US008244484B2

(12) United States Patent
Lee et al.

(10) Patent No.: US 8,244,484 B2
(45) Date of Patent: Aug. 14, 2012

(54) PROTEOME EPITOPE TAGS AND METHODS OF USE THEREOF IN PROTEIN MODIFICATION ANALYSIS

(75) Inventors: Frank D. Lee, Chestnut Hill, MA (US); Xun Meng, Newton, MA (US); Noubar B. Afeyan, Lexington, MA (US)

(73) Assignee: EMD Millipore Corporation, Billerica, MA (US)

( * ) Notice: Subject to any disclaimer, the term of this patent is extended or adjusted under 35 U.S.C. 154(b) by 9 days.

(21) Appl. No.: 12/576,864

(22) Filed: Oct. 9, 2009

(65) Prior Publication Data

US 2010/0184613 A1 Jul. 22, 2010

Related U.S. Application Data

(63) Continuation of application No. 10/773,032, filed on Feb. 5, 2004, now Pat. No. 7,618,788, which is a continuation-in-part of application No. 10/712,425, filed on Nov. 13, 2003, now Pat. No. 7,460,960, which is a continuation-in-part of application No. 10/436,549, filed on May 12, 2003, now abandoned.

(60) Provisional application No. 60/433,319, filed on Dec. 13, 2002, provisional application No. 60/430,948, filed on Dec. 4, 2002, provisional application No. 60/393,197, filed on Jul. 1, 2002, provisional application No. 60/393,280, filed on Jul. 1, 2002, provisional application No. 60/393,223, filed on Jul. 1, 2002, provisional application No. 60/393,211, filed on Jul. 1, 2002, provisional application No. 60/393,235, filed on Jul. 1, 2002, provisional application No. 60/393,233, filed on Jul. 1, 2002, provisional application No. 60/393,137, filed on Jul. 1, 2002, provisional application No. 60/379,626, filed on May 10, 2002.

(51) Int. Cl.
*G01N 31/00* (2006.01)

(52) U.S. Cl. ........................................................ 702/27

(58) Field of Classification Search ..................... 702/27
See application file for complete search history.

(56) References Cited

U.S. PATENT DOCUMENTS

| | | | |
|---|---|---|---|
| 4,478,744 A | 10/1984 | Mezei et al. | |
| 4,658,022 A | 4/1987 | Knowles et al. | |
| 4,970,171 A | 11/1990 | Messenger et al. | |
| 5,061,790 A | 10/1991 | Elting et al. | |
| 5,223,441 A | 6/1993 | Ullman et al. | |
| 5,449,601 A | 9/1995 | Jean et al. | |
| 5,565,332 A | 10/1996 | Hoogenboom et al. | |
| 5,580,742 A | 12/1996 | Bodenmuller et al. | |
| 5,708,155 A | 1/1998 | Potter et al. | |
| 5,723,129 A | 3/1998 | Potter et al. | |
| 5,763,158 A | 6/1998 | Bohannon | |
| 5,790,155 A | 8/1998 | Usui et al. | |
| 5,798,155 A | 8/1998 | Yanagawa et al. | |
| 5,849,531 A | 12/1998 | Potter | |
| 5,872,234 A | 2/1999 | Bandman et al. | |
| 5,955,317 A | 9/1999 | Suzuki et al. | |
| 5,961,923 A | 10/1999 | Nova et al. | |
| 6,113,897 A | 9/2000 | Danø et al. | |
| 6,197,599 B1 | 3/2001 | Chin et al. | |
| 6,225,047 B1 | 5/2001 | Hutchens et al. | |
| 6,253,456 B1 | 7/2001 | Cooksey | |
| 6,261,569 B1 | 7/2001 | Comis et al. | |
| 6,329,209 B1 | 12/2001 | Wagner et al. | |
| 6,365,418 B1 | 4/2002 | Wagner et al. | |
| 6,406,921 B1 | 6/2002 | Wagner et al. | |
| 6,420,125 B1 | 7/2002 | Fledelius et al. | |
| 6,794,363 B2 | 9/2004 | Bejanin et al. | |
| 6,897,073 B2 * | 5/2005 | Wagner et al. | ................ 436/518 |
| 6,955,915 B2 | 10/2005 | Fodor et al. | |
| 7,022,486 B2 | 4/2006 | Campbell | |
| 7,460,960 B2 | 12/2008 | Lee et al. | |
| 7,964,362 B2 | 6/2011 | Lee et al. | |
| 2002/0042386 A1 | 4/2002 | Rosen et al. | |
| 2002/0055186 A1 | 5/2002 | Barry et al. | |
| 2002/0081617 A1 | 6/2002 | Buranda et al. | |
| 2002/0106702 A1 | 8/2002 | Wagner et al. | |
| 2002/0110843 A1 | 8/2002 | Dumas | |
| 2002/0110933 A1 | 8/2002 | Wagner et al. | |
| 2002/0119579 A1 | 8/2002 | Wagner | |
| 2002/0137119 A1 | 9/2002 | Katz | |
| 2003/0028330 A1 | 2/2003 | Cheng et al. | |
| 2003/0032039 A1 | 2/2003 | Cunningham et al. | |

(Continued)

FOREIGN PATENT DOCUMENTS

AU 2003302118 A1 6/2004

(Continued)

OTHER PUBLICATIONS

Holt et al. "By-passing Selection: Direction Screening for Anitibody-Antigen Interactions Using Protein Arrays," Nucleic Acids Research (2000) vol. 28, No. 15, pp. e72 (i-v).*

Arenkov et al. "Protein Microchips: Use for Immunoassay and Enzymatic Reactions", Analytical Biochemistry, vol. 278, 2000, pp. 123-131.

Arnheiter et al., "Physicochemical and antigenic properties of synthetic fragments of human leukocyte interferon" Nature 294, 1981, pp. 278-280.

Arnon "Synthetic Peptides as the Basis for Vaccine Design" Molecular Immunology, vol. 28(3), 1991, pp. 209-215.

(Continued)

*Primary Examiner* — Jerry Lin

(74) *Attorney, Agent, or Firm* — EMD Millipore Corporation

(57) ABSTRACT

Disclosed are methods for reliably detecting the presence of proteins, including proteins with various post-translational modifications (phosphorylation, glycosylation, methylation, acetylation, etc.) in a sample by the use of one or more capture agents that recognize and interact with recognition sequences uniquely characteristic of a protein or a set of proteins (Proteome Epitope Tags, or PETs) in the sample. Arrays comprising these capture agents or PETs are also provided.

20 Claims, 24 Drawing Sheets
(20 of 24 Drawing Sheet(s) Filed in Color)

U.S. PATENT DOCUMENTS

| | | | |
|---|---|---|---|
| 2003/0044862 | A1 | 3/2003 | Giaccia et al. |
| 2003/0054408 | A1 | 3/2003 | Ravi et al. |
| 2003/0143612 | A1* | 7/2003 | Ault-Riche et al. ............ 435/6 |
| 2004/0029292 | A1 | 2/2004 | Joos et al. |
| 2004/0038307 | A1 | 2/2004 | Lee et al. |
| 2004/0096901 | A1 | 5/2004 | Aversa et al. |
| 2004/0180380 | A1 | 9/2004 | Lee et al. |
| 2004/0229284 | A1 | 11/2004 | Luciw et al. |
| 2005/0069911 | A1 | 3/2005 | Lee et al. |
| 2005/0153298 | A1 | 7/2005 | Gembitsky et al. |
| 2005/0214304 | A1 | 9/2005 | Pastan et al. |
| 2005/0255491 | A1 | 11/2005 | Lee et al. |
| 2006/0014212 | A1 | 1/2006 | Bankovic et al. |
| 2006/0035270 | A1 | 2/2006 | Lee et al. |
| 2007/0224628 | A1 | 9/2007 | Gordon et al. |
| 2007/0224704 | A1 | 9/2007 | Gordon et al. |
| 2008/0248500 | A1 | 10/2008 | Semmes et al. |

FOREIGN PATENT DOCUMENTS

| | | | |
|---|---|---|---|
| DE | 40 23 945 | A1 | 1/1992 |
| DE | 100 54 055 | A1 | 5/2002 |
| EP | 0 267 355 | A1 | 5/1988 |
| EP | 0 337 057 | A1 | 10/1989 |
| EP | 0449269 | B1 | 5/1996 |
| EP | 1320754 | A2 | 6/2003 |
| JP | 4-223270 | A | 8/1992 |
| JP | 07-285999 | A | 10/1995 |
| JP | 2002-360278 | A | 12/2002 |
| WO | 94/08597 | A1 | 4/1994 |
| WO | 95/00851 | A1 | 1/1995 |
| WO | 96/05847 | A1 | 2/1996 |
| WO | 96/29629 | A2 | 9/1996 |
| WO | 97/07132 | A1 | 2/1997 |
| WO | 99/38013 | A2 | 7/1999 |
| WO | 99/39210 | A1 | 8/1999 |
| WO | 00/04389 | A2 | 1/2000 |
| WO | 00/45168 | A1 | 8/2000 |
| WO | 00/54046 | A2 | 9/2000 |
| WO | 0178652 | A2 | 10/2001 |
| WO | 02/06834 | A2 | 1/2002 |
| WO | 02/25287 | A2 | 3/2002 |
| WO | 02/37117 | A1 | 5/2002 |
| WO | 03/01879 | A2 | 1/2003 |
| WO | 03/58249 | A1 | 7/2003 |
| WO | 2004/046164 | A2 | 6/2004 |
| WO | 2005/050223 | A2 | 6/2005 |
| WO | 2005/050224 | A2 | 6/2005 |
| WO | 2005/078453 | A2 | 8/2005 |
| WO | 2007/112012 | A2 | 10/2007 |
| WO | 2007/123708 | A2 | 11/2007 |

OTHER PUBLICATIONS

Barbas III, et al. "Assembly of Combinatorial Antibody Libraries on Phage Surfaces: The Gene III Site", Proceedings of the National. Academy of Sciences, vol. 88, Sep. 1991, pp. 7978-7982.

Barry et al. "Competitive Assay Formats for High-Throughput Affinity Arrays", J. Biomol. Screen, 3, 2003, 257-263.

Bittner et al., "Molecular Classification of cutaneous malignant melanoma by gene expression profiling", Nature, 406, Aug. 3, 2000, pp. 536-540.

Borrebaeck et al., "Antibodies in Diagnostics—From Immunoassays to Protein Chips", Immunology Today, vol. 21 (8), 2000, 379-381.

Chames et al., "Antibody engineering and its applications in tumor targeting and intracellular immunization", FEMS Microbiology Letters, 189, 2000, pp. 1-8.

Chou et al., "Prediction of protein conformation", Biochemistry, vol. 13(2), Jan. 1974, pp. 222-245.

Clark et al., "Genomic analysis of metastasis reveals an essential role for RhoC", Nature, 406, 2000, pp. 532-535.

De Wildt et al. "Antibody arrays for high-throughput screening of antibody—antigen interactions", Nature Biotechnology, vol. 18(9), 2000, pp. 989-994.

Devereux et al., "A Comprehensive Set of Sequence Analysis Programs for the VAX", Nucleic Acids Research,12(1) 1984, pp. 387-395.

Dours-Zimmermann et al., "A Novel Glycosaminoglycan Attachment Domain Identified in Two Alternative Splice Variants of Human Versican" The Journal of Biological Chemistry, vol. 269(52), Dec. 30, 1994, pp. 32992-23998.

Partial European Search Report issued in Application No. EP 03808371, dated Jun. 1, 2006, 7 pages.

Erali et al., "ELISA for thyroglobulin in serum: recovery studies to evaluate autoantibody interference and reliability of thyroglobulin values" Clinical Chemistry 42:5, 1996, pp. 766-770.

Evans et al. "Effect of anticoagulants and storage temperatures on stability of plasma and serum hormones", Clinical Biochemistry, vol. 34(2), Mar. 2001, pp. 107-112.

Gembitsky et al., "A prototype antibody microarray platform to monitor changes in protein tyrosine phosphorylation", Molecular & Cellular Proteomics, 3(11), Nov. 2004, pp. 1102-1118.

Georges et al "Detection of P-glycoprotein isoforms by gene specific monoclonal antibodies", Proceedings of the National Academy of Sciences—USA, vol. 87, Jan. 1990, pp. 152-156.

Grimm et al., "Nanogram scale separations of proteins using capillary high-performance liquid chromatography with fully-automated on-line microfraction collection followed by matrix-assisted laser desorption ionisation time-of-flight mass spectrometry protein sequencing and western blot analysis." J. Chromatogr A. Mar. 1998, pp. 83-88.

Grubb et al. "Signal Pathway Profiling of Prostate Cancer using Reverse Phase Protein Arrays" Proteomics, 3(11), Nov. 2003, pp. 2142-2146.

Haab et al., "Protein Microarrays for highly parallel detection and quantitation of specific proteins and antibodies in complex solutions" Genome Biology, 2(2), 2001, research 0004.1-0004.13.

Harper et al., "Two-Dimensional Gel Electrophoresis", Current Protocols in Protein Science, Unit 10.4, 1998, pp. 10.4.1-10.4.36.

Haupt et al., "Plastic Antibodies: Developments and Applications", Trends in Biotechnology, vol. 16(11), Nov. 1998, pp. 468-475.

Hellmold "Identification of End Points Relevant to Detection of Potentially Adverse Drug Reactions", Toxicology Letters, 127(1), Feb. 2002, pp. 239-243.

Hemminki, et al., "Fine Tuning of an Anti-Testosterone Antibody Binding Site by Stepwise Optimisation of the CDRs" Immunotechnology, 4, 1989, pp. 59-69.

Henning et al., WinPep-ein Programm zur Analyse von Aminosauresequenzen Biospektrum Biospektrum, 4(5) 1989, pp. 49-50.

Hongo et al., "Identification of a second protein encoded by influenza C virus RNA segment 6" Journal General Virology, vol. 75, 1994, pp. 3503-3510.

Hoogenboom et al. "Antibody Phage Display Technology and its Applications" Immunotechnology 4, 1989, pp. 1-20.

Hoogenboom et al., "Natural and Designer Binding Sites Made by Phage Display Technology" Immunology Today, vol. 21(8), 2000, pp. 371-378.

Hopp et al., "A Computer Program for Predicting Protein Antigenic Determinants" Molecular Immunology, 20(4), 1983, pp. 483-489.

Huang et al., "The Plasticity of Dendric Cell Responses to Pathogens and Their Components" Science, 294(5543), Oct. 2001, pp. 870-875.

Hughes et al. "Functional Discovery via a Compendium of Express Profiles" Cell, 102(1), Jul. 2000, pp. 109-126.

Jean et al. "A Novel Protein Immunoassay with Predetermined Specificity Using Monoclonal Antibodies Against Tryptic Fragments: Application to HIV P24 Antigen" J. Immunol. Mehtods, vol. 185(1), 1995, pp. 103-114.

Jemmerson "Antigenicity and native structure of globular proteins: low frequency of peptide reactive antibodies" Proc. Natl. Acad. Sci. USA, vol. 84, Dec. 1987, pp. 9180-9184.

Keyomarsi et al. "Cyclin E and Survival in Patients with Breast Cancer" New England Journal of Medicine, 347(20) Nov. 2002, pp. 1566-1575.

Kohlberger et al., "Immunohistochemical Detection of CD44 Splice Variant Expression in Premalignant Lesions of the Cervix and Benign Cervical Epithelium" Gynecologic Oncology, vol. 66, 1997, pp. 227-232.

Kuruvilla et al. "Dissecting Glucose Signaling with Diversity-Oriented Synthesis and Small-Molecule Microarrays" Nature, vol. 416, 2002, pp. 653-657.

Kyte et al., "A Simple Method for Displaying the Hydropathic Character of a Protein", J. Mol. Biol. vol. 157, 1982, pp. 105-132.

Lerner "Antibodies of Predetermined Specificity in Biology and Medicine" Advances in Immunology, vol. 36(1), 1984, pp. 1-45.

Lesko "Use of Biomarkers and Surrogate Endpoints in Drug Development and Regulatory Decision Making: Criteria, Validation, Strategies", Annu. Rev. Pharmacol. Toxicol., vol. 41, 2001, pp. 347-366.

Levilliers et al., "Monoclonal and polyclonal antibodies detect a new type of post-translational modification of axonemal tubulin" Journal of Cell Science, vol. 108(9), 1995, pp. 3013-3028.

Li et al., "Application of Microfluidic Devices to proteomics Research: Identification of Trace-Level Protein Digests and Affinity Capture of Target Peptides" Molecular & Cellular Proteomics 1(2), Feb. 2002, pp. 157-168.

Li et al., "Applications of Display Technology in Protein Analysis" Nature Biotechnology, vol. 18, 2000, pp. 1251-1256.

Liu et al., "Motif-based construction of a functional map for mammalian olfactory receptors" Genomics 81(5), 2003, pp. 443-456.

Lizardi et al. "Mutation Detection and Single Molecule Counting Using Isothermal Rolling Circle Amplification" Nature Genetics vol. 19, 1998, pp. 225-232.

MacBeath et al. "Printing Proteins as Microarrays for High-Throughput Function Determination" Science, vol. 289 (5485), 2000, pp. 1760-1763.

Maggio Enzyme-immunoassay, 1980, pp. 53-70.

Mann et al. "Analysis of Protein Phosphorylation Using Mass Spectrometry: Deciphering the Phosphoproteome" Trends in Biotechnology, vol. 20(6), Jun. 2002, pp. 261-268.

Mariani et al. "Immunogenicity of a free synthetic peptide: Carrier-conjugation enhances antibody affinity for the native protein" Molecular Immunology, vol. 24(3), Mar. 1987, pp. 297-303.

Marks et al. "By—Passing Immunization: Building High Affinity Human Antibodies by Chain Shuffling", Nature Biotechnology, 10, 1992, pp. 779-783.

Martegani et al., "Structural Variability of CD44v Molecules and Reliability of Immunodetection of CD44 Isoforms Using mAbs Specific for CD44 Variant Exon Products", American J. Pathology, 154(1), 1999.

Michaud et al. "Analyzing Antibody Specificity with Whole Proteome Microarrays", Nat. Biotech, vol. 21(12), Dec. 2003, pp. 1509-1512.

Nelson et al., "Demystified . . . Monoclonal Antibodies", J. Clin. Pathol: Mol Pathol. 53, 2000, pp. 111-117.

Ohlin et al. "Light chain shuffling of a high affinity antibody results in a drift in epitope recognition", Molecular Immunology, vol. 33(1), Jan. 1996, pp. 47-56.

Park et al. "Thermal Denaturation: A Useful Technique in Peptide Mass Mapping", Anal. Chem, 72(11), 2000, pp. 2667-2670.

International Search Report of PCT/US2003/014846, dated Nov. 30, 2004, 5 pages.

International Search Report of PCT/US2004/038283, dated Dec. 22, 2005, 6 pages.

Phelps et al "Metabolomics and microarrays for improved understanding of phenotypic characteristics controlled by both genomics and environmental constraints" Curr. Opi. Biotech vol. 13(1), Feb. 2002, pp. 20-24.

Punglia et al., "Effect of Verification Bias on Screening for Prostate Cancer by Measurement of Prostate-Specific Antigen" New England Journal of Medicine, 349, 2003, pp. 335-342.

Rosenkranz "Biomarkers and Surrogate Endpoints in Clinical Drug Development" Applied Clinical Trials, Jul. 1, 2003, pp. 30-34 and 40.

Schweitzer et al. "Multiplexed Protein Profiling on Microarrays by Rolling-Circle Amplification" Nat. Biotechnolol. 20 (4), Apr. 2002, pp. 359-365.

Scrivener et al. "Peptidomics: A New Approach to Affinity Protein Microarrays" Protemics, 3, 2003, pp. 122-128.

Shea et al. "Immunologic Detection and Measurement of Glycated Apolipoprotein B with Site Specific Monocolonal Antibodies" J. Immunol. Methods, vol. 162(1), 1993, pp. 85-95.

Soderlind et al. "Complementary-Determining Region (CDR) Implantation: A Theme of Recombination" Immunotechnology, 4(3-4), Mar. 1999, pp. 279-285.

Soderlind et al. "Recombining Germline-Derived CDR Sequences for Creating Diverse Single-Framework Antibody Libraries" Nature Biotechnology, 18, 2000, pp. 852-856.

Soloviev et al., "Combinatorial Peptidomics: A Generic Approach for Protein Expression Profiling" Journal of Nanobiotechnology, 1:4, Jul. 3, 2003, pp. 1-19.

Sumner et al. "Plant metabolomics: large-scale phytochemistry in the functional genomics era", Phytochemistry, vol. 62(6), 2003, 817-836.

Vlatakis et al. "Drug Assay Using Antibody Mimics Made by Molecular Imprinting" J. Of Nanobiotechnology 1, 1993, pp. 1-19.

Weckwerth "Metabolomics in System Biology" Annu. Rev. Plant Biol. 54, 2003, pp. 669-689.

Werkmeister et al., "Multiple Antigenic Determinants on Type III Collagen" Biochem. J., 274, 1991, pp. 895-898.

Whaley et al. "Identification of Nearest-neighbor Peptides in Protease Digests by Mass Spectrometry for Construction of Sequence-ordered Tryptic Maps" Biological Mass Spectrometry, vol. 20, 1991, pp. 210-214.

Zhu et al. "Global Analysis of Protein Activities Using Proteome Chips", Science, 293(5537), Sep. 14, 2001, pp. 2101-2105.

Cazares et al., "Discovery of Prostate Cancer Biomarkers from Lazer Capture Microdissected (LCM) Cells Using Innovative Proteinchip SELDI Mass Spectroscopy", Proceedings of the Annual Meeting of the American Association for Cancer Research, 5407, vol. 41, Mar. 2000, p. 851.

Cottrell, John S., "Protein Identification by Peptide Mass Fingerprinting", Peptide Research, vol. 7, No. 3, 1994, pp. 115-124.

Geng et al., "Signature-peptide approach to detecting proteins in complex mixtures", Journal of Chromatography A, vol. 807, No. 1-2, 2000, pp. 295-313.

International Search Report recieved for PCT Application No. PCT/EP2001/012295, mailed on Apr. 5, 2002, 4 pages of International Search Report and 4 pages of English Translation.

International Preliminary Examination Report recieved for PCT Application No. PCT/EP2001/012295, mailed on Apr. 3, 2003, 7 pages of International Preliminary Examination report and 3 pages of English Translation.

International Search Report and Written Opinion recieved for PCT Application No. PCT/US2007/007268m mailed on Sep. 14, 2007, 8 pages.

International Preliminary Report on Patentability recieved for PCT Application No. PCT/US2007/007268, issued on Sep. 23, 2008, 6 pages.

* cited by examiner

Interleukin-8 receptor A: SeqID: ENSP00000295683
Sequence and pentamer URS distribution

- MSNITDPQMWDFDDLNFTGMPPADEDYSPCMLETETLNKYVVIIAYALVFLLSLLGNSLVMLVILYSR
  VGRSVTDVYLLNLALADLLFALTLPIWAASKVNGWIFGTFLCKVVSLLKEVNFYSGTILLACISVDRY
  LAIVHATRTLTQKRHLVKFVCLGCWGLSMNLSLPFFLFRQAYHPNNSSPVCYEVLGNDTAKWRMVLRI
  LPHTFGFIVPLFVMLFCYGFTLRTLFKAHMGQKHRAMRVIFAVVLIFLLCWLPYNLVLLADTLMRTQV
  IQESCERRNNIGRALDATEILGFLHSCLNPIIYAFIGQNFRHGFLKILAMHGLVSKEFLARHRVTSYT
  SSSVNVSSNL (SEQ ID NO. 546)

- ENSP00000295683: list of pentamer URS peptides: (total number: 35) AHMGQ (SEQ ID NO. 547) AKWRM (SEQ ID NO.548) AYHPN (SEQ ID NO. 549) CERRN (SEQ ID NO. 550) CLGCW (SEQ ID NO. 551) CYGFT (SEQ ID NO. 552) DLNFT (SEQ ID NO. 553) DPQMW (SEQ ID NO. 554) DTAKW (SEQ ID NO. 555) FCYGF (SEQ ID NO. 556) FKAHM (SEQ ID NO. 557) GQNFR (SEQ ID NO. 558) HTFGF (SEQ ID NO. 559) IWAAS (SEQ ID NO. 560) KWRMV (SEQ ID NO. 561) KYVVI (SEQ ID NO. 562) MGQKH (SEQ ID NO. 563) MPPAD (SEQ ID NO. 564) NFTGM (SEQ ID NO. 565) NGWIF (SEQ ID NO. 566) PQMWD (SEQ ID NO. 567) PYNLV (SEQ ID NO. 568) QKHRA (SEQ ID NO. 569) QMWDF (SEQ ID NO. 570) QNFRH (SEQ ID NO. 571) TAKWR (SEQ ID NO. 572) TDPQM (SEQ ID NO. 573) VCLGC (SEQ ID NO. 574) VCYEV (SEQ ID NO. 575) VMLFC (SEQ ID NO. 576) VNGWI (SEQ ID NO. 577) WDFDD (SEQ ID NO. 578) WIFGT (SEQ ID NO. 579) WRMVL (SEQ ID NO. 580) YSPCM (SEQ ID NO. 581)

- ___ : URS Penta-peptide

Figure 1

Histamine H1 receptor: SeqID: ENSP00000273023
Sequence and pentamer URS distribution

MSLPNSSCLLEDK!MCEGNK!TTMASPQLMPLVVVLSTICLVTVGLNLLVLYAVR!SER!K!LHTVGN

LYIVSLSVADLIVGAVVMPMNILYLLMSK!WSLGR!PLCLFWLSMDYVASTASIFSVFILCIDR!YR!

SVQQPLR!YLK!YR!TK!TR!ASATILGAWFLSFLWVIPILGWNHFMQQTSVR!R!EDK!CETDFYDV

TWFK!VMTAIINFYLPTLLMLWFYAK!IYK!AVR!QHCQHR!ELINR!SLPSFSEIK!LR!PENPK!G

DAK!K!PGK!ESPWEVLK!R!K!PK!DAGGGSVLK!SPSQTPK!EMK!SPVVFSQEDDR!EVDK!LYC

FPLDIVHMQAAAEGSSR!DYVAVNR!SHGQLK!TDEQGLNTHGASEISEDQMLGDSQSFSR!TDSDTT

TETAPGK!GK!LR!SGSNTGLDYIK!FTWK!R!LR!SHSR!QYVSGLHMNR!ER!K!AAK!QLGFIMA

AFILCWIPYFIFFMVIAFCK!NCCNEHLHMFTIWLGYINSTLNPLIYPLCNENFK!K!TFK!R!ILHI

R!S (SEQ ID NO. 582)

URS Penta-peptide: AIINF (SEQ ID NO. 583) CEGNK (SEQ ID NO. 584) CNENF (SEQ ID NO. 585) CWIPY (SEQ ID NO. 586) DFYDV (SEQ ID NO. 587) DQMLG (SEQ ID NO. 588) FILCI (SEQ ID NO. 589) FLWVI (SEQ ID NO. 590) FMQQT (SEQ ID NO. 591) FWLSM (SEQ ID NO. 592) GWNHF (SEQ ID NO. 593) HLHMF (SEQ ID NO. 594) HMFTI (SEQ ID NO. 595) HTVGN (SEQ ID NO. 596) IFFMV (SEQ ID NO. 597) ILCWI (SEQ ID NO. 598) LLMSK (SEQ ID NO. 599) LWFYA (SEQ ID NO. 600) MCEGN (SEQ ID NO. 601) MDYVA (SEQ ID NO. 602) MFTIW (SEQ ID NO. 603) MLWFY (SEQ ID NO. 604) NCCNE (SEQ ID NO. 605) NHFMQ (SEQ ID NO. 606) PLCLF (SEQ ID NO. 607) SPWEV (SEQ ID NO. 608) VIAFC (SEQ ID NO. 609) WFYAK (SEQ ID NO. 610) WNHFM (SEQ ID NO. 611) WVIPI (SEQ ID NO. 612) YCFPL (SEQ ID NO. 613)

!: trypsin cutting site, ___: URS Penta-peptide

| Protein | Parental Tryptic Peptide | Also Detect |
|---|---|---|
| BRAF | WSGSHQFEQLSGSILWMAPEVIR* (SEQ ID NO. 1327) | |
| DLK | MSFAGTVAWMAPEVIR (SEQ ID NO. 1328) | |
| GCK | SFIGTPYWMAPEVAAVER (SEQ ID NO. 1329) | |
| HH498 | WMAPEVFTQCTR (SEQ ID NO. 1330) | |
| HPK1 | LSFIGTPYWMAPEVAAVALK (SEQ ID NO. 1331) | |
| LOK | DSFIGTPYWMAPEVVMCETMK (SEQ ID NO. 1332) | KSH1,2, HPK1, SLK |
| LZK | MSFAGTVAWMAPEVIR (SEQ ID NO. 1333) | |
| MAP3K | SMHGTPYWMAPEVINESGYGR (SEQ ID NO. 1334) | |
| MST1 | NTVIGTPFWMAPEVIQEIGYNCVR (SEQ ID NO. 1335) | MST2 |
| MST4 | NTFVGTPFWMAPEVIQQSAYDSK (SEQ ID NO. 1336) | |
| MYO3A | NTSVGTPFWMAPEVIACEQQLDTTYDAR (SEQ ID NO. 1337) | MYO3B |
| MYO3B | NTSVGTPFWMAPEVIACEQQYDSSYDAR (SEQ ID NO. 1338) | MYO3A |
| ZC1/HGK | NTFIGTPYWMAPEVIACDENPDATYDYR (SEQ ID NO. 1339) | ZC2, ZC3 |
| OSR1 | TFVGTPCWMAPEVMEQVR (SEQ ID NO. 1340) | |
| PAK1 | STMVGTPYWMAPEVVTR (SEQ ID NO. 1341) | PAK2,3 |
| PAK5 | SLVGTPYWMAPEVISR (SEQ ID NO. 1342) | PAK6 |
| RAF1 | WSGSQQVEQPTGSVLWMAPEVIR (SEQ ID NO. 1343) | |
| STLK3 | TFVGTPCWMAPEVMEQVR (SEQ ID NO. 1344) | |
| TAO1 | ASMASPANSFVGTPYWMAPEVILAMDEGQYDGK (SEQ ID NO. 1345) | TAO3 |
| TAO2 | ASIMAPANSFVGTPYWMAPEVILAMDEGQYDGK (SEQ ID NO. 1346) | |
| TESK1 | EPLAVVGSPYWMAPEVLR (SEQ ID NO. 1347) | |
| ZAK | TTHMSLVGTFPWMAPEVIQSLR (SEQ ID NO. 1348) | |

BLUE = PET
RED = Commone Epitope

SEQUENCE LISTING

```
<160> NUMBER OF SEQ ID NOS: 1386

<210> SEQ ID NO 1
<211> LENGTH: 5
<212> TYPE: PRT
<213> ORGANISM: Homo sapiens

<400> SEQUENCE: 1

Ala Met Pro Val Ser
1               5

<210> SEQ ID NO 2
<211> LENGTH: 5
<212> TYPE: PRT
```

```
<213> ORGANISM: Homo sapiens

<400> SEQUENCE: 2

Cys Ala Thr Gln Gly
1               5

<210> SEQ ID NO 3
<211> LENGTH: 5
<212> TYPE: PRT
<213> ORGANISM: Homo sapiens

<400> SEQUENCE: 3

Cys Phe Thr Val Trp
1               5

<210> SEQ ID NO 4
<211> LENGTH: 5
<212> TYPE: PRT
<213> ORGANISM: Homo sapiens

<400> SEQUENCE: 4

Ile Cys Phe Thr Val
1               5

<210> SEQ ID NO 5
<211> LENGTH: 5
<212> TYPE: PRT
<213> ORGANISM: Homo sapiens

<400> SEQUENCE: 5

Met Pro Asn Ala Met
1               5

<210> SEQ ID NO 6
<211> LENGTH: 5
<212> TYPE: PRT
<213> ORGANISM: Homo sapiens

<400> SEQUENCE: 6

Pro Asn Ala Met Pro
1               5

<210> SEQ ID NO 7
<211> LENGTH: 5
<212> TYPE: PRT
<213> ORGANISM: Homo sapiens

<400> SEQUENCE: 7

Ser Arg Thr Trp Tyr
1               5

<210> SEQ ID NO 8
<211> LENGTH: 5
<212> TYPE: PRT
<213> ORGANISM: Homo sapiens

<400> SEQUENCE: 8

Thr Trp Tyr Val Gln
1               5

<210> SEQ ID NO 9
<211> LENGTH: 5
<212> TYPE: PRT
<213> ORGANISM: Homo sapiens

<400> SEQUENCE: 9
```

```
Trp Tyr Val Gln Ala
1               5

<210> SEQ ID NO 10
<211> LENGTH: 5
<212> TYPE: PRT
<213> ORGANISM: Homo sapiens

<400> SEQUENCE: 10

Cys Asp Phe Val Cys
1               5

<210> SEQ ID NO 11
<211> LENGTH: 5
<212> TYPE: PRT
<213> ORGANISM: Homo sapiens

<400> SEQUENCE: 11

Cys Gly Lys Glu Gln
1               5

<210> SEQ ID NO 12
<211> LENGTH: 5
<212> TYPE: PRT
<213> ORGANISM: Homo sapiens

<400> SEQUENCE: 12

Cys Trp Arg Thr Gly
1               5

<210> SEQ ID NO 13
<211> LENGTH: 5
<212> TYPE: PRT
<213> ORGANISM: Homo sapiens

<400> SEQUENCE: 13

Asp Asn Phe Asn Pro
1               5

<210> SEQ ID NO 14
<211> LENGTH: 5
<212> TYPE: PRT
<213> ORGANISM: Homo sapiens

<400> SEQUENCE: 14

Asp Asn His Cys Gly
1               5

<210> SEQ ID NO 15
<211> LENGTH: 5
<212> TYPE: PRT
<213> ORGANISM: Homo sapiens

<400> SEQUENCE: 15

Phe Arg Val Cys Arg
1               5

<210> SEQ ID NO 16
<211> LENGTH: 5
<212> TYPE: PRT
<213> ORGANISM: Homo sapiens

<400> SEQUENCE: 16

Phe Tyr Ser Cys Trp
1               5
```

-continued

<210> SEQ ID NO 17
<211> LENGTH: 5
<212> TYPE: PRT
<213> ORGANISM: Homo sapiens

<400> SEQUENCE: 17

Gly Met Glu Gln Phe
1               5

<210> SEQ ID NO 18
<211> LENGTH: 5
<212> TYPE: PRT
<213> ORGANISM: Homo sapiens

<400> SEQUENCE: 18

His Leu Ala Phe Trp
1               5

<210> SEQ ID NO 19
<211> LENGTH: 5
<212> TYPE: PRT
<213> ORGANISM: Homo sapiens

<400> SEQUENCE: 19

Ile Phe Asn Gly Ser
1               5

<210> SEQ ID NO 20
<211> LENGTH: 5
<212> TYPE: PRT
<213> ORGANISM: Homo sapiens

<400> SEQUENCE: 20

Ile Met Leu Ile Tyr
1               5

<210> SEQ ID NO 21
<211> LENGTH: 5
<212> TYPE: PRT
<213> ORGANISM: Homo sapiens

<400> SEQUENCE: 21

Ile Tyr Ile Phe Arg
1               5

<210> SEQ ID NO 22
<211> LENGTH: 5
<212> TYPE: PRT
<213> ORGANISM: Homo sapiens

<400> SEQUENCE: 22

Lys Gly Met Glu Gln
1               5

<210> SEQ ID NO 23
<211> LENGTH: 5
<212> TYPE: PRT
<213> ORGANISM: Homo sapiens

<400> SEQUENCE: 23

Lys Thr Cys Asp Leu
1               5

<210> SEQ ID NO 24

```
<211> LENGTH: 5
<212> TYPE: PRT
<213> ORGANISM: Homo sapiens

<400> SEQUENCE: 24

Met Phe Pro Phe Tyr
1               5

<210> SEQ ID NO 25
<211> LENGTH: 5
<212> TYPE: PRT
<213> ORGANISM: Homo sapiens

<400> SEQUENCE: 25

Met Ile Ser Cys Asn
1               5

<210> SEQ ID NO 26
<211> LENGTH: 5
<212> TYPE: PRT
<213> ORGANISM: Homo sapiens

<400> SEQUENCE: 26

Asn Glu Thr His Ile
1               5

<210> SEQ ID NO 27
<211> LENGTH: 5
<212> TYPE: PRT
<213> ORGANISM: Homo sapiens

<400> SEQUENCE: 27

Asn Trp Ile Met Leu
1               5

<210> SEQ ID NO 28
<211> LENGTH: 5
<212> TYPE: PRT
<213> ORGANISM: Homo sapiens

<400> SEQUENCE: 28

Pro Phe Tyr Ser Cys
1               5

<210> SEQ ID NO 29
<211> LENGTH: 5
<212> TYPE: PRT
<213> ORGANISM: Homo sapiens

<400> SEQUENCE: 29

Gln Asp Cys Phe Tyr
1               5

<210> SEQ ID NO 30
<211> LENGTH: 5
<212> TYPE: PRT
<213> ORGANISM: Homo sapiens

<400> SEQUENCE: 30

Gln Phe Pro His Leu
1               5

<210> SEQ ID NO 31
<211> LENGTH: 5
<212> TYPE: PRT
<213> ORGANISM: Homo sapiens
```

```
<400> SEQUENCE: 31

Arg Glu Ser Trp Gln
1               5

<210> SEQ ID NO 32
<211> LENGTH: 5
<212> TYPE: PRT
<213> ORGANISM: Homo sapiens

<400> SEQUENCE: 32

Ser Asn Trp Ile Met
1               5

<210> SEQ ID NO 33
<211> LENGTH: 5
<212> TYPE: PRT
<213> ORGANISM: Homo sapiens

<400> SEQUENCE: 33

Val Met Ile Ser Cys
1               5

<210> SEQ ID NO 34
<211> LENGTH: 5
<212> TYPE: PRT
<213> ORGANISM: Homo sapiens

<400> SEQUENCE: 34

Tyr Asp Asn His Cys
1               5

<210> SEQ ID NO 35
<211> LENGTH: 5
<212> TYPE: PRT
<213> ORGANISM: Homo sapiens

<400> SEQUENCE: 35

Tyr Ile Tyr Ile Phe
1               5

<210> SEQ ID NO 36
<211> LENGTH: 5
<212> TYPE: PRT
<213> ORGANISM: Homo sapiens

<400> SEQUENCE: 36

Tyr Lys Gly Gly Asp
1               5

<210> SEQ ID NO 37
<211> LENGTH: 5
<212> TYPE: PRT
<213> ORGANISM: Homo sapiens

<400> SEQUENCE: 37

Tyr Leu Phe Glu Met
1               5

<210> SEQ ID NO 38
<211> LENGTH: 5
<212> TYPE: PRT
<213> ORGANISM: Homo sapiens

<400> SEQUENCE: 38
```

```
Tyr Arg Gly Val Gly
1               5

<210> SEQ ID NO 39
<211> LENGTH: 5
<212> TYPE: PRT
<213> ORGANISM: Homo sapiens

<400> SEQUENCE: 39

Tyr Ser Cys Trp Arg
1               5

<210> SEQ ID NO 40
<211> LENGTH: 5
<212> TYPE: PRT
<213> ORGANISM: Homo sapiens

<400> SEQUENCE: 40

Ala Ser Asn Glu Cys
1               5

<210> SEQ ID NO 41
<211> LENGTH: 5
<212> TYPE: PRT
<213> ORGANISM: Homo sapiens

<400> SEQUENCE: 41

Pro Ala Ser Asn Glu
1               5

<210> SEQ ID NO 42
<211> LENGTH: 5
<212> TYPE: PRT
<213> ORGANISM: Homo sapiens

<400> SEQUENCE: 42

Ala Gln Pro Trp Ala
1               5

<210> SEQ ID NO 43
<211> LENGTH: 5
<212> TYPE: PRT
<213> ORGANISM: Homo sapiens

<400> SEQUENCE: 43

Ala Ser Thr Trp Arg
1               5

<210> SEQ ID NO 44
<211> LENGTH: 5
<212> TYPE: PRT
<213> ORGANISM: Homo sapiens

<400> SEQUENCE: 44

Cys Leu Cys Leu Val
1               5

<210> SEQ ID NO 45
<211> LENGTH: 5
<212> TYPE: PRT
<213> ORGANISM: Homo sapiens

<400> SEQUENCE: 45

Phe Val Ile Cys Ala
1               5
```

```
<210> SEQ ID NO 46
<211> LENGTH: 5
<212> TYPE: PRT
<213> ORGANISM: Homo sapiens

<400> SEQUENCE: 46

Leu Tyr Cys Cys Pro
1               5

<210> SEQ ID NO 47
<211> LENGTH: 5
<212> TYPE: PRT
<213> ORGANISM: Homo sapiens

<400> SEQUENCE: 47

Pro Arg Ala Asn Arg
1               5

<210> SEQ ID NO 48
<211> LENGTH: 5
<212> TYPE: PRT
<213> ORGANISM: Homo sapiens

<400> SEQUENCE: 48

Val Asn Val Leu Cys
1               5

<210> SEQ ID NO 49
<211> LENGTH: 5
<212> TYPE: PRT
<213> ORGANISM: Homo sapiens

<400> SEQUENCE: 49

Tyr Ala Gln Leu Trp
1               5

<210> SEQ ID NO 50
<211> LENGTH: 5
<212> TYPE: PRT
<213> ORGANISM: Homo sapiens

<400> SEQUENCE: 50

Tyr Cys Cys Pro Val
1               5

<210> SEQ ID NO 51
<211> LENGTH: 5
<212> TYPE: PRT
<213> ORGANISM: Homo sapiens

<400> SEQUENCE: 51

Ala Ile Gln Arg Met
1               5

<210> SEQ ID NO 52
<211> LENGTH: 5
<212> TYPE: PRT
<213> ORGANISM: Homo sapiens

<400> SEQUENCE: 52

Ala Lys Pro Asn Glu
1               5

<210> SEQ ID NO 53
<211> LENGTH: 5
```

```
<212> TYPE: PRT
<213> ORGANISM: Homo sapiens

<400> SEQUENCE: 53

Ala Met Cys His Leu
1               5

<210> SEQ ID NO 54
<211> LENGTH: 5
<212> TYPE: PRT
<213> ORGANISM: Homo sapiens

<400> SEQUENCE: 54

Ala Trp Asp Ile Ala
1               5

<210> SEQ ID NO 55
<211> LENGTH: 5
<212> TYPE: PRT
<213> ORGANISM: Homo sapiens

<400> SEQUENCE: 55

Cys Gln Gln Arg Ile
1               5

<210> SEQ ID NO 56
<211> LENGTH: 5
<212> TYPE: PRT
<213> ORGANISM: Homo sapiens

<400> SEQUENCE: 56

Glu Leu Lys Tyr Glu
1               5

<210> SEQ ID NO 57
<211> LENGTH: 5
<212> TYPE: PRT
<213> ORGANISM: Homo sapiens

<400> SEQUENCE: 57

Glu Met Pro Met Ile
1               5

<210> SEQ ID NO 58
<211> LENGTH: 5
<212> TYPE: PRT
<213> ORGANISM: Homo sapiens

<400> SEQUENCE: 58

Phe Val His Tyr Thr
1               5

<210> SEQ ID NO 59
<211> LENGTH: 5
<212> TYPE: PRT
<213> ORGANISM: Homo sapiens

<400> SEQUENCE: 59

His Ser Ile Val Tyr
1               5

<210> SEQ ID NO 60
<211> LENGTH: 5
<212> TYPE: PRT
<213> ORGANISM: Homo sapiens
```

```
<400> SEQUENCE: 60

His Tyr Thr Gly Trp
1               5

<210> SEQ ID NO 61
<211> LENGTH: 5
<212> TYPE: PRT
<213> ORGANISM: Homo sapiens

<400> SEQUENCE: 61

Leu Tyr Ala Asn Met
1               5

<210> SEQ ID NO 62
<211> LENGTH: 5
<212> TYPE: PRT
<213> ORGANISM: Homo sapiens

<400> SEQUENCE: 62

Met Ile Gly Asp Arg
1               5

<210> SEQ ID NO 63
<211> LENGTH: 5
<212> TYPE: PRT
<213> ORGANISM: Homo sapiens

<400> SEQUENCE: 63

Gln Lys Ser Asn Thr
1               5

<210> SEQ ID NO 64
<211> LENGTH: 5
<212> TYPE: PRT
<213> ORGANISM: Homo sapiens

<400> SEQUENCE: 64

Ser Trp Glu Met Asn
1               5

<210> SEQ ID NO 65
<211> LENGTH: 5
<212> TYPE: PRT
<213> ORGANISM: Homo sapiens

<400> SEQUENCE: 65

Ser Trp Leu Glu Tyr
1               5

<210> SEQ ID NO 66
<211> LENGTH: 5
<212> TYPE: PRT
<213> ORGANISM: Homo sapiens

<400> SEQUENCE: 66

Thr Glu Met Pro Met
1               5

<210> SEQ ID NO 67
<211> LENGTH: 5
<212> TYPE: PRT
<213> ORGANISM: Homo sapiens

<400> SEQUENCE: 67

Trp Glu Met Asn Ser
```

```
1               5

<210> SEQ ID NO 68
<211> LENGTH: 5
<212> TYPE: PRT
<213> ORGANISM: Homo sapiens

<400> SEQUENCE: 68

Tyr Ala Lys Pro Asn
1               5

<210> SEQ ID NO 69
<211> LENGTH: 5
<212> TYPE: PRT
<213> ORGANISM: Homo sapiens

<400> SEQUENCE: 69

Tyr Glu Ser Ser Phe
1               5

<210> SEQ ID NO 70
<211> LENGTH: 5
<212> TYPE: PRT
<213> ORGANISM: Homo sapiens

<400> SEQUENCE: 70

Tyr Pro Asn Asn Lys
1               5

<210> SEQ ID NO 71
<211> LENGTH: 5
<212> TYPE: PRT
<213> ORGANISM: Homo sapiens

<400> SEQUENCE: 71

Ala Thr Arg Asp Lys
1               5

<210> SEQ ID NO 72
<211> LENGTH: 5
<212> TYPE: PRT
<213> ORGANISM: Homo sapiens

<400> SEQUENCE: 72

Cys Pro Cys Glu Gly
1               5

<210> SEQ ID NO 73
<211> LENGTH: 5
<212> TYPE: PRT
<213> ORGANISM: Homo sapiens

<400> SEQUENCE: 73

Asp Lys Ser Cys Lys
1               5

<210> SEQ ID NO 74
<211> LENGTH: 5
<212> TYPE: PRT
<213> ORGANISM: Homo sapiens

<400> SEQUENCE: 74

Asp Thr His Asp Thr
1               5
```

```
<210> SEQ ID NO 75
<211> LENGTH: 5
<212> TYPE: PRT
<213> ORGANISM: Homo sapiens

<400> SEQUENCE: 75

Glu Trp Pro Arg Ser
1               5

<210> SEQ ID NO 76
<211> LENGTH: 5
<212> TYPE: PRT
<213> ORGANISM: Homo sapiens

<400> SEQUENCE: 76

Phe Glu Val Tyr Gln
1               5

<210> SEQ ID NO 77
<211> LENGTH: 5
<212> TYPE: PRT
<213> ORGANISM: Homo sapiens

<400> SEQUENCE: 77

Phe Gln Ile Pro Lys
1               5

<210> SEQ ID NO 78
<211> LENGTH: 5
<212> TYPE: PRT
<213> ORGANISM: Homo sapiens

<400> SEQUENCE: 78

Phe Ser Gly Tyr Arg
1               5

<210> SEQ ID NO 79
<211> LENGTH: 5
<212> TYPE: PRT
<213> ORGANISM: Homo sapiens

<400> SEQUENCE: 79

Gly Cys Pro Cys Glu
1               5

<210> SEQ ID NO 80
<211> LENGTH: 5
<212> TYPE: PRT
<213> ORGANISM: Homo sapiens

<400> SEQUENCE: 80

Gly His Leu Phe Glu
1               5

<210> SEQ ID NO 81
<211> LENGTH: 5
<212> TYPE: PRT
<213> ORGANISM: Homo sapiens

<400> SEQUENCE: 81

His Asp Thr Ala Pro
1               5

<210> SEQ ID NO 82
<211> LENGTH: 5
<212> TYPE: PRT
```

```
<213> ORGANISM: Homo sapiens

<400> SEQUENCE: 82

Ile Phe Ser His Glu
1               5

<210> SEQ ID NO 83
<211> LENGTH: 5
<212> TYPE: PRT
<213> ORGANISM: Homo sapiens

<400> SEQUENCE: 83

Lys Glu Met Thr Met
1               5

<210> SEQ ID NO 84
<211> LENGTH: 5
<212> TYPE: PRT
<213> ORGANISM: Homo sapiens

<400> SEQUENCE: 84

Lys Leu Gln Cys Thr
1               5

<210> SEQ ID NO 85
<211> LENGTH: 5
<212> TYPE: PRT
<213> ORGANISM: Homo sapiens

<400> SEQUENCE: 85

Lys Ser Cys Lys Leu
1               5

<210> SEQ ID NO 86
<211> LENGTH: 5
<212> TYPE: PRT
<213> ORGANISM: Homo sapiens

<400> SEQUENCE: 86

Lys Tyr Gly Asn Val
1               5

<210> SEQ ID NO 87
<211> LENGTH: 5
<212> TYPE: PRT
<213> ORGANISM: Homo sapiens

<400> SEQUENCE: 87

Leu Lys His Pro Thr
1               5

<210> SEQ ID NO 88
<211> LENGTH: 5
<212> TYPE: PRT
<213> ORGANISM: Homo sapiens

<400> SEQUENCE: 88

Met Gly Glu His His
1               5

<210> SEQ ID NO 89
<211> LENGTH: 5
<212> TYPE: PRT
<213> ORGANISM: Homo sapiens

<400> SEQUENCE: 89
```

```
Met Thr Met Gln Glu
1               5

<210> SEQ ID NO 90
<211> LENGTH: 5
<212> TYPE: PRT
<213> ORGANISM: Homo sapiens

<400> SEQUENCE: 90

Met Tyr Ser Ile Arg
1               5

<210> SEQ ID NO 91
<211> LENGTH: 5
<212> TYPE: PRT
<213> ORGANISM: Homo sapiens

<400> SEQUENCE: 91

Asn Val Phe Asp Pro
1               5

<210> SEQ ID NO 92
<211> LENGTH: 5
<212> TYPE: PRT
<213> ORGANISM: Homo sapiens

<400> SEQUENCE: 92

Gln Leu Trp Gln Leu
1               5

<210> SEQ ID NO 93
<211> LENGTH: 5
<212> TYPE: PRT
<213> ORGANISM: Homo sapiens

<400> SEQUENCE: 93

Arg Gly Ile Gln Ala
1               5

<210> SEQ ID NO 94
<211> LENGTH: 5
<212> TYPE: PRT
<213> ORGANISM: Homo sapiens

<400> SEQUENCE: 94

Arg Tyr Leu Asp Cys
1               5

<210> SEQ ID NO 95
<211> LENGTH: 5
<212> TYPE: PRT
<213> ORGANISM: Homo sapiens

<400> SEQUENCE: 95

Ser Thr Glu Trp Pro
1               5

<210> SEQ ID NO 96
<211> LENGTH: 5
<212> TYPE: PRT
<213> ORGANISM: Homo sapiens

<400> SEQUENCE: 96

Thr His Asp Thr Ala
1               5
```

<210> SEQ ID NO 97
<211> LENGTH: 5
<212> TYPE: PRT
<213> ORGANISM: Homo sapiens

<400> SEQUENCE: 97

Thr Arg Thr Phe Pro
1               5

<210> SEQ ID NO 98
<211> LENGTH: 5
<212> TYPE: PRT
<213> ORGANISM: Homo sapiens

<400> SEQUENCE: 98

Val Met Tyr Ser Ile
1               5

<210> SEQ ID NO 99
<211> LENGTH: 5
<212> TYPE: PRT
<213> ORGANISM: Homo sapiens

<400> SEQUENCE: 99

Val Arg Thr Cys Leu
1               5

<210> SEQ ID NO 100
<211> LENGTH: 5
<212> TYPE: PRT
<213> ORGANISM: Homo sapiens

<400> SEQUENCE: 100

Val Ser Thr Glu Trp
1               5

<210> SEQ ID NO 101
<211> LENGTH: 5
<212> TYPE: PRT
<213> ORGANISM: Homo sapiens

<400> SEQUENCE: 101

Trp Gln Leu Arg Trp
1               5

<210> SEQ ID NO 102
<211> LENGTH: 5
<212> TYPE: PRT
<213> ORGANISM: Homo sapiens

<400> SEQUENCE: 102

Trp Ser Val Met Tyr
1               5

<210> SEQ ID NO 103
<211> LENGTH: 5
<212> TYPE: PRT
<213> ORGANISM: Homo sapiens

<400> SEQUENCE: 103

Ala Cys Lys Cys Phe
1               5

<210> SEQ ID NO 104

```
<211> LENGTH: 5
<212> TYPE: PRT
<213> ORGANISM: Homo sapiens

<400> SEQUENCE: 104

Cys Lys Cys Phe Trp
1               5

<210> SEQ ID NO 105
<211> LENGTH: 5
<212> TYPE: PRT
<213> ORGANISM: Homo sapiens

<400> SEQUENCE: 105

Phe Trp Leu Trp Tyr
1               5

<210> SEQ ID NO 106
<211> LENGTH: 5
<212> TYPE: PRT
<213> ORGANISM: Homo sapiens

<400> SEQUENCE: 106

Lys Cys Phe Trp Leu
1               5

<210> SEQ ID NO 107
<211> LENGTH: 5
<212> TYPE: PRT
<213> ORGANISM: Homo sapiens

<400> SEQUENCE: 107

Leu Trp Tyr Pro His
1               5

<210> SEQ ID NO 108
<211> LENGTH: 5
<212> TYPE: PRT
<213> ORGANISM: Homo sapiens

<400> SEQUENCE: 108

Gln Lys Arg Arg Cys
1               5

<210> SEQ ID NO 109
<211> LENGTH: 5
<212> TYPE: PRT
<213> ORGANISM: Homo sapiens

<400> SEQUENCE: 109

Trp Leu Trp Tyr Pro
1               5

<210> SEQ ID NO 110
<211> LENGTH: 5
<212> TYPE: PRT
<213> ORGANISM: Homo sapiens

<400> SEQUENCE: 110

Trp Tyr Pro His Phe
1               5

<210> SEQ ID NO 111
<211> LENGTH: 5
<212> TYPE: PRT
<213> ORGANISM: Homo sapiens
```

<400> SEQUENCE: 111

Ala Met Glu Gln Thr
1               5

<210> SEQ ID NO 112
<211> LENGTH: 5
<212> TYPE: PRT
<213> ORGANISM: Homo sapiens

<400> SEQUENCE: 112

Ala Pro Cys Thr Ile
1               5

<210> SEQ ID NO 113
<211> LENGTH: 5
<212> TYPE: PRT
<213> ORGANISM: Homo sapiens

<400> SEQUENCE: 113

Ala Tyr Met Glu Arg
1               5

<210> SEQ ID NO 114
<211> LENGTH: 5
<212> TYPE: PRT
<213> ORGANISM: Homo sapiens

<400> SEQUENCE: 114

Cys Thr Ile Met Lys
1               5

<210> SEQ ID NO 115
<211> LENGTH: 5
<212> TYPE: PRT
<213> ORGANISM: Homo sapiens

<400> SEQUENCE: 115

Asp Gly Leu Cys Asn
1               5

<210> SEQ ID NO 116
<211> LENGTH: 5
<212> TYPE: PRT
<213> ORGANISM: Homo sapiens

<400> SEQUENCE: 116

Glu Gln Thr Trp Arg
1               5

<210> SEQ ID NO 117
<211> LENGTH: 5
<212> TYPE: PRT
<213> ORGANISM: Homo sapiens

<400> SEQUENCE: 117

Phe Arg Ser Tyr Gly
1               5

<210> SEQ ID NO 118
<211> LENGTH: 5
<212> TYPE: PRT
<213> ORGANISM: Homo sapiens

<400> SEQUENCE: 118

```
Gly Met Ala Tyr Met
1               5

<210> SEQ ID NO 119
<211> LENGTH: 5
<212> TYPE: PRT
<213> ORGANISM: Homo sapiens

<400> SEQUENCE: 119

Gly Tyr His Met Pro
1               5

<210> SEQ ID NO 120
<211> LENGTH: 5
<212> TYPE: PRT
<213> ORGANISM: Homo sapiens

<400> SEQUENCE: 120

His Ile Pro Asn Tyr
1               5

<210> SEQ ID NO 121
<211> LENGTH: 5
<212> TYPE: PRT
<213> ORGANISM: Homo sapiens

<400> SEQUENCE: 121

Lys Gly Arg Ile Pro
1               5

<210> SEQ ID NO 122
<211> LENGTH: 5
<212> TYPE: PRT
<213> ORGANISM: Homo sapiens

<400> SEQUENCE: 122

Lys Leu Asp Met Gly
1               5

<210> SEQ ID NO 123
<211> LENGTH: 5
<212> TYPE: PRT
<213> ORGANISM: Homo sapiens

<400> SEQUENCE: 123

Met Ala Tyr Met Glu
1               5

<210> SEQ ID NO 124
<211> LENGTH: 5
<212> TYPE: PRT
<213> ORGANISM: Homo sapiens

<400> SEQUENCE: 124

Met Glu Gln Thr Trp
1               5

<210> SEQ ID NO 125
<211> LENGTH: 5
<212> TYPE: PRT
<213> ORGANISM: Homo sapiens

<400> SEQUENCE: 125

Met Asn Lys Arg Glu
1               5
```

```
<210> SEQ ID NO 126
<211> LENGTH: 5
<212> TYPE: PRT
<213> ORGANISM: Homo sapiens

<400> SEQUENCE: 126

Pro Gly Met Asn Lys
1               5

<210> SEQ ID NO 127
<211> LENGTH: 5
<212> TYPE: PRT
<213> ORGANISM: Homo sapiens

<400> SEQUENCE: 127

Gln Gly Tyr His Met
1               5

<210> SEQ ID NO 128
<211> LENGTH: 5
<212> TYPE: PRT
<213> ORGANISM: Homo sapiens

<400> SEQUENCE: 128

Thr Met Ser Pro Lys
1               5

<210> SEQ ID NO 129
<211> LENGTH: 5
<212> TYPE: PRT
<213> ORGANISM: Homo sapiens

<400> SEQUENCE: 129

Thr Trp Arg Leu Asp
1               5

<210> SEQ ID NO 130
<211> LENGTH: 5
<212> TYPE: PRT
<213> ORGANISM: Homo sapiens

<400> SEQUENCE: 130

Val Glu Gln Gly Tyr
1               5

<210> SEQ ID NO 131
<211> LENGTH: 5
<212> TYPE: PRT
<213> ORGANISM: Homo sapiens

<400> SEQUENCE: 131

Val Asn Asp Gly Leu
1               5

<210> SEQ ID NO 132
<211> LENGTH: 5
<212> TYPE: PRT
<213> ORGANISM: Homo sapiens

<400> SEQUENCE: 132

Trp Asp Gln Thr Arg
1               5

<210> SEQ ID NO 133
<211> LENGTH: 5
```

```
<212> TYPE: PRT
<213> ORGANISM: Homo sapiens

<400> SEQUENCE: 133

Trp Arg Leu Asp Pro
1               5

<210> SEQ ID NO 134
<211> LENGTH: 5
<212> TYPE: PRT
<213> ORGANISM: Homo sapiens

<400> SEQUENCE: 134

Tyr Glu Ala Met Glu
1               5

<210> SEQ ID NO 135
<211> LENGTH: 5
<212> TYPE: PRT
<213> ORGANISM: Homo sapiens

<400> SEQUENCE: 135

Tyr His Met Pro Cys
1               5

<210> SEQ ID NO 136
<211> LENGTH: 5
<212> TYPE: PRT
<213> ORGANISM: Homo sapiens

<400> SEQUENCE: 136

Tyr Asn Pro Cys Gln
1               5

<210> SEQ ID NO 137
<211> LENGTH: 5
<212> TYPE: PRT
<213> ORGANISM: Homo sapiens

<400> SEQUENCE: 137

Ala Thr Tyr Tyr Lys
1               5

<210> SEQ ID NO 138
<211> LENGTH: 5
<212> TYPE: PRT
<213> ORGANISM: Homo sapiens

<400> SEQUENCE: 138

Cys Ala Thr Tyr Tyr
1               5

<210> SEQ ID NO 139
<211> LENGTH: 5
<212> TYPE: PRT
<213> ORGANISM: Homo sapiens

<400> SEQUENCE: 139

Cys Asp Asn Pro Tyr
1               5

<210> SEQ ID NO 140
<211> LENGTH: 5
<212> TYPE: PRT
<213> ORGANISM: Homo sapiens
```

```
<400> SEQUENCE: 140

Cys Glu Val Val Lys
1               5

<210> SEQ ID NO 141
<211> LENGTH: 5
<212> TYPE: PRT
<213> ORGANISM: Homo sapiens

<400> SEQUENCE: 141

Cys Ile Lys Thr Asp
1               5

<210> SEQ ID NO 142
<211> LENGTH: 5
<212> TYPE: PRT
<213> ORGANISM: Homo sapiens

<400> SEQUENCE: 142

Cys Ile Asn Ser Arg
1               5

<210> SEQ ID NO 143
<211> LENGTH: 5
<212> TYPE: PRT
<213> ORGANISM: Homo sapiens

<400> SEQUENCE: 143

Cys Lys Ser Pro Asp
1               5

<210> SEQ ID NO 144
<211> LENGTH: 5
<212> TYPE: PRT
<213> ORGANISM: Homo sapiens

<400> SEQUENCE: 144

Cys Lys Ser Ser Asn
1               5

<210> SEQ ID NO 145
<211> LENGTH: 5
<212> TYPE: PRT
<213> ORGANISM: Homo sapiens

<400> SEQUENCE: 145

Cys Asn Glu Leu Pro
1               5

<210> SEQ ID NO 146
<211> LENGTH: 5
<212> TYPE: PRT
<213> ORGANISM: Homo sapiens

<400> SEQUENCE: 146

Cys Gln Glu Asn Tyr
1               5

<210> SEQ ID NO 147
<211> LENGTH: 5
<212> TYPE: PRT
<213> ORGANISM: Homo sapiens

<400> SEQUENCE: 147

Cys Ser Glu Ser Phe
```

```
1               5

<210> SEQ ID NO 148
<211> LENGTH: 5
<212> TYPE: PRT
<213> ORGANISM: Homo sapiens

<400> SEQUENCE: 148

Cys Tyr Glu Arg Glu
1               5

<210> SEQ ID NO 149
<211> LENGTH: 5
<212> TYPE: PRT
<213> ORGANISM: Homo sapiens

<400> SEQUENCE: 149

Cys Tyr His Phe Gly
1               5

<210> SEQ ID NO 150
<211> LENGTH: 5
<212> TYPE: PRT
<213> ORGANISM: Homo sapiens

<400> SEQUENCE: 150

Cys Tyr Met Gly Lys
1               5

<210> SEQ ID NO 151
<211> LENGTH: 5
<212> TYPE: PRT
<213> ORGANISM: Homo sapiens

<400> SEQUENCE: 151

Asp Phe Thr Trp Phe
1               5

<210> SEQ ID NO 152
<211> LENGTH: 5
<212> TYPE: PRT
<213> ORGANISM: Homo sapiens

<400> SEQUENCE: 152

Asp Gly Trp Ser Ala
1               5

<210> SEQ ID NO 153
<211> LENGTH: 5
<212> TYPE: PRT
<213> ORGANISM: Homo sapiens

<400> SEQUENCE: 153

Asp Ile Pro Ile Cys
1               5

<210> SEQ ID NO 154
<211> LENGTH: 5
<212> TYPE: PRT
<213> ORGANISM: Homo sapiens

<400> SEQUENCE: 154

Asp Gln Thr Tyr Pro
1               5
```

```
<210> SEQ ID NO 155
<211> LENGTH: 5
<212> TYPE: PRT
<213> ORGANISM: Homo sapiens

<400> SEQUENCE: 155

Asp Arg Glu Tyr His
1               5

<210> SEQ ID NO 156
<211> LENGTH: 5
<212> TYPE: PRT
<213> ORGANISM: Homo sapiens

<400> SEQUENCE: 156

Glu Glu Met His Cys
1               5

<210> SEQ ID NO 157
<211> LENGTH: 5
<212> TYPE: PRT
<213> ORGANISM: Homo sapiens

<400> SEQUENCE: 157

Glu Phe Asp His Asn
1               5

<210> SEQ ID NO 158
<211> LENGTH: 5
<212> TYPE: PRT
<213> ORGANISM: Homo sapiens

<400> SEQUENCE: 158

Glu Phe Asn Cys Ser
1               5

<210> SEQ ID NO 159
<211> LENGTH: 5
<212> TYPE: PRT
<213> ORGANISM: Homo sapiens

<400> SEQUENCE: 159

Glu His Gly Trp Ala
1               5

<210> SEQ ID NO 160
<211> LENGTH: 5
<212> TYPE: PRT
<213> ORGANISM: Homo sapiens

<400> SEQUENCE: 160

Glu Ile Asn Tyr Arg
1               5

<210> SEQ ID NO 161
<211> LENGTH: 5
<212> TYPE: PRT
<213> ORGANISM: Homo sapiens

<400> SEQUENCE: 161

Glu Lys Ile Pro Cys
1               5

<210> SEQ ID NO 162
<211> LENGTH: 5
<212> TYPE: PRT
```

<213> ORGANISM: Homo sapiens

<400> SEQUENCE: 162

Glu Met His Cys Ser
1               5

<210> SEQ ID NO 163
<211> LENGTH: 5
<212> TYPE: PRT
<213> ORGANISM: Homo sapiens

<400> SEQUENCE: 163

Glu Ser Asn Thr Gly
1               5

<210> SEQ ID NO 164
<211> LENGTH: 5
<212> TYPE: PRT
<213> ORGANISM: Homo sapiens

<400> SEQUENCE: 164

Glu Ser Thr Cys Gly
1               5

<210> SEQ ID NO 165
<211> LENGTH: 5
<212> TYPE: PRT
<213> ORGANISM: Homo sapiens

<400> SEQUENCE: 165

Glu Ser Tyr Ala His
1               5

<210> SEQ ID NO 166
<211> LENGTH: 5
<212> TYPE: PRT
<213> ORGANISM: Homo sapiens

<400> SEQUENCE: 166

Glu Tyr His Phe Gly
1               5

<210> SEQ ID NO 167
<211> LENGTH: 5
<212> TYPE: PRT
<213> ORGANISM: Homo sapiens

<400> SEQUENCE: 167

Glu Tyr Tyr Cys Asn
1               5

<210> SEQ ID NO 168
<211> LENGTH: 5
<212> TYPE: PRT
<213> ORGANISM: Homo sapiens

<400> SEQUENCE: 168

Phe Glu Asn Ala Ile
1               5

<210> SEQ ID NO 169
<211> LENGTH: 5
<212> TYPE: PRT
<213> ORGANISM: Homo sapiens

<400> SEQUENCE: 169

Phe Gln Tyr Lys Cys
1               5

<210> SEQ ID NO 170
<211> LENGTH: 5
<212> TYPE: PRT
<213> ORGANISM: Homo sapiens

<400> SEQUENCE: 170

Phe Thr Trp Phe Lys
1               5

<210> SEQ ID NO 171
<211> LENGTH: 5
<212> TYPE: PRT
<213> ORGANISM: Homo sapiens

<400> SEQUENCE: 171

Gly Glu Trp Val Ala
1               5

<210> SEQ ID NO 172
<211> LENGTH: 5
<212> TYPE: PRT
<213> ORGANISM: Homo sapiens

<400> SEQUENCE: 172

Gly Asn Val Phe Glu
1               5

<210> SEQ ID NO 173
<211> LENGTH: 5
<212> TYPE: PRT
<213> ORGANISM: Homo sapiens

<400> SEQUENCE: 173

Gly Trp Thr Asn Asp
1               5

<210> SEQ ID NO 174
<211> LENGTH: 5
<212> TYPE: PRT
<213> ORGANISM: Homo sapiens

<400> SEQUENCE: 174

His Gly Arg Lys Phe
1               5

<210> SEQ ID NO 175
<211> LENGTH: 5
<212> TYPE: PRT
<213> ORGANISM: Homo sapiens

<400> SEQUENCE: 175

His Gly Thr Ile Asn
1               5

<210> SEQ ID NO 176
<211> LENGTH: 5
<212> TYPE: PRT
<213> ORGANISM: Homo sapiens

<400> SEQUENCE: 176

His Gly Trp Ala Gln
1               5

<210> SEQ ID NO 177
<211> LENGTH: 5
<212> TYPE: PRT
<213> ORGANISM: Homo sapiens

<400> SEQUENCE: 177

His Pro Gly Tyr Ala
1               5

<210> SEQ ID NO 178
<211> LENGTH: 5
<212> TYPE: PRT
<213> ORGANISM: Homo sapiens

<400> SEQUENCE: 178

His Pro Pro Ser Cys
1               5

<210> SEQ ID NO 179
<211> LENGTH: 5
<212> TYPE: PRT
<213> ORGANISM: Homo sapiens

<400> SEQUENCE: 179

His Thr Val Cys Ile
1               5

<210> SEQ ID NO 180
<211> LENGTH: 5
<212> TYPE: PRT
<213> ORGANISM: Homo sapiens

<400> SEQUENCE: 180

Ile His Gly Val Trp
1               5

<210> SEQ ID NO 181
<211> LENGTH: 5
<212> TYPE: PRT
<213> ORGANISM: Homo sapiens

<400> SEQUENCE: 181

Ile Lys His Arg Thr
1               5

<210> SEQ ID NO 182
<211> LENGTH: 5
<212> TYPE: PRT
<213> ORGANISM: Homo sapiens

<400> SEQUENCE: 182

Ile Met Val Cys Arg
1               5

<210> SEQ ID NO 183
<211> LENGTH: 5
<212> TYPE: PRT
<213> ORGANISM: Homo sapiens

<400> SEQUENCE: 183

Ile Asn Gly Arg Trp
1               5

<210> SEQ ID NO 184

```
<211> LENGTH: 5
<212> TYPE: PRT
<213> ORGANISM: Homo sapiens

<400> SEQUENCE: 184

Ile Pro Cys Ser Gln
1               5

<210> SEQ ID NO 185
<211> LENGTH: 5
<212> TYPE: PRT
<213> ORGANISM: Homo sapiens

<400> SEQUENCE: 185

Ile Pro Val Phe Met
1               5

<210> SEQ ID NO 186
<211> LENGTH: 5
<212> TYPE: PRT
<213> ORGANISM: Homo sapiens

<400> SEQUENCE: 186

Ile Val Cys Gly Tyr
1               5

<210> SEQ ID NO 187
<211> LENGTH: 5
<212> TYPE: PRT
<213> ORGANISM: Homo sapiens

<400> SEQUENCE: 187

Ile Tyr Lys Cys Arg
1               5

<210> SEQ ID NO 188
<211> LENGTH: 5
<212> TYPE: PRT
<213> ORGANISM: Homo sapiens

<400> SEQUENCE: 188

Ile Tyr Lys Glu Asn
1               5

<210> SEQ ID NO 189
<211> LENGTH: 5
<212> TYPE: PRT
<213> ORGANISM: Homo sapiens

<400> SEQUENCE: 189

Lys Cys Asn Met Gly
1               5

<210> SEQ ID NO 190
<211> LENGTH: 5
<212> TYPE: PRT
<213> ORGANISM: Homo sapiens

<400> SEQUENCE: 190

Lys Gly Glu Trp Val
1               5

<210> SEQ ID NO 191
<211> LENGTH: 5
<212> TYPE: PRT
<213> ORGANISM: Homo sapiens
```

```
<400> SEQUENCE: 191

Lys Ile Pro Cys Ser
1               5

<210> SEQ ID NO 192
<211> LENGTH: 5
<212> TYPE: PRT
<213> ORGANISM: Homo sapiens

<400> SEQUENCE: 192

Lys Pro Cys Asp Tyr
1               5

<210> SEQ ID NO 193
<211> LENGTH: 5
<212> TYPE: PRT
<213> ORGANISM: Homo sapiens

<400> SEQUENCE: 193

Lys Trp Ser His Pro
1               5

<210> SEQ ID NO 194
<211> LENGTH: 5
<212> TYPE: PRT
<213> ORGANISM: Homo sapiens

<400> SEQUENCE: 194

Leu Pro Ile Cys Tyr
1               5

<210> SEQ ID NO 195
<211> LENGTH: 5
<212> TYPE: PRT
<213> ORGANISM: Homo sapiens

<400> SEQUENCE: 195

Met Glu Asn Gly Trp
1               5

<210> SEQ ID NO 196
<211> LENGTH: 5
<212> TYPE: PRT
<213> ORGANISM: Homo sapiens

<400> SEQUENCE: 196

Met Gly Lys Trp Ser
1               5

<210> SEQ ID NO 197
<211> LENGTH: 5
<212> TYPE: PRT
<213> ORGANISM: Homo sapiens

<400> SEQUENCE: 197

Met Gly Tyr Glu Tyr
1               5

<210> SEQ ID NO 198
<211> LENGTH: 5
<212> TYPE: PRT
<213> ORGANISM: Homo sapiens

<400> SEQUENCE: 198
```

```
Met Ile Gly His Arg
1               5

<210> SEQ ID NO 199
<211> LENGTH: 5
<212> TYPE: PRT
<213> ORGANISM: Homo sapiens

<400> SEQUENCE: 199

Asn Cys Ser Met Ala
1               5

<210> SEQ ID NO 200
<211> LENGTH: 5
<212> TYPE: PRT
<213> ORGANISM: Homo sapiens

<400> SEQUENCE: 200

Asn Asp Phe Thr Trp
1               5

<210> SEQ ID NO 201
<211> LENGTH: 5
<212> TYPE: PRT
<213> ORGANISM: Homo sapiens

<400> SEQUENCE: 201

Asn Glu Gly Tyr Gln
1               5

<210> SEQ ID NO 202
<211> LENGTH: 5
<212> TYPE: PRT
<213> ORGANISM: Homo sapiens

<400> SEQUENCE: 202

Asn Glu Thr Thr Cys
1               5

<210> SEQ ID NO 203
<211> LENGTH: 5
<212> TYPE: PRT
<213> ORGANISM: Homo sapiens

<400> SEQUENCE: 203

Asn Gly Trp Ser Asp
1               5

<210> SEQ ID NO 204
<211> LENGTH: 5
<212> TYPE: PRT
<213> ORGANISM: Homo sapiens

<400> SEQUENCE: 204

Asn Met Gly Tyr Glu
1               5

<210> SEQ ID NO 205
<211> LENGTH: 5
<212> TYPE: PRT
<213> ORGANISM: Homo sapiens

<400> SEQUENCE: 205

Asn Gln Asn His Gly
1               5
```

```
<210> SEQ ID NO 206
<211> LENGTH: 5
<212> TYPE: PRT
<213> ORGANISM: Homo sapiens

<400> SEQUENCE: 206

Asn Ser Val Gln Cys
1               5

<210> SEQ ID NO 207
<211> LENGTH: 5
<212> TYPE: PRT
<213> ORGANISM: Homo sapiens

<400> SEQUENCE: 207

Asn Val Phe Glu Tyr
1               5

<210> SEQ ID NO 208
<211> LENGTH: 5
<212> TYPE: PRT
<213> ORGANISM: Homo sapiens

<400> SEQUENCE: 208

Asn Tyr Arg Asp Gly
1               5

<210> SEQ ID NO 209
<211> LENGTH: 5
<212> TYPE: PRT
<213> ORGANISM: Homo sapiens

<400> SEQUENCE: 209

Asn Tyr Arg Glu Cys
1               5

<210> SEQ ID NO 210
<211> LENGTH: 5
<212> TYPE: PRT
<213> ORGANISM: Homo sapiens

<400> SEQUENCE: 210

Pro Cys Asp Tyr Pro
1               5

<210> SEQ ID NO 211
<211> LENGTH: 5
<212> TYPE: PRT
<213> ORGANISM: Homo sapiens

<400> SEQUENCE: 211

Pro Glu Val Asn Cys
1               5

<210> SEQ ID NO 212
<211> LENGTH: 5
<212> TYPE: PRT
<213> ORGANISM: Homo sapiens

<400> SEQUENCE: 212

Pro Ile Cys Tyr Glu
1               5

<210> SEQ ID NO 213
<211> LENGTH: 5
```

```
<212> TYPE: PRT
<213> ORGANISM: Homo sapiens

<400> SEQUENCE: 213

Pro Pro Gln Cys Glu
1               5

<210> SEQ ID NO 214
<211> LENGTH: 5
<212> TYPE: PRT
<213> ORGANISM: Homo sapiens

<400> SEQUENCE: 214

Pro Pro Tyr Tyr Tyr
1               5

<210> SEQ ID NO 215
<211> LENGTH: 5
<212> TYPE: PRT
<213> ORGANISM: Homo sapiens

<400> SEQUENCE: 215

Pro Gln Cys Val Ala
1               5

<210> SEQ ID NO 216
<211> LENGTH: 5
<212> TYPE: PRT
<213> ORGANISM: Homo sapiens

<400> SEQUENCE: 216

Pro Tyr Ile Pro Asn
1               5

<210> SEQ ID NO 217
<211> LENGTH: 5
<212> TYPE: PRT
<213> ORGANISM: Homo sapiens

<400> SEQUENCE: 217

Gln Cys Tyr His Phe
1               5

<210> SEQ ID NO 218
<211> LENGTH: 5
<212> TYPE: PRT
<213> ORGANISM: Homo sapiens

<400> SEQUENCE: 218

Gln Ile Gln Leu Cys
1               5

<210> SEQ ID NO 219
<211> LENGTH: 5
<212> TYPE: PRT
<213> ORGANISM: Homo sapiens

<400> SEQUENCE: 219

Gln Tyr Lys Val Gly
1               5

<210> SEQ ID NO 220
<211> LENGTH: 5
<212> TYPE: PRT
<213> ORGANISM: Homo sapiens
```

```
<400> SEQUENCE: 220

Arg Asp Thr Ser Cys
1               5

<210> SEQ ID NO 221
<211> LENGTH: 5
<212> TYPE: PRT
<213> ORGANISM: Homo sapiens

<400> SEQUENCE: 221

Arg Glu Tyr His Phe
1               5

<210> SEQ ID NO 222
<211> LENGTH: 5
<212> TYPE: PRT
<213> ORGANISM: Homo sapiens

<400> SEQUENCE: 222

Arg Ile Lys His Arg
1               5

<210> SEQ ID NO 223
<211> LENGTH: 5
<212> TYPE: PRT
<213> ORGANISM: Homo sapiens

<400> SEQUENCE: 223

Arg Lys Gly Glu Trp
1               5

<210> SEQ ID NO 224
<211> LENGTH: 5
<212> TYPE: PRT
<213> ORGANISM: Homo sapiens

<400> SEQUENCE: 224

Arg Pro Cys Gly His
1               5

<210> SEQ ID NO 225
<211> LENGTH: 5
<212> TYPE: PRT
<213> ORGANISM: Homo sapiens

<400> SEQUENCE: 225

Arg Val Arg Tyr Gln
1               5

<210> SEQ ID NO 226
<211> LENGTH: 5
<212> TYPE: PRT
<213> ORGANISM: Homo sapiens

<400> SEQUENCE: 226

Arg Trp Gln Ser Ile
1               5

<210> SEQ ID NO 227
<211> LENGTH: 5
<212> TYPE: PRT
<213> ORGANISM: Homo sapiens

<400> SEQUENCE: 227

Ser Cys Asp Asn Pro
```

```
1               5
```

<210> SEQ ID NO 228
<211> LENGTH: 5
<212> TYPE: PRT
<213> ORGANISM: Homo sapiens

<400> SEQUENCE: 228

```
Ser Asp Gln Thr Tyr
1               5
```

<210> SEQ ID NO 229
<211> LENGTH: 5
<212> TYPE: PRT
<213> ORGANISM: Homo sapiens

<400> SEQUENCE: 229

```
Ser Phe Thr Met Ile
1               5
```

<210> SEQ ID NO 230
<211> LENGTH: 5
<212> TYPE: PRT
<213> ORGANISM: Homo sapiens

<400> SEQUENCE: 230

```
Ser Ile Thr Cys Gly
1               5
```

<210> SEQ ID NO 231
<211> LENGTH: 5
<212> TYPE: PRT
<213> ORGANISM: Homo sapiens

<400> SEQUENCE: 231

```
Ser Arg Trp Thr Gly
1               5
```

<210> SEQ ID NO 232
<211> LENGTH: 5
<212> TYPE: PRT
<213> ORGANISM: Homo sapiens

<400> SEQUENCE: 232

```
Ser Thr Gly Trp Ile
1               5
```

<210> SEQ ID NO 233
<211> LENGTH: 5
<212> TYPE: PRT
<213> ORGANISM: Homo sapiens

<400> SEQUENCE: 233

```
Ser Val Glu Phe Asn
1               5
```

<210> SEQ ID NO 234
<211> LENGTH: 5
<212> TYPE: PRT
<213> ORGANISM: Homo sapiens

<400> SEQUENCE: 234

```
Ser Trp Ser Asp Gln
1               5
```

```
<210> SEQ ID NO 235
<211> LENGTH: 5
<212> TYPE: PRT
<213> ORGANISM: Homo sapiens

<400> SEQUENCE: 235

Thr Ala Lys Cys Thr
1               5

<210> SEQ ID NO 236
<211> LENGTH: 5
<212> TYPE: PRT
<213> ORGANISM: Homo sapiens

<400> SEQUENCE: 236

Thr Cys Ile His Gly
1               5

<210> SEQ ID NO 237
<211> LENGTH: 5
<212> TYPE: PRT
<213> ORGANISM: Homo sapiens

<400> SEQUENCE: 237

Thr Cys Ile Asn Ser
1               5

<210> SEQ ID NO 238
<211> LENGTH: 5
<212> TYPE: PRT
<213> ORGANISM: Homo sapiens

<400> SEQUENCE: 238

Thr Cys Met Glu Asn
1               5

<210> SEQ ID NO 239
<211> LENGTH: 5
<212> TYPE: PRT
<213> ORGANISM: Homo sapiens

<400> SEQUENCE: 239

Thr Cys Tyr Met Gly
1               5

<210> SEQ ID NO 240
<211> LENGTH: 5
<212> TYPE: PRT
<213> ORGANISM: Homo sapiens

<400> SEQUENCE: 240

Thr Met Ile Gly His
1               5

<210> SEQ ID NO 241
<211> LENGTH: 5
<212> TYPE: PRT
<213> ORGANISM: Homo sapiens

<400> SEQUENCE: 241

Thr Asn Asp Ile Pro
1               5

<210> SEQ ID NO 242
<211> LENGTH: 5
<212> TYPE: PRT
```

<213> ORGANISM: Homo sapiens

<400> SEQUENCE: 242

Thr Ser Thr Gly Trp
1               5

<210> SEQ ID NO 243
<211> LENGTH: 5
<212> TYPE: PRT
<213> ORGANISM: Homo sapiens

<400> SEQUENCE: 243

Thr Trp Phe Lys Leu
1               5

<210> SEQ ID NO 244
<211> LENGTH: 5
<212> TYPE: PRT
<213> ORGANISM: Homo sapiens

<400> SEQUENCE: 244

Thr Tyr Lys Cys Phe
1               5

<210> SEQ ID NO 245
<211> LENGTH: 5
<212> TYPE: PRT
<213> ORGANISM: Homo sapiens

<400> SEQUENCE: 245

Val Ala Ile Asp Lys
1               5

<210> SEQ ID NO 246
<211> LENGTH: 5
<212> TYPE: PRT
<213> ORGANISM: Homo sapiens

<400> SEQUENCE: 246

Val Cys Gly Tyr Asn
1               5

<210> SEQ ID NO 247
<211> LENGTH: 5
<212> TYPE: PRT
<213> ORGANISM: Homo sapiens

<400> SEQUENCE: 247

Val Glu Phe Asn Cys
1               5

<210> SEQ ID NO 248
<211> LENGTH: 5
<212> TYPE: PRT
<213> ORGANISM: Homo sapiens

<400> SEQUENCE: 248

Val Phe Glu Tyr Gly
1               5

<210> SEQ ID NO 249
<211> LENGTH: 5
<212> TYPE: PRT
<213> ORGANISM: Homo sapiens

<400> SEQUENCE: 249

Val Ile Met Val Cys
1               5

<210> SEQ ID NO 250
<211> LENGTH: 5
<212> TYPE: PRT
<213> ORGANISM: Homo sapiens

<400> SEQUENCE: 250

Val Asn Cys Ser Met
1               5

<210> SEQ ID NO 251
<211> LENGTH: 5
<212> TYPE: PRT
<213> ORGANISM: Homo sapiens

<400> SEQUENCE: 251

Val Thr Tyr Lys Cys
1               5

<210> SEQ ID NO 252
<211> LENGTH: 5
<212> TYPE: PRT
<213> ORGANISM: Homo sapiens

<400> SEQUENCE: 252

Trp Asp His Ile His
1               5

<210> SEQ ID NO 253
<211> LENGTH: 5
<212> TYPE: PRT
<213> ORGANISM: Homo sapiens

<400> SEQUENCE: 253

Trp Phe Lys Leu Asn
1               5

<210> SEQ ID NO 254
<211> LENGTH: 5
<212> TYPE: PRT
<213> ORGANISM: Homo sapiens

<400> SEQUENCE: 254

Trp Ile His Thr Val
1               5

<210> SEQ ID NO 255
<211> LENGTH: 5
<212> TYPE: PRT
<213> ORGANISM: Homo sapiens

<400> SEQUENCE: 255

Trp Gln Ser Ile Pro
1               5

<210> SEQ ID NO 256
<211> LENGTH: 5
<212> TYPE: PRT
<213> ORGANISM: Homo sapiens

<400> SEQUENCE: 256

Trp Ser Asp Gln Thr
1               5

<210> SEQ ID NO 257
<211> LENGTH: 5
<212> TYPE: PRT
<213> ORGANISM: Homo sapiens

<400> SEQUENCE: 257

Trp Thr Asn Asp Ile
1               5

<210> SEQ ID NO 258
<211> LENGTH: 5
<212> TYPE: PRT
<213> ORGANISM: Homo sapiens

<400> SEQUENCE: 258

Tyr Cys Asn Pro Arg
1               5

<210> SEQ ID NO 259
<211> LENGTH: 5
<212> TYPE: PRT
<213> ORGANISM: Homo sapiens

<400> SEQUENCE: 259

Tyr His Glu Asn Met
1               5

<210> SEQ ID NO 260
<211> LENGTH: 5
<212> TYPE: PRT
<213> ORGANISM: Homo sapiens

<400> SEQUENCE: 260

Tyr His Phe Gly Gln
1               5

<210> SEQ ID NO 261
<211> LENGTH: 5
<212> TYPE: PRT
<213> ORGANISM: Homo sapiens

<400> SEQUENCE: 261

Tyr Lys Cys Phe Glu
1               5

<210> SEQ ID NO 262
<211> LENGTH: 5
<212> TYPE: PRT
<213> ORGANISM: Homo sapiens

<400> SEQUENCE: 262

Tyr Lys Cys Asn Met
1               5

<210> SEQ ID NO 263
<211> LENGTH: 5
<212> TYPE: PRT
<213> ORGANISM: Homo sapiens

<400> SEQUENCE: 263

Tyr Lys Cys Arg Pro
1               5

<210> SEQ ID NO 264

```
<211> LENGTH: 5
<212> TYPE: PRT
<213> ORGANISM: Homo sapiens

<400> SEQUENCE: 264

Tyr Lys Ile Glu Gly
1               5

<210> SEQ ID NO 265
<211> LENGTH: 5
<212> TYPE: PRT
<213> ORGANISM: Homo sapiens

<400> SEQUENCE: 265

Tyr Met Gly Lys Trp
1               5

<210> SEQ ID NO 266
<211> LENGTH: 5
<212> TYPE: PRT
<213> ORGANISM: Homo sapiens

<400> SEQUENCE: 266

Tyr Asn Gly Trp Ser
1               5

<210> SEQ ID NO 267
<211> LENGTH: 5
<212> TYPE: PRT
<213> ORGANISM: Homo sapiens

<400> SEQUENCE: 267

Tyr Asn Gln Asn His
1               5

<210> SEQ ID NO 268
<211> LENGTH: 5
<212> TYPE: PRT
<213> ORGANISM: Homo sapiens

<400> SEQUENCE: 268

Tyr Pro Asp Ile Lys
1               5

<210> SEQ ID NO 269
<211> LENGTH: 5
<212> TYPE: PRT
<213> ORGANISM: Homo sapiens

<400> SEQUENCE: 269

Tyr Gln Cys Arg Asn
1               5

<210> SEQ ID NO 270
<211> LENGTH: 5
<212> TYPE: PRT
<213> ORGANISM: Homo sapiens

<400> SEQUENCE: 270

Tyr Gln Tyr Gly Glu
1               5

<210> SEQ ID NO 271
<211> LENGTH: 5
<212> TYPE: PRT
<213> ORGANISM: Homo sapiens
```

<400> SEQUENCE: 271

Tyr Ser Glu Arg Gly
1               5

<210> SEQ ID NO 272
<211> LENGTH: 5
<212> TYPE: PRT
<213> ORGANISM: Homo sapiens

<400> SEQUENCE: 272

Tyr Trp Asp His Ile
1               5

<210> SEQ ID NO 273
<211> LENGTH: 5
<212> TYPE: PRT
<213> ORGANISM: Homo sapiens

<400> SEQUENCE: 273

Tyr Tyr Lys Met Asp
1               5

<210> SEQ ID NO 274
<211> LENGTH: 5
<212> TYPE: PRT
<213> ORGANISM: Homo sapiens

<400> SEQUENCE: 274

Cys Val Ser Lys Gly
1               5

<210> SEQ ID NO 275
<211> LENGTH: 5
<212> TYPE: PRT
<213> ORGANISM: Homo sapiens

<400> SEQUENCE: 275

Glu Ile Ile Ile Ile
1               5

<210> SEQ ID NO 276
<211> LENGTH: 5
<212> TYPE: PRT
<213> ORGANISM: Homo sapiens

<400> SEQUENCE: 276

Gly Ile Asn Tyr Glu
1               5

<210> SEQ ID NO 277
<211> LENGTH: 5
<212> TYPE: PRT
<213> ORGANISM: Homo sapiens

<400> SEQUENCE: 277

Gly Met Lys His Ala
1               5

<210> SEQ ID NO 278
<211> LENGTH: 5
<212> TYPE: PRT
<213> ORGANISM: Homo sapiens

<400> SEQUENCE: 278

Gly Trp Asp Leu Lys
1               5

<210> SEQ ID NO 279
<211> LENGTH: 5
<212> TYPE: PRT
<213> ORGANISM: Homo sapiens

<400> SEQUENCE: 279

His Gly Met Lys His
1               5

<210> SEQ ID NO 280
<211> LENGTH: 5
<212> TYPE: PRT
<213> ORGANISM: Homo sapiens

<400> SEQUENCE: 280

His His Pro Lys Phe
1               5

<210> SEQ ID NO 281
<211> LENGTH: 5
<212> TYPE: PRT
<213> ORGANISM: Homo sapiens

<400> SEQUENCE: 281

Ile Glu Lys Cys Val
1               5

<210> SEQ ID NO 282
<211> LENGTH: 5
<212> TYPE: PRT
<213> ORGANISM: Homo sapiens

<400> SEQUENCE: 282

Ile Ile Met Asp Ala
1               5

<210> SEQ ID NO 283
<211> LENGTH: 5
<212> TYPE: PRT
<213> ORGANISM: Homo sapiens

<400> SEQUENCE: 283

Ile Asn Tyr Glu Ile
1               5

<210> SEQ ID NO 284
<211> LENGTH: 5
<212> TYPE: PRT
<213> ORGANISM: Homo sapiens

<400> SEQUENCE: 284

Lys Gly Tyr Val Phe
1               5

<210> SEQ ID NO 285
<211> LENGTH: 5
<212> TYPE: PRT
<213> ORGANISM: Homo sapiens

<400> SEQUENCE: 285

Met Glu Met Ile Val
1               5

```
<210> SEQ ID NO 286
<211> LENGTH: 5
<212> TYPE: PRT
<213> ORGANISM: Homo sapiens

<400> SEQUENCE: 286

Met Ile Val Arg Ala
1               5

<210> SEQ ID NO 287
<211> LENGTH: 5
<212> TYPE: PRT
<213> ORGANISM: Homo sapiens

<400> SEQUENCE: 287

Asn Tyr Thr Ile Gly
1               5

<210> SEQ ID NO 288
<211> LENGTH: 5
<212> TYPE: PRT
<213> ORGANISM: Homo sapiens

<400> SEQUENCE: 288

Gln Met Glu Met Ile
1               5

<210> SEQ ID NO 289
<211> LENGTH: 5
<212> TYPE: PRT
<213> ORGANISM: Homo sapiens

<400> SEQUENCE: 289

Ser His His Pro Lys
1               5

<210> SEQ ID NO 290
<211> LENGTH: 5
<212> TYPE: PRT
<213> ORGANISM: Homo sapiens

<400> SEQUENCE: 290

Thr Gly Ser Phe Arg
1               5

<210> SEQ ID NO 291
<211> LENGTH: 5
<212> TYPE: PRT
<213> ORGANISM: Homo sapiens

<400> SEQUENCE: 291

Thr Arg Tyr Lys Gly
1               5

<210> SEQ ID NO 292
<211> LENGTH: 5
<212> TYPE: PRT
<213> ORGANISM: Homo sapiens

<400> SEQUENCE: 292

Val Tyr Gly Trp Asp
1               5

<210> SEQ ID NO 293
<211> LENGTH: 5
```

```
<212> TYPE: PRT
<213> ORGANISM: Homo sapiens

<400> SEQUENCE: 293

Tyr Gly Glu Ser Lys
1               5

<210> SEQ ID NO 294
<211> LENGTH: 5
<212> TYPE: PRT
<213> ORGANISM: Homo sapiens

<400> SEQUENCE: 294

Tyr Gly Trp Asp Leu
1               5

<210> SEQ ID NO 295
<211> LENGTH: 5
<212> TYPE: PRT
<213> ORGANISM: Homo sapiens

<400> SEQUENCE: 295

Tyr Ile His Gly Met
1               5

<210> SEQ ID NO 296
<211> LENGTH: 5
<212> TYPE: PRT
<213> ORGANISM: Homo sapiens

<400> SEQUENCE: 296

Tyr Asn Glu Arg Glu
1               5

<210> SEQ ID NO 297
<211> LENGTH: 5
<212> TYPE: PRT
<213> ORGANISM: Homo sapiens

<400> SEQUENCE: 297

Tyr Thr Ile Gly Glu
1               5

<210> SEQ ID NO 298
<211> LENGTH: 5
<212> TYPE: PRT
<213> ORGANISM: Homo sapiens

<400> SEQUENCE: 298

Tyr Val Phe Gln Met
1               5

<210> SEQ ID NO 299
<211> LENGTH: 5
<212> TYPE: PRT
<213> ORGANISM: Homo sapiens

<400> SEQUENCE: 299

Gly Arg Tyr Gln Arg
1               5

<210> SEQ ID NO 300
<211> LENGTH: 5
<212> TYPE: PRT
<213> ORGANISM: Homo sapiens
```

```
<400> SEQUENCE: 300

Lys Asn Met Gly Ile
1               5

<210> SEQ ID NO 301
<211> LENGTH: 5
<212> TYPE: PRT
<213> ORGANISM: Homo sapiens

<400> SEQUENCE: 301

Met Gly Glu Arg Phe
1               5

<210> SEQ ID NO 302
<211> LENGTH: 5
<212> TYPE: PRT
<213> ORGANISM: Homo sapiens

<400> SEQUENCE: 302

Pro Ile Lys Gln His
1               5

<210> SEQ ID NO 303
<211> LENGTH: 5
<212> TYPE: PRT
<213> ORGANISM: Homo sapiens

<400> SEQUENCE: 303

Gln Arg Asn Ala Arg
1               5

<210> SEQ ID NO 304
<211> LENGTH: 5
<212> TYPE: PRT
<213> ORGANISM: Homo sapiens

<400> SEQUENCE: 304

Arg Tyr Gln Arg Asn
1               5

<210> SEQ ID NO 305
<211> LENGTH: 5
<212> TYPE: PRT
<213> ORGANISM: Homo sapiens

<400> SEQUENCE: 305

Tyr Asp Met Leu Met
1               5

<210> SEQ ID NO 306
<211> LENGTH: 5
<212> TYPE: PRT
<213> ORGANISM: Homo sapiens

<400> SEQUENCE: 306

Ala His Ser Ala Thr
1               5

<210> SEQ ID NO 307
<211> LENGTH: 5
<212> TYPE: PRT
<213> ORGANISM: Homo sapiens

<400> SEQUENCE: 307

Ala Lys Phe Phe Asn
```

```
1               5

<210> SEQ ID NO 308
<211> LENGTH: 5
<212> TYPE: PRT
<213> ORGANISM: Homo sapiens

<400> SEQUENCE: 308

Cys Lys Trp Gly Trp
1               5

<210> SEQ ID NO 309
<211> LENGTH: 5
<212> TYPE: PRT
<213> ORGANISM: Homo sapiens

<400> SEQUENCE: 309

Cys Met Thr Ile Asp
1               5

<210> SEQ ID NO 310
<211> LENGTH: 5
<212> TYPE: PRT
<213> ORGANISM: Homo sapiens

<400> SEQUENCE: 310

Asp Lys Leu Ser Trp
1               5

<210> SEQ ID NO 311
<211> LENGTH: 5
<212> TYPE: PRT
<213> ORGANISM: Homo sapiens

<400> SEQUENCE: 311

Asp Gln Ala Lys Phe
1               5

<210> SEQ ID NO 312
<211> LENGTH: 5
<212> TYPE: PRT
<213> ORGANISM: Homo sapiens

<400> SEQUENCE: 312

Asp Val Trp Tyr Thr
1               5

<210> SEQ ID NO 313
<211> LENGTH: 5
<212> TYPE: PRT
<213> ORGANISM: Homo sapiens

<400> SEQUENCE: 313

Glu Tyr Ser Trp Asn
1               5

<210> SEQ ID NO 314
<211> LENGTH: 5
<212> TYPE: PRT
<213> ORGANISM: Homo sapiens

<400> SEQUENCE: 314

Phe Asp Gln Ala Lys
1               5
```

```
<210> SEQ ID NO 315
<211> LENGTH: 5
<212> TYPE: PRT
<213> ORGANISM: Homo sapiens

<400> SEQUENCE: 315

Phe Glu Trp Phe His
1               5

<210> SEQ ID NO 316
<211> LENGTH: 5
<212> TYPE: PRT
<213> ORGANISM: Homo sapiens

<400> SEQUENCE: 316

Phe Asn Ala Asn Gln
1               5

<210> SEQ ID NO 317
<211> LENGTH: 5
<212> TYPE: PRT
<213> ORGANISM: Homo sapiens

<400> SEQUENCE: 317

Phe Trp Trp Tyr Trp
1               5

<210> SEQ ID NO 318
<211> LENGTH: 5
<212> TYPE: PRT
<213> ORGANISM: Homo sapiens

<400> SEQUENCE: 318

Phe Tyr Thr Cys Ser
1               5

<210> SEQ ID NO 319
<211> LENGTH: 5
<212> TYPE: PRT
<213> ORGANISM: Homo sapiens

<400> SEQUENCE: 319

His Lys Trp Glu Asn
1               5

<210> SEQ ID NO 320
<211> LENGTH: 5
<212> TYPE: PRT
<213> ORGANISM: Homo sapiens

<400> SEQUENCE: 320

His Pro Lys Ala Ile
1               5

<210> SEQ ID NO 321
<211> LENGTH: 5
<212> TYPE: PRT
<213> ORGANISM: Homo sapiens

<400> SEQUENCE: 321

His Gln Met Pro Cys
1               5

<210> SEQ ID NO 322
<211> LENGTH: 5
<212> TYPE: PRT
```

<213> ORGANISM: Homo sapiens

<400> SEQUENCE: 322

His Thr Trp Arg Ser
1               5

<210> SEQ ID NO 323
<211> LENGTH: 5
<212> TYPE: PRT
<213> ORGANISM: Homo sapiens

<400> SEQUENCE: 323

Ile His Gln Met Pro
1               5

<210> SEQ ID NO 324
<211> LENGTH: 5
<212> TYPE: PRT
<213> ORGANISM: Homo sapiens

<400> SEQUENCE: 324

Ile Pro Lys Tyr Val
1               5

<210> SEQ ID NO 325
<211> LENGTH: 5
<212> TYPE: PRT
<213> ORGANISM: Homo sapiens

<400> SEQUENCE: 325

Ile Tyr Glu Thr His
1               5

<210> SEQ ID NO 326
<211> LENGTH: 5
<212> TYPE: PRT
<213> ORGANISM: Homo sapiens

<400> SEQUENCE: 326

Lys Phe Phe Asn Ala
1               5

<210> SEQ ID NO 327
<211> LENGTH: 5
<212> TYPE: PRT
<213> ORGANISM: Homo sapiens

<400> SEQUENCE: 327

Lys Trp Glu Asn Cys
1               5

<210> SEQ ID NO 328
<211> LENGTH: 5
<212> TYPE: PRT
<213> ORGANISM: Homo sapiens

<400> SEQUENCE: 328

Lys Trp Gly Trp Ala
1               5

<210> SEQ ID NO 329
<211> LENGTH: 5
<212> TYPE: PRT
<213> ORGANISM: Homo sapiens

<400> SEQUENCE: 329

Lys Trp Pro Thr Ser
1               5

<210> SEQ ID NO 330
<211> LENGTH: 5
<212> TYPE: PRT
<213> ORGANISM: Homo sapiens

<400> SEQUENCE: 330

Leu Met Asn Ile Gly
1               5

<210> SEQ ID NO 331
<211> LENGTH: 5
<212> TYPE: PRT
<213> ORGANISM: Homo sapiens

<400> SEQUENCE: 331

Leu Pro His Lys Trp
1               5

<210> SEQ ID NO 332
<211> LENGTH: 5
<212> TYPE: PRT
<213> ORGANISM: Homo sapiens

<400> SEQUENCE: 332

Met Pro Cys Lys Trp
1               5

<210> SEQ ID NO 333
<211> LENGTH: 5
<212> TYPE: PRT
<213> ORGANISM: Homo sapiens

<400> SEQUENCE: 333

Met Arg Pro Gln Glu
1               5

<210> SEQ ID NO 334
<211> LENGTH: 5
<212> TYPE: PRT
<213> ORGANISM: Homo sapiens

<400> SEQUENCE: 334

Asn Ala Asn Gln Trp
1               5

<210> SEQ ID NO 335
<211> LENGTH: 5
<212> TYPE: PRT
<213> ORGANISM: Homo sapiens

<400> SEQUENCE: 335

Asn Cys Met Thr Ile
1               5

<210> SEQ ID NO 336
<211> LENGTH: 5
<212> TYPE: PRT
<213> ORGANISM: Homo sapiens

<400> SEQUENCE: 336

Asn Tyr Pro Pro Ser
1               5

<210> SEQ ID NO 337
<211> LENGTH: 5
<212> TYPE: PRT
<213> ORGANISM: Homo sapiens

<400> SEQUENCE: 337

Asn Tyr Gln Pro Glu
1               5

<210> SEQ ID NO 338
<211> LENGTH: 5
<212> TYPE: PRT
<213> ORGANISM: Homo sapiens

<400> SEQUENCE: 338

Pro Cys Lys Trp Gly
1               5

<210> SEQ ID NO 339
<211> LENGTH: 5
<212> TYPE: PRT
<213> ORGANISM: Homo sapiens

<400> SEQUENCE: 339

Pro Asp Gln Tyr Trp
1               5

<210> SEQ ID NO 340
<211> LENGTH: 5
<212> TYPE: PRT
<213> ORGANISM: Homo sapiens

<400> SEQUENCE: 340

Pro His Lys Trp Glu
1               5

<210> SEQ ID NO 341
<211> LENGTH: 5
<212> TYPE: PRT
<213> ORGANISM: Homo sapiens

<400> SEQUENCE: 341

Gln Met Gly Ser Trp
1               5

<210> SEQ ID NO 342
<211> LENGTH: 5
<212> TYPE: PRT
<213> ORGANISM: Homo sapiens

<400> SEQUENCE: 342

Gln Tyr Trp Asn Ser
1               5

<210> SEQ ID NO 343
<211> LENGTH: 5
<212> TYPE: PRT
<213> ORGANISM: Homo sapiens

<400> SEQUENCE: 343

Arg Asn Arg Thr Asp
1               5

<210> SEQ ID NO 344

```
<211> LENGTH: 5
<212> TYPE: PRT
<213> ORGANISM: Homo sapiens

<400> SEQUENCE: 344

Ser Cys Gly Gly Asn
1               5

<210> SEQ ID NO 345
<211> LENGTH: 5
<212> TYPE: PRT
<213> ORGANISM: Homo sapiens

<400> SEQUENCE: 345

Ser Lys His His Glu
1               5

<210> SEQ ID NO 346
<211> LENGTH: 5
<212> TYPE: PRT
<213> ORGANISM: Homo sapiens

<400> SEQUENCE: 346

Thr Cys Ser Asp Arg
1               5

<210> SEQ ID NO 347
<211> LENGTH: 5
<212> TYPE: PRT
<213> ORGANISM: Homo sapiens

<400> SEQUENCE: 347

Thr His Thr Trp Arg
1               5

<210> SEQ ID NO 348
<211> LENGTH: 5
<212> TYPE: PRT
<213> ORGANISM: Homo sapiens

<400> SEQUENCE: 348

Thr Ile His Gln Met
1               5

<210> SEQ ID NO 349
<211> LENGTH: 5
<212> TYPE: PRT
<213> ORGANISM: Homo sapiens

<400> SEQUENCE: 349

Thr Asn Asp Arg Trp
1               5

<210> SEQ ID NO 350
<211> LENGTH: 5
<212> TYPE: PRT
<213> ORGANISM: Homo sapiens

<400> SEQUENCE: 350

Thr Pro Asp Val Trp
1               5

<210> SEQ ID NO 351
<211> LENGTH: 5
<212> TYPE: PRT
<213> ORGANISM: Homo sapiens
```

<400> SEQUENCE: 351

Thr Arg Phe Asp Pro
1               5

<210> SEQ ID NO 352
<211> LENGTH: 5
<212> TYPE: PRT
<213> ORGANISM: Homo sapiens

<400> SEQUENCE: 352

Thr Val Val Thr Asn
1               5

<210> SEQ ID NO 353
<211> LENGTH: 5
<212> TYPE: PRT
<213> ORGANISM: Homo sapiens

<400> SEQUENCE: 353

Val Arg Gly Thr Val
1               5

<210> SEQ ID NO 354
<211> LENGTH: 5
<212> TYPE: PRT
<213> ORGANISM: Homo sapiens

<400> SEQUENCE: 354

Val Val Thr Asn Asp
1               5

<210> SEQ ID NO 355
<211> LENGTH: 5
<212> TYPE: PRT
<213> ORGANISM: Homo sapiens

<400> SEQUENCE: 355

Trp Glu Asn Cys Met
1               5

<210> SEQ ID NO 356
<211> LENGTH: 5
<212> TYPE: PRT
<213> ORGANISM: Homo sapiens

<400> SEQUENCE: 356

Trp Phe Asp Gln Ala
1               5

<210> SEQ ID NO 357
<211> LENGTH: 5
<212> TYPE: PRT
<213> ORGANISM: Homo sapiens

<400> SEQUENCE: 357

Trp Phe Trp Trp Tyr
1               5

<210> SEQ ID NO 358
<211> LENGTH: 5
<212> TYPE: PRT
<213> ORGANISM: Homo sapiens

<400> SEQUENCE: 358

```
Trp Gly Ser Glu Tyr
1               5

<210> SEQ ID NO 359
<211> LENGTH: 5
<212> TYPE: PRT
<213> ORGANISM: Homo sapiens

<400> SEQUENCE: 359

Trp Gly Trp Ala Leu
1               5

<210> SEQ ID NO 360
<211> LENGTH: 5
<212> TYPE: PRT
<213> ORGANISM: Homo sapiens

<400> SEQUENCE: 360

Trp Asn Trp Asn Ala
1               5

<210> SEQ ID NO 361
<211> LENGTH: 5
<212> TYPE: PRT
<213> ORGANISM: Homo sapiens

<400> SEQUENCE: 361

Trp Arg Ser Gln Asn
1               5

<210> SEQ ID NO 362
<211> LENGTH: 5
<212> TYPE: PRT
<213> ORGANISM: Homo sapiens

<400> SEQUENCE: 362

Trp Trp Tyr Trp Gln
1               5

<210> SEQ ID NO 363
<211> LENGTH: 5
<212> TYPE: PRT
<213> ORGANISM: Homo sapiens

<400> SEQUENCE: 363

Tyr Glu Asp Phe Gly
1               5

<210> SEQ ID NO 364
<211> LENGTH: 5
<212> TYPE: PRT
<213> ORGANISM: Homo sapiens

<400> SEQUENCE: 364

Tyr Glu Thr His Thr
1               5

<210> SEQ ID NO 365
<211> LENGTH: 5
<212> TYPE: PRT
<213> ORGANISM: Homo sapiens

<400> SEQUENCE: 365

Tyr Asn Pro Gly His
1               5
```

```
<210> SEQ ID NO 366
<211> LENGTH: 5
<212> TYPE: PRT
<213> ORGANISM: Homo sapiens

<400> SEQUENCE: 366

Tyr Ser Trp Asn Trp
1               5

<210> SEQ ID NO 367
<211> LENGTH: 5
<212> TYPE: PRT
<213> ORGANISM: Homo sapiens

<400> SEQUENCE: 367

Tyr Val Glu Phe Met
1               5

<210> SEQ ID NO 368
<211> LENGTH: 5
<212> TYPE: PRT
<213> ORGANISM: Homo sapiens

<400> SEQUENCE: 368

Tyr Tyr Ser Leu Phe
1               5

<210> SEQ ID NO 369
<211> LENGTH: 5
<212> TYPE: PRT
<213> ORGANISM: Homo sapiens

<400> SEQUENCE: 369

Ala Met Asn Asp Ala
1               5

<210> SEQ ID NO 370
<211> LENGTH: 5
<212> TYPE: PRT
<213> ORGANISM: Homo sapiens

<400> SEQUENCE: 370

Ala Asn His Gly Glu
1               5

<210> SEQ ID NO 371
<211> LENGTH: 5
<212> TYPE: PRT
<213> ORGANISM: Homo sapiens

<400> SEQUENCE: 371

Ala Gln Trp Arg Asn
1               5

<210> SEQ ID NO 372
<211> LENGTH: 5
<212> TYPE: PRT
<213> ORGANISM: Homo sapiens

<400> SEQUENCE: 372

Cys Val Lys Leu Pro
1               5

<210> SEQ ID NO 373
<211> LENGTH: 5
```

```
<212> TYPE: PRT
<213> ORGANISM: Homo sapiens

<400> SEQUENCE: 373

Cys Val Gln Tyr Lys
1               5

<210> SEQ ID NO 374
<211> LENGTH: 5
<212> TYPE: PRT
<213> ORGANISM: Homo sapiens

<400> SEQUENCE: 374

Asp Ala His Lys Arg
1               5

<210> SEQ ID NO 375
<211> LENGTH: 5
<212> TYPE: PRT
<213> ORGANISM: Homo sapiens

<400> SEQUENCE: 375

Asp Cys Val Gln Tyr
1               5

<210> SEQ ID NO 376
<211> LENGTH: 5
<212> TYPE: PRT
<213> ORGANISM: Homo sapiens

<400> SEQUENCE: 376

Asp Ile Glu Gln Arg
1               5

<210> SEQ ID NO 377
<211> LENGTH: 5
<212> TYPE: PRT
<213> ORGANISM: Homo sapiens

<400> SEQUENCE: 377

Asp Met Ala Glu Arg
1               5

<210> SEQ ID NO 378
<211> LENGTH: 5
<212> TYPE: PRT
<213> ORGANISM: Homo sapiens

<400> SEQUENCE: 378

Asp Pro Asp Lys Trp
1               5

<210> SEQ ID NO 379
<211> LENGTH: 5
<212> TYPE: PRT
<213> ORGANISM: Homo sapiens

<400> SEQUENCE: 379

Asp Thr Ala Asn His
1               5

<210> SEQ ID NO 380
<211> LENGTH: 5
<212> TYPE: PRT
<213> ORGANISM: Homo sapiens
```

```
<400> SEQUENCE: 380

Glu Val Ser Phe Met
1               5

<210> SEQ ID NO 381
<211> LENGTH: 5
<212> TYPE: PRT
<213> ORGANISM: Homo sapiens

<400> SEQUENCE: 381

Glu Tyr Val Ile Asp
1               5

<210> SEQ ID NO 382
<211> LENGTH: 5
<212> TYPE: PRT
<213> ORGANISM: Homo sapiens

<400> SEQUENCE: 382

Phe Glu Gln Tyr Glu
1               5

<210> SEQ ID NO 383
<211> LENGTH: 5
<212> TYPE: PRT
<213> ORGANISM: Homo sapiens

<400> SEQUENCE: 383

Phe Phe Glu Gln Tyr
1               5

<210> SEQ ID NO 384
<211> LENGTH: 5
<212> TYPE: PRT
<213> ORGANISM: Homo sapiens

<400> SEQUENCE: 384

Phe Gly Asp Cys Val
1               5

<210> SEQ ID NO 385
<211> LENGTH: 5
<212> TYPE: PRT
<213> ORGANISM: Homo sapiens

<400> SEQUENCE: 385

Phe Met Asn Glu Thr
1               5

<210> SEQ ID NO 386
<211> LENGTH: 5
<212> TYPE: PRT
<213> ORGANISM: Homo sapiens

<400> SEQUENCE: 386

His Glu Ile Tyr Arg
1               5

<210> SEQ ID NO 387
<211> LENGTH: 5
<212> TYPE: PRT
<213> ORGANISM: Homo sapiens

<400> SEQUENCE: 387

His Glu Arg Phe Leu
```

```
1               5

<210> SEQ ID NO 388
<211> LENGTH: 5
<212> TYPE: PRT
<213> ORGANISM: Homo sapiens

<400> SEQUENCE: 388

His Phe Asp Gln Thr
1               5

<210> SEQ ID NO 389
<211> LENGTH: 5
<212> TYPE: PRT
<213> ORGANISM: Homo sapiens

<400> SEQUENCE: 389

His Lys Gln Trp Lys
1               5

<210> SEQ ID NO 390
<211> LENGTH: 5
<212> TYPE: PRT
<213> ORGANISM: Homo sapiens

<400> SEQUENCE: 390

His Lys Arg Ala Phe
1               5

<210> SEQ ID NO 391
<211> LENGTH: 5
<212> TYPE: PRT
<213> ORGANISM: Homo sapiens

<400> SEQUENCE: 391

His Thr Ala Met Asn
1               5

<210> SEQ ID NO 392
<211> LENGTH: 5
<212> TYPE: PRT
<213> ORGANISM: Homo sapiens

<400> SEQUENCE: 392

His Trp Ile Gln Gln
1               5

<210> SEQ ID NO 393
<211> LENGTH: 5
<212> TYPE: PRT
<213> ORGANISM: Homo sapiens

<400> SEQUENCE: 393

Lys His Phe Asp Gln
1               5

<210> SEQ ID NO 394
<211> LENGTH: 5
<212> TYPE: PRT
<213> ORGANISM: Homo sapiens

<400> SEQUENCE: 394

Lys Met Leu Asn Gln
1               5
```

```
<210> SEQ ID NO 395
<211> LENGTH: 5
<212> TYPE: PRT
<213> ORGANISM: Homo sapiens

<400> SEQUENCE: 395

Lys Gln Met Thr Ser
1               5

<210> SEQ ID NO 396
<211> LENGTH: 5
<212> TYPE: PRT
<213> ORGANISM: Homo sapiens

<400> SEQUENCE: 396

Lys Gln Tyr Ala Gln
1               5

<210> SEQ ID NO 397
<211> LENGTH: 5
<212> TYPE: PRT
<213> ORGANISM: Homo sapiens

<400> SEQUENCE: 397

Lys Arg Ala Phe His
1               5

<210> SEQ ID NO 398
<211> LENGTH: 5
<212> TYPE: PRT
<213> ORGANISM: Homo sapiens

<400> SEQUENCE: 398

Lys Trp Glu Arg Phe
1               5

<210> SEQ ID NO 399
<211> LENGTH: 5
<212> TYPE: PRT
<213> ORGANISM: Homo sapiens

<400> SEQUENCE: 399

Leu Asn Gly Arg Trp
1               5

<210> SEQ ID NO 400
<211> LENGTH: 5
<212> TYPE: PRT
<213> ORGANISM: Homo sapiens

<400> SEQUENCE: 400

Leu Pro His Trp Ile
1               5

<210> SEQ ID NO 401
<211> LENGTH: 5
<212> TYPE: PRT
<213> ORGANISM: Homo sapiens

<400> SEQUENCE: 401

Met Phe Ala Thr Met
1               5

<210> SEQ ID NO 402
<211> LENGTH: 5
<212> TYPE: PRT
```

<213> ORGANISM: Homo sapiens

<400> SEQUENCE: 402

Met Lys Phe Met Asn
1               5

<210> SEQ ID NO 403
<211> LENGTH: 5
<212> TYPE: PRT
<213> ORGANISM: Homo sapiens

<400> SEQUENCE: 403

Met Lys Met Glu Phe
1               5

<210> SEQ ID NO 404
<211> LENGTH: 5
<212> TYPE: PRT
<213> ORGANISM: Homo sapiens

<400> SEQUENCE: 404

Met Leu Asn Gln Ser
1               5

<210> SEQ ID NO 405
<211> LENGTH: 5
<212> TYPE: PRT
<213> ORGANISM: Homo sapiens

<400> SEQUENCE: 405

Met Pro Gln Glu Gly
1               5

<210> SEQ ID NO 406
<211> LENGTH: 5
<212> TYPE: PRT
<213> ORGANISM: Homo sapiens

<400> SEQUENCE: 406

Met Tyr Val Lys Ala
1               5

<210> SEQ ID NO 407
<211> LENGTH: 5
<212> TYPE: PRT
<213> ORGANISM: Homo sapiens

<400> SEQUENCE: 407

Asn Leu Pro His Trp
1               5

<210> SEQ ID NO 408
<211> LENGTH: 5
<212> TYPE: PRT
<213> ORGANISM: Homo sapiens

<400> SEQUENCE: 408

Asn Thr Asp Ala His
1               5

<210> SEQ ID NO 409
<211> LENGTH: 5
<212> TYPE: PRT
<213> ORGANISM: Homo sapiens

<400> SEQUENCE: 409

Asn Val Leu Lys His
1               5

<210> SEQ ID NO 410
<211> LENGTH: 5
<212> TYPE: PRT
<213> ORGANISM: Homo sapiens

<400> SEQUENCE: 410

Pro His Trp Ile Gln
1               5

<210> SEQ ID NO 411
<211> LENGTH: 5
<212> TYPE: PRT
<213> ORGANISM: Homo sapiens

<400> SEQUENCE: 411

Pro Val Met Asp Ala
1               5

<210> SEQ ID NO 412
<211> LENGTH: 5
<212> TYPE: PRT
<213> ORGANISM: Homo sapiens

<400> SEQUENCE: 412

Gln Ala Asp Glu Met
1               5

<210> SEQ ID NO 413
<211> LENGTH: 5
<212> TYPE: PRT
<213> ORGANISM: Homo sapiens

<400> SEQUENCE: 413

Gln Glu Asn Cys Lys
1               5

<210> SEQ ID NO 414
<211> LENGTH: 5
<212> TYPE: PRT
<213> ORGANISM: Homo sapiens

<400> SEQUENCE: 414

Gln His Thr Ala Met
1               5

<210> SEQ ID NO 415
<211> LENGTH: 5
<212> TYPE: PRT
<213> ORGANISM: Homo sapiens

<400> SEQUENCE: 415

Gln Asn Tyr Val Ser
1               5

<210> SEQ ID NO 416
<211> LENGTH: 5
<212> TYPE: PRT
<213> ORGANISM: Homo sapiens

<400> SEQUENCE: 416

Gln Trp Lys Asp Leu
1               5

<210> SEQ ID NO 417
<211> LENGTH: 5
<212> TYPE: PRT
<213> ORGANISM: Homo sapiens

<400> SEQUENCE: 417

Gln Tyr Ala Gln Ala
1               5

<210> SEQ ID NO 418
<211> LENGTH: 5
<212> TYPE: PRT
<213> ORGANISM: Homo sapiens

<400> SEQUENCE: 418

Arg Val Pro Val Met
1               5

<210> SEQ ID NO 419
<211> LENGTH: 5
<212> TYPE: PRT
<213> ORGANISM: Homo sapiens

<400> SEQUENCE: 419

Ser Phe Tyr Asp Ser
1               5

<210> SEQ ID NO 420
<211> LENGTH: 5
<212> TYPE: PRT
<213> ORGANISM: Homo sapiens

<400> SEQUENCE: 420

Ser His Glu Arg Phe
1               5

<210> SEQ ID NO 421
<211> LENGTH: 5
<212> TYPE: PRT
<213> ORGANISM: Homo sapiens

<400> SEQUENCE: 421

Thr Cys Asp Glu Met
1               5

<210> SEQ ID NO 422
<211> LENGTH: 5
<212> TYPE: PRT
<213> ORGANISM: Homo sapiens

<400> SEQUENCE: 422

Thr Asp Ala His Lys
1               5

<210> SEQ ID NO 423
<211> LENGTH: 5
<212> TYPE: PRT
<213> ORGANISM: Homo sapiens

<400> SEQUENCE: 423

Thr Lys Leu Met Pro
1               5

<210> SEQ ID NO 424

```
<211> LENGTH: 5
<212> TYPE: PRT
<213> ORGANISM: Homo sapiens

<400> SEQUENCE: 424

Thr Val Val Arg Tyr
1               5

<210> SEQ ID NO 425
<211> LENGTH: 5
<212> TYPE: PRT
<213> ORGANISM: Homo sapiens

<400> SEQUENCE: 425

Thr Tyr Gln Ile Leu
1               5

<210> SEQ ID NO 426
<211> LENGTH: 5
<212> TYPE: PRT
<213> ORGANISM: Homo sapiens

<400> SEQUENCE: 426

Val Met Asp Ala Gln
1               5

<210> SEQ ID NO 427
<211> LENGTH: 5
<212> TYPE: PRT
<213> ORGANISM: Homo sapiens

<400> SEQUENCE: 427

Val Met Lys Phe Met
1               5

<210> SEQ ID NO 428
<211> LENGTH: 5
<212> TYPE: PRT
<213> ORGANISM: Homo sapiens

<400> SEQUENCE: 428

Val Pro Val Met Asp
1               5

<210> SEQ ID NO 429
<211> LENGTH: 5
<212> TYPE: PRT
<213> ORGANISM: Homo sapiens

<400> SEQUENCE: 429

Val Arg Tyr Leu Phe
1               5

<210> SEQ ID NO 430
<211> LENGTH: 5
<212> TYPE: PRT
<213> ORGANISM: Homo sapiens

<400> SEQUENCE: 430

Val Ser Phe Met Asn
1               5

<210> SEQ ID NO 431
<211> LENGTH: 5
<212> TYPE: PRT
<213> ORGANISM: Homo sapiens
```

```
<400> SEQUENCE: 431

Trp Asp Arg Tyr Gly
1               5

<210> SEQ ID NO 432
<211> LENGTH: 5
<212> TYPE: PRT
<213> ORGANISM: Homo sapiens

<400> SEQUENCE: 432

Trp Glu Arg Phe Glu
1               5

<210> SEQ ID NO 433
<211> LENGTH: 5
<212> TYPE: PRT
<213> ORGANISM: Homo sapiens

<400> SEQUENCE: 433

Trp Ile Ile Lys Tyr
1               5

<210> SEQ ID NO 434
<211> LENGTH: 5
<212> TYPE: PRT
<213> ORGANISM: Homo sapiens

<400> SEQUENCE: 434

Trp Ile Gln Gln His
1               5

<210> SEQ ID NO 435
<211> LENGTH: 5
<212> TYPE: PRT
<213> ORGANISM: Homo sapiens

<400> SEQUENCE: 435

Trp Ile Ser Thr Asn
1               5

<210> SEQ ID NO 436
<211> LENGTH: 5
<212> TYPE: PRT
<213> ORGANISM: Homo sapiens

<400> SEQUENCE: 436

Trp Lys Asp Tyr Thr
1               5

<210> SEQ ID NO 437
<211> LENGTH: 5
<212> TYPE: PRT
<213> ORGANISM: Homo sapiens

<400> SEQUENCE: 437

Trp Lys Lys His Val
1               5

<210> SEQ ID NO 438
<211> LENGTH: 5
<212> TYPE: PRT
<213> ORGANISM: Homo sapiens

<400> SEQUENCE: 438
```

Tyr Ala Gln Ala Asp
1               5

<210> SEQ ID NO 439
<211> LENGTH: 5
<212> TYPE: PRT
<213> ORGANISM: Homo sapiens

<400> SEQUENCE: 439

Tyr Glu Val Thr Tyr
1               5

<210> SEQ ID NO 440
<211> LENGTH: 5
<212> TYPE: PRT
<213> ORGANISM: Homo sapiens

<400> SEQUENCE: 440

Tyr Gly Arg Arg Glu
1               5

<210> SEQ ID NO 441
<211> LENGTH: 5
<212> TYPE: PRT
<213> ORGANISM: Homo sapiens

<400> SEQUENCE: 441

Tyr Thr Asp Cys Val
1               5

<210> SEQ ID NO 442
<211> LENGTH: 5
<212> TYPE: PRT
<213> ORGANISM: Homo sapiens

<400> SEQUENCE: 442

Tyr Val Lys Ala Asp
1               5

<210> SEQ ID NO 443
<211> LENGTH: 5
<212> TYPE: PRT
<213> ORGANISM: Homo sapiens

<400> SEQUENCE: 443

Cys Phe Lys Glu Asn
1               5

<210> SEQ ID NO 444
<211> LENGTH: 5
<212> TYPE: PRT
<213> ORGANISM: Homo sapiens

<400> SEQUENCE: 444

Asp Gly Gly Phe Asp
1               5

<210> SEQ ID NO 445
<211> LENGTH: 5
<212> TYPE: PRT
<213> ORGANISM: Homo sapiens

<400> SEQUENCE: 445

Phe Asp Leu Gly Asp
1               5

```
<210> SEQ ID NO 446
<211> LENGTH: 5
<212> TYPE: PRT
<213> ORGANISM: Homo sapiens

<400> SEQUENCE: 446

Lys Leu Cys Phe Lys
1               5

<210> SEQ ID NO 447
<211> LENGTH: 5
<212> TYPE: PRT
<213> ORGANISM: Homo sapiens

<400> SEQUENCE: 447

Lys Pro Met Pro Asn
1               5

<210> SEQ ID NO 448
<211> LENGTH: 5
<212> TYPE: PRT
<213> ORGANISM: Homo sapiens

<400> SEQUENCE: 448

Met Pro Asn Pro Asn
1               5

<210> SEQ ID NO 449
<211> LENGTH: 5
<212> TYPE: PRT
<213> ORGANISM: Homo sapiens

<400> SEQUENCE: 449

Pro Asn Pro Asn His
1               5

<210> SEQ ID NO 450
<211> LENGTH: 5
<212> TYPE: PRT
<213> ORGANISM: Homo sapiens

<400> SEQUENCE: 450

Asp Arg Cys Leu His
1               5

<210> SEQ ID NO 451
<211> LENGTH: 5
<212> TYPE: PRT
<213> ORGANISM: Homo sapiens

<400> SEQUENCE: 451

Glu Glu His Tyr Ser
1               5

<210> SEQ ID NO 452
<211> LENGTH: 5
<212> TYPE: PRT
<213> ORGANISM: Homo sapiens

<400> SEQUENCE: 452

Glu His Tyr Ser His
1               5

<210> SEQ ID NO 453
<211> LENGTH: 5
```

```
<212> TYPE: PRT
<213> ORGANISM: Homo sapiens

<400> SEQUENCE: 453

Glu Asn Glu Val His
1               5

<210> SEQ ID NO 454
<211> LENGTH: 5
<212> TYPE: PRT
<213> ORGANISM: Homo sapiens

<400> SEQUENCE: 454

Glu Tyr Phe His Glu
1               5

<210> SEQ ID NO 455
<211> LENGTH: 5
<212> TYPE: PRT
<213> ORGANISM: Homo sapiens

<400> SEQUENCE: 455

Phe Phe Asp Trp Glu
1               5

<210> SEQ ID NO 456
<211> LENGTH: 5
<212> TYPE: PRT
<213> ORGANISM: Homo sapiens

<400> SEQUENCE: 456

Phe His Glu Pro Asn
1               5

<210> SEQ ID NO 457
<211> LENGTH: 5
<212> TYPE: PRT
<213> ORGANISM: Homo sapiens

<400> SEQUENCE: 457

Phe Ser Trp Pro His
1               5

<210> SEQ ID NO 458
<211> LENGTH: 5
<212> TYPE: PRT
<213> ORGANISM: Homo sapiens

<400> SEQUENCE: 458

Phe Tyr Asn His Met
1               5

<210> SEQ ID NO 459
<211> LENGTH: 5
<212> TYPE: PRT
<213> ORGANISM: Homo sapiens

<400> SEQUENCE: 459

Gly Arg Asp Arg Cys
1               5

<210> SEQ ID NO 460
<211> LENGTH: 5
<212> TYPE: PRT
<213> ORGANISM: Homo sapiens
```

```
<400> SEQUENCE: 460

Gly Val Ala Pro Asn
1               5

<210> SEQ ID NO 461
<211> LENGTH: 5
<212> TYPE: PRT
<213> ORGANISM: Homo sapiens

<400> SEQUENCE: 461

His Glu Tyr Phe His
1               5

<210> SEQ ID NO 462
<211> LENGTH: 5
<212> TYPE: PRT
<213> ORGANISM: Homo sapiens

<400> SEQUENCE: 462

His Phe Phe Asp Trp
1               5

<210> SEQ ID NO 463
<211> LENGTH: 5
<212> TYPE: PRT
<213> ORGANISM: Homo sapiens

<400> SEQUENCE: 463

His Ile Val Asp Gly
1               5

<210> SEQ ID NO 464
<211> LENGTH: 5
<212> TYPE: PRT
<213> ORGANISM: Homo sapiens

<400> SEQUENCE: 464

His Lys Pro Tyr Pro
1               5

<210> SEQ ID NO 465
<211> LENGTH: 5
<212> TYPE: PRT
<213> ORGANISM: Homo sapiens

<400> SEQUENCE: 465

His Met Gln Lys His
1               5

<210> SEQ ID NO 466
<211> LENGTH: 5
<212> TYPE: PRT
<213> ORGANISM: Homo sapiens

<400> SEQUENCE: 466

His Met Gln Asn Trp
1               5

<210> SEQ ID NO 467
<211> LENGTH: 5
<212> TYPE: PRT
<213> ORGANISM: Homo sapiens

<400> SEQUENCE: 467

His Pro Gln Val Asp
```

```
<210> SEQ ID NO 468
<211> LENGTH: 5
<212> TYPE: PRT
<213> ORGANISM: Homo sapiens

<400> SEQUENCE: 468

His Val His Met Gln
1               5

<210> SEQ ID NO 469
<211> LENGTH: 5
<212> TYPE: PRT
<213> ORGANISM: Homo sapiens

<400> SEQUENCE: 469

Lys Gly Arg Ala His
1               5

<210> SEQ ID NO 470
<211> LENGTH: 5
<212> TYPE: PRT
<213> ORGANISM: Homo sapiens

<400> SEQUENCE: 470

Lys His Lys Pro Tyr
1               5

<210> SEQ ID NO 471
<211> LENGTH: 5
<212> TYPE: PRT
<213> ORGANISM: Homo sapiens

<400> SEQUENCE: 471

Lys Thr Pro Ala Tyr
1               5

<210> SEQ ID NO 472
<211> LENGTH: 5
<212> TYPE: PRT
<213> ORGANISM: Homo sapiens

<400> SEQUENCE: 472

Met Gln Asn Trp Leu
1               5

<210> SEQ ID NO 473
<211> LENGTH: 5
<212> TYPE: PRT
<213> ORGANISM: Homo sapiens

<400> SEQUENCE: 473

Asn His Met Gln Lys
1               5

<210> SEQ ID NO 474
<211> LENGTH: 5
<212> TYPE: PRT
<213> ORGANISM: Homo sapiens

<400> SEQUENCE: 474

Gln Lys His Lys Pro
1               5
```

```
<210> SEQ ID NO 475
<211> LENGTH: 5
<212> TYPE: PRT
<213> ORGANISM: Homo sapiens

<400> SEQUENCE: 475

Gln Asn Trp Leu Arg
1               5

<210> SEQ ID NO 476
<211> LENGTH: 5
<212> TYPE: PRT
<213> ORGANISM: Homo sapiens

<400> SEQUENCE: 476

Arg Val Tyr Ser Met
1               5

<210> SEQ ID NO 477
<211> LENGTH: 5
<212> TYPE: PRT
<213> ORGANISM: Homo sapiens

<400> SEQUENCE: 477

Ser Met Asn Pro Ser
1               5

<210> SEQ ID NO 478
<211> LENGTH: 5
<212> TYPE: PRT
<213> ORGANISM: Homo sapiens

<400> SEQUENCE: 478

Ser Trp Pro His Gln
1               5

<210> SEQ ID NO 479
<211> LENGTH: 5
<212> TYPE: PRT
<213> ORGANISM: Homo sapiens

<400> SEQUENCE: 479

Thr Phe Asp Trp His
1               5

<210> SEQ ID NO 480
<211> LENGTH: 5
<212> TYPE: PRT
<213> ORGANISM: Homo sapiens

<400> SEQUENCE: 480

Thr Gln Val Phe Tyr
1               5

<210> SEQ ID NO 481
<211> LENGTH: 5
<212> TYPE: PRT
<213> ORGANISM: Homo sapiens

<400> SEQUENCE: 481

Trp Glu Glu His Tyr
1               5

<210> SEQ ID NO 482
<211> LENGTH: 5
<212> TYPE: PRT
```

<213> ORGANISM: Homo sapiens

<400> SEQUENCE: 482

Tyr Cys Leu Arg Asp
1               5

<210> SEQ ID NO 483
<211> LENGTH: 5
<212> TYPE: PRT
<213> ORGANISM: Homo sapiens

<400> SEQUENCE: 483

Tyr His Val His Met
1               5

<210> SEQ ID NO 484
<211> LENGTH: 5
<212> TYPE: PRT
<213> ORGANISM: Homo sapiens

<400> SEQUENCE: 484

Tyr Asn His Met Gln
1               5

<210> SEQ ID NO 485
<211> LENGTH: 5
<212> TYPE: PRT
<213> ORGANISM: Homo sapiens

<400> SEQUENCE: 485

Tyr Pro Ser Ile Glu
1               5

<210> SEQ ID NO 486
<211> LENGTH: 5
<212> TYPE: PRT
<213> ORGANISM: Homo sapiens

<400> SEQUENCE: 486

Ala Asp Ile Arg Met
1               5

<210> SEQ ID NO 487
<211> LENGTH: 5
<212> TYPE: PRT
<213> ORGANISM: Homo sapiens

<400> SEQUENCE: 487

Ala Trp Pro Ser Phe
1               5

<210> SEQ ID NO 488
<211> LENGTH: 5
<212> TYPE: PRT
<213> ORGANISM: Homo sapiens

<400> SEQUENCE: 488

Cys Leu Val Asn Lys
1               5

<210> SEQ ID NO 489
<211> LENGTH: 5
<212> TYPE: PRT
<213> ORGANISM: Homo sapiens

<400> SEQUENCE: 489

Cys Gln Ala Tyr Gly
1               5

<210> SEQ ID NO 490
<211> LENGTH: 5
<212> TYPE: PRT
<213> ORGANISM: Homo sapiens

<400> SEQUENCE: 490

Cys Thr Tyr Val Asn
1               5

<210> SEQ ID NO 491
<211> LENGTH: 5
<212> TYPE: PRT
<213> ORGANISM: Homo sapiens

<400> SEQUENCE: 491

Asp His Asp Arg Met
1               5

<210> SEQ ID NO 492
<211> LENGTH: 5
<212> TYPE: PRT
<213> ORGANISM: Homo sapiens

<400> SEQUENCE: 492

Asp Pro Ser Phe Ile
1               5

<210> SEQ ID NO 493
<211> LENGTH: 5
<212> TYPE: PRT
<213> ORGANISM: Homo sapiens

<400> SEQUENCE: 493

Asp Arg Met Tyr Val
1               5

<210> SEQ ID NO 494
<211> LENGTH: 5
<212> TYPE: PRT
<213> ORGANISM: Homo sapiens

<400> SEQUENCE: 494

Gly His Cys Cys Leu
1               5

<210> SEQ ID NO 495
<211> LENGTH: 5
<212> TYPE: PRT
<213> ORGANISM: Homo sapiens

<400> SEQUENCE: 495

Gly Ile Glu Thr His
1               5

<210> SEQ ID NO 496
<211> LENGTH: 5
<212> TYPE: PRT
<213> ORGANISM: Homo sapiens

<400> SEQUENCE: 496

Gly Tyr Trp Arg His
1               5

<210> SEQ ID NO 497
<211> LENGTH: 5
<212> TYPE: PRT
<213> ORGANISM: Homo sapiens

<400> SEQUENCE: 497

His Cys Cys Leu Val
1               5

<210> SEQ ID NO 498
<211> LENGTH: 5
<212> TYPE: PRT
<213> ORGANISM: Homo sapiens

<400> SEQUENCE: 498

His Asp Ile Asn Arg
1               5

<210> SEQ ID NO 499
<211> LENGTH: 5
<212> TYPE: PRT
<213> ORGANISM: Homo sapiens

<400> SEQUENCE: 499

His Asp Arg Met Tyr
1               5

<210> SEQ ID NO 500
<211> LENGTH: 5
<212> TYPE: PRT
<213> ORGANISM: Homo sapiens

<400> SEQUENCE: 500

His Gln Tyr Cys Gln
1               5

<210> SEQ ID NO 501
<211> LENGTH: 5
<212> TYPE: PRT
<213> ORGANISM: Homo sapiens

<400> SEQUENCE: 501

His Arg Cys Gln Ala
1               5

<210> SEQ ID NO 502
<211> LENGTH: 5
<212> TYPE: PRT
<213> ORGANISM: Homo sapiens

<400> SEQUENCE: 502

Ile Glu Thr His Phe
1               5

<210> SEQ ID NO 503
<211> LENGTH: 5
<212> TYPE: PRT
<213> ORGANISM: Homo sapiens

<400> SEQUENCE: 503

Ile Phe Tyr Leu Glu
1               5

<210> SEQ ID NO 504

```
<211> LENGTH: 5
<212> TYPE: PRT
<213> ORGANISM: Homo sapiens

<400> SEQUENCE: 504

Ile His Gln Tyr Cys
1               5

<210> SEQ ID NO 505
<211> LENGTH: 5
<212> TYPE: PRT
<213> ORGANISM: Homo sapiens

<400> SEQUENCE: 505

Ile Ile His Trp Ala
1               5

<210> SEQ ID NO 506
<211> LENGTH: 5
<212> TYPE: PRT
<213> ORGANISM: Homo sapiens

<400> SEQUENCE: 506

Ile Asn Phe Met Arg
1               5

<210> SEQ ID NO 507
<211> LENGTH: 5
<212> TYPE: PRT
<213> ORGANISM: Homo sapiens

<400> SEQUENCE: 507

Ile Gln Pro Trp Asn
1               5

<210> SEQ ID NO 508
<211> LENGTH: 5
<212> TYPE: PRT
<213> ORGANISM: Homo sapiens

<400> SEQUENCE: 508

Lys Met Pro Tyr Pro
1               5

<210> SEQ ID NO 509
<211> LENGTH: 5
<212> TYPE: PRT
<213> ORGANISM: Homo sapiens

<400> SEQUENCE: 509

Lys Trp Leu Phe Gln
1               5

<210> SEQ ID NO 510
<211> LENGTH: 5
<212> TYPE: PRT
<213> ORGANISM: Homo sapiens

<400> SEQUENCE: 510

Leu Ile Ile His Trp
1               5

<210> SEQ ID NO 511
<211> LENGTH: 5
<212> TYPE: PRT
<213> ORGANISM: Homo sapiens
```

<400> SEQUENCE: 511

Leu Ile Gln Pro Trp
1               5

<210> SEQ ID NO 512
<211> LENGTH: 5
<212> TYPE: PRT
<213> ORGANISM: Homo sapiens

<400> SEQUENCE: 512

Met Cys Thr Tyr Val
1               5

<210> SEQ ID NO 513
<211> LENGTH: 5
<212> TYPE: PRT
<213> ORGANISM: Homo sapiens

<400> SEQUENCE: 513

Met Pro Tyr Pro Arg
1               5

<210> SEQ ID NO 514
<211> LENGTH: 5
<212> TYPE: PRT
<213> ORGANISM: Homo sapiens

<400> SEQUENCE: 514

Met Arg Ser His Pro
1               5

<210> SEQ ID NO 515
<211> LENGTH: 5
<212> TYPE: PRT
<213> ORGANISM: Homo sapiens

<400> SEQUENCE: 515

Asn Asn Phe Lys His
1               5

<210> SEQ ID NO 516
<211> LENGTH: 5
<212> TYPE: PRT
<213> ORGANISM: Homo sapiens

<400> SEQUENCE: 516

Asn Pro Ile Arg Gln
1               5

<210> SEQ ID NO 517
<211> LENGTH: 5
<212> TYPE: PRT
<213> ORGANISM: Homo sapiens

<400> SEQUENCE: 517

Asn Ser Arg Trp Leu
1               5

<210> SEQ ID NO 518
<211> LENGTH: 5
<212> TYPE: PRT
<213> ORGANISM: Homo sapiens

<400> SEQUENCE: 518

Asn Thr Thr Asp Tyr
1               5

<210> SEQ ID NO 519
<211> LENGTH: 5
<212> TYPE: PRT
<213> ORGANISM: Homo sapiens

<400> SEQUENCE: 519

Asn Tyr Gln Trp Met
1               5

<210> SEQ ID NO 520
<211> LENGTH: 5
<212> TYPE: PRT
<213> ORGANISM: Homo sapiens

<400> SEQUENCE: 520

Pro Ile Arg Gln Cys
1               5

<210> SEQ ID NO 521
<211> LENGTH: 5
<212> TYPE: PRT
<213> ORGANISM: Homo sapiens

<400> SEQUENCE: 521

Pro Arg Asn Arg Arg
1               5

<210> SEQ ID NO 522
<211> LENGTH: 5
<212> TYPE: PRT
<213> ORGANISM: Homo sapiens

<400> SEQUENCE: 522

Pro Val Lys Thr Met
1               5

<210> SEQ ID NO 523
<211> LENGTH: 5
<212> TYPE: PRT
<213> ORGANISM: Homo sapiens

<400> SEQUENCE: 523

Pro Trp Asn Arg Thr
1               5

<210> SEQ ID NO 524
<211> LENGTH: 5
<212> TYPE: PRT
<213> ORGANISM: Homo sapiens

<400> SEQUENCE: 524

Gln Asp Tyr Ile Phe
1               5

<210> SEQ ID NO 525
<211> LENGTH: 5
<212> TYPE: PRT
<213> ORGANISM: Homo sapiens

<400> SEQUENCE: 525

Gln Gly Tyr Trp Arg
1               5

```
<210> SEQ ID NO 526
<211> LENGTH: 5
<212> TYPE: PRT
<213> ORGANISM: Homo sapiens

<400> SEQUENCE: 526

Gln Thr Ala Met Arg
1               5

<210> SEQ ID NO 527
<211> LENGTH: 5
<212> TYPE: PRT
<213> ORGANISM: Homo sapiens

<400> SEQUENCE: 527

Arg Cys Gln Ala Tyr
1               5

<210> SEQ ID NO 528
<211> LENGTH: 5
<212> TYPE: PRT
<213> ORGANISM: Homo sapiens

<400> SEQUENCE: 528

Arg Met Val Phe Asn
1               5

<210> SEQ ID NO 529
<211> LENGTH: 5
<212> TYPE: PRT
<213> ORGANISM: Homo sapiens

<400> SEQUENCE: 529

Ser Lys Asp Tyr Val
1               5

<210> SEQ ID NO 530
<211> LENGTH: 5
<212> TYPE: PRT
<213> ORGANISM: Homo sapiens

<400> SEQUENCE: 530

Ser Asn Ala Asn Lys
1               5

<210> SEQ ID NO 531
<211> LENGTH: 5
<212> TYPE: PRT
<213> ORGANISM: Homo sapiens

<400> SEQUENCE: 531

Thr Gly Ala Trp Pro
1               5

<210> SEQ ID NO 532
<211> LENGTH: 5
<212> TYPE: PRT
<213> ORGANISM: Homo sapiens

<400> SEQUENCE: 532

Val Gly Val Thr His
1               5

<210> SEQ ID NO 533
<211> LENGTH: 5
```

```
<212> TYPE: PRT
<213> ORGANISM: Homo sapiens

<400> SEQUENCE: 533

Val Ile Asn Phe Met
1               5

<210> SEQ ID NO 534
<211> LENGTH: 5
<212> TYPE: PRT
<213> ORGANISM: Homo sapiens

<400> SEQUENCE: 534

Val Lys Trp Leu Phe
1               5

<210> SEQ ID NO 535
<211> LENGTH: 5
<212> TYPE: PRT
<213> ORGANISM: Homo sapiens

<400> SEQUENCE: 535

Trp Asp Gly Gln Ala
1               5

<210> SEQ ID NO 536
<211> LENGTH: 5
<212> TYPE: PRT
<213> ORGANISM: Homo sapiens

<400> SEQUENCE: 536

Trp Pro Ser Phe Pro
1               5

<210> SEQ ID NO 537
<211> LENGTH: 5
<212> TYPE: PRT
<213> ORGANISM: Homo sapiens

<400> SEQUENCE: 537

Trp Arg His Val Pro
1               5

<210> SEQ ID NO 538
<211> LENGTH: 5
<212> TYPE: PRT
<213> ORGANISM: Homo sapiens

<400> SEQUENCE: 538

Tyr Ala Gly Val Tyr
1               5

<210> SEQ ID NO 539
<211> LENGTH: 5
<212> TYPE: PRT
<213> ORGANISM: Homo sapiens

<400> SEQUENCE: 539

Tyr Cys Gln Gly Tyr
1               5

<210> SEQ ID NO 540
<211> LENGTH: 5
<212> TYPE: PRT
<213> ORGANISM: Homo sapiens
```

```
<400> SEQUENCE: 540

Tyr Asn Pro Met Cys
1               5

<210> SEQ ID NO 541
<211> LENGTH: 5
<212> TYPE: PRT
<213> ORGANISM: Homo sapiens

<400> SEQUENCE: 541

Tyr Asn Ser Arg Trp
1               5

<210> SEQ ID NO 542
<211> LENGTH: 5
<212> TYPE: PRT
<213> ORGANISM: Homo sapiens

<400> SEQUENCE: 542

Tyr Pro Leu Gln Arg
1               5

<210> SEQ ID NO 543
<211> LENGTH: 5
<212> TYPE: PRT
<213> ORGANISM: Homo sapiens

<400> SEQUENCE: 543

Tyr Gln Ala Val Tyr
1               5

<210> SEQ ID NO 544
<211> LENGTH: 5
<212> TYPE: PRT
<213> ORGANISM: Homo sapiens

<400> SEQUENCE: 544

Tyr Gln Trp Met Pro
1               5

<210> SEQ ID NO 545
<211> LENGTH: 5
<212> TYPE: PRT
<213> ORGANISM: Homo sapiens

<400> SEQUENCE: 545

Tyr Trp Arg His Val
1               5

<210> SEQ ID NO 546
<211> LENGTH: 350
<212> TYPE: PRT
<213> ORGANISM: Homo sapiens

<400> SEQUENCE: 546

Met Ser Asn Ile Thr Asp Pro Gln Met Trp Asp Phe Asp Asp Leu Asn
1               5                   10                  15

Phe Thr Gly Met Pro Pro Ala Asp Glu Asp Tyr Ser Pro Cys Met Leu
                20                  25                  30

Glu Thr Glu Thr Leu Asn Lys Tyr Val Val Ile Ile Ala Tyr Ala Leu
            35                  40                  45

Val Phe Leu Leu Ser Leu Leu Gly Asn Ser Leu Val Met Leu Val Ile
        50                  55                  60
```

Leu Tyr Ser Arg Val Gly Arg Ser Val Thr Asp Val Tyr Leu Leu Asn
 65                  70                  75                  80

Leu Ala Leu Ala Asp Leu Leu Phe Ala Leu Thr Leu Pro Ile Trp Ala
             85                  90                  95

Ala Ser Lys Val Asn Gly Trp Ile Phe Gly Thr Phe Leu Cys Lys Val
        100                 105                 110

Val Ser Leu Leu Lys Glu Val Asn Phe Tyr Ser Gly Ile Leu Leu Leu
    115                 120                 125

Ala Cys Ile Ser Val Asp Arg Tyr Leu Ala Ile Val His Ala Thr Arg
130                 135                 140

Thr Leu Thr Gln Lys Arg His Leu Val Lys Phe Val Cys Leu Gly Cys
145                 150                 155                 160

Trp Gly Leu Ser Met Asn Leu Ser Leu Pro Phe Phe Leu Phe Arg Gln
                165                 170                 175

Ala Tyr His Pro Asn Asn Ser Ser Pro Val Cys Tyr Glu Val Leu Gly
            180                 185                 190

Asn Asp Thr Ala Lys Trp Arg Met Val Leu Arg Ile Leu Pro His Thr
        195                 200                 205

Phe Gly Phe Ile Val Pro Leu Phe Val Met Leu Phe Cys Tyr Gly Phe
    210                 215                 220

Thr Leu Arg Thr Leu Phe Lys Ala His Met Gly Gln Lys His Arg Ala
225                 230                 235                 240

Met Arg Val Ile Phe Ala Val Val Leu Ile Phe Leu Leu Cys Trp Leu
                245                 250                 255

Pro Tyr Asn Leu Val Leu Leu Ala Asp Thr Leu Met Arg Thr Gln Val
            260                 265                 270

Ile Gln Glu Ser Cys Glu Arg Arg Asn Asn Ile Gly Arg Ala Leu Asp
        275                 280                 285

Ala Thr Glu Ile Leu Gly Phe Leu His Ser Cys Leu Asn Pro Ile Ile
290                 295                 300

Tyr Ala Phe Ile Gly Gln Asn Phe Arg His Gly Phe Leu Lys Ile Leu
305                 310                 315                 320

Ala Met His Gly Leu Val Ser Lys Glu Phe Leu Ala Arg His Arg Val
                325                 330                 335

Thr Ser Tyr Thr Ser Ser Ser Val Asn Val Ser Ser Asn Leu
            340                 345                 350

```
<210> SEQ ID NO 547
<211> LENGTH: 5
<212> TYPE: PRT
<213> ORGANISM: Homo sapiens

<400> SEQUENCE: 547
```

Ala His Met Gly Gln
1               5

```
<210> SEQ ID NO 548
<211> LENGTH: 5
<212> TYPE: PRT
<213> ORGANISM: Homo sapiens

<400> SEQUENCE: 548
```

Ala Lys Trp Arg Met
1               5

```
<210> SEQ ID NO 549
<211> LENGTH: 5
<212> TYPE: PRT
```

<213> ORGANISM: Homo sapiens

<400> SEQUENCE: 549

Ala Tyr His Pro Asn
1               5

<210> SEQ ID NO 550
<211> LENGTH: 5
<212> TYPE: PRT
<213> ORGANISM: Homo sapiens

<400> SEQUENCE: 550

Cys Glu Arg Arg Asn
1               5

<210> SEQ ID NO 551
<211> LENGTH: 5
<212> TYPE: PRT
<213> ORGANISM: Homo sapiens

<400> SEQUENCE: 551

Cys Leu Gly Cys Trp
1               5

<210> SEQ ID NO 552
<211> LENGTH: 5
<212> TYPE: PRT
<213> ORGANISM: Homo sapiens

<400> SEQUENCE: 552

Cys Tyr Gly Phe Thr
1               5

<210> SEQ ID NO 553
<211> LENGTH: 5
<212> TYPE: PRT
<213> ORGANISM: Homo sapiens

<400> SEQUENCE: 553

Asp Leu Asn Phe Thr
1               5

<210> SEQ ID NO 554
<211> LENGTH: 5
<212> TYPE: PRT
<213> ORGANISM: Homo sapiens

<400> SEQUENCE: 554

Asp Pro Gln Met Trp
1               5

<210> SEQ ID NO 555
<211> LENGTH: 5
<212> TYPE: PRT
<213> ORGANISM: Homo sapiens

<400> SEQUENCE: 555

Asp Thr Ala Lys Trp
1               5

<210> SEQ ID NO 556
<211> LENGTH: 5
<212> TYPE: PRT
<213> ORGANISM: Homo sapiens

<400> SEQUENCE: 556

Phe Cys Tyr Gly Phe
1               5

<210> SEQ ID NO 557
<211> LENGTH: 5
<212> TYPE: PRT
<213> ORGANISM: Homo sapiens

<400> SEQUENCE: 557

Phe Lys Ala His Met
1               5

<210> SEQ ID NO 558
<211> LENGTH: 5
<212> TYPE: PRT
<213> ORGANISM: Homo sapiens

<400> SEQUENCE: 558

Gly Gln Asn Phe Arg
1               5

<210> SEQ ID NO 559
<211> LENGTH: 5
<212> TYPE: PRT
<213> ORGANISM: Homo sapiens

<400> SEQUENCE: 559

His Thr Phe Gly Phe
1               5

<210> SEQ ID NO 560
<211> LENGTH: 5
<212> TYPE: PRT
<213> ORGANISM: Homo sapiens

<400> SEQUENCE: 560

Ile Trp Ala Ala Ser
1               5

<210> SEQ ID NO 561
<211> LENGTH: 5
<212> TYPE: PRT
<213> ORGANISM: Homo sapiens

<400> SEQUENCE: 561

Lys Trp Arg Met Val
1               5

<210> SEQ ID NO 562
<211> LENGTH: 5
<212> TYPE: PRT
<213> ORGANISM: Homo sapiens

<400> SEQUENCE: 562

Lys Tyr Val Val Ile
1               5

<210> SEQ ID NO 563
<211> LENGTH: 5
<212> TYPE: PRT
<213> ORGANISM: Homo sapiens

<400> SEQUENCE: 563

Met Gly Gln Lys His
1               5

<210> SEQ ID NO 564
<211> LENGTH: 5
<212> TYPE: PRT
<213> ORGANISM: Homo sapiens

<400> SEQUENCE: 564

Met Pro Pro Ala Asp
1               5

<210> SEQ ID NO 565
<211> LENGTH: 5
<212> TYPE: PRT
<213> ORGANISM: Homo sapiens

<400> SEQUENCE: 565

Asn Phe Thr Gly Met
1               5

<210> SEQ ID NO 566
<211> LENGTH: 5
<212> TYPE: PRT
<213> ORGANISM: Homo sapiens

<400> SEQUENCE: 566

Asn Gly Trp Ile Phe
1               5

<210> SEQ ID NO 567
<211> LENGTH: 5
<212> TYPE: PRT
<213> ORGANISM: Homo sapiens

<400> SEQUENCE: 567

Pro Gln Met Trp Asp
1               5

<210> SEQ ID NO 568
<211> LENGTH: 5
<212> TYPE: PRT
<213> ORGANISM: Homo sapiens

<400> SEQUENCE: 568

Pro Tyr Asn Leu Val
1               5

<210> SEQ ID NO 569
<211> LENGTH: 5
<212> TYPE: PRT
<213> ORGANISM: Homo sapiens

<400> SEQUENCE: 569

Gln Lys His Arg Ala
1               5

<210> SEQ ID NO 570
<211> LENGTH: 5
<212> TYPE: PRT
<213> ORGANISM: Homo sapiens

<400> SEQUENCE: 570

Gln Met Trp Asp Phe
1               5

<210> SEQ ID NO 571

```
<211> LENGTH: 5
<212> TYPE: PRT
<213> ORGANISM: Homo sapiens

<400> SEQUENCE: 571

Gln Asn Phe Arg His
1               5

<210> SEQ ID NO 572
<211> LENGTH: 5
<212> TYPE: PRT
<213> ORGANISM: Homo sapiens

<400> SEQUENCE: 572

Thr Ala Lys Trp Arg
1               5

<210> SEQ ID NO 573
<211> LENGTH: 5
<212> TYPE: PRT
<213> ORGANISM: Homo sapiens

<400> SEQUENCE: 573

Thr Asp Pro Gln Met
1               5

<210> SEQ ID NO 574
<211> LENGTH: 5
<212> TYPE: PRT
<213> ORGANISM: Homo sapiens

<400> SEQUENCE: 574

Val Cys Leu Gly Cys
1               5

<210> SEQ ID NO 575
<211> LENGTH: 5
<212> TYPE: PRT
<213> ORGANISM: Homo sapiens

<400> SEQUENCE: 575

Val Cys Tyr Glu Val
1               5

<210> SEQ ID NO 576
<211> LENGTH: 5
<212> TYPE: PRT
<213> ORGANISM: Homo sapiens

<400> SEQUENCE: 576

Val Met Leu Phe Cys
1               5

<210> SEQ ID NO 577
<211> LENGTH: 5
<212> TYPE: PRT
<213> ORGANISM: Homo sapiens

<400> SEQUENCE: 577

Val Asn Gly Trp Ile
1               5

<210> SEQ ID NO 578
<211> LENGTH: 5
<212> TYPE: PRT
<213> ORGANISM: Homo sapiens
```

<400> SEQUENCE: 578

Trp Asp Phe Asp Asp
1               5

<210> SEQ ID NO 579
<211> LENGTH: 5
<212> TYPE: PRT
<213> ORGANISM: Homo sapiens

<400> SEQUENCE: 579

Trp Ile Phe Gly Thr
1               5

<210> SEQ ID NO 580
<211> LENGTH: 5
<212> TYPE: PRT
<213> ORGANISM: Homo sapiens

<400> SEQUENCE: 580

Trp Arg Met Val Leu
1               5

<210> SEQ ID NO 581
<211> LENGTH: 5
<212> TYPE: PRT
<213> ORGANISM: Homo sapiens

<400> SEQUENCE: 581

Tyr Ser Pro Cys Met
1               5

<210> SEQ ID NO 582
<211> LENGTH: 487
<212> TYPE: PRT
<213> ORGANISM: Homo sapiens

<400> SEQUENCE: 582

Met Ser Leu Pro Asn Ser Ser Cys Leu Leu Glu Asp Lys Met Cys Glu
1               5                   10                  15

Gly Asn Lys Thr Thr Met Ala Ser Pro Gln Leu Met Pro Leu Val Val
                20                  25                  30

Val Leu Ser Thr Ile Cys Leu Val Thr Val Gly Leu Asn Leu Leu Val
            35                  40                  45

Leu Tyr Ala Val Arg Ser Glu Arg Lys Leu His Thr Val Gly Asn Leu
        50                  55                  60

Tyr Ile Val Ser Leu Ser Val Ala Asp Leu Ile Val Gly Ala Val Val
65                  70                  75                  80

Met Pro Met Asn Ile Leu Tyr Leu Leu Met Ser Lys Trp Ser Leu Gly
                85                  90                  95

Arg Pro Leu Cys Leu Phe Trp Leu Ser Met Asp Tyr Val Ala Ser Thr
                100                 105                 110

Ala Ser Ile Phe Ser Val Phe Ile Leu Cys Ile Asp Arg Tyr Arg Ser
            115                 120                 125

Val Gln Gln Pro Leu Arg Tyr Leu Lys Tyr Arg Thr Lys Thr Arg Ala
        130                 135                 140

Ser Ala Thr Ile Leu Gly Ala Trp Phe Leu Ser Phe Leu Trp Val Ile
145                 150                 155                 160

Pro Ile Leu Gly Trp Asn His Phe Met Gln Gln Thr Ser Val Arg Arg
                165                 170                 175

```
Glu Asp Lys Cys Glu Thr Asp Phe Tyr Asp Val Thr Trp Phe Lys Val
            180                 185                 190
Met Thr Ala Ile Ile Asn Phe Tyr Leu Pro Thr Leu Leu Met Leu Trp
        195                 200                 205
Phe Tyr Ala Lys Ile Tyr Lys Ala Val Arg Gln His Cys Gln His Arg
210                 215                 220
Glu Leu Ile Asn Arg Ser Leu Pro Ser Phe Ser Glu Ile Lys Leu Arg
225                 230                 235                 240
Pro Glu Asn Pro Lys Gly Asp Ala Lys Lys Pro Gly Lys Glu Ser Pro
                245                 250                 255
Trp Glu Val Leu Lys Arg Lys Pro Lys Asp Ala Gly Gly Gly Ser Val
            260                 265                 270
Leu Lys Ser Pro Ser Gln Thr Pro Lys Glu Met Lys Ser Pro Val Val
        275                 280                 285
Phe Ser Gln Glu Asp Asp Arg Glu Val Asp Lys Leu Tyr Cys Phe Pro
290                 295                 300
Leu Asp Ile Val His Met Gln Ala Ala Glu Gly Ser Ser Arg Asp
305                 310                 315                 320
Tyr Val Ala Val Asn Arg Ser His Gly Gln Leu Lys Thr Asp Glu Gln
                325                 330                 335
Gly Leu Asn Thr His Gly Ala Ser Glu Ile Ser Glu Asp Gln Met Leu
            340                 345                 350
Gly Asp Ser Gln Ser Phe Ser Arg Thr Asp Ser Asp Thr Thr Thr Glu
        355                 360                 365
Thr Ala Pro Gly Lys Gly Lys Leu Arg Ser Gly Ser Asn Thr Gly Leu
370                 375                 380
Asp Tyr Ile Lys Phe Thr Trp Lys Arg Leu Arg Ser His Ser Arg Gln
385                 390                 395                 400
Tyr Val Ser Gly Leu His Met Asn Arg Glu Arg Lys Ala Ala Lys Gln
                405                 410                 415
Leu Gly Phe Ile Met Ala Ala Phe Ile Leu Cys Trp Ile Pro Tyr Phe
            420                 425                 430
Ile Phe Phe Met Val Ile Ala Phe Cys Lys Asn Cys Cys Asn Glu His
        435                 440                 445
Leu His Met Phe Thr Ile Trp Leu Gly Tyr Ile Asn Ser Thr Leu Asn
450                 455                 460
Pro Leu Ile Tyr Pro Leu Cys Asn Glu Asn Phe Lys Lys Thr Phe Lys
465                 470                 475                 480
Arg Ile Leu His Ile Arg Ser
                485

<210> SEQ ID NO 583
<211> LENGTH: 5
<212> TYPE: PRT
<213> ORGANISM: Homo sapiens

<400> SEQUENCE: 583

Ala Ile Ile Asn Phe
1               5

<210> SEQ ID NO 584
<211> LENGTH: 5
<212> TYPE: PRT
<213> ORGANISM: Homo sapiens

<400> SEQUENCE: 584

Cys Glu Gly Asn Lys
```

-continued

<210> SEQ ID NO 585
<211> LENGTH: 5
<212> TYPE: PRT
<213> ORGANISM: Homo sapiens

<400> SEQUENCE: 585

Cys Asn Glu Asn Phe
1               5

<210> SEQ ID NO 586
<211> LENGTH: 5
<212> TYPE: PRT
<213> ORGANISM: Homo sapiens

<400> SEQUENCE: 586

Cys Trp Ile Pro Tyr
1               5

<210> SEQ ID NO 587
<211> LENGTH: 5
<212> TYPE: PRT
<213> ORGANISM: Homo sapiens

<400> SEQUENCE: 587

Asp Phe Tyr Asp Val
1               5

<210> SEQ ID NO 588
<211> LENGTH: 5
<212> TYPE: PRT
<213> ORGANISM: Homo sapiens

<400> SEQUENCE: 588

Asp Gln Met Leu Gly
1               5

<210> SEQ ID NO 589
<211> LENGTH: 5
<212> TYPE: PRT
<213> ORGANISM: Homo sapiens

<400> SEQUENCE: 589

Phe Ile Leu Cys Ile
1               5

<210> SEQ ID NO 590
<211> LENGTH: 5
<212> TYPE: PRT
<213> ORGANISM: Homo sapiens

<400> SEQUENCE: 590

Phe Leu Trp Val Ile
1               5

<210> SEQ ID NO 591
<211> LENGTH: 5
<212> TYPE: PRT
<213> ORGANISM: Homo sapiens

<400> SEQUENCE: 591

Phe Met Gln Gln Thr
1               5

```
<210> SEQ ID NO 592
<211> LENGTH: 5
<212> TYPE: PRT
<213> ORGANISM: Homo sapiens

<400> SEQUENCE: 592

Phe Trp Leu Ser Met
1               5

<210> SEQ ID NO 593
<211> LENGTH: 5
<212> TYPE: PRT
<213> ORGANISM: Homo sapiens

<400> SEQUENCE: 593

Gly Trp Asn His Phe
1               5

<210> SEQ ID NO 594
<211> LENGTH: 5
<212> TYPE: PRT
<213> ORGANISM: Homo sapiens

<400> SEQUENCE: 594

His Leu His Met Phe
1               5

<210> SEQ ID NO 595
<211> LENGTH: 5
<212> TYPE: PRT
<213> ORGANISM: Homo sapiens

<400> SEQUENCE: 595

His Met Phe Thr Ile
1               5

<210> SEQ ID NO 596
<211> LENGTH: 5
<212> TYPE: PRT
<213> ORGANISM: Homo sapiens

<400> SEQUENCE: 596

His Thr Val Gly Asn
1               5

<210> SEQ ID NO 597
<211> LENGTH: 5
<212> TYPE: PRT
<213> ORGANISM: Homo sapiens

<400> SEQUENCE: 597

Ile Phe Phe Met Val
1               5

<210> SEQ ID NO 598
<211> LENGTH: 5
<212> TYPE: PRT
<213> ORGANISM: Homo sapiens

<400> SEQUENCE: 598

Ile Leu Cys Trp Ile
1               5

<210> SEQ ID NO 599
<211> LENGTH: 5
<212> TYPE: PRT
```

<213> ORGANISM: Homo sapiens

<400> SEQUENCE: 599

Leu Leu Met Ser Lys
1               5

<210> SEQ ID NO 600
<211> LENGTH: 5
<212> TYPE: PRT
<213> ORGANISM: Homo sapiens

<400> SEQUENCE: 600

Leu Trp Phe Tyr Ala
1               5

<210> SEQ ID NO 601
<211> LENGTH: 5
<212> TYPE: PRT
<213> ORGANISM: Homo sapiens

<400> SEQUENCE: 601

Met Cys Glu Gly Asn
1               5

<210> SEQ ID NO 602
<211> LENGTH: 5
<212> TYPE: PRT
<213> ORGANISM: Homo sapiens

<400> SEQUENCE: 602

Met Asp Tyr Val Ala
1               5

<210> SEQ ID NO 603
<211> LENGTH: 5
<212> TYPE: PRT
<213> ORGANISM: Homo sapiens

<400> SEQUENCE: 603

Met Phe Thr Ile Trp
1               5

<210> SEQ ID NO 604
<211> LENGTH: 5
<212> TYPE: PRT
<213> ORGANISM: Homo sapiens

<400> SEQUENCE: 604

Met Leu Trp Phe Tyr
1               5

<210> SEQ ID NO 605
<211> LENGTH: 5
<212> TYPE: PRT
<213> ORGANISM: Homo sapiens

<400> SEQUENCE: 605

Asn Cys Cys Asn Glu
1               5

<210> SEQ ID NO 606
<211> LENGTH: 5
<212> TYPE: PRT
<213> ORGANISM: Homo sapiens

<400> SEQUENCE: 606

Asn His Phe Met Gln
1               5

<210> SEQ ID NO 607
<211> LENGTH: 5
<212> TYPE: PRT
<213> ORGANISM: Homo sapiens

<400> SEQUENCE: 607

Pro Leu Cys Leu Phe
1               5

<210> SEQ ID NO 608
<211> LENGTH: 5
<212> TYPE: PRT
<213> ORGANISM: Homo sapiens

<400> SEQUENCE: 608

Ser Pro Trp Glu Val
1               5

<210> SEQ ID NO 609
<211> LENGTH: 5
<212> TYPE: PRT
<213> ORGANISM: Homo sapiens

<400> SEQUENCE: 609

Val Ile Ala Phe Cys
1               5

<210> SEQ ID NO 610
<211> LENGTH: 5
<212> TYPE: PRT
<213> ORGANISM: Homo sapiens

<400> SEQUENCE: 610

Trp Phe Tyr Ala Lys
1               5

<210> SEQ ID NO 611
<211> LENGTH: 5
<212> TYPE: PRT
<213> ORGANISM: Homo sapiens

<400> SEQUENCE: 611

Trp Asn His Phe Met
1               5

<210> SEQ ID NO 612
<211> LENGTH: 5
<212> TYPE: PRT
<213> ORGANISM: Homo sapiens

<400> SEQUENCE: 612

Trp Val Ile Pro Ile
1               5

<210> SEQ ID NO 613
<211> LENGTH: 5
<212> TYPE: PRT
<213> ORGANISM: Homo sapiens

<400> SEQUENCE: 613

Tyr Cys Phe Pro Leu
1               5

<210> SEQ ID NO 614
<211> LENGTH: 25
<212> TYPE: PRT
<213> ORGANISM: Homo sapiens

<400> SEQUENCE: 614

Tyr Asp Val Pro Asp Tyr Ala Gly Gly Asp Tyr Lys Ala Phe Asp Glu
1               5                   10                  15

Gln Lys Leu Ile Ser Glu Glu Asp Leu
            20                  25

<210> SEQ ID NO 615
<211> LENGTH: 5
<212> TYPE: PRT
<213> ORGANISM: Artificial Sequence
<220> FEATURE:
<223> OTHER INFORMATION: Linker peptide

<400> SEQUENCE: 615

Gly Ser Ser Ser Ser
1               5

<210> SEQ ID NO 616
<211> LENGTH: 17
<212> TYPE: PRT
<213> ORGANISM: Unknown
<220> FEATURE:
<223> OTHER INFORMATION: peptide related to Anti-Cyclin F

<400> SEQUENCE: 616

Thr Ala Ser Pro Thr Ser Ser Val Asp Gly Gly Leu Gly Ala Leu Pro
1               5                   10                  15

Lys

<210> SEQ ID NO 617
<211> LENGTH: 8
<212> TYPE: PRT
<213> ORGANISM: Unknown
<220> FEATURE:
<223> OTHER INFORMATION: Peptide related to Anti-Cyclin F

<400> SEQUENCE: 617

Ser Ala Ser Ile Asp Gly Gly Leu
1               5

<210> SEQ ID NO 618
<211> LENGTH: 8
<212> TYPE: PRT
<213> ORGANISM: Unknown
<220> FEATURE:
<223> OTHER INFORMATION: Peptide related to Anti-Cyclin F

<400> SEQUENCE: 618

Ser Ser Ser Ser Asp Gly Gly Leu
1               5

<210> SEQ ID NO 619
<211> LENGTH: 8
<212> TYPE: PRT
<213> ORGANISM: Unknown
<220> FEATURE:
<223> OTHER INFORMATION: Peptide related to Anti-Cyclin F

<400> SEQUENCE: 619

Thr Gly Ser Val Asp Gly Gly Ala

```
<210> SEQ ID NO 620
<211> LENGTH: 8
<212> TYPE: PRT
<213> ORGANISM: Unknown
<220> FEATURE:
<223> OTHER INFORMATION: Peptide related to Anti-Cyclin F

<400> SEQUENCE: 620

Glu Ser Ser Ser Asp Gly Gly Leu
1               5

<210> SEQ ID NO 621
<211> LENGTH: 23
<212> TYPE: PRT
<213> ORGANISM: Homo sapiens

<400> SEQUENCE: 621

Phe Ala Gly Met Pro Ile Thr Leu Thr Val Ser Thr Ser Ser Leu Asn
1               5                   10                  15

Leu Met Ala Ala Asp Cys Lys
            20

<210> SEQ ID NO 622
<211> LENGTH: 8
<212> TYPE: PRT
<213> ORGANISM: Unknown
<220> FEATURE:
<223> OTHER INFORMATION: Peptide related to Anti-phospho SHC

<400> SEQUENCE: 622

Ile Ser Thr Ala Ser Leu Asn Leu
1               5

<210> SEQ ID NO 623
<211> LENGTH: 8
<212> TYPE: PRT
<213> ORGANISM: Unknown
<220> FEATURE:
<223> OTHER INFORMATION: Peptide related to Anti-phospho SHC

<400> SEQUENCE: 623

Ile Ser Thr Ser Ser Leu Asn Val
1               5

<210> SEQ ID NO 624
<211> LENGTH: 8
<212> TYPE: PRT
<213> ORGANISM: Unknown
<220> FEATURE:
<223> OTHER INFORMATION: Peptide related to Anti-phospho SHC

<400> SEQUENCE: 624

Val Ser Leu Ser Ser Leu Asn Leu
1               5

<210> SEQ ID NO 625
<211> LENGTH: 8
<212> TYPE: PRT
<213> ORGANISM: Unknown
<220> FEATURE:
<223> OTHER INFORMATION: Peptide related to Anti-phospho SHC

<400> SEQUENCE: 625

Met Asp Thr Ser Ser Leu Asn Leu
1               5
```

```
<210> SEQ ID NO 626
<211> LENGTH: 15
<212> TYPE: PRT
<213> ORGANISM: Homo sapiens

<400> SEQUENCE: 626

Glu Glu Glu Ala Asp Ile Asn Gln Leu Thr Glu Glu Phe Phe Lys
1               5                   10                  15

<210> SEQ ID NO 627
<211> LENGTH: 8
<212> TYPE: PRT
<213> ORGANISM: Unknown
<220> FEATURE:
<223> OTHER INFORMATION: Peptide related to Anti-phospho-PP2A

<400> SEQUENCE: 627

Ala Asp Leu Asn Gln Leu Thr Gln
1               5

<210> SEQ ID NO 628
<211> LENGTH: 8
<212> TYPE: PRT
<213> ORGANISM: Unknown
<220> FEATURE:
<223> OTHER INFORMATION: Peptide related to Anti-phospho-PP2A

<400> SEQUENCE: 628

Arg Asp Ile Asn Gln Leu Ser Glu
1               5

<210> SEQ ID NO 629
<211> LENGTH: 8
<212> TYPE: PRT
<213> ORGANISM: Unknown
<220> FEATURE:
<223> OTHER INFORMATION: Peptide related to Anti-phospho-PP2A

<400> SEQUENCE: 629

Ala Asp Phe Asn Gln Leu Ala Glu
1               5

<210> SEQ ID NO 630
<211> LENGTH: 8
<212> TYPE: PRT
<213> ORGANISM: Unknown
<220> FEATURE:
<223> OTHER INFORMATION: Peptide related to Anti-phospho-PP2A

<400> SEQUENCE: 630

Ala Asp Ile Asn Met Val Thr Glu
1               5

<210> SEQ ID NO 631
<211> LENGTH: 15
<212> TYPE: PRT
<213> ORGANISM: Homo sapiens

<400> SEQUENCE: 631

Ala Thr Ser Gln Gln Pro Pro Gln Tyr Ser His Gln Thr His Arg
1               5                   10                  15

<210> SEQ ID NO 632
<211> LENGTH: 8
<212> TYPE: PRT
<213> ORGANISM: Unknown
```

```
<220> FEATURE:
<223> OTHER INFORMATION: Peptide related to Anti-Cdk8

<400> SEQUENCE: 632

Gln Glu Pro Pro Gln Tyr Ser His
1               5

<210> SEQ ID NO 633
<211> LENGTH: 8
<212> TYPE: PRT
<213> ORGANISM: Unknown
<220> FEATURE:
<223> OTHER INFORMATION: Peptide related to Anti-Cdk8

<400> SEQUENCE: 633

Gln Gln Gln Pro Gln Phe Ser His
1               5

<210> SEQ ID NO 634
<211> LENGTH: 8
<212> TYPE: PRT
<213> ORGANISM: Unknown
<220> FEATURE:
<223> OTHER INFORMATION: Peptide related to Anti-Cdk8

<400> SEQUENCE: 634

Gln Gln Pro Pro Gln His Ser Lys
1               5

<210> SEQ ID NO 635
<211> LENGTH: 8
<212> TYPE: PRT
<213> ORGANISM: Unknown
<220> FEATURE:
<223> OTHER INFORMATION: Peptide related to Anti-Cdk8

<400> SEQUENCE: 635

Gln Gln Pro Pro Gln Gln Gln His
1               5

<210> SEQ ID NO 636
<211> LENGTH: 11
<212> TYPE: PRT
<213> ORGANISM: Unknown
<220> FEATURE:
<223> OTHER INFORMATION: Peptide used to illustrate phosphorylation site

<400> SEQUENCE: 636

Tyr Leu Arg Arg Ala Ser Leu Ala Gln Leu Thr
1               5                   10

<210> SEQ ID NO 637
<211> LENGTH: 8
<212> TYPE: PRT
<213> ORGANISM: Unknown
<220> FEATURE:
<223> OTHER INFORMATION: Peptide used to illustrate phosphorylation site

<400> SEQUENCE: 637

Phe Arg Arg Leu Ser Ile Ser Thr
1               5

<210> SEQ ID NO 638
<211> LENGTH: 11
<212> TYPE: PRT
<213> ORGANISM: Unknown
<220> FEATURE:
<223> OTHER INFORMATION: Peptide used to illustrate phosphorylation site
```

```
<400> SEQUENCE: 638

Ala Gly Ala Arg Arg Lys Ala Ser Gly Pro Pro
1               5                   10

<210> SEQ ID NO 639
<211> LENGTH: 11
<212> TYPE: PRT
<213> ORGANISM: Unknown
<220> FEATURE:
<223> OTHER INFORMATION: Peptide used to illustrate phosphorylation site
<220> FEATURE:
<221> NAME/KEY: MOD_RES
<222> LOCATION: (4)
<223> OTHER INFORMATION: phosphoSer

<400> SEQUENCE: 639

Arg Thr Leu Ser Val Ser Ser Leu Pro Gly Leu
1               5                   10

<210> SEQ ID NO 640
<211> LENGTH: 10
<212> TYPE: PRT
<213> ORGANISM: Unknown
<220> FEATURE:
<223> OTHER INFORMATION: Peptide used to illustrate phosphorylation site
<220> FEATURE:
<221> NAME/KEY: MOD_RES
<222> LOCATION: (4)
<223> OTHER INFORMATION: phosphoSer
<220> FEATURE:
<221> NAME/KEY: MOD_RES
<222> LOCATION: (6)
<223> OTHER INFORMATION: phosphoSer

<400> SEQUENCE: 640

Asp Ile Gly Ser Glu Ser Thr Glu Asp Gln
1               5                   10

<210> SEQ ID NO 641
<211> LENGTH: 10
<212> TYPE: PRT
<213> ORGANISM: Unknown
<220> FEATURE:
<223> OTHER INFORMATION: Peptide used to illustrate phosphorylation site

<400> SEQUENCE: 641

Ala Asp Ser Glu Ser Glu Asp Glu Glu Asp
1               5                   10

<210> SEQ ID NO 642
<211> LENGTH: 11
<212> TYPE: PRT
<213> ORGANISM: Unknown
<220> FEATURE:
<223> OTHER INFORMATION: Peptide used to illustrate phosphorylation site

<400> SEQUENCE: 642

Leu Glu Ser Glu Glu Glu Gly Val Pro Ser Thr
1               5                   10

<210> SEQ ID NO 643
<211> LENGTH: 11
<212> TYPE: PRT
<213> ORGANISM: Unknown
<220> FEATURE:
<223> OTHER INFORMATION: Peptide used to illustrate phosphorylation site

<400> SEQUENCE: 643
```

```
Glu Asp Asn Ser Glu Asp Glu Ile Ser Asn Leu
1               5                   10

<210> SEQ ID NO 644
<211> LENGTH: 9
<212> TYPE: PRT
<213> ORGANISM: Unknown
<220> FEATURE:
<223> OTHER INFORMATION: Peptide used to illustrate phosphorylation site
<220> FEATURE:
<221> NAME/KEY: MOD_RES
<222> LOCATION: (9)
<223> OTHER INFORMATION: phosphoSer

<400> SEQUENCE: 644

Ser Val Pro Pro Ser Pro Ser Leu Ser
1               5

<210> SEQ ID NO 645
<211> LENGTH: 9
<212> TYPE: PRT
<213> ORGANISM: Unknown
<220> FEATURE:
<223> OTHER INFORMATION: Peptide used to illustrate phosphorylation site
<220> FEATURE:
<221> NAME/KEY: MOD_RES
<222> LOCATION: (5)
<223> OTHER INFORMATION: phosphoSer
<220> FEATURE:
<221> NAME/KEY: MOD_RES
<222> LOCATION: (9)
<223> OTHER INFORMATION: phosphoSer

<400> SEQUENCE: 645

Ser Val Pro Pro Ser Pro Ser Leu Ser
1               5

<210> SEQ ID NO 646
<211> LENGTH: 7
<212> TYPE: PRT
<213> ORGANISM: Unknown
<220> FEATURE:
<223> OTHER INFORMATION: Peptide used to illustrate phosphorylation site

<400> SEQUENCE: 646

Pro Ala Lys Thr Pro Val Lys
1               5

<210> SEQ ID NO 647
<211> LENGTH: 10
<212> TYPE: PRT
<213> ORGANISM: Unknown
<220> FEATURE:
<223> OTHER INFORMATION: Peptide used to illustrate phosphorylation site

<400> SEQUENCE: 647

His Ser Thr Pro Pro Lys Lys Lys Arg Lys
1               5                   10

<210> SEQ ID NO 648
<211> LENGTH: 11
<212> TYPE: PRT
<213> ORGANISM: Unknown
<220> FEATURE:
<223> OTHER INFORMATION: Peptide used to illustrate phosphorylation site

<400> SEQUENCE: 648

Asn Tyr Leu Arg Arg Arg Leu Ser Asp Ser Asn
1               5                   10
```

```
<210> SEQ ID NO 649
<211> LENGTH: 10
<212> TYPE: PRT
<213> ORGANISM: Unknown
<220> FEATURE:
<223> OTHER INFORMATION: Peptide used to illustrate phosphorylation site

<400> SEQUENCE: 649

Lys Met Ala Arg Val Phe Ser Val Leu Arg
1               5                   10

<210> SEQ ID NO 650
<211> LENGTH: 4
<212> TYPE: PRT
<213> ORGANISM: Unknown
<220> FEATURE:
<223> OTHER INFORMATION: Peptide used to illustrate phosphorylation site

<400> SEQUENCE: 650

Pro Leu Ser Pro
1

<210> SEQ ID NO 651
<211> LENGTH: 4
<212> TYPE: PRT
<213> ORGANISM: Unknown
<220> FEATURE:
<223> OTHER INFORMATION: Peptide used to illustrate phosphorylation site

<400> SEQUENCE: 651

Pro Ser Ser Pro
1

<210> SEQ ID NO 652
<211> LENGTH: 4
<212> TYPE: PRT
<213> ORGANISM: Unknown
<220> FEATURE:
<223> OTHER INFORMATION: Peptide used to illustrate phosphorylation site

<400> SEQUENCE: 652

Val Leu Ser Pro
1

<210> SEQ ID NO 653
<211> LENGTH: 11
<212> TYPE: PRT
<213> ORGANISM: Unknown
<220> FEATURE:
<223> OTHER INFORMATION: Peptide used to illustrate phosphorylation site

<400> SEQUENCE: 653

Gly Lys Lys Arg Lys Arg Ser Arg Lys Glu Ser
1               5                   10

<210> SEQ ID NO 654
<211> LENGTH: 8
<212> TYPE: PRT
<213> ORGANISM: Unknown
<220> FEATURE:
<223> OTHER INFORMATION: Peptide used to illustrate phosphorylation site

<400> SEQUENCE: 654

Phe Arg Arg Leu Ser Ile Ser Thr
1               5

<210> SEQ ID NO 655
```

```
<211> LENGTH: 12
<212> TYPE: PRT
<213> ORGANISM: Unknown
<220> FEATURE:
<223> OTHER INFORMATION: Peptide used to illustrate phosphorylation site

<400> SEQUENCE: 655

Asp Gln Glu Lys Arg Lys Gln Ile Ser Val Arg Gly
1               5                   10

<210> SEQ ID NO 656
<211> LENGTH: 10
<212> TYPE: PRT
<213> ORGANISM: Unknown
<220> FEATURE:
<223> OTHER INFORMATION: Peptide used to illustrate phosphorylation site

<400> SEQUENCE: 656

Pro Leu Ser Arg Thr Leu Ser Val Ser Ser
1               5                   10

<210> SEQ ID NO 657
<211> LENGTH: 9
<212> TYPE: PRT
<213> ORGANISM: Unknown
<220> FEATURE:
<223> OTHER INFORMATION: Peptide used to illustrate phosphorylation site

<400> SEQUENCE: 657

His Glu Gly Thr His Ser Thr Lys Arg
1               5

<210> SEQ ID NO 658
<211> LENGTH: 10
<212> TYPE: PRT
<213> ORGANISM: Unknown
<220> FEATURE:
<223> OTHER INFORMATION: Peptide used to illustrate phosphorylation site

<400> SEQUENCE: 658

Pro Leu Ser Arg Thr Leu Ser Val Ser Ser
1               5                   10

<210> SEQ ID NO 659
<211> LENGTH: 11
<212> TYPE: PRT
<213> ORGANISM: Unknown
<220> FEATURE:
<223> OTHER INFORMATION: Peptide used to illustrate phosphorylation site

<400> SEQUENCE: 659

Gln Lys Arg Pro Ser Gln Arg Ser Lys Tyr Leu
1               5                   10

<210> SEQ ID NO 660
<211> LENGTH: 11
<212> TYPE: PRT
<213> ORGANISM: Unknown
<220> FEATURE:
<223> OTHER INFORMATION: Peptide used to illustrate phosphorylation site

<400> SEQUENCE: 660

Arg Glu Asn Ala Glu Tyr Leu Arg Val Ala Pro
1               5                   10

<210> SEQ ID NO 661
<211> LENGTH: 10
<212> TYPE: PRT
```

```
<213> ORGANISM: Unknown
<220> FEATURE:
<223> OTHER INFORMATION: Peptide used to illustrate phosphorylation site

<400> SEQUENCE: 661

Ala Glu Pro Asp Tyr Gly Ala Leu Tyr Glu
1               5                   10

<210> SEQ ID NO 662
<211> LENGTH: 8
<212> TYPE: PRT
<213> ORGANISM: Homo sapiens

<400> SEQUENCE: 662

Tyr Val Leu Glu Gly Val Pro His
1               5

<210> SEQ ID NO 663
<211> LENGTH: 8
<212> TYPE: PRT
<213> ORGANISM: Human severe acute respiratory syndrome virus

<400> SEQUENCE: 663

Ile Ser Leu Cys Ser Cys Ile Cys
1               5

<210> SEQ ID NO 664
<211> LENGTH: 8
<212> TYPE: PRT
<213> ORGANISM: Human severe acute respiratory syndrome virus

<400> SEQUENCE: 664

Ser Leu Cys Ser Cys Ile Cys Thr
1               5

<210> SEQ ID NO 665
<211> LENGTH: 8
<212> TYPE: PRT
<213> ORGANISM: Human severe acute respiratory syndrome virus

<400> SEQUENCE: 665

Leu Cys Ser Cys Ile Cys Thr Val
1               5

<210> SEQ ID NO 666
<211> LENGTH: 8
<212> TYPE: PRT
<213> ORGANISM: Human severe acute respiratory syndrome virus

<400> SEQUENCE: 666

Cys Ser Cys Ile Cys Thr Val Val
1               5

<210> SEQ ID NO 667
<211> LENGTH: 8
<212> TYPE: PRT
<213> ORGANISM: Human severe acute respiratory syndrome virus

<400> SEQUENCE: 667

Ser Cys Ile Cys Thr Val Val Gln
1               5

<210> SEQ ID NO 668
<211> LENGTH: 8
<212> TYPE: PRT
<213> ORGANISM: Human severe acute respiratory syndrome virus
```

```
<400> SEQUENCE: 668

Cys Ile Cys Thr Val Val Gln Arg
1               5

<210> SEQ ID NO 669
<211> LENGTH: 8
<212> TYPE: PRT
<213> ORGANISM: Human severe acute respiratory syndrome virus

<400> SEQUENCE: 669

Ile Cys Thr Val Val Gln Arg Cys
1               5

<210> SEQ ID NO 670
<211> LENGTH: 8
<212> TYPE: PRT
<213> ORGANISM: Human severe acute respiratory syndrome virus

<400> SEQUENCE: 670

Cys Thr Val Val Gln Arg Cys Ala
1               5

<210> SEQ ID NO 671
<211> LENGTH: 8
<212> TYPE: PRT
<213> ORGANISM: Human severe acute respiratory syndrome virus

<400> SEQUENCE: 671

His Val Leu Glu Asp Pro Cys Lys
1               5

<210> SEQ ID NO 672
<211> LENGTH: 8
<212> TYPE: PRT
<213> ORGANISM: Human severe acute respiratory syndrome virus

<400> SEQUENCE: 672

Val Leu Glu Asp Pro Cys Lys Val
1               5

<210> SEQ ID NO 673
<211> LENGTH: 8
<212> TYPE: PRT
<213> ORGANISM: Human severe acute respiratory syndrome virus

<400> SEQUENCE: 673

Leu Glu Asp Pro Cys Lys Val Gln
1               5

<210> SEQ ID NO 674
<211> LENGTH: 8
<212> TYPE: PRT
<213> ORGANISM: Human severe acute respiratory syndrome virus

<400> SEQUENCE: 674

Glu Asp Pro Cys Lys Val Gln His
1               5

<210> SEQ ID NO 675
<211> LENGTH: 8
<212> TYPE: PRT
<213> ORGANISM: Human severe acute respiratory syndrome virus

<400> SEQUENCE: 675
```

```
Met Asn Glu Leu Thr Leu Ile Asp
1               5

<210> SEQ ID NO 676
<211> LENGTH: 8
<212> TYPE: PRT
<213> ORGANISM: Human severe acute respiratory syndrome virus

<400> SEQUENCE: 676

Asn Glu Leu Thr Leu Ile Asp Phe
1               5

<210> SEQ ID NO 677
<211> LENGTH: 8
<212> TYPE: PRT
<213> ORGANISM: Human severe acute respiratory syndrome virus

<400> SEQUENCE: 677

Glu Leu Thr Leu Ile Asp Phe Tyr
1               5

<210> SEQ ID NO 678
<211> LENGTH: 8
<212> TYPE: PRT
<213> ORGANISM: Human severe acute respiratory syndrome virus

<400> SEQUENCE: 678

Leu Thr Leu Ile Asp Phe Tyr Leu
1               5

<210> SEQ ID NO 679
<211> LENGTH: 8
<212> TYPE: PRT
<213> ORGANISM: Human severe acute respiratory syndrome virus

<400> SEQUENCE: 679

Thr Leu Ile Asp Phe Tyr Leu Cys
1               5

<210> SEQ ID NO 680
<211> LENGTH: 8
<212> TYPE: PRT
<213> ORGANISM: Human severe acute respiratory syndrome virus

<400> SEQUENCE: 680

Leu Ile Asp Phe Tyr Leu Cys Phe
1               5

<210> SEQ ID NO 681
<211> LENGTH: 8
<212> TYPE: PRT
<213> ORGANISM: Human severe acute respiratory syndrome virus

<400> SEQUENCE: 681

Ile Asp Phe Tyr Leu Cys Phe Leu
1               5

<210> SEQ ID NO 682
<211> LENGTH: 8
<212> TYPE: PRT
<213> ORGANISM: Human severe acute respiratory syndrome virus

<400> SEQUENCE: 682

Asp Phe Tyr Leu Cys Phe Leu Ala
1               5
```

```
<210> SEQ ID NO 683
<211> LENGTH: 8
<212> TYPE: PRT
<213> ORGANISM: Human severe acute respiratory syndrome virus

<400> SEQUENCE: 683

Phe Tyr Leu Cys Phe Leu Ala Phe
1               5

<210> SEQ ID NO 684
<211> LENGTH: 8
<212> TYPE: PRT
<213> ORGANISM: Human severe acute respiratory syndrome virus

<400> SEQUENCE: 684

Tyr Leu Cys Phe Leu Ala Phe Leu
1               5

<210> SEQ ID NO 685
<211> LENGTH: 8
<212> TYPE: PRT
<213> ORGANISM: Human severe acute respiratory syndrome virus

<400> SEQUENCE: 685

Leu Cys Phe Leu Ala Phe Leu Leu
1               5

<210> SEQ ID NO 686
<211> LENGTH: 8
<212> TYPE: PRT
<213> ORGANISM: Human severe acute respiratory syndrome virus

<400> SEQUENCE: 686

Cys Phe Leu Ala Phe Leu Leu Phe
1               5

<210> SEQ ID NO 687
<211> LENGTH: 8
<212> TYPE: PRT
<213> ORGANISM: Human severe acute respiratory syndrome virus

<400> SEQUENCE: 687

Phe Leu Ala Phe Leu Leu Phe Leu
1               5

<210> SEQ ID NO 688
<211> LENGTH: 8
<212> TYPE: PRT
<213> ORGANISM: Human severe acute respiratory syndrome virus

<400> SEQUENCE: 688

Leu Ala Phe Leu Leu Phe Leu Val
1               5

<210> SEQ ID NO 689
<211> LENGTH: 8
<212> TYPE: PRT
<213> ORGANISM: Human severe acute respiratory syndrome virus

<400> SEQUENCE: 689

Ala Phe Leu Leu Phe Leu Val Leu
1               5

<210> SEQ ID NO 690
<211> LENGTH: 8
```

```
<212> TYPE: PRT
<213> ORGANISM: Human severe acute respiratory syndrome virus

<400> SEQUENCE: 690

Phe Leu Leu Phe Leu Val Leu Ile
1               5

<210> SEQ ID NO 691
<211> LENGTH: 8
<212> TYPE: PRT
<213> ORGANISM: Human severe acute respiratory syndrome virus

<400> SEQUENCE: 691

Leu Leu Phe Leu Val Leu Ile Met
1               5

<210> SEQ ID NO 692
<211> LENGTH: 8
<212> TYPE: PRT
<213> ORGANISM: Human severe acute respiratory syndrome virus

<400> SEQUENCE: 692

Leu Phe Leu Val Leu Ile Met Leu
1               5

<210> SEQ ID NO 693
<211> LENGTH: 8
<212> TYPE: PRT
<213> ORGANISM: Human severe acute respiratory syndrome virus

<400> SEQUENCE: 693

Phe Leu Val Leu Ile Met Leu Ile
1               5

<210> SEQ ID NO 694
<211> LENGTH: 8
<212> TYPE: PRT
<213> ORGANISM: Human severe acute respiratory syndrome virus

<400> SEQUENCE: 694

Leu Val Leu Ile Met Leu Ile Ile
1               5

<210> SEQ ID NO 695
<211> LENGTH: 8
<212> TYPE: PRT
<213> ORGANISM: Human severe acute respiratory syndrome virus

<400> SEQUENCE: 695

Val Leu Ile Met Leu Ile Ile Phe
1               5

<210> SEQ ID NO 696
<211> LENGTH: 8
<212> TYPE: PRT
<213> ORGANISM: Human severe acute respiratory syndrome virus

<400> SEQUENCE: 696

Leu Ile Met Leu Ile Ile Phe Trp
1               5

<210> SEQ ID NO 697
<211> LENGTH: 8
<212> TYPE: PRT
<213> ORGANISM: Human severe acute respiratory syndrome virus
```

```
<400> SEQUENCE: 697

Ile Met Leu Ile Ile Phe Trp Phe
1               5

<210> SEQ ID NO 698
<211> LENGTH: 8
<212> TYPE: PRT
<213> ORGANISM: Human severe acute respiratory syndrome virus

<400> SEQUENCE: 698

Met Leu Ile Ile Phe Trp Phe Ser
1               5

<210> SEQ ID NO 699
<211> LENGTH: 8
<212> TYPE: PRT
<213> ORGANISM: Human severe acute respiratory syndrome virus

<400> SEQUENCE: 699

Leu Ile Ile Phe Trp Phe Ser Leu
1               5

<210> SEQ ID NO 700
<211> LENGTH: 8
<212> TYPE: PRT
<213> ORGANISM: Human severe acute respiratory syndrome virus

<400> SEQUENCE: 700

Ile Ile Phe Trp Phe Ser Leu Glu
1               5

<210> SEQ ID NO 701
<211> LENGTH: 8
<212> TYPE: PRT
<213> ORGANISM: Human severe acute respiratory syndrome virus

<400> SEQUENCE: 701

Ile Phe Trp Phe Ser Leu Glu Ile
1               5

<210> SEQ ID NO 702
<211> LENGTH: 8
<212> TYPE: PRT
<213> ORGANISM: Human severe acute respiratory syndrome virus

<400> SEQUENCE: 702

Phe Trp Phe Ser Leu Glu Ile Gln
1               5

<210> SEQ ID NO 703
<211> LENGTH: 8
<212> TYPE: PRT
<213> ORGANISM: Human severe acute respiratory syndrome virus

<400> SEQUENCE: 703

Trp Phe Ser Leu Glu Ile Gln Asp
1               5

<210> SEQ ID NO 704
<211> LENGTH: 8
<212> TYPE: PRT
<213> ORGANISM: Human severe acute respiratory syndrome virus

<400> SEQUENCE: 704

Phe Ser Leu Glu Ile Gln Asp Leu
```

```
<210> SEQ ID NO 705
<211> LENGTH: 8
<212> TYPE: PRT
<213> ORGANISM: Human severe acute respiratory syndrome virus

<400> SEQUENCE: 705

Ser Leu Glu Ile Gln Asp Leu Glu
1               5

<210> SEQ ID NO 706
<211> LENGTH: 8
<212> TYPE: PRT
<213> ORGANISM: Human severe acute respiratory syndrome virus

<400> SEQUENCE: 706

Leu Glu Ile Gln Asp Leu Glu Glu
1               5

<210> SEQ ID NO 707
<211> LENGTH: 8
<212> TYPE: PRT
<213> ORGANISM: Human severe acute respiratory syndrome virus

<400> SEQUENCE: 707

Glu Ile Gln Asp Leu Glu Glu Pro
1               5

<210> SEQ ID NO 708
<211> LENGTH: 8
<212> TYPE: PRT
<213> ORGANISM: Human severe acute respiratory syndrome virus

<400> SEQUENCE: 708

Ile Gln Asp Leu Glu Glu Pro Cys
1               5

<210> SEQ ID NO 709
<211> LENGTH: 8
<212> TYPE: PRT
<213> ORGANISM: Human severe acute respiratory syndrome virus

<400> SEQUENCE: 709

Gln Asp Leu Glu Glu Pro Cys Thr
1               5

<210> SEQ ID NO 710
<211> LENGTH: 8
<212> TYPE: PRT
<213> ORGANISM: Human severe acute respiratory syndrome virus

<400> SEQUENCE: 710

Asp Leu Glu Glu Pro Cys Thr Lys
1               5

<210> SEQ ID NO 711
<211> LENGTH: 8
<212> TYPE: PRT
<213> ORGANISM: Human severe acute respiratory syndrome virus

<400> SEQUENCE: 711

Leu Glu Glu Pro Cys Thr Lys Val
1               5
```

```
<210> SEQ ID NO 712
<211> LENGTH: 8
<212> TYPE: PRT
<213> ORGANISM: Human severe acute respiratory syndrome virus

<400> SEQUENCE: 712

Asp Glu Glu Pro Met Glu Leu Asx
1               5

<210> SEQ ID NO 713
<211> LENGTH: 8
<212> TYPE: PRT
<213> ORGANISM: Human severe acute respiratory syndrome virus

<400> SEQUENCE: 713

Glu Glu Pro Met Glu Leu Asx Tyr
1               5

<210> SEQ ID NO 714
<211> LENGTH: 8
<212> TYPE: PRT
<213> ORGANISM: Human severe acute respiratory syndrome virus

<400> SEQUENCE: 714

Glu Pro Met Glu Leu Asx Tyr Pro
1               5

<210> SEQ ID NO 715
<211> LENGTH: 8
<212> TYPE: PRT
<213> ORGANISM: Human severe acute respiratory syndrome virus

<400> SEQUENCE: 715

Asp Glu Glu Pro Met Glu Leu Asp
1               5

<210> SEQ ID NO 716
<211> LENGTH: 8
<212> TYPE: PRT
<213> ORGANISM: Human severe acute respiratory syndrome virus

<400> SEQUENCE: 716

Glu Glu Pro Met Glu Leu Asp Tyr
1               5

<210> SEQ ID NO 717
<211> LENGTH: 8
<212> TYPE: PRT
<213> ORGANISM: Human severe acute respiratory syndrome virus

<400> SEQUENCE: 717

Glu Pro Met Glu Leu Asp Tyr Pro
1               5

<210> SEQ ID NO 718
<211> LENGTH: 8
<212> TYPE: PRT
<213> ORGANISM: Human severe acute respiratory syndrome virus

<400> SEQUENCE: 718

Ser Glu Leu Asp Asp Glu Glu Leu
1               5

<210> SEQ ID NO 719
<211> LENGTH: 8
<212> TYPE: PRT
```

-continued

<213> ORGANISM: Human severe acute respiratory syndrome virus

<400> SEQUENCE: 719

Glu Leu Asp Asp Glu Glu Leu Met
1               5

<210> SEQ ID NO 720
<211> LENGTH: 8
<212> TYPE: PRT
<213> ORGANISM: Human severe acute respiratory syndrome virus

<400> SEQUENCE: 720

Leu Asp Asp Glu Glu Leu Met Glu
1               5

<210> SEQ ID NO 721
<211> LENGTH: 8
<212> TYPE: PRT
<213> ORGANISM: Human severe acute respiratory syndrome virus

<400> SEQUENCE: 721

Asp Asp Glu Glu Leu Met Glu Leu
1               5

<210> SEQ ID NO 722
<211> LENGTH: 8
<212> TYPE: PRT
<213> ORGANISM: Human severe acute respiratory syndrome virus

<400> SEQUENCE: 722

Asp Glu Glu Leu Met Glu Leu Asp
1               5

<210> SEQ ID NO 723
<211> LENGTH: 8
<212> TYPE: PRT
<213> ORGANISM: Human severe acute respiratory syndrome virus

<400> SEQUENCE: 723

Glu Glu Leu Met Glu Leu Asp Tyr
1               5

<210> SEQ ID NO 724
<211> LENGTH: 8
<212> TYPE: PRT
<213> ORGANISM: Human severe acute respiratory syndrome virus

<400> SEQUENCE: 724

Glu Leu Met Glu Leu Asp Tyr Pro
1               5

<210> SEQ ID NO 725
<211> LENGTH: 8
<212> TYPE: PRT
<213> ORGANISM: Human severe acute respiratory syndrome virus

<400> SEQUENCE: 725

Met Leu Pro Pro Cys Tyr Asn Phe
1               5

<210> SEQ ID NO 726
<211> LENGTH: 8
<212> TYPE: PRT
<213> ORGANISM: Human severe acute respiratory syndrome virus

<400> SEQUENCE: 726

```
Leu Pro Pro Cys Tyr Asn Phe Leu
1               5

<210> SEQ ID NO 727
<211> LENGTH: 8
<212> TYPE: PRT
<213> ORGANISM: Human severe acute respiratory syndrome virus

<400> SEQUENCE: 727

Pro Pro Cys Tyr Asn Phe Leu Lys
1               5

<210> SEQ ID NO 728
<211> LENGTH: 8
<212> TYPE: PRT
<213> ORGANISM: Human severe acute respiratory syndrome virus

<400> SEQUENCE: 728

Pro Cys Tyr Asn Phe Leu Lys Glu
1               5

<210> SEQ ID NO 729
<211> LENGTH: 8
<212> TYPE: PRT
<213> ORGANISM: Human severe acute respiratory syndrome virus

<400> SEQUENCE: 729

Cys Tyr Asn Phe Leu Lys Glu Gln
1               5

<210> SEQ ID NO 730
<211> LENGTH: 8
<212> TYPE: PRT
<213> ORGANISM: Human severe acute respiratory syndrome virus

<400> SEQUENCE: 730

Tyr Asn Phe Leu Lys Glu Gln His
1               5

<210> SEQ ID NO 731
<211> LENGTH: 8
<212> TYPE: PRT
<213> ORGANISM: Human severe acute respiratory syndrome virus

<400> SEQUENCE: 731

Asn Phe Leu Lys Glu Gln His Cys
1               5

<210> SEQ ID NO 732
<211> LENGTH: 8
<212> TYPE: PRT
<213> ORGANISM: Human severe acute respiratory syndrome virus

<400> SEQUENCE: 732

Phe Leu Lys Glu Gln His Cys Gln
1               5

<210> SEQ ID NO 733
<211> LENGTH: 8
<212> TYPE: PRT
<213> ORGANISM: Human severe acute respiratory syndrome virus

<400> SEQUENCE: 733

Leu Lys Glu Gln His Cys Gln Lys
1               5
```

<210> SEQ ID NO 734
<211> LENGTH: 8
<212> TYPE: PRT
<213> ORGANISM: Human severe acute respiratory syndrome virus

<400> SEQUENCE: 734

Lys Glu Gln His Cys Gln Lys Ala
1               5

<210> SEQ ID NO 735
<211> LENGTH: 8
<212> TYPE: PRT
<213> ORGANISM: Human severe acute respiratory syndrome virus

<400> SEQUENCE: 735

Glu Gln His Cys Gln Lys Ala Ser
1               5

<210> SEQ ID NO 736
<211> LENGTH: 8
<212> TYPE: PRT
<213> ORGANISM: Human severe acute respiratory syndrome virus

<400> SEQUENCE: 736

Gln His Cys Gln Lys Ala Ser Thr
1               5

<210> SEQ ID NO 737
<211> LENGTH: 8
<212> TYPE: PRT
<213> ORGANISM: Human severe acute respiratory syndrome virus

<400> SEQUENCE: 737

His Cys Gln Lys Ala Ser Thr Gln
1               5

<210> SEQ ID NO 738
<211> LENGTH: 8
<212> TYPE: PRT
<213> ORGANISM: Human severe acute respiratory syndrome virus

<400> SEQUENCE: 738

Cys Gln Lys Ala Ser Thr Gln Arg
1               5

<210> SEQ ID NO 739
<211> LENGTH: 8
<212> TYPE: PRT
<213> ORGANISM: Human severe acute respiratory syndrome virus

<400> SEQUENCE: 739

Gln Lys Ala Ser Thr Gln Arg Glu
1               5

<210> SEQ ID NO 740
<211> LENGTH: 8
<212> TYPE: PRT
<213> ORGANISM: Human severe acute respiratory syndrome virus

<400> SEQUENCE: 740

Lys Ala Ser Thr Gln Arg Glu Ala
1               5

<210> SEQ ID NO 741

```
<211> LENGTH: 8
<212> TYPE: PRT
<213> ORGANISM: Human severe acute respiratory syndrome virus

<400> SEQUENCE: 741

Ala Ser Thr Gln Arg Glu Ala Glu
1               5

<210> SEQ ID NO 742
<211> LENGTH: 8
<212> TYPE: PRT
<213> ORGANISM: Human severe acute respiratory syndrome virus

<400> SEQUENCE: 742

Ser Thr Gln Arg Glu Ala Glu Ala
1               5

<210> SEQ ID NO 743
<211> LENGTH: 8
<212> TYPE: PRT
<213> ORGANISM: Human severe acute respiratory syndrome virus

<400> SEQUENCE: 743

Thr Gln Arg Glu Ala Glu Ala Ala
1               5

<210> SEQ ID NO 744
<211> LENGTH: 8
<212> TYPE: PRT
<213> ORGANISM: Human severe acute respiratory syndrome virus

<400> SEQUENCE: 744

Gln Arg Glu Ala Glu Ala Ala Val
1               5

<210> SEQ ID NO 745
<211> LENGTH: 8
<212> TYPE: PRT
<213> ORGANISM: Human severe acute respiratory syndrome virus

<400> SEQUENCE: 745

Arg Glu Ala Glu Ala Ala Val Lys
1               5

<210> SEQ ID NO 746
<211> LENGTH: 8
<212> TYPE: PRT
<213> ORGANISM: Human severe acute respiratory syndrome virus

<400> SEQUENCE: 746

Glu Ala Glu Ala Ala Val Lys Pro
1               5

<210> SEQ ID NO 747
<211> LENGTH: 8
<212> TYPE: PRT
<213> ORGANISM: Human severe acute respiratory syndrome virus

<400> SEQUENCE: 747

Ala Glu Ala Ala Val Lys Pro Leu
1               5

<210> SEQ ID NO 748
<211> LENGTH: 8
<212> TYPE: PRT
<213> ORGANISM: Human severe acute respiratory syndrome virus
```

<400> SEQUENCE: 748

Glu Ala Ala Val Lys Pro Leu Leu
1               5

<210> SEQ ID NO 749
<211> LENGTH: 8
<212> TYPE: PRT
<213> ORGANISM: Human severe acute respiratory syndrome virus

<400> SEQUENCE: 749

Ala Ala Val Lys Pro Leu Leu Ala
1               5

<210> SEQ ID NO 750
<211> LENGTH: 8
<212> TYPE: PRT
<213> ORGANISM: Human severe acute respiratory syndrome virus

<400> SEQUENCE: 750

Ala Val Lys Pro Leu Leu Ala Pro
1               5

<210> SEQ ID NO 751
<211> LENGTH: 8
<212> TYPE: PRT
<213> ORGANISM: Human severe acute respiratory syndrome virus

<400> SEQUENCE: 751

Val Lys Pro Leu Leu Ala Pro His
1               5

<210> SEQ ID NO 752
<211> LENGTH: 8
<212> TYPE: PRT
<213> ORGANISM: Human severe acute respiratory syndrome virus

<400> SEQUENCE: 752

Lys Pro Leu Leu Ala Pro His His
1               5

<210> SEQ ID NO 753
<211> LENGTH: 8
<212> TYPE: PRT
<213> ORGANISM: Human severe acute respiratory syndrome virus

<400> SEQUENCE: 753

Pro Leu Leu Ala Pro His His Val
1               5

<210> SEQ ID NO 754
<211> LENGTH: 8
<212> TYPE: PRT
<213> ORGANISM: Human severe acute respiratory syndrome virus

<400> SEQUENCE: 754

Leu Leu Ala Pro His His Val Val
1               5

<210> SEQ ID NO 755
<211> LENGTH: 8
<212> TYPE: PRT
<213> ORGANISM: Human severe acute respiratory syndrome virus

<400> SEQUENCE: 755

```
Leu Ala Pro His His Val Val Ala
1               5

<210> SEQ ID NO 756
<211> LENGTH: 8
<212> TYPE: PRT
<213> ORGANISM: Human severe acute respiratory syndrome virus

<400> SEQUENCE: 756

Ala Pro His His Val Val Ala Val
1               5

<210> SEQ ID NO 757
<211> LENGTH: 8
<212> TYPE: PRT
<213> ORGANISM: Human severe acute respiratory syndrome virus

<400> SEQUENCE: 757

Pro His His Val Val Ala Val Ile
1               5

<210> SEQ ID NO 758
<211> LENGTH: 8
<212> TYPE: PRT
<213> ORGANISM: Human severe acute respiratory syndrome virus

<400> SEQUENCE: 758

His His Val Val Ala Val Ile Gln
1               5

<210> SEQ ID NO 759
<211> LENGTH: 8
<212> TYPE: PRT
<213> ORGANISM: Human severe acute respiratory syndrome virus

<400> SEQUENCE: 759

His Val Val Ala Val Ile Gln Glu
1               5

<210> SEQ ID NO 760
<211> LENGTH: 8
<212> TYPE: PRT
<213> ORGANISM: Human severe acute respiratory syndrome virus

<400> SEQUENCE: 760

Val Val Ala Val Ile Gln Glu Ile
1               5

<210> SEQ ID NO 761
<211> LENGTH: 8
<212> TYPE: PRT
<213> ORGANISM: Human severe acute respiratory syndrome virus

<400> SEQUENCE: 761

Val Ala Val Ile Gln Glu Ile Gln
1               5

<210> SEQ ID NO 762
<211> LENGTH: 8
<212> TYPE: PRT
<213> ORGANISM: Human severe acute respiratory syndrome virus

<400> SEQUENCE: 762

Ala Val Ile Gln Glu Ile Gln Leu
1               5
```

```
<210> SEQ ID NO 763
<211> LENGTH: 8
<212> TYPE: PRT
<213> ORGANISM: Human severe acute respiratory syndrome virus

<400> SEQUENCE: 763

Val Ile Gln Glu Ile Gln Leu Leu
1               5

<210> SEQ ID NO 764
<211> LENGTH: 8
<212> TYPE: PRT
<213> ORGANISM: Human severe acute respiratory syndrome virus

<400> SEQUENCE: 764

Ile Gln Glu Ile Gln Leu Leu Ala
1               5

<210> SEQ ID NO 765
<211> LENGTH: 8
<212> TYPE: PRT
<213> ORGANISM: Human severe acute respiratory syndrome virus

<400> SEQUENCE: 765

Gln Glu Ile Gln Leu Leu Ala Ala
1               5

<210> SEQ ID NO 766
<211> LENGTH: 8
<212> TYPE: PRT
<213> ORGANISM: Human severe acute respiratory syndrome virus

<400> SEQUENCE: 766

Glu Ile Gln Leu Leu Ala Ala Val
1               5

<210> SEQ ID NO 767
<211> LENGTH: 8
<212> TYPE: PRT
<213> ORGANISM: Human severe acute respiratory syndrome virus

<400> SEQUENCE: 767

Ile Gln Leu Leu Ala Ala Val Gly
1               5

<210> SEQ ID NO 768
<211> LENGTH: 8
<212> TYPE: PRT
<213> ORGANISM: Human severe acute respiratory syndrome virus

<400> SEQUENCE: 768

Gln Leu Leu Ala Ala Val Gly Glu
1               5

<210> SEQ ID NO 769
<211> LENGTH: 8
<212> TYPE: PRT
<213> ORGANISM: Human severe acute respiratory syndrome virus

<400> SEQUENCE: 769

Leu Leu Ala Ala Val Gly Glu Ile
1               5

<210> SEQ ID NO 770
<211> LENGTH: 8
```

<212> TYPE: PRT
<213> ORGANISM: Human severe acute respiratory syndrome virus

<400> SEQUENCE: 770

Leu Ala Ala Val Gly Glu Ile Leu
1               5

<210> SEQ ID NO 771
<211> LENGTH: 8
<212> TYPE: PRT
<213> ORGANISM: Human severe acute respiratory syndrome virus

<400> SEQUENCE: 771

Ala Ala Val Gly Glu Ile Leu Leu
1               5

<210> SEQ ID NO 772
<211> LENGTH: 8
<212> TYPE: PRT
<213> ORGANISM: Human severe acute respiratory syndrome virus

<400> SEQUENCE: 772

Ala Val Gly Glu Ile Leu Leu Leu
1               5

<210> SEQ ID NO 773
<211> LENGTH: 8
<212> TYPE: PRT
<213> ORGANISM: Human severe acute respiratory syndrome virus

<400> SEQUENCE: 773

Val Gly Glu Ile Leu Leu Leu Glu
1               5

<210> SEQ ID NO 774
<211> LENGTH: 8
<212> TYPE: PRT
<213> ORGANISM: Human severe acute respiratory syndrome virus

<400> SEQUENCE: 774

Gly Glu Ile Leu Leu Leu Glu Trp
1               5

<210> SEQ ID NO 775
<211> LENGTH: 8
<212> TYPE: PRT
<213> ORGANISM: Human severe acute respiratory syndrome virus

<400> SEQUENCE: 775

Glu Ile Leu Leu Leu Glu Trp Leu
1               5

<210> SEQ ID NO 776
<211> LENGTH: 8
<212> TYPE: PRT
<213> ORGANISM: Human severe acute respiratory syndrome virus

<400> SEQUENCE: 776

Ile Leu Leu Leu Glu Trp Leu Ala
1               5

<210> SEQ ID NO 777
<211> LENGTH: 8
<212> TYPE: PRT
<213> ORGANISM: Human severe acute respiratory syndrome virus -continued

```
<400> SEQUENCE: 777

Leu Leu Leu Glu Trp Leu Ala Glu
1               5

<210> SEQ ID NO 778
<211> LENGTH: 8
<212> TYPE: PRT
<213> ORGANISM: Human severe acute respiratory syndrome virus

<400> SEQUENCE: 778

Leu Leu Glu Trp Leu Ala Glu Val
1               5

<210> SEQ ID NO 779
<211> LENGTH: 8
<212> TYPE: PRT
<213> ORGANISM: Human severe acute respiratory syndrome virus

<400> SEQUENCE: 779

Leu Glu Trp Leu Ala Glu Val Val
1               5

<210> SEQ ID NO 780
<211> LENGTH: 8
<212> TYPE: PRT
<213> ORGANISM: Human severe acute respiratory syndrome virus

<400> SEQUENCE: 780

Glu Trp Leu Ala Glu Val Val Lys
1               5

<210> SEQ ID NO 781
<211> LENGTH: 8
<212> TYPE: PRT
<213> ORGANISM: Human severe acute respiratory syndrome virus

<400> SEQUENCE: 781

Trp Leu Ala Glu Val Val Lys Leu
1               5

<210> SEQ ID NO 782
<211> LENGTH: 8
<212> TYPE: PRT
<213> ORGANISM: Human severe acute respiratory syndrome virus

<400> SEQUENCE: 782

Leu Ala Glu Val Val Lys Leu Pro
1               5

<210> SEQ ID NO 783
<211> LENGTH: 8
<212> TYPE: PRT
<213> ORGANISM: Human severe acute respiratory syndrome virus

<400> SEQUENCE: 783

Ala Glu Val Val Lys Leu Pro Ser
1               5

<210> SEQ ID NO 784
<211> LENGTH: 8
<212> TYPE: PRT
<213> ORGANISM: Human severe acute respiratory syndrome virus

<400> SEQUENCE: 784

Glu Val Val Lys Leu Pro Ser Arg
```

```
<210> SEQ ID NO 785
<211> LENGTH: 8
<212> TYPE: PRT
<213> ORGANISM: Human severe acute respiratory syndrome virus

<400> SEQUENCE: 785

Val Val Lys Leu Pro Ser Arg Tyr
1               5

<210> SEQ ID NO 786
<211> LENGTH: 8
<212> TYPE: PRT
<213> ORGANISM: Human severe acute respiratory syndrome virus

<400> SEQUENCE: 786

Val Lys Leu Pro Ser Arg Tyr Cys
1               5

<210> SEQ ID NO 787
<211> LENGTH: 8
<212> TYPE: PRT
<213> ORGANISM: Human severe acute respiratory syndrome virus

<400> SEQUENCE: 787

Lys Leu Pro Ser Arg Tyr Cys Cys
1               5

<210> SEQ ID NO 788
<211> LENGTH: 8
<212> TYPE: PRT
<213> ORGANISM: Human severe acute respiratory syndrome virus

<400> SEQUENCE: 788

Val Leu Leu Phe Leu Ala Phe Met
1               5

<210> SEQ ID NO 789
<211> LENGTH: 8
<212> TYPE: PRT
<213> ORGANISM: Human severe acute respiratory syndrome virus

<400> SEQUENCE: 789

Leu Leu Phe Leu Ala Phe Met Val
1               5

<210> SEQ ID NO 790
<211> LENGTH: 8
<212> TYPE: PRT
<213> ORGANISM: Human severe acute respiratory syndrome virus

<400> SEQUENCE: 790

Leu Phe Leu Ala Phe Met Val Phe
1               5

<210> SEQ ID NO 791
<211> LENGTH: 8
<212> TYPE: PRT
<213> ORGANISM: Human severe acute respiratory syndrome virus

<400> SEQUENCE: 791

Phe Leu Ala Phe Met Val Phe Leu
1               5
```

```
<210> SEQ ID NO 792
<211> LENGTH: 8
<212> TYPE: PRT
<213> ORGANISM: Human severe acute respiratory syndrome virus

<400> SEQUENCE: 792

Leu Ala Phe Met Val Phe Leu Leu
1               5

<210> SEQ ID NO 793
<211> LENGTH: 8
<212> TYPE: PRT
<213> ORGANISM: Human severe acute respiratory syndrome virus

<400> SEQUENCE: 793

Ala Phe Met Val Phe Leu Leu Val
1               5

<210> SEQ ID NO 794
<211> LENGTH: 8
<212> TYPE: PRT
<213> ORGANISM: Human severe acute respiratory syndrome virus

<400> SEQUENCE: 794

Phe Met Val Phe Leu Leu Val Thr
1               5

<210> SEQ ID NO 795
<211> LENGTH: 8
<212> TYPE: PRT
<213> ORGANISM: Human severe acute respiratory syndrome virus

<400> SEQUENCE: 795

Met Val Phe Leu Leu Val Thr Leu
1               5

<210> SEQ ID NO 796
<211> LENGTH: 8
<212> TYPE: PRT
<213> ORGANISM: Human severe acute respiratory syndrome virus

<400> SEQUENCE: 796

Val Leu Leu Phe Leu Ala Phe Val
1               5

<210> SEQ ID NO 797
<211> LENGTH: 8
<212> TYPE: PRT
<213> ORGANISM: Human severe acute respiratory syndrome virus

<400> SEQUENCE: 797

Leu Leu Phe Leu Ala Phe Val Val
1               5

<210> SEQ ID NO 798
<211> LENGTH: 8
<212> TYPE: PRT
<213> ORGANISM: Human severe acute respiratory syndrome virus

<400> SEQUENCE: 798

Leu Phe Leu Ala Phe Val Val Phe
1               5

<210> SEQ ID NO 799
<211> LENGTH: 8
<212> TYPE: PRT
```

-continued

<213> ORGANISM: Human severe acute respiratory syndrome virus

<400> SEQUENCE: 799

Phe Leu Ala Phe Val Val Phe Leu
1               5

<210> SEQ ID NO 800
<211> LENGTH: 8
<212> TYPE: PRT
<213> ORGANISM: Human severe acute respiratory syndrome virus

<400> SEQUENCE: 800

Leu Ala Phe Val Val Phe Leu Leu
1               5

<210> SEQ ID NO 801
<211> LENGTH: 8
<212> TYPE: PRT
<213> ORGANISM: Human severe acute respiratory syndrome virus

<400> SEQUENCE: 801

Ala Phe Val Val Phe Leu Leu Val
1               5

<210> SEQ ID NO 802
<211> LENGTH: 8
<212> TYPE: PRT
<213> ORGANISM: Human severe acute respiratory syndrome virus

<400> SEQUENCE: 802

Phe Val Val Phe Leu Leu Val Thr
1               5

<210> SEQ ID NO 803
<211> LENGTH: 8
<212> TYPE: PRT
<213> ORGANISM: Human severe acute respiratory syndrome virus

<400> SEQUENCE: 803

Val Val Phe Leu Leu Val Thr Leu
1               5

<210> SEQ ID NO 804
<211> LENGTH: 8
<212> TYPE: PRT
<213> ORGANISM: Human severe acute respiratory syndrome virus

<400> SEQUENCE: 804

Met Cys Leu Lys Ile Leu Val Arg
1               5

<210> SEQ ID NO 805
<211> LENGTH: 8
<212> TYPE: PRT
<213> ORGANISM: Human severe acute respiratory syndrome virus

<400> SEQUENCE: 805

Cys Leu Lys Ile Leu Val Arg Tyr
1               5

<210> SEQ ID NO 806
<211> LENGTH: 8
<212> TYPE: PRT
<213> ORGANISM: Human severe acute respiratory syndrome virus

<400> SEQUENCE: 806

Leu Lys Ile Leu Val Arg Tyr Asn
1               5

<210> SEQ ID NO 807
<211> LENGTH: 8
<212> TYPE: PRT
<213> ORGANISM: Human severe acute respiratory syndrome virus

<400> SEQUENCE: 807

Lys Ile Leu Val Arg Tyr Asn Thr
1               5

<210> SEQ ID NO 808
<211> LENGTH: 8
<212> TYPE: PRT
<213> ORGANISM: Human severe acute respiratory syndrome virus

<400> SEQUENCE: 808

Ile Leu Val Arg Tyr Asn Thr Arg
1               5

<210> SEQ ID NO 809
<211> LENGTH: 8
<212> TYPE: PRT
<213> ORGANISM: Human severe acute respiratory syndrome virus

<400> SEQUENCE: 809

Leu Val Arg Tyr Asn Thr Arg Gly
1               5

<210> SEQ ID NO 810
<211> LENGTH: 8
<212> TYPE: PRT
<213> ORGANISM: Human severe acute respiratory syndrome virus

<400> SEQUENCE: 810

Val Arg Tyr Asn Thr Arg Gly Asn
1               5

<210> SEQ ID NO 811
<211> LENGTH: 8
<212> TYPE: PRT
<213> ORGANISM: Human severe acute respiratory syndrome virus

<400> SEQUENCE: 811

Thr Ala Ala Phe Arg Asp Val Leu
1               5

<210> SEQ ID NO 812
<211> LENGTH: 8
<212> TYPE: PRT
<213> ORGANISM: Human severe acute respiratory syndrome virus

<400> SEQUENCE: 812

Ala Ala Phe Arg Asp Val Leu Val
1               5

<210> SEQ ID NO 813
<211> LENGTH: 8
<212> TYPE: PRT
<213> ORGANISM: Human severe acute respiratory syndrome virus

<400> SEQUENCE: 813

Ala Phe Arg Asp Val Leu Val Val
1               5

<210> SEQ ID NO 814
<211> LENGTH: 8
<212> TYPE: PRT
<213> ORGANISM: Human severe acute respiratory syndrome virus

<400> SEQUENCE: 814

Phe Arg Asp Val Leu Val Val Leu
1               5

<210> SEQ ID NO 815
<211> LENGTH: 8
<212> TYPE: PRT
<213> ORGANISM: Human severe acute respiratory syndrome virus

<400> SEQUENCE: 815

Arg Asp Val Leu Val Val Leu Asn
1               5

<210> SEQ ID NO 816
<211> LENGTH: 8
<212> TYPE: PRT
<213> ORGANISM: Human severe acute respiratory syndrome virus

<400> SEQUENCE: 816

Asp Val Leu Val Val Leu Asn Lys
1               5

<210> SEQ ID NO 817
<211> LENGTH: 8
<212> TYPE: PRT
<213> ORGANISM: Human severe acute respiratory syndrome virus

<400> SEQUENCE: 817

Val Leu Val Val Leu Asn Lys Arg
1               5

<210> SEQ ID NO 818
<211> LENGTH: 8
<212> TYPE: PRT
<213> ORGANISM: Human severe acute respiratory syndrome virus

<400> SEQUENCE: 818

Leu Val Val Leu Asn Lys Arg Thr
1               5

<210> SEQ ID NO 819
<211> LENGTH: 8
<212> TYPE: PRT
<213> ORGANISM: Human severe acute respiratory syndrome virus

<400> SEQUENCE: 819

Met Asp Pro Asn Gln Thr Asn Val
1               5

<210> SEQ ID NO 820
<211> LENGTH: 8
<212> TYPE: PRT
<213> ORGANISM: Human severe acute respiratory syndrome virus

<400> SEQUENCE: 820

Asp Pro Asn Gln Thr Asn Val Val
1               5

<210> SEQ ID NO 821

```
<211> LENGTH: 8
<212> TYPE: PRT
<213> ORGANISM: Human severe acute respiratory syndrome virus

<400> SEQUENCE: 821

Pro Asn Gln Thr Asn Val Val Pro
1               5

<210> SEQ ID NO 822
<211> LENGTH: 8
<212> TYPE: PRT
<213> ORGANISM: Human severe acute respiratory syndrome virus

<400> SEQUENCE: 822

Asn Gln Thr Asn Val Val Pro Pro
1               5

<210> SEQ ID NO 823
<211> LENGTH: 8
<212> TYPE: PRT
<213> ORGANISM: Human severe acute respiratory syndrome virus

<400> SEQUENCE: 823

Gln Thr Asn Val Val Pro Pro Ala
1               5

<210> SEQ ID NO 824
<211> LENGTH: 8
<212> TYPE: PRT
<213> ORGANISM: Human severe acute respiratory syndrome virus

<400> SEQUENCE: 824

Thr Asn Val Val Pro Pro Ala Leu
1               5

<210> SEQ ID NO 825
<211> LENGTH: 8
<212> TYPE: PRT
<213> ORGANISM: Human severe acute respiratory syndrome virus

<400> SEQUENCE: 825

Asn Val Val Pro Pro Ala Leu His
1               5

<210> SEQ ID NO 826
<211> LENGTH: 8
<212> TYPE: PRT
<213> ORGANISM: Human severe acute respiratory syndrome virus

<400> SEQUENCE: 826

Val Val Pro Pro Ala Leu His Leu
1               5

<210> SEQ ID NO 827
<211> LENGTH: 8
<212> TYPE: PRT
<213> ORGANISM: Human severe acute respiratory syndrome virus

<400> SEQUENCE: 827

Val Pro Pro Ala Leu His Leu Val
1               5

<210> SEQ ID NO 828
<211> LENGTH: 8
<212> TYPE: PRT
<213> ORGANISM: Human severe acute respiratory syndrome virus
```

```
<400> SEQUENCE: 828

Pro Pro Ala Leu His Leu Val Asp
1               5

<210> SEQ ID NO 829
<211> LENGTH: 8
<212> TYPE: PRT
<213> ORGANISM: Human severe acute respiratory syndrome virus

<400> SEQUENCE: 829

Pro Ala Leu His Leu Val Asp Pro
1               5

<210> SEQ ID NO 830
<211> LENGTH: 8
<212> TYPE: PRT
<213> ORGANISM: Human severe acute respiratory syndrome virus

<400> SEQUENCE: 830

Ala Leu His Leu Val Asp Pro Gln
1               5

<210> SEQ ID NO 831
<211> LENGTH: 8
<212> TYPE: PRT
<213> ORGANISM: Human severe acute respiratory syndrome virus

<400> SEQUENCE: 831

Leu His Leu Val Asp Pro Gln Ile
1               5

<210> SEQ ID NO 832
<211> LENGTH: 8
<212> TYPE: PRT
<213> ORGANISM: Human severe acute respiratory syndrome virus

<400> SEQUENCE: 832

His Leu Val Asp Pro Gln Ile Gln
1               5

<210> SEQ ID NO 833
<211> LENGTH: 8
<212> TYPE: PRT
<213> ORGANISM: Human severe acute respiratory syndrome virus

<400> SEQUENCE: 833

Leu Val Asp Pro Gln Ile Gln Leu
1               5

<210> SEQ ID NO 834
<211> LENGTH: 8
<212> TYPE: PRT
<213> ORGANISM: Human severe acute respiratory syndrome virus

<400> SEQUENCE: 834

Val Asp Pro Gln Ile Gln Leu Thr
1               5

<210> SEQ ID NO 835
<211> LENGTH: 8
<212> TYPE: PRT
<213> ORGANISM: Human severe acute respiratory syndrome virus

<400> SEQUENCE: 835
```

```
Asp Pro Gln Ile Gln Leu Thr Ile
1               5

<210> SEQ ID NO 836
<211> LENGTH: 8
<212> TYPE: PRT
<213> ORGANISM: Human severe acute respiratory syndrome virus

<400> SEQUENCE: 836

Pro Gln Ile Gln Leu Thr Ile Thr
1               5

<210> SEQ ID NO 837
<211> LENGTH: 8
<212> TYPE: PRT
<213> ORGANISM: Human severe acute respiratory syndrome virus

<400> SEQUENCE: 837

Gln Ile Gln Leu Thr Ile Thr Arg
1               5

<210> SEQ ID NO 838
<211> LENGTH: 8
<212> TYPE: PRT
<213> ORGANISM: Human severe acute respiratory syndrome virus

<400> SEQUENCE: 838

Ile Gln Leu Thr Ile Thr Arg Met
1               5

<210> SEQ ID NO 839
<211> LENGTH: 8
<212> TYPE: PRT
<213> ORGANISM: Human severe acute respiratory syndrome virus

<400> SEQUENCE: 839

Gln Leu Thr Ile Thr Arg Met Glu
1               5

<210> SEQ ID NO 840
<211> LENGTH: 8
<212> TYPE: PRT
<213> ORGANISM: Human severe acute respiratory syndrome virus

<400> SEQUENCE: 840

Leu Thr Ile Thr Arg Met Glu Asp
1               5

<210> SEQ ID NO 841
<211> LENGTH: 8
<212> TYPE: PRT
<213> ORGANISM: Human severe acute respiratory syndrome virus

<400> SEQUENCE: 841

Thr Ile Thr Arg Met Glu Asp Ala
1               5

<210> SEQ ID NO 842
<211> LENGTH: 8
<212> TYPE: PRT
<213> ORGANISM: Human severe acute respiratory syndrome virus

<400> SEQUENCE: 842

Ile Thr Arg Met Glu Asp Ala Met
1               5
```

```
<210> SEQ ID NO 843
<211> LENGTH: 8
<212> TYPE: PRT
<213> ORGANISM: Human severe acute respiratory syndrome virus

<400> SEQUENCE: 843

Thr Arg Met Glu Asp Ala Met Gly
1               5

<210> SEQ ID NO 844
<211> LENGTH: 8
<212> TYPE: PRT
<213> ORGANISM: Human severe acute respiratory syndrome virus

<400> SEQUENCE: 844

Arg Met Glu Asp Ala Met Gly Gln
1               5

<210> SEQ ID NO 845
<211> LENGTH: 8
<212> TYPE: PRT
<213> ORGANISM: Human severe acute respiratory syndrome virus

<400> SEQUENCE: 845

Met Glu Asp Ala Met Gly Gln Gly
1               5

<210> SEQ ID NO 846
<211> LENGTH: 8
<212> TYPE: PRT
<213> ORGANISM: Human severe acute respiratory syndrome virus

<400> SEQUENCE: 846

Glu Asp Ala Met Gly Gln Gly Gln
1               5

<210> SEQ ID NO 847
<211> LENGTH: 8
<212> TYPE: PRT
<213> ORGANISM: Human severe acute respiratory syndrome virus

<400> SEQUENCE: 847

Asp Ala Met Gly Gln Gly Gln Asn
1               5

<210> SEQ ID NO 848
<211> LENGTH: 8
<212> TYPE: PRT
<213> ORGANISM: Human severe acute respiratory syndrome virus

<400> SEQUENCE: 848

Ala Met Gly Gln Gly Gln Asn Ser
1               5

<210> SEQ ID NO 849
<211> LENGTH: 8
<212> TYPE: PRT
<213> ORGANISM: Human severe acute respiratory syndrome virus

<400> SEQUENCE: 849

Met Gly Gln Gly Gln Asn Ser Ala
1               5

<210> SEQ ID NO 850
<211> LENGTH: 8
```

```
<212> TYPE: PRT
<213> ORGANISM: Human severe acute respiratory syndrome virus

<400> SEQUENCE: 850

Gly Gln Gly Gln Asn Ser Ala Asp
1               5

<210> SEQ ID NO 851
<211> LENGTH: 8
<212> TYPE: PRT
<213> ORGANISM: Human severe acute respiratory syndrome virus

<400> SEQUENCE: 851

Gln Gly Gln Asn Ser Ala Asp Pro
1               5

<210> SEQ ID NO 852
<211> LENGTH: 8
<212> TYPE: PRT
<213> ORGANISM: Human severe acute respiratory syndrome virus

<400> SEQUENCE: 852

Gly Gln Asn Ser Ala Asp Pro Lys
1               5

<210> SEQ ID NO 853
<211> LENGTH: 8
<212> TYPE: PRT
<213> ORGANISM: Human severe acute respiratory syndrome virus

<400> SEQUENCE: 853

Gln Asn Ser Ala Asp Pro Lys Val
1               5

<210> SEQ ID NO 854
<211> LENGTH: 8
<212> TYPE: PRT
<213> ORGANISM: Human severe acute respiratory syndrome virus

<400> SEQUENCE: 854

Asn Ser Ala Asp Pro Lys Val Tyr
1               5

<210> SEQ ID NO 855
<211> LENGTH: 8
<212> TYPE: PRT
<213> ORGANISM: Human severe acute respiratory syndrome virus

<400> SEQUENCE: 855

Ser Ala Asp Pro Lys Val Tyr Pro
1               5

<210> SEQ ID NO 856
<211> LENGTH: 8
<212> TYPE: PRT
<213> ORGANISM: Human severe acute respiratory syndrome virus

<400> SEQUENCE: 856

Ala Asp Pro Lys Val Tyr Pro Ile
1               5

<210> SEQ ID NO 857
<211> LENGTH: 8
<212> TYPE: PRT
<213> ORGANISM: Human severe acute respiratory syndrome virus
```

```
<400> SEQUENCE: 857

Asp Pro Lys Val Tyr Pro Ile Ile
1               5

<210> SEQ ID NO 858
<211> LENGTH: 8
<212> TYPE: PRT
<213> ORGANISM: Human severe acute respiratory syndrome virus

<400> SEQUENCE: 858

Pro Lys Val Tyr Pro Ile Ile Leu
1               5

<210> SEQ ID NO 859
<211> LENGTH: 8
<212> TYPE: PRT
<213> ORGANISM: Human severe acute respiratory syndrome virus

<400> SEQUENCE: 859

Lys Val Tyr Pro Ile Ile Leu Arg
1               5

<210> SEQ ID NO 860
<211> LENGTH: 8
<212> TYPE: PRT
<213> ORGANISM: Human severe acute respiratory syndrome virus

<400> SEQUENCE: 860

Val Tyr Pro Ile Ile Leu Arg Leu
1               5

<210> SEQ ID NO 861
<211> LENGTH: 8
<212> TYPE: PRT
<213> ORGANISM: Human severe acute respiratory syndrome virus

<400> SEQUENCE: 861

Tyr Pro Ile Ile Leu Arg Leu Gly
1               5

<210> SEQ ID NO 862
<211> LENGTH: 8
<212> TYPE: PRT
<213> ORGANISM: Human severe acute respiratory syndrome virus

<400> SEQUENCE: 862

Pro Ile Ile Leu Arg Leu Gly Ser
1               5

<210> SEQ ID NO 863
<211> LENGTH: 8
<212> TYPE: PRT
<213> ORGANISM: Human severe acute respiratory syndrome virus

<400> SEQUENCE: 863

Ile Ile Leu Arg Leu Gly Ser Gln
1               5

<210> SEQ ID NO 864
<211> LENGTH: 8
<212> TYPE: PRT
<213> ORGANISM: Human severe acute respiratory syndrome virus

<400> SEQUENCE: 864

Ile Leu Arg Leu Gly Ser Gln Leu
```

<210> SEQ ID NO 865
<211> LENGTH: 8
<212> TYPE: PRT
<213> ORGANISM: Human severe acute respiratory syndrome virus

<400> SEQUENCE: 865

Leu Arg Leu Gly Ser Gln Leu Ser
1               5

<210> SEQ ID NO 866
<211> LENGTH: 8
<212> TYPE: PRT
<213> ORGANISM: Human severe acute respiratory syndrome virus

<400> SEQUENCE: 866

Arg Leu Gly Ser Gln Leu Ser Leu
1               5

<210> SEQ ID NO 867
<211> LENGTH: 8
<212> TYPE: PRT
<213> ORGANISM: Human severe acute respiratory syndrome virus

<400> SEQUENCE: 867

Leu Gly Ser Gln Leu Ser Leu Ser
1               5

<210> SEQ ID NO 868
<211> LENGTH: 8
<212> TYPE: PRT
<213> ORGANISM: Human severe acute respiratory syndrome virus

<400> SEQUENCE: 868

Gly Ser Gln Leu Ser Leu Ser Met
1               5

<210> SEQ ID NO 869
<211> LENGTH: 8
<212> TYPE: PRT
<213> ORGANISM: Human severe acute respiratory syndrome virus

<400> SEQUENCE: 869

Ser Gln Leu Ser Leu Ser Met Ala
1               5

<210> SEQ ID NO 870
<211> LENGTH: 8
<212> TYPE: PRT
<213> ORGANISM: Human severe acute respiratory syndrome virus

<400> SEQUENCE: 870

Gln Leu Ser Leu Ser Met Ala Arg
1               5

<210> SEQ ID NO 871
<211> LENGTH: 8
<212> TYPE: PRT
<213> ORGANISM: Human severe acute respiratory syndrome virus

<400> SEQUENCE: 871

Leu Ser Leu Ser Met Ala Arg Arg
1               5

```
<210> SEQ ID NO 872
<211> LENGTH: 8
<212> TYPE: PRT
<213> ORGANISM: Human severe acute respiratory syndrome virus

<400> SEQUENCE: 872

Ser Leu Ser Met Ala Arg Arg Asn
1               5

<210> SEQ ID NO 873
<211> LENGTH: 8
<212> TYPE: PRT
<213> ORGANISM: Human severe acute respiratory syndrome virus

<400> SEQUENCE: 873

Leu Ser Met Ala Arg Arg Asn Leu
1               5

<210> SEQ ID NO 874
<211> LENGTH: 8
<212> TYPE: PRT
<213> ORGANISM: Human severe acute respiratory syndrome virus

<400> SEQUENCE: 874

Ser Met Ala Arg Arg Asn Leu Asp
1               5

<210> SEQ ID NO 875
<211> LENGTH: 8
<212> TYPE: PRT
<213> ORGANISM: Human severe acute respiratory syndrome virus

<400> SEQUENCE: 875

Met Ala Arg Arg Asn Leu Asp Ser
1               5

<210> SEQ ID NO 876
<211> LENGTH: 8
<212> TYPE: PRT
<213> ORGANISM: Human severe acute respiratory syndrome virus

<400> SEQUENCE: 876

Ala Arg Arg Asn Leu Asp Ser Leu
1               5

<210> SEQ ID NO 877
<211> LENGTH: 8
<212> TYPE: PRT
<213> ORGANISM: Human severe acute respiratory syndrome virus

<400> SEQUENCE: 877

Arg Arg Asn Leu Asp Ser Leu Glu
1               5

<210> SEQ ID NO 878
<211> LENGTH: 8
<212> TYPE: PRT
<213> ORGANISM: Human severe acute respiratory syndrome virus

<400> SEQUENCE: 878

Arg Asn Leu Asp Ser Leu Glu Ala
1               5

<210> SEQ ID NO 879
<211> LENGTH: 8
<212> TYPE: PRT
```

<213> ORGANISM: Human severe acute respiratory syndrome virus

<400> SEQUENCE: 879

Asn Leu Asp Ser Leu Glu Ala Arg
1               5

<210> SEQ ID NO 880
<211> LENGTH: 8
<212> TYPE: PRT
<213> ORGANISM: Human severe acute respiratory syndrome virus

<400> SEQUENCE: 880

Leu Asp Ser Leu Glu Ala Arg Ala
1               5

<210> SEQ ID NO 881
<211> LENGTH: 8
<212> TYPE: PRT
<213> ORGANISM: Human severe acute respiratory syndrome virus

<400> SEQUENCE: 881

Asp Ser Leu Glu Ala Arg Ala Phe
1               5

<210> SEQ ID NO 882
<211> LENGTH: 8
<212> TYPE: PRT
<213> ORGANISM: Human severe acute respiratory syndrome virus

<400> SEQUENCE: 882

Ser Leu Glu Ala Arg Ala Phe Gln
1               5

<210> SEQ ID NO 883
<211> LENGTH: 8
<212> TYPE: PRT
<213> ORGANISM: Human severe acute respiratory syndrome virus

<400> SEQUENCE: 883

Leu Glu Ala Arg Ala Phe Gln Ser
1               5

<210> SEQ ID NO 884
<211> LENGTH: 8
<212> TYPE: PRT
<213> ORGANISM: Human severe acute respiratory syndrome virus

<400> SEQUENCE: 884

Glu Ala Arg Ala Phe Gln Ser Thr
1               5

<210> SEQ ID NO 885
<211> LENGTH: 8
<212> TYPE: PRT
<213> ORGANISM: Human severe acute respiratory syndrome virus

<400> SEQUENCE: 885

Ala Arg Ala Phe Gln Ser Thr Pro
1               5

<210> SEQ ID NO 886
<211> LENGTH: 8
<212> TYPE: PRT
<213> ORGANISM: Human severe acute respiratory syndrome virus

<400> SEQUENCE: 886

Arg Ala Phe Gln Ser Thr Pro Ile
1               5

<210> SEQ ID NO 887
<211> LENGTH: 8
<212> TYPE: PRT
<213> ORGANISM: Human severe acute respiratory syndrome virus

<400> SEQUENCE: 887

Ala Phe Gln Ser Thr Pro Ile Val
1               5

<210> SEQ ID NO 888
<211> LENGTH: 8
<212> TYPE: PRT
<213> ORGANISM: Human severe acute respiratory syndrome virus

<400> SEQUENCE: 888

Phe Gln Ser Thr Pro Ile Val Val
1               5

<210> SEQ ID NO 889
<211> LENGTH: 8
<212> TYPE: PRT
<213> ORGANISM: Human severe acute respiratory syndrome virus

<400> SEQUENCE: 889

Gln Ser Thr Pro Ile Val Val Gln
1               5

<210> SEQ ID NO 890
<211> LENGTH: 8
<212> TYPE: PRT
<213> ORGANISM: Human severe acute respiratory syndrome virus

<400> SEQUENCE: 890

Ser Thr Pro Ile Val Val Gln Met
1               5

<210> SEQ ID NO 891
<211> LENGTH: 8
<212> TYPE: PRT
<213> ORGANISM: Human severe acute respiratory syndrome virus

<400> SEQUENCE: 891

Thr Pro Ile Val Val Gln Met Thr
1               5

<210> SEQ ID NO 892
<211> LENGTH: 8
<212> TYPE: PRT
<213> ORGANISM: Human severe acute respiratory syndrome virus

<400> SEQUENCE: 892

Pro Ile Val Val Gln Met Thr Lys
1               5

<210> SEQ ID NO 893
<211> LENGTH: 8
<212> TYPE: PRT
<213> ORGANISM: Human severe acute respiratory syndrome virus

<400> SEQUENCE: 893

Ile Val Val Gln Met Thr Lys Leu
1               5

<210> SEQ ID NO 894
<211> LENGTH: 8
<212> TYPE: PRT
<213> ORGANISM: Human severe acute respiratory syndrome virus

<400> SEQUENCE: 894

Val Val Gln Met Thr Lys Leu Ala
1               5

<210> SEQ ID NO 895
<211> LENGTH: 8
<212> TYPE: PRT
<213> ORGANISM: Human severe acute respiratory syndrome virus

<400> SEQUENCE: 895

Val Gln Met Thr Lys Leu Ala Thr
1               5

<210> SEQ ID NO 896
<211> LENGTH: 8
<212> TYPE: PRT
<213> ORGANISM: Human severe acute respiratory syndrome virus

<400> SEQUENCE: 896

Gln Met Thr Lys Leu Ala Thr Thr
1               5

<210> SEQ ID NO 897
<211> LENGTH: 8
<212> TYPE: PRT
<213> ORGANISM: Human severe acute respiratory syndrome virus

<400> SEQUENCE: 897

Met Thr Lys Leu Ala Thr Thr Glu
1               5

<210> SEQ ID NO 898
<211> LENGTH: 8
<212> TYPE: PRT
<213> ORGANISM: Human severe acute respiratory syndrome virus

<400> SEQUENCE: 898

Thr Lys Leu Ala Thr Thr Glu Glu
1               5

<210> SEQ ID NO 899
<211> LENGTH: 8
<212> TYPE: PRT
<213> ORGANISM: Human severe acute respiratory syndrome virus

<400> SEQUENCE: 899

Lys Leu Ala Thr Thr Glu Glu Leu
1               5

<210> SEQ ID NO 900
<211> LENGTH: 8
<212> TYPE: PRT
<213> ORGANISM: Human severe acute respiratory syndrome virus

<400> SEQUENCE: 900

Leu Ala Thr Thr Glu Glu Leu Pro
1               5

<210> SEQ ID NO 901

```
<211> LENGTH: 8
<212> TYPE: PRT
<213> ORGANISM: Human severe acute respiratory syndrome virus

<400> SEQUENCE: 901

Ala Thr Thr Glu Glu Leu Pro Asp
1               5

<210> SEQ ID NO 902
<211> LENGTH: 8
<212> TYPE: PRT
<213> ORGANISM: Human severe acute respiratory syndrome virus

<400> SEQUENCE: 902

Thr Thr Glu Glu Leu Pro Asp Glu
1               5

<210> SEQ ID NO 903
<211> LENGTH: 8
<212> TYPE: PRT
<213> ORGANISM: Human severe acute respiratory syndrome virus

<400> SEQUENCE: 903

Thr Glu Glu Leu Pro Asp Glu Phe
1               5

<210> SEQ ID NO 904
<211> LENGTH: 8
<212> TYPE: PRT
<213> ORGANISM: Human severe acute respiratory syndrome virus

<400> SEQUENCE: 904

Glu Glu Leu Pro Asp Glu Phe Val
1               5

<210> SEQ ID NO 905
<211> LENGTH: 8
<212> TYPE: PRT
<213> ORGANISM: Human severe acute respiratory syndrome virus

<400> SEQUENCE: 905

Glu Leu Pro Asp Glu Phe Val Val
1               5

<210> SEQ ID NO 906
<211> LENGTH: 8
<212> TYPE: PRT
<213> ORGANISM: Human severe acute respiratory syndrome virus

<400> SEQUENCE: 906

Leu Pro Asp Glu Phe Val Val Val
1               5

<210> SEQ ID NO 907
<211> LENGTH: 8
<212> TYPE: PRT
<213> ORGANISM: Human severe acute respiratory syndrome virus

<400> SEQUENCE: 907

Pro Asp Glu Phe Val Val Val Thr
1               5

<210> SEQ ID NO 908
<211> LENGTH: 8
<212> TYPE: PRT
<213> ORGANISM: Human severe acute respiratory syndrome virus
```

```
<400> SEQUENCE: 908

Asp Glu Phe Val Val Val Thr Ala
1               5

<210> SEQ ID NO 909
<211> LENGTH: 8
<212> TYPE: PRT
<213> ORGANISM: Human severe acute respiratory syndrome virus

<400> SEQUENCE: 909

Glu Phe Val Val Val Thr Ala Lys
1               5

<210> SEQ ID NO 910
<211> LENGTH: 8
<212> TYPE: PRT
<213> ORGANISM: Human severe acute respiratory syndrome virus

<400> SEQUENCE: 910

Ile Ser Leu Cys Ser Cys Ile Arg
1               5

<210> SEQ ID NO 911
<211> LENGTH: 8
<212> TYPE: PRT
<213> ORGANISM: Human severe acute respiratory syndrome virus

<400> SEQUENCE: 911

Ser Leu Cys Ser Cys Ile Arg Thr
1               5

<210> SEQ ID NO 912
<211> LENGTH: 8
<212> TYPE: PRT
<213> ORGANISM: Human severe acute respiratory syndrome virus

<400> SEQUENCE: 912

Leu Cys Ser Cys Ile Arg Thr Val
1               5

<210> SEQ ID NO 913
<211> LENGTH: 8
<212> TYPE: PRT
<213> ORGANISM: Human severe acute respiratory syndrome virus

<400> SEQUENCE: 913

Cys Ser Cys Ile Arg Thr Val Val
1               5

<210> SEQ ID NO 914
<211> LENGTH: 8
<212> TYPE: PRT
<213> ORGANISM: Human severe acute respiratory syndrome virus

<400> SEQUENCE: 914

Ser Cys Ile Arg Thr Val Val Gln
1               5

<210> SEQ ID NO 915
<211> LENGTH: 8
<212> TYPE: PRT
<213> ORGANISM: Human severe acute respiratory syndrome virus

<400> SEQUENCE: 915
```

-continued

```
Cys Ile Arg Thr Val Val Gln Arg
1               5

<210> SEQ ID NO 916
<211> LENGTH: 8
<212> TYPE: PRT
<213> ORGANISM: Human severe acute respiratory syndrome virus

<400> SEQUENCE: 916

Ile Arg Thr Val Val Gln Arg Cys
1               5

<210> SEQ ID NO 917
<211> LENGTH: 8
<212> TYPE: PRT
<213> ORGANISM: Human severe acute respiratory syndrome virus

<400> SEQUENCE: 917

Arg Thr Val Val Gln Arg Cys Ala
1               5

<210> SEQ ID NO 918
<211> LENGTH: 8
<212> TYPE: PRT
<213> ORGANISM: Human severe acute respiratory syndrome virus

<400> SEQUENCE: 918

His Val Leu Glu Asp Pro Cys Pro
1               5

<210> SEQ ID NO 919
<211> LENGTH: 8
<212> TYPE: PRT
<213> ORGANISM: Human severe acute respiratory syndrome virus

<400> SEQUENCE: 919

Val Leu Glu Asp Pro Cys Pro Thr
1               5

<210> SEQ ID NO 920
<211> LENGTH: 8
<212> TYPE: PRT
<213> ORGANISM: Human severe acute respiratory syndrome virus

<400> SEQUENCE: 920

Leu Glu Asp Pro Cys Pro Thr Gly
1               5

<210> SEQ ID NO 921
<211> LENGTH: 8
<212> TYPE: PRT
<213> ORGANISM: Human severe acute respiratory syndrome virus

<400> SEQUENCE: 921

Glu Asp Pro Cys Pro Thr Gly Tyr
1               5

<210> SEQ ID NO 922
<211> LENGTH: 8
<212> TYPE: PRT
<213> ORGANISM: Human severe acute respiratory syndrome virus

<400> SEQUENCE: 922

Asp Pro Cys Pro Thr Gly Tyr Gln
1               5
```

<210> SEQ ID NO 923
<211> LENGTH: 8
<212> TYPE: PRT
<213> ORGANISM: Human severe acute respiratory syndrome virus

<400> SEQUENCE: 923

Pro Cys Pro Thr Gly Tyr Gln Pro
1               5

<210> SEQ ID NO 924
<211> LENGTH: 8
<212> TYPE: PRT
<213> ORGANISM: Human severe acute respiratory syndrome virus

<400> SEQUENCE: 924

Cys Pro Thr Gly Tyr Gln Pro Glu
1               5

<210> SEQ ID NO 925
<211> LENGTH: 8
<212> TYPE: PRT
<213> ORGANISM: Human severe acute respiratory syndrome virus

<400> SEQUENCE: 925

Pro Thr Gly Tyr Gln Pro Glu Trp
1               5

<210> SEQ ID NO 926
<211> LENGTH: 8
<212> TYPE: PRT
<213> ORGANISM: Human severe acute respiratory syndrome virus

<400> SEQUENCE: 926

Thr Gly Tyr Gln Pro Glu Trp Asn
1               5

<210> SEQ ID NO 927
<211> LENGTH: 8
<212> TYPE: PRT
<213> ORGANISM: Human severe acute respiratory syndrome virus

<400> SEQUENCE: 927

Gly Tyr Gln Pro Glu Trp Asn Ile
1               5

<210> SEQ ID NO 928
<211> LENGTH: 8
<212> TYPE: PRT
<213> ORGANISM: Human severe acute respiratory syndrome virus

<400> SEQUENCE: 928

Tyr Gln Pro Glu Trp Asn Ile Arg
1               5

<210> SEQ ID NO 929
<211> LENGTH: 8
<212> TYPE: PRT
<213> ORGANISM: Human severe acute respiratory syndrome virus

<400> SEQUENCE: 929

Gln Pro Glu Trp Asn Ile Arg Tyr
1               5

<210> SEQ ID NO 930
<211> LENGTH: 8

```
<212> TYPE: PRT
<213> ORGANISM: Human severe acute respiratory syndrome virus

<400> SEQUENCE: 930

Pro Glu Trp Asn Ile Arg Tyr Asn
1               5

<210> SEQ ID NO 931
<211> LENGTH: 8
<212> TYPE: PRT
<213> ORGANISM: Human severe acute respiratory syndrome virus

<400> SEQUENCE: 931

Glu Trp Asn Ile Arg Tyr Asn Thr
1               5

<210> SEQ ID NO 932
<211> LENGTH: 8
<212> TYPE: PRT
<213> ORGANISM: Human severe acute respiratory syndrome virus

<400> SEQUENCE: 932

Trp Asn Ile Arg Tyr Asn Thr Arg
1               5

<210> SEQ ID NO 933
<211> LENGTH: 8
<212> TYPE: PRT
<213> ORGANISM: Human severe acute respiratory syndrome virus

<400> SEQUENCE: 933

Asn Ile Arg Tyr Asn Thr Arg Gly
1               5

<210> SEQ ID NO 934
<211> LENGTH: 8
<212> TYPE: PRT
<213> ORGANISM: Human severe acute respiratory syndrome virus

<400> SEQUENCE: 934

Ile Arg Tyr Asn Thr Arg Gly Asn
1               5

<210> SEQ ID NO 935
<211> LENGTH: 8
<212> TYPE: PRT
<213> ORGANISM: Human severe acute respiratory syndrome virus

<400> SEQUENCE: 935

Thr Ala Ala Phe Arg Asp Val Phe
1               5

<210> SEQ ID NO 936
<211> LENGTH: 8
<212> TYPE: PRT
<213> ORGANISM: Human severe acute respiratory syndrome virus

<400> SEQUENCE: 936

Ala Ala Phe Arg Asp Val Phe Val
1               5

<210> SEQ ID NO 937
<211> LENGTH: 8
<212> TYPE: PRT
<213> ORGANISM: Human severe acute respiratory syndrome virus
```

```
<400> SEQUENCE: 937

Ala Phe Arg Asp Val Phe Val Val
1               5

<210> SEQ ID NO 938
<211> LENGTH: 8
<212> TYPE: PRT
<213> ORGANISM: Human severe acute respiratory syndrome virus

<400> SEQUENCE: 938

Phe Arg Asp Val Phe Val Val Leu
1               5

<210> SEQ ID NO 939
<211> LENGTH: 8
<212> TYPE: PRT
<213> ORGANISM: Human severe acute respiratory syndrome virus

<400> SEQUENCE: 939

Arg Asp Val Phe Val Val Leu Asn
1               5

<210> SEQ ID NO 940
<211> LENGTH: 8
<212> TYPE: PRT
<213> ORGANISM: Human severe acute respiratory syndrome virus

<400> SEQUENCE: 940

Asp Val Phe Val Val Leu Asn Lys
1               5

<210> SEQ ID NO 941
<211> LENGTH: 8
<212> TYPE: PRT
<213> ORGANISM: Human severe acute respiratory syndrome virus

<400> SEQUENCE: 941

Val Phe Val Val Leu Asn Lys Arg
1               5

<210> SEQ ID NO 942
<211> LENGTH: 8
<212> TYPE: PRT
<213> ORGANISM: Human severe acute respiratory syndrome virus

<400> SEQUENCE: 942

Phe Val Val Leu Asn Lys Arg Thr
1               5

<210> SEQ ID NO 943
<211> LENGTH: 8
<212> TYPE: PRT
<213> ORGANISM: Human severe acute respiratory syndrome virus

<400> SEQUENCE: 943

Met Lys Ile Ile Leu Phe Leu Thr
1               5

<210> SEQ ID NO 944
<211> LENGTH: 8
<212> TYPE: PRT
<213> ORGANISM: Human severe acute respiratory syndrome virus

<400> SEQUENCE: 944

Lys Ile Ile Leu Phe Leu Thr Leu
```

```
1               5

<210> SEQ ID NO 945
<211> LENGTH: 8
<212> TYPE: PRT
<213> ORGANISM: Human severe acute respiratory syndrome virus

<400> SEQUENCE: 945

Ile Ile Leu Phe Leu Thr Leu Ile
1               5

<210> SEQ ID NO 946
<211> LENGTH: 8
<212> TYPE: PRT
<213> ORGANISM: Human severe acute respiratory syndrome virus

<400> SEQUENCE: 946

Ile Leu Phe Leu Thr Leu Ile Val
1               5

<210> SEQ ID NO 947
<211> LENGTH: 8
<212> TYPE: PRT
<213> ORGANISM: Human severe acute respiratory syndrome virus

<400> SEQUENCE: 947

Leu Phe Leu Thr Leu Ile Val Phe
1               5

<210> SEQ ID NO 948
<211> LENGTH: 8
<212> TYPE: PRT
<213> ORGANISM: Human severe acute respiratory syndrome virus

<400> SEQUENCE: 948

Phe Leu Thr Leu Ile Val Phe Thr
1               5

<210> SEQ ID NO 949
<211> LENGTH: 8
<212> TYPE: PRT
<213> ORGANISM: Human severe acute respiratory syndrome virus

<400> SEQUENCE: 949

Leu Thr Leu Ile Val Phe Thr Ser
1               5

<210> SEQ ID NO 950
<211> LENGTH: 8
<212> TYPE: PRT
<213> ORGANISM: Human severe acute respiratory syndrome virus

<400> SEQUENCE: 950

Thr Leu Ile Val Phe Thr Ser Cys
1               5

<210> SEQ ID NO 951
<211> LENGTH: 8
<212> TYPE: PRT
<213> ORGANISM: Human severe acute respiratory syndrome virus

<400> SEQUENCE: 951

Leu Ile Val Phe Thr Ser Cys Glu
1               5
```

```
<210> SEQ ID NO 952
<211> LENGTH: 8
<212> TYPE: PRT
<213> ORGANISM: Human severe acute respiratory syndrome virus

<400> SEQUENCE: 952

Ile Val Phe Thr Ser Cys Glu Leu
1               5

<210> SEQ ID NO 953
<211> LENGTH: 8
<212> TYPE: PRT
<213> ORGANISM: Human severe acute respiratory syndrome virus

<400> SEQUENCE: 953

Val Phe Thr Ser Cys Glu Leu Tyr
1               5

<210> SEQ ID NO 954
<211> LENGTH: 8
<212> TYPE: PRT
<213> ORGANISM: Human severe acute respiratory syndrome virus

<400> SEQUENCE: 954

Phe Thr Ser Cys Glu Leu Tyr His
1               5

<210> SEQ ID NO 955
<211> LENGTH: 8
<212> TYPE: PRT
<213> ORGANISM: Human severe acute respiratory syndrome virus

<400> SEQUENCE: 955

Thr Ser Cys Glu Leu Tyr His Tyr
1               5

<210> SEQ ID NO 956
<211> LENGTH: 8
<212> TYPE: PRT
<213> ORGANISM: Human severe acute respiratory syndrome virus

<400> SEQUENCE: 956

Ser Cys Glu Leu Tyr His Tyr Gln
1               5

<210> SEQ ID NO 957
<211> LENGTH: 8
<212> TYPE: PRT
<213> ORGANISM: Human severe acute respiratory syndrome virus

<400> SEQUENCE: 957

Cys Glu Leu Tyr His Tyr Gln Glu
1               5

<210> SEQ ID NO 958
<211> LENGTH: 8
<212> TYPE: PRT
<213> ORGANISM: Human severe acute respiratory syndrome virus

<400> SEQUENCE: 958

Glu Leu Tyr His Tyr Gln Glu Cys
1               5

<210> SEQ ID NO 959
<211> LENGTH: 8
<212> TYPE: PRT
```

-continued

<213> ORGANISM: Human severe acute respiratory syndrome virus

<400> SEQUENCE: 959

Leu Tyr His Tyr Gln Glu Cys Val
1               5

<210> SEQ ID NO 960
<211> LENGTH: 8
<212> TYPE: PRT
<213> ORGANISM: Human severe acute respiratory syndrome virus

<400> SEQUENCE: 960

Tyr His Tyr Gln Glu Cys Val Arg
1               5

<210> SEQ ID NO 961
<211> LENGTH: 8
<212> TYPE: PRT
<213> ORGANISM: Human severe acute respiratory syndrome virus

<400> SEQUENCE: 961

His Tyr Gln Glu Cys Val Arg Gly
1               5

<210> SEQ ID NO 962
<211> LENGTH: 8
<212> TYPE: PRT
<213> ORGANISM: Human severe acute respiratory syndrome virus

<400> SEQUENCE: 962

Tyr Gln Glu Cys Val Arg Gly Thr
1               5

<210> SEQ ID NO 963
<211> LENGTH: 8
<212> TYPE: PRT
<213> ORGANISM: Human severe acute respiratory syndrome virus

<400> SEQUENCE: 963

Gln Glu Cys Val Arg Gly Thr Thr
1               5

<210> SEQ ID NO 964
<211> LENGTH: 8
<212> TYPE: PRT
<213> ORGANISM: Human severe acute respiratory syndrome virus

<400> SEQUENCE: 964

Glu Cys Val Arg Gly Thr Thr Val
1               5

<210> SEQ ID NO 965
<211> LENGTH: 8
<212> TYPE: PRT
<213> ORGANISM: Human severe acute respiratory syndrome virus

<400> SEQUENCE: 965

Cys Val Arg Gly Thr Thr Val Leu
1               5

<210> SEQ ID NO 966
<211> LENGTH: 8
<212> TYPE: PRT
<213> ORGANISM: Human severe acute respiratory syndrome virus

<400> SEQUENCE: 966

```
Val Arg Gly Thr Thr Val Leu Leu
1               5

<210> SEQ ID NO 967
<211> LENGTH: 8
<212> TYPE: PRT
<213> ORGANISM: Human severe acute respiratory syndrome virus

<400> SEQUENCE: 967

Arg Gly Thr Thr Val Leu Leu Lys
1               5

<210> SEQ ID NO 968
<211> LENGTH: 8
<212> TYPE: PRT
<213> ORGANISM: Human severe acute respiratory syndrome virus

<400> SEQUENCE: 968

Gly Thr Thr Val Leu Leu Lys Glu
1               5

<210> SEQ ID NO 969
<211> LENGTH: 8
<212> TYPE: PRT
<213> ORGANISM: Human severe acute respiratory syndrome virus

<400> SEQUENCE: 969

Thr Thr Val Leu Leu Lys Glu Pro
1               5

<210> SEQ ID NO 970
<211> LENGTH: 8
<212> TYPE: PRT
<213> ORGANISM: Human severe acute respiratory syndrome virus

<400> SEQUENCE: 970

Thr Val Leu Leu Lys Glu Pro Cys
1               5

<210> SEQ ID NO 971
<211> LENGTH: 8
<212> TYPE: PRT
<213> ORGANISM: Human severe acute respiratory syndrome virus

<400> SEQUENCE: 971

Val Leu Leu Lys Glu Pro Cys Pro
1               5

<210> SEQ ID NO 972
<211> LENGTH: 8
<212> TYPE: PRT
<213> ORGANISM: Human severe acute respiratory syndrome virus

<400> SEQUENCE: 972

Leu Leu Lys Glu Pro Cys Pro Ser
1               5

<210> SEQ ID NO 973
<211> LENGTH: 8
<212> TYPE: PRT
<213> ORGANISM: Human severe acute respiratory syndrome virus

<400> SEQUENCE: 973

Leu Lys Glu Pro Cys Pro Ser Gly
1               5
```

<210> SEQ ID NO 974
<211> LENGTH: 8
<212> TYPE: PRT
<213> ORGANISM: Human severe acute respiratory syndrome virus

<400> SEQUENCE: 974

Lys Glu Pro Cys Pro Ser Gly Thr
1               5

<210> SEQ ID NO 975
<211> LENGTH: 8
<212> TYPE: PRT
<213> ORGANISM: Human severe acute respiratory syndrome virus

<400> SEQUENCE: 975

Glu Pro Cys Pro Ser Gly Thr Tyr
1               5

<210> SEQ ID NO 976
<211> LENGTH: 8
<212> TYPE: PRT
<213> ORGANISM: Human severe acute respiratory syndrome virus

<400> SEQUENCE: 976

Pro Cys Pro Ser Gly Thr Tyr Glu
1               5

<210> SEQ ID NO 977
<211> LENGTH: 8
<212> TYPE: PRT
<213> ORGANISM: Human severe acute respiratory syndrome virus

<400> SEQUENCE: 977

Cys Pro Ser Gly Thr Tyr Glu Gly
1               5

<210> SEQ ID NO 978
<211> LENGTH: 8
<212> TYPE: PRT
<213> ORGANISM: Human severe acute respiratory syndrome virus

<400> SEQUENCE: 978

Pro Ser Gly Thr Tyr Glu Gly Asn
1               5

<210> SEQ ID NO 979
<211> LENGTH: 8
<212> TYPE: PRT
<213> ORGANISM: Human severe acute respiratory syndrome virus

<400> SEQUENCE: 979

Ser Gly Thr Tyr Glu Gly Asn Ser
1               5

<210> SEQ ID NO 980
<211> LENGTH: 8
<212> TYPE: PRT
<213> ORGANISM: Human severe acute respiratory syndrome virus

<400> SEQUENCE: 980

Gly Thr Tyr Glu Gly Asn Ser Pro
1               5

<210> SEQ ID NO 981

```
<211> LENGTH: 8
<212> TYPE: PRT
<213> ORGANISM: Human severe acute respiratory syndrome virus

<400> SEQUENCE: 981

Thr Tyr Glu Gly Asn Ser Pro Phe
1               5

<210> SEQ ID NO 982
<211> LENGTH: 8
<212> TYPE: PRT
<213> ORGANISM: Human severe acute respiratory syndrome virus

<400> SEQUENCE: 982

Tyr Glu Gly Asn Ser Pro Phe His
1               5

<210> SEQ ID NO 983
<211> LENGTH: 8
<212> TYPE: PRT
<213> ORGANISM: Human severe acute respiratory syndrome virus

<400> SEQUENCE: 983

Glu Gly Asn Ser Pro Phe His Pro
1               5

<210> SEQ ID NO 984
<211> LENGTH: 8
<212> TYPE: PRT
<213> ORGANISM: Human severe acute respiratory syndrome virus

<400> SEQUENCE: 984

Gly Asn Ser Pro Phe His Pro Leu
1               5

<210> SEQ ID NO 985
<211> LENGTH: 8
<212> TYPE: PRT
<213> ORGANISM: Human severe acute respiratory syndrome virus

<400> SEQUENCE: 985

Asn Ser Pro Phe His Pro Leu Ala
1               5

<210> SEQ ID NO 986
<211> LENGTH: 8
<212> TYPE: PRT
<213> ORGANISM: Human severe acute respiratory syndrome virus

<400> SEQUENCE: 986

Ser Pro Phe His Pro Leu Ala Asp
1               5

<210> SEQ ID NO 987
<211> LENGTH: 8
<212> TYPE: PRT
<213> ORGANISM: Human severe acute respiratory syndrome virus

<400> SEQUENCE: 987

Pro Phe His Pro Leu Ala Asp Asn
1               5

<210> SEQ ID NO 988
<211> LENGTH: 8
<212> TYPE: PRT
<213> ORGANISM: Human severe acute respiratory syndrome virus
```

```
<400> SEQUENCE: 988

Phe His Pro Leu Ala Asp Asn Lys
1               5

<210> SEQ ID NO 989
<211> LENGTH: 8
<212> TYPE: PRT
<213> ORGANISM: Human severe acute respiratory syndrome virus

<400> SEQUENCE: 989

His Pro Leu Ala Asp Asn Lys Phe
1               5

<210> SEQ ID NO 990
<211> LENGTH: 8
<212> TYPE: PRT
<213> ORGANISM: Human severe acute respiratory syndrome virus

<400> SEQUENCE: 990

Pro Leu Ala Asp Asn Lys Phe Ala
1               5

<210> SEQ ID NO 991
<211> LENGTH: 8
<212> TYPE: PRT
<213> ORGANISM: Human severe acute respiratory syndrome virus

<400> SEQUENCE: 991

Leu Ala Asp Asn Lys Phe Ala Leu
1               5

<210> SEQ ID NO 992
<211> LENGTH: 8
<212> TYPE: PRT
<213> ORGANISM: Human severe acute respiratory syndrome virus

<400> SEQUENCE: 992

Ala Asp Asn Lys Phe Ala Leu Thr
1               5

<210> SEQ ID NO 993
<211> LENGTH: 8
<212> TYPE: PRT
<213> ORGANISM: Human severe acute respiratory syndrome virus

<400> SEQUENCE: 993

Asp Asn Lys Phe Ala Leu Thr Cys
1               5

<210> SEQ ID NO 994
<211> LENGTH: 8
<212> TYPE: PRT
<213> ORGANISM: Human severe acute respiratory syndrome virus

<400> SEQUENCE: 994

Asn Lys Phe Ala Leu Thr Cys Thr
1               5

<210> SEQ ID NO 995
<211> LENGTH: 8
<212> TYPE: PRT
<213> ORGANISM: Human severe acute respiratory syndrome virus

<400> SEQUENCE: 995
```

```
Lys Phe Ala Leu Thr Cys Thr Ser
1               5

<210> SEQ ID NO 996
<211> LENGTH: 8
<212> TYPE: PRT
<213> ORGANISM: Human severe acute respiratory syndrome virus

<400> SEQUENCE: 996

Phe Ala Leu Thr Cys Thr Ser Thr
1               5

<210> SEQ ID NO 997
<211> LENGTH: 8
<212> TYPE: PRT
<213> ORGANISM: Human severe acute respiratory syndrome virus

<400> SEQUENCE: 997

Ala Leu Thr Cys Thr Ser Thr His
1               5

<210> SEQ ID NO 998
<211> LENGTH: 8
<212> TYPE: PRT
<213> ORGANISM: Human severe acute respiratory syndrome virus

<400> SEQUENCE: 998

Leu Thr Cys Thr Ser Thr His Phe
1               5

<210> SEQ ID NO 999
<211> LENGTH: 8
<212> TYPE: PRT
<213> ORGANISM: Human severe acute respiratory syndrome virus

<400> SEQUENCE: 999

Thr Cys Thr Ser Thr His Phe Ala
1               5

<210> SEQ ID NO 1000
<211> LENGTH: 8
<212> TYPE: PRT
<213> ORGANISM: Human severe acute respiratory syndrome virus

<400> SEQUENCE: 1000

Cys Thr Ser Thr His Phe Ala Phe
1               5

<210> SEQ ID NO 1001
<211> LENGTH: 8
<212> TYPE: PRT
<213> ORGANISM: Human severe acute respiratory syndrome virus

<400> SEQUENCE: 1001

Thr Ser Thr His Phe Ala Phe Ala
1               5

<210> SEQ ID NO 1002
<211> LENGTH: 8
<212> TYPE: PRT
<213> ORGANISM: Human severe acute respiratory syndrome virus

<400> SEQUENCE: 1002

Ser Thr His Phe Ala Phe Ala Cys
1               5
```

```
<210> SEQ ID NO 1003
<211> LENGTH: 8
<212> TYPE: PRT
<213> ORGANISM: Human severe acute respiratory syndrome virus

<400> SEQUENCE: 1003

Thr His Phe Ala Phe Ala Cys Ala
1               5

<210> SEQ ID NO 1004
<211> LENGTH: 8
<212> TYPE: PRT
<213> ORGANISM: Human severe acute respiratory syndrome virus

<400> SEQUENCE: 1004

His Phe Ala Phe Ala Cys Ala Asp
1               5

<210> SEQ ID NO 1005
<211> LENGTH: 8
<212> TYPE: PRT
<213> ORGANISM: Human severe acute respiratory syndrome virus

<400> SEQUENCE: 1005

Phe Ala Phe Ala Cys Ala Asp Gly
1               5

<210> SEQ ID NO 1006
<211> LENGTH: 8
<212> TYPE: PRT
<213> ORGANISM: Human severe acute respiratory syndrome virus

<400> SEQUENCE: 1006

Ala Phe Ala Cys Ala Asp Gly Thr
1               5

<210> SEQ ID NO 1007
<211> LENGTH: 8
<212> TYPE: PRT
<213> ORGANISM: Human severe acute respiratory syndrome virus

<400> SEQUENCE: 1007

Phe Ala Cys Ala Asp Gly Thr Arg
1               5

<210> SEQ ID NO 1008
<211> LENGTH: 8
<212> TYPE: PRT
<213> ORGANISM: Human severe acute respiratory syndrome virus

<400> SEQUENCE: 1008

Ala Cys Ala Asp Gly Thr Arg His
1               5

<210> SEQ ID NO 1009
<211> LENGTH: 8
<212> TYPE: PRT
<213> ORGANISM: Human severe acute respiratory syndrome virus

<400> SEQUENCE: 1009

Cys Ala Asp Gly Thr Arg His Thr
1               5

<210> SEQ ID NO 1010
<211> LENGTH: 8
```

```
<212> TYPE: PRT
<213> ORGANISM: Human severe acute respiratory syndrome virus

<400> SEQUENCE: 1010

Ala Asp Gly Thr Arg His Thr Tyr
1               5

<210> SEQ ID NO 1011
<211> LENGTH: 8
<212> TYPE: PRT
<213> ORGANISM: Human severe acute respiratory syndrome virus

<400> SEQUENCE: 1011

Asp Gly Thr Arg His Thr Tyr Gln
1               5

<210> SEQ ID NO 1012
<211> LENGTH: 8
<212> TYPE: PRT
<213> ORGANISM: Human severe acute respiratory syndrome virus

<400> SEQUENCE: 1012

Gly Thr Arg His Thr Tyr Gln Leu
1               5

<210> SEQ ID NO 1013
<211> LENGTH: 8
<212> TYPE: PRT
<213> ORGANISM: Human severe acute respiratory syndrome virus

<400> SEQUENCE: 1013

Thr Arg His Thr Tyr Gln Leu Arg
1               5

<210> SEQ ID NO 1014
<211> LENGTH: 8
<212> TYPE: PRT
<213> ORGANISM: Human severe acute respiratory syndrome virus

<400> SEQUENCE: 1014

Arg His Thr Tyr Gln Leu Arg Ala
1               5

<210> SEQ ID NO 1015
<211> LENGTH: 8
<212> TYPE: PRT
<213> ORGANISM: Human severe acute respiratory syndrome virus

<400> SEQUENCE: 1015

His Thr Tyr Gln Leu Arg Ala Arg
1               5

<210> SEQ ID NO 1016
<211> LENGTH: 8
<212> TYPE: PRT
<213> ORGANISM: Human severe acute respiratory syndrome virus

<400> SEQUENCE: 1016

Thr Tyr Gln Leu Arg Ala Arg Ser
1               5

<210> SEQ ID NO 1017
<211> LENGTH: 8
<212> TYPE: PRT
<213> ORGANISM: Human severe acute respiratory syndrome virus
```

```
<400> SEQUENCE: 1017

Tyr Gln Leu Arg Ala Arg Ser Val
1               5

<210> SEQ ID NO 1018
<211> LENGTH: 8
<212> TYPE: PRT
<213> ORGANISM: Human severe acute respiratory syndrome virus

<400> SEQUENCE: 1018

Gln Leu Arg Ala Arg Ser Val Ser
1               5

<210> SEQ ID NO 1019
<211> LENGTH: 8
<212> TYPE: PRT
<213> ORGANISM: Human severe acute respiratory syndrome virus

<400> SEQUENCE: 1019

Leu Arg Ala Arg Ser Val Ser Pro
1               5

<210> SEQ ID NO 1020
<211> LENGTH: 8
<212> TYPE: PRT
<213> ORGANISM: Human severe acute respiratory syndrome virus

<400> SEQUENCE: 1020

Arg Ala Arg Ser Val Ser Pro Lys
1               5

<210> SEQ ID NO 1021
<211> LENGTH: 8
<212> TYPE: PRT
<213> ORGANISM: Human severe acute respiratory syndrome virus

<400> SEQUENCE: 1021

Ala Arg Ser Val Ser Pro Lys Leu
1               5

<210> SEQ ID NO 1022
<211> LENGTH: 8
<212> TYPE: PRT
<213> ORGANISM: Human severe acute respiratory syndrome virus

<400> SEQUENCE: 1022

Arg Ser Val Ser Pro Lys Leu Phe
1               5

<210> SEQ ID NO 1023
<211> LENGTH: 8
<212> TYPE: PRT
<213> ORGANISM: Human severe acute respiratory syndrome virus

<400> SEQUENCE: 1023

Ser Val Ser Pro Lys Leu Phe Ile
1               5

<210> SEQ ID NO 1024
<211> LENGTH: 8
<212> TYPE: PRT
<213> ORGANISM: Human severe acute respiratory syndrome virus

<400> SEQUENCE: 1024

Val Ser Pro Lys Leu Phe Ile Arg
```

-continued

```
1               5

<210> SEQ ID NO 1025
<211> LENGTH: 8
<212> TYPE: PRT
<213> ORGANISM: Human severe acute respiratory syndrome virus

<400> SEQUENCE: 1025

Ser Pro Lys Leu Phe Ile Arg Gln
1               5

<210> SEQ ID NO 1026
<211> LENGTH: 8
<212> TYPE: PRT
<213> ORGANISM: Human severe acute respiratory syndrome virus

<400> SEQUENCE: 1026

Pro Lys Leu Phe Ile Arg Gln Glu
1               5

<210> SEQ ID NO 1027
<211> LENGTH: 8
<212> TYPE: PRT
<213> ORGANISM: Human severe acute respiratory syndrome virus

<400> SEQUENCE: 1027

Lys Leu Phe Ile Arg Gln Glu Glu
1               5

<210> SEQ ID NO 1028
<211> LENGTH: 8
<212> TYPE: PRT
<213> ORGANISM: Human severe acute respiratory syndrome virus

<400> SEQUENCE: 1028

Leu Phe Ile Arg Gln Glu Glu Val
1               5

<210> SEQ ID NO 1029
<211> LENGTH: 8
<212> TYPE: PRT
<213> ORGANISM: Human severe acute respiratory syndrome virus

<400> SEQUENCE: 1029

Phe Ile Arg Gln Glu Glu Val Gln
1               5

<210> SEQ ID NO 1030
<211> LENGTH: 8
<212> TYPE: PRT
<213> ORGANISM: Human severe acute respiratory syndrome virus

<400> SEQUENCE: 1030

Ile Arg Gln Glu Glu Val Gln Gln
1               5

<210> SEQ ID NO 1031
<211> LENGTH: 8
<212> TYPE: PRT
<213> ORGANISM: Human severe acute respiratory syndrome virus

<400> SEQUENCE: 1031

Arg Gln Glu Glu Val Gln Gln Glu
1               5
```

```
<210> SEQ ID NO 1032
<211> LENGTH: 8
<212> TYPE: PRT
<213> ORGANISM: Human severe acute respiratory syndrome virus

<400> SEQUENCE: 1032

Gln Glu Glu Val Gln Gln Glu Leu
1               5

<210> SEQ ID NO 1033
<211> LENGTH: 8
<212> TYPE: PRT
<213> ORGANISM: Human severe acute respiratory syndrome virus

<400> SEQUENCE: 1033

Glu Glu Val Gln Gln Glu Leu Tyr
1               5

<210> SEQ ID NO 1034
<211> LENGTH: 8
<212> TYPE: PRT
<213> ORGANISM: Human severe acute respiratory syndrome virus

<400> SEQUENCE: 1034

Glu Val Gln Gln Glu Leu Tyr Ser
1               5

<210> SEQ ID NO 1035
<211> LENGTH: 8
<212> TYPE: PRT
<213> ORGANISM: Human severe acute respiratory syndrome virus

<400> SEQUENCE: 1035

Val Gln Gln Glu Leu Tyr Ser Pro
1               5

<210> SEQ ID NO 1036
<211> LENGTH: 8
<212> TYPE: PRT
<213> ORGANISM: Human severe acute respiratory syndrome virus

<400> SEQUENCE: 1036

Gln Gln Glu Leu Tyr Ser Pro Leu
1               5

<210> SEQ ID NO 1037
<211> LENGTH: 8
<212> TYPE: PRT
<213> ORGANISM: Human severe acute respiratory syndrome virus

<400> SEQUENCE: 1037

Gln Glu Leu Tyr Ser Pro Leu Phe
1               5

<210> SEQ ID NO 1038
<211> LENGTH: 8
<212> TYPE: PRT
<213> ORGANISM: Human severe acute respiratory syndrome virus

<400> SEQUENCE: 1038

Glu Leu Tyr Ser Pro Leu Phe Leu
1               5

<210> SEQ ID NO 1039
<211> LENGTH: 8
<212> TYPE: PRT
```

-continued

<213> ORGANISM: Human severe acute respiratory syndrome virus

<400> SEQUENCE: 1039

Leu Tyr Ser Pro Leu Phe Leu Ile
1               5

<210> SEQ ID NO 1040
<211> LENGTH: 8
<212> TYPE: PRT
<213> ORGANISM: Human severe acute respiratory syndrome virus

<400> SEQUENCE: 1040

Tyr Ser Pro Leu Phe Leu Ile Val
1               5

<210> SEQ ID NO 1041
<211> LENGTH: 8
<212> TYPE: PRT
<213> ORGANISM: Human severe acute respiratory syndrome virus

<400> SEQUENCE: 1041

Ser Pro Leu Phe Leu Ile Val Ala
1               5

<210> SEQ ID NO 1042
<211> LENGTH: 8
<212> TYPE: PRT
<213> ORGANISM: Human severe acute respiratory syndrome virus

<400> SEQUENCE: 1042

Pro Leu Phe Leu Ile Val Ala Ala
1               5

<210> SEQ ID NO 1043
<211> LENGTH: 8
<212> TYPE: PRT
<213> ORGANISM: Human severe acute respiratory syndrome virus

<400> SEQUENCE: 1043

Leu Phe Leu Ile Val Ala Ala Leu
1               5

<210> SEQ ID NO 1044
<211> LENGTH: 8
<212> TYPE: PRT
<213> ORGANISM: Human severe acute respiratory syndrome virus

<400> SEQUENCE: 1044

Phe Leu Ile Val Ala Ala Leu Val
1               5

<210> SEQ ID NO 1045
<211> LENGTH: 8
<212> TYPE: PRT
<213> ORGANISM: Human severe acute respiratory syndrome virus

<400> SEQUENCE: 1045

Leu Ile Val Ala Ala Leu Val Phe
1               5

<210> SEQ ID NO 1046
<211> LENGTH: 8
<212> TYPE: PRT
<213> ORGANISM: Human severe acute respiratory syndrome virus

<400> SEQUENCE: 1046

-continued

```
Ile Val Ala Ala Leu Val Phe Leu
1               5

<210> SEQ ID NO 1047
<211> LENGTH: 8
<212> TYPE: PRT
<213> ORGANISM: Human severe acute respiratory syndrome virus

<400> SEQUENCE: 1047

Val Ala Ala Leu Val Phe Leu Ile
1               5

<210> SEQ ID NO 1048
<211> LENGTH: 8
<212> TYPE: PRT
<213> ORGANISM: Human severe acute respiratory syndrome virus

<400> SEQUENCE: 1048

Ala Ala Leu Val Phe Leu Ile Leu
1               5

<210> SEQ ID NO 1049
<211> LENGTH: 8
<212> TYPE: PRT
<213> ORGANISM: Human severe acute respiratory syndrome virus

<400> SEQUENCE: 1049

Ala Leu Val Phe Leu Ile Leu Cys
1               5

<210> SEQ ID NO 1050
<211> LENGTH: 8
<212> TYPE: PRT
<213> ORGANISM: Human severe acute respiratory syndrome virus

<400> SEQUENCE: 1050

Leu Val Phe Leu Ile Leu Cys Phe
1               5

<210> SEQ ID NO 1051
<211> LENGTH: 8
<212> TYPE: PRT
<213> ORGANISM: Human severe acute respiratory syndrome virus

<400> SEQUENCE: 1051

Val Phe Leu Ile Leu Cys Phe Thr
1               5

<210> SEQ ID NO 1052
<211> LENGTH: 8
<212> TYPE: PRT
<213> ORGANISM: Human severe acute respiratory syndrome virus

<400> SEQUENCE: 1052

Phe Leu Ile Leu Cys Phe Thr Ile
1               5

<210> SEQ ID NO 1053
<211> LENGTH: 8
<212> TYPE: PRT
<213> ORGANISM: Human severe acute respiratory syndrome virus

<400> SEQUENCE: 1053

Leu Ile Leu Cys Phe Thr Ile Lys
1               5
```

<210> SEQ ID NO 1054
<211> LENGTH: 8
<212> TYPE: PRT
<213> ORGANISM: Human severe acute respiratory syndrome virus

<400> SEQUENCE: 1054

Ile Leu Cys Phe Thr Ile Lys Arg
1               5

<210> SEQ ID NO 1055
<211> LENGTH: 8
<212> TYPE: PRT
<213> ORGANISM: Human severe acute respiratory syndrome virus

<400> SEQUENCE: 1055

Leu Cys Phe Thr Ile Lys Arg Lys
1               5

<210> SEQ ID NO 1056
<211> LENGTH: 8
<212> TYPE: PRT
<213> ORGANISM: Human severe acute respiratory syndrome virus

<400> SEQUENCE: 1056

Cys Phe Thr Ile Lys Arg Lys Thr
1               5

<210> SEQ ID NO 1057
<211> LENGTH: 8
<212> TYPE: PRT
<213> ORGANISM: Human severe acute respiratory syndrome virus

<400> SEQUENCE: 1057

Phe Thr Ile Lys Arg Lys Thr Glu
1               5

<210> SEQ ID NO 1058
<211> LENGTH: 8
<212> TYPE: PRT
<213> ORGANISM: Human severe acute respiratory syndrome virus
<220> FEATURE:
<221> NAME/KEY: MOD_RES
<222> LOCATION: (8)..(8)
<223> OTHER INFORMATION: Xaa can be any amino acid

<400> SEQUENCE: 1058

Ile Leu Ser Asp Asp Gly Val Xaa
1               5

<210> SEQ ID NO 1059
<211> LENGTH: 8
<212> TYPE: PRT
<213> ORGANISM: Human severe acute respiratory syndrome virus
<220> FEATURE:
<221> NAME/KEY: MOD_RES
<222> LOCATION: (7)
<223> OTHER INFORMATION: Xaa can be any amino acid

<400> SEQUENCE: 1059

Leu Ser Asp Asp Gly Val Xaa Val
1               5

<210> SEQ ID NO 1060
<211> LENGTH: 8
<212> TYPE: PRT
<213> ORGANISM: Human severe acute respiratory syndrome virus

```
<220> FEATURE:
<221> NAME/KEY: MOD_RES
<222> LOCATION: (6)..(6)
<223> OTHER INFORMATION: Xaa can be any amino acid

<400> SEQUENCE: 1060

Ser Asp Asp Gly Val Xaa Val Leu
1               5

<210> SEQ ID NO 1061
<211> LENGTH: 8
<212> TYPE: PRT
<213> ORGANISM: Human severe acute respiratory syndrome virus
<220> FEATURE:
<221> NAME/KEY: MOD_RES
<222> LOCATION: (5)..(5)
<223> OTHER INFORMATION: Xaa can be any amino acid

<400> SEQUENCE: 1061

Asp Asp Gly Val Xaa Val Leu Asn
1               5

<210> SEQ ID NO 1062
<211> LENGTH: 8
<212> TYPE: PRT
<213> ORGANISM: Human severe acute respiratory syndrome virus

<400> SEQUENCE: 1062

Leu Leu Ile Gln Gln Trp Ile Pro
1               5

<210> SEQ ID NO 1063
<211> LENGTH: 8
<212> TYPE: PRT
<213> ORGANISM: Human severe acute respiratory syndrome virus

<400> SEQUENCE: 1063

Leu Ile Gln Gln Trp Ile Pro Phe
1               5

<210> SEQ ID NO 1064
<211> LENGTH: 8
<212> TYPE: PRT
<213> ORGANISM: Human severe acute respiratory syndrome virus

<400> SEQUENCE: 1064

Ile Gln Gln Trp Ile Pro Phe Met
1               5

<210> SEQ ID NO 1065
<211> LENGTH: 8
<212> TYPE: PRT
<213> ORGANISM: Human severe acute respiratory syndrome virus

<400> SEQUENCE: 1065

Gln Gln Trp Ile Pro Phe Met Met
1               5

<210> SEQ ID NO 1066
<211> LENGTH: 8
<212> TYPE: PRT
<213> ORGANISM: Human severe acute respiratory syndrome virus

<400> SEQUENCE: 1066

Gln Trp Ile Pro Phe Met Met Ser
1               5
```

```
<210> SEQ ID NO 1067
<211> LENGTH: 8
<212> TYPE: PRT
<213> ORGANISM: Human severe acute respiratory syndrome virus

<400> SEQUENCE: 1067

Trp Ile Pro Phe Met Met Ser Arg
1               5

<210> SEQ ID NO 1068
<211> LENGTH: 8
<212> TYPE: PRT
<213> ORGANISM: Human severe acute respiratory syndrome virus

<400> SEQUENCE: 1068

Ile Pro Phe Met Met Ser Arg Arg
1               5

<210> SEQ ID NO 1069
<211> LENGTH: 8
<212> TYPE: PRT
<213> ORGANISM: Human severe acute respiratory syndrome virus

<400> SEQUENCE: 1069

Pro Phe Met Met Ser Arg Arg Arg
1               5

<210> SEQ ID NO 1070
<211> LENGTH: 8
<212> TYPE: PRT
<213> ORGANISM: Human severe acute respiratory syndrome virus

<400> SEQUENCE: 1070

Gln Ile Gln Leu Ser Leu Leu Gln
1               5

<210> SEQ ID NO 1071
<211> LENGTH: 8
<212> TYPE: PRT
<213> ORGANISM: Human severe acute respiratory syndrome virus

<400> SEQUENCE: 1071

Ile Gln Leu Ser Leu Leu Gln Val
1               5

<210> SEQ ID NO 1072
<211> LENGTH: 8
<212> TYPE: PRT
<213> ORGANISM: Human severe acute respiratory syndrome virus

<400> SEQUENCE: 1072

Gln Leu Ser Leu Leu Gln Val Thr
1               5

<210> SEQ ID NO 1073
<211> LENGTH: 8
<212> TYPE: PRT
<213> ORGANISM: Human severe acute respiratory syndrome virus

<400> SEQUENCE: 1073

Leu Ser Leu Leu Gln Val Thr Ala
1               5

<210> SEQ ID NO 1074
<211> LENGTH: 8
```

```
<212> TYPE: PRT
<213> ORGANISM: Human severe acute respiratory syndrome virus

<400> SEQUENCE: 1074

Ser Leu Leu Gln Val Thr Ala Phe
1               5

<210> SEQ ID NO 1075
<211> LENGTH: 8
<212> TYPE: PRT
<213> ORGANISM: Human severe acute respiratory syndrome virus

<400> SEQUENCE: 1075

Leu Leu Gln Val Thr Ala Phe Gln
1               5

<210> SEQ ID NO 1076
<211> LENGTH: 8
<212> TYPE: PRT
<213> ORGANISM: Human severe acute respiratory syndrome virus

<400> SEQUENCE: 1076

Leu Gln Val Thr Ala Phe Gln His
1               5

<210> SEQ ID NO 1077
<211> LENGTH: 8
<212> TYPE: PRT
<213> ORGANISM: Human severe acute respiratory syndrome virus

<400> SEQUENCE: 1077

Gln Val Thr Ala Phe Gln His Gln
1               5

<210> SEQ ID NO 1078
<211> LENGTH: 8
<212> TYPE: PRT
<213> ORGANISM: Human severe acute respiratory syndrome virus

<400> SEQUENCE: 1078

Ser Thr Ala Leu Gln Glu Leu Gln
1               5

<210> SEQ ID NO 1079
<211> LENGTH: 8
<212> TYPE: PRT
<213> ORGANISM: Human severe acute respiratory syndrome virus

<400> SEQUENCE: 1079

Thr Ala Leu Gln Glu Leu Gln Ile
1               5

<210> SEQ ID NO 1080
<211> LENGTH: 8
<212> TYPE: PRT
<213> ORGANISM: Human severe acute respiratory syndrome virus

<400> SEQUENCE: 1080

Ala Leu Gln Glu Leu Gln Ile Gln
1               5

<210> SEQ ID NO 1081
<211> LENGTH: 8
<212> TYPE: PRT
<213> ORGANISM: Human severe acute respiratory syndrome virus
```

-continued

```
<400> SEQUENCE: 1081

Leu Gln Glu Leu Gln Ile Gln Gln
1               5

<210> SEQ ID NO 1082
<211> LENGTH: 8
<212> TYPE: PRT
<213> ORGANISM: Human severe acute respiratory syndrome virus

<400> SEQUENCE: 1082

Gln Glu Leu Gln Ile Gln Gln Trp
1               5

<210> SEQ ID NO 1083
<211> LENGTH: 8
<212> TYPE: PRT
<213> ORGANISM: Human severe acute respiratory syndrome virus

<400> SEQUENCE: 1083

Glu Leu Gln Ile Gln Gln Trp Ile
1               5

<210> SEQ ID NO 1084
<211> LENGTH: 8
<212> TYPE: PRT
<213> ORGANISM: Human severe acute respiratory syndrome virus

<400> SEQUENCE: 1084

Leu Gln Ile Gln Gln Trp Ile Gln
1               5

<210> SEQ ID NO 1085
<211> LENGTH: 8
<212> TYPE: PRT
<213> ORGANISM: Human severe acute respiratory syndrome virus

<400> SEQUENCE: 1085

Gln Ile Gln Gln Trp Ile Gln Phe
1               5

<210> SEQ ID NO 1086
<211> LENGTH: 8
<212> TYPE: PRT
<213> ORGANISM: Human severe acute respiratory syndrome virus

<400> SEQUENCE: 1086

Leu Leu Ile Gln Gln Trp Ile Gln
1               5

<210> SEQ ID NO 1087
<211> LENGTH: 8
<212> TYPE: PRT
<213> ORGANISM: Human severe acute respiratory syndrome virus

<400> SEQUENCE: 1087

Leu Ile Gln Gln Trp Ile Gln Phe
1               5

<210> SEQ ID NO 1088
<211> LENGTH: 8
<212> TYPE: PRT
<213> ORGANISM: Human severe acute respiratory syndrome virus

<400> SEQUENCE: 1088

Gln Asp Ala Val Ala Ser Lys Ile
```

```
<210> SEQ ID NO 1089
<211> LENGTH: 8
<212> TYPE: PRT
<213> ORGANISM: Human severe acute respiratory syndrome virus

<400> SEQUENCE: 1089

Asp Ala Val Ala Ser Lys Ile Leu
1               5

<210> SEQ ID NO 1090
<211> LENGTH: 8
<212> TYPE: PRT
<213> ORGANISM: Human severe acute respiratory syndrome virus

<400> SEQUENCE: 1090

Tyr Val Asp Thr Glu Asn Asn Leu
1               5

<210> SEQ ID NO 1091
<211> LENGTH: 8
<212> TYPE: PRT
<213> ORGANISM: Human severe acute respiratory syndrome virus

<400> SEQUENCE: 1091

Leu Ala Cys Phe Val Leu Ala Val
1               5

<210> SEQ ID NO 1092
<211> LENGTH: 8
<212> TYPE: PRT
<213> ORGANISM: Human severe acute respiratory syndrome virus

<400> SEQUENCE: 1092

Ala Cys Phe Val Leu Ala Val Val
1               5

<210> SEQ ID NO 1093
<211> LENGTH: 8
<212> TYPE: PRT
<213> ORGANISM: Human severe acute respiratory syndrome virus

<400> SEQUENCE: 1093

Cys Phe Val Leu Ala Val Val Tyr
1               5

<210> SEQ ID NO 1094
<211> LENGTH: 8
<212> TYPE: PRT
<213> ORGANISM: Human severe acute respiratory syndrome virus

<400> SEQUENCE: 1094

Phe Val Leu Ala Val Val Tyr Arg
1               5

<210> SEQ ID NO 1095
<211> LENGTH: 8
<212> TYPE: PRT
<213> ORGANISM: Human severe acute respiratory syndrome virus

<400> SEQUENCE: 1095

Val Leu Ala Val Val Tyr Arg Ile
1               5
```

```
<210> SEQ ID NO 1096
<211> LENGTH: 8
<212> TYPE: PRT
<213> ORGANISM: Human severe acute respiratory syndrome virus

<400> SEQUENCE: 1096

Leu Ala Val Val Tyr Arg Ile Asn
1               5

<210> SEQ ID NO 1097
<211> LENGTH: 8
<212> TYPE: PRT
<213> ORGANISM: Human severe acute respiratory syndrome virus

<400> SEQUENCE: 1097

Ala Val Val Tyr Arg Ile Asn Trp
1               5

<210> SEQ ID NO 1098
<211> LENGTH: 8
<212> TYPE: PRT
<213> ORGANISM: Human severe acute respiratory syndrome virus

<400> SEQUENCE: 1098

Val Val Tyr Arg Ile Asn Trp Val
1               5

<210> SEQ ID NO 1099
<211> LENGTH: 8
<212> TYPE: PRT
<213> ORGANISM: Human severe acute respiratory syndrome virus

<400> SEQUENCE: 1099

His Leu Arg Met Ala Gly His Pro
1               5

<210> SEQ ID NO 1100
<211> LENGTH: 8
<212> TYPE: PRT
<213> ORGANISM: Human severe acute respiratory syndrome virus

<400> SEQUENCE: 1100

Leu Arg Met Ala Gly His Pro Leu
1               5

<210> SEQ ID NO 1101
<211> LENGTH: 8
<212> TYPE: PRT
<213> ORGANISM: Human severe acute respiratory syndrome virus

<400> SEQUENCE: 1101

Arg Met Ala Gly His Pro Leu Gly
1               5

<210> SEQ ID NO 1102
<211> LENGTH: 8
<212> TYPE: PRT
<213> ORGANISM: Human severe acute respiratory syndrome virus

<400> SEQUENCE: 1102

Met Ala Gly His Pro Leu Gly Arg
1               5

<210> SEQ ID NO 1103
<211> LENGTH: 8
<212> TYPE: PRT
```

<213> ORGANISM: Human severe acute respiratory syndrome virus

<400> SEQUENCE: 1103

Ala Gly His Pro Leu Gly Arg Cys
1               5

<210> SEQ ID NO 1104
<211> LENGTH: 8
<212> TYPE: PRT
<213> ORGANISM: Human severe acute respiratory syndrome virus

<400> SEQUENCE: 1104

Gly His Pro Leu Gly Arg Cys Asp
1               5

<210> SEQ ID NO 1105
<211> LENGTH: 8
<212> TYPE: PRT
<213> ORGANISM: Human severe acute respiratory syndrome virus

<400> SEQUENCE: 1105

His Pro Leu Gly Arg Cys Asp Ile
1               5

<210> SEQ ID NO 1106
<211> LENGTH: 8
<212> TYPE: PRT
<213> ORGANISM: Human severe acute respiratory syndrome virus

<400> SEQUENCE: 1106

Pro Leu Gly Arg Cys Asp Ile Lys
1               5

<210> SEQ ID NO 1107
<211> LENGTH: 8
<212> TYPE: PRT
<213> ORGANISM: Human severe acute respiratory syndrome virus

<400> SEQUENCE: 1107

Leu Cys Trp Lys Cys Lys Ser Gln
1               5

<210> SEQ ID NO 1108
<211> LENGTH: 8
<212> TYPE: PRT
<213> ORGANISM: Human severe acute respiratory syndrome virus

<400> SEQUENCE: 1108

Cys Trp Lys Cys Lys Ser Gln Asn
1               5

<210> SEQ ID NO 1109
<211> LENGTH: 8
<212> TYPE: PRT
<213> ORGANISM: Human severe acute respiratory syndrome virus

<400> SEQUENCE: 1109

Trp Lys Cys Lys Ser Gln Asn Pro
1               5

<210> SEQ ID NO 1110
<211> LENGTH: 8
<212> TYPE: PRT
<213> ORGANISM: Human severe acute respiratory syndrome virus

<400> SEQUENCE: 1110

```
Lys Cys Lys Ser Gln Asn Pro Leu
1               5
```

<210> SEQ ID NO 1111
<211> LENGTH: 8
<212> TYPE: PRT
<213> ORGANISM: Human severe acute respiratory syndrome virus

<400> SEQUENCE: 1111

```
Cys Lys Ser Gln Asn Pro Leu Leu
1               5
```

<210> SEQ ID NO 1112
<211> LENGTH: 8
<212> TYPE: PRT
<213> ORGANISM: Human severe acute respiratory syndrome virus

<400> SEQUENCE: 1112

```
Lys Ser Gln Asn Pro Leu Leu Tyr
1               5
```

<210> SEQ ID NO 1113
<211> LENGTH: 8
<212> TYPE: PRT
<213> ORGANISM: Human severe acute respiratory syndrome virus

<400> SEQUENCE: 1113

```
Ser Gln Asn Pro Leu Leu Tyr Asp
1               5
```

<210> SEQ ID NO 1114
<211> LENGTH: 8
<212> TYPE: PRT
<213> ORGANISM: Human severe acute respiratory syndrome virus

<400> SEQUENCE: 1114

```
Gln Asn Pro Leu Leu Tyr Asp Ala
1               5
```

<210> SEQ ID NO 1115
<211> LENGTH: 8
<212> TYPE: PRT
<213> ORGANISM: Human severe acute respiratory syndrome virus

<400> SEQUENCE: 1115

```
Thr Asp Thr Ile Val Val Thr Ala
1               5
```

<210> SEQ ID NO 1116
<211> LENGTH: 8
<212> TYPE: PRT
<213> ORGANISM: Human severe acute respiratory syndrome virus

<400> SEQUENCE: 1116

```
Asp Thr Ile Val Val Thr Ala Gly
1               5
```

<210> SEQ ID NO 1117
<211> LENGTH: 8
<212> TYPE: PRT
<213> ORGANISM: Human severe acute respiratory syndrome virus

<400> SEQUENCE: 1117

```
Thr Ile Val Val Thr Ala Gly Asp
1               5
```

<210> SEQ ID NO 1118
<211> LENGTH: 8
<212> TYPE: PRT
<213> ORGANISM: Human severe acute respiratory syndrome virus

<400> SEQUENCE: 1118

Ile Val Val Thr Ala Gly Asp Gly
1               5

<210> SEQ ID NO 1119
<211> LENGTH: 8
<212> TYPE: PRT
<213> ORGANISM: Human severe acute respiratory syndrome virus

<400> SEQUENCE: 1119

Val Val Thr Ala Gly Asp Gly Ile
1               5

<210> SEQ ID NO 1120
<211> LENGTH: 8
<212> TYPE: PRT
<213> ORGANISM: Human severe acute respiratory syndrome virus

<400> SEQUENCE: 1120

Val Thr Ala Gly Asp Gly Ile Ser
1               5

<210> SEQ ID NO 1121
<211> LENGTH: 8
<212> TYPE: PRT
<213> ORGANISM: Human severe acute respiratory syndrome virus

<400> SEQUENCE: 1121

Thr Ala Gly Asp Gly Ile Ser Thr
1               5

<210> SEQ ID NO 1122
<211> LENGTH: 8
<212> TYPE: PRT
<213> ORGANISM: Human severe acute respiratory syndrome virus

<400> SEQUENCE: 1122

Ala Gly Asp Gly Ile Ser Thr Pro
1               5

<210> SEQ ID NO 1123
<211> LENGTH: 8
<212> TYPE: PRT
<213> ORGANISM: Human severe acute respiratory syndrome virus

<400> SEQUENCE: 1123

Ile Gly Gly Tyr Ser Glu Asp Trp
1               5

<210> SEQ ID NO 1124
<211> LENGTH: 8
<212> TYPE: PRT
<213> ORGANISM: Human severe acute respiratory syndrome virus

<400> SEQUENCE: 1124

Gly Gly Tyr Ser Glu Asp Trp His
1               5

<210> SEQ ID NO 1125

-continued

```
<211> LENGTH: 8
<212> TYPE: PRT
<213> ORGANISM: Human severe acute respiratory syndrome virus

<400> SEQUENCE: 1125

Gly Tyr Ser Glu Asp Trp His Ser
1               5

<210> SEQ ID NO 1126
<211> LENGTH: 8
<212> TYPE: PRT
<213> ORGANISM: Human severe acute respiratory syndrome virus

<400> SEQUENCE: 1126

Tyr Ser Glu Asp Trp His Ser Gly
1               5

<210> SEQ ID NO 1127
<211> LENGTH: 8
<212> TYPE: PRT
<213> ORGANISM: Human severe acute respiratory syndrome virus

<400> SEQUENCE: 1127

Ser Glu Asp Trp His Ser Gly Val
1               5

<210> SEQ ID NO 1128
<211> LENGTH: 8
<212> TYPE: PRT
<213> ORGANISM: Human severe acute respiratory syndrome virus

<400> SEQUENCE: 1128

Glu Asp Trp His Ser Gly Val Lys
1               5

<210> SEQ ID NO 1129
<211> LENGTH: 8
<212> TYPE: PRT
<213> ORGANISM: Human severe acute respiratory syndrome virus

<400> SEQUENCE: 1129

Asp Trp His Ser Gly Val Lys Asp
1               5

<210> SEQ ID NO 1130
<211> LENGTH: 8
<212> TYPE: PRT
<213> ORGANISM: Human severe acute respiratory syndrome virus

<400> SEQUENCE: 1130

Trp His Ser Gly Val Lys Asp Tyr
1               5

<210> SEQ ID NO 1131
<211> LENGTH: 8
<212> TYPE: PRT
<213> ORGANISM: Human severe acute respiratory syndrome virus

<400> SEQUENCE: 1131

Phe Met Arg Phe Phe Thr Leu Arg
1               5

<210> SEQ ID NO 1132
<211> LENGTH: 8
<212> TYPE: PRT
<213> ORGANISM: Human severe acute respiratory syndrome virus
```

```
<400> SEQUENCE: 1132

Met Arg Phe Phe Thr Leu Arg Ser
1               5

<210> SEQ ID NO 1133
<211> LENGTH: 8
<212> TYPE: PRT
<213> ORGANISM: Human severe acute respiratory syndrome virus

<400> SEQUENCE: 1133

Arg Phe Phe Thr Leu Arg Ser Ile
1               5

<210> SEQ ID NO 1134
<211> LENGTH: 8
<212> TYPE: PRT
<213> ORGANISM: Human severe acute respiratory syndrome virus

<400> SEQUENCE: 1134

Phe Phe Thr Leu Arg Ser Ile Thr
1               5

<210> SEQ ID NO 1135
<211> LENGTH: 8
<212> TYPE: PRT
<213> ORGANISM: Human severe acute respiratory syndrome virus

<400> SEQUENCE: 1135

Phe Thr Leu Arg Ser Ile Thr Ala
1               5

<210> SEQ ID NO 1136
<211> LENGTH: 8
<212> TYPE: PRT
<213> ORGANISM: Human severe acute respiratory syndrome virus

<400> SEQUENCE: 1136

Thr Leu Arg Ser Ile Thr Ala Gln
1               5

<210> SEQ ID NO 1137
<211> LENGTH: 8
<212> TYPE: PRT
<213> ORGANISM: Human severe acute respiratory syndrome virus

<400> SEQUENCE: 1137

Leu Arg Ser Ile Thr Ala Gln Pro
1               5

<210> SEQ ID NO 1138
<211> LENGTH: 8
<212> TYPE: PRT
<213> ORGANISM: Human severe acute respiratory syndrome virus

<400> SEQUENCE: 1138

Arg Ser Ile Thr Ala Gln Pro Val
1               5

<210> SEQ ID NO 1139
<211> LENGTH: 8
<212> TYPE: PRT
<213> ORGANISM: Human severe acute respiratory syndrome virus

<400> SEQUENCE: 1139
```

```
Arg Ser Ser Ser Arg Ser Arg Cys
1               5

<210> SEQ ID NO 1140
<211> LENGTH: 8
<212> TYPE: PRT
<213> ORGANISM: Human severe acute respiratory syndrome virus

<400> SEQUENCE: 1140

Ser Ser Ser Arg Ser Arg Cys Asn
1               5

<210> SEQ ID NO 1141
<211> LENGTH: 8
<212> TYPE: PRT
<213> ORGANISM: Human severe acute respiratory syndrome virus

<400> SEQUENCE: 1141

Ser Ser Arg Ser Arg Cys Asn Ser
1               5

<210> SEQ ID NO 1142
<211> LENGTH: 8
<212> TYPE: PRT
<213> ORGANISM: Human severe acute respiratory syndrome virus

<400> SEQUENCE: 1142

Ser Arg Ser Arg Cys Asn Ser Arg
1               5

<210> SEQ ID NO 1143
<211> LENGTH: 8
<212> TYPE: PRT
<213> ORGANISM: Human severe acute respiratory syndrome virus

<400> SEQUENCE: 1143

Arg Ser Arg Cys Asn Ser Arg Asn
1               5

<210> SEQ ID NO 1144
<211> LENGTH: 8
<212> TYPE: PRT
<213> ORGANISM: Human severe acute respiratory syndrome virus

<400> SEQUENCE: 1144

Ser Arg Cys Asn Ser Arg Asn Ser
1               5

<210> SEQ ID NO 1145
<211> LENGTH: 8
<212> TYPE: PRT
<213> ORGANISM: Human severe acute respiratory syndrome virus

<400> SEQUENCE: 1145

Arg Cys Asn Ser Arg Asn Ser Thr
1               5

<210> SEQ ID NO 1146
<211> LENGTH: 8
<212> TYPE: PRT
<213> ORGANISM: Human severe acute respiratory syndrome virus

<400> SEQUENCE: 1146

Cys Asn Ser Arg Asn Ser Thr Pro
1               5
```

```
<210> SEQ ID NO 1147
<211> LENGTH: 8
<212> TYPE: PRT
<213> ORGANISM: Human severe acute respiratory syndrome virus

<400> SEQUENCE: 1147

Pro Gln Gly Leu Pro Asn Asn Ile
1               5

<210> SEQ ID NO 1148
<211> LENGTH: 8
<212> TYPE: PRT
<213> ORGANISM: Human severe acute respiratory syndrome virus

<400> SEQUENCE: 1148

Gln Gly Leu Pro Asn Asn Ile Ala
1               5

<210> SEQ ID NO 1149
<211> LENGTH: 8
<212> TYPE: PRT
<213> ORGANISM: Human severe acute respiratory syndrome virus

<400> SEQUENCE: 1149

Gly Leu Pro Asn Asn Ile Ala Ser
1               5

<210> SEQ ID NO 1150
<211> LENGTH: 8
<212> TYPE: PRT
<213> ORGANISM: Human severe acute respiratory syndrome virus

<400> SEQUENCE: 1150

Leu Pro Asn Asn Ile Ala Ser Trp
1               5

<210> SEQ ID NO 1151
<211> LENGTH: 8
<212> TYPE: PRT
<213> ORGANISM: Human severe acute respiratory syndrome virus

<400> SEQUENCE: 1151

Pro Asn Asn Ile Ala Ser Trp Phe
1               5

<210> SEQ ID NO 1152
<211> LENGTH: 8
<212> TYPE: PRT
<213> ORGANISM: Human severe acute respiratory syndrome virus

<400> SEQUENCE: 1152

Asn Asn Ile Ala Ser Trp Phe Thr
1               5

<210> SEQ ID NO 1153
<211> LENGTH: 8
<212> TYPE: PRT
<213> ORGANISM: Human severe acute respiratory syndrome virus

<400> SEQUENCE: 1153

Asn Ile Ala Ser Trp Phe Thr Ala
1               5

<210> SEQ ID NO 1154
<211> LENGTH: 8
```

```
<212> TYPE: PRT
<213> ORGANISM: Human severe acute respiratory syndrome virus

<400> SEQUENCE: 1154

Ile Ala Ser Trp Phe Thr Ala Leu
1               5

<210> SEQ ID NO 1155
<211> LENGTH: 8
<212> TYPE: PRT
<213> ORGANISM: Human severe acute respiratory syndrome virus

<400> SEQUENCE: 1155

His Thr Ser Pro Asp Val Asp Phe
1               5

<210> SEQ ID NO 1156
<211> LENGTH: 8
<212> TYPE: PRT
<213> ORGANISM: Human severe acute respiratory syndrome virus

<400> SEQUENCE: 1156

Thr Ser Pro Asp Val Asp Phe Gly
1               5

<210> SEQ ID NO 1157
<211> LENGTH: 8
<212> TYPE: PRT
<213> ORGANISM: Human severe acute respiratory syndrome virus

<400> SEQUENCE: 1157

Ser Pro Asp Val Asp Phe Gly Asp
1               5

<210> SEQ ID NO 1158
<211> LENGTH: 8
<212> TYPE: PRT
<213> ORGANISM: Human severe acute respiratory syndrome virus

<400> SEQUENCE: 1158

Pro Asp Val Asp Phe Gly Asp Ile
1               5

<210> SEQ ID NO 1159
<211> LENGTH: 8
<212> TYPE: PRT
<213> ORGANISM: Human severe acute respiratory syndrome virus

<400> SEQUENCE: 1159

Asp Val Asp Phe Gly Asp Ile Ser
1               5

<210> SEQ ID NO 1160
<211> LENGTH: 8
<212> TYPE: PRT
<213> ORGANISM: Human severe acute respiratory syndrome virus

<400> SEQUENCE: 1160

Val Asp Phe Gly Asp Ile Ser Gly
1               5

<210> SEQ ID NO 1161
<211> LENGTH: 8
<212> TYPE: PRT
<213> ORGANISM: Human severe acute respiratory syndrome virus
```

```
<400> SEQUENCE: 1161

Asp Phe Gly Asp Ile Ser Gly Ile
1               5

<210> SEQ ID NO 1162
<211> LENGTH: 8
<212> TYPE: PRT
<213> ORGANISM: Human severe acute respiratory syndrome virus

<400> SEQUENCE: 1162

Phe Gly Asp Ile Ser Gly Ile Asn
1               5

<210> SEQ ID NO 1163
<211> LENGTH: 8
<212> TYPE: PRT
<213> ORGANISM: Human severe acute respiratory syndrome virus

<400> SEQUENCE: 1163

Arg Ala Ile Leu Thr Ala Phe Leu
1               5

<210> SEQ ID NO 1164
<211> LENGTH: 8
<212> TYPE: PRT
<213> ORGANISM: Human severe acute respiratory syndrome virus

<400> SEQUENCE: 1164

Ala Ile Leu Thr Ala Phe Leu Pro
1               5

<210> SEQ ID NO 1165
<211> LENGTH: 8
<212> TYPE: PRT
<213> ORGANISM: Human severe acute respiratory syndrome virus

<400> SEQUENCE: 1165

Ile Leu Thr Ala Phe Leu Pro Ala
1               5

<210> SEQ ID NO 1166
<211> LENGTH: 8
<212> TYPE: PRT
<213> ORGANISM: Human severe acute respiratory syndrome virus

<400> SEQUENCE: 1166

Leu Thr Ala Phe Leu Pro Ala Gln
1               5

<210> SEQ ID NO 1167
<211> LENGTH: 8
<212> TYPE: PRT
<213> ORGANISM: Human severe acute respiratory syndrome virus

<400> SEQUENCE: 1167

Thr Ala Phe Leu Pro Ala Gln Asp
1               5

<210> SEQ ID NO 1168
<211> LENGTH: 8
<212> TYPE: PRT
<213> ORGANISM: Human severe acute respiratory syndrome virus

<400> SEQUENCE: 1168

Ala Phe Leu Pro Ala Gln Asp Thr
```

```
1               5

<210> SEQ ID NO 1169
<211> LENGTH: 8
<212> TYPE: PRT
<213> ORGANISM: Human severe acute respiratory syndrome virus

<400> SEQUENCE: 1169

Phe Leu Pro Ala Gln Asp Thr Trp
1               5

<210> SEQ ID NO 1170
<211> LENGTH: 8
<212> TYPE: PRT
<213> ORGANISM: Human severe acute respiratory syndrome virus

<400> SEQUENCE: 1170

Leu Pro Ala Gln Asp Thr Trp Gly
1               5

<210> SEQ ID NO 1171
<211> LENGTH: 8
<212> TYPE: PRT
<213> ORGANISM: Human severe acute respiratory syndrome virus

<400> SEQUENCE: 1171

Asn Phe Arg Val Val Pro Ser Arg
1               5

<210> SEQ ID NO 1172
<211> LENGTH: 8
<212> TYPE: PRT
<213> ORGANISM: Human severe acute respiratory syndrome virus

<400> SEQUENCE: 1172

Phe Arg Val Val Pro Ser Arg Asp
1               5

<210> SEQ ID NO 1173
<211> LENGTH: 8
<212> TYPE: PRT
<213> ORGANISM: Human severe acute respiratory syndrome virus

<400> SEQUENCE: 1173

Arg Val Val Pro Ser Arg Asp Val
1               5

<210> SEQ ID NO 1174
<211> LENGTH: 8
<212> TYPE: PRT
<213> ORGANISM: Human severe acute respiratory syndrome virus

<400> SEQUENCE: 1174

Val Val Pro Ser Arg Asp Val Val
1               5

<210> SEQ ID NO 1175
<211> LENGTH: 8
<212> TYPE: PRT
<213> ORGANISM: Human severe acute respiratory syndrome virus

<400> SEQUENCE: 1175

Val Pro Ser Arg Asp Val Val Arg
1               5
```

```
<210> SEQ ID NO 1176
<211> LENGTH: 8
<212> TYPE: PRT
<213> ORGANISM: Human severe acute respiratory syndrome virus

<400> SEQUENCE: 1176

Pro Ser Arg Asp Val Val Arg Phe
1               5

<210> SEQ ID NO 1177
<211> LENGTH: 8
<212> TYPE: PRT
<213> ORGANISM: Human severe acute respiratory syndrome virus

<400> SEQUENCE: 1177

Ser Arg Asp Val Val Arg Phe Pro
1               5

<210> SEQ ID NO 1178
<211> LENGTH: 8
<212> TYPE: PRT
<213> ORGANISM: Human severe acute respiratory syndrome virus

<400> SEQUENCE: 1178

Arg Asp Val Val Arg Phe Pro Asn
1               5

<210> SEQ ID NO 1179
<211> LENGTH: 8
<212> TYPE: PRT
<213> ORGANISM: Human severe acute respiratory syndrome virus

<400> SEQUENCE: 1179

Val Tyr Ala Trp Glu Arg Lys Arg
1               5

<210> SEQ ID NO 1180
<211> LENGTH: 8
<212> TYPE: PRT
<213> ORGANISM: Human severe acute respiratory syndrome virus

<400> SEQUENCE: 1180

Tyr Ala Trp Glu Arg Lys Arg Ile
1               5

<210> SEQ ID NO 1181
<211> LENGTH: 8
<212> TYPE: PRT
<213> ORGANISM: Human severe acute respiratory syndrome virus

<400> SEQUENCE: 1181

Ala Trp Glu Arg Lys Arg Ile Ser
1               5

<210> SEQ ID NO 1182
<211> LENGTH: 8
<212> TYPE: PRT
<213> ORGANISM: Human severe acute respiratory syndrome virus

<400> SEQUENCE: 1182

Trp Glu Arg Lys Arg Ile Ser Asn
1               5

<210> SEQ ID NO 1183
<211> LENGTH: 8
<212> TYPE: PRT
```

<213> ORGANISM: Human severe acute respiratory syndrome virus

<400> SEQUENCE: 1183

Glu Arg Lys Arg Ile Ser Asn Cys
1               5

<210> SEQ ID NO 1184
<211> LENGTH: 8
<212> TYPE: PRT
<213> ORGANISM: Human severe acute respiratory syndrome virus

<400> SEQUENCE: 1184

Arg Lys Arg Ile Ser Asn Cys Val
1               5

<210> SEQ ID NO 1185
<211> LENGTH: 8
<212> TYPE: PRT
<213> ORGANISM: Human severe acute respiratory syndrome virus

<400> SEQUENCE: 1185

Lys Arg Ile Ser Asn Cys Val Ala
1               5

<210> SEQ ID NO 1186
<211> LENGTH: 8
<212> TYPE: PRT
<213> ORGANISM: Human severe acute respiratory syndrome virus

<400> SEQUENCE: 1186

Arg Ile Ser Asn Cys Val Ala Asp
1               5

<210> SEQ ID NO 1187
<211> LENGTH: 8
<212> TYPE: PRT
<213> ORGANISM: Human severe acute respiratory syndrome virus

<400> SEQUENCE: 1187

Tyr Arg Val Val Val Leu Ser Tyr
1               5

<210> SEQ ID NO 1188
<211> LENGTH: 8
<212> TYPE: PRT
<213> ORGANISM: Human severe acute respiratory syndrome virus

<400> SEQUENCE: 1188

Arg Val Val Val Leu Ser Tyr Glu
1               5

<210> SEQ ID NO 1189
<211> LENGTH: 8
<212> TYPE: PRT
<213> ORGANISM: Human severe acute respiratory syndrome virus

<400> SEQUENCE: 1189

Val Val Val Leu Ser Tyr Glu Leu
1               5

<210> SEQ ID NO 1190
<211> LENGTH: 8
<212> TYPE: PRT
<213> ORGANISM: Human severe acute respiratory syndrome virus

<400> SEQUENCE: 1190

Val Val Leu Ser Tyr Glu Leu Leu
1               5

<210> SEQ ID NO 1191
<211> LENGTH: 8
<212> TYPE: PRT
<213> ORGANISM: Human severe acute respiratory syndrome virus

<400> SEQUENCE: 1191

Val Leu Ser Tyr Glu Leu Leu Asn
1               5

<210> SEQ ID NO 1192
<211> LENGTH: 8
<212> TYPE: PRT
<213> ORGANISM: Human severe acute respiratory syndrome virus

<400> SEQUENCE: 1192

Leu Ser Tyr Glu Leu Leu Asn Ala
1               5

<210> SEQ ID NO 1193
<211> LENGTH: 8
<212> TYPE: PRT
<213> ORGANISM: Human severe acute respiratory syndrome virus

<400> SEQUENCE: 1193

Ser Tyr Glu Leu Leu Asn Ala Pro
1               5

<210> SEQ ID NO 1194
<211> LENGTH: 8
<212> TYPE: PRT
<213> ORGANISM: Human severe acute respiratory syndrome virus

<400> SEQUENCE: 1194

Tyr Glu Leu Leu Asn Ala Pro Ala
1               5

<210> SEQ ID NO 1195
<211> LENGTH: 8
<212> TYPE: PRT
<213> ORGANISM: Human severe acute respiratory syndrome virus

<400> SEQUENCE: 1195

Tyr Lys Thr Pro Thr Leu Lys Asp
1               5

<210> SEQ ID NO 1196
<211> LENGTH: 8
<212> TYPE: PRT
<213> ORGANISM: Human severe acute respiratory syndrome virus

<400> SEQUENCE: 1196

Lys Thr Pro Thr Leu Lys Asp Phe
1               5

<210> SEQ ID NO 1197
<211> LENGTH: 8
<212> TYPE: PRT
<213> ORGANISM: Human severe acute respiratory syndrome virus

<400> SEQUENCE: 1197

Thr Pro Thr Leu Lys Asp Phe Gly
1               5

<210> SEQ ID NO 1198
<211> LENGTH: 8
<212> TYPE: PRT
<213> ORGANISM: Human severe acute respiratory syndrome virus

<400> SEQUENCE: 1198

Pro Thr Leu Lys Asp Phe Gly Gly
1               5

<210> SEQ ID NO 1199
<211> LENGTH: 8
<212> TYPE: PRT
<213> ORGANISM: Human severe acute respiratory syndrome virus

<400> SEQUENCE: 1199

Thr Leu Lys Asp Phe Gly Gly Phe
1               5

<210> SEQ ID NO 1200
<211> LENGTH: 8
<212> TYPE: PRT
<213> ORGANISM: Human severe acute respiratory syndrome virus

<400> SEQUENCE: 1200

Leu Lys Asp Phe Gly Gly Phe Asn
1               5

<210> SEQ ID NO 1201
<211> LENGTH: 8
<212> TYPE: PRT
<213> ORGANISM: Human severe acute respiratory syndrome virus

<400> SEQUENCE: 1201

Lys Asp Phe Gly Gly Phe Asn Phe
1               5

<210> SEQ ID NO 1202
<211> LENGTH: 8
<212> TYPE: PRT
<213> ORGANISM: Human severe acute respiratory syndrome virus

<400> SEQUENCE: 1202

Asp Phe Gly Gly Phe Asn Phe Ser
1               5

<210> SEQ ID NO 1203
<211> LENGTH: 8
<212> TYPE: PRT
<213> ORGANISM: Human severe acute respiratory syndrome virus

<400> SEQUENCE: 1203

Ile Leu Pro Asp Pro Leu Lys Ser
1               5

<210> SEQ ID NO 1204
<211> LENGTH: 8
<212> TYPE: PRT
<213> ORGANISM: Human severe acute respiratory syndrome virus

<400> SEQUENCE: 1204

Leu Pro Asp Pro Leu Lys Ser Thr
1               5

<210> SEQ ID NO 1205

```
<211> LENGTH: 8
<212> TYPE: PRT
<213> ORGANISM: Human severe acute respiratory syndrome virus

<400> SEQUENCE: 1205

Pro Asp Pro Leu Lys Ser Thr Lys
1               5

<210> SEQ ID NO 1206
<211> LENGTH: 8
<212> TYPE: PRT
<213> ORGANISM: Human severe acute respiratory syndrome virus

<400> SEQUENCE: 1206

Asp Pro Leu Lys Ser Thr Lys Arg
1               5

<210> SEQ ID NO 1207
<211> LENGTH: 8
<212> TYPE: PRT
<213> ORGANISM: Human severe acute respiratory syndrome virus

<400> SEQUENCE: 1207

Pro Leu Lys Ser Thr Lys Arg Ser
1               5

<210> SEQ ID NO 1208
<211> LENGTH: 8
<212> TYPE: PRT
<213> ORGANISM: Human severe acute respiratory syndrome virus

<400> SEQUENCE: 1208

Leu Lys Ser Thr Lys Arg Ser Phe
1               5

<210> SEQ ID NO 1209
<211> LENGTH: 8
<212> TYPE: PRT
<213> ORGANISM: Human severe acute respiratory syndrome virus

<400> SEQUENCE: 1209

Lys Ser Thr Lys Arg Ser Phe Ile
1               5

<210> SEQ ID NO 1210
<211> LENGTH: 8
<212> TYPE: PRT
<213> ORGANISM: Human severe acute respiratory syndrome virus

<400> SEQUENCE: 1210

Ser Thr Lys Arg Ser Phe Ile Glu
1               5

<210> SEQ ID NO 1211
<211> LENGTH: 8
<212> TYPE: PRT
<213> ORGANISM: Human severe acute respiratory syndrome virus

<400> SEQUENCE: 1211

Ile Leu Asp Ile Ser Pro Cys Ala
1               5

<210> SEQ ID NO 1212
<211> LENGTH: 8
<212> TYPE: PRT
<213> ORGANISM: Human severe acute respiratory syndrome virus
```

```
<400> SEQUENCE: 1212

Leu Asp Ile Ser Pro Cys Ala Phe
1               5

<210> SEQ ID NO 1213
<211> LENGTH: 8
<212> TYPE: PRT
<213> ORGANISM: Human severe acute respiratory syndrome virus

<400> SEQUENCE: 1213

Asp Ile Ser Pro Cys Ala Phe Gly
1               5

<210> SEQ ID NO 1214
<211> LENGTH: 8
<212> TYPE: PRT
<213> ORGANISM: Human severe acute respiratory syndrome virus

<400> SEQUENCE: 1214

Ile Ser Pro Cys Ala Phe Gly Gly
1               5

<210> SEQ ID NO 1215
<211> LENGTH: 8
<212> TYPE: PRT
<213> ORGANISM: Human severe acute respiratory syndrome virus

<400> SEQUENCE: 1215

Ser Pro Cys Ala Phe Gly Gly Val
1               5

<210> SEQ ID NO 1216
<211> LENGTH: 8
<212> TYPE: PRT
<213> ORGANISM: Human severe acute respiratory syndrome virus

<400> SEQUENCE: 1216

Pro Cys Ala Phe Gly Gly Val Ser
1               5

<210> SEQ ID NO 1217
<211> LENGTH: 8
<212> TYPE: PRT
<213> ORGANISM: Human severe acute respiratory syndrome virus

<400> SEQUENCE: 1217

Cys Ala Phe Gly Gly Val Ser Val
1               5

<210> SEQ ID NO 1218
<211> LENGTH: 8
<212> TYPE: PRT
<213> ORGANISM: Human severe acute respiratory syndrome virus

<400> SEQUENCE: 1218

Ala Phe Gly Gly Val Ser Val Ile
1               5

<210> SEQ ID NO 1219
<211> LENGTH: 8
<212> TYPE: PRT
<213> ORGANISM: Human severe acute respiratory syndrome virus

<400> SEQUENCE: 1219
```

```
Ala Phe Ser Pro Ala Gln Asp Thr
1               5

<210> SEQ ID NO 1220
<211> LENGTH: 8
<212> TYPE: PRT
<213> ORGANISM: Human severe acute respiratory syndrome virus

<400> SEQUENCE: 1220

Phe Ser Pro Ala Gln Asp Thr Trp
1               5

<210> SEQ ID NO 1221
<211> LENGTH: 8
<212> TYPE: PRT
<213> ORGANISM: Human severe acute respiratory syndrome virus

<400> SEQUENCE: 1221

Ser Pro Ala Gln Asp Thr Trp Gly
1               5

<210> SEQ ID NO 1222
<211> LENGTH: 8
<212> TYPE: PRT
<213> ORGANISM: Human severe acute respiratory syndrome virus

<400> SEQUENCE: 1222

Asp Ala Leu Cys Glu Lys Ala Ser
1               5

<210> SEQ ID NO 1223
<211> LENGTH: 8
<212> TYPE: PRT
<213> ORGANISM: Human severe acute respiratory syndrome virus

<400> SEQUENCE: 1223

Ala Leu Cys Glu Lys Ala Ser Lys
1               5

<210> SEQ ID NO 1224
<211> LENGTH: 8
<212> TYPE: PRT
<213> ORGANISM: Human severe acute respiratory syndrome virus

<400> SEQUENCE: 1224

Leu Cys Glu Lys Ala Ser Lys Tyr
1               5

<210> SEQ ID NO 1225
<211> LENGTH: 8
<212> TYPE: PRT
<213> ORGANISM: Human severe acute respiratory syndrome virus

<400> SEQUENCE: 1225

Cys Glu Lys Ala Ser Lys Tyr Leu
1               5

<210> SEQ ID NO 1226
<211> LENGTH: 8
<212> TYPE: PRT
<213> ORGANISM: Human severe acute respiratory syndrome virus

<400> SEQUENCE: 1226

Glu Lys Ala Ser Lys Tyr Leu Pro
1               5
```

```
<210> SEQ ID NO 1227
<211> LENGTH: 8
<212> TYPE: PRT
<213> ORGANISM: Human severe acute respiratory syndrome virus

<400> SEQUENCE: 1227

Lys Ala Ser Lys Tyr Leu Pro Ile
1               5

<210> SEQ ID NO 1228
<211> LENGTH: 8
<212> TYPE: PRT
<213> ORGANISM: Human severe acute respiratory syndrome virus

<400> SEQUENCE: 1228

Ala Ser Lys Tyr Leu Pro Ile Asp
1               5

<210> SEQ ID NO 1229
<211> LENGTH: 8
<212> TYPE: PRT
<213> ORGANISM: Human severe acute respiratory syndrome virus

<400> SEQUENCE: 1229

Ser Lys Tyr Leu Pro Ile Asp Lys
1               5

<210> SEQ ID NO 1230
<211> LENGTH: 8
<212> TYPE: PRT
<213> ORGANISM: Human severe acute respiratory syndrome virus

<400> SEQUENCE: 1230

Ser Val Ile Asp Leu Leu Leu Asn
1               5

<210> SEQ ID NO 1231
<211> LENGTH: 8
<212> TYPE: PRT
<213> ORGANISM: Human severe acute respiratory syndrome virus

<400> SEQUENCE: 1231

Leu Leu Leu Asn Asp Phe Val Glu
1               5

<210> SEQ ID NO 1232
<211> LENGTH: 8
<212> TYPE: PRT
<213> ORGANISM: Human severe acute respiratory syndrome virus

<400> SEQUENCE: 1232

Leu Leu Asn Asp Phe Val Glu Ile
1               5

<210> SEQ ID NO 1233
<211> LENGTH: 8
<212> TYPE: PRT
<213> ORGANISM: Human severe acute respiratory syndrome virus

<400> SEQUENCE: 1233

Leu Asn Asp Phe Val Glu Ile Ile
1               5

<210> SEQ ID NO 1234
<211> LENGTH: 8
```

```
<212> TYPE: PRT
<213> ORGANISM: Human severe acute respiratory syndrome virus

<400> SEQUENCE: 1234

Asn Asp Phe Val Glu Ile Ile Lys
1               5

<210> SEQ ID NO 1235
<211> LENGTH: 8
<212> TYPE: PRT
<213> ORGANISM: Human severe acute respiratory syndrome virus

<400> SEQUENCE: 1235

Leu Val Asp Ser Asp Leu Asn Glu
1               5

<210> SEQ ID NO 1236
<211> LENGTH: 8
<212> TYPE: PRT
<213> ORGANISM: Human severe acute respiratory syndrome virus

<400> SEQUENCE: 1236

Val Asp Ser Asp Leu Asn Glu Phe
1               5

<210> SEQ ID NO 1237
<211> LENGTH: 8
<212> TYPE: PRT
<213> ORGANISM: Human severe acute respiratory syndrome virus

<400> SEQUENCE: 1237

Asp Ser Asp Leu Asn Glu Phe Val
1               5

<210> SEQ ID NO 1238
<211> LENGTH: 8
<212> TYPE: PRT
<213> ORGANISM: Human severe acute respiratory syndrome virus

<400> SEQUENCE: 1238

Ser Asp Leu Asn Glu Phe Val Ser
1               5

<210> SEQ ID NO 1239
<211> LENGTH: 8
<212> TYPE: PRT
<213> ORGANISM: Human severe acute respiratory syndrome virus

<400> SEQUENCE: 1239

Asp Leu Asn Glu Phe Val Ser Asp
1               5

<210> SEQ ID NO 1240
<211> LENGTH: 8
<212> TYPE: PRT
<213> ORGANISM: Human severe acute respiratory syndrome virus

<400> SEQUENCE: 1240

Leu Asn Glu Phe Val Ser Asp Ala
1               5

<210> SEQ ID NO 1241
<211> LENGTH: 8
<212> TYPE: PRT
<213> ORGANISM: Human severe acute respiratory syndrome virus
```

```
<400> SEQUENCE: 1241

Asn Glu Phe Val Ser Asp Ala Asp
1               5

<210> SEQ ID NO 1242
<211> LENGTH: 8
<212> TYPE: PRT
<213> ORGANISM: Human severe acute respiratory syndrome virus

<400> SEQUENCE: 1242

Glu Phe Val Ser Asp Ala Asp Ser
1               5

<210> SEQ ID NO 1243
<211> LENGTH: 8
<212> TYPE: PRT
<213> ORGANISM: Human severe acute respiratory syndrome virus

<400> SEQUENCE: 1243

Ala Asn Tyr Ile Phe Trp Arg Lys
1               5

<210> SEQ ID NO 1244
<211> LENGTH: 8
<212> TYPE: PRT
<213> ORGANISM: Human severe acute respiratory syndrome virus

<400> SEQUENCE: 1244

Asn Tyr Ile Phe Trp Arg Lys Thr
1               5

<210> SEQ ID NO 1245
<211> LENGTH: 8
<212> TYPE: PRT
<213> ORGANISM: Human severe acute respiratory syndrome virus

<400> SEQUENCE: 1245

Tyr Ile Phe Trp Arg Lys Thr Asn
1               5

<210> SEQ ID NO 1246
<211> LENGTH: 8
<212> TYPE: PRT
<213> ORGANISM: Human severe acute respiratory syndrome virus

<400> SEQUENCE: 1246

Ile Phe Trp Arg Lys Thr Asn Pro
1               5

<210> SEQ ID NO 1247
<211> LENGTH: 8
<212> TYPE: PRT
<213> ORGANISM: Human severe acute respiratory syndrome virus

<400> SEQUENCE: 1247

Phe Trp Arg Lys Thr Asn Pro Ile
1               5

<210> SEQ ID NO 1248
<211> LENGTH: 8
<212> TYPE: PRT
<213> ORGANISM: Human severe acute respiratory syndrome virus

<400> SEQUENCE: 1248

Trp Arg Lys Thr Asn Pro Ile Gln
```

-continued 1          5

<210> SEQ ID NO 1249
<211> LENGTH: 8
<212> TYPE: PRT
<213> ORGANISM: Human severe acute respiratory syndrome virus

<400> SEQUENCE: 1249

Arg Lys Thr Asn Pro Ile Gln Leu
1               5

<210> SEQ ID NO 1250
<211> LENGTH: 8
<212> TYPE: PRT
<213> ORGANISM: Human severe acute respiratory syndrome virus

<400> SEQUENCE: 1250

Lys Thr Asn Pro Ile Gln Leu Ser
1               5

<210> SEQ ID NO 1251
<211> LENGTH: 8
<212> TYPE: PRT
<213> ORGANISM: Human severe acute respiratory syndrome virus

<400> SEQUENCE: 1251

Ser Ala Asp Ala Ser Thr Phe Phe
1               5

<210> SEQ ID NO 1252
<211> LENGTH: 8
<212> TYPE: PRT
<213> ORGANISM: Human severe acute respiratory syndrome virus

<400> SEQUENCE: 1252

Ala Asp Ala Ser Thr Phe Phe Lys
1               5

<210> SEQ ID NO 1253
<211> LENGTH: 8
<212> TYPE: PRT
<213> ORGANISM: Human severe acute respiratory syndrome virus

<400> SEQUENCE: 1253

Asp Ala Ser Thr Phe Phe Lys Arg
1               5

<210> SEQ ID NO 1254
<211> LENGTH: 8
<212> TYPE: PRT
<213> ORGANISM: Human severe acute respiratory syndrome virus

<400> SEQUENCE: 1254

Ala Ser Thr Phe Phe Lys Arg Val
1               5

<210> SEQ ID NO 1255
<211> LENGTH: 8
<212> TYPE: PRT
<213> ORGANISM: Human severe acute respiratory syndrome virus

<400> SEQUENCE: 1255

Ser Thr Phe Phe Lys Arg Val Cys
1               5

```
<210> SEQ ID NO 1256
<211> LENGTH: 8
<212> TYPE: PRT
<213> ORGANISM: Human severe acute respiratory syndrome virus

<400> SEQUENCE: 1256

Thr Phe Phe Lys Arg Val Cys Gly
1               5

<210> SEQ ID NO 1257
<211> LENGTH: 8
<212> TYPE: PRT
<213> ORGANISM: Human severe acute respiratory syndrome virus

<400> SEQUENCE: 1257

Phe Phe Lys Arg Val Cys Gly Val
1               5

<210> SEQ ID NO 1258
<211> LENGTH: 8
<212> TYPE: PRT
<213> ORGANISM: Human severe acute respiratory syndrome virus

<400> SEQUENCE: 1258

Phe Lys Arg Val Cys Gly Val Ser
1               5

<210> SEQ ID NO 1259
<211> LENGTH: 8
<212> TYPE: PRT
<213> ORGANISM: Human severe acute respiratory syndrome virus

<400> SEQUENCE: 1259

Lys Arg Val Cys Gly Val Ser Ala
1               5

<210> SEQ ID NO 1260
<211> LENGTH: 8
<212> TYPE: PRT
<213> ORGANISM: Human severe acute respiratory syndrome virus

<400> SEQUENCE: 1260

Glu Leu Phe Tyr Ser Tyr Ala Ile
1               5

<210> SEQ ID NO 1261
<211> LENGTH: 8
<212> TYPE: PRT
<213> ORGANISM: Human severe acute respiratory syndrome virus

<400> SEQUENCE: 1261

Leu Phe Tyr Ser Tyr Ala Ile His
1               5

<210> SEQ ID NO 1262
<211> LENGTH: 8
<212> TYPE: PRT
<213> ORGANISM: Human severe acute respiratory syndrome virus

<400> SEQUENCE: 1262

Phe Tyr Ser Tyr Ala Ile His His
1               5

<210> SEQ ID NO 1263
<211> LENGTH: 8
<212> TYPE: PRT
```

-continued

<213> ORGANISM: Human severe acute respiratory syndrome virus

<400> SEQUENCE: 1263

Tyr Ser Tyr Ala Ile His His Asp
1               5

<210> SEQ ID NO 1264
<211> LENGTH: 8
<212> TYPE: PRT
<213> ORGANISM: Human severe acute respiratory syndrome virus

<400> SEQUENCE: 1264

Ser Tyr Ala Ile His His Asp Lys
1               5

<210> SEQ ID NO 1265
<211> LENGTH: 8
<212> TYPE: PRT
<213> ORGANISM: Human severe acute respiratory syndrome virus

<400> SEQUENCE: 1265

Tyr Ala Ile His His Asp Lys Phe
1               5

<210> SEQ ID NO 1266
<211> LENGTH: 8
<212> TYPE: PRT
<213> ORGANISM: Human severe acute respiratory syndrome virus

<400> SEQUENCE: 1266

Ala Ile His His Asp Lys Phe Thr
1               5

<210> SEQ ID NO 1267
<211> LENGTH: 8
<212> TYPE: PRT
<213> ORGANISM: Human severe acute respiratory syndrome virus

<400> SEQUENCE: 1267

Ile His His Asp Lys Phe Thr Asp
1               5

<210> SEQ ID NO 1268
<211> LENGTH: 14
<212> TYPE: PRT
<213> ORGANISM: Unknown
<220> FEATURE:
<223> OTHER INFORMATION: Illustrative peptide having high affinity for
      its antigen

<400> SEQUENCE: 1268

Gly Ala Thr Pro Glu Asp Leu Asn Gln Lys Leu Ala Gly Asn
1               5                   10

<210> SEQ ID NO 1269
<211> LENGTH: 17
<212> TYPE: PRT
<213> ORGANISM: Tobacco mosaic virus

<400> SEQUENCE: 1269

Cys Arg Gly Thr Gly Ser Tyr Asn Arg Ser Ser Phe Glu Ser Ser Ser
1               5                   10                  15
Gly

<210> SEQ ID NO 1270

```
<211> LENGTH: 15
<212> TYPE: PRT
<213> ORGANISM: Unknown
<220> FEATURE:
<223> OTHER INFORMATION: Illustrative peptide having high affinity for
      its antigen

<400> SEQUENCE: 1270

Asn Tyr Arg Ala Tyr Ala Thr Glu Pro His Ala Lys Lys Lys Ser
1               5                   10                  15

<210> SEQ ID NO 1271
<211> LENGTH: 10
<212> TYPE: PRT
<213> ORGANISM: Homo sapiens

<400> SEQUENCE: 1271

Arg Tyr Asp Ile Glu Ala Lys Val Thr Lys
1               5                   10

<210> SEQ ID NO 1272
<211> LENGTH: 8
<212> TYPE: PRT
<213> ORGANISM: Unknown
<220> FEATURE:
<223> OTHER INFORMATION: Illustrative peptide having high affinity for
      its antigen

<400> SEQUENCE: 1272

Asp Arg Val Tyr Ile His Pro Phe
1               5

<210> SEQ ID NO 1273
<211> LENGTH: 12
<212> TYPE: PRT
<213> ORGANISM: Homo sapiens

<400> SEQUENCE: 1273

Pro Gln Ser Asp Pro Ser Val Glu Pro Pro Leu Ser
1               5                   10

<210> SEQ ID NO 1274
<211> LENGTH: 8
<212> TYPE: PRT
<213> ORGANISM: Artificial Sequence
<220> FEATURE:
<223> OTHER INFORMATION: Synthetic HA tag

<400> SEQUENCE: 1274

Tyr Asp Val Pro Asp Tyr Ala Ser
1               5

<210> SEQ ID NO 1275
<211> LENGTH: 8
<212> TYPE: PRT
<213> ORGANISM: Artificial Sequence
<220> FEATURE:
<223> OTHER INFORMATION: Synthetic FLAG tag

<400> SEQUENCE: 1275

Met Asp Tyr Lys Ala Phe Asp Asn
1               5

<210> SEQ ID NO 1276
<211> LENGTH: 5
<212> TYPE: PRT
<213> ORGANISM: Artificial Sequence
<220> FEATURE:
```

<223> OTHER INFORMATION: Synthetic 5-His tag

<400> SEQUENCE: 1276

His His His His His
1               5

<210> SEQ ID NO 1277
<211> LENGTH: 8
<212> TYPE: PRT
<213> ORGANISM: Homo sapiens

<400> SEQUENCE: 1277

Glu Pro Ala Glu Leu Thr Asp Ala
1               5

<210> SEQ ID NO 1278
<211> LENGTH: 8
<212> TYPE: PRT
<213> ORGANISM: Homo sapiens

<400> SEQUENCE: 1278

Tyr Glu Val Gln Gly Glu Val Phe
1               5

<210> SEQ ID NO 1279
<211> LENGTH: 8
<212> TYPE: PRT
<213> ORGANISM: Homo sapiens

<400> SEQUENCE: 1279

Gly Tyr Ser Ile Phe Ser Tyr Ala
1               5

<210> SEQ ID NO 1280
<211> LENGTH: 12
<212> TYPE: PRT
<213> ORGANISM: Homo sapiens

<400> SEQUENCE: 1280

Leu Ser Glu Pro Ala Glu Leu Thr Asp Ala Val Lys
1               5                   10

<210> SEQ ID NO 1281
<211> LENGTH: 16
<212> TYPE: PRT
<213> ORGANISM: Homo sapiens

<400> SEQUENCE: 1281

Asp Glu Pro Val Glu Leu Thr Ser Ala Pro Thr Gly His Thr Phe Ser
1               5                   10                  15

<210> SEQ ID NO 1282
<211> LENGTH: 17
<212> TYPE: PRT
<213> ORGANISM: Homo sapiens

<400> SEQUENCE: 1282

Ala Gly Glu Ala Ala Glu Leu Gln Asp Ala Glu Val Glu Ser Ser Ala
1               5                   10                  15
Lys

<210> SEQ ID NO 1283
<211> LENGTH: 15
<212> TYPE: PRT
<213> ORGANISM: Homo sapiens

```
<400> SEQUENCE: 1283

Leu Gln Glu Pro Ala Glu Leu Val Glu Ser Asp Gly Val Pro Lys
1               5                   10                  15

<210> SEQ ID NO 1284
<211> LENGTH: 12
<212> TYPE: PRT
<213> ORGANISM: Homo sapiens

<400> SEQUENCE: 1284

Ala Gln Pro Ala Glu Leu Val Asp Ser Ser Gly Trp
1               5                   10

<210> SEQ ID NO 1285
<211> LENGTH: 14
<212> TYPE: PRT
<213> ORGANISM: Homo sapiens

<400> SEQUENCE: 1285

Gly Leu Asp Pro Thr Gln Leu Thr Asp Ala Leu Thr Gln Arg
1               5                   10

<210> SEQ ID NO 1286
<211> LENGTH: 10
<212> TYPE: PRT
<213> ORGANISM: Homo sapiens

<400> SEQUENCE: 1286

Tyr Glu Val Gln Gly Glu Val Phe Thr Lys
1               5                   10

<210> SEQ ID NO 1287
<211> LENGTH: 11
<212> TYPE: PRT
<213> ORGANISM: Homo sapiens

<400> SEQUENCE: 1287

His Val Glu Val Asn Gly Glu Val Phe Gln Lys
1               5                   10

<210> SEQ ID NO 1288
<211> LENGTH: 11
<212> TYPE: PRT
<213> ORGANISM: Homo sapiens

<400> SEQUENCE: 1288

Ser Tyr Glu Val Leu Gly Glu Glu Phe Asp Arg
1               5                   10

<210> SEQ ID NO 1289
<211> LENGTH: 13
<212> TYPE: PRT
<213> ORGANISM: Homo sapiens

<400> SEQUENCE: 1289

Gln Tyr Ala Val Ser Gly Glu Ile Phe Val Val Asp Arg
1               5                   10

<210> SEQ ID NO 1290
<211> LENGTH: 11
<212> TYPE: PRT
<213> ORGANISM: Homo sapiens

<400> SEQUENCE: 1290
```

```
Val Tyr Glu Glu Gln Gly Glu Ile Ile Leu Lys
1               5                   10

<210> SEQ ID NO 1291
<211> LENGTH: 11
<212> TYPE: PRT
<213> ORGANISM: Homo sapiens

<400> SEQUENCE: 1291

Leu Tyr Glu Val Arg Gly Glu Thr Tyr Leu Lys
1               5                   10

<210> SEQ ID NO 1292
<211> LENGTH: 8
<212> TYPE: PRT
<213> ORGANISM: Homo sapiens

<400> SEQUENCE: 1292

Glu Pro Val Glu Leu Thr Ser Ala
1               5

<210> SEQ ID NO 1293
<211> LENGTH: 8
<212> TYPE: PRT
<213> ORGANISM: Homo sapiens

<400> SEQUENCE: 1293

Asp Pro Thr Gln Leu Thr Asp Ala
1               5

<210> SEQ ID NO 1294
<211> LENGTH: 8
<212> TYPE: PRT
<213> ORGANISM: Homo sapiens

<400> SEQUENCE: 1294

Val Glu Val Asn Gly Glu Val Phe
1               5

<210> SEQ ID NO 1295
<211> LENGTH: 8
<212> TYPE: PRT
<213> ORGANISM: Homo sapiens

<400> SEQUENCE: 1295

Tyr Glu Val Leu Gly Glu Glu Phe
1               5

<210> SEQ ID NO 1296
<211> LENGTH: 24
<212> TYPE: PRT
<213> ORGANISM: Homo sapiens

<400> SEQUENCE: 1296

His Ser Gln Pro Trp Gln Val Ala Val Tyr Ser His Gly Trp Ala His
1               5                   10                  15

Cys Gly Gly Val Leu Val His Arg
            20

<210> SEQ ID NO 1297
<211> LENGTH: 33
<212> TYPE: PRT
<213> ORGANISM: Homo sapiens

<400> SEQUENCE: 1297
```

Ile Val Gly Gly Trp Glu Cys Glu Gln His Ser Gln Pro Trp Gln Ala
1               5                   10                  15

Ala Leu Tyr His Phe Ser Thr Phe Gln Cys Gly Gly Ile Leu Val His
                20                  25                  30

Lys

<210> SEQ ID NO 1298
<211> LENGTH: 24
<212> TYPE: PRT
<213> ORGANISM: Homo sapiens

<400> SEQUENCE: 1298

Gly Ser Gln Pro Trp Gln Val Ser Leu Phe Asn Gly Leu Ser Phe His
1               5                   10                  15

Cys Ala Gly Val Leu Val Asp Arg
                20

<210> SEQ ID NO 1299
<211> LENGTH: 16
<212> TYPE: PRT
<213> ORGANISM: Homo sapiens

<400> SEQUENCE: 1299

Asn Ser Gln Pro Trp Gln Val Gly Leu Phe Glu Gly Thr Ser Leu Arg
1               5                   10                  15

<210> SEQ ID NO 1300
<211> LENGTH: 29
<212> TYPE: PRT
<213> ORGANISM: Homo sapiens

<400> SEQUENCE: 1300

His Glu Cys Gln Pro His Ser Gln Pro Trp Gln Ala Ala Leu Phe Gln
1               5                   10                  15

Gly Gln Gln Leu Leu Cys Gly Gly Val Leu Val Gly Arg
                20                  25

<210> SEQ ID NO 1301
<211> LENGTH: 29
<212> TYPE: PRT
<213> ORGANISM: Homo sapiens

<400> SEQUENCE: 1301

Glu Asp Cys Ser Pro His Ser Gln Pro Trp Gln Ala Ala Leu Val Met
1               5                   10                  15

Glu Asn Glu Leu Phe Cys Ser Gly Val Leu Val His Arg
                20                  25

<210> SEQ ID NO 1302
<211> LENGTH: 33
<212> TYPE: PRT
<213> ORGANISM: Homo sapiens

<400> SEQUENCE: 1302

Val Leu Asn Thr Asn Gly Thr Ser Gly Phe Leu Pro Gly Gly Tyr Thr
1               5                   10                  15

Cys Phe Pro His Ser Gln Pro Trp Gln Ala Ala Leu Leu Val Gln Gly
                20                  25                  30

Arg

<210> SEQ ID NO 1303
<211> LENGTH: 21

-continued

```
<212> TYPE: PRT
<213> ORGANISM: Homo sapiens

<400> SEQUENCE: 1303

Leu Leu Glu Gly Asp Glu Cys Ala Pro His Ser Gln Pro Trp Gln Val
1               5                   10                  15

Ala Leu Tyr Glu Arg
            20

<210> SEQ ID NO 1304
<211> LENGTH: 15
<212> TYPE: PRT
<213> ORGANISM: Homo sapiens

<400> SEQUENCE: 1304

Pro Asn Ser Gln Pro Trp Gln Ala Gly Leu Phe His Leu Thr Arg
1               5                   10                  15

<210> SEQ ID NO 1305
<211> LENGTH: 22
<212> TYPE: PRT
<213> ORGANISM: Homo sapiens

<400> SEQUENCE: 1305

Cys Val Thr Ala Gly Thr Ser Cys Leu Ile Ser Gly Trp Gly Ser Thr
1               5                   10                  15

Ser Ser Pro Gln Leu Arg
            20

<210> SEQ ID NO 1306
<211> LENGTH: 32
<212> TYPE: PRT
<213> ORGANISM: Homo sapiens

<400> SEQUENCE: 1306

Val Met Asp Leu Pro Thr Gln Glu Pro Ala Leu Gly Thr Thr Cys Tyr
1               5                   10                  15

Ala Ser Gly Trp Gly Ser Ile Glu Pro Glu Glu Phe Leu Thr Pro Lys
            20                  25                  30

<210> SEQ ID NO 1307
<211> LENGTH: 44
<212> TYPE: PRT
<213> ORGANISM: Homo sapiens

<400> SEQUENCE: 1307

Arg Leu Asn Pro Gln Val Arg Pro Ala Val Leu Pro Thr Arg Cys Pro
1               5                   10                  15

His Pro Gly Glu Ala Cys Val Val Ser Gly Trp Gly Leu Val Ser His
            20                  25                  30

Glu Pro Gly Thr Ala Gly Ser Pro Arg Ser Gln Gly
        35                  40

<210> SEQ ID NO 1308
<211> LENGTH: 5
<212> TYPE: PRT
<213> ORGANISM: Homo sapiens

<400> SEQUENCE: 1308

Arg Leu Asn Pro Gln
1               5

<210> SEQ ID NO 1309
```

```
<211> LENGTH: 40
<212> TYPE: PRT
<213> ORGANISM: Homo sapiens

<400> SEQUENCE: 1309

Arg Leu Asn Pro Gln Gly Asp Ser Gly Pro Leu Val Cys Gly Gly
1               5                   10                  15

Ile Leu Gln Gly Ile Val Ser Trp Gly Asp Val Pro Cys Asp Asn Thr
            20                  25                  30

Thr Lys Pro Gly Val Tyr Thr Lys
        35                  40

<210> SEQ ID NO 1310
<211> LENGTH: 8
<212> TYPE: PRT
<213> ORGANISM: Homo sapiens

<400> SEQUENCE: 1310

Ser Gly Trp Gly Leu Val Ser His
1               5

<210> SEQ ID NO 1311
<211> LENGTH: 8
<212> TYPE: PRT
<213> ORGANISM: Homo sapiens

<400> SEQUENCE: 1311

Ala Gly Trp Gly Ile Val Asn His
1               5

<210> SEQ ID NO 1312
<211> LENGTH: 8
<212> TYPE: PRT
<213> ORGANISM: Homo sapiens

<400> SEQUENCE: 1312

Ser Gly Trp Gly Ile Thr Asn His
1               5

<210> SEQ ID NO 1313
<211> LENGTH: 8
<212> TYPE: PRT
<213> ORGANISM: Homo sapiens

<400> SEQUENCE: 1313

Ser Gly Trp Gly Met Val Thr Glu
1               5

<210> SEQ ID NO 1314
<211> LENGTH: 8
<212> TYPE: PRT
<213> ORGANISM: Homo sapiens

<400> SEQUENCE: 1314

Trp Gly Asp Val Pro Cys Asp Asn
1               5

<210> SEQ ID NO 1315
<211> LENGTH: 8
<212> TYPE: PRT
<213> ORGANISM: Homo sapiens

<400> SEQUENCE: 1315

Trp Lys Asp Val Pro Cys Glu Asp
1               5
```

```
<210> SEQ ID NO 1316
<211> LENGTH: 8
<212> TYPE: PRT
<213> ORGANISM: Homo sapiens

<400> SEQUENCE: 1316

Trp Asn Asp Ala Pro Cys Asp Ser
1               5

<210> SEQ ID NO 1317
<211> LENGTH: 8
<212> TYPE: PRT
<213> ORGANISM: Homo sapiens

<400> SEQUENCE: 1317

Trp Asn Asp Ala Pro Cys Asp Lys
1               5

<210> SEQ ID NO 1318
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide tag

<400> SEQUENCE: 1318

Met Asp Tyr Lys Ala Phe Asp Asn Leu Glu Gln Lys Leu Ile Ser Glu
1               5                   10                  15

Glu Asp Leu

<210> SEQ ID NO 1319
<211> LENGTH: 28
<212> TYPE: PRT
<213> ORGANISM: Homo sapiens
<220> FEATURE:
<221> NAME/KEY: MOD_RES
<222> LOCATION: (8)
<223> OTHER INFORMATION: phosphoTyr
<220> FEATURE:
<221> NAME/KEY: MOD_RES
<222> LOCATION: (25)
<223> OTHER INFORMATION: phosphoSer

<400> SEQUENCE: 1319

Asn Ser Phe Asn Asn Pro Ala Tyr Tyr Val Leu Glu Gly Val Pro His
1               5                   10                  15

Gln Leu Leu Pro Pro Glu Pro Pro Ser Pro Ala Arg
            20                  25

<210> SEQ ID NO 1320
<211> LENGTH: 8
<212> TYPE: PRT
<213> ORGANISM: Homo sapiens

<400> SEQUENCE: 1320

Tyr Leu Thr Glu Gly Val Pro His
1               5

<210> SEQ ID NO 1321
<211> LENGTH: 8
<212> TYPE: PRT
<213> ORGANISM: Homo sapiens

<400> SEQUENCE: 1321
```

```
Tyr Ile Leu Glu Ser Met Pro His
1               5

<210> SEQ ID NO 1322
<211> LENGTH: 8
<212> TYPE: PRT
<213> ORGANISM: Homo sapiens

<400> SEQUENCE: 1322

Tyr Val Ile Met Gly Met Pro His
1               5

<210> SEQ ID NO 1323
<211> LENGTH: 15
<212> TYPE: PRT
<213> ORGANISM: Homo sapiens
<220> FEATURE:
<221> NAME/KEY: MOD_RES
<222> LOCATION: (6)
<223> OTHER INFORMATION: phosphoTyr

<400> SEQUENCE: 1323

Leu Gly Gly Gly Gln Tyr Gly Glu Val Tyr Glu Gly Val Trp Lys
1               5                   10                  15

<210> SEQ ID NO 1324
<211> LENGTH: 8
<212> TYPE: PRT
<213> ORGANISM: Homo sapiens

<400> SEQUENCE: 1324

Glu Val Tyr Val Gly Val Trp Lys
1               5

<210> SEQ ID NO 1325
<211> LENGTH: 8
<212> TYPE: PRT
<213> ORGANISM: Homo sapiens

<400> SEQUENCE: 1325

Glu Val Phe Glu Gly Leu Trp Lys
1               5

<210> SEQ ID NO 1326
<211> LENGTH: 8
<212> TYPE: PRT
<213> ORGANISM: Homo sapiens

<400> SEQUENCE: 1326

Glu Val Tyr Glu Gly Val Tyr Thr
1               5

<210> SEQ ID NO 1327
<211> LENGTH: 23
<212> TYPE: PRT
<213> ORGANISM: Unknown
<220> FEATURE:
<223> OTHER INFORMATION: Description of Unknown Organism:  Illustrative
      parental tryptic peptide

<400> SEQUENCE: 1327

Trp Ser Gly Ser His Gln Phe Glu Gln Leu Ser Gly Ser Ile Leu Trp
1               5                   10                  15

Met Ala Pro Glu Val Ile Arg
            20
```

```
<210> SEQ ID NO 1328
<211> LENGTH: 16
<212> TYPE: PRT
<213> ORGANISM: Unknown
<220> FEATURE:
<223> OTHER INFORMATION: Description of Unknown Organism: Illustrative
      parental tryptic peptide

<400> SEQUENCE: 1328

Met Ser Phe Ala Gly Thr Val Ala Trp Met Ala Pro Glu Val Ile Arg
1               5                   10                  15

<210> SEQ ID NO 1329
<211> LENGTH: 18
<212> TYPE: PRT
<213> ORGANISM: Unknown
<220> FEATURE:
<223> OTHER INFORMATION: Description of Unknown Organism: Illustrative
      parental tryptic peptide

<400> SEQUENCE: 1329

Ser Phe Ile Gly Thr Pro Tyr Trp Met Ala Pro Glu Val Ala Ala Val
1               5                   10                  15

Glu Arg

<210> SEQ ID NO 1330
<211> LENGTH: 12
<212> TYPE: PRT
<213> ORGANISM: Unknown
<220> FEATURE:
<223> OTHER INFORMATION: Description of Unknown Organism: Illustrative
      parental tryptic peptide

<400> SEQUENCE: 1330

Trp Met Ala Pro Glu Val Phe Thr Gln Cys Thr Arg
1               5                   10

<210> SEQ ID NO 1331
<211> LENGTH: 20
<212> TYPE: PRT
<213> ORGANISM: Unknown
<220> FEATURE:
<223> OTHER INFORMATION: Description of Unknown Organism: Illustrative
      parental tryptic peptide

<400> SEQUENCE: 1331

Leu Ser Phe Ile Gly Thr Pro Tyr Trp Met Ala Pro Glu Val Ala Ala
1               5                   10                  15

Val Ala Leu Lys
            20

<210> SEQ ID NO 1332
<211> LENGTH: 21
<212> TYPE: PRT
<213> ORGANISM: Unknown
<220> FEATURE:
<223> OTHER INFORMATION: Description of Unknown Organism: Illustrative
      parental tryptic peptide

<400> SEQUENCE: 1332

Asp Ser Phe Ile Gly Thr Pro Tyr Trp Met Ala Pro Glu Val Val Met
1               5                   10                  15

Cys Glu Thr Met Lys
            20

<210> SEQ ID NO 1333
<211> LENGTH: 16
```

```
<212> TYPE: PRT
<213> ORGANISM: Unknown
<220> FEATURE:
<223> OTHER INFORMATION: Description of Unknown Organism:  Illustrative
      parental tryptic peptide

<400> SEQUENCE: 1333

Met Ser Phe Ala Gly Thr Val Ala Trp Met Ala Pro Glu Val Ile Arg
1               5                   10                  15

<210> SEQ ID NO 1334
<211> LENGTH: 21
<212> TYPE: PRT
<213> ORGANISM: Unknown
<220> FEATURE:
<223> OTHER INFORMATION: Description of Unknown Organism:  Illustrative
      parental tryptic peptide

<400> SEQUENCE: 1334

Ser Met His Gly Thr Pro Tyr Trp Met Ala Pro Glu Val Ile Asn Glu
1               5                   10                  15

Ser Gly Tyr Gly Arg
            20

<210> SEQ ID NO 1335
<211> LENGTH: 24
<212> TYPE: PRT
<213> ORGANISM: Unknown
<220> FEATURE:
<223> OTHER INFORMATION: Description of Unknown Organism:  Illustrative
      parental tryptic peptide

<400> SEQUENCE: 1335

Asn Thr Val Ile Gly Thr Pro Phe Trp Met Ala Pro Glu Val Ile Gln
1               5                   10                  15

Glu Ile Gly Tyr Asn Cys Val Arg
            20

<210> SEQ ID NO 1336
<211> LENGTH: 23
<212> TYPE: PRT
<213> ORGANISM: Unknown
<220> FEATURE:
<223> OTHER INFORMATION: Description of Unknown Organism:  Illustrative
      parental tryptic peptide

<400> SEQUENCE: 1336

Asn Thr Phe Val Gly Thr Pro Phe Trp Met Ala Pro Glu Val Ile Gln
1               5                   10                  15

Gln Ser Ala Tyr Asp Ser Lys
            20

<210> SEQ ID NO 1337
<211> LENGTH: 28
<212> TYPE: PRT
<213> ORGANISM: Unknown
<220> FEATURE:
<223> OTHER INFORMATION: Description of Unknown Organism:  Illustrative
      parental tryptic peptide

<400> SEQUENCE: 1337

Asn Thr Ser Val Gly Thr Pro Phe Trp Met Ala Pro Glu Val Ile Ala
1               5                   10                  15

Cys Glu Gln Gln Leu Asp Thr Thr Tyr Asp Ala Arg
            20                  25
```

-continued

```
<210> SEQ ID NO 1338
<211> LENGTH: 28
<212> TYPE: PRT
<213> ORGANISM: Unknown
<220> FEATURE:
<223> OTHER INFORMATION: Description of Unknown Organism:  Illustrative
      parental tryptic peptide

<400> SEQUENCE: 1338

Asn Thr Ser Val Gly Thr Pro Phe Trp Met Ala Pro Glu Val Ile Ala
1               5                   10                  15

Cys Glu Gln Gln Tyr Asp Ser Ser Tyr Asp Ala Arg
            20                  25

<210> SEQ ID NO 1339
<211> LENGTH: 28
<212> TYPE: PRT
<213> ORGANISM: Unknown
<220> FEATURE:
<223> OTHER INFORMATION: Description of Unknown Organism:  Illustrative
      parental tryptic peptide

<400> SEQUENCE: 1339

Asn Thr Phe Ile Gly Thr Pro Tyr Trp Met Ala Pro Glu Val Ile Ala
1               5                   10                  15

Cys Asp Glu Asn Pro Asp Ala Thr Tyr Asp Tyr Arg
            20                  25

<210> SEQ ID NO 1340
<211> LENGTH: 18
<212> TYPE: PRT
<213> ORGANISM: Unknown
<220> FEATURE:
<223> OTHER INFORMATION: Description of Unknown Organism:  Illustrative
      parental tryptic peptide

<400> SEQUENCE: 1340

Thr Phe Val Gly Thr Pro Cys Trp Met Ala Pro Glu Val Met Glu Gln
1               5                   10                  15

Val Arg

<210> SEQ ID NO 1341
<211> LENGTH: 17
<212> TYPE: PRT
<213> ORGANISM: Unknown
<220> FEATURE:
<223> OTHER INFORMATION: Description of Unknown Organism:  Illustrative
      parental tryptic peptide

<400> SEQUENCE: 1341

Ser Thr Met Val Gly Thr Pro Tyr Trp Met Ala Pro Glu Val Val Thr
1               5                   10                  15

Arg

<210> SEQ ID NO 1342
<211> LENGTH: 16
<212> TYPE: PRT
<213> ORGANISM: Unknown
<220> FEATURE:
<223> OTHER INFORMATION: Description of Unknown Organism:  Illustrative
      parental tryptic peptide

<400> SEQUENCE: 1342

Ser Leu Val Gly Thr Pro Tyr Trp Met Ala Pro Glu Val Ile Ser Arg
1               5                   10                  15
```

```
<210> SEQ ID NO 1343
<211> LENGTH: 23
<212> TYPE: PRT
<213> ORGANISM: Unknown
<220> FEATURE:
<223> OTHER INFORMATION: Description of Unknown Organism: Illustrative
      parental tryptic peptide

<400> SEQUENCE: 1343

Trp Ser Gly Ser Gln Gln Val Glu Gln Pro Thr Gly Ser Val Leu Trp
1               5                   10                  15

Met Ala Pro Glu Val Ile Arg
            20

<210> SEQ ID NO 1344
<211> LENGTH: 18
<212> TYPE: PRT
<213> ORGANISM: Unknown
<220> FEATURE:
<223> OTHER INFORMATION: Description of Unknown Organism: Illustrative
      parental tryptic peptide

<400> SEQUENCE: 1344

Thr Phe Val Gly Thr Pro Cys Trp Met Ala Pro Glu Val Met Glu Gln
1               5                   10                  15

Val Arg

<210> SEQ ID NO 1345
<211> LENGTH: 33
<212> TYPE: PRT
<213> ORGANISM: Unknown
<220> FEATURE:
<223> OTHER INFORMATION: Description of Unknown Organism: Illustrative
      parental tryptic peptide

<400> SEQUENCE: 1345

Ala Ser Met Ala Ser Pro Ala Asn Ser Phe Val Gly Thr Pro Tyr Trp
1               5                   10                  15

Met Ala Pro Glu Val Ile Leu Ala Met Asp Glu Gly Gln Tyr Asp Gly
            20                  25                  30

Lys

<210> SEQ ID NO 1346
<211> LENGTH: 33
<212> TYPE: PRT
<213> ORGANISM: Unknown
<220> FEATURE:
<223> OTHER INFORMATION: Description of Unknown Organism: Illustrative
      parental tryptic peptide

<400> SEQUENCE: 1346

Ala Ser Ile Met Ala Pro Ala Asn Ser Phe Val Gly Thr Pro Tyr Trp
1               5                   10                  15

Met Ala Pro Glu Val Ile Leu Ala Met Asp Glu Gly Gln Tyr Asp Gly
            20                  25                  30

Lys

<210> SEQ ID NO 1347
<211> LENGTH: 18
<212> TYPE: PRT
<213> ORGANISM: Unknown
<220> FEATURE:
<223> OTHER INFORMATION: Description of Unknown Organism: Illustrative
      parental tryptic peptide

<400> SEQUENCE: 1347
```

```
Glu Pro Leu Ala Val Val Gly Ser Pro Tyr Trp Met Ala Pro Glu Val
1               5                   10                  15

Leu Arg

<210> SEQ ID NO 1348
<211> LENGTH: 22
<212> TYPE: PRT
<213> ORGANISM: Unknown
<220> FEATURE:
<223> OTHER INFORMATION: Description of Unknown Organism:  Illustrative
      parental tryptic peptide

<400> SEQUENCE: 1348

Thr Thr His Met Ser Leu Val Gly Thr Phe Pro Trp Met Ala Pro Glu
1               5                   10                  15

Val Ile Gln Ser Leu Arg
            20

<210> SEQ ID NO 1349
<211> LENGTH: 63
<212> TYPE: PRT
<213> ORGANISM: Human severe acute respiratory system virus

<400> SEQUENCE: 1349

Met Phe His Leu Val Asp Phe Gln Val Thr Ile Ala Glu Ile Leu Ile
1               5                   10                  15

Ile Ile Met Arg Thr Phe Arg Ile Ala Ile Trp Asn Leu Asp Val Ile
            20                  25                  30

Ile Ser Ser Ile Val Arg Gln Leu Phe Lys Pro Leu Thr Lys Lys Asn
        35                  40                  45

Tyr Ser Glu Leu Asp Asp Glu Pro Met Glu Leu Asp Tyr Pro
    50                  55                  60

<210> SEQ ID NO 1350
<211> LENGTH: 8
<212> TYPE: PRT
<213> ORGANISM: Homo sapiens

<400> SEQUENCE: 1350

Met Phe Asp Leu Val Asp Tyr Lys
1               5

<210> SEQ ID NO 1351
<211> LENGTH: 8
<212> TYPE: PRT
<213> ORGANISM: Homo sapiens

<400> SEQUENCE: 1351

Met Phe His Pro Met Asp Phe Glu
1               5

<210> SEQ ID NO 1352
<211> LENGTH: 8
<212> TYPE: PRT
<213> ORGANISM: Unknown
<220> FEATURE:
<223> OTHER INFORMATION: Description of Unknown Organism: Coronavirus
      peptide

<400> SEQUENCE: 1352

Ser Phe His Phe Ile Asp Phe Tyr
1               5
```

<210> SEQ ID NO 1353
<211> LENGTH: 8
<212> TYPE: PRT
<213> ORGANISM: Homo sapiens

<400> SEQUENCE: 1353

Tyr Ser Glu Leu Asp Gly Glu Glu
1               5

<210> SEQ ID NO 1354
<211> LENGTH: 8
<212> TYPE: PRT
<213> ORGANISM: Unknown
<220> FEATURE:
<223> OTHER INFORMATION: Description of Unknown Organism: Coronavirus
      peptide

<400> SEQUENCE: 1354

Tyr Ser Ser Leu Asn Asp Glu Phe
1               5

<210> SEQ ID NO 1355
<211> LENGTH: 36
<212> TYPE: PRT
<213> ORGANISM: Homo sapiens

<400> SEQUENCE: 1355

Lys Val Leu Ala Leu Tyr Asn Gln His Asn Pro Gly Ala Ser Ala Ala
1               5                   10                  15

Pro Cys Cys Val Pro Gln Ala Leu Glu Pro Leu Pro Ile Val Tyr Tyr
            20                  25                  30

Val Gly Arg Lys
        35

<210> SEQ ID NO 1356
<211> LENGTH: 8
<212> TYPE: PRT
<213> ORGANISM: Homo sapiens

<400> SEQUENCE: 1356

Asn His His Ser Pro Gly Gly Ser
1               5

<210> SEQ ID NO 1357
<211> LENGTH: 8
<212> TYPE: PRT
<213> ORGANISM: Homo sapiens

<400> SEQUENCE: 1357

Gln Gln His Asn Pro Ala Ala Asn
1               5

<210> SEQ ID NO 1358
<211> LENGTH: 8
<212> TYPE: PRT
<213> ORGANISM: Homo sapiens

<400> SEQUENCE: 1358

Asn Lys His Gly Pro Gly Val Ser
1               5

<210> SEQ ID NO 1359
<211> LENGTH: 8
<212> TYPE: PRT
<213> ORGANISM: Homo sapiens

```
<400> SEQUENCE: 1359

Glu Pro Leu Thr Ile Leu Tyr Tyr
1               5

<210> SEQ ID NO 1360
<211> LENGTH: 8
<212> TYPE: PRT
<213> ORGANISM: Homo sapiens

<400> SEQUENCE: 1360

Asp Pro Leu Pro Val Arg Tyr Tyr
1               5

<210> SEQ ID NO 1361
<211> LENGTH: 8
<212> TYPE: PRT
<213> ORGANISM: Homo sapiens

<400> SEQUENCE: 1361

Glu Pro Leu Pro Ser Gln Tyr Tyr
1               5

<210> SEQ ID NO 1362
<211> LENGTH: 36
<212> TYPE: PRT
<213> ORGANISM: Homo sapiens

<400> SEQUENCE: 1362

Arg Val Leu Ser Leu Tyr Asn Thr Ile Asn Pro Glu Ala Ser Ala Ser
1               5                   10                  15

Pro Cys Cys Val Ser Gln Asp Leu Glu Pro Leu Thr Ile Leu Tyr Tyr
                20                  25                  30

Ile Gly Lys Thr
            35

<210> SEQ ID NO 1363
<211> LENGTH: 8
<212> TYPE: PRT
<213> ORGANISM: Homo sapiens

<400> SEQUENCE: 1363

Asn Thr Leu Asn Pro Glu Ala Ser
1               5

<210> SEQ ID NO 1364
<211> LENGTH: 8
<212> TYPE: PRT
<213> ORGANISM: Homo sapiens

<400> SEQUENCE: 1364

Asn Lys Leu Asp Pro Glu Ala Ser
1               5

<210> SEQ ID NO 1365
<211> LENGTH: 8
<212> TYPE: PRT
<213> ORGANISM: Homo sapiens

<400> SEQUENCE: 1365

Asn Thr Ala Asn Pro Glu Arg Ser
1               5

<210> SEQ ID NO 1366
<211> LENGTH: 8
```

```
<212> TYPE: PRT
<213> ORGANISM: Homo sapiens

<400> SEQUENCE: 1366

Pro Gln Asp Leu Glu Pro Leu Thr
1               5

<210> SEQ ID NO 1367
<211> LENGTH: 8
<212> TYPE: PRT
<213> ORGANISM: Homo sapiens

<400> SEQUENCE: 1367

Ser Glu Asp Leu Glu Pro Leu Ala
1               5

<210> SEQ ID NO 1368
<211> LENGTH: 8
<212> TYPE: PRT
<213> ORGANISM: Homo sapiens

<400> SEQUENCE: 1368

Ser Gln Asp Leu Asp Pro Met Ala
1               5

<210> SEQ ID NO 1369
<211> LENGTH: 44
<212> TYPE: PRT
<213> ORGANISM: Homo sapiens

<400> SEQUENCE: 1369

Arg Ser Ala Asp Thr Thr His Ser Thr Val Leu Gly Leu Tyr Asn Thr
1               5                   10                  15

Leu Asn Pro Glu Ala Ser Ala Ser Pro Cys Cys Val Pro Gln Asp Leu
                20                  25                  30

Glu Pro Leu Thr Ile Leu Tyr Tyr Val Gly Arg Thr
            35                  40

<210> SEQ ID NO 1370
<211> LENGTH: 8
<212> TYPE: PRT
<213> ORGANISM: Homo sapiens

<400> SEQUENCE: 1370

Ser Ala His Ser Thr His Ser Thr
1               5

<210> SEQ ID NO 1371
<211> LENGTH: 8
<212> TYPE: PRT
<213> ORGANISM: Homo sapiens

<400> SEQUENCE: 1371

Ser Ser Asp Thr Thr His Ala Ser
1               5

<210> SEQ ID NO 1372
<211> LENGTH: 8
<212> TYPE: PRT
<213> ORGANISM: Homo sapiens

<400> SEQUENCE: 1372

Ala Ala Glu Ala Thr His Ser Thr
1               5
```

<210> SEQ ID NO 1373
<211> LENGTH: 8
<212> TYPE: PRT
<213> ORGANISM: Homo sapiens

<400> SEQUENCE: 1373

Asn Thr Ile Asn Pro Glu Ala Ser
1               5

<210> SEQ ID NO 1374
<211> LENGTH: 8
<212> TYPE: PRT
<213> ORGANISM: Homo sapiens

<400> SEQUENCE: 1374

Asn Lys Leu Asp Pro Glu Ala Ser
1               5

<210> SEQ ID NO 1375
<211> LENGTH: 8
<212> TYPE: PRT
<213> ORGANISM: Homo sapiens

<400> SEQUENCE: 1375

Asn Thr Ala Asn Pro Glu Arg Ser
1               5

<210> SEQ ID NO 1376
<211> LENGTH: 41
<212> TYPE: PRT
<213> ORGANISM: Homo sapiens

<400> SEQUENCE: 1376

Met Lys Trp Ala Lys Asn Trp Val Leu Glu Pro Pro Gly Phe Leu Ala
1               5                   10                  15

Tyr Glu Cys Val Gly Thr Cys Gln Gln Pro Pro Glu Ala Leu Ala Phe
            20                  25                  30

Asn Trp Pro Phe Leu Gly Pro Arg Gln
        35                  40

<210> SEQ ID NO 1377
<211> LENGTH: 8
<212> TYPE: PRT
<213> ORGANISM: Homo sapiens

<400> SEQUENCE: 1377

Asn Trp Ala Val Asp Pro Pro Gly
1               5

<210> SEQ ID NO 1378
<211> LENGTH: 8
<212> TYPE: PRT
<213> ORGANISM: Homo sapiens

<400> SEQUENCE: 1378

His Trp Val Val Ser Pro Pro Gly
1               5

<210> SEQ ID NO 1379
<211> LENGTH: 8
<212> TYPE: PRT
<213> ORGANISM: Homo sapiens

<400> SEQUENCE: 1379

```
Asn Trp Val Arg Leu Pro Pro Gly
1               5

<210> SEQ ID NO 1380
<211> LENGTH: 8
<212> TYPE: PRT
<213> ORGANISM: Homo sapiens

<400> SEQUENCE: 1380

Gln Pro Pro Glu Ala Phe Gly Phe
1               5

<210> SEQ ID NO 1381
<211> LENGTH: 8
<212> TYPE: PRT
<213> ORGANISM: Homo sapiens

<400> SEQUENCE: 1381

Lys Pro Pro Glu Ala Leu Ala Met
1               5

<210> SEQ ID NO 1382
<211> LENGTH: 8
<212> TYPE: PRT
<213> ORGANISM: Homo sapiens

<400> SEQUENCE: 1382

Gln Pro Pro Glu Ala Lys Lys Phe
1               5

<210> SEQ ID NO 1383
<211> LENGTH: 6
<212> TYPE: PRT
<213> ORGANISM: Homo sapiens

<400> SEQUENCE: 1383

Arg His Arg Arg Ala Leu
1               5

<210> SEQ ID NO 1384
<211> LENGTH: 6
<212> TYPE: PRT
<213> ORGANISM: Homo sapiens

<400> SEQUENCE: 1384

Arg Lys Lys Arg Ala Leu
1               5

<210> SEQ ID NO 1385
<211> LENGTH: 6
<212> TYPE: PRT
<213> ORGANISM: Homo sapiens

<400> SEQUENCE: 1385

Arg Lys Lys Arg Ala Leu
1               5

<210> SEQ ID NO 1386
<211> LENGTH: 4
<212> TYPE: PRT
<213> ORGANISM: Homo sapiens

<400> SEQUENCE: 1386

Arg His Arg Arg
1
```

PROTEOME EPITOPE TAGS AND METHODS OF USE THEREOF IN PROTEIN MODIFICATION ANALYSIS

CROSS-REFERENCE TO RELATED APPLICATIONS

This application is a continuation of U.S. Ser. No. 10/773,032, filed on Feb. 5, 2004, which is a continuation-in-part application of U.S. Ser. No. 10/712,425, filed on Nov. 13, 2003, which is a continuation-in-part application of U.S. Ser. No. 10/436,549, filed on May 12, 2003, which claims the benefit of and priority to U.S. Provisional Application No. 60/379,626, filed on May 10, 2002; U.S. Provisional Application Nos. 60/393,137, 60/393,233, 60/393,235, 60/393,211, 60/393,223, 60/393,280, and 60/393,197, all filed on Jul. 1, 2002; U.S. Provisional Application No. 60/430,948, filed on Dec. 4, 2002; and U.S. Provisional Application No. 60/433,319, filed on Dec. 13, 2002, the entire contents of each of which are incorporated herein by reference.

BACKGROUND OF THE INVENTION

Genomic studies are now approaching "industrial" speed and scale, thanks to advances in gene sequencing and the increasing availability of high-throughput methods for studying genes, the proteins they encode, and the pathways in which they are involved. The development of DNA microarrays has enabled massively parallel studies of gene expression as well as genomic DNA variations.

DNA microarrays have shown promise in advanced medical diagnostics. More specifically, several groups have shown that when the gene expression patterns of normal and diseased tissues are compared at the whole genome level, patterns of expression characteristic of the particular disease state can be observed. Bittner et al., (2000) Nature 406:536-540; Clark et al., (2000) Nature 406:532-535; Huang et al., (2001) Science 294:870-875; and Hughes et al., (2000) Cell 102:109-126. For example, tissue samples from patients with malignant forms of prostate cancer display a recognizably different pattern of mRNA expression to tissue samples from patients with a milder form of the disease. C. f., Dhanasekaran et al., (2001) Nature 412 (2001), pp. 822-826.

However, as James Watson pointed out recently proteins are really the "actors in biology" ("*A Cast of Thousands*" *Nature Biotechnology* March 2003). A more attractive approach would be to monitor key proteins directly. These might be biomarkers identified by DNA microarray analysis. In this case, the assay required might be relatively simple, examining only 5-10 proteins. Another approach would be to use an assay that detects hundreds or thousands of protein features, such as for the direct analysis of blood, sputum or urine samples, etc. It is reasonable to believe that the body would react in a specific way to a particular disease state and produce a distinct "biosignature" in a complex data set, such as the levels of 500 proteins in the blood. One could imagine that in the future a single blood test could be used to diagnose most conditions.

The motivation for the development of large-scale protein detection assays as basic research tools is different to that for their development for medical diagnostics. The utility of biosignatures is one aspect researchers desire in order to understand the molecular basis of cellular response to a particular genetic, physiological or environmental stimulus. DNA microarrays do a good job in this role, but detection of proteins would allow for more accurate determination of protein levels and, more importantly, could be designed to quantitate the presence of different splice variants or isoforms. These events, to which DNA microarrays are largely or completely blind, often have pronounced effects on protein activities.

This has sparked great interest in the development of devices such as protein-detecting microarrays (PDMs) to allow similar experiments to be done at the protein level, particularly in the development of devices capable of monitoring the levels of hundreds or thousands of proteins simultaneously.

Prior to the present invention, PDMs that even approach the complexity of DNA microarrays do not exist. There are several problems with the current approaches to massively parallel, e.g., cell-wide or proteome wide, protein detection. First, reagent generation is difficult: One needs to first isolate every individual target protein in order to isolate a detection a gent against e very protein in an organism and then develop detection agents against the purified protein. Since the number of proteins in the human organism is currently estimated to be about 30,000 this requires a lot of time (years) and resources. Furthermore, detection agents against native proteins have less defined specificity since it is a difficult task to know which part of the proteins the detection agents recognize. This problem causes considerable cross-reactivity of when multiple detection agents are arrayed together, making large-scale protein detection array difficult to construct. Second, current methods achieve poor coverage of all possible proteins in an organism. These methods typically include only the soluble proteins in biological samples. They often fail to distinguish splice variants, which are now appreciated as being ubiquitous. They exclude a large number of proteins that are bound in organellar and cellular membranes or are insoluble when the sample is processed for detection. Third, current methods are not general to all proteins or to all types of biological samples. Proteins vary quite widely in their chemical character. Groups of proteins require different processing conditions in order to keep them stably solubilized for detection. Any one condition may not suit all the proteins. Further, biological samples vary in their chemical character. Individual cells considered identical express different proteins over the course of their generation and ultimate death. Physiological fluids like urine and blood serum are relatively simple, but biopsy tissue samples are very complex. Different protocols need to be used to process each type of sample and achieve maximal solubilization and stabilization of proteins.

Current detection methods are either not effective over all proteins uniformly or cannot be highly multiplexed to enable simultaneous detection of a large number of proteins (e.g., >5,000). Optical detection methods would be most cost effective but suffer from lack of uniformity over different proteins. Proteins in a sample have to be labeled with dye molecules and the different chemical character of proteins leads to inconsistency in efficiency of labeling. Labels may also interfere with the interactions between the detection agents and the analyte protein leading to further errors in quantitation. Non-optical detection methods have been developed but are quite expensive in instrumentation and are very difficult to multiplex for parallel detection of even moderately large samples (e.g., >100 samples).

Another problem with current technologies is that they are burdened by intracellular life processes involving a complex web of protein complex formation, multiple enzymatic reactions altering protein structure, and protein conformational changes. These processes can mask or expose binding sites known to be present in a sample. For example, prostate specific antigen (PSA) is known to exist in serum in multiple forms including free (unbound) forms, e.g., pro-PSA, BPSA (BPH-associated free PSA), and complexed forms, e.g., PSA- ACT, PSA-A2M (PSA-alpha$_2$-macroglobulin), and PSA-API (PSA-alpha$_1$-protease inhibitor) (see Stephan C. et al. (2002) *Urology* 59:2-8). Similarly, Cyclin E is known to exist not only as a full length 50 kD protein, but also in five other low molecular weight forms ranging in size from 34 to 49 kD. In fact, the low molecular weight forms of cyclin E are believed to be more sensitive markers for breast cancer than the full length protein (see Keyomarsi K. et al. (2002) *N. Eng. J. Med.* 347(20):1566-1575).

Sample collection and handling prior to a detection assay may also affect the nature of proteins that are present in a sample and, thus, the ability to detect these proteins. As indicated by Evans M. J. et al. (2001) *Clinical Biochemistry* 34:107-112 and Zhang D. J. et al. (1998) *Clinical Chemistry* 44(6):1325-1333, standardizing immunoassays is difficult due to the variability in sample handling and protein stability in plasma or serum. For example, PSA sample handling, such as sample freezing, affects the stability and the relative levels of the different forms of PSA in the sample (Leinonen J, Stenman U H (2000) *Tumour Biol.* 21(1):46-53).

Finally, current technologies are burdened by the presence of autoantibodies which affect the outcome of immunoassays in unpredictable ways, e.g., by leading to analytical errors (Fitzmaurice T. F. et al. (1998) *Clinical Chemistry* 44(10): 2212-2214).

These problems prompted the question whether it is even possible to standardize immunoassays for hetergenous protein antigens. (Stenman U-H. (2001) Immunoassay Standardization: Is it possible? Who is responsible? Who is capable? Clinical Chemistry 47 (5) 815-820). Thus, a great need exists in the art for efficient and simple methods of parallel detection of proteins that are expressed in a biological sample and, particularly, for methods that can overcome the imprecisions caused by the complexity of protein chemistry and for methods which can detect all or a majority of the proteins expressed in a given cell type at a given time, or for proteome-wide detection and quantitation of proteins expressed in biological samples.

SUMMARY OF THE INVENTION

The present invention is directed to methods and reagents for reproducible protein detection and quantitation, e.g., parallel detection and quantitation, in complex biological samples. Salient features to certain embodiments of the present invention reduce the complexity of reagent generation, achieve greater coverage of all protein classes in an organism, greatly simplify the sample processing and analyte stabilization process, and enable effective and reliable parallel detection, e.g., by optical or other automated detection methods, and quantitation of proteins and/or post-translationally modified forms, and, enable multiplexing of standardized capture agents for proteins with minimal cross-reactivity and well-defined specificity for large-scale, proteome-wide protein detection.

Embodiments of the present invention also overcome the imprecisions indetection methods caused by: the existence of proteins in multiple forms in a sample (e.g., various post-trnslationally modified forms or various complexed or aggregated forms); the variability in sample handling and protein stability in a sample, such as plasma or serum; and the presence of autoantibodies in samples. In certain embodiments, using a targeted fragmentation protocol, the methods of the present invention assure that a binding site on a protein of interest, which may have been masked due to one of the foregoing reasons, is made available to interact with a capture agent. In other embodiments, the sample proteins are subjected to conditions in which they are denatured, and optionally are alkylated, so as to render buried (or otherwise cryptic) PET moieties accessible to solvent and interaction with capture agents. As a result, the present invention allows for detection methods having increased sensitivity and more accurate protein quantitation capabilities. This advantage of the present invention will be particularly useful in, for example, protein marker-type disease detection assays (e.g., PSA or Cyclin E based assays) as it will allow for an improvement in the predictive value, sensitivity, and reproducibility of these assays. The present invention can standardize detection and measurement assays for all proteins from all samples.

For example, a recent study by Punglia et al. (*N. Engl. J. Med.* 349(4): 335-42, July, 2003) indicated that, in the standard PSA-based screening for prostate cancer, if the threshold PSA value for undergoing biopsy were set at 4.1 ng per milliliter, 82 percent of cancers in younger men and 65 percent of cancers in older men would be missed. Thus a lower threshold level of PSA for recommending prostate biopsy, particularly in younger men, may improve the clinical value of the PSA test. However, at lower detection limits, background can become a significant issue. It would be immensely advantageous if the sensitivity/selectivity of the assay can be improved by, for example, the method of the instant invention.

In a specific embodiment, the invention provides a method to detect and quantitate the presence of specific modified polypeptides in a sample. In a general sense, the invention provides a method to identify a URS or PET uniquely associated with a modification site on a peptide fragment, which PET can then be captured and detected/quantitated by specific capture agents. The method applies to virtually all kinds of post-translational modifications, including but are not limited to phosphorylation, glycosylation, etc., as long as the modification can be reliably detected, for example, by phospho-antibodies. The method also applies to the detection of alternative splicing forms of otherwise identical proteins.

The present invention is based, at least in part, on the realization that exploitation of unique recognition sequences (URSs) or Proteome Epitope Tags (PETs) present within individual proteins can enable reproducible detection and quantitation of individual proteins in parallel in a milieu of proteins in a biological sample. As a result of this PET-based approach, the methods of the invention detect specific proteins in a manner that does not require preservation of the whole protein, nor even its native tertiary structure, for analysis. Moreover, the methods of the invention are suitable for the detection of most or all proteins in a sample, including insoluble proteins such as cell membrane bound and organelle membrane bound proteins.

The present invention is also based, at least in part, on the realization that PETs can serve as Proteome Epitope Tags characteristic of a specific organism's proteome and can enable the recognition and detection of a specific organism.

The present invention is also based, at least in part, on the realization that high-affinity agents (such as antibodies) with predefined specificity can be generated for defined, short length peptides and when antibodies recognize protein or peptide epitopes, only 4-6 (on average) amino acids are critical. See, for example, Lerner R A (1984) *Advances In Immunology.* 36:1-45.

The present invention is also based, at least in part, on the realization that by denaturing (including thermo- and/or chemical-denaturation) and/or fragmenting (such as by protease digestion including digestion by thermo-protease) all proteins in a sample to produce a soluble set of protein analytes, e.g., in which even otherwise buried PETs including PETs in protein complexes/aggregates are solvent accessible, the subject method provides a reproducible and accurate (intra-assay and inter-assay) measurement of proteins.

The present invention is also based, at least in part, on the realization that protein modifications associated with PETs on a fragmented peptide can be readily detected and quantitated by isolating the associated PET followed by detection/quantitation of the modification.

Accordingly, in one aspect, the present invention provides a method for globally detecting the presence of a protein(s) (e.g., membrane bound protein(s)) in an organism's proteome. The method includes providing a sample which has been denatured and/or fragmented to generate a collection of soluble polypeptide analytes; contacting the polypeptide analytes with a plurality of capture agents (e.g., capture agents immobilized on a solid support such as an array) under conditions such that interaction of the capture agents with corresponding unique recognition sequences occurs, thereby globally detecting the presence of protein(s) in an organism's proteome.

The method is suitable for use in, for example, diagnosis (e.g., clinical diagnosis or environmental diagnosis), drug discovery, protein sequencing or protein profiling. In one embodiment, at least 50%, 55%, 60%, 65%, 70%, 75%, 80%, 85%, 90%, 95% or 100% of an organism's proteome is detectable from arrayed capture agents.

The capture agent may be a protein, a peptide, an antibody, e.g., a single chain antibody, an artificial protein, an RNA or DNA aptamer, an allosteric ribozyme, a small molecule or electronic means of capturing a PET.

The sample to be tested (e.g., a human, yeast, mouse, C. elegans, Drosophila melanogaster or Arabidopsis thaliana sample, such whole cell lysate) may be fragmented by the use of a proteolytic agent. The proteolytic agent can be any agent, which is capable of predictably cleaving polypeptides between specific amino acid residues (i.e., the proteolytic cleavage pattern). The predictability of cleavage allows a computer to generate fragmentation patterns in sillico, which will greatly aid the process of searching PETs unique to a sample.

According to one embodiment of this aspect of the present invention a proteolytic agent is a proteolytic enzyme. Examples of proteolytic enzymes, include but are not limited to trypsin, calpain, carboxypeptidase, chymotrypsin, V8 protease, pepsin, papain, subtilisin, thrombin, elastase, gluc-C, endo lys-C or proteinase K, caspase-1, caspase-2, caspase-3, caspase-4, caspase-5, caspase-6, caspase-7, caspase-8, MetAP-2, a denovirus protease, HIV protease and the like.

The following table summarizes the result of analyzing pentamer PETs in the human proteome using different proteases. A total of 23,446 sequences are tagged before protease digestion.

| Protease | Cleavage Site | Fragment Length | Tagged Proteins |
|---|---|---|---|
| Chymotrypsin | after W, F, Y | 12.7 | 21,990 |
| S.A. V-8 E specific | after E | 13.7 | 23,120 |
| Post-Proline Cleaving Enzyme | after P | 15.7 | 23,009 |
| Trypsin | after K, R | 8.5 | 22,408 |

According to another embodiment of this aspect of the present invention a proteolytic agent is a proteolytic chemical such as cyanogen bromide and 2-nitro-5-thiocyanobenzoate. In still other embodiments, the proteins of the test sample can be fragmented by physical shearing; by sonication, or some combination of these or other treatment steps.

An important feature for certain embodiments, particularly when analyzing complex samples, is to develop a fragmentation protocol that is known to reproducibly generate peptides, preferably soluble peptides, which serve as the unique recognition sequences. The collection of polypeptide analytes generated from the fragmentation may be 5-30, 5-20, 5-10, 10-20, 20-30, or 10-30 amino acids long, or longer. Ranges intermediate to the above recited values, e.g., 7-15 or 15-25 are also intended to be part of this invention. For example, ranges using a combination of any of the above recited values as upper and/or lower limits are intended to be included.

The unique recognition sequence may be a linear sequence or a non-contiguous sequence and may be 5, 6, 7, 8, 9, 10, 11, 12, 13, 14, 15, 16, 17, 18, 19, 20, 25, or 30 amino acids in length. In certain embodiments, the unique recognition sequence is selected from the group consisting of SEQ ID NOs:1-546 or a sub-collection thereof.

In one embodiment, the protein(s) being detected is characteristic of a pathogenic organism, e.g., anthrax, small pox, cholera toxin, Staphylococcus aureus α-toxin, Shiga toxin, cytotoxic necrotizing factor type 1, Escherichia coli heat-stable toxin, botulinum toxins, or tetanus neurotoxins.

In another aspect, the present invention provides a method for detecting the presence of a protein, preferably simultaneous or parallel detection of multiple proteins, in a sample. The method includes providing a sample which has been denatured and/or fragmented to generate a collection of soluble polypeptide analytes; providing an array comprising a support having a plurality of discrete regions to which are bound a plurality of capture agents, wherein each of the capture agents is bound to a different discrete region and wherein each of the capture agents is able to recognize and interact with a unique recognition sequence within a protein; contacting the array of capture agents with the polypeptide analytes; and determining which discrete regions show specific binding to the sample, thereby detecting the presence of a protein in a sample.

To further illustrate, the present invention provides a packaged protein detection array. Such arrays may include an addressable array having a plurality of features, each feature independently including a discrete type of capture agent that selectively interacts with a unique recognition sequence (URS) or PET of an analyte protein, e.g., under conditions in which the analyte protein is a soluble protein produced by proteolysis and/or denaturation. The features of the array are disposed in a pattern or with a label to provide the identity of interactions between analytes and the capture a gents, e.g., to ascertain the identity and/or quantity of a protein occurring in the sample. The packaged array may also include instructions for (i) contacting the addressable array with a sample containing polypeptide analytes produced by denaturation and/or cleavage of proteins at amide backbone positions; (ii) detecting interaction of said polypeptide analytes with said capture agent moieties; (iii) and determining the identity of polypeptide analytes, or native proteins from which they are derived, based on interaction with capture agent moieties.

In yet a further aspect, the present invention provides a method for detecting the presence of a protein in a sample by providing a sample which has been denatured and/or fragmented to generate a collection of soluble polypeptide analytes; contacting the sample with a plurality of capture agents, wherein each of the capture agents is able to recognize and interact with a unique recognition sequence within a protein, under conditions such that the presence of a protein in the sample is detected.

In another aspect, the present invention provides a method for detecting the presence of a protein in a sample by providing an array of capture agents comprising a support having a plurality of discrete regions (features) to which are bound a plurality of capture agents, wherein each of the capture agents is bound to a different discrete region and wherein the plurality of capture agents are capable of interacting with at least 50% of an organism's proteome; contacting the array with the sample; and determining which discrete regions show specific binding to the sample, thereby detecting the presence of a protein in the sample.

In a further aspect, the present invention provides a method for globally detecting the presence of a protein(s) in an organism's proteome by providing a sample comprising the protein and contacting the sample with a plurality of capture agents under conditions such that interaction of the capture agents with corresponding unique recognition sequences occurs, thereby globally detecting the presence of protein(s) in an organism's proteome.

In another aspect, the present invention provides a plurality of capture agents, wherein the plurality of capture agents are capable of interacting with at least 50%, 55%, 60%, 65%, 70%, 75%, 80%, 85%, 90%, 95% or 100% of an organism's proteome and wherein each of the capture agents is able to recognize and interact with a unique recognition sequence within a protein.

In yet another aspect, the present invention provides an array of capture agents, which includes a support having a plurality of discrete regions to which are bound a plurality of capture agents (, e.g., at least 10, 20, 30, 40, 50, 60, 70, 80, 90, 100, 200, 300, 400, 500, 1000, 2000, 3000, 4000, 5000, 6000, 7000, 8000, 9000, 10000, 11000, 12000 or 13000 different capture agents), wherein each of the capture agents is bound to a different discrete region and wherein each of the capture agents is able to recognize and interact with a unique recognition sequence within a protein. The capture agents may be attached to the support, e.g., via a linker, at a density of 50, 100, 150, 200, 250, 300, 350, 400, 450, 500 or 1000 capture agents/cm$^2$. In one embodiment, each of the discrete regions is physically separated from each of the other discrete regions.

The capture agent array can be produced on any suitable solid surface, including silicon, plastic, glass, polymer, such as cellulose, polyacrylamide, nylon, polystyrene, polyvinyl chloride or polypropylene, ceramic, photoresist or rubber surface. Preferably, the silicon surface is a silicon dioxide or a silicon nitride surface. Also preferably, the array is made in a chip format. The solid surfaces may be in the form of tubes, beads, discs. silicon chips, microplates, polyvinylidene difluoride (PVDF) membrane, nitrocellulose membrane, nylon membrane, other purous membrane, non-porous membrane, e.g., plastic, polymer, perspex, silicon, amongst others, a plurality of polymeric pins, or a plurality of microtitre wells, or any other surface suitable for immobilizing proteins and/or conducting an immunoassay or other binding assay.

The capture agent may be a protein, a peptide, an antibody, e.g., a single chain antibody, an artificial protein, an RNA or DNA aptamer, an allosteric ribozyme or a small molecule.

In a further aspect, the present invention provides a composition comprising a plurality of isolated unique recognition sequences, wherein the unique recognition sequences are derived from at least 50%, 55%, 60%, 65%, 70%, 75%, 80%, 85%, 90%, 95% or 100% of an organism's proteome. In one embodiment, each of the unique recognition sequences is derived from a different protein.

In another aspect, the present invention provides a method for preparing an array of capture agents. The method includes providing a plurality of isolated unique recognition sequences, the plurality of unique recognition sequences derived from at least 50%, 55%, 60%, 65%, 70%, 75%, 80%, 85%, 90%, 95% or 100% of an organism's proteome; generating a plurality of capture agents capable of binding the plurality of unique recognition sequences; and attaching the plurality of capture agents to a support having a plurality of discrete regions, wherein each of the capture agents is bound to a different discrete region, thereby preparing an array of capture agents.

In one fundamental aspect, the invention provides an apparatus for detecting simultaneously the presence of plural specific proteins in a multi-protein sample, e.g., a body fluid sample or a cell sample produced by lysing a natural tissue sample or microorganism sample. The apparatus comprises a plurality of immobilized capture agents for contact with the sample and which include at least a subset of agents which respectively bind specifically with individual unique recognition sequences, and means for detecting binding events between respective capture agents and the unique recognition sequences, e.g., probes for detecting the presence and/or concentration of unique recognition sequences bound to the capture agents. The unique recognition sequences are selected such that the presence of each sequence is unambiguously indicative of the presence in the sample (before it is fragmented) of a target protein from which it was derived. Each sample is treated with a set proteolytic protocol so that the unique recognition sequences are generated reproducibly. Optionally, the means for detecting binding events may include means for detecting data indicative of the amount of bound unique recognition sequence. This permits assessment of the relative quantity of at least two target proteins in said sample.

The invention also provides methods for simultaneously detecting the presence of plural specific proteins in a multi-protein sample. The method comprises denaturing and/or fragmenting proteins in a sample using a predetermined protocol to generate plural unique recognition sequences, the presence of which in the sample are indicative unambiguously of the presence of target proteins from which they were derived. At least a portion of the Recognition Sequences in the sample are contacted with plural capture agents which bind specifically to at least a portion of the unique recognition sequences. Detection of binding events to particular unique recognition sequences indicate the presence of target proteins corresponding to those sequences.

In another aspect, the present invention provides methods for improving the reproducibility of protein binding assays conducted on biological samples. The improvement enables detecting the presence of the target protein with greater effective sensitivity, or quantitating the protein more reliably (i.e., reducing standard deviation). The methods include: (1) treating the sample using a pre-determined protocol which A) inhibits masking of the target protein caused by target protein-protein non covalent or covalent complexation or aggregation, target protein degradation or denaturing, target protein post-translational modification, or environmentally induced alteration in target protein tertiary structure, and B) fragments the target protein to, thereby, produce at least one peptide epitope (i.e., a PET) whose concentration is directly proportional to the true concentration of the target protein in the sample; (2) contacting the so treated sample with a capture agent for the PET under suitable binding conditions, and (3) detecting binding events qualitatively or quantitatively.

For certain embodiments of the subject assay, the capture agents that are made available according to the teachings herein can be used to develop multiplex assays having increased sensitivity, dynamic range and/or recovery rates relative to, for example ELISA and other immunoassays. Such improved performance characteristics can include one or more of the following: a regression coefficient (R2) of 0.95 or greater for a reference standard, e.g., a comparable control sample, more preferably an R2 greater than 0.97, 0.99 or even 0.995; an average recovery rate of at least 50 percent, and more preferably at least 60, 75, 80 or even 90 percent; a average positive predictive value for the occurrence of proteins in a sample of at least 90 percent, more preferably at least 95, 98 or even 99 percent; an average diagnostic sensitivity (DSN) for the occurrence of proteins in a sample of 99 percent or higher, more preferably at least 99.5 or even 99.8 percent; an average diagnostic specificity (DSP) for the occurrence of proteins in a sample of 99 percent or higher, more preferably at least 99.5 or even 99.8 percent.

Another aspect of the invention provides a method for detecting the presence of a post-translational modification on a target protein within a sample, comprising: (1) computationally analyzing amino acid sequence of said target protein to identify one or more candidate site for said post-translational modification; (2) computationally identifying the amino acid sequence of one or more fragment of said target protein, said fragment predictably results from a treatment of said target protein within said sample, and said fragment encompasses said potential post-translational modification site and a PET (proteome epitope tag) unique to said fragment within said sample; (3) generating a capture agent that specifically binds said PET, and immobilizing said capture agent to a support; (4) subjecting said sample to said treatment to render said fragment soluble in solution, and contacting said sample after said treatment to said capture agent; (5) detecting, on said fragment bound to said capture agent, the presence or absence of said post-translational modification.

In one embodiment, said post-translational modification is acetylation, amidation, deamidation, prenylation, formylation, glycosylation, hydroxylation, methylation, myristoylation, phosphorylation, ubiquitination, ribosylation or sulphation.

In one embodiment, said post-translational modification is phosphorylation on tyrosine, serine or threonine.

In one embodiment, said step of computationally analyzing amino acid sequences includes a Nearest-Neighbor Analysis that identifies said PET based on criteria that also include one or more of pI, charge, steric, solubility, hydrophobicity, polarity and solvent exposed area.

In one embodiment, the method further comprises determining the specificity of said capture agent generated in (3) against one or more nearest neighbor(s), if any, of said PET.

In one embodiment, peptide competition assay is used in determining the specificity of said capture agent generated in (3) against said nearest neighbor(s) of said PET.

In one embodiment, said step of computationally analyzing amino acid sequences includes a solubility analysis that identifies said PET that are predicted to have at least a threshold solubility under a designated solution condition.

In one embodiment, the length of said PET is selected from 5-10 amino acids, 10-15 amino acids, 15-20 amino acids, 20-25 amino acids, 25-30 amino acids, or 30-40 amino acids.

In one embodiment, said capture agent is a full-length antibody, or a functional antibody fragment selected from: an Fab fragment, an F(ab')2 fragment, an Fd fragment, an Fv fragment, a dAb fragment, an isolated complementarity determining region (CDR), a single chain antibody (scFv), or derivative thereof.

In one embodiment, said capture agent is nucleotides; nucleic acids; PNA (peptide nucleic acids); proteins; peptides; carbohydrates; artificial polymers; or small organic molecules.

In one embodiment, said capture agent is aptamers, scaffolded peptides, or small organic molecules.

In one embodiment, said treatment is denaturation and/or fragmentation of said sample by a protease, a chemical agent, physical shearing, or sonication.

In one embodiment, said denaturation is thermo-denaturation or chemical denaturation.

In one embodiment, said thermo-denaturation is followed by or concurrent with proteolysis using thermo-stable proteases.

In one embodiment, said thermo-denaturation comprises two or more cycles of thermo-denaturation followed by protease digestion.

In one embodiment, said fragmentation is carried out by a protease selected from trypsin, chymotrypsin, pepsin, papain, carboxypeptidase, calpain, subtilisin, gluc-C, endo lys-C, or proteinase K.

In one embodiment, said sample is a body fluid selected from: saliva, mucous, sweat, whole blood, serum, urine, amniotic fluid, genital fluid, fecal material, marrow, plasma, spinal fluid, pericardial fluid, gastric fluid, abdominal fluid, peritoneal fluid, pleural fluid, synovial fluid, cyst fluid, cerebrospinal fluid, lung lavage fluid, lymphatic fluid, tears, prostatitc fluid, extraction from other body parts, or secretion from other glands; or from supernatant, whole cell lysate, or cell fraction obtained by lysis and fractionation of cellular material, extract or fraction of cells obtained directly from a biological entity or cells grown in an artificial environment.

In one embodiment, said sample is obtained from human, mouse, rat, frog (*Xenopus*), fish (zebra fish), fly (*Drosophila melanogaster*), nematode (*C. elegans*), fission or budding yeast, or plant (*Arabidopsis thaliana*).

In one embodiment, said sample is produced by treatment of membrane bound proteins.

In one embodiment, said treatment is carried out under conditions to preserve said post-translational modification.

In one embodiment, said PET and said candidate site for said post-translational modification do not overlap.

In one embodiment, said capture agent is optimized for selectivity for said PET under denaturing conditions.

In one embodiment, step (5) is effectuated by using a secondary capture agent specific for said post-translational modification, wherein said secondary capture agent is labeled by a detectable moiety selected from: an enzyme, a fluorescent label, a stainable dye, a chemilumninescent compound, a colloidal particle, a radioactive isotope, a near-infrared dye, a DNA dendrimer, a water-soluble quantum dot, a latex bead, a selenium particle, or a europium nanoparticle.

In one embodiment, said post-translational modification is phosphorylation, and said secondary capture agent is a labeled secondary antibody specific for phosphorylated tyrosine, phosphorylated serine, or phosphorylated threonine.

In one embodiment, said secondary antibody is labeled by an enzyme or a fluorescent group.

In one embodiment, said enzyme is HRP (horse radish peroxidase).

In one embodiment, said post-translational modification is phosphorylation, and said secondary capture agent is a fluoresent dye that specifically stains phosphoamino acids.

In one embodiment, said fluoresent dye is Pro-Q Diamond dye.

In one embodiment, said post-translational modification is glycosylation, and said labeled secondary capture agent is a labeled lectin specific for one or more sugar moieties attached to the glycosylation site.

In one embodiment, said post-translational modification is ubiquitination, and said labeled secondary capture agent is a labeled secondary antibody specific for ubiquitin.

In one embodiment, said sample contains billion molar excess of unrelated proteins or fragments thereof relative to said fragment.

In one embodiment, the method further comprises qantitating the amount of said fragment bound to said capture agent.

In one embodiment, step (3) is effectuated by immunizing an animal with an antigen comprising said PET sequence.

In one embodiment, the N- or C-terminus, or both, of said PET sequence are blocked to eliminate free N- or C-terminus, or both.

In one embodiment, the N- or C-terminus of said PET sequence are blocked by fusing the PET sequence to a heterologous carrier polypeptide, or blocked by a small chemical group.

In one embodiment, said carrier is KLH or BSA.

Another aspect of the invention provides an array of capture agents for identifying all potential substrates of a kinase within a proteome, comprising a plurality of capture agents, each immobilized on a distinct addressable location on solid support, each of said capture agents specifically binds a PET uniquely associated with a peptide fragment that predictably results from a treatment of all proteins within said proteome, wherein said peptide fragment encompasses one or more potential phosphorylation sites of said kinase.

In one embodiment, said solid support is beads or an array device in a manner that encodes the identity of said capture agents disposed thereon.

In one embodiment, said array includes 100 or more different capture agents.

In one embodiment, said array device includes a diffractive grating surface.

In one embodiment, said capture agents are antibodies or antigen binding portions thereof, and said array is an arrayed ELISA.

In one embodiment, said array device is a surface plasmon resonance array.

In one embodiment, said beads are encoded as a virtual array.

Another aspect of the invention provides a method of identifying, in a sample, potential substrates of a kinase, comprising: (1) computationally analyzing amino acid sequences of all proteins in a proteome to identify all candidate phosphorylation sites for said kinase; (2) computationally identifying all peptide fragments encompassing one or more said candidate phosphorylation sites, said fragments predictably result from a treatment of all proteins within said proteome; (3) for each said fragments identified in (2), identifying one PET unique to said fragment within said sample; (4) obtaining capture agents specific for each PET identified in (3), respectively, and immobilizing said capture agents to generate the array of the subject invention; (5) contacting said array of capture agents with a sample of said proteome subjected to said treatment, and (6) detecting the presence of phosphorylated residues within any fragments bound to said capture agents, if any, wherein the presence of phosphorylated residues within a specific fragment bound to a specific capture agent is indicative that the protein, from which said specific fragment is derived from, is a substrate of said kinase.

In one embodiment, said proteome is a human proteome.

In one embodiment, said candidate phosphorylation sites are predicted based on the consensus sequence of phosphorylation by said kinase.

In one embodiment, said consensus sequence is obtained from a phosphorylation site database.

In one embodiment, said sample is pre-treated by an agent that is a known agonist of said kinase, or a known agonist of the signaling pathway to which said kinase belongs.

In one embodiment, said treatment is carried out under conditions to preserve phosphorylation.

In one embodiment, the method further comprises verifying phosphorylation of said identified substrate by said kinase in vitro or in vivo.

In one embodiment, said proteome and said kinase are from the same organism.

In one embodiment, step (6) is effectuated by using a labeled secondary capture agent specific for phosphorylated residues.

Another aspect of the invention provides an array of capture agents for identifying all potential substrates of an enzyme catalyzing post-translational modification within a proteome, comprising a plurality of capture agents, each immobilized on a distinct addressable location on solid support, each of said capture agents specifically binds a PET uniquely associated with a peptide fragment that predictably results from a treatment of all proteins within said proteome, wherein said peptide fragment encompasses one or more potential post-translational modification sites of said enzyme.

Another aspect of the invention provides a method of identifying, in a sample, potential substrates of an enzyme that catalyze a post-translational modification selected from acetylation, amidation, deamidation, prenylation, formylation, glycosylation, hydroxylation, methylation, myristoylation, phosphorylation, ubiquitination, ribosylation or sulphation, comprising: (1) computationally analyzing amino acid sequences of all proteins in a proteome to identify all candidate post-translational modification sites for said enzyme; (2) computationally identifying all peptide fragments encompassing one or more said candidate post-translational modification sites, said fragments predictably result from a treatment of all proteins within said proteome; (3) for each said fragments identified in (2), identifying one PET unique to said fragment within said sample; (4) obtaining capture agents specific for each PET identified in (3), respectively, and immobilizing said capture agents in the array of the subject invention; (5) contacting said array of capture agents with a sample of said proteome subjected to said treatment, and (6) detecting the presence of residues with said post-translational modification within any fragments bound to said capture agents, if any, wherein the presence of residues with said post-translational modification within a specific fragment bound to a specific capture agent is indicative that the protein, from which said specific fragment is derived from, is a substrate of said enzyme.

Another aspect of the invention provides an array of capture agents for determining which, if any, of a selected number of signal transduction pathways within a proteome is activated or inhibited in response to a stimulation, comprising: a plurality of capture agents, each immobilized on a distinct addressable location on solid support, each of said capture agents specifically binds a unique PET associated with a peptide fragment that predictably results from a treatment of one or more key proteins of said signal transduction pathways, said peptide fragment encompasses one or more sites predictably post-translationally modified upon activation or inhibition of said pathway; wherein each of said signal transduction pathways is represented by one or more said key proteins.

In one embodiment, said signal transduction pathways are immune pathways activated by IL-4, IL-13, or Token-like receptor; seven-transmembrane receptor pathways activated by adrenergic, PAC1 receptor, *Dictyostelium discoideum* cAMP chemotaxis, Wnt/$Ca^{2+}$/cGMP, or G Protein-independent seven transmembrane receptor; circadian rhythm pathway of murine or *Drosophila*; insulin pathway; FAS pathway; TNF pathway; G-Protein coupled receptor pathways; integrin pathways; mitogen-activated protein kinase pathways of MAPK, JNK, or p38; estrogen receptor pathway; phosphoinositide 3-kinase pathway; Transforming Growth Factor-β (TGF-β) pathway; B Cell antigen receptor pathway; Jak-STAT pathway; STATS pathway; T Cell signal transduction pathway; Type 1 Interferon (α/β) pathway; jasmonate biochemical pathway; or jasmonate signaling pathway.

In one embodiment, said proteome is that of human, mouse, rat, frog (*Xenopus*), fish (zebra fish), fly (*Drosophila melanogaster*), nematode (*C. elegans*), fission or budding yeast, or plant (*Arabidopsis thaliana*).

In one embodiment, said post-translational modification is phosphorylation on a tyrosine, a serine, or a threonine residue.

In one embodiment, said stimulation is treatment of cells by a growth factor, a cytokine, a hormone, a steroid, a lipid, an antigen, a small molecule ($Ca^{2+}$, cAMP, cGMP), an osmotic shock, a heat or cold shock, a pH change, a change in ionic strength, a mechanical force, a viral or bacterial infection, or an attachment or detachment from a neighboring cell or a surface with or without a coated protein.

In one embodiment, activation or inhibition of at least one of said signal transduction pathways is manifested by a type of post-translational modification different from those of other signal transduction pathways.

In one embodiment, at least 3, 5, 10, 20, 50, 100, 200, 500, or 1000 signaling pathways are represented.

In one embodiment, signaling pathways of at least two different organisms are represented.

In one embodiment, similar signaling pathways of different organisms are represented.

In one embodiment, all capture agents are specific for proteins belonging to the same signal transduction pathway, and wherein all proteins of said signal transduction pathway that are predictably post-translationally modified are represented.

In one embodiment, one or more of said key proteins are post-translationally modified upon activation or inhibition of at least two of said signal transduction pathways. In this embodiment, the status of post-translational modification of these key proteins may indicate cross-talk between different, or even seemingly irrelavent, signaling pathways, since signals converge to these key proteins from many different pathways.

In one embodiment, the array further includes instructions for: (1) denaturing and/or fragmentation of a sample containing polypeptide analytes, in a way compatible with the array; (2) detecting interaction of said polypeptide analytes or fragments thereof with said capture agents.

In one embodiment, the instructions further includes one or more of: data for calibration procedures and preparation procedures, and statistical data on performance characteristics of the capture agents.

In one embodiment, the array has a recovery rate of at least 50 percent.

In one embodiment, the array has an overall positive predictive value for occurrence of proteins in said sample of at least 90 percent.

In one embodiment, the array has an overall diagnostic sensitivity (DSN) for occurrence of proteins in said sample of 99 percent or higher.

In one embodiment, said array comprises at least 1,000 or 10,000 different capture agents bound to said support.

In one embodiment, said capture agents are bound to said support at a density of 100 capture agents/$cm^2$.

In one embodiment, the array further includes one or more labeled reference peptides including PET portions that bind to said capture agents, wherein said binding of said capture agents with said polypeptide analytes is detected by a competitive binding assay with said reference peptides.

In one embodiment, the addressable array is collection of beads, each of which comprises a discrete species of capture agent and one or more labels which identify the bead.

Another aspect of the invention provides a method of using the array of the subject invention for determining which, if any, of a selected number of signal transduction pathways within a sample from a proteome is activated or inhibited in response to a stimulation, comprising: (1) subjecting said sample to said stimulation; (2) subjecting said sample to the treatment of the subject invention to render said peptide fragment of the subject invention soluble in solution; (3) contacting said sample after said treatment to the array of the subject invention; (4) detecting the presence, and/or quantitate the amount of post-translationally modified residues within any fragments bound to said capture agents, if any, wherein a change in the presence and/or amount of post-translationally modified residues within a specific fragment bound to a specific capture agent on said array, after said stimulation, is indicative that the signal transduction pathway represented by said specific fragment is activated or inhibited.

In one embodiment, said stimulation is effectuated by a candidate analog of a drug, and wherein activation or inhibition of a specific signal transduction pathway is monitored.

In one embodiment, said specific signal transduction pathway is one that is affected by said drug.

In one embodiment, the method further comprises comparing the degree of activation/inhibition of said specific signal transduction pathway by said analog and said drug.

In one embodiment, said specific signal transduction pathway is one that mediates a side effect of said drug.

Another aspect of the invention provides a business method for a biotechnology or pharmaceutical business, the method comprising: (i) identifying, using the method of the subject invention, one or more substrates for an enzyme catalyzing a post-translational modification; (ii) optionally, verifying the post-translational modification of said substrates by said enzyme; (iii) licensing to a third party the right to manufacture, or explore the use of said substrate as a target of said enzyme.

Another aspect of the invention provides a business method for providing protein detection arrays for identifying substrates of a post-translational modification enzyme, the method comprising: (i) identifying, within a proteome, one or more protein(s) or fragments thereof that have at least one site for said potential post-translational modification; (ii) identifying one or more PETs for each of one or more protein(s) or fragments thereof identified in (i); (iii) generating one or more capture agent(s) for each of said PETs identified in (ii), each of said capture agent(s) specifically bind one of said PETs for which said capture agent(s) is generated; (iv) fabricating arrays of capture agent(s) generated in (iii), wherein each of said capture agents is bound to a different discrete region or address of said solid support; (v) packaging said arrays of capture agent(s) in (iv) for use in diagnostic and/or research experimentation.

In one embodiment, the business method further comprises marketing said arrays of capture agent(s).

In one embodiment, the business method further comprises distributing said arrays of capture agent(s).

Another aspect of the invention provides a composition comprising a plurality of capture agents, wherein said plurality of capture agents are, collectively, capable of specifically interacting with all potential substrates of a post-translational modification enzyme within an organism's proteome, and wherein each of said capture agents is able to recognize and interact with only one PET within said potential substrate or fragment thereof containing the post-translational modification site.

In one embodiment, said capture agents are s elected from the group consisting of: nucleotides; nucleic acids; PNA (peptide nucleic acids); proteins; peptides; carbohydrates; artificial polymers; and small organic molecules.

In one embodiment, said capture agents are antibodies, or antigen binding fragments thereof.

In one embodiment, said capture agent is a full-length antibody, or a functional antibody fragment selected from: an Fab fragment, an F(ab')2 fragment, an Fd fragment, an Fv fragment, a dAb fragment, an isolated complementarity determining region (CDR), a single chain antibody (scFv), or derivative thereof.

In one embodiment, each of said capture agents is a single chain antibody.

Another aspect of the invention provides a business method for generating arrays of capture agents for marketing in research and development, the method comprising: (1) identifying one or more protein(s), a post-translational modification of which protein(s) represent the activation of at least one signal transduction pathway within an organism; (2) identifying one or more PETs for each of said protein(s), or fragment thereof containing at least one site for said post-translational modification; (3) generating one or more capture agent(s) for each of said PETs identified in (2), each of said capture agent(s) specifically bind one of said PETs for which said capture agent(s) is generated; (4) fabricating arrays of capture a gent(s) generated in (3) on solid support, wherein each of said capture agents is bound to a different discrete region of said solid support; (5) packaging said arrays of capture agent(s) in (4) for diagnosis and/or research use in commercial and/or academic laboratories.

In one embodiment, the business method further comprises marketing said arrays of capture agent(s) in (4) or said packaged arrays of capture agent(s) in (5) to potential customers and/or distributors.

In one embodiment, the business method further comprises distributing said arrays of capture agent(s) in (4) or said packaged arrays of capture agent(s) in (5) to customers and/or distributors.

Another aspect of the invention provides a business method for generating arrays of capture agents for marketing in research and development, the method comprising: (1) identifying one or more protein(s), a post-translational modification of which protein(s) represent the activation of at least one signal transduction pathway within an organism; (2) identifying one or more PETs for each of said protein(s), or fragment thereof containing at least one site for said post-translational modification; (3) licensing to a third party the right to manufacture or use said one or more PET(s) identified in (2).

Another aspect of the invention provides a method of immunizing a host animal against a disease condition associated with the presence or overexpression of a protein, comprising: (1) computationally analyzing the amino acid sequence of said protein to identify one or more PET(s) unique to said protein within the proteome of said host animal; (2) administering said one or more PET(s) identified in (1) to said host animal as an immunogen.

In one embodiment, said one or more PET(s) is administered to said host animal in a formulation designed to enhance the immune response of said host animal.

In one embodiment, said formulation comprises liposomes with or without additional adjuvants selected from: lipopolysaccharide (LPS), lipid A, muramyl dipeptide (MDP), glucan or cytokine.

In one embodiment, said cytokine is an interleukin, an interferon, or an colony stimulating factor.

In one embodiment, said formulation comprises a viral or bacterial vector encoding said one or more PET(s).

In one embodiment, said protein is from an organism different from the host animal.

In one embodiment, said protein is from a tumor cell, an infectious agent or a parasitic agent.

In one embodiment, said infectious agent is SARS virus.

Another aspect of the invention provides a method of generating antibodies specific for a marker protein for use in immunohistochemistry, the method comprising computationally analyzing the amino acid sequence of said marker protein to identify one or more PET(s) unique to said marker protein, wherein said PET(s) is located on the surface of said marker protein.

In one embodiment, said PET(s) excludes residues known to form cross-links under the fixation condition to be used in immunohistochemistry.

Another aspect of the invention provides a method for simultaneous unambiguous detection/quantification of a family of related proteins in a sample, comprising: (1) computationally analyzing amino acid sequences for said family of related proteins expected to be present in a sample of proteins, and identifying a common PET sequence unique to the said family of proteins; (2) generating a capture agent that selectively and specifically binds said common PET; (3) contacting said sample with said capture agent identified in (2); and (4) detecting the presence and/or measuring the amount of proteins bound to said capture agent, thereby simultaneously detecting/quantifying said family of related proteins in said sample.

In one embodiment, said family of related proteins are denatured and digested by protease or chemical agents prior to step (3).

In one embodiment, the method further comprises identifying at least one PET unique to each member of said family of related proteins to facilitate detection/quantification of said each member.

In one embodiment, said family of related proteins comprises a family of related kinases or cytokines.

In one embodiment, said sample is a body fluid selected from: saliva, mucous, sweat, whole blood, serum, urine, amniotic fluid, genital fluid, fecal material, marrow, plasma, spinal fluid, pericardial fluid, gastric fluid, abdominal fluid, peritoneal fluid, pleural fluid, synovial fluid, cyst fluid, cerebrospinal fluid, lung lavage fluid, lymphatic fluid, tears, prostatitc fluid, extraction from other body parts, or secretion from other glands; or from supernatant, whole cell lysate, or cell fraction obtained by lysis and fractionation of cellular material, extract or fraction of cells obtained directly from a biological entity or cells grown in an artificial environment.

Another aspect of the invention provides a method of processing a sample for use in PET-associated detection/quantitation of a target protein therein, the method comprising denaturing all proteins of said sample, and/or fragmenting all proteins of said sample by a protease, a chemical agent, physical shearing, or sonication.

In one embodiment, said denaturation is thermo-denaturation or chemical denaturation.

In one embodiment, said thermo-denaturation is followed by or concurrent with proteolysis using thermo-stable proteases.

In one embodiment, said thermo-denaturation comprises two or more cycles of thermo-denaturation followed by protease digestion.

In one embodiment, each of said two or more cycles of thermo-denaturation is carried out by denaturing at about 90° C. followed by protease digestion at about 50° C.

In one embodiment, wherein said fragmentation is carried out by a protease selected from trypsin, chymotrypsin, pepsin, papain, carboxypeptidase, calpain, subtilisin, gluc-C, endo lys-C, or proteinase K.

In one embodiment, said sample is a body fluid selected from: saliva, mucous, sweat, whole blood, serum, urine, amniotic fluid, genital fluid, fecal material, marrow, plasma, spinal fluid, pericardial fluid, gastric fluid, abdominal fluid, peritoneal fluid, pleural fluid, synovial fluid, cyst fluid, cerebrospinal fluid, lung lavage fluid, lymphatic fluid, tears, prostatitc fluid, extraction from other body parts, or secretion from other glands; or from supernatant, whole cell lysate, or cell fraction obtained by lysis and fractionation of cellular material, extract or fraction of cells obtained directly from a biological entity or cells grown in an artificial environment.

In one embodiment, said target protein forms or tends to form complexes or aggregates with other proteins within said sample.

In one embodiment, said target protein is a TGF-beta protein.

Another aspect of the invention provides a SARS virus-specific PET amino acid sequence as listed in Table SARS.

Another aspect of the invention provides a method of generating antibodies specific for a PET sequence, the method comprising: (1) administering to an animal a peptide immunogen comprising said PET sequence; (2) screening for antibodies specific for said PET sequence using a peptide fragment comprising said PET sequence, said peptide fragment predictably results from a treatment of a protein comprising said PET sequence.

In one embodiment, said peptide immunogen consists essentially of said PET sequence.

In one embodiment, the N- or C-terminus, or both, of said PET sequence are blocked to eliminate free N- or C-terminus, or both.

In one embodiment, more than one peptide immunogens, each comprising a PET sequence, are adminitered to said animal.

In one embodiment, said more than one peptide immunogens encompasses PET sequences derived from different proteins.

In one embodiment, said peptide immunogen comprises more than one PET sequences.

In one embodiment, said more than one PET sequences are linked by short linker sequences.

In one embodiment, said more than one PET sequences are derived from different proteins.

Another aspect of the invention provides a method for achieving high sensitivity detection and/or high accuracy quantitation of a target protein in a biological sample, comprising: (1) providing two or more different capture agents for detecting a target protein in a test sample, which capture agents are provided as an addressable array, and each of which capture agents selectively interacts with a peptide epitope tag (PET) of said target protein; (2) contacting said array with a solution of polypeptide analytes produced by denaturation and/or cleavage of proteins from the test sample; (3) detecting the presence and amount of said target protein in the sample from the interaction of said polypeptide analytes with each said capture agents; (4) quantitating, if present, the amount of the target protein in the sample by averaging the results obtained from each said capture agents in (3).

In one embodiment, each said different capture agents specifically bind a different PET of said target protein.

In one embodiment, said different capture agents belong to the same category of capture agent.

In one embodiment, said category of capture agent includes: antibody, non-antibody polypeptide, PNA (peptide nucleic acids), scaffolded peptide, peptidomimetic compound, polynucleotide, carbohydrates, artificial polymers, plastibody, chimeric binding agent derived from low-affinity ligand, and small organic molecules.

In one embodiment, at least two of said different capture agents belong to different categorys of capture agent selected from antibody, non-antibody polypeptide, PNA (peptide nucleic acids), scaffolded peptide, peptidomimetic compound, polynucleotide, carbohydrates, artificial polymers, plastibody, chimeric binding agent derived from low-affinity ligand, and small organic molecules.

In one embodiment, a subset of said capture agents bind to the same PET, and wherein each capture agents of said subset belong to different category of capture agent selected from: antibody, non-antibody polypeptide, PNA (peptide nucleic acids), scaffolded peptide, peptidomimetic compound, polynucleotide, carbohydrates, artificial polymers, plastibody, chimeric binding agent derived from low-affinity ligand, and small organic molecules.

In one embodiment, said target protein has two or more different forms within said biological sample.

In one embodiment, said different forms include unprocessed/pro-form and processed/mature form.

In one embodiment, said different forms include different alternative splicing forms.

In one embodiment, said different forms include unmodified and post-translationally modified form with respect to one or more post-translational modification(s).

In one embodiment, said post-translational modification includes: acetylation, amidation, deamidation, prenylation, formylation, glycosylation, hydroxylation, methylation, myristoylation, phosphorylation, ubiquitination, ribosylation and sulphation.

In one embodiment, a subset of said capture agents are specific for PET(s) only found in certain forms but not in other forms.

In one embodiment, the method further comprise determining the percentage of one form of said target protein as compared to the total target protein, or ratio of a first form of said target protein to a second form of said target protein.

In one embodiment, the method further comprises detecting other target proteins within said biological sample with capture agents specific for PETs of said other target proteins.

In one embodiment, two or more different capture agents are used for detecting and/or quantitating at least one of said other target proteins.

In one embodiment, for each capture agent, the method has a regression coefficient ($R^2$) of 0.95 or greater.

In one embodiment, the array has a recovery rate of at least 50 percent.

In one embodiment, the accuracy is 90%.

In one embodiment, said sample is a body fluid selected from: saliva, mucous, sweat, whole blood, serum, urine, amniotic fluid, genital fluid, fecal material, marrow, plasma, spinal fluid, pericardial fluid, gastric fluid, abdominal fluid, peritoneal fluid, pleural fluid, synovial fluid, cyst fluid, cerebrospinal fluid, lung lavage fluid, lymphatic fluid, tears, prostatitc fluid, extraction from other body parts, or secretion from other glands; or from supernatant, whole cell lysate, or cell fraction obtained by lysis and fractionation of cellular material, extract or fraction of cells obtained directly from a biological entity or cells grown in an artificial environment.

In one embodiment, said sample is obtained from human, mouse, rat, frog (*Xenopus*), fish (zebra fish), fly (*Drosophila melanogaster*), nematode (*C. elegans*), fission or budding yeast, or plant (*Arabidopsis thaliana*).

In one embodiment, said sample is produced by treatment of membrane bound proteins.

In one embodiment, step (3) is effectuated by directly detecting and measuring captured PET-containing polypeptides using mass spectrometry, colorimetric resonant reflection using a SWS or SRVD biosensor, surface plasmon resonance (SPR), interferometry, gravimetry, ellipsometry, an evanascent wave device, resonance light scattering, reflectometry, a fluorescent polymer superquenching-based bioassay, or arrays of nanosensors comprising nanowires or nanotubes.

In one embodiment, step (3) is effectuated by using secondary capture agents specific for captured polypeptide analytes, wherein said secondary capture agent is labeled by a detectable moiety selected from: an enzyme, a fluorescent label, a stainable dye, a chemilumninescent compound, a colloidal particle, a radioactive isotope, a near-infrared dye, a DNA dendrimer, a water-soluble quantum dot, a latex bead, a selenium particle, or a europium nanoparticle.

In one embodiment, said secondary capture agent is specific for a post-translational modification.

In one embodiment, said secondary capture agent is a labeled secondary antibody specific for phosphorylated tyrosine, phosphorylated serine, or phosphorylated threonine.

In one embodiment, said sample contains billion molar excess of unrelated proteins or fragments thereof relative to said target protein.

In one embodiment, said PET is identified based on one or more of the protein sources selected from: sequenced genome or virtually translated proteome, virtually translated transcriptome, or mass spectrometry database of tryptic fragments.

In one embodiment, the target protein is a biomarker with a concentration of about 1-5 pM in said sample.

In one embodiment, the target protein is a biomarker with relatively small concentration change of no more than 50%, 40%, 30%, 20%, 10%, 5%, or 1% in a disease sample.

Another aspect of the invention provides an array of capture agents for detecting and quantitating a target protein within a biological sample, comprising a plurality of capture agents, each immobilized on a distinct addressable location on solid support, each of said capture agents specifically binds a PET uniquely associated with a peptide fragment of said target protein that predictably results from a treatment of said biological sample.

In one embodiment, said solid support is beads or an array device in a manner that encodes the identity of said capture agents disposed thereon.

In one embodiment, said array includes 2-100 or more different capture agents.

In one embodiment, said array device includes a diffractive grating surface.

In one embodiment, said capture agents are antibodies or antigen binding portions thereof, and said array is an arrayed ELISA.

In one embodiment, said array device is a surface plasmon resonance array.

In one embodiment, said beads are encoded as a virtual array.

Another aspect of the invention provides a composition comprising a plurality of capture agents, wherein each of said capture agents recognizes and interacts with one PET of a target protein.

In one embodiment, said capture agents is independently selected from: antibody, non-antibody polypeptide, PNA (peptide nucleic acids), scaffolded peptide, peptidomimetic compound, polynucleotide, carbohydrates, artificial polymers, plastibody, chimeric binding agent derived from low-affinity ligand, and small organic molecules.

In one embodiment, said capture agents are antibodies, or antigen binding fragments thereof.

In one embodiment, said capture agent is a full-length antibody, or a functional antibody fragment selected from: an Fab fragment, an F(ab')$_2$ fragment, an Fd fragment, an Fv fragment, a dAb fragment, an isolated complementarity determining region (CDR), a single chain antibody (scFv), or derivative thereof.

In one embodiment, each of said capture agents is a single chain antibody.

It is also contemplated that all embodiments of the invention, including those specifically described for different aspects of the invention, can be combined with any other embodiments of the invention as appropriate.

Other features and advantages of the invention will be apparent from the following detailed description and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 depicts the sequence of the Interleukin-8 receptor A and the pentamer unique recognition sequences (URS) or PETs within this sequence.

FIG. 2 depicts the sequence of the Histamine H1 receptor and the pentamer unique recognition sequences (URS) or PETs within this sequence that are not destroyed by trypsin digestion.

FIG. 19 illustrates the common PETs and kinase-specific PETs useful for the detection of related kinases.

DETAILED DESCRIPTION OF THE INVENTION

The present invention provides methods, reagents and systems for detecting, e.g., globally detecting, the presence of a protein or a panel of proteins, especially protein with a specific type of modification (phosphorylation, glycosylation, alternative splicing, mutation, etc.) in a sample. In certain embodiments, the method may be used to quantitate the level of expression or post-translational modification of one or more proteins in the sample. The method includes providing a sample which has, preferably, been fragmented and/or denatured to generate a collection of peptides, and contacting the sample with a plurality of capture agents, wherein each of the capture agents is able to recognize and interact with a unique recognition sequence (URS) or PET characteristic of a specific protein or modified state. Through detection and deconvolution of binding data, the presence and/or amount of a protein in the sample is determined.

Figure 4:
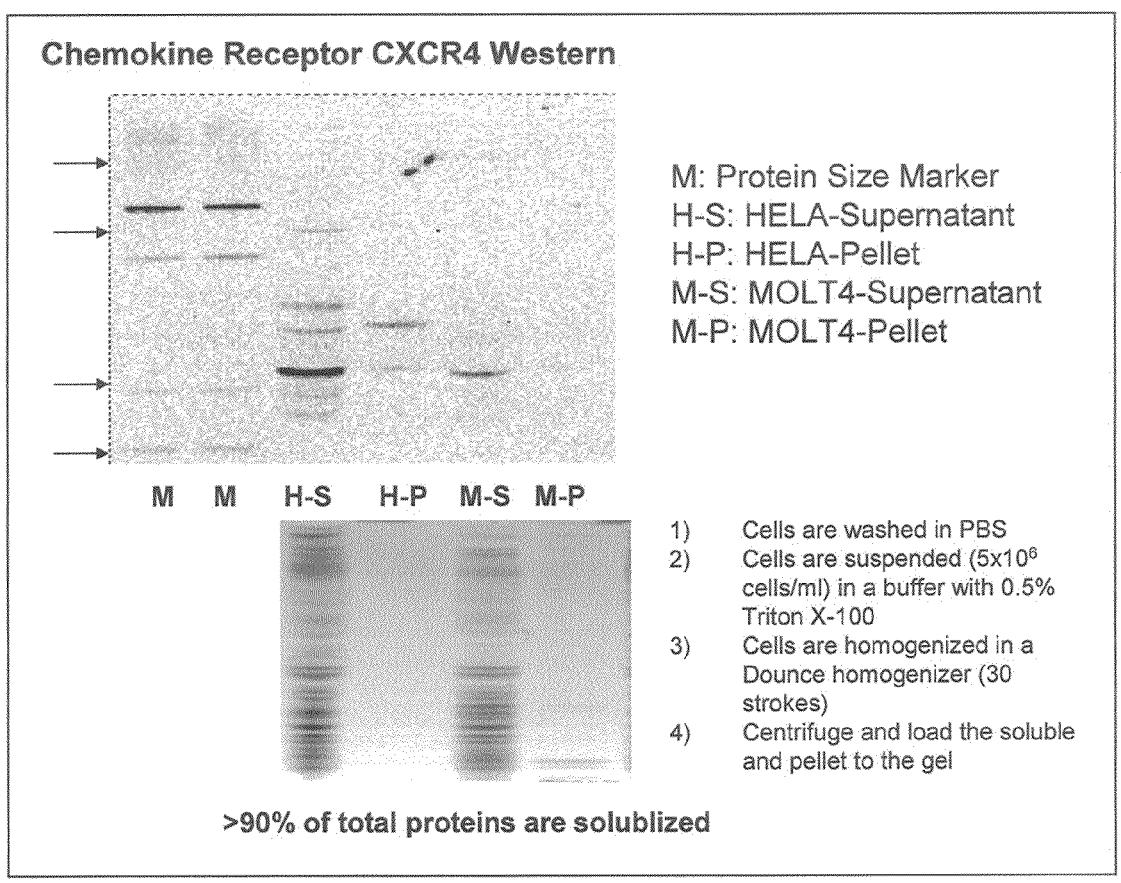
FIG. 4 illustrates the result of extraction of intracellular and membrane proteins. Top Panel: M: Protein Size Marker; H-S: HELA-Supernatant; H-P: HELA-Pellet; M-S: MOLT4-Supernatant; M-P: MOLT4-Pellet. Bottom panel shows that >90% of the proteins are solublized. Briefly, cells were washed in PBS, then suspended (5×10⁶ cells/ml) in a buffer with 0.5% Triton X-100 and homogenized in a Dounce homogenizer (30 strokes). The homogenized cells were centrifuged to separate the soluble portion and the pellet, which were both loaded to the gel.

In the first step, a biological sample is obtained. The biological sample as used herein refers to any body sample such as blood (serum or plasma), sputum, ascites fluids, pleural effusions, urine, biopsy specimens, isolated cells and/or cell membrane preparation (see FIG. 4). Methods of obtaining tissue biopsies and body fluids from mammals are well known in the art.

Retrieved biological samples can be further solubilized using detergent-based or detergent free (i.e., sonication) methods, depending on the biological specimen and the nature of the examined polypeptide (i.e., secreted, membrane anchored or intracellular soluble polypeptide).

In certain embodiment, the sample may be denatured by detergent-free methods, such as thermo-denaturation. This is especially useful in applications where detergent needs to be removed or is preferably removed in future analysis.

In certain embodiments, the solubilized biological sample is contacted with one or more proteolytic agents. Digestion is effected under effective conditions and for a period of time sufficient to ensure complete digestion of the diagnosed polypeptide(s). Agents that are capable of digesting a biological sample under moderate conditions in terms of temperature and buffer stringency are preferred. Measures are taken not to allow non-specific sample digestion, thus the quantity of the digesting agent, reaction mixture conditions (i.e., salinity and acidity), digestion time and temperature are carefully selected. At the end of incubation time proteolytic activity is terminated to avoid non-specific proteolytic activity, which may evolve from elongated digestion period, and to a void further proteolysis of other peptide-based molecules (i.e., protein-derived capture agents), which are added to the mixture in following steps.

If the sample is thermo-denatured, protease active at high temperatures, such as those isolated from thermophilic bacteria, can be used after the denaturation.

In the next method step the rendered biological sample is contacted with one or more capture agents, which are capable of discriminately binding one or more protein analytes through interaction via PET binding, and the products of such binding interactions examined and, as necessary, deconvolved, in order to identify and/or quantitate proteins found in the sample.

The present invention is based, at least in part, on the realization that unique recognition sequences (URSs) or PETs, which can be identified by computational analysis, can characterize individual proteins in a given sample, e.g., identify a particular protein from amongst others and/or identify a particular post-translationally modified form of a protein. The use of agents that bind PETs can be exploited for the detection and quantitation of individual proteins from a milieu of several or many proteins in a biological sample. The subject method can be used to assess the status of proteins or protein modifications in, for example, bodily fluids, cell or tissue samples, cell lystates, cell membranes, etc. In certain embodiments, the method utilizes a set of capture agents which discriminate between splice variants, allelic variants and/or point mutations (e.g., altered amino acid sequences arising from single nucleotide polymorphisms).

As a result of the sample preparation, namely denaturation and/or proteolysis, the subject method can be used to detect specific proteins/modifications in a manner that does not require the homogeneity of the target protein for analysis and is relatively refractory to small but otherwise significant differences between samples. The methods of the invention are suitable for the detection of all or any selected subset of all proteins in a sample, including cell membrane bound and organelle membrane bound proteins.

In certain embodiments, the detection step(s) of the method are not sensitive to post-translational modifications of the native protein; while in other embodiments, the preparation steps are designed to preserve a post-translational modification of interest, and the detection step(s) use a set of capture agents able to discriminate between modified and unmodified forms of the protein. Exemplary post-translational modifications that the subject method can be used to detect and quantitate include acetylation, amidation, deamidation, prenylation (such as farnesylation or geranylation), formylation, glycosylation, hydroxylation, methylation, myristoylation, phosphorylation, ubiquitination, ribosylation and sulphation. In one specific embodiment, the phosphorylation to be assessed is phosphorylation on tyrosine, serine, threonine or histidine residue. In another specific embodiment, the addition of a hydrophobic group to be assessed is the addition of a fatty acid, e.g., myristate or palmitate, or addition of a glycosyl-phosphatidyl inositol anchor. In certain embodiment, the present method can be used to assess protein modification profile of a particular disease or disorder, such as infection, neoplasm (neoplasia), cancer, an immune system disease or disorder, a metabolism disease or disorder, a muscle and bone disease or disorder, a nervous system disease or disorder, a signal disease or disorder, or a transporter disease or disorder.

As used herein, the term "unique recognition sequence," "URS," "Proteome Epitope Tag," or "PET" is intended to mean an amino acid sequence that, when detected in a particular sample, unambiguously indicates that the protein from which it was derived is present in the sample. For instance, a PET is selected such that its presence in a sample, as indicated by detection of an authentic binding event with a capture agent designed to selectively bind with the sequence, necessarily means that the protein which comprises the sequence is present in the sample. A useful PET must present a binding surface that is solvent accessible when a protein mixture is denatured and/or fragmented, and must bind with significant specificity to a selected capture agent with minimal cross reactivity. A unique recognition sequence is present within the protein from which it is derived and in no other protein that may be present in the sample, cell type, or species under investigation. Moreover, a PET will preferably not have any closely related sequence, such as determined by a nearest neighbor analysis, among the other proteins that may be present in the sample. A PET can be derived from a surface region of a protein, buried regions, splice junctions, or post translationally modified regions.

Perhaps the ideal PET is a peptide sequence which is present in only one protein in the proteome of a species. But a peptide comprising a PET useful in a human sample may in fact be present within the structure of proteins of other organisms. A PET useful in an adult cell sample is "unique" to that sample even though it may be present in the structure of other different proteins of the same organism at other times in its life, such as during embryology, or is present in other tissues or cell types different from the sample under investigation. A PET may be unique even though the same amino acid sequence is present in the sample from a different protein provided one or more of its amino acids are derivatized, and a binder can be developed which resolves the peptides.

When referring herein to "uniqueness" with respect to a PET, the reference is always made in relation to the foregoing. Thus, within the human genome, a PET may be an amino acid sequence that is truly unique to the protein from which it is derived. Alternatively, it may be unique just to the sample from which it is derived, but the same amino acid sequence may be present in, for example, the murine genome. Likewise, when referring to a sample which may contain proteins from multiple different organism, uniqueness refers to the ability to unambiguously identify and discriminate between proteins from the different organisms, such as being from a host or from a pathogen.

Thus, a PET may be present within more than one protein in the species, provided it is unique to the sample from which it is derived. For example, a PET may be an amino acid sequence that is unique to: a certain cell type, e.g., a liver, brain, heart, kidney or muscle cell; a certain biological sample, e.g., a plasma, urine, amniotic fluid, genital fluid, marrow, spinal fluid, or pericardial fluid sample; a certain biological pathway, e.g., a G-protein coupled receptor signaling pathway or a tumor necrosis factor (TNF) signaling pathway.

In this sense, the instant invention provides a method to identify application-specific PETs, depending on the type of proteins present in a given sample. This information may be readily obtained from a variety of sources. For example, when the whole genome of an organism is concerned, the sequenced genome provides each and every protein sequences that can be encoded by this genome, sometimes even including hypothetical proteins. This "virtually translated proteome" obtained from the sequenced genome is expected to be the most comprehensive in terms of representing all proteins in the sample. Alternatively, the type of transcribed mRNA species ("virtually translated transcriptome") within a sample may also provide useful information as to what type of proteins may be present within the sample. The mRNA species present may be identified by DNA microarrays, SNP analysis, or any other suitable RNA analysis tools available in the art of molecular biology. An added advantage of RNA analysis is that it may also provide information such as alternative splicing and mutations. Finally, direct protein analysis using techniques such as mass spectrometry may help to identify the presence of specific post-translation modifications and mutations, which may aid the design of specific PETs for specific applications. For example, WO 03/001879 A2 describes methods for determining the phosphorylaion status or sulfation state of a polypeptide or a cell using mass spectrometry, especially ICP-MS. In a related aspect, mass spectrometry, when coupled with separation techniques such as 2-D electrophoresis, GC/LC, etc., has provide a wealth of information regarding the profile of expressed proteins in specific samples.

For instance, plasma, the soluble component of the human blood, is believed to harbor thousands of distinct proteins, which originate from a variety of cells and tissues through either active secretion or leakage from blood cells or tissues. The dynamic range of plasma protein concentrations comprises at least nine orders of magnitude. Proteins involved in coagulation, immune defense, small molecule transport, and protease inhibition, many of them present in high abundance in this body fluid, have been functionally characterized and associated with disease processes. Pieper et al. (Proteomics 3: 1345-1364, 2003) fractionated blood serum proteins prior to display on two-dimensional electrophoresis (2-DE) gels using immunoaffinity chromatography to remove the most abundant serum proteins, followed by sequential anionexchange and size-exclusion chromatography. Serum proteins from 74 fractions were displayed on 2-DE gels. This approach succeeded in resolving approximately 3700 distinct protein spots, many of the post-translationally modified variants of plasma proteins. About 1800 distinct serum protein spots were identified by mass spectrometry. They collapsed into 325 distinct proteins, after sequence homology and similarity searches were carried out to eliminate redundant protein annotations. Coomassie Brillant Blue G-250 was used to visualize protein spots, and several proteins known to be present in serum in <10 ng/mL concentrations were identified such as interleukin-6, cathepsins, and peptide hormones.

The above article examplifies a typical approach for MS-based protein profiling study. In a typical such study, proteins from a specific sample are first separated using a chosen appropriate method (such as 2-DE). To identify a sepated protein, a gel spot or band is cut out, and in-gel tryptic digestion is performed thereafter. The gel must be stained with a mass spectrometry-compatible stain, for example colloidal Coommasie Brilliant Blue R-250 or Farmer's silver stain. The tryptic digest is then analyzed by MS such as MALDI-MS. The resulting mass spectrum of peptides, the peptide mass fingerprint or PMF, is searched against a sequence database. The PMF is compared to the masses of all theoretical tryptic peptides generated in silico by the search program. Programs such as Prospector, Sequest, and MasCot (Matrix Science, Ltd., London, UK) can be used for the database searching. For example, MasCot produces a statistically-based Mowse score indicates if any matches are significant or not. MS/MS is typically used to increase the likelihood of getting a database match. The PMF only contains the masses of the peptides. CID-MS/MS (collision induced dissociation of tandem MS) of peptides gives a spectrum of fragment ions that contain information about the amino-acid sequence. Adding this information to the peptide mass fingerprint allows Mascot to increase the statistical significance of a match. It is also possible in some cases to identify a protein by submitting only the raw MS/MS spectrum of a single peptide, a so-called MS/MS Ion Search, such is the amount of information contained in these spectra. MS/MS of peptides in a PMF can also greatly increase the confidence of a protein indentification, sometimes giving very high Mowse scores, especially with spectra from a TOF/TOF™.

Applied Biosystems 4700 Proteomics Analyzer, a MALDI-TOF/TOF™ tandem mass spectrometer, is unrivalled for the identification of proteins from tryptic digests, because of its sensitivity and speed. High-speed batch data acquisition is coupled to automated database searching using a locally-running copy of the Mascot search engine. When proteins cannot be identified by peptide mass mapping unambiguously, the digest can be further analyzed by a hybrid nanospray/ESI-Quadrupole-TOF-MS and MS/MS in a QSTAR mass spectrometer (Applied Biosystems Inc., Foster City, Calif.) for de novo peptide sequencing, sequence tag search, and/or MS/MS ion search. The static nanospray MS/MS is especially useful used when the target protein is not known (database absent). Applied Biosystems QSTAR® Pulsar i tandem mass spectrometer with a Dionex UltiMate capillary nanoLC system can be used for ES-LC-MS and MDLC (Multi-Dimensional Liquid Chromatography) analysis of peptide mixtures. A combination of these instruments can also perform MALDI-MS/MS, MDLC-ES-MS/MS, LC-MALDI, and Gel-C-MS/MS. With the Probot™ micro-fraction collector, HPLC can be interfaced with MALDI and spot peptides eluting from the nanoLC directly onto a MALDI target plate. This new LC-MALDI workflow for proteomics allows maximal potential for detecting proteins in complex mixtures by complementing the conventional 2-DE-based approach. For the traditional 2-DE approach, new and improved instruments, such as the Bio-Rad Protean 6-gel 2-DE apparatus and Packard MultiProbe II-EX robotic sample handler, in conjunction with the Applied Biosystems 4700 Proteomics Analyzer, allow higher sample throughputs for complete proteome characterisations.

Studies such as this, using equivalent instruments described above, have accumulated a large amount of MS data regarding expressed proteins and their specific protease digestion fragments, mostly tryptic fragment, stored in the form of many MS database. See, for example, MSDB (a non-identical protein sequence database maintained by the Proteomics Department at the Hammersmith Campus of Imperial College London. MSDB is designed specifically for mass spectrometry applications). PET analysis can be done on these tryptic peptides to identify PETs, which in turn is used for PET-specific antibody generation. The advantage of this approach is that it is known for certain that these (tryptic) peptide fragments will be generated in the sample of interest.

PETs identified based on the different methods described above may be combined. For example, in certain embodiments of the invention, multiple PETs need to be identified for any given target protein. Some of the PETs may be identified from sequenced genome data, while others may be identified from tryptic peptide databases.

The PET may be found in the native protein from which it is derived as a contiguous or as a non-contiguous amino acid sequence. It typically will comprise a portion of the sequence of a larger peptide or protein, recognizable by a capture agent either on the surface of an intact or partially degraded or digested protein, or on a fragment of the protein produced by a predetermined fragmentation protocol. The PET may be 5, 6, 7, 8, 9, 10, 11, 12, 13, 14, 15, 16, 17, 18, 19 or 20 amino acid residues in length. In a preferred embodiment, the PET is 6, 7, 8, 9 or 10 amino acid residues, preferably 8 amino acids in length.

The term "discriminate", as in "capture agents able to discriminate between", refers to a relative difference in the binding of a capture agent to its intended protein analyte and background binding to other proteins (or compounds) present in the sample. In particular, a capture agent can discriminate between two different species of proteins (or species of modifications) if the difference in binding constants is such that a statistically significant difference in binding is produced under the assay protocols and detection sensitivities. In preferred embodiments, the capture agent will have a discriminating index (D.I.) of at least 0.5, and even more preferably at least 0.1, 0.001, or even 0.0001, wherein D.I. is defined as $K_d(a)/K_d(b)$, $K_d(a)$ being the dissociation constant for the intended analyte, $K_d(b)$ is the dissociation constant for any other protein (or modified form as the case may be) present in sample.

As used herein, the term "capture agent" includes any agent which is capable of binding to a protein that includes a unique recognition sequence, e.g., with at least detectable selectivity. A capture agent is capable of specifically interacting with (directly or indirectly), or binding to (directly or indirectly) a unique recognition sequence. The capture agent is preferably able to produce a signal that may be detected. In a preferred embodiment, the capture agent is an antibody or a fragment thereof, such as a single chain antibody, or a peptide selected from a displayed library. In other embodiments, the capture agent may be an artificial protein, an RNA or DNA aptamer, an allosteric ribozyme or a small molecule. In other embodiments, the capture agent may allow for electronic (e.g., computer-based or information-based) recognition of a unique recognition sequence. In one embodiment, the capture agent is an agent that is not naturally found in a cell.

As used herein, the term "globally detecting" includes detecting at least 40% of the proteins in the sample. In a preferred embodiment, the term "globally detecting" includes detecting at least 50%, 60%, 65%, 70%, 75%, 80%, 85%, 90%, 95% or 100% of the proteins in the sample. Ranges intermediate to the above recited values, e.g., 50%-70% or 75%-95%, are also intended to be part of this invention. For example, ranges using a combination of any of the above recited values as upper and/or lower limits are intended to be included.

As used herein, the term "proteome" refers to the complete set of chemically distinct proteins found in an organism.

As used herein, the term "organism" includes any living organism including animals, e.g., avians, insects, mammals such as humans, mice, rats, monkeys, or rabbits; microorganisms such as bacteria, yeast, and fungi, e.g., *Escherichia coli, Campylobacter, Listeria, Legionella, Staphylococcus, Streptococcus, Salmonella, Bordatella, Pneumococcus, Rhizobium, Chlamydia, Rickettsia, Streptomyces, Mycoplasma, Helicobacter pylori, Chlamydia pneumoniae, Coxiella burnetii, Bacillus Anthracis*, and *Neisseria*; protozoa, e.g., *Trypanosoma brucei*; viruses, e.g., human immunodeficiency virus, rhinoviruses, rotavirus, influenza virus, Ebola virus, simian immunodeficiency virus, feline leukemia virus, respiratory syncytial virus, herpesvirus, pox virus, polio virus, parvoviruses, Kaposi's Sarcoma-Associated Herpesvirus (KSHV), adeno-associated virus (AAV), Sindbis virus, Lassa virus, West Nile virus, enteroviruses, such as 23 Coxsackie A viruses, 6 Coxsackie B viruses, and 28 echoviruses, Epstein-Barr virus, caliciviruses, astroviruses, and Norwalk virus; fungi, e.g., *Rhizopus, neurospora*, yeast, or *puccinia*; tapeworms, e.g., *Echinococcus granulosus, E. multilocularis, E. vogeli* and *E. oligarthrus*; and plants, e.g., *Arabidopsis thaliana*, rice, wheat, maize, tomato, alfalfa, oilseed rape, soybean, cotton, sunflower or canola.

As used herein, "sample" refers to anything which may contain a protein analyte. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The sample may also be a mixture of target protein containing molecules prepared in vitro.

As used herein, "a comparable control sample" refers to a control sample that is only different in one or more defined aspects relative to a test sample, and the present methods, kits or arrays are used to identify the effects, if any, of these defined difference(s) between the test sample and the control sample, e.g., on the amounts and types of proteins expressed and/or on the protein modification profile. For example, the control biosample can be derived from physiological normal conditions and/or can be subjected to different physical, chemical, physiological or drug treatments, or can be derived from different biological stages, etc.

"Predictably result from a treatment" means that a peptide fragment can be reliably generated by certain treatments, such as site specific protease digestion or chemical fragmentation. Since the digestion sites are quite specific, the peptide fragment generated by specific treatments can be reliably predicted in silico.

A report by MacBeath and Schreiber (*Science* 289 (2000), pp. 1760-1763) in 2000 established that proteins could be printed and assayed in a microarray format, and thereby had a large role in renewing the excitement for the prospect of a protein chip. Shortly after this, Snyder and co-workers reported the preparation of a protein chip comprising nearly 6000 yeast gene products and used this chip to identify new classes of calmodulin- and phospholipid-binding proteins (Zhu et al., *Science* 293 (2001), pp. 2101-2105). The proteins were generated by cloning the open reading frames and overproducing each of the proteins as glutathione-S-transferase- (GST) and His-tagged fusions. The fusions were used to facilitate the purification of each protein and the His-tagged family were also used in the immobilization of proteins. This and other references in the art established that microarrays containing thousands of proteins could be prepared and used to discover binding interactions. They also reported that proteins immobilized by way of the His tag—and therefore uniformly oriented at the surface—gave superior signals to proteins randomly attached to aldehyde surfaces.

Related work has addressed the construction of antibody arrays (de Wildt et al., Antibody arrays for high-throughput screening of antibody—antigen interactions. *Nat. Biotechnol.* 18 (2000), pp. 989-994; Haab, B. B. et al. (2001) Protein microarrays for highly parallel detection and quantitation of specific proteins and antibodies in complex solutions. *Genome Biol.* 2, RESEARCH0004.1-RESEARCH0004.13). Specifically, in an early landmark report, de Wildt and Tomlinson immobilized phage libraries presenting scFv antibody fragments on filter paper to select antibodies for specific antigens in complex mixtures (supra). The use of arrays for this purpose greatly increased the throughput when evaluating antibodies, allowing nearly 20,000 unique clones to be screened in one cycle. Brown and co-workers extended this concept to create molecularly defined arrays wherein antibodies were directly attached to aldehyde-modified glass. They printed 115 commercially available antibodies and analyzed their interactions with cognate antigens with semi-quantitative results (supra). Kingsmore and co-workers used an analogous approach to prepare arrays of antibodies recognizing 75 distinct cytokines and, using the rolling-circle amplification strategy (Lizardi et al., Mutation detection and single molecule counting using isothermal rolling circle amplification. *Nat. Genet.* 19 (1998), pp. 225-233), could measure cytokines at femtomolar concentrations (Schweitzer et al., Multiplexed protein profiling on microarrays by rolling-circle amplification. *Nat. Biotechnol.* 20 (2002), pp. 359-365).

These examples demonstrate the many important roles that protein chips can play, and give evidence for the widespread activity in fabrication of these tools. The following subsections describes in further detail about various aspects of the invention.

I. Type of Capture Agents

In certain preferred embodiments, the capture agents used should be capable of selective affinity reactions with PET moieties. Generally, such ineraction will be non-covalent in nature, though the present invention also contemplates the use of capture reagents that become covalently linked to the PET.

Examples of capture agents which can be used include, but are not limited to: nucleotides; nucleic acids including oligonucleotides, double stranded or single stranded nucleic acids (linear or circular), nucleic acid aptamers and ribozymes; PNA (peptide nucleic acids); proteins, including antibodies (such as monoclonal or recombinantly engineered antibodies or antibody fragments), T cell receptor and MHC complexes, lectins and scaffolded peptides; peptides; other naturally occurring polymers such as carbohydrates; artificial polymers, including plastibodies; small organic molecules such as drugs, metabolites and natural products; and the like.

In certain embodiments, the capture agents are immobilized, permanently or reversibly, on a solid support such as a bead, chip, or slide. When employed to analyze a complex mixture of proteins, the immobilized capture agent are arrayed and/or otherwise labeled for deconvolution of the binding data to yield identity of the capture agent (and therefore of the protein to which it binds) and (optionally) to quantitate binding. Alternatively, the capture agents can be provided free in solution (soluble), and other methods can be used for deconvolving PET binding in parallel.

In one embodiment, the capture agents are conjugated with a reporter molecule such as a fluorescent molecule or an enzyme, and used to detect the presence of bound PET on a substrate (such as a chip or bead), in for example, a "sandwich" type assay in which one capture agent is immobilized on a support to capture a PET, while a second, labeled capture agent also specific for the captured PET may be added to detect/quantitate the captured PET. In this embodiment, the peptide fragment contains two unique, non-overlapping PETs, one recognized by the immobilized the capture agent, the other recognized by the labled detecting capture agent. In a related embodiment, one PET unique to the peptide fragment can be used in conjunction with a common PET shared among several protein family members. The spacial arrangement of these two PET is such that binding by one capture agent will not substantially affect the binding by the other capture agent. In addition, the length of the peptide fragment is such that it encompasses two PETs properly spaced from each other. Preferably, peptide fragments is at least about 15 residues for sandwich assay. In other embodiments a labeled-PET peptide is used in a competitive binding assay to determine the amount of unlabeled PET (from the sample) binds to the capture agent. In this embodiment, the peptide fragment need only be long enough to encompass one PET, so peptides as short as 5-8 residues may be suitable.

Generally, the sandwich assay tend to be more (e.g., about 10, 100, or 1000 fold more) sensitive than the competitive binding assay.

An important advantage of the invention is that useful capture agents can be identified and/or synthesized even in the absence of a sample of the protein to be detected. With the completion of the whole genome in a number of organisms, such as human, fly (*Drosophila melanogaster*) and nematode (*C. elegans*), PET of a given length or combination thereof can be identified for any single given protein in a certain organism, and capture agents for any of these proteins of interest can then be made without ever cloning and expressing the full length protein.

In addition, the suitability of any PET to serve as an antigen or target of a capture agent can be further checked against other available information. For example, since amino acid sequence of many proteins can now be inferred from available genomic data, sequence from the structure of the proteins unique to the sample can be determined by computer aided searching, and the location of the peptide in the protein, and whether it will be accessible in the intact protein, can be determined. Once a suitable PET peptide is found, it can be synthesized using known techniques. With a sample of the PET in hand, an agent that interacts with the peptide such as an antibody or peptidic binder, can be raised against it or panned from a library. In this situation, care must be taken to assure that any chosen fragmentation protocol for the sample does not restrict the protein in a way that destroys or masks the PET. This can be determined theoretically and/or experimentally, and the process can be repeated until the selected PET is reliably retrieved by a capture agent(s).

The PET set selected according to the teachings of the present invention can be used to generate peptides either through enzymatic cleavage of the protein from which they were generated and selection of peptides, or preferably through peptide synthesis methods.

Proteolytically cleaved peptides can be separated by chromatographic or electrophoretic procedures and purified and renatured via well known prior art methods.

Synthetic peptides can be prepared by classical methods known in the art, for example, by using standard solid phase techniques. The standard methods include exclusive solid phase synthesis, partial solid phase synthesis methods, fragment condensation, classical solution synthesis, and even by recombinant DNA technology. See, e.g., Merrifield, J. Am. Chem. Soc., 85:2149 (1963), incorporated herein by reference. Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. W H Freeman and Co. N.Y.] and the composition of which can be confirmed via amino acid sequencing.

In addition, other additives such as stabilizers, buffers, blockers and the like may also be provided with the capture agent.

A. Antibodies

In one embodiment, the capture agent is an antibody or an antibody-like molecule (collectively "antibody"). Thus an antibody useful as capture agent may be a full length antibody or a fragment thereof, which includes an "antigen-binding portion" of an antibody. The term "antigen-binding portion," as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L, V_H, C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al. (1988) Science 242:423-426; and Huston et al. (1988) Proc. Natl. Acad. Sci. USA 85:5879-5883; and Osbourn et al. 1998, Nature Biotechnology 16: 778). Such single chain antibodies are also intended to be encompassed within the term "antigen-binding portion" of an antibody. Any $V_H$ and $V_L$ sequences of specific scFv can be linked to human immunoglobulin constant region cDNA or genomic sequences, in order to generate expression vectors encoding complete IgG molecules or other isotypes. $V_H$ and $V_L$ can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques.

Antibodies may be polyclonal or monoclonal. The terms "monoclonal antibodies" and "monoclonal antibody composition," as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition, typically displays a single binding affinity for a particular antigen with which it immunoreacts.

Any art-recognized methods can be used to generate an PET-directed antibody. For example, a PET (alone or linked to a hapten) can be used to immunize a suitable subject, (e.g., rabbit, goat, mouse or other mammal or vertebrate). For example, the methods described in U.S. Pat. Nos. 5,422,110; 5,837,268; 5,708,155; 5,723,129; and 5,849,531 (the contents of each of which are incorporated herein by reference) can be used. The immunogenic preparation can further include an adjuvant, such as Freund's complete or incomplete adjuvant, or similar immunostimulatory agent. Immunization of a suitable subject with a PET induces a polyclonal anti-PET antibody response. The anti-PET antibody titer in the immunized subject can be monitored over time by standard techniques, such as with an enzyme linked immunosorbent assay (ELISA) using immobilized PET.

The antibody molecules directed against a PET can be isolated from the mammal (e.g., from the blood) and further purified by well known techniques, such as protein A chromatography to obtain the IgG fraction. At an appropriate time after immunization, e.g., when the anti-PET antibody titers are highest, antibody-producing cells can be obtained from the subject and used to prepare, e.g., monoclonal antibodies by standard techniques, such as the hybridoma technique originally described by Kohler and Milstein (1975) Nature 256:495-497) (see also, Brown et al. (1981) J. Immunol. 127:539-46; Brown et al. (1980) J. Biol. Chem. 255:4980-83; Yeh et al. (1976) Proc. Natl. Acad. Sci. USA 76:2927-31; and Yeh et al. (1982) Int. J. Cancer 29:269-75), the more recent human B cell hybridoma technique (Kozbor et al. (1983) Immunol Today 4:72), or the EBV-hybridoma technique (Cole et al. (1985), Monoclonal Antibodies and Cancer Therapy, Alan R. Liss, Inc., pp. 77-96). The technology for producing monoclonal antibody hybridomas is well known (see generally R. H. Kenneth, in Monoclonal Antibodies: A New Dimension In Biological Analyses, Plenum Publishing Corp., New York, N.Y. (1980); E. A. Lerner (1981) Yale J. Biol. Med., 54:387-402; M. L. Gefter et al. (1977) Somatic Cell Genet. 3:231-36). Briefly, an immortal cell line (typically a myeloma) is fused to lymphocytes (typically splenocytes) from a mammal immunized with a PET immunogen as described above, and the culture supernatants of the resulting hybridoma cells are screened to identify a hybridoma producing a monoclonal antibody that binds a PET.

Any of the many well known protocols used for fusing lymphocytes and immortalized cell lines can be applied for the purpose of generating an anti-PET monoclonal antibody (see, e.g., G. Galfre et al. (1977) Nature 266:55052; Gefter et al. Somatic Cell Genet., cited supra; Lerner, Yale J. Biol. Med., cited supra; Kenneth, Monoclonal Antibodies, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, a minopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a PET, e.g., using a standard ELISA assay.

In addition, automated screening of antibody or scaffold libraries against arrays of target proteins/PETs will be the most rapid way of developing thousands of reagents that can be used for protein expression profiling. Furthermore, polyclonal antisera, hybridomas or selection from library systems may also be used to quickly generate the necessary capture agents. A high-throughput process for antibody isolation is described by Hayhurst and Georgiou in *Curr Opin Chem Biol* 5(6):683-9, December 2001 (incorporated by reference).

Figure 5:
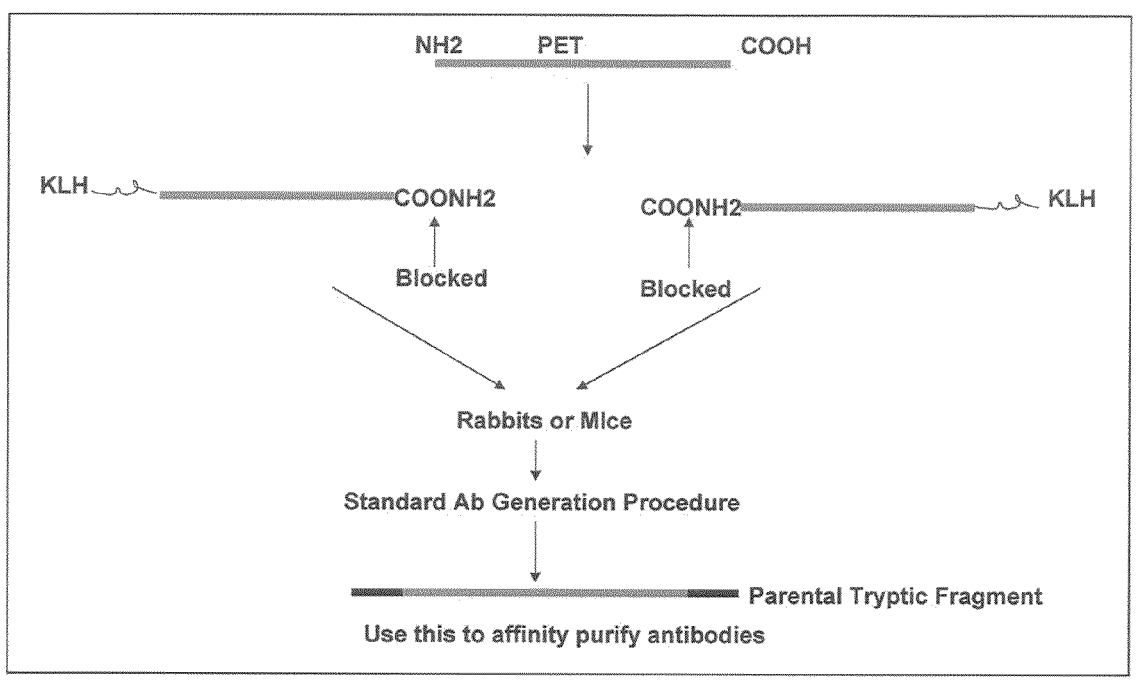
FIG. 5 illustrates the process for PET-specific antibody generation.

The PET antigens used for the generation of PET-specific antibodies are preferably blocked at either the N- or C-terminal end, most preferably at both ends (see FIG. 5) to generate neutral groups, since antibodies raised against peptides with non-neutralized ends may not be functional for the methods of the invention. The PET antigens can be most easily synthesized using standard molecular biology or chemical methods, for example, with a peptide synthesizer. The terminals can be blocked with NH2- or COO— groups as appropriate, or any other blocking agents to eliminate free ends. In a preferred embodiment, one end (either N- or C-terminus) of the PET will be conjugated with a carrier protein such as KLH or BSA to facilitate antibody generation. KLH represents Keyhole-limpet hemocyanin, an oxygen carrying copper protein found in the keyhole-limpet (*Megathura crenulata*), a primitive mollusk sea snail. KLH has a complex molecular arrangement and contains a diverse antigenic structure and elicits a strong nonspecific immune response in host animals. Therefore, when small peptides (which may not be very immunogenic) are used as immunogens, they are preferably conjugated to KLH or other carrier proteins (BSA) for enhanced immune responses in the host animal. The resulting antibodies can be affinity purified using a polypeptide corresponding to the PET-containing tryptic peptide of interest (see FIG. 5).

Blocking the ends of PET in antibody generation may be advantageous, since in many (if not most) cases, the selected PETs are contained within larger (tryptic) fragments. In these cases, the PET-specific antibodies are required to bind PETs in the middle of a peptide fragment. Therefore, blocking both the C- and N-terminus of the PETs best simulates the antibody binding of peptide fragments in a digested sample. Similarly, if the selected PET sequence happens to be at the N- or C-terminal end of a target fragment, then only the other end of the immunogen needs to be blocked, preferably by a carrier such as KLH or BSA.

Figure 24:
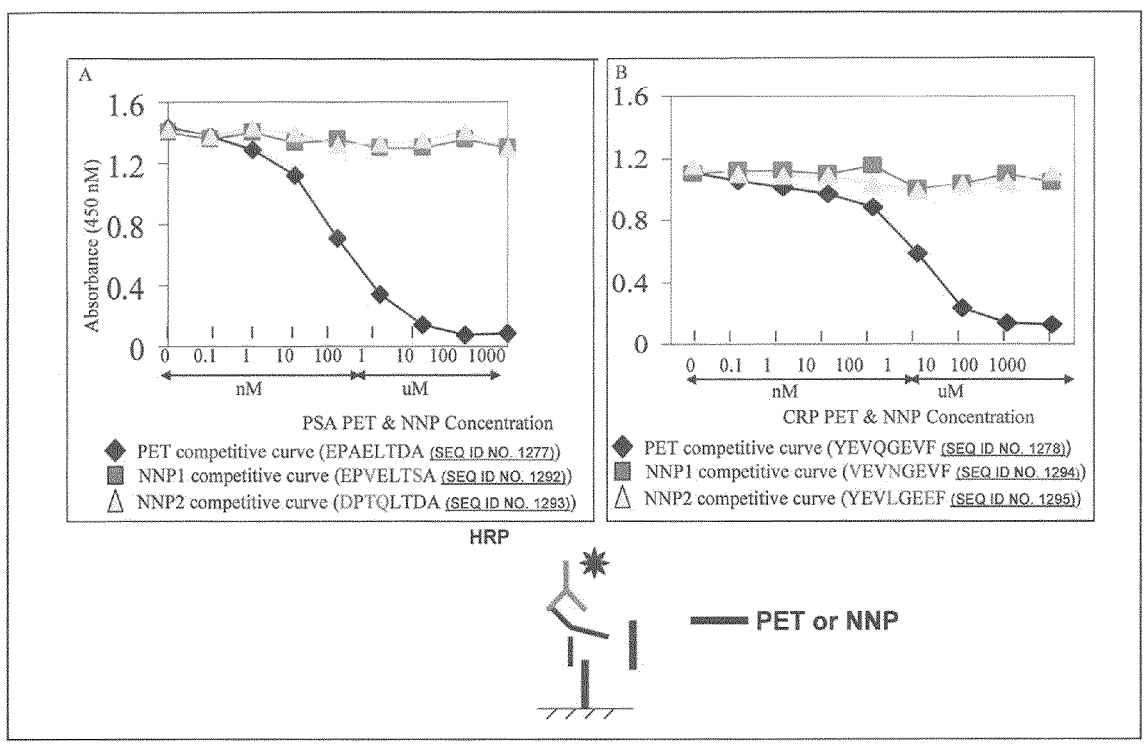
FIG. 24 illustrates that PET-specific antibodies are highly specific for the PET antigen and do not bind the nearest neighbors of the PET antigen.

FIG. 24 below shows that PET-specific antibodies are highly specific and have high affinity for their respective PET-antigens.

When generating PET-specific antibodies, preferably monoclonal antibodies, a peptide immunogen comprising essentially of the target PET sequence may be administered to an animal according to standard antibody generation protocol for short peptide antigens. In one embodiment, the short peptide antigen may be conjugated with a carrier such as KLH. However, when screening for antibodies specific for the PET sequence, it is preferred that the parental peptide fragments containing the PET sequence (such as the fragment resulting from trypsin digestion) is used. This ensures that the identified antibodies will be not only specific for the original PET sequence, but also able to recognize the PET peptide fragment for which the antibody is designed. Optionally, the specificity of the identified antibody can be further verified by reacting with the original immunogen such as the end-blocked PET sequence itself.

In certain embodiments, several different immunogens for different PET sequences may be simultaneously administered to the same animal, so that different antibodies may be generated in one animal. Obviously, for each immunogen, a separate screen would be needed to identify antibodies specific for the immunogen.

In an alternative embodiment, different PETs may be linked together in a single, longer immunogen for administration to an animal. The linker sequence can be flexible linkers such as GS, GSSSS (SEQ ID NO. 615) or repeats thereof (such as three-peats).

In both embodiments described above, the different immunogens may be from the same or different organisms or proteomes. These methods are all potential means of reducing costs in antibody generation. An unexpected advantage of using linked PET sequences as immunogen is that longer immunogens may at certain situations produce higher affinity antibodies than those produced using short PET sequences.

(i) PET-Specific Antibody Knowledge Database

The instant invention also provides an antibody knowledge database, which provides various important information pertaining to these antibodies. A specific subset of the antibodies will be PET-specific antibodies, which are either generated de novo based on the criteria set forth in the instant application, or generated by others in the prior art, which happens to recognize certain PETs.

Information to be included in the knowledge database can be quite comprehensive. Such knowledge may be further classified as public or proprietary. Examples of public information may include: target protein name, antibody source, catalog number, potential applications, etc. Exemplary proprietary information includes parental tryptic fragments in one or more organisms or specific samples, immunogen peptide sequences and whether or not they are PETs, affinity for the target PET, degree of cross-reactivity with other related epitopes (such as the closest nearest neighbors), and usefulness for various PET assays.

To this end, such information about 1000 anti-peptide antibodies are already collected/generated in the knowledge database. Among them, about 128 antibodies are deemed compatible for trypsin digested samples. Certain commercially available antibodies, the immunogen and the PET sequences they happen to contain, and the nearest neighbors of these PETs are listed below.

| Commercial Anti-PET Antibodies | | |
|---|---|---|
| Protein | PTP (Immunogen/ PET underlined) | Nearest Neighbors |
| Anti-Cyclin F | TASPTSSVDGGLGALP.K (SEQ ID NO. 616) | SASIDGGL (SEQ ID NO. 617); SSSSDGGL (SEQ ID NO. 618); TGSVDGGA (SEQ ID NO. 619); ESSSDGGL (SEQ ID NO. 620) |

-continued

Commercial Anti-PET Antibodies

| Protein | PTP (Immunogen/ PET underlined) | Nearest Neighbors |
|---|---|---|
| Anti-phospho SHC (Tyr239) | FAGMPITLTVSTSSLNLMAADCK (SEQ ID NO. 621) | ISTASLNL (SEQ ID NO. 622); ISTSSLNV (SEQ ID NO. 623); VSLSSLNL (SEQ ID NO. 624); MDTSSLNL (SEQ ID NO. 625); |
| Anti-phospho-PP2A (Tyr307) | EEEADINQLTEEFF.K (SEQ ID NO. 626) | ADLNQLTQ (SEQ ID NO. 627); RDINQLSE (SEQ ID NO. 628); ADFNQLAE (SEQ ID NO. 629); ADINMVTE (SEQ ID NO. 630); |
| Anti-Cdk8 | ATSQQPPQYSHQTHR (SEQ ID NO. 631) | QEPPQYSH (SEQ ID NO. 632); QQQPQFSH (SEQ ID NO. 633); QQPPQHSK (SEQ ID NO. 634); QQPPQQQH (SEQ ID NO. 635); |

B. Proteins and Peptides

Other methods for generating the capture agents of the present invention include phage-display technology described in, for example, Dower et al., WO 91/17271, McCafferty et al., WO 92/01047, Herzig et al., U.S. Pat. No. 5,877,218, Winter et al., U.S. Pat. No. 5,871,907, Winter et al., U.S. Pat. No. 5,858,657, Holliger et al., U.S. Pat. No. 5,837,242, Johnson et al., U.S. Pat. No. 5,733,743 and Hoogenboom et al., U.S. Pat. No. 5,565,332 (the contents of each of which are incorporated by reference). In these methods, libraries of phage are produced in which members display different antibodies, antibody binding sites, or peptides on their outer surfaces. Antibodies are usually displayed as Fv or Fab fragments. Phage displaying sequences with a desired specificity are selected by affinity enrichment to a specific PET.

Methods such as yeast display and in vitro ribosome display may also be used to generate the capture agents of the present invention. The foregoing methods are described in, for example, Methods in Enzymology Vol 328-Part C: Protein-protein interactions & Genomics and Bradbury A. (2001) Nature Biotechnology 19:528-529, the contents of each of which are incorporated herein by reference.

In a related embodiment, proteins or polypeptides may also act as capture agents of the present invention. These peptide capture agents also specifically bind to an given PET, and can be identified, for example, using phage display screening against an immobilized PET, or using any other art-recognized methods. Once identified, the peptidic capture agents may be prepared by any of the well known methods for preparing peptidic sequences. For example, the peptidic capture agents may be produced in prokaryotic or eukaryotic host cells by expression of polynucleotides encoding the particular peptide sequence. Alternatively, such peptidic capture agents may be synthesized by chemical methods. Methods for expression of heterologous peptides in recombinant hosts, chemical synthesis of peptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken, I. M. (1981) *CRC Crit. Rev. Biochem.* 11:255; Kaiser et al. (1989) *Science* 243:187; Merrifield, B. (1986) *Science* 232:342; Kent, S. B. H. (1988) *Ann. Rev. Biochem.* 57:957; and Offord, R. E. (1980) *Semisynthetic Proteins*, Wiley Publishing, which are incorporated herein in their entirety by reference).

The peptidic capture agents may also be prepared by any suitable method for chemical peptide synthesis, including solution-phase and solid-phase chemical synthesis. Preferably, the peptides are synthesized on a solid support. Methods for chemically synthesizing peptides are well known in the art (see, e.g., Bodansky, M. *Principles of Peptide Synthesis*, Springer Verlag, Berlin (1993) and Grant, G. A (ed.). *Synthetic Peptides: A User's Guide*, W. H. Freeman and Company, New York (1992). Automated peptide synthesizers useful to make the peptidic capture agents are commercially available.

C. Scaffolded Peptides

An alternative approach to generating capture agents for use in the present invention makes use of antibodies are scaffolded peptides, e.g., peptides displayed on the surface of a protein. The idea is that restricting the degrees of freedom of a peptide by incorporating it into a surface-exposed protein loop could reduce the entropic cost of binding to a target protein, resulting in higher affinity. Thioredoxin, fibronectin, avian pancreatic polypeptide (aPP) and albumin, as examples, are small, stable proteins with surface loops that will tolerate a great deal of sequence variation. To identify scaffolded peptides that selectively bind a target PET, libraries of chimeric proteins can be generated in which random peptides are used to replace the native loop sequence, and through a process of affinity maturation, those which selectively bind a PET of interest are identified.

D. Simple Peptides and Peptidomimetic Compounds

Peptides are also attractive candidates for capture agents because they combine advantages of small molecules and proteins. Large, diverse libraries can be made either biologically or synthetically, and the "hits" obtained in binding screens against PET moieties can be made synthetically in large quantities.

Peptide-like oligomers (Soth et al. (1997) Curr. Opin. Chem. Biol. 1:120-129) such as peptoids (Figliozzi et al., (1996) *Methods Enzymol.* 267:437-447) can also be used as capture reagents, and can have certain advantages over peptides. They are impervious to proteases and their synthesis can be simpler and cheaper than that of peptides, particularly if one considers the use of functionality that is not found in the 20 common amino acids.

E. Nucleic Acids

In another embodiment, aptamers binding specifically to a PET may also be used as capture agents. As used herein, the term "aptamer," e.g., RNA aptamer or DNA aptamer, includes single-stranded oligonucleotides that bind specifically to a target molecule. Aptamers are selected, for example, by employing an in vitro evolution protocol called systematic evolution of ligands by exponential enrichment. Aptamers bind tightly and specifically to target molecules; most aptamers to proteins bind with a $K_d$ (equilibrium dissociation constant) in the range of 1 pM to 1 nM. Aptamers and methods of preparing them are described in, for example, E. N. Brody et al. (1999) Mol. Diagn. 4:381-388, the contents of which are incorporated herein by reference.

In one embodiment, the subject aptamers can be generated using SELEX, a method for generating very high affinity receptors that are composed of nucleic acids instead of proteins. See, for example, Brody et al. (1999) *Mol. Diagn.* 4:381-388. SELEX offers a completely in vitro combinatorial chemistry alternative to traditional protein-based antibody technology. Similar to phage display, SELEX is advantageous in terms of obviating animal hosts, reducing production time and labor, and simplifying purification involved in generating specific binding agents to a particular target PET.

To further illustrate, SELEX can be performed by synthesizing a random oligonucleotide library, e.g., of greater than 20 bases in length, which is flanked by known primer sequences. Synthesis of the random region can be achieved by mixing all four nucleotides at each position in the sequence. Thus, the diversity of the random sequence is maximally $4^n$, where n is the length of the sequence, minus the frequency of palindromes and symmetric sequences. The greater degree of diversity conferred by SELEX affords greater opportunity to select for oligonuclotides that form 3-dimensional binding sites. Selection of high affinity oligonucleotides is achieved by exposing a random SELEX library to an immobilized target PET. Sequences, which bind readily without washing away, are retained and amplified by the PCR, for subsequent rounds of SELEX consisting of alternating affinity selection and PCR amplification of bound nucleic acid sequences. Four to five rounds of SELEX are typically sufficient to produce a high affinity set of aptamers.

Therefore, hundreds to thousands of aptamers can be made in an economically feasible fashion. Blood and urine can be analyzed on aptamer chips that capture and quantitate proteins. SELEX has also been adapted to the use of 5-bromo (5-Br) and 5-iodo (5-I) deoxyuridine residues. These halogenated bases can be specifically cross-linked to proteins. Selection pressure during in vitro evolution can be applied for both binding specificity and specific photo-cross-linkability. These are sufficiently independent parameters to allow one reagent, a photo-cross-linkable aptamer, to substitute for two reagents, the capture antibody and the detection antibody, in a typical sandwich array. After a cycle of binding, washing, cross-linking, and detergent washing, proteins will be specifically and covalently linked to their cognate aptamers. Because no other proteins are present on the chips, protein-specific stain will now show a meaningful array of pixels on the chip. Combined with learning algorithms and retrospective studies, this technique should lead to a robust yet simple diagnostic chip.

In yet another related embodiment, a capture agent may be an allosteric ribozyme. The term "allosteric ribozymes," as used herein, includes single-stranded oligonucleotides that perform catalysis when triggered with a variety of effectors, e.g., nucleotides, second messengers, enzyme cofactors, pharmaceutical agents, proteins, and oligonucleotides. Allosteric ribozymes and methods for preparing them are described in, for example, S. Seetharaman et al. (2001) *Nature Biotechnol.* 19: 336-341, the contents of which are incorporated herein by reference. According to Seetharaman et al., a prototype biosensor array has been assembled from engineered RNA molecular switches that undergo ribozyme-mediated self-cleavage when triggered by specific effectors. Each type of switch is prepared with a 5'-thiotriphosphate moiety that permits immobilization on gold to form individually addressable pixels. The ribozymes comprising each pixel become active only when presented with their corresponding effector, such that each type of switch serves as a specific analyte sensor. An addressed array created with seven different RNA switches was used to report the status of targets in complex mixtures containing metal ion, enzyme cofactor, metabolite, and drug analytes. The RNA switch array also was used to determine the phenotypes of *Escherichia coli* strains for adenylate cyclase function by detecting naturally produced 3',5'-cyclic adenosine monophosphate (cAMP) in bacterial culture media.

F. Plastibodies

In certain embodiments the subject capture agent is a plastibody. The term "plastibody" refers to polymers imprinted with selected template molecules. See, for example, Bruggemann (2002) *Adv Biochem Eng Biotechnol* 76:127-63; and Haupt et al. (1998) *Trends Biotech.* 16:468-475. The plastibody principle is based on molecular imprinting, namely, a recognition site that can be generated by stereoregular display of pendant functional groups that are grafted to the sidechains of a polymeric chain to thereby mimic the binding site of, for example, an antibody.

G. Chimeric Binding Agents Derived from Two Low-affinity Ligands

Still another strategy for generating suitable capture agents is to link two or more modest-affinity ligands and generate high affinity capture agent. Given the appropriate linker, such chimeric compounds can exhibit affinities that approach the product of the affinities for the two individual ligands for the PET. To illustrate, a collection of compounds is screened at high concentrations for weak interactors of a target PET. The compounds that do not compete with one another are then identified and a library of chimeric compounds is made with linkers of different length. This library is then screened for binding to the PET at much lower concentrations to identify high affinity binders. Such a technique may also be applied to peptides or any other type of modest-affinity PET-binding compound.

H. Labels for Capture Agents

The capture agents of the present invention may be modified to enable detection using techniques known to one of ordinary skill in the art, such as fluorescent, radioactive, chromatic, optical, and other physical or chemical labels, as described herein below.

I. Miscellaneous

In addition, for any given PET, multiple capture agents belonging to each of the above described categories of capture agents may be available. These multiple capture agents may have different properties, such as affinity/avidity/specificity for the PET. Different affinities are useful in covering the wide dynamic ranges of expression which some proteins can exhibit. Depending on specific use, in any given array of capture agents, different types/amounts of capture agents may be present on a single chip/array to achieve optimal overall performance.

In a preferred embodiment, capture agents are raised against PETs that are located on the surface of the protein of interest, e.g., hydrophilic regions. PETs that are located on the surface of the protein of interest may be identified using any of the well known software available in the art. For example, the Naccess program may be used.

Naccess is a program that calculates the accessible area of a molecule from a PDB (Protein Data Bank) format file. It can calculate the atomic and residue a ccessibilities for both proteins and nucleic acids. Naccess calculates the atomic accessible area when a probe is rolled around the Van der Waal's surface of a macromolecule. Such three-dimensional coordinate sets are available from the PDB at the Brookhaven National laboratory. The program uses the Lee & Richards (1971) *J. Mol. Biol.*, 55, 379-400 method, whereby a probe of given radius is rolled around the surface of the molecule, and the path traced out by its center is the accessible surface.

The solvent accessibility method described in Boger, J., Emini, E. A. & Schmidt, A., Surface probability profile-An heuristic approach to the selection of synthetic peptide antigens, Reports on the Sixth International Congress in Immunology (Toronto) 1986 p. 250 also may be used to identify PETs that are located on the surface of the protein of interest. The package MOLMOL (Koradi, R. et al. (1996) *J. Mol. Graph.* 14:51-55) and Eisenhaber's ASC method (Eisenhaber and Argos (1993) *J. Comput. Chem.* 14:1272-1280; Eisenhaber et al. (1995) *J. Comput. Chem.* 16:273-284) may also be used.

In another embodiment, capture agents are raised that are designed to bind with peptides generated by digestion of intact proteins rather than with accessible peptidic surface regions on the proteins. In this embodiment, it is preferred to employ a fragmentation protocol which reproducibly generates all of the PETs in the sample under study.

II. Tools Comprising Capture Agents (Arrays, etc.)

In certain embodiments, to construct arrays, e.g., high-density arrays, of capture agents for efficient screening of complex chemical or biological samples or large numbers of compounds, the capture agents need to be immobilized onto a solid support (e.g., a planar support or a bead). A variety of methods are known in the art for attaching biological molecules to solid supports. See, generally, Affinity Techniques, Enzyme Purification: Part B, Meth. Enz. 34 (ed. W. B. Jakoby and M. Wilchek, Acad. Press, N.Y. 1974) and Immobilized Biochemicals and Affinity Chromatography, Adv. Exp. Med. Biol. 42 (ed. R. Dunlap, Plenum Press, N.Y. 1974). The following are a few considerations when constructing arrays.

A. Formats and Surfaces Consideration

Protein arrays have been designed as a miniaturisation of familiar immunoassay methods such as ELISA and dot blotting, often utilizing fluorescent readout, and facilitated by robotics and high throughput detection systems to enable multiple assays to be carried out in parallel. Common physical supports include glass slides, silicon, microwells, nitrocellulose or PVDF membranes, and magnetic and other microbeads. While microdrops of protein delivered onto planar surfaces are widely used, related alternative architectures include CD centrifugation devices based on developments in microfluidics [Gyros] and specialized chip designs, such as engineered microchannels in a plate [The Living Chip™, Biotrove] and tiny 3D posts on a silicon surface [Zyomyx]. Particles in suspension can also be used as the basis of arrays, providing they are coded for identification; systems include color coding for microbeads [Luminex, Bio-Rad] and semiconductor nanocrystals [QDots™, Quantum Dots], and barcoding for beads [UltraPlex™, Smartbeads] and multimetal microrods [Nanobarcodes™ particles, Surromed]. Beads can also be assembled into planar arrays on semiconductor chips [LEAPS technology, BioArray Solutions].

B. Immobilisation Considerations

The variables in immobilization of proteins such as antibodies include both the coupling reagent and the nature of the surface being coupled to. Ideally, the immobilization method used should be reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally requires site-specific labeling of the protein.

The properties of a good protein array support surface are that it should be chemically stable before and after the coupling procedures, allow good spot morphology, display minimal nonspecific binding, not contribute a background in detection systems, and be compatible with different detection systems.

Both covalent and noncovalent methods of protein immobilization are used and have various pros and cons. Passive adsorption to surfaces is methodologically simple, but allows little quantitative or orientational control; it may or may not alter the functional properties of the protein, and reproducibility and efficiency are variable. Covalent coupling methods provide a stable linkage, can be applied to a range of proteins and have good reproducibility; however, orientation may be variable, chemical dramatization may alter the function of the protein and requires a stable interactive surface. Biological capture methods utilizing a tag on the protein provide a stable linkage and bind the protein specifically and in reproducible orientation, but the biological reagent must first be immobilized adequately and the array may require special handling and have variable stability.

Several immobilization chemistries and tags have been described for fabrication of protein arrays. Substrates for covalent attachment include glass slides coated with amino- or aldehyde-containing silane reagents [Telechem]. In the Versalinx™ system [Prolinx], reversible covalent coupling is achieved by interaction between the protein derivatized with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HydroGel™ [PerkinElmer], based on a 3-dimensional polyacrylamide gel; this substrate is reported to give a particularly low background on glass microarrays, with a high capacity and retention of protein function. Widely used biological capture methods are through biotin/streptavidin or hexahistidine/Ni interactions, having modified the protein appropriately. Biotin may be conjugated to a poly-lysine backbone immobilized on a surface such as titanium dioxide [Zyomyx] or tantalum pentoxide [Zeptosens].

Arenkov et al., for example, have described a way to immobilize proteins while preserving their function by using microfabricated polyacrylamide gel pads to capture proteins, and then accelerating diffusion through the matrix by microelectrophoresis (Arenkov et al. (2000), Anal Biochem 278(2): 123-31). The patent literature also describes a number of different methods for attaching biological molecules to solid supports. For example, U.S. Pat. No. 4,282,287 describes a method for modifying a polymer surface through the successive application of multiple layers of biotin, avidin, and extenders. U.S. Pat. No. 4,562,157 describes a technique for attaching biochemical ligands to surfaces by attachment to a photochemically reactive arylazide. U.S. Pat. No. 4,681,870 describes a method for introducing free amino or carboxyl groups onto a silica matrix, in which the groups may subsequently be covalently linked to a protein in the presence of a carbodiimide. In addition, U.S. Pat. No. 4,762,881 describes a method for attaching a polypeptide chain to a solid substrate by incorporating a light-sensitive unnatural amino acid group into the polypeptide chain and exposing the product to low-energy ultraviolet light.

The surface of the support is chosen to possess, or is chemically derivatized to possess, at least one reactive chemical group that can be used for further attachment chemistry. There may be optional flexible adapter molecules interposed between the support and the capture agents. In one embodiment, the capture agents are physically adsorbed onto the support.

In certain embodiments of the invention, a capture agent is immobilized on a support in ways that separate the capture agent's PET binding site region and the region where it is linked to the support. In a preferred embodiment, the capture agent is engineered to form a covalent bond between one of its termini to an adapter molecule on the support. Such a covalent bond may be formed through a Schiff-base linkage, a linkage generated by a Michael addition, or a thioether linkage.

In order to allow attachment by an adapter or directly by a capture agent, the surface of the substrate may require preparation to create suitable reactive groups. Such reactive groups could include simple chemical moieties such as amino, hydroxyl, carboxyl, carboxylate, aldehyde, ester, amide, amine, nitrile, sulfonyl, phosphoryl, or similarly chemically reactive groups. Alternatively, reactive groups may comprise more complex moieties that include, but are not limited to, sulfo-N-hydroxysuccinimide, nitrilotriacetic acid, activated hydroxyl, haloacetyl (e.g., bromoacetyl, iodoacetyl), activated carboxyl, hydrazide, epoxy, aziridine, sulfonylchloride, trifluoromethyldiaziridine, pyridyldisulfide, N-acyl-imidazole, imidazolecarbamate, succinimidylcarbonate, arylazide, anhydride, diazoacetate, benzophenone, isothiocyanate, isocyanate, imidoester, fluorobenzene, biotin and avidin. Techniques of placing such reactive groups on a substrate by mechanical, physical, electrical or chemical means are well known in the art, such as described by U.S. Pat. No. 4,681,870, incorporated herein by reference.

Once the initial preparation of reactive groups on the substrate is completed (if necessary), adapter molecules optionally may be added to the surface of the substrate to make it suitable for further attachment chemistry. Such adapters covalently join the reactive groups already on the substrate and the capture agents to be immobilized, having a backbone of chemical bonds forming a continuous connection between the reactive groups on the substrate and the capture agents, and having a plurality of freely rotating bonds along that backbone. Substrate adapters may be selected from any suitable class of compounds and may comprise polymers or copolymers of organic acids, aldehydes, alcohols, thiols, amines and the like. For example, polymers or copolymers of hydroxy-, amino-, or di-carboxylic acids, such as glycolic acid, lactic acid, sebacic acid, or sarcosine may be employed. Alternatively, polymers or copolymers of saturated or unsaturated hydrocarbons such as ethylene glycol, propylene glycol, saccharides, and the like may be employed. Preferably, the substrate adapter should be of an appropriate length to allow the capture agent, which is to be attached, to interact freely with molecules in a sample solution and to form effective binding. The substrate adapters may be either branched or unbranched, but this and other structural attributes of the adapter should not interfere stereochemically with relevant functions of the capture agents, such as a PET interaction. Protection groups, known to those skilled in the art, may be used to prevent the adapter's end groups from undesired or premature reactions. For instance, U.S. Pat. No. 5,412,087, incorporated herein by reference, describes the use of photoremovable protection groups on a adapter's thiol group.

To preserve the binding affinity of a capture agent, it is preferred that the capture agent be modified so that it binds to the support substrate at a region separate from the region responsible for interacting with it's ligand, i.e., the PET.

Methods of coupling the capture agent to the reactive end groups on the surface of the substrate or on the adapter include reactions that form linkage such as thioether bonds, disulfide bonds, amide bonds, carbamate bonds, urea linkages, ester bonds, carbonate bonds, ether bonds, hydrazone linkages, Schiff-base linkages, and noncovalent linkages mediated by, for example, ionic or hydrophobic interactions. The form of reaction will depend, of course, upon the available reactive groups on both the substrate/adapter and capture agent.

C. Array Fabrication Consideration

Preferably, the immobilized capture agents are arranged in an array on a solid support, such as a silicon-based chip or glass slide. One or more capture agents designed to detect the presence (and optionally the concentration) of a given known protein (one previously recognized as existing) is immobilized at each of a plurality of cells/regions in the array. Thus, a signal at a particular cell/region indicates the presence of a known protein in the sample, and the identity of the protein is revealed by the position of the cell. Alternatively, capture agents for one or a plurality of PET are immobilized on beads, which optionally are labeled to identify their intended target analyte, or are distributed in an array such as a microwell plate.

In one embodiment, the microarray is high density, with a density over about 100, preferably over about 1000, 1500, 2000, 3000, 4000, 5000 and further preferably over about 9000, 10000, 11000, 12000 or 13000 spots per $cm^2$, formed by attaching capture agents onto a support surface which has been functionalized to create a high density of reactive groups or which has been functionalized by the addition of a high density of adapters bearing reactive groups. In another embodiment, the microarray comprises a relatively small number of capture agents, e.g., 10 to 50, selected to detect in a sample various combinations of specific proteins which generate patterns probative of disease diagnosis, cell type determination, pathogen identification, etc.

Although the characteristics of the substrate or support may vary depending upon the intended use, the shape, material and surface modification of the substrates must be considered. Although it is preferred that the substrate have at least one surface which is substantially planar or flat, it may also include indentations, protuberances, steps, ridges, terraces and the like and may have any geometric form (e.g., cylindrical, conical, spherical, concave surface, convex surface, string, or a combination of any of these). Suitable substrate materials include, but are not limited to, glasses, ceramics, plastics, metals, alloys, carbon, papers, agarose, silica, quartz, cellulose, polyacrylamide, polyamide, and gelatin, as well as other polymer supports, other solid-material supports, or flexible membrane supports. Polymers that may be used as substrates include, but are not limited to: polystyrene; poly (tetra)fluoroethylene (PTFE); polyvinylidenedifluoride; polycarbonate; polymethylmethacrylate; polyvinylethylene; polyethyleneimine; polyoxymethylene (POM); polyvinylphenol; polylactides; polymethacrylimide (PMI); polyalkenesulfone (PAS); polypropylene; polyethylene; polyhydroxyethylmethacrylate (HEMA); polydimethylsiloxane; polyacrylamide; polyimide; and various block co-polymers. The substrate can also comprise a combination of materials, whether water-permeable or not, in multi-layer configurations. A preferred embodiment of the substrate is a plain 2.5 cm×7.5 cm glass slide with surface Si—OH functionalities.

Array fabrication methods include robotic contact printing, ink-jetting, piezoelectric spotting and photolithography.

A number of commercial arrayers are available [e.g. Packard Biosience] as well as manual equipment [V & P Scientific]. Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85 sq microns, equivalent to 25 million spots per sq cm, at the limit for optical detection; their readout methods are fluorescence and atomic force microscopy (AFM).

A microfluidics system for automated sample incubation with arrays on glass slides and washing has been codeveloped by NextGen and PerkinElmer Lifesciences.

For example, capture agent microarrays may be produced by a number of means, including "spotting" wherein small amounts of the reactants are dispensed to particular positions on the surface of the substrate. Methods for spotting include, but are not limited to, microfluidics printing, microstamping (see, e.g., U.S. Pat. Nos. 5,515,131, 5,731,152, Martin, B. D. et al. (1998), *Langmuir* 14: 3971-3975 and Haab, B et al. (2001) *Genome Biol* 2 and MacBeath, G. et al. (2000) *Science* 289: 1760-1763), microcontact printing (see, e.g., PCT Publication WO 96/29629), inkjet head printing (Roda, A. et al. (2000) *BioTechniques* 28: 492-496, and Silzel, J. W. et al. (1998) *Clin Chem* 44: 2036-2043), microfluidic direct application (Rowe, C. A. et al. (1999) *Anal Chem* 71: 433-439 and Bernard, A. et al. (2001), *Anal Chem* 73: 8-12) and electrospray deposition (Morozov, V. N. et al. (1999) *Anal Chem* 71: 1415-1420 and Moerman R. et al. (2001) *Anal Chem* 73: 2183-2189). Generally, the dispensing device includes calibrating means for controlling the amount of sample deposition, and may also include a structure for moving and positioning the sample in relation to the support surface. The volume of fluid to be dispensed per capture agent in an array varies with the intended use of the array, and available equipment. Preferably, a volume formed by one dispensation is less than 100 nL, more preferably less than 10 nL, and most preferably about 1 nL. The size of the resultant spots will vary as well, and in preferred embodiments these spots are less than 20,000 µm in diameter, more preferably less than 2,000 µm in diameter, and most preferably about 150-200 µm in diameter (to yield about 1600 spots per square centimeter). Solutions of blocking agents may be applied to the microarrays to prevent non-specific binding by reactive groups that have not bound to a capture agent. Solutions of bovine serum albumin (BSA), casein, or nonfat milk, for example, may be used as blocking agents to reduce background binding in subsequent assays.

In preferred embodiments, high-precision, contact-printing robots are used to pick up small volumes of dissolved capture agents from the wells of a microtiter plate and to repetitively deliver approximately 1 nL of the solutions to defined locations on the surfaces of substrates, such as chemically-derivatized glass microscope slides. Examples of such robots include the GMS 417 Arrayer, commercially available from Affymetrix of Santa Clara, Calif., and a split pin arrayer constructed according to instructions downloadable from the Brown lab website at http://cmgm.stanford.edu/pbrown. This results in the formation of microscopic spots of compounds on the slides. It will be appreciated by one of ordinary skill in the art, however, that the current invention is not limited to the delivery of 1 nL volumes of solution, to the use of particular robotic devices, or to the use of chemically derivatized glass slides, and that alternative means of delivery can be used that are capable of delivering picoliter or smaller volumes. Hence, in addition to a high precision array robot, other means for delivering the compounds can be used, including, but not limited to, ink jet printers, piezoelectric printers, and small volume pipetting robots.

In one embodiment, the compositions, e.g., microarrays or beads, comprising the capture agents of the present invention may also comprise other components, e.g., molecules that recognize and bind specific peptides, metabolites, drugs or drug candidates, RNA, DNA, lipids, and the like. Thus, an array of capture agents only some of which bind a PET can comprise an embodiment of the invention.

As an alternative to planar microarrays, bead-based assays combined with fluorescence-activated cell sorting (FACS) have been developed to perform multiplexed immunoassays. Fluorescence-activated cell sorting has been routinely used in diagnostics for more than 20 years. Using mAbs, cell surface markers are identified on normal and neoplastic cell populations enabling the classification of various forms of leukemia or disease monitoring (recently reviewed by Herzenberg et al. *Immunol Today* 21 (2000), pp. 383-390).

Bead-based assay systems employ microspheres as solid support for the capture molecules instead of a planar substrate, which is conventionally used for microarray assays. In each individual immunoassay, the capture agent is coupled to a distinct type of microsphere. The reaction takes place on the surface of the microspheres. The individual microspheres are color-coded by a uniform and distinct mixture of red and orange fluorescent dyes. After coupling to the appropriate capture molecule, the different color-coded bead sets can be pooled and the immunoassay is performed in a single reaction vial. Product formation of the PET targets with t heir respective capture agents on the different bead types can be detected with a fluorescence-based reporter system. The signal intensities are measured in a flow cytometer, which is able to quantify the amount of captured targets on each individual bead. Each bead type and thus each immobilized target is identified using the color code measured by a second fluorescence signal. This allows the multiplexed quantification of multiple targets from a single sample. Sensitivity, reliability and accuracy are similar to those observed with standard microtiter ELISA procedures. Color-coded microspheres can be used to perform up to a hundred different assay types simultaneously (LabMAP system, Laboratory Muliple Analyte Profiling, Luminex, Austin, Tex., USA). For example, microsphere-based systems have been used to simultaneously quantify cytokines or autoantibodies from biological samples (Carson and Vignali, *J Immunol Methods* 227 (1999), pp. 41-52; Chen et al., *Clin Chem* 45 (1999), pp. 1693-1694; Fulton et al., *Clin Chem* 43 (1997), pp. 1749-1756). Bellisario et al. (*Early Hum Dev* 64 (2001), pp. 21-25) have used this technology to simultaneously measure antibodies to three HIV-1 antigens from newborn dried bloodspot specimens.

Bead-based systems have several advantages. As the capture molecules are coupled to distinct microspheres, each individual coupling event can be perfectly analyzed. Thus, only quality-controlled beads can be pooled for multiplexed immunoassays. Furthermore, if an additional parameter has to be included into the assay, one must only add a new type of loaded bead. No washing steps are required when performing the assay. The sample is incubated with the different bead types together with fluorescently labeled detection antibodies. After formation of the sandwich immuno-complex, only the fluorophores that are definitely bound to the surface of the microspheres are counted in the flow cytometer.

D. Related Non-array Formats

An alternative to an array of capture agents is one made through the so-called "molecular imprinting" technology, in which peptides (e.g. selected PETs) are used as templates to generate structurally complementary, sequence-specific cavities in a polymerisable matrix; the cavities can then specifically capture (digested) proteins which have the appropriate primary amino acid sequence [ProteinPrint™, Aspira Biosystems]. To illustrate, a chosen PET can be synthesized, and a universal matrix of polymerizable monomers is allowed to self assemble around the peptide and crosslinked into place. The PET, or template, is then removed, leaving behind a cavity complementary in shape and functionality. The cavities can be formed on a film, discrete sites of an array or the surface of beads. When a sample of fragmented proteins is exposed to the capture agent, the polymer will selectively retain the target protein containing the PET and exclude all others. After the washing, only the bound PET-containing peptides remain. Common staining and tagging procedures, or any of the non-labeling techniques described below can be used to detect expression levels and/or post translational modifications. See, for example, WO 01/61354 A1 and WO 01/61355 A1.

Alternatively, the captured peptides can be eluted for further analysis such as mass spectrometry analysis. Although several well-established chemical methods for the sequencing of peptides, polypeptides and proteins are known (for example, the Edman degradation), mass spectrometric methods are becoming increasingly important in view of their speed and ease of use. Mass spectrometric methods have been developed to the point at which they are capable of sequencing peptides in a mixture even without any prior chemical purification or separation, typically using electrospray ionization and tandem mass spectrometry (MS/MS). For example, see Yates III (J. Mass Spectrom, 1998 vol. 33 pp. 1-19), Papayannopoulos (Mass Spectrom. Rev. 1995, vol. 14 pp. 49-73), and Yates III, McCormack, and Eng (Anal. Chem. 1996 vol. 68 (17) pp. 534A-540A). Thus, in a typical MS/MS sequencing experiment, molecular ions of a particular peptide are selected by the first mass analyzer and fragmented by collisions with neutral gas molecules in a collision cell. The second mass analyzer is then used to record the fragment ion spectrum that generally contains enough information to allow at least a partial, and often the complete, sequence to be determined. See, for example, U.S. Pat. Nos. 6,489,608, 5,470,753, 5,246,865, all incorporated hereion by reference, and related applications/patents.

Another methodology which can be used diagnostically and in expression profiling is the ProteinChip® array [Ciphergen], in which solid phase chromatographic surfaces bind proteins with similar characteristics of charge or hydrophobicity from mixtures such as plasma or tumor extracts, and SELDI-TOF mass spectrometry is used to detection the retained proteins. The ProteinChip® is credited with the ability to identify novel disease markers. However, this technology differs from the protein arrays under discussion here since, in general, it does not involve immobilization of individual proteins for detection of specific ligand interactions.

E. Single Assay Format

PET-specific affinity capture agents can also be used in a single assay format. For example, such agents can be used to develop a better assay for detecting circulating agents, such as PSA, by providing increased sensitivity, dynamic range and/or recovery rate. For instance, the single assays can have functional performance characteristics which exceed traditional ELISA and other immunoassays, such as one or more of the following: a regression coefficient (R2) of 0.95 or greater for a reference standard, e.g., a comparable control sample, more preferably an R2 greater than 0.97, 0.99 or even 0.995; a recovery rate of at least 50 percent, and more preferably at least 60, 75, 80 or even 90 percent; a positive predictive value for occurrence of the protein in a sample of at least 90 percent, more preferably at least 95, 98 or even 99 percent; a diagnostic sensitivity (DSN) for occurrence of the protein in a sample of 99 percent or higher, more preferably at least 99.5 or even 99.8 percent; a diagnostic specificity (DSP) for occurrence of the protein in a sample of 99 percent or higher, more preferably at least 99.5 or even 99.8 percent.

III. Methods of Detecting Binding Events

The capture agents of the invention, as well as compositions, e.g., microarrays or beads, comprising these capture agents have a wide range of applications in the health care industry, e.g., in therapy, in clinical diagnostics, in in vivo imaging or in drug discovery. The capture agents of the present invention also have industrial and environmental applications, e.g., in environmental diagnostics, industrial diagnostics, food safety, toxicology, catalysis of reactions, or high-throughput screening; as well as applications in the agricultural industry and in basic research, e.g., protein sequencing.

The capture agents of the present invention are a powerful analytical tool that enables a user to detect a specific protein, or group of proteins of interest present within complex samples. In addition, the invention allow for efficient and rapid analysis of samples; sample conservation and direct sample comparison. The invention enables "multi-parametric" analysis of protein samples. As used herein, a "multi-parametric" analysis of a protein sample is intended to include an analysis of a protein sample based on a plurality of parameters. For example, a protein sample may be contacted with a plurality of PETs, each of the PETs being able to detect a different protein within the sample. Based on the combination and, preferably the relative concentration, of the proteins detected in the sample the skilled artisan would be able to determine the identity of a sample, diagnose a disease or pre-disposition to a disease, or determine the stage of a disease The capture agents of the present invention may be used in any method suitable for detection of a protein or a polypeptide, such as, for example, in immunoprecipitations, immunocytochemistry, Western Blots or nuclear magnetic resonance spectroscopy (NMR).

To detect the presence of a protein that interacts with a capture agent, a variety of art known methods may be used. The protein to be detected may be labeled with a detectable label, and the amount of bound label directly measured. The term "label" is used herein in a broad sense to refer to agents that are capable of providing a detectable signal, either directly or through interaction with one or more additional members of a signal producing system. Labels that are directly detectable and may find use in the present invention include, for example, fluorescent labels such as fluorescein, rhodamine, BODIPY, cyanine dyes (e.g. from Amersham Pharmacia), Alexa dyes (e.g. from Molecular Probes, Inc.), fluorescent dye phosphoramidites, beads, chemilumninescent compounds, colloidal particles, and the like. Suitable fluorescent dyes are known in the art, including fluorescein-isothiocyanate (FITC); rhodamine and rhodamine derivatives; Texas Red; phycoerythrin; allophycocyanin; 6-carboxyfluorescein (6-FAM); 2',7'-dimethoxy-41,51-dichloro carboxyfluorescein (JOE); 6-carboxy-X-rhodamine (ROX); 6-carboxy-21,41,71,4,7-hexachlorofluorescein (HEX); 5-carboxyfluorescein (5-FAM); N,N,N1,N'-tetramethyl carboxyrhodamine (TAMRA); sulfonated rhodamine; Cy3;

Cy5, etc. Radioactive isotopes, such as $^{35}$S, $^{32}$P, $^3$H, $^{125}$I, etc., and the like can also be used for labeling. In addition, labels may also include near-infrared dyes (Wang et al., *Anal. Chem.*, 72:5907-5917 (2000), upconverting phosphors (Hampl et al., *Anal. Biochem.*, 288:176-187 (2001), DNA dendrimers (Stears et al., *Physiol. Genomics* 3: 93-99 (2000), quantum dots (Bruchez et al., *Science* 281:2013-2016 (1998), latex beads (Okana et al., *Anal. Biochem.* 202:120-125 (1992), selenium particles (Stimpson et al., *Proc. Natl. Acad. Sci.* 92:6379-6383 (1995), and europium nanoparticles (Harma et al., *Clin. Chem.* 47:561-568 (2001). The label is one that preferably does not provide a variable signal, but instead provides a constant and reproducible signal over a given period of time.

A very useful labeling agent is water-soluble quantum dots, or so-called "functionalized nanocrystals" or "semiconductor nanocrystals" as described in U.S. Pat. No. 6,114,038. Generally, quantum dots can be prepared which result in relative monodispersity (e.g., the diameter of the core varying approximately less than 10% between quantum dots in the preparation), as has been described previously (Bawendi et al., 1993, J. Am. Chem. Soc. 115:8706). Examples of quantum dots are known in the art to have a core selected from the group consisting of CdSe, CdS, and CdTe (collectively referred to as "CdX") (see, e.g., Norris et al., 1996, Physical Review B. 53:16338-16346; Nirmal et al., 1996, Nature 383: 802-804; Empedocles et al., 1996, Physical Review Letters 77:3873-3876; Murray et al., 1996, Science 270: 1355-1338; Effros et al., 1996, Physical Review B. 54:4843-4856; Sacra et al., 1996, J. Chem. Phys. 103:5236-5245; Murakoshi et al., 1998, J. Colloid Interface Sci. 203:225-228; Optical Materials and Engineering News, 1995, Vol. 5, No. 12; and Murray et al., 1993, J. Am. Chem. Soc. 115:8706-8714; the disclosures of which are hereby incorporated by reference).

CdX quantum dots have been passivated with an inorganic coating ("shell") uniformly deposited thereon. Passivating the surface of the core quantum dot can result in an increase in the quantum yield of the luminescence emission, depending on the nature of the inorganic coating. The shell which is used to passivate the quantum dot is preferably comprised of YZ wherein Y is Cd or Zn, and Z is S, or Se. Quantum dots having a CdX core and a YZ shell have been described in the art (see, e.g., Danek et al., 1996, Chem. Mater. 8:173-179; Dabbousi et al., 1997, J. Phys. Chem. B 101:9463; Rodriguez-Viejo et al., 1997, Appl. Phys. Lett. 70:2132-2134; Peng et al., 1997, J. Am. Chem. Soc. 119:7019-7029; 1996, Phys. Review B. 53:16338-16346; the disclosures of which are hereby incorporated by reference). However, the above described quantum dots, passivated using an inorganic shell, have only been soluble in organic, non-polar (or weakly polar) solvents. To make quantum dots useful in biological applications, it is desirable that the quantum dots are water-soluble. " Water-soluble" is used herein to mean sufficiently soluble or suspendable in an aqueous-based solution, such as in water or water-based solutions or buffer solutions, including those used in biological or molecular detection systems as known by those skilled in the art.

U.S. Pat. No. 6,114,038 provides a composition comprising functionalized nanocrystals for use in non-isotopic detection systems. The composition comprises quantum dots (capped with a layer of a capping compound) that are water-soluble and functionalized by operably linking, in a successive manner, one or more additional compounds. In a preferred embodiment, the one or more additional compounds form successive layers over the nanocrystal. More particularly, the functionalized nanocrystals comprise quantum dots capped with the capping compound, and have at least a diaminocarboxylic acid which is operatively linked to the capping compound. Thus, the functionalized nanocrystals may have a first layer comprising the capping compound, and a second layer comprising a diaminocarboxylic acid; and may further comprise one or more successive layers including a layer of amino acid, a layer of affinity ligand, or multiple layers comprising a combination thereof. The composition comprises a class of quantum dots that can be excited with a single wavelength of light resulting in detectable luminescence emissions of high quantum yield and with discrete luminescence peaks. Such functionalized nanocrystal may be used to label capture agents of the instant invention for their use in the detection and/or quantitation of the binding events.

U.S. Pat. No. 6,326,144 describes quantum dots (QDs) having a characteristic spectral emission, which is tunable to a desired energy by selection of the particle size of the quantum dot. For example, a 2 nanometer quantum dot emits green light, while a 5 nanometer quantum dot emits red light. The emission spectra of quantum dots have line widths as narrow as 25-30 nm depending on the size heterogeneity of the sample, and lineshapes that are symmetric, gaussian or nearly gaussian with an absence of a tailing region. The combination of tunability, narrow linewidths, and symmetric emission spectra without a tailing region provides for high resolution of multiply-sized quantum dots within a system and enables researchers to examine simultaneously a variety of biological moieties tagged with QDs. In addition, the range of excitation wavelengths of the nanocrystal quantum dots is broad and can be higher in energy than the emission wavelengths of all available quantum dots. Consequently, this allows the simultaneous excitation of all quantum dots in a system with a single light source, usually in the ultraviolet or blue region of the spectrum. QDs are also more robust than conventional organic fluorescent dyes and are more resistant to photobleaching than the organic dyes. The robustness of the QD also alleviates the problem of contamination of the degradation products of the organic dyes in the system being examined. These QDs can be used for labeling capture agents of protein, nucleic acid, and other biological molecules in nature. Cadmium Selenide quantum dot nanocrystals are available from Quantum Dot Corporation of Hayward, Calif.

Alternatively, the sample to be tested is not labeled, but a second stage labeled reagent is added in order to detect the presence or quantitate the amount of protein in the sample. Such "sandwich based" methods of detection have the disadvantage that two capture agents must be developed for each protein, one to capture the PET and one to label it once captured. Such methods have the advantage that they are characterized by an inherently improved signal to noise ratio as they exploit two binding reactions at different points on a peptide, thus the presence and/or concentration of the protein can be measured with more accuracy and precision because of the increased signal to noise ratio.

In yet another embodiment, the subject capture array can be a "virtual arrays". For example, a virtual array can be generated in which antibodies or other capture agents are immobilized on beads whose identity, with respect to the particular PET it is specific for as a consequence to the associated capture agent, is encoded by a particular ratio of two or more covalently attached dyes. Mixtures of encoded PET-beads are added to a sample, resulting in capture of the PET entities recognized by the immobilized capture agents.

Figure 3:
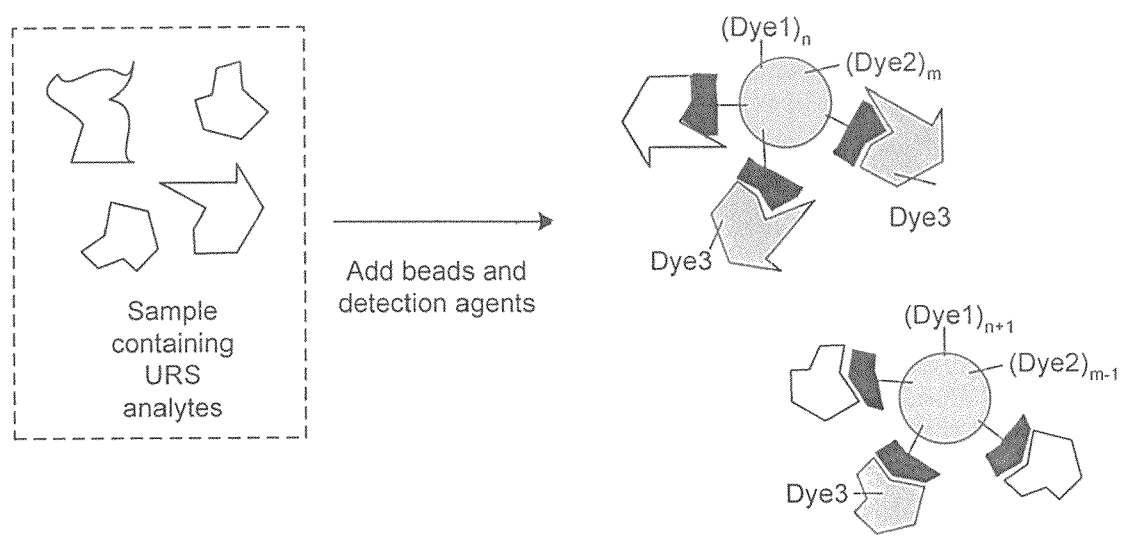
FIG. 3 is an alternative format for the parallel detection of PET from a complex sample. In this type of "virtual array" each of many different beads displays a capture agent directed against a different PET. Each different bead is color-coded by covalent linkage of two dyes (dye1 and dye2) at a characteristic ratio. Only two different beads are shown for clarity. Upon application of the sample, the capture agent binds a cognate PET, if present in the sample. Then a mixture of secondary binding ligands (in this case labeled PET peptides) conjugated to a third fluorescent tag is applied to the mixture of beads. The beads can then be analyzed using flow cytometry other detection method that can resolve, on a bead-by-bead basis, the ratio of dye1 and dye2 and thus identify the PET captured on the bead, while the fluorescence intensity of dye3 is read to quantitate the amount of labeled PET on the bead (which will in inversely reflect the analyte PET level).

To quantitate the captured species, a sandwich assay with fluorescently labeled antibodies that bind the captured PET, or a competitive binding assay with a fluorescently labeled ligand for the capture agent, are added to the mix. In one embodiment, the labeled ligand is a labeled PET that competes with the analyte PET for binding to the capture agent. The beads are then introduced into an instrument, such as a flow cytometer, that reads the intensity of the various fluorescence signals on each bead, and the identity of the bead can be determined by measuring the ratio of the dyes (FIG. 3). This technology is relatively fast and efficient, and can be adapted by researchers to monitor almost any set of PET of interest.

In another embodiment, an array of capture agents are embedded in a matrix suitable for ionization (such as described in Fung et al. (2001) *Curr. Opin. Biotechnol.* 12:65-69). After application of the sample and removal of unbound molecules (by washing), the retained PET proteins are analyzed by mass spectrometry. In some instances, further proteolytic digestion of the bound species with trypsin may be required before ionization, particularly if electrospray is the means for ionizing the peptides.

All the above named reagents may be used to label the capture agents. Preferably, the capture agent to be labeled is combined with an activated dye that reacts with a group present on the protein to be detected, e.g., amine groups, thiol groups, or aldehyde groups.

The label may also be a covalently bound enzyme capable of providing a detectable product signal after addition of suitable substrate. Examples of suitable enzymes for use in the present invention include horseradish peroxidase, alkaline phosphatase, malate dehydrogenase and the like.

Enzyme-Linked Immunosorbent Assay (ELISA) may also be used for detection of a protein that interacts with a capture agent. In an ELISA, the indicator molecule is covalently coupled to an enzyme and may be quantified by determining with a spectrophotometer the initial rate at which the enzyme converts a clear substrate to a correlated product. Methods for performing ELISA are well known in the art and described in, for example, Perlmann, H. and Perlmann, P. (1994). Enzyme-Linked Immunosorbent Assay. In: Cell Biology: A Laboratory Handbook. San Diego, Calif., Academic Press, Inc., 322-328; Crowther, J. R. (1995). Methods in Molecular Biology, Vol. 42-ELISA: Theory and Practice. Humana Press, Totowa, N.J.; and Harlow, E. and Lane, D. (1988). Antibodies: A Laboratory Manual. Cold Spring Harbor Laboratory Press, Cold Spring Harbor, N.Y., 553-612, the contents of each of which are incorporated by reference. Sandwich (capture) ELISA may also be used to detect a protein that interacts with two capture agents. The two capture agents may be able to specifically interact with two PETs that are present on the same peptide (e.g., the peptide which has been generated by fragmentation of the sample of interest, as described above). Alternatively, the two capture agents may be able to specifically interact with one PET and one non-unique amino acid sequence, both present on the same peptide (e.g., the peptide which has been generated by fragmentation of the sample of interest, as described above). Sandwich ELISAs for the quantitation of proteins of interest are especially valuable when the concentration of the protein in the sample is low and/or the protein of interest is present in a sample that contains high concentrations of contaminating proteins.

A fully-automated, microarray-based approach for high-throughput, ELISAs was described by Mendoza et al. (*BioTechniques* 27:778-780,782-786,788, 1999). This system consisted of an optically flat glass plate with 96 wells separated by a Teflon mask. More than a hundred capture molecules were immobilized in each well. Sample incubation, washing and fluorescence-based detection were performed with an automated liquid pipettor. The microarrays were quantitatively imaged with a scanning charge-coupled device (CCD) detector. Thus, the feasibility of multiplex detection of arrayed antigens in a high-throughput fashion using marker antigens could be successfully demonstrated. In addition, Silzel et al. (*Clin Chem* 44 pp. 2036-2043, 1998) could demonstrate that multiple IgG subclasses can be detected simultaneously using microarray technology. Wiese et al. (*Clin Chem* 47 pp. 1451-1457, 2001) were able to measure prostate-specific antigen (PSA), -(1)-antichymotrypsin-bound PSA and interleukin-6 in a microarray format. Arenkov et al. (supra) carried out microarray sandwich immunoassays and direct antigen or antibody detection experiments using a modified polyacrylamide gel as substrate for immobilized capture molecules.

Most of the microarray assay formats described in the art rely on chemiluminescence- or fluorescence-based detection methods. A further improvement with regard to sensitivity involves the application of fluorescent labels and waveguide technology. A fluorescence-based array immunosensor was developed by Rowe et al. (*Anal Chem* 71 (1999), pp. 433-439; and *Biosens Bioelectron* 15 (2000), pp. 579-589) and applied for the simultaneous detection of clinical analytes using the sandwich immunoassay format. Biotinylated capture antibodies were immobilized on avidin-coated waveguides using a flow-chamber module system. Discrete regions of capture molecules were vertically arranged on the surface of the waveguide. Samples of interest were incubated to allow the targets to bind to their capture molecules. Captured targets were then visualized with appropriate fluorescently labeled detection molecules. This array immunosensor was shown to be appropriate for the detection and measurement of targets at physiologically relevant concentrations in a variety of clinical samples.

A further increase in the sensitivity using waveguide technology was achieved with the development of the planar waveguide technology (Duveneck et al., *Sens Actuators B* B38 (1997), pp. 88-95). Thin-film waveguides are generated from a high-refractive material such as $Ta_2O_5$ that is deposited on a transparent substrate. Laser light of desired wavelength is coupled to the planar waveguide by means of diffractive grating. The light propagates in the planar waveguide and an area of more than a square centimeter can be homogeneously illuminated. At the surface, the propagating light generates a so-called evanescent field. This extends into the solution and activates only fluorophores that are bound to the surface. Fluorophores in the surrounding solution are not excited. Close to the surface, the excitation field intensities can be a hundred times higher than those achieved with standard confocal excitation. A CCD camera is used to identify signals simultaneously across the entire area of the planar waveguide. Thus, the immobilization of the capture molecules in a microarray format on the planar waveguide allows the performance of highly sensitive miniaturized and parallelized immunoassays. This system was successfully employed to detect interleukin-6 at concentrations as low as 40 fM and has the additional advantage that the assay can be performed without washing steps that are usually required to remove unbound detection molecules (Weinberger et al., *Pharmacogenomics* 1 (2000), pp. 395-416).

Alternative strategies pursued to increase sensitivity are based on signal amplification procedures. For example, immunoRCA (immuno rolling circle amplification) involves an oligonucleotide primer that is covalently attached to a detection molecule (such as a second capture agent in a sandwich-type assay format). Using circular DNA as template, which is complementary to the attached oligonucleotide, DNA polymerase will extend the attached oligonucleotide and generate a long DNA molecule consisting of hundreds of copies of the circular DNA, which remains attached to the detection molecule. The incorporation of thousands of fluorescently labeled nucleotides will generate a strong signal. Schweitzer et al. (*Proc Natl Acad Sci USA* 97 (2000), pp. 10113-10119) have evaluated this detection technology for use in microarray-based assays. Sandwich immunoassays for huIgE and prostate-specific antigens were performed in a microarray format. The antigens could be detected at femtomolar concentrations and it was possible to score single, specifically captured antigens by counting discrete fluorescent signals that arose from the individual antibody-antigen complexes. The authors demonstrated that immunoassays employing rolling circle DNA amplification are a versatile platform for the ultra-sensitive detection of antigens and thus are well suited for use in protein microarray technology.

Radioimmunoassays (RIA) may also be used for detection of a protein that interacts with a capture agent. In a RIA, the indicator molecule is labeled with a radioisotope and it may be quantified by counting radioactive decay events in a scintillation counter. Methods for performing direct or competitive RIA are well known in the art and described in, for example, Cell Biology: A Laboratory Handbook. San Diego, Calif., Academic Press, Inc., the contents of which are incorporated herein by reference.

Other immunoassays commonly used to quantitate the levels of proteins in cell samples, and are well-known in the art, can be adapted for use in the instant invention. The invention is not limited to a particular assay procedure, and therefore is intended to include both homogeneous and heterogeneous procedures. Exemplary other immunoassays which can be conducted according to the invention include fluorescence polarization immunoassay (FPIA), fluorescence immunoassay (FIA), enzyme immunoassay (EIA), nephelometric inhibition immunoassay (NIA). An indicator moiety, or label group, can be attached to the subject antibodies and is selected so as to meet the needs of various uses of the method which are often dictated by the availability of assay equipment and compatible immunoassay procedures. General techniques to be used in performing the various immunoassays noted above are known to those of ordinary skill in the art. In one embodiment, the determination of protein level in a biological sample may be performed by a microarray analysis (protein chip).

In several other embodiments, detection of the presence of a protein that interacts with a capture agent may be achieved without labeling. For example, determining the ability of a protein to bind to a capture agent can be accomplished using a technology such as real-time Biomolecular Interaction Analysis (BIA). Sjolander, S. and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore).

In another embodiment, a biosensor with a special diffractive grating surface may be used to detect/quantitate binding between non-labeled PET-containing peptides in a treated (digested) biological sample and immobilized capture agents at the surface of the biosensor. Details of the technology is described in more detail in B. Cunningham, P. Li, B. Lin, J. Pepper, "Colorimetric resonant reflection as a direct biochemical assay technique," Sensors and Actuators B, Volume 81, p. 316-328, Jan. 5, 2002, and in PCT No. WO 02/061429 A2 and US 2003/0032039. Briefly, a guided mode resonant phenomenon is used to produce an optical structure that, when illuminated with collimated white light, is designed to reflect only a single wavelength (color). When molecules are attached to the surface of the biosensor, the reflected wavelength (color) is shifted due to the change of the optical path of light that is coupled into the grating. By linking receptor molecules to the grating surface, complementary binding molecules can be detected/quantitated without the use of any kind of fluorescent probe or particle label. The spectral shifts may be analyzed to determine the expression data provided, and to indicate the presence or absence of a particular indication.

The biosensor typically comprises: a two-dimensional grating comprised of a material having a high refractive index, a substrate layer that supports the two-dimensional grating, and one or more detection probes immobilized on the surface of the two-dimensional grating opposite of the substrate layer. When the biosensor is illuminated a resonant grating effect is produced on the reflected radiation spectrum. The depth and period of the two-dimensional grating are less than the wavelength of the resonant grating effect.

A narrow band of optical wavelengths can be reflected from the biosensor when it is illuminated with a broad band of optical wavelengths. The substrate can comprise glass, plastic or epoxy. The two-dimensional grating can comprise a material selected from the group consisting of zinc sulfide, titanium dioxide, tantalum oxide, and silicon nitride.

The substrate and two-dimensional grating can optionally comprise a single unit. The surface of the single unit comprising the two-dimensional grating is coated with a material having a high refractive index, and the one or more detection probes are immobilized on the surface of the material having a high refractive index opposite of the single unit. The single unit can be comprised of a material selected from the group consisting of glass, plastic, and epoxy.

The biosensor can optionally comprise a cover layer on the surface of the two-dimensional grating opposite oft he substrate layer. The one or more detection probes are immobilized on the surface of the cover layer opposite of the two-dimensional grating. The cover layer can comprise a material that has a lower refractive index than the high refractive index material of the two-dimensional grating. For example, a cover layer can comprise glass, epoxy, and plastic.

A two-dimensional grating can be comprised of a repeating pattern of shapes selected from the group consisting of lines, squares, circles, ellipses, triangles, trapezoids, sinusoidal waves, ovals, rectangles, and hexagons. The repeating pattern of shapes can be arranged in a linear grid, i.e., a grid of parallel lines, a rectangular grid, or a hexagonal grid. The two-dimensional grating can have a period of about 0.01 microns to about I micron and a depth of about 0.01 microns to about 1 micron.

To illustrate, biochemical interactions occurring on a surface of a calorimetric resonant optical biosensor embedded into a surface of a microarray slide, microtiter plate or other device, can be directly detected and measured on the sensor's surface without the use of fluorescent tags or calorimetric labels. The sensor surface contains an optical structure that, when illuminated with collimated white light, is designed to reflect only a narrow band of wavelengths (color). The narrow wavelength is described as a wavelength "peak." The "peak wavelength value" (PWV) changes when biological material is deposited or removed from the sensor surface, such as when binding occurs. Such binding-induced change of PWV can be measured using a measurement instrument disclosed in US2003/0032039.

In one embodiment, the instrument illuminates the biosensor surface by directing a collimated white light on to the sensor structure. The illuminated light may take the form of a spot of collimated light. Alternatively, the light is generated in the form of a fan beam. The instrument collects light reflected from the illuminated biosensor surface. The instrument may gather this reflected light from multiple locations on the biosensor surface simultaneously. The instrument can include a plurality of illumination probes that direct the light to a discrete number of positions across the biosensor surface. The instrument measures the Peak Wavelength Values (PWVs) of separate locations within the biosensor-embedded microtiter plate using a spectrometer. In one embodiment, the spectrometer is a single-point spectrometer. Alternatively, an imaging spectrometer is used. The spectrometer can produce a PWV image map of the sensor surface. In one embodiment, the measuring instrument spatially resolves PWV images with less than 200 micron resolution.

In one embodiment, a subwavelength structured surface (SWS) may be used to create a sharp optical resonant reflection at a particular wavelength that can be used to track with high sensitivity the interaction of biological materials, such as specific binding substances or binding partners or both. A colormetric resonant diffractive grating surface acts as a surface binding platform for specific binding substances (such as immobilized capture agents of the instant invention). SWS is an unconventional type of diffractive optic that can mimic the effect of thin-film coatings. (Peng & Morris, "Resonant scattering from two-dimensional gratings," J. Opt. Soc. Am. A, Vol. 13, No. 5, p. 993, May; Magnusson, & Wang, "New principle for optical filters," Appl. Phys. Lett., 61, No. 9, p. 1022, August, 1992; Peng & Morris, "Experimental demonstration of resonant anomalies in diffraction from two-dimensional gratings," Optics Letters, Vol. 21, No. 8, p. 549, April, 1996). A SWS structure contains a surface-relief, two-dimensional grating in which the grating period is small compared to the wavelength of incident light so that no diffractive orders other than the reflected and transmitted zeroth orders are allowed to propagate. A SWS surface narrowband filter can comprise a two-dimensional grating sandwiched between a substrate layer and a cover layer that fills the grating grooves. Optionally, a cover layer is not used. When the effective index of refraction of the grating region is greater than the substrate or the cover layer, a waveguide is created. When a filter is designed accordingly, incident light passes into the waveguide region. A two-dimensional grating structure selectively couples light at a narrow band of wavelengths into the waveguide. The light propagates only a short distance (on the order of 10-100 micrometers), undergoes scattering, and couples with the forward- and backward-propagating zeroth-order light. This sensitive coupling condition can produce a resonant grating effect on the reflected radiation spectrum, resulting in a narrow band of reflected or transmitted wavelengths (colors). The depth and period of the two-dimensional grating are less than the wavelength of the resonant grating effect.

The reflected or transmitted color of this structure can be modulated by the addition of molecules such as capture agents or their PET-containing binding partners or both, to the upper surface of the cover layer or the two-dimensional grating surface. The added molecules increase the optical path length of incident radiation through the structure, and thus modify the wavelength (color) at which maximum reflectance or transmittance will occur. Thus in one embodiment, a biosensor, when illuminated with white light, is designed to reflect only a single wavelength. When specific binding substances are attached to the surface of the biosensor, the reflected wavelength (color) is shifted due to the change of the optical path of light that is coupled into the grating. By linking specific binding substances to a biosensor surface, complementary binding partner molecules can be detected without the use of any kind of fluorescent probe or particle label. The detection technique is capable of resolving changes of, for example, about 0.1 nm thickness of protein binding, and can be performed with the biosensor surface either immersed in fluid or dried. This PWV change can be detected by a detection system consists of, for example, a light source that illuminates a small spot of a biosensor at normal incidence through, for example, a fiber optic probe. A spectrometer collects the reflected light through, for example, a second fiber optic probe also at normal incidence. Because no physical contact occurs between the excitation/detection system and the biosensor surface, no special coupling prisms are required. The biosensor can, therefore, be adapted to a commonly used assay platform including, for example, microliter plates and microarray slides. A spectrometer reading can be performed in several milliseconds, thus it is possible to efficiently measure a large number of molecular interactions taking place in parallel upon a biosensor surface, and to monitor reaction kinetics in real time.

Various embodiments, variations of the biosensor described above can be found in US2003/0032039, incorporated herein by reference in its entirety.

One or more specific capture agents may be immobilized on the two-dimensional grating or cover layer, if present. Immobilization may occur by any of the above described methods. Suitable capture agents can be, for example, a nucleic acid, polypeptide, antigen, polyclonal antibody, monoclonal antibody, single chain antibody (scFv), F(ab) fragment, F(ab')2 fragment, Fv fragment, small organic molecule, even cell, virus, or bacteria. A biological sample can be obtained and/or described from, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatitc fluid. Preferably, one or more specific capture agents are arranged in a microarray of distinct locations on a biosensor. A microarray of capture agents comprises one or more specific capture agents on a surface of a biosensor such that a biosensor surface contains a plurality of distinct locations, each with a different capture agent or with a different amount of a specific capture agent. For example, an array can comprise 1, 10, 100, 1,000, 10,000, or 100,000 distinct locations. A biosensor surface with a large number of distinct locations is called a microarray because one or more specific capture agents are typically laid out in a regular grid pattern in x-y coordinates. However, a microarray can comprise one or more specific capture agents laid out in a regular or irregular pattern.

A microarray spot can range from about 50 to about 500 microns in diameter. Alternatively, a microarray spot can range from about 150 to about 200 microns in diameter. One or more specific capture agents can be bound to their specific PET-containing binding partners.

In one biosensor embodiment, a microarray on a biosensor is created by placing microdroplets of one or more specific capture agents onto, for example, an x-y grid of locations on a two-dimensional grating or cover layer surface. When the biosensor is exposed to a test sample comprising one or more PET binding partners, the binding partners will be preferentially attracted to distinct locations on the microarray that comprise capture agents that have high affinity for the PET binding partners. Some of the distinct locations will gather binding partners onto their surface, while other locations will not. Thus a specific capture agent specifically binds to its PET binding partner, but does not substantially bind other PET binding partners added to the surface of a biosensor. In an alternative embodiment, a nucleic acid microarray (such as an aptamer array) is provided, in which each distinct location within the array contains a different aptamer capture agent.

By application of specific capture agents with a microarray spotter onto a biosensor, specific binding substance densities of 10,000 specific binding substances/in$^2$ can be obtained. By focusing an illumination beam of a fiber optic probe to interrogate a single microarray location, a biosensor can be used as a label-free microarray readout system.

For the detection of PET binding partners at concentrations of less than about 0.1 ng/ml, one may amplify and transduce binding partners bound to a biosensor into an additional layer on the biosensor surface. The increased mass deposited on the biosensor can be detected as a consequence of increased optical path length. By incorporating greater mass onto a biosensor surface, an optical density of binding partners on the surface is also increased, thus rendering a greater resonant wavelength shift than would occur without the added mass. The addition of mass can be accomplished, for example, enzymatically, through a "sandwich" assay, or by direct application of mass (such as a second capture agent specific for the PET peptide) to the biosensor surface in the form of appropriately conjugated beads or polymers of various size and composition. Since the capture agents are PET-specific, multiple capture agents of different types and specificity can be added together to the captured PETs. This principle has been exploited for other types of optical biosensors to demonstrate sensitivity increases over 1500× beyond sensitivity limits achieved without mass amplification. See, e.g., Jenison et al., "Interference-based detection of nucleic acid targets on optically coated silicon," Nature Biotechnology, 19: 62-65, 2001.

In an alternative embodiment, a biosensor comprises volume surface-relief volume diffractive structures (a SRVD biosensor). SRVD biosensors have a surface that reflects predominantly at a particular narrow band of optical wavelengths when illuminated with a broad band of optical wavelengths. Where specific capture agents and/or PET binding partners are immobilized on a SRVD biosensor, the reflected wavelength of light is shifted. One-dimensional surfaces, such as thin film interference filters and Bragg reflectors, can select a narrow range of reflected or transmitted wavelengths from a broadband excitation source. However, the deposition of additional material, such as specific capture agents and/or PET binding partners onto their upper surface results only in a change in the resonance linewidth, rather than the resonance wavelength. In contrast, SRVD biosensors have the ability to alter the reflected wavelength with the addition of material, such as specific capture agents and/or binding partners to the surface.

A SRVD biosensor comprises a sheet material having a first and second surface. The first surface of the sheet material defines relief volume diffraction structures. Sheet material can comprise, for example, plastic, glass, semiconductor wafer, or metal film. A relief volume diffractive structure can be, for example, a two-dimensional grating, as described above, or a three-dimensional surface-relief volume diffractive grating. The depth and period of relief volume diffraction structures are less than the resonance wavelength of light reflected from a biosensor. A three-dimensional surface-relief volume diffractive grating can be, for example, a three-dimensional phase-quantized terraced surface relief pattern whose groove pattern resembles a stepped pyramid. When such a grating is illuminated by a beam of broadband radiation, light will be coherently reflected from the equally spaced terraces at a wavelength given by twice the step spacing times the index of refraction of the surrounding medium. Light of a given wavelength is resonantly diffracted or reflected from the steps that are a half-wavelength apart, and with a bandwidth that is inversely proportional to the number of steps.

The reflected or diffracted color can be controlled by the deposition of a dielectric layer so that a new wavelength is selected, depending on the index of refraction of the coating.

A stepped-phase structure can be produced first in photoresist by coherently exposing a thin photoresist film to three laser beams, as described previously. See e.g., Cowen, "The recording and large scale replication of crossed holographic grating arrays using multiple beam interferometry," in International Conference on the Application, Theory, and Fabrication of Periodic Structures, Diffraction Gratings, and Moire Phenomena II, Lerner, ed., Proc. Soc. Photo-Opt. Instrum. Eng., 503, 120-129, 1984; Cowen, "Holographic honeycomb microlens," Opt. Eng. 24, 796-802 (1985); Cowen & Slafer, "The recording and replication of holographic micropatterns for the ordering of photographic emulsion grains in film systems," J Imaging Sci. 31, 100-107, 1987. The nonlinear etching characteristics of photoresist are used to develop the exposed film to create a three-dimensional relief pattern. The photoresist structure is then replicated using standard embossing procedures. For example, a thin silver film may be deposited over the photoresist structure to form a conducting layer upon which a thick film of nickel can be electroplated. The nickel "master" plate is then used to emboss directly into a plastic film, such as vinyl, that has been softened by heating or solvent. A theory describing the design and fabrication of three-dimensional phase-quantized terraced surface relief pattern that resemble stepped pyramids is described: Cowen, "Aztec surface-relief volume diffractive structure," J. Opt. Soc. Am. A, 7:1529 (1990). An example of a three-dimensional phase-quantized terraced surface relief pattern may be a pattern that resembles a stepped pyramid. Each inverted pyramid is approximately 1 micron in diameter. Preferably, each inverted pyramid can be about 0.5 to about 5 microns diameter, including for example, about 1 micron. The pyramid structures can be close-packed so that a typical microarray spot with a diameter of 150-200 microns can incorporate several hundred stepped pyramid structures. The relief volume diffraction structures have a period of about 0.1 to about 1 micron and a depth of about 0.1 to about 1 micron.

One or more specific binding substances, as described above, are immobilized on the reflective material of a SRVD biosensor. One or more specific binding substances can be arranged in microarray of distinct locations, as described above, on the reflective material.

A SRVD biosensor reflects light predominantly at a first single optical wavelength when illuminated with a broad band of optical wavelengths, and reflects light at a second single optical wavelength when one or more specific binding substances are immobilized on the reflective surface. The reflection at the second optical wavelength results from optical interference. A SRVD biosensor also reflects light at a third single optical wavelength when the one or more specific capture agents are bound to their respective PET binding partners, due to optical interference. Readout of the reflected color can be performed serially by focusing a microscope objective onto individual microarray spots and reading the reflected spectrum with the aid of a spectrograph or imaging spectrometer, or in parallel by, for example, projecting the reflected image of the microarray onto an imaging spectrometer incorporating a high resolution color CCD camera.

A SRVD biosensor can be manufactured by, for example, producing a metal master plate, and stamping a relief volume diffractive structure into, for example, a plastic material like vinyl. After stamping, the surface is made reflective by blanket deposition of, for example, a thin metal film such as gold, silver, or aluminum. Compared to MEMS-based biosensors that rely upon photolithography, etching, and wafer bonding procedures, the manufacture of a SRVD biosensor is very inexpensive.

A SWS or SRVD biosensor embodiment can comprise an inner surface. In one preferred embodiment, such an inner surface is a bottom surface of a liquid-containing vessel. A liquid-containing vessel can be, for example, a microtiter plate well, a test tube, a petri dish, or a microfluidic channel. In one embodiment, a SWS or SRVD biosensor is incorporated into a microtiter plate. For example, a SWS biosensor or SRVD biosensor can be incorporated into the bottom surface of a microtiter plate by assembling the walls of the reaction vessels over the resonant reflection surface, so that each reaction "spot" can be exposed to a distinct test sample. Therefore, each individual microtiter plate well can act as a separate reaction vessel. Separate chemical reactions can, therefore, occur within adjacent wells without intermixing reaction fluids and chemically distinct test solutions can be applied to individual wells.

This technology is useful in applications where large numbers of biomolecular interactions are measured in parallel, particularly when molecular labels would alter or inhibit the functionality of the molecules under study. High-throughput screening of pharmaceutical compound libraries with protein targets, and microarray screening of protein-protein interactions for proteomics are examples of applications that require the sensitivity and throughput afforded by the compositions and methods of the invention.

Unlike surface plasmon resonance, resonant mirrors, and waveguide biosensors, the described compositions and methods enable many thousands of individual binding reactions to take place simultaneously upon the biosensor surface. This technology is useful in applications where large numbers of biomolecular interactions are measured in parallel (such as in an array), particularly when molecular labels alter or inhibit the functionality of the molecules under study. These biosensors are especially suited for high-throughput screening of pharmaceutical compound libraries with protein targets, and microarray screening of protein-protein interactions for proteomics. A biosensor of the invention can be manufactured, for example, in large areas using a plastic embossing process, and thus can be inexpensively incorporated into common disposable laboratory assay platforms such as microtiter plates and microarray slides.

Other similar biosensors may also be used in the instant invention. Numerous biosensors have been developed to detect a variety of biomolecular complexes including oligonucleotides, antibody-antigen interactions, hormone-receptor interactions, and enzyme-substrate interactions. In general, these biosensors consist of two components: a highly specific recognition element and a transducer that converts the molecular recognition event into a quantifiable signal. Signal transduction has been accomplished by many methods, including fluorescence, interferometry (Jenison et al., "Interference-based detection of nucleic acid targets on optically coated silicon," Nature Biotechnology, 19, p. 62-65; Lin et al., "A porous silicon-based optical interferometric biosensor," Science, 278, p. 840-843, 1997), and gravimetry (A. Cunningham, Bioanalytical Sensors, John Wiley & Sons (1998)). Of the optically-based transduction methods, direct methods that do not require labeling of analytes with fluorescent compounds are of interest due to the relative assay simplicity and ability to study the interaction of small molecules and proteins that are not readily labeled.

These direct optical methods include surface plasmon resonance (SPR) (Jordan & Corn, "Surface Plasmon Resonance Imaging Measurements of Electrostatic Biopolymer Adsorption onto Chemically Modified Gold Surfaces," Anal. Chem., 69:1449-1456 (1997); plasmom-resonant particles (PRPs) (Schultz et al., Proc. Nat. Acad. Sci., 97: 996-1001 (2000); grating couplers (Morhard et al., "Immobilization of antibodies in micropatterns for cell detection by optical diffraction," Sensors and Actuators B, 70, p. 232-242, 2000); ellipsometry (Jin et al., "A biosensor concept based on imaging ellipsometry for visualization of biomolecular interactions," Analytical Biochemistry, 232, p. 69-72, 1995), evanascent wave devices (Huber et al., "Direct optical immunosensing (sensitivity and selectivity)," Sensors and Actuators B, 6, p.122.126, 1992), resonance light scattering (Bao et al., Anal. Chem., 74:1792-1797 (2002), and reflectometry (Brecht & Gauglitz, "Optical probes and transducers," Biosensors and Bioelectronics, 10, p. 923-936, 1995). Changes in the optical phenomenon of surface plasmon resonance (SPR) can be used as an indication of real-time reactions between biological molecules. Theoretically predicted detection limits of these detection methods have been determined and experimentally confirmed to be feasible down to diagnostically relevant concentration ranges.

Surface plasmon resonance (SPR) has been successfully incorporated into an immunosensor format for the simple, rapid, and nonlabeled assay of various biochemical analytes. Proteins, complex conjugates, toxins, allergens, drugs, and pesticides can be determined directly using either natural antibodies or synthetic receptors with high sensitivity and selectivity as the sensing element. Immunosensors are capable of real-time monitoring of the antigen-antibody reaction. A wide range of molecules can be detected with lower limits ranging between $10^{-9}$ and $10^{-13}$ mol/L. Several successful commercial developments of SPR immunosensors are available and their web pages are rich in technical information. Wayne et al. (Methods 22: 77-91, 2000) reviewed and highlighted many recent developments in SPR-based immunoassay, functionalizations of the gold surface, novel receptors in molecular recognition, and advanced techniques for sensitivity enhancement.

Utilization of the optical phenomenon surface plasmon resonance (SPR) has seen extensive growth since its initial observation by Wood in 1902 (Phil. Mag. 4 (1902), pp. 396-402). SPR is a simple and direct sensing technique that can be used to probe refractive index ($\eta$) changes that occur in the very close vicinity of a thin metal film surface (Otto Z. Phys. 216 (1968), p. 398). The sensing mechanism exploits the properties of an evanescent field generated at the site of total internal reflection. This field penetrates into the metal film, with exponentially decreasing amplitude from the glass-metal interface. Surface plasmons, which oscillate and propagate along the upper surface of the metal film, absorb some of the plane-polarized light energy from this evanescent field to change the total internal reflection light intensity $I_r$. A plot of $I_r$ versus incidence (or reflection) angle $\theta$ produces an angular intensity profile that exhibits a sharp dip. The exact location of the dip minimum (or the SPR angle $\theta_r$) can be determined by using a polynomial algorithm to fit the $I_r$ signals from a few diodes close to the minimum. The binding of molecules on the upper metal surface causes a change in $\eta$ of the surface medium that can be observed as a shift in $\theta_r$.

The potential of SPR for biosensor purposes was realized in 1982-1983 by Liedberg et al., who adsorbed an immunoglobulin G (IgG) antibody overlayer on the gold sensing film, resulting in the subsequent selective binding and detection of IgG (Nylander et al., Sens. Actuators 3 (1982), pp. 79-84; Liedberg et al., Sens. Actuators 4 (1983), pp. 229-304). The principles of SPR as a biosensing technique have been reviewed previously (Daniels et al., Sens. Actuators 15

(1988), pp. 11-18; VanderNoot and Lai, *Spectroscopy* 6 (1991), pp. 28-33; Lundström *Biosens. Bioelectron.* 9 (1994), pp. 725-736; Liedberg et al., *Biosens. Bioelectron.* 10 (1995); Morgan et al., *Clin. Chem.* 42 (1996), pp. 193-209; Tapuchi et al., *S. Afr. J. Chem.* 49 (1996), pp. 8-25). Applications of SPR to biosensing were demonstrated for a wide range of molecules, from virus particles to sex hormone-binding globulin and syphilis. Most importantly, SPR has an inherent advantage over other types of biosensors in its versatility and capability of monitoring binding interactions without the need for fluorescence or radioisotope labeling of the biomolecules. This approach has also shown promise in the real-time determination of concentration, kinetic constant, and binding specificity of individual biomolecular interaction steps. Antibody-antigen interactions, peptide/protein-protein interactions, DNA hybridization conditions, biocompatibility studies of polymers, biomolecule-cell receptor interactions, and DNA/receptor-ligand interactions can all be analyzed (Pathak and Savelkoul, *Immunol. Today* 18 (1997), pp. 464-467). Commercially, the use of SPR-based immunoassay has been promoted by companies such as Biacore (Uppsala, Sweden) (Jönsson et al., *Ann. Biol. Clin.* 51 (1993), pp. 19-26), Windsor Scientific (U.K.) (WWW URL for Windsor Scientific IBIS Biosensor), Quantech (Minnesota) (WWW URL for Quantech), and Texas Instruments (Dallas, Tex.) (WWW URL for Texas Instruments).

In yet another embodiment, a fluorescent polymer superquenching-based bioassays as disclosed in WO 02/074997 may be used for detecting binding of the unlabeled PET to its capture agents. In this embodiment, a capture agent that is specific for both a target PET peptide and a chemical moiety is used. The chemical moiety includes (a) a recognition element for the capture agent, (b) a fluorescent property-altering element, and (c) a tethering element linking the recognition element and the property-altering element. A composition comprising a fluorescent polymer and the capture agent are co-located on a support. When the chemical moiety is bound to the capture agent, the property-altering element of the chemical moiety is sufficiently close to the fluorescent polymer to alter (quench) the fluorescence emitted by the polymer. When an analyte sample is introduced, the target PET peptide, if present, binds to the capture agent, thereby displacing the chemical moiety from the receptor, resulting in de-quenching and an increase of detected fluorescence. Assays for detecting the presence of a target biological agent are also disclosed in the application.

In another related embodiment, the binding event between the capture agents and the PET can be detected by using a water-soluble luminescent quantum dot as described in US2003/0008414A1. In one embodiment, a water-soluble luminescent semiconductor quantum dot comprises a core, a cap and a hydrophilic attachment group. The "core" is a nanoparticle-sized semiconductor. While any core of the IIB-VIB, IIIB-VB or IVB-IVB semiconductors can be used in this context, the core must be such that, upon combination with a cap, a luminescent quantum dot results. A IIB-VIB semiconductor is a compound that contains at least one element from Group IEB and at least one element from Group VIB of the periodic table, and so on. Preferably, the core is a IIB-VIB, IIIB-VB or IVB-IVB semiconductor that ranges in size from about 1 nm to about 10 nm. The core is more preferably a IIB-VIB semiconductor and ranges in size from about 2 nm to about 5 nm. Most preferably, the core is CdS or CdSe. In this regard, CdSe is especially preferred as the core, in particular at a size of about 4.2 nm.

The "cap" is a semiconductor that differs from the semiconductor of the core and binds to the core, thereby forming a surface layer on the core. The cap must be such that, upon combination with a given semiconductor core, results in a luminescent quantum dot. The cap should passivate the core by having a higher band gap than the core. In this regard, the cap is preferably a IIB-VIB semiconductor of high band gap. More preferably, the cap is ZnS or CdS. Most preferably, the cap is ZnS. In particular, the cap is preferably ZnS when the core is CdSe or CdS and the cap is preferably CdS when the core is CdSe.

The "attachment group" as that term is used herein refers to any organic group that can be attached, such as by any stable physical or chemical association, to the surface of the cap of the luminescent semiconductor quantum dot and can render the quantum dot water-soluble without rendering the quantum dot no longer luminescent. Accordingly, the attachment group comprises a hydrophilic moiety. Preferably, the attachment group enables the hydrophilic quantum dot to remain in solution for at least about one hour, one day, one week, or one month. Desirably, the attachment group is attached to the cap by covalent bonding and is attached to the cap in such a manner that the hydrophilic moiety is exposed. Preferably, the hydrophilic attachment group is attached to the quantum dot via a sulfur atom. More preferably, the hydrophilic attachment group is an organic group comprising a sulfur atom and at least one hydrophilic attachment group. Suitable hydrophilic attachment groups include, for example, a carboxylic acid or salt thereof, a sulfonic acid or salt thereof, a sulfamic acid or salt thereof, an amino substituent, a quaternary ammonium salt, and a hydroxy. The organic group of the hydrophilic attachment group of the present invention is preferably a C1-C6 alkyl group or an aryl group, more preferably a C1-C6 alkyl group, even more preferably a C1-C3 alkyl group. Therefore, in a preferred embodiment, the attachment group of the present invention is a thiol carboxylic acid or thiol alcohol. More preferably, the attachment group is a thiol carboxylic acid. Most preferably, the attachment group is mercaptoacetic acid.

Accordingly, a preferred embodiment of a water-soluble luminescent semiconductor quantum dot is one that comprises a CdSe core of about 4.2 nm in size, a ZnS cap and an attachment group. Another preferred embodiment of a water-soluble luminescent semiconductor quantum dot is one that comprises a CdSe core, a ZnS cap and the attachment group mercaptoacetic acid. An especially preferred water-soluble luminescent semiconductor quantum dot comprises a CdSe core of about 4.2 nm, a ZnS cap of about 1 nm and a mercaptoacetic acid attachment group.

The capture agent of the instant invention can be attached to the quantum dot via the hydrophilic attachment group and forms a conjugate. The capture agent can be attached, such as by any stable physical or chemical association, to the hydrophilic attachment group of the water-soluble luminescent quantum dot directly or indirectly by any suitable means, through one or more covalent bonds, via an optional linker that does not impair the function of the capture agent or the quantum dot. For example, if the attachment group is mercaptoacetic acid and a nucleic acid biomolecule is being attached to the attachment group, the linker preferably is a primary amine, a thiol, streptavidin, neutravidin, biotin, or a like molecule. If the attachment group is mercaptoacetic acid and a protein biomolecule or a fragment thereof is being attached to the attachment group, the linker preferably is strepavidin, neutravidin, biotin, or a like molecule.

By using the quantum dot-capture agent conjugate, a PET-containing sample, when contacted with a conjugate as described above, will promote the emission of luminescence when the capture agent of the conjugate specifically binds to the PET peptide. This is particularly useful when the capture agent is a nucleic acid aptamer or an antibody. When the aptamer is used, an alternative embodiment may be employed, in which a fluorescent quencher may be positioned adjacent to the quantum dot via a self-pairing stem-loop structure when the aptamer is not bound to a PET-containing sequence. When the aptamer binds to the PET, the stem-loop structure is opened, thus releasing the quenching effect and generates luminescence.

In another related embodiment, arrays of nanosensors comprising nanowires or nanotubes as described in US2002/0117659A1 may be used for detection and/or quantitation of PET-capture agent interaction. Briefly, a "nanowire" is an elongated nanoscale semiconductor, which can have a cross-sectional dimension of as thin as 1 nanometer. Similarly, a "nanotube" is a nanowire that has a hollowed-out core, and includes those nanotubes know to those of ordinary skill in the art. A "wire" refers to any material having a conductivity at least that of a semiconductor or metal. These nanowires/nanotubes may be used in a system constructed and arranged to determine an analyte (e.g., PET peptide) in a sample to which the nanowire(s) is exposed. The surface of the nanowire is functionalized by coating with a capture agent. Binding of an analyte to the functionalized nanowire causes a detectable change in electrical conductivity of the nanowire or optical properties. Thus, presence of the analyte can be determined by determining a change in a characteristic in the nanowire, typically an electrical characteristic or an optical characteristic. A variety of biomolecular entities can be used for coating, including, but not limited to, amino acids, proteins, sugars, DNA, antibodies, antigens, and enzymes, etc. For more details such as construction of nanowires, functionalization with various biomolecules (such as the capture agents of the instant invention), and detection in nanowire devices, see US2002/0117659A1 (incorporated by reference). Since multiple nanowires can be used in parallel, each with a different capture agent as the functionalized group, this technology is ideally suited for large scale arrayed detection of PET-containing peptides in biological samples without the need to label the PET peptides. This nanowire detection technology has been successfully used to detect pH change ($H^+$ binding), biotin-streptavidin binding, antibody-antigen binding, metal ($Ca^{2+}$) binding with picomolar sensitivity and in real time (Cui et al., *Science* 293: 1289-1292).

Matrix-assisted laser desorption/ionization time-of-flight mass spectrometry (MALDI-TOF MS), uses a laser pulse to desorb proteins from the surface followed by mass spectrometry to identify the molecular weights of the proteins (Gilligan et al., Mass spectrometry after capture and small-volume elution of analyte from a surface plasmon resonance biosensor. *Anal. Chem.* 74 (2002), pp. 2041-2047). Because this method only measures the mass of proteins at the interface, and because the desorption protocol is sufficiently mild that it does not result in fragmentation, MALDI can provide straightforward useful information such as confirming the identity of the bound PET peptide, or any enzymatic modification of a PET peptide. For this matter, MALDI can be used to identify proteins that are bound to immobilized capture agents. An important technique for identifying bound proteins relies on treating the array (and the proteins that are selectively bound to the array) with proteases and then analyzing the resulting peptides to obtain sequence data.

IV. Samples and Their Preparation

The capture agents or an array of capture agents typically are contacted with a sample, e.g., a biological fluid, a water sample, or a food sample, which has been fragmented to generate a collection of peptides, under conditions suitable for binding a PET corresponding to a protein of interest.

Samples to be assayed using the capture agents of the present invention may be drawn from various physiological, environmental or artificial sources. In particular, physiological samples such as body fluids or tissue samples of a patient or an organism may be used as assay samples. Such fluids include, but are not limited to, saliva, mucous, sweat, whole blood, serum, urine, amniotic fluid, genital fluids, fecal material, marrow, plasma, spinal fluid, pericardial fluids, gastric fluids, abdominal fluids, peritoneal fluids, pleural fluids and extraction from other body parts, and secretion from other glands. Alternatively, biological samples drawn from cells taken from the patient or grown in culture may be employed. Such samples include supernatants, whole cell lysates, or cell fractions obtained by lysis and fractionation of cellular material. Extracts of cells and fractions thereof, including those directly from a biological entity and those grown in an artificial environment, can also be used. In addition, a biological sample can be obtained and/or described from, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatitc fluid.

Figure 6:
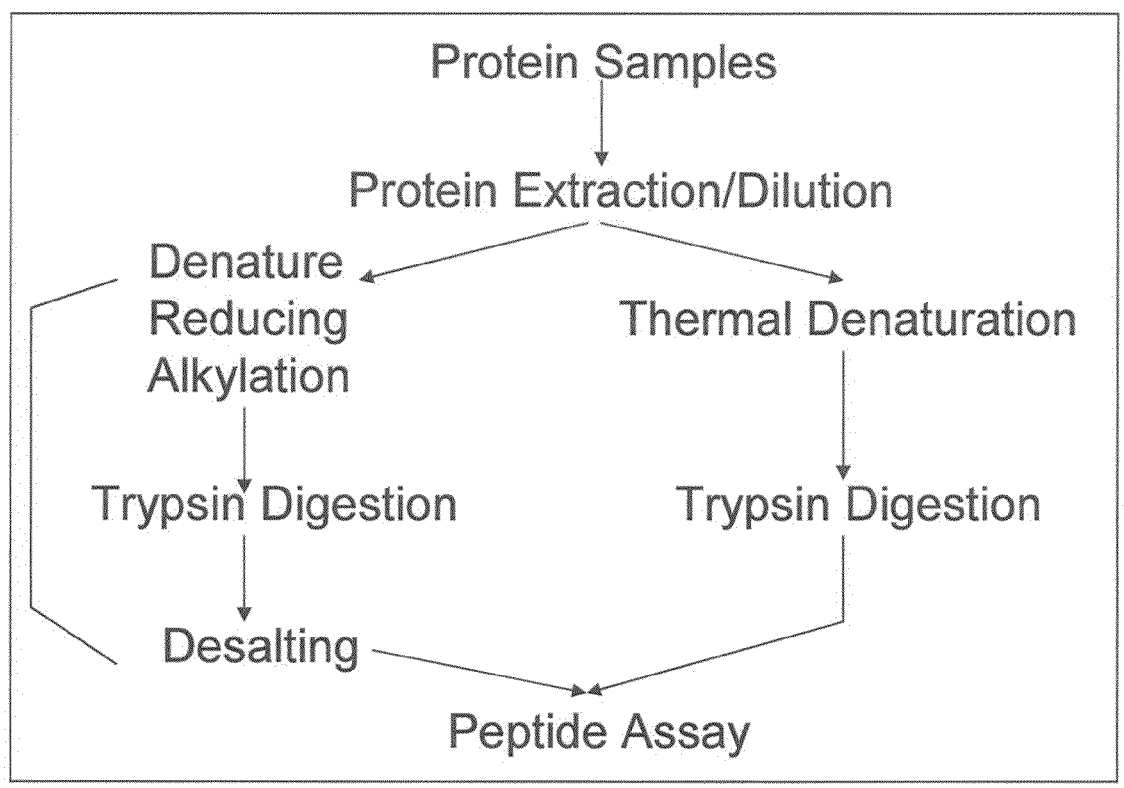
FIG. 6 illustrates a general scheme of sample preparation prior to its use in the methods of the instant invention. The left side shows the process for chemical denaturation followed by protease digestion, the right side illustrates the preferred thermo-denaturation and fragmentation. Although the most commonly used protease trypsin is depicted in this illustration, any other suitable proteases described in the instant application may be used. The process is simple, robust & reproducible, and is generally applicable to main sample types including serum, cell lysates and tissues.

A general scheme of sample preparation prior to its use in the methods of the instant invention is described in FIG. 6 (slide 45 of D2). Briefly, a sample can be pretreated by extraction and/or dilution to minimize the interference from certain substances present in the sample. The sample can then be either chemically reduced, denatured, alkylated, or subjected to thermo-denaturation. Regardless of the denaturation step, the denatured sample is then digested by a protease, such as trypsin, before it is used in subsequent assays. A desalting step may also be added just after protease digestion if chemical denaturation if used. This process is generally simple, robust and reproducible, and is generally applicable to main sample types including serum, cell lysates and tissues.

The sample may be pre treated to remove extraneous materials, stabilized, buffered, preserved, filtered, or otherwise conditioned as desired or necessary. Proteins in the sample typically are fragmented, either as part of the methods of the invention or in advance of performing these methods. Fragmentation can be performed using any art-recognized desired method, such as by using chemical cleavage (e.g., cyanogen bromide); enzymatic means (e.g., using a protease such as trypsin, chymotrypsin, pepsin, papain, carboxypeptidase, calpain, subtilisin, gluc-C, endo lys-C and proteinase K, or a collection or sub-collection thereof); or physical means (e.g., fragmentation by physical shearing or fragmentation by sonication). As used herein, the terms "fragmentation" "cleavage," "proteolytic cleavage," "proteolysis" "restriction" and the like are used interchangeably and refer to scission of a chemical bond, typically a peptide bond, within proteins to produce a collection of peptides (i.e., protein fragments).

The purpose of the fragmentation is to generate peptides comprising PET which are soluble and available for binding with a capture agent. In essence, the sample preparation is designed to assure to the extent possible that all PET present on or within relevant proteins that may be present in the sample are available for reaction with the capture agents. T his strategy can avoid many of the problems encountered with previous attempts to design protein chips caused by protein-protein complexation, post translational modifications and the like.

In one embodiment, the sample of interest is treated using a pre-determined protocol which: (A) inhibits masking of the target protein caused by target protein-protein non covalent or covalent complexation or aggregation, target protein degradation or denaturing, target protein post-translational modification, or environmentally induced alteration in target protein tertiary structure, and (B) fragments the target protein to, thereby, produce at least one peptide epitope (i.e., a PET) whose concentration is directly proportional to the true concentration of the target protein in the sample. The sample treatment protocol is designed and empirically tested to result reproducibly in the generation of a PET that is available for reaction with a given capture agent. The treatment can involve protein separations; protein fractionations; solvent modifications such as polarity changes, osmolarity changes, dilutions, or pH changes; heating; freezing; precipitating; extractions; reactions with a reagent such as an endo-, exo- or site specific protease; non proteolytic digestion; oxidations; reductions; neutralization of some biological activity, and other steps known to one of skill in the art.

For example, the sample may be treated with an alkylating agent and a reducing agent in order to prevent the formation of dimers or other aggregates through disulfide/dithiol exchange. The sample of PET-containing peptides may also be treated to remove secondary modifications, including but are not limited to, phosphorylation, methylation, glycosylation, acetylation, prenylation, using, for example, respective modification-specific enzymes such as phosphatases, etc.

In one embodiment, proteins of a sample will be denatured, reduced and/or alkylated, but will not be proteolytically cleaved. Proteins can be denatured by thermal denaturation or organic solvents, then subjected to direct detection or optionally, further proteolytic cleavage.

The use of thermal denaturation (50-90° C. for about 20 minutes) of proteins prior to enzyme digestion in solution is preferred over chemical denaturation (such as 6-8 M guanidine HCl or urea) because it does not require purification/ concentration, which might be preferred or required prior to subsequent analysis. Park and Russell reported that enzymatic digestions of proteins that are resistant to proteolysis are significantly enhanced by thermal denaturation (*Anal. Chem.*, 72 (11): 2667 -2670, 2000). Native proteins that are sensitive to proteolysis show similar or just slightly lower digestion yields following thermal denaturation. Proteins that are resistant to digestion become more susceptible to digestion, independent of protein size, following thermal denaturation. For example, amino acid sequence coverage from digest fragments increases from 15 to 86% in myoglobin and from 0 to 43% in ovalbumin. This leads to more rapid and reliable protein identification by the instant invention, especially to protease resistant proteins.

Although some proteins aggregate upon thermal denaturation, the protein aggregates are easily digested by trypsin and generate sufficient numbers of digest fragments for protein identification. In fact, protein aggregation may be the reason thermal denaturation facilitates digestion in most cases. Protein aggregates are believed to be the oligomerization products of the denatured form of protein (Copeland, R. A. *Methods for Protein Analysis*; Chapman & Hall: New York, N.Y., 1994). In general, hydrophobic parts of the protein are located inside and relatively less hydrophobic parts of the protein are exposed to the aqueous environment. During the thermal denaturation, intact proteins are gradually unfolded into a denatured conformation and sufficient energy is provided to prevent a fold back to its native conformation. The probability for interactions with other denatured proteins is increased, thus allowing hydrophobic interactions between exposed hydrophobic parts of the proteins. In addition, protein aggregates of the denatured protein can have a more protease-labile structure than nondenatured proteins because more cleavage sites are exposed to the environment. Protein aggregates are easily digested, so that protein aggregates are not observed at the end of 3 h of trypsin digestion (Park and Russell, *Anal. Chem.*, 72 (11): 2667-2670, 2000). Moreover, trypsin digestion of protein aggregates generates more specific cleavage products.

Ordinary proteases such as trypsin may be used after denaturation. The process may be repeated by one or more rounds after the first round of denaturation and digestion. Alternatively, this thermal denaturation process can be further assisted by using thermophilic trypsin-like enzymes, so that denaturation and digestion can be done simultaneously. For example, Nongporn Towatana et al. (*J of Bioscience and Bioengineering* 87(5): 581-587, 1999) reported the purification to apparent homogeneity of an alkaline protease from culture supernatants of *Bacillus* sp. PS719, a novel alkaliphilic, thermophilic bacterium isolated from a thermal spring soil sample. The protease exhibited maximum activity towards azocasein at pH 9.0 and at 75° C. The enzyme was stable in the pH range 8.0 to 10.0 and up to 80° C. in the absence of $Ca^{2+}$. This enzyme appears to be a trypsin-like serine protease, since phenylmethylsulfonyl fluoride (PMSF) and 3,4-dichloroisocoumarin (DCI) in addition to N-α-p-tosyl-L-lysine chloromethyl ketone (TLCK) completely inhibited the activity. Among the various oligopeptidyl-p-nitroanilides tested, the protease showed a preference for cleavage at arginine residues on the carboxylic side of the scissile bond of the substrate, liberating p-nitroaniline from N-carbobenzoxy (CBZ)-L-arginine-p-nitroanilide with the $K_m$ and $V_{max}$ values of 0.6 mM and 1.0 μmol $min^{-1}mg$ $protein^{-1}$, respectively.

Alternatively, existing proteases may be chemically modified to achieve enhanced thermostability for use in this type of application. Mozhaev et al. (*Eur J Biochem.* 173(1):147-54, 1988) experimentally verified the idea presented earlier that the contact of nonpolar clusters located on the surface of protein molecules with water destabilizes proteins. It was demonstrated that protein stabilization could be achieved by artificial hydrophilization of the surface area of protein globules by chemical modification. Two experimental systems were studied for the verification of the hydrophilization approach. In one experiment, the surface tyrosine residues of trypsin were transformed to aminotyrosines using a two-step modification procedure: nitration by tetranitromethane followed by reduction with sodium dithionite. The modified enzyme was much more stable against irreversible thermo-inactivation: the stabilizing effect increased with the number of aminotyrosine residues in trypsin and the modified enzyme could become even 100 times more stable than the native one. In another experiment, alpha-chymotrypsin was covalently modified by treatment with anhydrides or chloroanhydrides of aromatic carboxylic acids. As a result, different numbers of additional carboxylic groups (up to five depending on the structure of the modifying reagent) were introduced into each Lys residue modified. Acylation of all available amino groups of alpha-chymotrypsin by cyclic anhydrides of pyromellitic and mellitic acids resulted in a substantial hydrophilization of the protein as estimated by partitioning in an aqueous Ficoll-400/Dextran-70 biphasic system. These modified enzyme preparations were extremely stable against irreversible thermal inactivation at elevated temperatures (65-98° C.); their thermostability was practically equal to the stability of proteolytic enzymes from extremely thermophilic bacteria, the most stable proteinases known to date. Similar approaches may be used to any other chosen proteases for the subject method.

In other embodiments, samples can be pre-treated with reducing agents such as b-mercaptoethanol or DTT to reduce the disulfide bonds to facilitate digestion.

Fractionation may be performed using any single or multidimensional chromatography, such as reversed phase chromatography (RPC), ion exchange chromatography, hydrophobic interaction chromatography, size exclusion chromatography, or affinity fractionation such as immunoaffinity and immobilized metal affinity chromatography. Preferably, the fractionation involves surface-mediated selection strategies. Electrophoresis, either slab gel or capillary electrophoresis, can also be used to fractionate the peptides in the sample. Examples of slab gel electrophoretic methods include sodium dodecyl sulfate polyacrylamide gel electrophoresis (SDS-PAGE) and native gel electrophoresis. Capillary electrophoresis methods that can be used for fractionation include capillary gel electrophoresis (CGE), capillary zone electrophoresis (CZE) and capillary electrochromatography (CEC), capillary isoelectric focusing, immobilized metal affinity chromatography and affinity electrophoresis.

Protein precipitation may be performed using techniques well known in the art. For example, precipitation may be achieved using known precipitants, such as potassium thiocyanate, trichloroacetic acid and ammonium sulphate.

Subsequent to fragmentation, the sample may be contacted with the capture agents of the present invention, e.g., capture agents immobilized on a planar support or on a bead, as described herein. Alternatively, the fragmented sample (containing a collection of peptides) may be fractionated based on, for example, size, post-translational modifications (e.g., glycosylation or phosphorylation) or antigenic properties, and then contacted with the capture agents of the present invention, e.g., capture agents immobilized on a planar support or on a bead.

Figure 7:
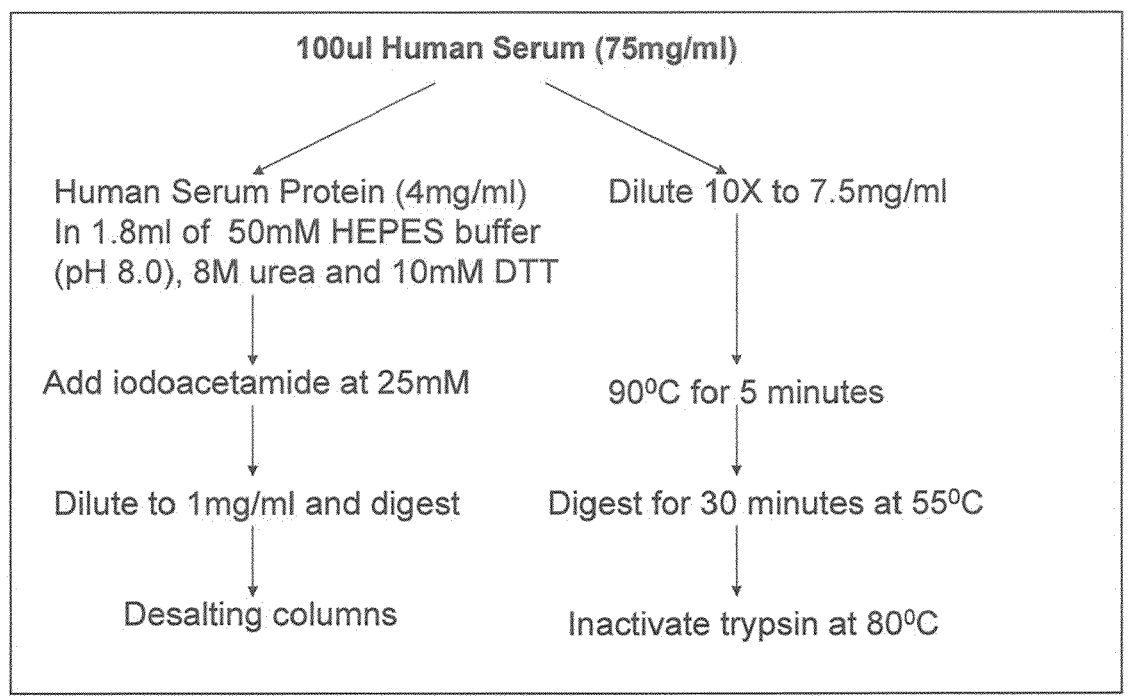
FIG. 7 provides an illustrative example of serum sample pre-treatment using either the thermo-denaturation or the chemical denaturation as described in FIG. 6.

FIG. 7 provides an illustrative example of serum sample pre-treatment using either the thermo-denaturation or the chemical denaturation. Briefly, for thermo-denaturation, 100 μL of human serum (about 75 mg/mL total protein) is first diluted 10-fold to about 7.5 mg/mL. The diluted sample is then heated to 90° C. for 5 minutes to denature the proteins, followed by 30 minutes of trypsin digestion at 55° C. The trypsin is inactivated at 80° C. after the digestion.

For chemical denaturation, about 1.8 mL of human serum proteins diluted to about 4 mg/mL is denatured in a final concentration of 50 mM HEPES buffer (pH 8.0), 8M urea and 10 mM DTT. Iodoacetamide is then added to 25 mM final concentration. The denatured sample is then further diluted to about 1 mg/mL for protease digestion. The digested sample will pass through a desalting column before being used in subsequent assays.

Figure 8:
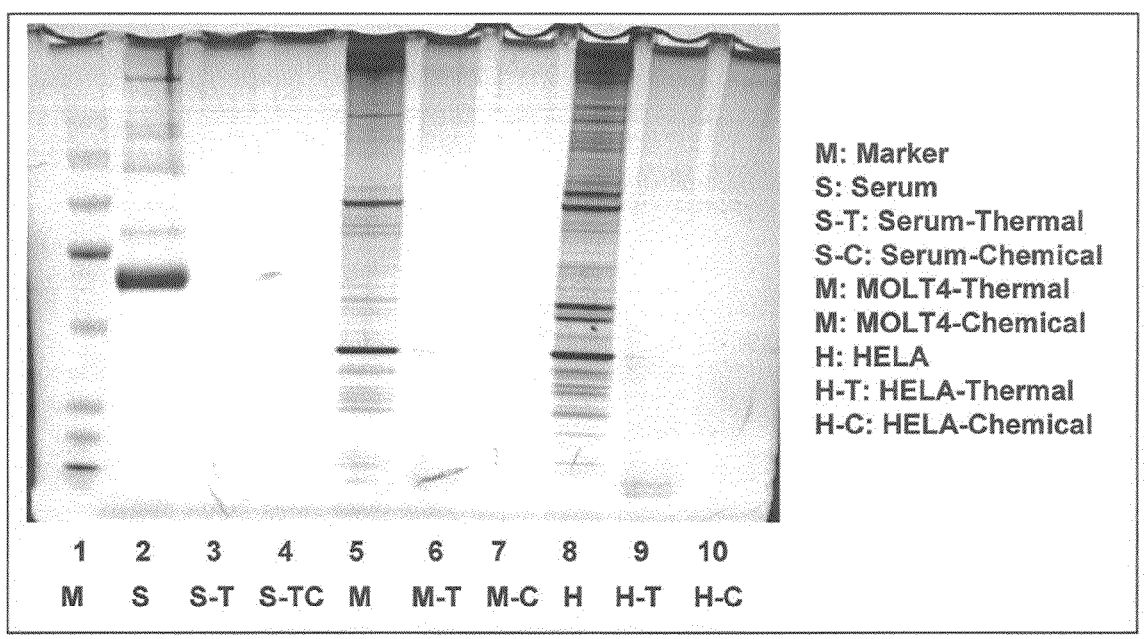
FIG. 8 shows the result of thermo-denaturation and chemical denaturation of serum proteins and cell lysates (MOLT4 and Hela cells).

FIG. 8 shows the result of thermo-denaturation and chemical denaturation of serum proteins, cell lysates (MOLT4 and Hela cells). It is evident that denaturation was successful for the majority, if not all of the proteins in both the thermo- and chemical-denaturation lanes, and both methods achieved comparable results in terms of protein denaturation and fragmentation.

The above example is for illustrative purpose only and is by no means limiting. Minor alterations of the protocol depending on specific uses can be easily achieved for optimal results in individual assays.

V. Selection of PET

One advantages of the PET of the instant invention is that PET can be determined in silico and generated in vitro (such as by peptide synthesis) without cloning or purifying the protein it belongs. PET is also advantageous over the full-length tryptic fragments (or for that matter, any other fragments that predictably results from any other treatments) since full-length tryptic fragments tend to contain one or more PETs themselves, though the tryptic fragment itself may be unique simply because of its length (the longer a stretch of peptide, the more likely it will be unique). A direct implication is that, by using relatively short and unique PETs rather than the full-length (tryptic) peptide fragments, the method of the instant invention has greatly reduced, if not completely eliminated, the risk of having multiple antibodies with unique specificities against the same peptide fragment—a source of antibody cross-reactivity. An additional advantage may be added due to the PETs election process, such as the nearest-neighbor analysis and ranking prioritization(see below), which further eliminates the chance of cross-reactivity. All these features make the PET-based methods particularly suitable for genome-wise analysis using multiplexing techniques.

The PET of the instant invention can be selected in various ways. In the simplest embodiment, the PET for a given organism or biological sample can be generated or identified by a brute force search of the relevant database, using all theoretically possible PET with a given length. This process is preferably carried out computationally using, for example, any of the sequence search tools available in the art or variations thereof. For example, to identify PET of 5 amino acids in length (a total of 3.2 million possible PET candidates, see table 2.2.2 below), each of the 3.2 million candidates may be used as a query sequence to search against the human proteom as described below. Any candidate that has more than one hit (found in two or more proteins) is immediately eliminated before further searching is done. At the end of the search, a list of human proteins that have one or more PETs can be obtained (see Example 1 below). The same or similar procedure can be used for any pre-determined organism or database.

For example, PETs for each human protein can be identified using the following procedure. A Perl program is developed to calculate the occurrence of all possible peptides, given by $20^N$, of defined length N (amino acids) in human proteins. For example, the total tag space is 160,000 ($20^4$) for tetramer peptides, 3.2 M ($20^5$) for pentamer peptides, and 64 M ($20^6$) for hexamer peptides, so on. Predicted human protein sequences are analyzed for the presence or absence of all possible peptides of N amino acids. PET are the peptide sequences that occur only once in the human proteome. Thus the presence of a specific PET is an intrinsic property of the protein sequence and is operational independent. According to this approach, a definitive set of PETs can be defined and used regardless of the sample processing procedure (operational independence).

In one embodiment, to speed up the searching process, computer algorithms may be developed or modified to eliminate unnecessary searches before the actual search begins.

Using the example above, two highly related (say differ only in a few amino acid positions) human proteins may be aligned, and a large number of candidate PET can be eliminated based on the sequence of the identical regions. For example, if there is a stretch of identical sequence of 20 amino acids, then sixteen 5-amino acid PETs can be eliminated without searching, by virtue of their simultaneous appearance in two non-identical human proteins. This elimination process can be continued using as many highly related protein pairs or families as possible, such as the evolutionary conserved proteins such as histones, globins, etc.

In another embodiment, the identified PET for a given protein may be rank-ordered based on certain criteria, so that higher ranking PETs are preferred to be used in generating specific capture agents.

For example, certain PET may naturally exist on protein surface, thus making good candidates for being a soluble peptide when digested by a protease. On the other hand, certain PET may exist in an internal or core region of a protein, and may not be readily soluble even after digestion. Such solubility property may be evaluated by available softwares. The solvent accessibility method described in Boger, J., Emini, E. A. & Schmidt, A., Surface probability profile-An heuristic approach to the selection of synthetic peptide antigens, Reports on the Sixth International Congress in Immunology (Toronto) 1986 p. 250 also may be used to identify PETs that are located on the surface of the protein of interest. The package MOLMOL (Koradi, R. et al. (1996) *J. Mol. Graph.* 14:51-55) and Eisenhaber's ASC method (Eisenhaber and Argos (1993) *J. Comput. Chem.* 14:1272-1280; Eisenhaber et al. (1995) *J. Comput. Chem.* 16:273-284) may also be used. Surface PETs generally have higher ranking than internal PETs. In one embodiment, the logP or logD values that can be calculated for a PET, or proteolytic fragment containing a PET, can be calculated and used to rank order the PET's based on likely solubility under conditions that a protein sample is to be contacted with a capture agent.

Regardless of the manner the PETs are generated, an ideal PET preferably is 8 amino acids in length, and the parental tryptic peptide should be smaller than 20 amino acid long. This is because antibodies typically recognize peptide epitopes of 4-8 amino acids, thus peptides of 12-20 amino acids are conventionally used for antibody production.

Since trypsin is a preferred digestion enzyme in certain embodiments, a PET in these embodiments should not contain K or R in the middle of the sequence so that the PET will not be cleaved by trypsin during sample preparation. In a more general sense, the selected PET should not contain or overlap a digestion site such that the PET is expected to be destroyed after digestion, unless an assay specifically prefer that a PET be destroyed after digestion.

In addition, an ideal PET preferably does not have hydrophobic parental tryptic peptide, is highly antigenic, and has the smallest numbers (preferably none) of closest related peptides (nearest neighbor peptides or NNP) defined by nearest neighbor analysis.

Any PET may also be associated with an annotation, which may contain useful information such as: whether the PET may be destroyed by a certain protease (such as trypsin), whether it is likely to appear on a digested peptide with a relatively rigid or flexible structure, etc. These characteristics may help to rank order the PETs for use if generating specific capture agents, especially when there are a large number of PETs associated with a given protein. Since PET may change depending on particular use in a given organism, ranking order may change depending on specific usages. A PET may be low ranking due to its probability of being destroyed by a certain protease may rank higher in a different fragmentation scheme using a different protease.

In another embodiment, the computational algorithm for selecting optimal PET from a protein for antibody generation takes antibody-peptide interaction data into consideration. A process such as Nearest-Neighbor Analysis (NNA), can be used to select most unique PET for each protein. Each PET in a protein is given a relative score, or PET Uniqueness Index, that is based on the number of nearest neighbors it has. The higher the PET Uniqueness Index, the more unique the PET is. The PET Uniqueness Index can be calculated using an Amino Acid Replacement Matrix such as the one in Table VIII of Getzoff, E D, Tainer J A and Lerner R A. *The chemistry and mechanism of antibody binding to protein antigens.* 1988. *Advances. Immunol.* 43: 1-97. In this matrix, the replaceability of each amino acid by the remaining 19 amino acids was calculated based on experimental data on antibody cross-reactivity to a large number of peptides of single mutations (replacing each amino acid in a peptide sequence by the remaining 19 amino acids). For example, each octamer PET from a protein is compared to 8.7 million octamers present in human proteome and a PET Uniqueness Index is calculated. This process not only selects the most unique PET for particular protein, it also identifies Nearest Neighbor Peptides for this PET. This becomes important for defining cross-reactivity of PET-specific antibodies since Nearest Neighbor Peptides are the ones most likely will cross-react with particular antibody.

Besides PET Uniqueness Index, the following parameters for each PET may also be calculated and help to rank the PETs:

a) PET Solubility Index: which involves calculating LogP and LogD of the PET.

b) PET Hydrophobicity & water accessibility: only hydrophilic peptides and peptides with good water accessibility will be selected.

c) PET Length: since longer peptides tend to have conformations in solution, we use PET peptides with defined length of 8 amino acids. PET-specific antibodies will have better defined specificity due to limited number of epitopes in a shorter peptide sequences. This is very important for multiplexing assays using these antibodies. In one embodiment, only antibodies generated by this way will be used for multiplexing assays.

d) Evolutionary Conservation Index: each human PET will be compared with other species to see whether a PET sequence is conserved cross species. Ideally, PET with minimal conservation, for example, between mouse and human sequences will be selected. This will maximize the possibility to generate good immunoresponse and monoclonal antibodies in mouse.

VI. Applications of the Invention

A. Investigative and Diagnostic Applications

The capture agents of the present invention provide a powerful tool in probing living systems and in diagnostic applications (e.g., clinical, environmental and industrial, and food safety diagnostic applications). For clinical diagnostic applications, the capture agents are designed such that they bind to one or more PET corresponding to one or more diagnostic targets (e.g., a disease related protein, collection of proteins, or pattern of proteins). Specific individual disease related proteins include, for example, prostate-specific antigen (PSA), prostatic acid phosphatase (PAP) or prostate specific membrane antigen (PSMA) (for diagnosing prostate cancer); Cyclin E for diagnosing breast cancer; Annexin, e.g., Annexin V (for diagnosing cell death in, for example, cancer, ischemia, or transplant rejection); or β-amyloid plaques (for diagnosing Alzheimer's Disease).

Thus, PETs and the capture agents of the present invention may be used as a source of surrogate markers. For example, they can be used as markers of disorders or disease states, as markers for precursors of disease states, as markers for predisposition of disease states, as markers of drug activity, or as markers of the pharmacogenomic profile of protein expression.

As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the causation of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using a PET corresponding to a protein associated with a cardiovascular disease as a surrogate marker, and an analysis of HIV infection may be made using a PET corresponding to an HIV protein as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35:258-264; and James (1994) *AIDS Treatment News Archive* 209.

Perhaps the most significant use of the invention is that it enables practice of a powerful new protein expression analysis technique: analyses of samples for the presence of specific combinations of proteins and specific levels of expression of combinations of proteins. This is valuable in molecular biology investigations generally, and particularly in development of novel assays. Thus, this invention permits one to identify proteins, groups of proteins, and protein expression patterns present in a sample which are characteristic of some disease, physiologic state, or species identity. Such multiparametric assay protocols may be particularly informative if the proteins being detected are from disconnected or remotely connected pathways. For example, the invention might be used to compare protein expression patterns in tissue, urine, or blood from normal patients and cancer patients, and to discover that in the presence of a particular type of cancer a first group of proteins are expressed at a higher level than normal and another group are expressed at a lower level. As another example, the protein chips might be used to survey protein expression levels in various strains of bacteria, to discover patterns of expression which characterize different strains, and to determine which strains are susceptible to which antibiotic. Furthermore, the invention enables production of specialty assay devices comprising arrays or other arrangements of capture agents for detecting specific patterns of specific proteins. Thus, to continue the example, in accordance with the practice of the invention, one can produce a chip which can be exposed to a cell lysate preparation from a patient or a body fluid to reveal the presence or absence or pattern of expression informative that the patient is cancer free, or is suffering from a particular cancer type. Alternatively, one might produce a protein chip that would be exposed to a sample and read to indicate the species of bacteria in an infection and the antibiotic that will destroy it.

A junction PET is a peptide which spans the region of a protein corresponding to a splice site of the RNA which encodes it. Capture agents designed to bind to a junction PET may be included in such analyses to detect splice variants as well as gene fusions generated by chromosomal rearrangements, e.g., cancer-associated chromosomal rearrangements. Detection of such rearrangements may lead to a diagnosis of a disease, e.g., cancer. It is now becoming apparent that splice variants are common and that mechanisms for controlling RNA splicing have evolved as a control mechanism for various physiological processes. The invention permits detection of expression of proteins encoded by such species, and correlation of the presence of such proteins with disease or abnormality. Examples of cancer-associated chromosomal rearrangements include: translocation t(16;21)(p11;q22) between genes FUS-ERG associated with myeloid leukemia and non-lymphocytic, acute leukemia (see Ichikawa H. et al. (1994) *Cancer Res.* 54(11):2865-8); translocation t(21;22) (q22;q12) between genes ERG-EWS associated with Ewing's sarcoma and neuroepithelioma (see Kaneko Y. et al. (1997) *Genes Chromosomes Cancer* 18(3):228-31); translocation t(14;18)(q32;q21) involving the bcl2 gene and associated with follicular lymphoma; and translocations juxtaposing the coding regions of the PAX3 gene on chromosome 2 and the FKHR gene on chromosome 13 associated with alveolar rhabdomyosarcoma (see Barr F. G. et al. (1996) *Hum. Mol. Genet.* 5:15-21).

For applications in environmental and industrial diagnostics the capture agents are designed such that they bind to one or more PET corresponding to a biowarfare agent (e.g., anthrax, small pox, cholera toxin) and/or one or more PET corresponding to other environmental toxins (*Staphylococcus aureus* a-toxin, Shiga toxin, cytotoxic necrotizing factor type 1, *Escherichia coli* heat-stable toxin, and botulinum and tetanus neurotoxins) or allergens. The capture agents may also be designed to bind to one or more PET corresponding to an infectious agent such as a bacterium, a prion, a parasite, or a PET corresponding to a virus (e.g., human immunodeficiency virus-1 (HIV-1), HIV-2, simian immunodeficiency virus (SIV), hepatitis C virus (HCV), hepatitis B virus (HBV), Influenza, Foot and Mouth Disease virus, and Ebola virus).

The following part illustrates the general idea of diagnostic use of the instant invention in one specific setting—serum biomarker assays.

The proteins found in human plasma perform many important functions in the body. Over or under expression of these proteins can thus cause disease directly, or reveal its presence. Studies have shown that complex serum proteomic patterns might reflect the underlying pathological state of an organ such as the ovary (Petricoin et al., Lancet 359: 572-577, 2002). Therefore, the easy accessibility of serum samples, and the fact that serum comprehensively samples the human phenotype—the state of the body at a particular point in time—make serum an attractive option for a broad array of applications, including clinical and diagnostics applications (early detection and diagnosis of disease, monitor disease progression, monitor therapy etc.), discovery applications (such as novel biomarker discovery), and drug development (drug efficacy and toxicity, and personalized medicine). In fact, over $1 billion annually is spent on immunoassays to measure proteins in plasma as indicators of disease (Plasma Proteome Institute (PPI), Washington, D.C.).

Despite decades of research, only a handful of proteins (about 20) among the 500 or so detected proteins in plasma are measured routinely for diagnostic purposes. These include: cardiac proteins (troponins, myoglobin, creatine kinase) as indicators of heart attack; insulin, for management of diabetes; liver enzymes (alanine or aspartate transaminases) as indicators of drug toxicity; and coagulation factors for management of clotting disorders. About 150 proteins in plasma are measured by some laboratory for diagnosis of less common diseases.

IN addition, proteins in plasma differ in concentration by at least one billion-fold. For example, serum albumin has a normal concentration range of 35-50 mg/mL ($35\text{-}50 \times 10^9$ pg/mL) and is measured clinically as an indication of severe liver disease or malnutrition, while interleukin 6 (IL-6) has a normal range of just 0-5 pg/mL, and is measured as a sensitive indicator of inflammation or infection.

Thus, there is a need for reference levels of all serum proteins, and reliable assays for measuring serum protein levels under any conditions. However, standardization of immunoassays for heterogeneous antigens is nearly impossible about 10 years ago (Ekins, Scand J Clin Lab Invest. 205: 33-46, 1991). One of the major obstacle is the apparent need of having identical standard and analyte. This is the case with only a few small peptides. With larger peptides and proteins, the problems tend to become more complicated because biological samples often contain proforms, splice variants, fragments, and complexes of the analyte (Stenman, Clinical Chemistry 47: 815-820, 2001). One such problem is illustrated by measuring serum TGF-beta levels.

Figure 9:
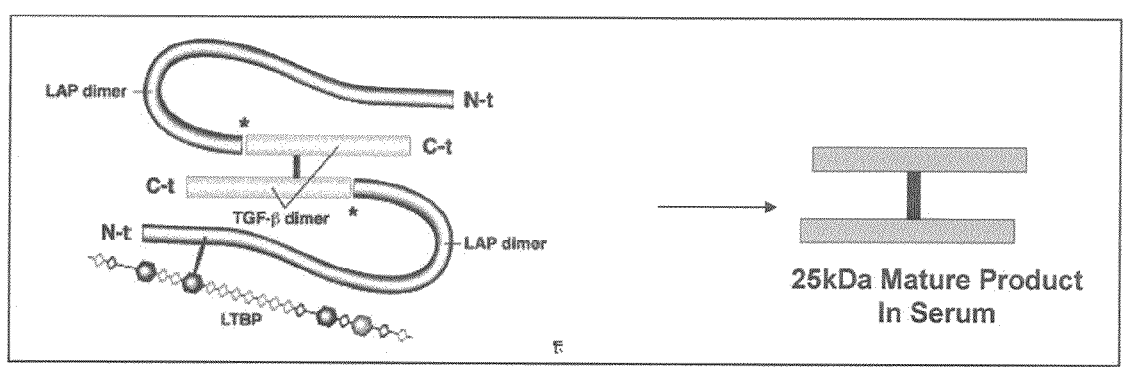
FIG. 9 illustrates the structure of mature TGF-beta dimer, and one complex form of mature TGF-beta with LAP and LTBP.

The TGF-beta superfamily proteins are a collection of structurally related multi-function proteins that have a diverse array of biological functions including wound healing, development, oncogenesis, and atherosclerosis. There are at least three known mammalian TGF-beta proteins (beta1, beta2 and beta3), which are thought to have similar functions, at least in vitro. Each of the three isoforms are produced as pre-proproteins, which rapidly dimerizes. After the loss of the signal sequences, sugar moieties are added to the proproteins regions known as the Latency Associated Peptide, or LAP. In addition, there is proteolytic cleavage between the LAPs and the mature dimers (the functional portion), but the cleaved LAPs still associate with the mature dimer, forming a complex known as the small latent complex. Either prior to secretion, or in the extracellular milieu, the small latent complex can bind to a large number of other proteins forming a large number of higher molecular weight latent complexes. The best characterized of these proteins are the latent TGF-beta binding protein family LTBP1-4 and fibrillin-1 and -2 (see FIG. 9). Once in the extracellular environment, the TGF-beta complex may bind even more proteins to form other complexes. Known soluble TGF-beta binding proteins include: decorin, alpha-fetoprotein (AFP), betaglycan extracellular domain, β-amyloid precursor, and fetuin. Given the various isoforms, complexes, processing stages, etc., it is very difficult to accurately measure serum TGF-beta protein levels, and a range of 100-fold differences in serum level of TBG-beta1 are reported by different groups (see Grainger et al., *Cytokine & Growth Factor Reviews* 11: 133-145, 2000).

The other problem arises from the false positive/negative effects of anti-animal antibodies on immunoassays. Specifically, in a sandwich-type assay for a specific antigen in a serum sample, instead of capturing the desired antigen, the immobilized capture antibody may bind to anti-animal antibodies in the serum sample, which in turn can be bound by the labeled secondary antibody and gives rise to false positive result. On the other hand, too much anti-animal antibodies may block the interaction between the capture antibody and the desired antigen, and the interaction between the labeled secondary antibody and the desired antigen, leading to false negative result. This is a serious problem demonstrated in a recent study by Rotmensch and Cole (Lancet 355: 712-715, 2000), which shows that in all 12 cases where women were diagnosed of having postgestational choriocarcinoma on the basis of persistently positive human chorionic gonadotropin (hCG) test results in the absence of pregnancy, a false diagnosis had been made, and most of the women had been subjected to needless surgery or chemotherapy. Such diagnostic problems associated with anti-animal antibodies have also been reported elsewhere (Hennig et al., The influence of naturally occurring heterophilic anti-immunoglobulin antibodies on direct measurement of serum proteins using sandwich ELISAs. *Journal of Immunological Methods* 235: 71-80, 2000; Covinsky et al., *An IgMl Antibody to Escherichia coli Produces False-Positive Results in Multiple Immunometric Assays. Clinical Chemistry* 46: 1157-1161, 2000).

All these problems can be efficiently solved by the methods of the instant invention. By digesting serum samples and converting all forms of the target protein to a uniform PET-containing peptide, the methods of the instant invention greatly reduce the complexity of the sample. Anti-animal antibodies, proteins complexes, various isoforms are no longer expected to be a significant factor in the digested serum sample, thus facilitating more reliable, reproducible, and accurate results from assay to assay.

The method of the instant invention is by no means limited to one particular serum protein such as TGF-beta. It has broad applications in a wide range of serum proteins, including peptide hormones, candidate disease biomarkers (such as PSA, CA125, MMPs, etc.), serum disease and non-disease biomarkers, and acute phase response proteins. For example, measuring the following types of serum biomarkers will have broad applications in clinical and diagnostic uses: 1) disease state markers (such as markers for inflammation, infection, etc.), and 2) non-disease state markers, including markers indicating drug and hormone effects (e.g., alcohol, androgens, anti-epileptics, estrogen, pregnancy, hormone replacement therapy, etc.). Exemplary serum proteins that can be measured include: ApoA-I, Andogens, AAT, AAG, A2M, Alb, Apo-B, AT III, C3, Cp, C4, CRP, SAA, Hp, AGP, Fb, AP, FIB, FER, PAL, PSM, Tf, IgA, IgG, IgM, IgE, FN, B2M, and RBP.

One preferred assay method for these serum proteins is the sandwich assay using a PET-specific capture agent and at least one labeled secondary capture agent(s) for detection of binding. These assays may be performed in an array format according to the teaching of the instant application, in that different capture agents (such as PET-specific antibodies) can be arrayed on a single (or a few) microarrays for use in simultaneous detection/quantitation of a large number of serum biomarkers.

Foundation for Blood Research (FBR, Scarborough, Me.) has developed a 152-page guide on serum protein utility and interpretation for day to day use by practitioners and laboratorians. This guide contains a distillation of the world's literature on the subject, is fully indexed, and is presented by a given disease state (Section I), as well as by individual proteins (Section II). This book is generally useful for interpretation of test results, as well as providing guidance regarding which test is (or is not) appropriate to order and why (or why not). Section II, which covers general information on serum proteins, is also helpful regarding background information about each protein. The entire content of which is incorporated herein by reference.

B. High-Throughput Screening

Compositions containing the capture agents of the invention, e.g., microarrays, beads or chips enable the high-throughput screening of very large numbers of compounds to identify those compounds capable of interacting with a particular capture agent, or to detect molecules which compete for binding with the PETs. Microarrays are useful for screening large libraries of natural or synthetic compounds to identify competitors of natural or non-natural ligands for the capture agent, which may be of diagnostic, prognostic, therapeutic or scientific interest.

The use of microarray technology with the capture agents of the present invention enables comprehensive profiling of large numbers of proteins from normal and diseased-state serum, cells, and tissues.

For example, once the microarray has been formed, it may be used for high-throughput drug discovery (e.g., screening libraries of compounds for their ability to bind to or modulate the activity of a target protein); for high-throughput target identification (e.g., correlating a protein with a disease process); for high-throughput target validation (e.g., manipulating a protein by, for example, mutagenesis and monitoring the effects of the manipulation on the protein or on other proteins); or in basic research (e.g., to study patterns of protein expression at, for example, key developmental or cell cycle time points or to study patterns of protein expression in response to various stimuli).

In one embodiment, the invention provides a method for identifying a test compound, e.g., a small molecule, that modulates the activity of a ligand of interest. According to this embodiment, a capture agent is exposed to a ligand and a test compound. The presence or the absence of binding between the capture agent and the ligand is then detected to determine the modulatory effect of the test compound on the ligand. In a preferred embodiment, a microarray of capture agents, that bind to ligands acting in the same cellular pathway, are used to profile the regulatory effect of a test compound on all these proteins in a parallel fashion.

C. Pharmacoproteomics

The capture agents or arrays comprising the capture agents of the present invention may also be used to study the relationship between a subject's protein expression profile and that subject's response to a foreign compound or drug. Differences in metabolism of therapeutics can lead to severe toxicity or therapeutic failure by altering the relation between dose and blood concentration of the pharmacologically active drug. Thus, use of the capture agents in the foregoing manner may aid a physician or clinician in determining whether to administer a pharmacologically active drug to a subject, as well as in tailoring the dosage and/or therapeutic regimen of treatment with the drug.

D. Protein Profiling

As indicated above, capture agents of the present invention enable the characterization of any biological state via protein profiling. The term "protein profile," as used herein, includes the pattern of protein expression obtained for a given tissue or cell under a given set of conditions. Such conditions may include, but are not limited to, cellular growth, apoptosis, proliferation, differentiation, transformation, tumorigenesis, metastasis, and carcinogen exposure.

The capture agents of the present invention may also be used to compare the protein expression patterns of two cells or different populations of cells. Methods of comparing the protein expression of two cells or populations of cells are particularly useful for the understanding of biological processes. For example, using these methods, the protein expression patterns of identical cells or closely related cells exposed to different conditions can be compared. Most typically, the protein content of one cell or population of cells is compared to the protein content of a control cell or population of cells. As indicated above, one of the cells or populations of cells may be neoplastic and the other cell is not. In another embodiment, one of the two cells or populations of cells being assayed may be infected with a pathogen. Alternatively, one of the two cells or populations of cells has been exposed to a chemical, environmental, or thermal stress and the other cell or population of cells serves as a control. In a further embodiment, one of the cells or populations of cells may be exposed to a drug or a potential drug and its protein expression pattern compared to a control cell.

Such methods of assaying differential protein expression are useful in the identification and validation of new potential drug targets as well as for drug screening. For instance, the capture agents and the methods of the invention may be used to identify a protein which is overexpressed in tumor cells, but not in normal cells. This protein may be a target for drug intervention. Inhibitors to the action of the overexpressed protein can then be developed. Alternatively, antisense strategies to inhibit the overexpression may be developed. In another instance, the protein expression pattern of a cell, or population of cells, which has been exposed to a drug or potential drug can be compared to that of a cell, or population of cells, which has not been exposed to the drug. This comparison will provide insight as to whether the drug has had the desired effect on a target protein (drug efficacy) and whether other proteins of the cell, or population of cells, have also been affected (drug specificity).

E. Protein Sequencing, Purification and Characterization

The capture agents of the present invention may also be used in protein sequencing. Briefly, capture agents are raised that interact with a known combination of unique recognition sequences. Subsequently, a protein of interest is fragmented using the methods described herein to generate a collection of peptides and then the sample is allowed to interact with the capture agents. Based on the interaction pattern between the collection of peptides and the capture agents, the amino acid sequence of the collection of peptides may be deciphered. In a preferred embodiment, the capture agents are immobilized on an array in pre-determined positions that allow for easy determination of peptide-capture agent interactions. These sequencing methods would further allow the identification of amino acid polymorphisms, e.g., single amino acid polymorphisms, or mutations in a protein of interest.

In another embodiment, the capture agents of the present invention may also be used in protein purification. In this embodiment, the PET acts as a ligand/affinity tag and allows for affinity purification of a protein. A capture agent raised against a PET exposed on a surface of a protein may be coupled to a column of interest using art known techniques. The choice of a column will depend on the amino acid sequence of the capture agent and which end will be linked to the matrix. For example, if the amino-terminal end of the capture agent is to be linked to the matrix, matrices such as the Affigel (by Biorad) may be used. If a linkage via a cysteine residue is desired, an Epoxy-Sepharose-6B column (by Pharmacia) may be used. A sample containing the protein of interest may then be run through the column and the protein of interest may be eluted using art known techniques as described in, for example, J. Nilsson et al. (1997) "Affinity fusion strategies for detection, purification, and immobilization of recombinant proteins," *Protein Expression and Purification,* 11:11-16, the contents of which are incorporated by reference. This embodiment of the invention also allows for the characterization of protein-protein interactions under native conditions, without the need to introduce artificial affinity tags in the protein(s) to be studied.

In yet another embodiment, the capture agents of the present invention may be used in protein characterization. Capture agents can be generated that differentiate between alternative forms of the same gene product, e.g., between proteins having different post-translational modifications (e.g., phosphorylated versus non-phosphorylated versions of the same protein or glycosylated versus non-glycosylated versions of the same protein) or between alternatively spliced gene products.

The utility of the invention is not limited to diagnosis. The system and methods described herein may also be useful for screening, making prognosis of disease outcomes, and providing treatment modality suggestion based on the profiling of the pathologic cells, prognosis of the outcome of a normal lesion and susceptibility of lesions to malignant transformation.

F. Detection of Post-translational Modifications

The subject computer generated PETs can also be analyzed according to the likely presence or absence of post-translational modifications. More than 100 different such modifications of amino acid residues are known, examples include but are not limited to acetylation, amidation, deamidation, prenylation (such as farnesylation or geranylation), formylation, glycosylation, hydroxylation, methylation, myristoylation, phosphorylation, ubiquitination, ribosylation and sulphation. Sequence analysis softwares which are capable of determining putative post-translational modification in a given amino acid sequence include the NetPhos server which produces neural network predictions for serine, threonine and tyrosine phosphorylation sites in eukaryotic proteins (available through http://www.cbs.dtu.dk/services/Net-Phos/), GPI Modification Site Prediction (available through http://mendel.imp.univie.ac.at/gpi) and the ExPASy proteomics server for total protein analysis (available through www.expasy.ch/tools/)

In certain embodiments, preferred PET moieties are those lacking any post-translational modification sites, since post-translationally modified amino acid sequences may complicate sample preparation and/or interaction with a capture agent. Notwithstanding the above, capture agents that can discriminate between post-translationally forms of a PET, which may indicate a biological activity of the polypeptide-of-interest, can be generated and used in the present invention. A very common example is the phosphorylation of OH group of the amino acid side chain of a serine, a threonine, or a tyrosine group in a polypeptide. Depending on the polypeptide, this modification can increase or decrease its functional activity. In one embodiment, the subject invention provides an array of capture agents that are variegated so as to provide discriminatory binding and identification of various post-translationally modified forms of one or more proteins. In a preferred alternative embodiment, the subject invention provides an array of capture agents that are variegated so as to provide specific binding to one or more PET uniquely associated with a modification of interest, which modification itself can be readily detected and/or quantitated by additional agents, such as a labeled secondary antibody specifically recognizing the modification (e.g., a phospho-tyrosine antibody).

In a general sense, the invention provides a general means to detect/quantitate protein modifications. "Modification" here refers generally to any kind of non-wildtype changes in amino acid sequence, including post-translational modification, alternative splicing, polymorphysm, insertion, deletion, point mutation, etc. To detect/quantitate a specific modification within a potential target protein present in a sample, the sequence of the target protein is first analyzed to identify potential modification sites (such as phosphorylation sites for a specific kinase). Next, a potential fragment of the target protein containing such modification site is identified. The fragment is specific for a selected method of treatment, such as tryptic digestion or digestion by another protease or reliable chemical fragmentation. PET within (and unique) to the modification site-containing fragment can then be identified using the method of the instant invention. Fragmentation using a combination of two or more methods is also contemplated. Absolute predictability of the fragment size is desired, but not necessary, as long as the fragment always contains the desired PET and the modification site.

Figure 22:
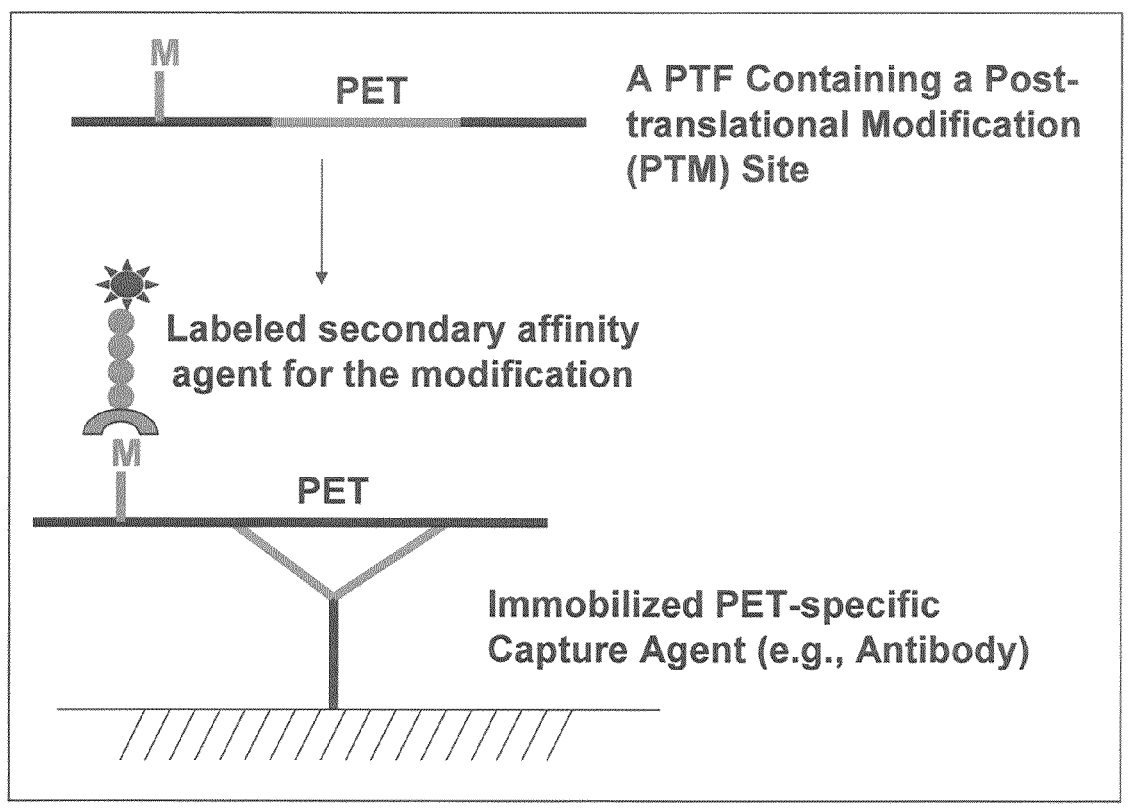
FIG. 22 is a schematic drawing showing the general princial of detecting PET-associated protein modification using sandwich assay.

Antibody or other capture agents specific for the identified PET is obtained. The capture agent is then used in a sandwich ELISA format to detect captured fragments containing the modification (see FIG. 22). The site of the PET is proximal to the post-translational modification site(s). Thus a binding to the PET by a capture agent will not interfere with the binding of a detection agent specific for the modified residue.

Figure 23:
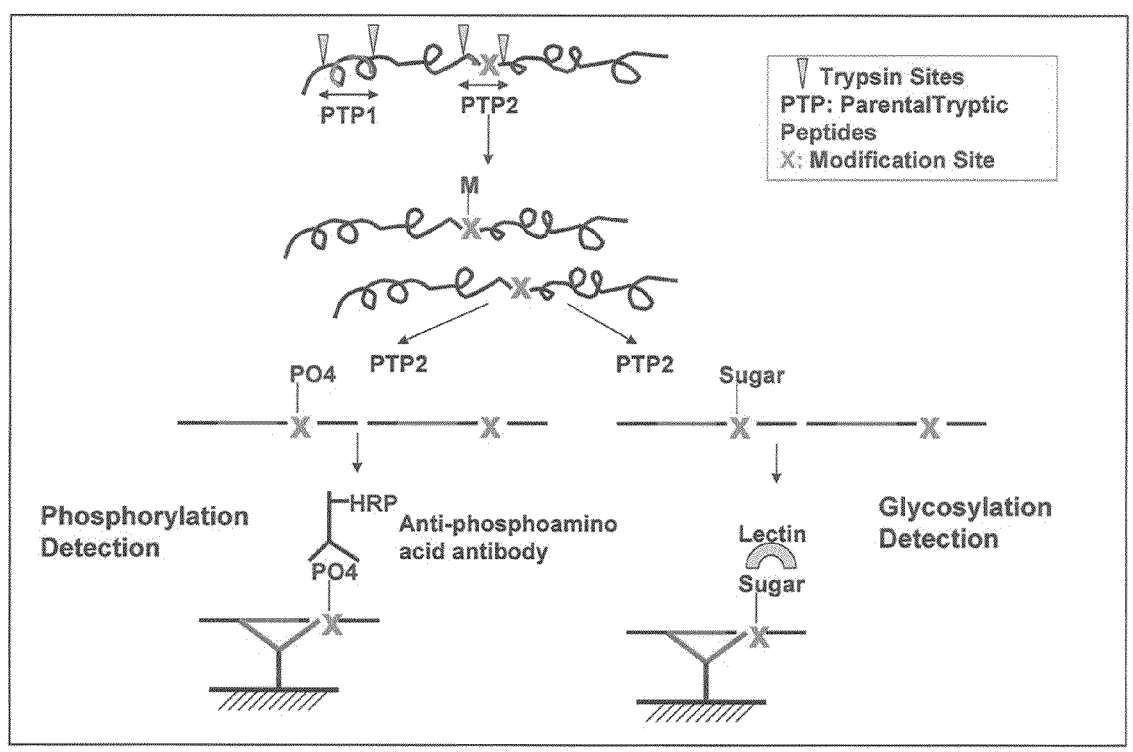
FIG. 23 is a schematic diagram of one embodiment of the detection of post-translational modification (e.g., phosphorylation or glycosylation). A target peptide is digested by a protease, such as Trypsin to yield smaller, PET-containing fragments. One of the fragments (PTP2) also contains at least one modification of interest. Once the fragments are isolated by capture agents on a support, the presence of phosphorylation can be detected by, for example, HRP-conjugated anti-phospho-amino acid antibodies; and the presence of sugar modification can be detected by, for example, lectin.

A few specific embodiments of this aspect of the invention are described in more detail below (see FIG. 23). For illustrative purpose only, the capture agents described below in various embodiments of the invention are antibodies specific for PETs. However, it should be understood that any capture agents described above can be used in each of the following embodiments.

(i) Phosphorylation

The reversible addition of phosphate groups to proteins is important for the transmission of signals within eukaryotic cells and, as a result, protein phosphorylation and dephosphorylation regulate many diverse cellular processes. To detect the presence and/or quantitate the amount of a phosphorylated peptide in a sample, anti-phospho-amino acid antibodies can be used to detect the presence of phosphopeptides.

There are numerous commercially available phospho-tyrosine specific antibodies that can be adapted to be used in the instant invention. Merely to illustrate, phosphotyrosine antibody (ab2287) [13F9] of Abcam Ltd (Cambridge, UK) is a mouse IgG1 isotype monoclonal antibody reacts specifically with phosphotyrosine and shows minimal reactivity by ELISA and competitive ELISA with phosphoserine or phosphothreonine. The antibody reacts with free phosphotyrosine, phosphotyrosine conjugated to carriers such as thyroglobulin or BSA, and detects the presence of phosphotyrosine in proteins of both unstimulated and stimulated cell lysates.

Similarly, RESEARCH DIAGNOSTICS INC (Flanders, N.J.) provides a few similar anti-phosphotyrosine antibodies. Among them, RDI-PHOSTYRabmb is a mouse mIgG2b isotype monoclonal antibody reacts strongly and specifically with phosphotyrosine-containing proteins and can be blocked specifically with phosphotyrosine. No reaction with either phosphothreonine or phosphoserine is detected. This antibody appears to have broad cross-species reactivity, and is reactive with various tyrosine-phosphorylated proteins of human, chick, frog, rat, mouse and dog origin.

RESEARCH DIAGNOSTICS INC also provides phosphoserine-specific antibodies, such as RDI-PHOSSERabr, which is an affinity-purified rabbit antibody made against phosphoserine containing proteins. The antibody reacts specifically with serine phosphorylated proteins and shows no significant cross reactivity to other phosphothreonine or phosphotyrosine by western blot analysis. This antibody is suitable for ELISA according to the manufacture's suggestion. The company also provides a mouse IgG1 monoclonal anti-phosphoserine antibody RDI-PHOSSEabm, which reacts specifically with phosphorylated serine, both as free amino acid or conjugated to carriers as BSA or KLH. No cross reactivity is observed with non-phosphorylated serine, phosphothreonine, phosphotyrosine, AmpMP or ATP.

RDI-PHOSTHRabr is an affinity isolated rabbit anti-phosphothreonine antibody (anti-pT) provided by RESEARCH DIAGNOSTICS INC. Both antigen-capture and antibody-capture ELISA indicated that the anti-phosphothreonine antibodies can recognize threonine-phosphorylated protein, phosphothreonine and lysine-phosphothreonine-glycine random polymer, respectively. Direct, competitive antigen-capture ELISA demonstrated that the antibodies are specifically inhibited by free phosphothreonine, phosvitin but not by free phosphoserine, phosphotyrosine, threonine and ATP. The company also provides a mouse IgG2b monoclonal anti-phosphothreonine antibody RDI-PHOSTHabm, which reacts specifically with phosphorylated threonine, both as free amino acid or conjugated to carriers as BSA or KLH. No cross reactivity is observed with non-phosphorylated threonine, phophoserine, phosphotyrosine, AmpMP or ATP.

Molecular Probe (Eugene, Oreg.) has developed a small molecule fluorophore phosphosensor, referred to as Pro-Q Diamond dye, which is capable of ultrasensitive global detection and quantitation of phosphorylated amino acid residues in peptides and proteins displayed on microarrays. The utility of the fluorescent Pro-Q Diamond phosphosensor dye technology is demonstrated using phosphoproteins and phosphopeptides as well as with protein kinase reactions performed in miniaturized microarray assay format (Martin, et al., *Proteomics* 3: 1244-1255, 2003). Instead of applying a phospho-amino acid-selective antibody labeled with a fluorescent or enzymatic tag for detection, a small, fluorescent probe is employed as a universal sensor of phosphorylation status. The detection limit for phosphoproteins on a variety of different commercially available protein array substrates was found to be 312-625 fg, depending upon the number of phosphate residues. Characterization of the enzymatic phosphorylation of immobilized peptide targets with Pro-Q Diamond dye readily permits differentiation between specific and non-specific peptide labeling at picogram to subpicogram levels of detection sensitivity. Martin et al. (supra) also describe in detail the suitable protocols, instruments for using the Pro-Q stain, especially for peptides on microarrays, the entire contents of which are incorporated herein by reference.

One of the advantages of the method over other methods, such as identification of modified amino acids in proteins by mass spectrometry, is that the instant invention provides a much simpler technique that does not rely on expensive instruments, and thus can be easily adapted to be used in small or large laboratories, in industry or academic settings alike.

In one embodiment, the instant invention can be used to identify potential substrates of a specific kinase or kinase subfamily. As the number of known protein kinases has increased at an ever-accelerating pace, it has become more challenging to determine which protein kinases interact with which substrates in the cell.

The determination of consensus phosphorylation site motifs by amino acid sequence alignment of known substrates has proven useful in this pursuit. These motifs can be helpful for predicting phosphorylation sites for specific protein kinases within a potential protein substrate. The table below summarizes merely some of the known data about specificity motifs for various well-studied protein kinases, along with examples of known phosphorylation sites in specific proteins (for a more extensive list, see Pearson, R. B., and Kemp, B. E. (1991). In T. Hunter and B. M. Sefton (Eds.), Methods in Enzymology Vol. 200, pp. 62-81. San Diego: Academic Press, incorporated by reference). Phosphoacceptor residue is indicated in bold, amino acids which can function interchangeably at a particular residue are separated by a slash (/), and residues which do not appear to contribute strongly to recognition are indicated by an "X." Some protein kinases such as CKI and GSK-3 contain phosphoamino acid residues in their recognition motifs, and have been termed "hierarchical" protein kinases (see Roach, *J. Biol. Chem.* 266, 14139-14142, 1991 for review). They often require prior phosphorylation by another kinase at a residue in the vicinity of their own phosphorylation site. S(p) represents such pre-existing phosphoserine residues.

| Protein Kinase | Recognition MOtifS$^a$ | Phosphorylation Sites$_b$ | Protein Substrate (reference) |
|---|---|---|---|
| cAMP-dependent Protein Kinase (PKA, cAPK) | R-X-S/T$^c$<br>R-R/K-X-S/T | Y$_7$LRRASLAQLT<br>(SEQ ID NO. 636)<br>F$_1$RRLSIST<br>(SEQ ID NO. 637)<br>A$_{29}$GARRKASGPP<br>(SEQ ID NO. 638) | pyruvate kinase (2)<br>phosphorylase kinase, a chain (2)<br>histone H1, bovine (2) |
| Casein Kinase I (CK1, CK-1) | S(P)-X-X-S/T | R$_4$TLS(P)VSSLPGL<br>(SEQ ID NO. 639)<br>D$_{43}$IGS(p)ES(p)TEDQ<br>(SEQ ID NO. 640) | glycogen synthase, rabbit muscle (4)<br>a$_{s1}$-casein (4) |
| Casein Kinase II (CKII, CK-2) | S/T-X-X-E | A$_{72}$DSESEDEED<br>(SEQ ID NO. 641)<br>L$_{37}$ESEEEGVPST<br>(SEQ ID NO. 642)<br>E$_{26}$DNSEDEISNL<br>(SEQ ID NO. 643) | PKA regulatory subunit, R$_{11}$ (2)<br>p34$^{cdc2}$, human (5)<br>acetyl-CoA carboxylase (2) |
| Glycogen Synthase Kinase 3 (GSK-3) | S-X-X-X-S(p) | S$_{641}$VPPSPSLS(p)<br>(SEQ ID NO. 644)<br>S$_{641}$VPPS(p)PSLS(p)<br>(SEQ ID NO. 645) | glycogen synthase, human (site 3b) (6, 2)<br>glycogen synthase, human (site 3a) (6, 2) |
| Cdc2 Protein Kinase | S/T-P-X-R/K$^c$ | P$_{13}$AKTPVK<br>(SEQ ID NO. 646)<br>H$_{122}$STPPKKKRK<br>(SEQ ID NO. 647) | histone H1, calf thymus (2)<br>large T antigen (2) |
| Calmodulin-dependent Protein Kinase II (CaMK | R-X-X-S/T<br>R-X-X-S/T-V | N$_2$YLRRRLSDSN<br>(SEQ ID NO. 648)<br>K$_{191}$MARVFSVLR | synapsin (site 1) (2)<br>calcineurin (2) |

-continued

| Protein Kinase | Recognition Motifs[a] | Phosphorylation Sites[b] | Protein Substrate (reference) |
|---|---|---|---|
| II) | | (SEQ ID NO. 649) | |
| Mitogen-activated Protein Kinase (Extracellular Signal-regulated Kinase)(MAPK, Erk) | P-X-S/T-P[d] X-X-S/T-P | P$_{244}$LSP (SEQ ID NO. 650) P$_{92}$SSP (SEQ ID NO. 651) V$_{420}$LSP (SEQ ID NO. 652) | c-Jun (7) cyclin B (7) Elk-1 (7) |
| cGMP-dependent Protein Kinase (cGPK) | R/K-X-S/T R/K-X-X-S/T | G$_{26}$KKRKRSRKES (SEQ ID NO. 653) F$_1$RRLSIST (SEQ ID NO. 654) | histone H2B (2) phosphorylase kinase (a chain)(2) |
| Phosphorylase Kinase (PhK) | K/R-X-X-S-V/I | D$_6$QEKRKQISVRG (SEQ ID NO. 655) P$_1$LSRTLSVSS (SEQ ID NO. 656) | phosphorylase (2) glycogen synthase (site 2) (2) |
| Protein Kinase C (PKC) | S/T-X-K/R K/R-X-X-S/T K/R-X-S/T | H$_{594}$EGTHSTKR (SEQ ID NO. 657) P$_1$LSRTLSVSS (SEQ ID NO. 658) Q$_4$KRPSQRSKYL (SEQ ID NO. 659) | fibrinogen (2) glycogen synthase (site 2)(2) myelin basic protein (2) |
| Abl Tyrosine Kinase | I/V/L-Y-X-X-P/F[e] | | |
| Epidermal Growth Factor Receptor Kinase (EGF-RK) | E/D-Y-X E/D-Y-I/L/V | R$_{1168}$ENAEYLRVAP (SEQ ID NO. 660) A$_{767}$EPDYGALYE (SEQ ID NO. 661) | autophosphorylation (2) phospholipase C-g(2) |

Single-letter Amino Acid Code:
[a]Recognition motifs are taken from Pearson and Kemp (supra) except where noted. Consult Pearson and Kemp for a comprehensive list of phosphorylation site sequences and specificity motifs.
[b]Subscripted numbers refer to the position of the first residue within the given polypeptide chain.
[c]From (1).
[d]From (7).
[e]From (8). See refs (8) and (9) for discussion of substrate recognition by Abl.
A = alanine, C = cysteine, D = aspartic acid, E = glutamic acid, F = phenylalanine, G = glycine, H = histidine, I = isoleucine, K = lysine, L = leucine, M = methionine, N = asparagine, P = proline, Q = glutamine, R = arginine, S = serine, T = threonine, W = tryptophan, V = valine, V = tyrosine, X = any amino acid References Used in the Table Above:
1. Kennelly, P. J., and Krebs, E. G. (1991) J. Biol. Chem. 266, 15555-15558.
2. Pearson, R. B., and Kemp, B. E. (1991). In T. Hunter and B. M. Sefton (Eds.), Methods in Enzymology Vol. 200, (pp. 62-81). San Diego: Academic Press.
3. Roach, P. J. (1991) J. Biol. Chem. 266, 14139-14142.
4. Flotow, H. et al. (1990) J. Biol. Chem. 265, 14264-14269.
5. Russo, G. L. et al. (1992) J. Biol. Chem. 267, 20317-20325.
6. Fiol, C. J. et al. (1990) J. Biol. Chem. 265, 6061-6065.
7. Davis, R. J. (1993) J. Biol. Chem. 268, 14553-14556.
8. Songyang, Z. et al. (1995) Nature 373, 536-539.
9. Geahlen, R. L. and Harrison, M. L. (1990). In B. E. Kemp (Ed.), Peptides and Protein Phosphorylation, (pp. 239-253). Boca Raton: CRC Press.

However, since the determinants of protein kinase specificity involve complex 3-dimensional interactions, these motifs, short amino-acid sequences describing the primary structure around the phosphoacceptor residue, are a significant oversimplification of the issue. They do not take into account possible secondary and tertiary structural elements, or determinants from other polypeptide chains or from distant locations within the same chain. Furthermore, not all of the residues described in a particular specificity motif may carry the same weight in determining recognition and phosphorylation by the kinase. In addition, the potential recognition sequence maybe buried deep inside a tertiary structure of within a protein complex under physiological conditions and thus may never be accessible in vivo. As a consequence, they should be used with some caution. The instant invention provides a fast and convenient way to determine, on a proteome-wide basis, the identity of all potential kinase substrates that actually do become phopshorylated by the kinase of interest in vivo (or in vitro).

Figure 10:
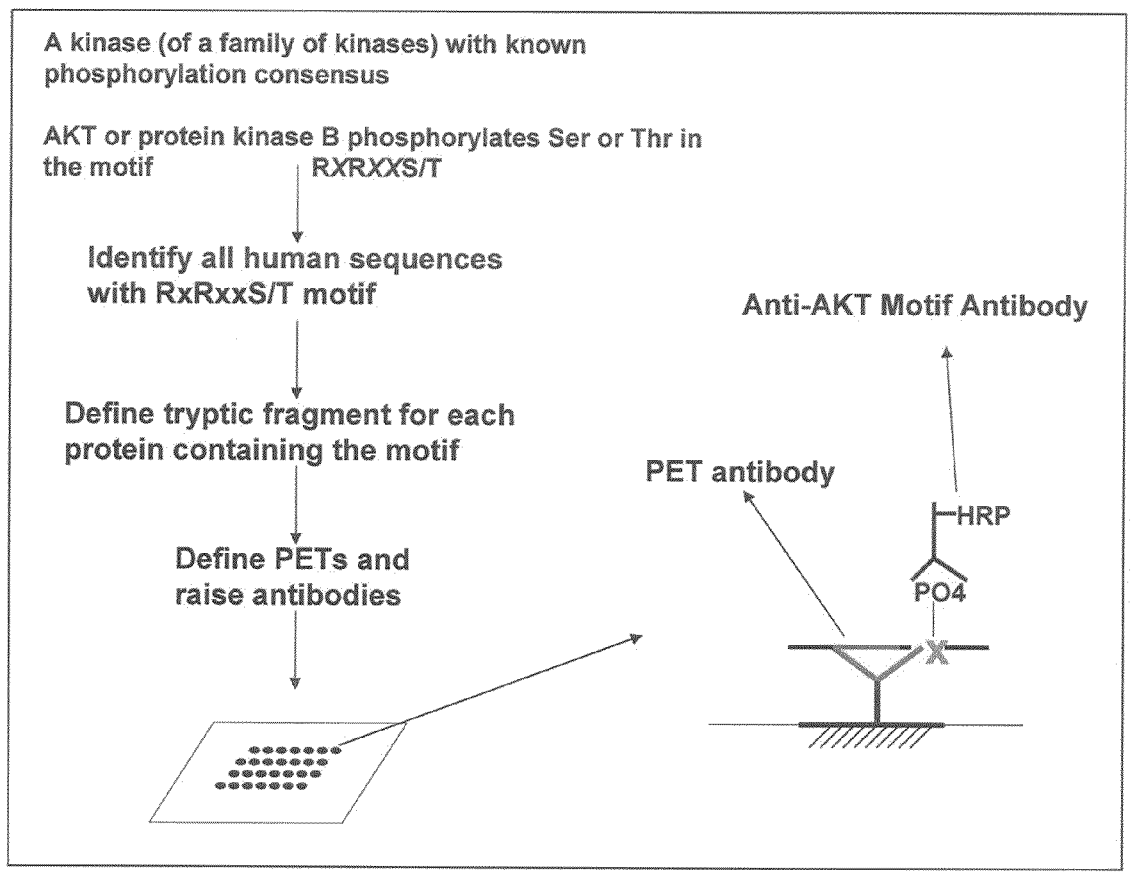
FIG. 10 depicts PET-based array for (AKT) kinase substrate identification.

Specifically, consensus recognition sequences of a kinase (or a kinase subfamily sharing substrate specificity) can be identified based on, for example, Pearson and Kemp or other kinase substrate motif database. For example, AKT (or PKB) kinase has a consensus phosphorylation site sequence of RXRXXS/T. All proteins in an organism (e.g., human) that contains this potential recognition sequence can be readily identified through routine sequence searches. Using the method of the instant invention, peptide fragments of these potential substrates, after a pre-determined treatment (such as trypsin digestion), which contain both the recognition motif and at least one PET can then be generated. Antibodies (or other capture agents) against each of these identified PETs can be raised and printed on an array to generate a so-called "kinase chip," in this case, an AKT chip. Using this chip, any sample to be studied can be treated as described above and then be incubated with the chip so that all potential recognition site-containing fragments are captured. The presence or absence of phosphorylation on any given "spot"—a specific potential substrate—can be detected/quantitated by, for example, labeled secondary antibodies (see FIG. 10). Thus, the identity of all AKT substrates in this organism under this condition may be identified in one experiment. The array can be reused for other samples by eluting the bound peptides on the array. Different arrays can be used in combination, preferably in the same experiment, to determine the substrates for multiple kinases.

The reversible phosphorylation of tyrosine residues is an important mechanism for modulating biological processes such as cellular signaling, differentiation, and growth, and if deregulated, can result in various types of cancer. Therefore, an understanding of these dynamic cellular processes at the molecular level requires the ability to assess changes in the sites of tyrosine phosphorylation across numerous proteins simultaneously as well as over time. Thus in another embodiment, the instant invention provides a method to identify the various signal transduction pathways activated after a specific treatment to a sample, such as before and after a specific growth factor or cytokine treatment to a sample cell. The same method can also be used to compare the status of signal transduction pathways in a diseased sample from a patient and a normal sample from the same patient.

Know ledges about the various signal transduction pathways existing in various organisms are accumulating at an astonishing pace. Science magazine's STKE (Signal Transduction Knowledge Environment) maintains a comprehensive and expanding list of known signal transduction pathways, their important components, relationship between the components (inhibit, stimulation, etc.), and cross-talk between key members of the different pathways. The "Connections Map" provides a dynamic graphical interface into a cellular signaling database, which currently covers at least the following broad pathways: immune pathways (IL-4, IL-13, Token-like receptor); seven-transmembrane receptor pathways (Adrenergic, PACl receptor, Dictyostelium discoideum cAMP Chemotaxis, Wnt/$Ca^{2+}$/cyclic GMP, G Protein-Independent 7 Transmembrane Receptor); Circadian Rhythm pathway (murine and *Drosophila*); Insulin pathway; FAS pathway; TNF pathway; G-Protein Coupled Receptor pathways; Integrin pathways; Mitogen-Activated Protein Kinase Pathways (MAPK, JNK, p38); Estrogen Receptor Pathway; Phosphoinositide 3-Kinase Pathway; Transforming Growth Factor-β (TGF-β) Pathway; B Cell Antigen Receptor Pathway; Jak-STAT Pathway; STAT3 Pathway; T Cell Signal Transduction Pathway; Type 1 Interferon (α/β) Pathway; Jasmonate Biochemical Pathway; and Jasmonate Signaling Pathway. Many other well-known signal transduction pathways not yet included are described in detail in other scientific literatures which can be readily identified in PubMed or other common search tools. Activation of most, if not all of these signal transduction pathways are generally characterized by changes in phosphorylation levels of one or more members of each pathway.

Thus in a general sense, the status of any given number of signaling pathways in a sample can be determined by taking a "snap shot" of the phosphorylation status of one or more key members of these selected pathways. For example, the Mitogen-activated protein (MAP) 1 kinase pathways are evolutionarily conserved in eukaryotic cells. The pathways are essential for physiological processes, such as embryonic development and immune response, and regulate cell survival, apoptosis, proliferation, differentiation, and migration. In mammals, three major classes of MAP kinases (MAPKs) have been identified, which differ in their substrate specificity and regulation. These subgroups compose the extracellular signal-regulated kinases (ERKs), the c-Jun N-terminal kinases (JNKs), and the p38/RK/CSBP kinases. ERKs are activated by a range of stimuli including growth factors, cell adhesion, tumor-promoting phorbol esters, and oncogenes, whereas JNK and p38 are preferentially activated by proinflammatory cytokines, and a variety of environmental stresses such as UV and osmotic stress. For this reason, the latter are classified as stress-activated protein kinases. Activation of the MAPKs is achieved by dual phosphorylation on threonine and tyrosine residues within a Thr-Xaa-Tyr motif located in the kinase subdomain VIII. This phosphorylation is mediated by a dual specificity protein kinase, MAPK kinase (MAPKK), and MAPKK is in turn activated by phosphorylation mediated by a serine/threonine protein kinase, MAPKK kinase. In addition to these activating kinases, several types of protein phosphatases have been also shown to control MAPK pathways by dephosphorylating the MAPKs or their upstream kinases. These protein phosphatases include tyrosine-specific phosphatases, serine/threonine-specific phosphatases, and dual specificity phosphatases (DSPs). Therefore, the activities of MAPKs can be regulated by upstream activating kinases and protein phosphatases, and the activation status can be determined by the phosphorylation status of, for example, ERK1/2, JNK, and p38.

Specifically, fragments of ERK1/2, JNK, and p38 containing the signature phosphorylation sites and PETs can be identified using the methods of the instant invention. Capture agents specifically recognizing such phosphorylation site-associated PETs can then be raised and immobilized on an array/chip. A sample (treated or untreated, thus containing high or low levels of phosphorylation of these pathway markers) can be digested and incubated with the chip, so as to determine the presence/absence of activation, and degree, time course, duration of activation, etc.

In the same principal, many other related or perceived unrelated pathways may be manufactured on the same chip, since each pathway may be represented by from just one, to possibly all of the known pathway components. This type of chip may provide a comprehensive view of the various pathways that may be activated after a drug treatment. Pathway specific chips may also be used in conjunction to further determine the status of individual components within a pathway of interest.

Because of the important functions of the kinases in virtually all kinds of signal transduction pathways, it is not surprising to see that many drugs directly or indirectly affects phosphorylation status of various kinase substrates. Thus this type of array may also be used in drug target identification. Briefly, samples treated by different drug candidates may be incubated with the same kind of array to generate a series of activation profiles of certain chosen targets. These profiles may be compared, preferably automatically, to determine which drug candidate has the same or similar activation profile as that of the lead molecule.

This type of experiment will also yield useful information concerning the selectivity of candidate drugs, since it can be easily determined whether a candidate drug or drug analog actually have differential effects on various pathways, and if so, whether the difference is significant.

The same type of experiments can also be adapted to screen for drug candidates that lacks undesired side effects or toxicity.

One aspect of this type of application relates to the selection of specific protease(s) for fragmentation. The following table presents data resulting from analysis of protease sensitivity of potential phosphorylation sites in the human "kinome" (all kinases). This table may aid the selection of proteases among the several most frequently used proteases.

| Enzymes | Total Peptide Fragments | Peptide Fragments with S/T/Y | |
|---|---|---|---|
| | | =<10 aa | >10 aa |
| Chymotrypsin | 34,094 | 10930 (43%) | 14985 (57%) |
| S.A. V-8 E specific Enzyme | 34,233 | 6753 (32%) | 14917 (68%) |
| Post-Proline Cleaving Enzyme | 29,715 | 7077 (37%) | 12224 (63%) |
| Trypsin | 54,260 | 15,217 (53%) | 13311 (47%) |

(ii) Glycosylation

A wide variety of eukaryotic membrane-bound and secreted proteins are glycosylated, that is they contain covalently-bound carbohydrate, and therefore are termed glycoproteins. In addition, certain intracellular eukaryotic proteins are also glycoproteins. Glycosylation of polypeptides in eukaryotes occurs principally in three ways (Parekh et al., *Trends Biotechnol.* 7: 117, 1989). Glycosylation through a glycosidic bond to an asparagine side-chain is known as N-glycosylation. Such asparagine residues only occur in the amino acid triplet sequence of Asn-Xaa-Ser/Thr, where Xaa can be any amino acid. The carbohydrate portion of a glycoprotein is also known as a glycan. O-glycans are linked to serine or threonine side-chains, through O-glycosidic bonds. In human, 284,535 octamer tags contains this NX(S/T) sequence, and 228,256 octamer PETs contains the NX(S/T) sequence. The latter is about 2.6% of the total octamer peptide tags in human. The N- and O-linked glycosylation are two of the most complex post-translational modifications. The polypeptide may also be linked to a phosphatidylinositol lipid anchor through a carbohydrate "bridge", the whole assembly being known as the glycosyl-phosphatidylinositol (GPI) anchor.

In recent years, the functional significance of the carbohydrate moieties has been increasingly appreciated (Rademacher et al., *Ann. Rev. Biochem.* 57: 785, 1988). Carbohydrates covalently attached to polypeptide chains can confer many functions to the glycoprotein, for example resistance to proteolytic degradation, the transduction of information between cells, and intercellular adhesion through ligand-receptor interactions (Gesundheit et al., *J. Biol. Chem.* 262: 5197, 1987; Ashwell & Harford, *Ann. Rev. Biochem.* 51: 531, 1982; Podskalny et al., *J. Biol. Chem.* 261: 14076, 1986; Dennis et al., *Science* 236: 582, 1987). As glycoforms are the product of a series of biochemical modifications, perturbations within a cell can have profound effects on their structure. With the increase in understanding of carbohydrate functions, the need for rapid, reliable and sensitive methods for carbohydrate detection and analysis has grown considerably.

Lectins are proteins that interact specifically and reversibly with certain sugar residues. Their specificity enables binding to polysaccharides and glycoproteins (even agglutination of erythrocytes and tumor cells). The binding reaction between a lectin and a specific sugar residue is analogous to the interaction between an antibody and an antigen. Substances bound to lectin may be resolved with a competitive binding substance or an ionic strength gradient. In addition, among other procedures, lectins can be labeled with biotin or digoxigenin, and subsequently detected by avidin-conjugated peroxidase or anti-digoxigenin antibodies coupled with alkaline phosphatase, respectively (Carlsson S R: *Isolation and characterization of glycoproteins*. In: *Glycobiology. A Practical Approach*. Fukuda M and Kobata A (eds). Oxford University Press, Oxford, pp 1-25, 1993, incorporated herein by reference).

For example, Concanavalin A (Con A) binds molecules that contain α-D-mannose, α-D-glucose and sterically related residues with available C-3, C-4, or C-5 hydroxyl groups. Like Con A, lentil lectin binds α-D-mannose, α-D-glucose, and sterically related residues, but lentil lectin distinguishes less sharply between glucosyl and mannosyl residues and binds simple sugars with lower affinity. Agarose wheat germ lectin specifically binds to N-acetyl-β-glucosaminyl residues. Wheat germ lectin specifically binds to N-acetyl-β-D-glucosaminyl residues. Psathyrella velutina lectin (PVL) preferentially interacts with the N-acetylglucosamine beta 1→2 Man group. All these lectins can be used to detect the presence of various kinds of glycosylated peptides fragments after these PET-associated glycosylated peptide fragments are captured from the sample by capture agents.

The GlycoTrack Kit from Glyko, Inc. (a Prozyme company, San Leandro, Calif.) detect glycosylation by using a specific carbohydrate oxidation reaction prior to binding of a high amplification color generating reagent. Briefly, a sample, either in solution or already immobilized to a support, is oxidized with periodate. This generates aldehyde groups that can react spontaneously with certain hydrazides at room temperature in aqueous conditions. Use of biotin-hydrazide following periodate oxidation leads to the incorporation of biotin into the carbohydrate (9). The biotinylated compound is detected by reaction with a streptavidin-alkaline phosphatase conjugate. Subsequently visualization is achieved using a substrate that reacts with the alkaline phosphatase bound to glycoproteins on the membrane, forming a colored precipitate.

Molecular Probes (Eugene, Oreg.) offer a proprietary Pro-Q Emerald 300 fluorescent glycoprotein stain for detection of glycoproteins. The new Pro-Q Emerald 300 fluorescent glycoprotein stain reacts with periodate-oxidized carbohydrate groups, creating a bright green-fluorescent signal on glycoproteins. Depending upon the nature and the degree of glycosylation, this stain may be 50-fold more sensitive than the standard periodic acid—Schiff base method using acidic fuchsin dye. According to the manufacture, detection using the Pro-Q Emerald 300 glycoprotein stain is much easier than detection of glycoproteins using biotin hydrazide with streptavidin-horseradish peroxidase and ECL detection (Amersham Pharmacia Biotech). The stain can detect 50 ng of a typical glycosylated protein. Since the captured glycosylated PET-containing peptide fragments are much smaller than a typocal peptide, as little as low nanogram to high picograms of captured peptides can be detected using this dye.

Thus to detect the presence and quantitation of glycosylation in a sample, all proteins or a subpopulation thereof which contains the potential glycosylation site NXS/T may be identified, and peptide fragments resulting from a specific predetermined treatment may be analyzed to identify associated PETs. Capture agents against these PETs can then be raised. In a method analogous to the phosphorylation detection as described above, glycosylation can be detected/quantitated using the various detection methods (iii) Other Post-translational Modifications Capture agents, such as antibodies specific for other post-translationally modified residues are also readily available.

There are at least 46 anti-ubiquitin commercial antibodies available from 14 different vendors. For example, Cell Signaling Technology (Beverly, Mass.) offers mouse anti-Ubiquitin monoclonal antibody, clone P4D1 (IgG1 isotype, Cat. No. 3936), which is specific for all species of ubiquitin, polyubiquitin, and ubiquitinated peptides.

Anti-acetylated amino acid antibodies have also been commercialized. See anti-acetylated-histon H3 and H4 antibodies (Catalog #06-599 and Catalog #06-598) from Upstate Biotechnology (Lake Placid, N.Y.). In fact, Alpha Diagnostic International, Inc. (San Antonio, Tex.) offers custom synthesis of anti-acetylated amino acid antibodies.

Arginine methylation, a protein modification discovered almost 30 years ago, has recently experienced a renewed interest as several new arginine methyltransferases have been identified and numerous proteins were found to be regulated by methylation on arginine residues. Mowen and David published detailed protocols on Science's STKE (www.stke.org/cgi/content/full/OC_sigtrans;2001/93/p11) that provide guidelines for the straightforward identification of arginine-methylated proteins, made possible by the availability of novel, commercially available reagents. Specifically, two anti-methylated arginine antibodies are described: mouse monoclonal antibody to methylarginine, clone 7E6 (IgG1) (Abcam, Cambridge, UK) (Data sheet: www.abcam.com/public/ab_detail.cfm?intAbID=412, which reacts with mono- and asymmetric dimethylated arginine residues; and mouse monoclonal antibody to methylarginine, clone 21C7 (IgM) (Abcam) (Data sheet: www.abcam.com/public/ab_detail.cfm?intAbID=413), which reacts with asymmetric dimethylated arginine residues. Detailed protocols for in vitro and in vivo analysis of arginine methylation are provided. See Mowen et al., *Cell* 104: 731-741, 2001.

Even if there is no reported antibodies at present for certain specific modifications, it is well within the capability of a skilled artisan to raise antibodies against that specific type of modified residues. There is no compelling reason to believe that such antibodies cannot be obtained, especially in view of the prior success in raising antibodies against relatively small groups such as phosphorylated amino acids. The anti-post-translational modification antibody should be checked against the same antigen that is un-modified to verify that the reactivity is depending upon the presence of the post-translational modification.

G. Immunohistochemistry (IHC)

Immunohistochemical analysis of tumor tissues/biopsy has traditionally played an important role in diagnosis, monitoring, and prognosis analysis of cancer. IHC is typically performed on disease tissue sections using antibodies (monoclonal or polyclonal) to specific disease markers. However, two major problems have hampered this useful procedure, such that it is frequently difficult to get reproducible, quantitative data. One problem is associated with the poor quality of antibodies used in the assay. Many antibodies lack specificity to a target biomarker, and tend to cross-react with other proteins not associated with disease status, resulting in high background. The other complication is that antibody may have difficulties accessing unknown epitopes after tissue/cell fixation.

For example, Press et al. (*Cancer Res.* 54(10): 2771-7, 1994) compared immunohistochemical staining results obtained with 7 polyclonal and 21 monoclonal antibodies in sections from paraffin-embedded blocks of breast cancer samples. It was found that the ability of these antibodies to detect the HER2/neu antigen overexpression was extremely variable, providing an important explanation for the variable overexpression rate reported in the literature.

The other problem is associated with sample processing before IHC. Generally, the efficiency of antigen retrieval is unpredictable in the concurrent protocol. It is also reported that heating coupled with enzyme digestion tends to give better results. But since epitopes for antibodies are not known, heating/digestion may cause different degree of problems for antibody recognition.

Therefore, PET-derived antibodies represent a unique solution as standardized reagents for IHC. In certain preferred embodiments, PETs present on the surface of the target protein will be chosen for easy accessibility by the PET-specific antibodies. The chemistry of cell fixation may also be taken into account to select optimum amino acid sequences of PETs. For example, if certain residues are known to form cross-links after fixation, these residues will be selected against in PET selection. Similarly, epitopes that overlap with enzyme recognition sites will not be chosen. These measures will help to achieve consistent, reproducible results and high rate of success in IHC experiments.

VII. Use of Multiple PETs in Highly Accurate Functional Measurement of Proteins

In certain embodiments of the invention, it may be advantageous to produce two or more PETs for each protein of interest. For example, trypsin digestion (or any other protease treatment or chemical fragmentation methods described above) may be incomplete or biased for/against certain fragments. Similarly, recovery of fragmented polypeptides by PET-specific capture agents may occasionally be incomplete and/or biased. Therefore, there may be certain risks associated with using one specific PET-specific capture agent for measurement of a target polypeptide.

To overcome this potential problem, or at least to compensate for the above-described incomplete digestion/recovery problems, two or more PETs specific to the polypeptide of interest may be generated, and used on the same array of the instant invention, or used in the same set of competition assays to independently detect different PETs of the same polypeptide. The average measurement results obtained by using such redundant PET-specific capture agents should be much more accurate and reliable when compared to results obtained using single PET-specific capture agents.

On the other hand, certain proteins may have different forms within the same biological sample. For example, proteins may be post-translationally modified on one or more specific positions. There are more than 100 different kinds of post-translational modifications, with the most common ones being acetylation, amidation, deamidation, prenylation, formylation, glycosylation, hydroxylation, methylation, myristoylation, phosphorylation, ubiquitination, ribosylation and sulphation. For a specific type of modification, such as phosphorylation, a PET peptide phosphorylated at a site may not be recognized by a capture agent raised against the same but unphosphorylated PET peptide. Therefore, by comparing the result of a first capture agent specific for un-modified PET peptide of a target protein (which represents unmodified target protein), with the result of a second capture agent specific for another PET within the same target protein (which does not contain any phosphorylation sites and thus representing the total amount of the target protein), one can determine the percentage of phosphorylated target protein within said sample.

The same principle applies to all target proteins with different forms, including unprocessed/pre-form and processed/ mature form in certain growth factors, cytokines, and proteases; alternative splicing forms; and all types of post-translational modifications.

In certain embodiments, capture agents specific for different PETs of the same target protein need not be of the same category (e.g., one could be an antibody specific for PET1, the other could be non-antibody binding protein for PET2, etc.)

In other embodiments, the presence or absence of one or more PETs is indicative of certain functional states of the target protein. For example, some PETs may be only present in unprocessed forms of certain proteins (such as peptide hormones, growth factors, cytokines, etc.), but not present in the corresponding mature/processed forms of the same proteins. This usually arises from the situation where the processing site resides within the PETs. On the other hand, other PETs might be common to both precessed and unprocessed forms (e.g., do not contain any processing sites). If both types of PETs are used in the same array, or in the same competition assay, the abundance and ratio of processed/unprocessed target protein can be assessed.

In other embodiments, due to the vastly improved overall accuracy of the measurement using multiple PET-specific capture agents, the invention is applicable to the detection of certain previously unsuitable biomarkers because they have low detectable level (such as 1-5 pM) which is easily obscured by background signals. For example, as described above, Punglia et al. (*N. Engl. J. Med.* 349(4): 335-42, July, 2003) indicated that, in the standard PSA-based screening for prostate cancer, if the threshold PSA value for undergoing biopsy were set at 4.1 ng per milliliter, 82 percent of cancers in younger men and 65 percent of cancers in older men would be missed. Thus a lower threshold level of PSA for recommending prostate biopsy, particularly in younger men, may improve the clinical value of the PSA test. However, at lower detection limits, background can become a significant issue. The sensitivity/selectivity of the multiple PET-specific capture agent assay can be used to reliably and accurately detect low levels of PSA.

Similarly, due to the increased accuracy of measurements, small changes in concentration are more easily and reliably detected. Thus, the same method can also be used for other proteins previously unrecognized as disease biomarkers, by monitoring very small changes of protein levels very accurately. "Small changes" refers to a change in concentration of no more than about 50%, 40%, 30%, 20%, 15%, 10%, 5%, 1% or less when comparing a disease sample with a normal/control sample.

Accuracy of a measurement is usually defined by the degree of variation among individual measurements when compared to the true value, which can be reasonably accurately represented by the mean value of multiple independent measurements. The more accurate a method is, the closer a random measurement will be as compared to the mean value. A x % accuracy measurement means that x % of the measurements will be within one standardized deviation of the mean value. The method of the invention is usually at least about 70% accurate, preferably 80%, 90% or more accurate.

Detection of the presence and amount of the captured PET-containing polypeptide fragments can be effectuated using any of the methods described above that are generally applicable for detecting/quantitating the binding event.

To reiterate, for example, for each primary capture agent on an array, a specific, detectable secondary capture agent might be generated to bind the PET-containing peptide to be captured by the primary capture agent. The secondary capture agent may be specific for a second PET sequence on the to be captured polypeptide analyte, or may be specific for a post-translational modification (such as phosphorylation) present on the to-be-captured polypeptide analyte. To facilitate detection/quantitation, the secondary capture agent may be labeled by a detectable moiety selected from: an enzyme, a fluorescent label, a stainable dye, a chemiluminescent compound, a colloidal particle, a radioactive isotope, a near-infrared dye, a DNA dendrimer, a water-soluble quantum dot, a latex bead, a selenium particle, or a europium nanoparticle.

Alternatively, the captured PET-containing polypeptide analytes may be detected directly using mass spectrometry, colorimetric resonant reflection using a SWS or SRVD biosensor, surface plasmon resonance (SPR), interferometry, gravimetry, ellipsometry, an evanescent wave device, resonance light scattering, reflectometry, a fluorescent polymer superquenching-based bioassay, or arrays of nanosensors comprising nanowires or nanotubes.

Another aspect of the invention provides arrays comprising redundant capture agents specific for one or more target proteins within a sample. Such arrays are useful to carry out the methods described above (e.g. high accuracy functional measurement of the target proteins). In one embodiment, several different capture agents are arrayed to detect different PET-containing peptide fragment derived from the same target protein. In other embodiments, the array may be used to detect several different target proteins, at least some (but may be not all) of which may be detected more than once by using capture agents specific for different PETs of those target proteins.

Another aspect of the invention provides a composition comprising a plurality of capture agents, wherein each of said capture agents recognizes and interacts with one PET of a target protein. The composition can be used in an array format in an array device as described above.

VIII. Other Aspects of the Invention

In another aspect, the invention provides compositions comprising a plurality of isolated unique recognition sequences, wherein the unique recognition sequences are derived from at least 50%, 55%, 60%, 65%, 70%, 75%, 80%, 85%, 90% 95% or 100% of an organism's proteome. In one embodiment, each of the unique recognition sequences is derived from a different protein.

The present invention further provides methods for identifying and/or detecting a specific organism based on the organism's Proteome Epitope Tag. The methods include contacting a sample containing an organism of interest (e.g., a sample that has been fragmented using the methods described herein to generate a collection of peptides) with a collection of unique recognition sequences that characterize, and/or that are unique to, the proteome of the organism. In one embodiment, the collection of unique recognition sequences that comprise the Proteome Epitope Tag are immobilized on an array. These methods can be used to, for example, distinguish a specific bacterium or virus from a pool of other bacteria or viruses.

The unique recognition sequences of the present invention may also be used in a protein detection assay in which the unique recognition sequences are coupled to a plurality of capture agents that are attached to a support. The support is contacted with a sample of interest and, in the situation where the sample contains a protein that is recognized by one of the capture agents, the unique recognition sequence will be displaced from being bound to the capture agent. The unique recognition sequences may be labeled, e.g., fluorescently labeled, such that loss of signal from the support would indicate that the unique recognition sequence was displaced and that the sample contains a protein is recognized by one or more of the capture agents.

The PETs of the present invention may also be used in therapeutic applications, e.g., to prevent or treat a disease in a subject. Specifically, the PETs may be used as vaccines to elicit a desired immune response in a subject, such as an immune response against a tumor cell, an infectious agent or a parasitic agent. In this embodiment of the invention, a PET is selected that is unique to or is over-represented in, for example, a tissue of interest, an infectious agent of interest or a parasitic agent of interest. A PET is administered to a subject using art known techniques, such as those described in, for example, U.S. Pat. No. 5,925,362 and international publication Nos. WO 91/11465 and WO 95/24924, the contents of each of which are incorporated herein by reference. Briefly, the PET may be administered to a subject in a formulation designed to enhance the immune response. Suitable formulations include, but are not limited to, liposomes with or without additional adjuvants and/or cloning DNA encoding the PET into a viral or bacterial vector. The formulations, e.g., liposomal formulations, incorporating the PET may also include immune system adjuvants, including one or more of lipopolysaccharide (LPS), lipid A, muramyl dipeptide (MDP), glucan or certain cytokines, including interleukins, interferons, and colony stimulating factors, such as IL1, IL2, gamma interferon, and GM-CSF.

EXAMPLES

This invention is further illustrated by the following examples which should not be construed as limiting. The contents of all references, patents and published patent applications cited throughout this application, as well as the Figures are hereby incorporated by reference.

Example 1

Identification of Unique Recognition Sequences within the Human Proteome

As any one of the total 20 amino acids could be at one specific position of a peptide, the total possible combination for a tetramer (a peptide containing 4 amino acid residues) is $20^4$; the total possible combination for a pentamer (a peptide containing 5 amino acid residues) is $20^5$ and the total possible combination for a hexamer (a peptide containing 6 amino acid residues) is $20^6$. In order to identify unique recognition sequences within the human proteome, each possible tetramer, pentamer or hexamer was searched against the human proteome (total number: 9,076; Source of human proteome: EBI Ensembl project release v 4.28.1 on Mar. 12, 2002, http://www.ensembl.org/Homo_sapiens/).

The results of this analysis, set forth below, indicate that using a pentamer as a unique recognition sequence, 80.6% (23,446 sequences) of the human proteome have their own unique recognition sequence(s). Using a hexamer as a unique recognition sequence, 89.7% of the human proteome have their own unique recognition sequence(s). In contrast, when a tetramer is used as a unique recognition sequence, only 2.4% of the human proteome have their own unique recognition sequence(s).

Results and Data 2.1. Tetramer Analysis:
2.1.1. Sequence Space:

| | | |
|---|---|---|
| Total number of human protein sequences | 29,076 | 100% |
| *Number of sequences with 1 or more unique tetramer tag | 684 | 2.4% |
| Number of sequences with 0 unique tetramer tag | 28,392 | 97.6% |

*For these 684 sequences, average Tag/sequence: 1.1.

2.1.2. Tag Space:

| | | |
|---|---|---|
| Total number of tetramers | $20^4$ = 160,000 | 100% |
| Tetramers found in 0 sequence | 393 | 0.2% |
| #Tetramers found in 1 sequence only | 745 | 0.5% |
| Tetramers found in more than 1 sequences | 158,862 | 99.3% |

These are signature tetra-peptides 2.2. Pentamer Analysis:
2.2.1. Sequence Space:

| | | |
|---|---|---|
| Total number of human protein sequences | 29,076 | 100% |
| *Number of sequences with 1 or more unique pentamer tag | 23,446 | 80.6% |
| Number of sequences with 0 unique pentamer tag | 5,630 | 19.4% |

*For these 23,446 sequences, Average Tag/sequence: 23.9

2.2.2. Tag Space:

| | | |
|---|---|---|
| Total number of pentamers | $20^5$ = 3,200,000 | 100% |
| Pentamers found in 0 sequence | 955,007 | 29.8% |
| #Pentamers found in 1 sequence only | 560,309 | 17.5% |
| Pentamers found in more than 1 sequences | 1,684,684 | 52.6% |

These are signature penta-peptides 2.3. Hexamer Analysis:
2.3.1. Sequence Space:

| | | |
|---|---|---|
| Total number of human protein sequences | 29,076 | 100% |
| *Number of sequences with 1 or more unique hexamer tag | 26,069 | 89.7% |
| Number of sequences with 0 unique hexamer tag | 3,007 | 10.3% |

*For these 26069 sequences, Average Tag/sequence: 177

2.3.2. Tag Space:

| | | |
|---|---|---|
| Total number of hexamers | $20^6$ = 64,000,000 | 100% |
| hexamers found in 0 sequence | 57,040,296 | 89.1% |
| #hexamers found in 1 sequence only | 4,609,172 | 7.2% |
| hexamers found in more than 1 sequences | 2,350,532 | 3.7% |

These are signature hexa-peptides.

Similar analysis in the human proteome was done for PET sequences of 7-10 amino acids in length, and the results are combinedly summarized in the table below:

| PET Length (Amino Acids) | Tagged Sequences (Number) | Tagged Sequences (% of total - 29076) | Average PET (Number/Tagged Protein) |
|---|---|---|---|
| 4 | 684 | 2.35% | 3 |
| 5 | 23,446 | 80.64% | 24 |
| 6 | 26,069 | 89.66% | 177 |
| 7 | 26,184 | 90.05% | 254 |
| 8 | 26,216 | 90.16% | 268 |
| 9 | 26,238 | 90.24% | 272 |
| 10 | 26,250 | 90.28% | 275 |

Example 2

Identification of Unique Recognition Sequences (or PET) within all Bacterial Proteomes In order to identify pentamer PETs that can be used to, for example, distinguish a specific bacterium from a pool of all other bacteria, each possible pentamer was searched against the NCBI database (http://www.ncbi.nlm.nih.gov/PMGifs/Genomes/eub_g.html, updated as of Apr. 10, 2002). The results from this analysis are set forth below.

Results and Data:

| Number of unique pentamers | Database ID (NCBI RefSeq ID) | Species Name |
|---|---|---|
| 6 | NC_000922 | Chlamydophila pneumoniae CWL029 |
| 37 | NC_002745 | Staphylococcus aureus N315 chromosome |
| 40 | NC_001733 | Methanococcus jannaschii small extra-chromosomal element |
| 58 | NC_002491 | Chlamydophila pneumoniae J138 |
| 84 | NC_002179 | Chlamydophila pneumoniae AR39 |
| 135 | NC_000909 | Methanococcus jannaschii |
| 206 | NC_003305 | Agrobacterium tumefaciens str. C58 (U. Washington) linear chromosome |
| 298 | NC_002758 | Staphylococcus aureus Mu50 chromosome |
| 356 | NC_002655 | Escherichia coli O157: H7 EDL933 |
| 386 | NC_003063 | Agrobacterium tumefaciens str. C58 (Cereon) linear chromosome |
| 479 | NC_000962 | Mycobacterium tuberculosis |
| 481 | NC_002737 | Streptococcus pyogenes |
| 495 | NC_003304 | Agrobacterium tumefaciens str. C58 (U. Washington) circular chromosome |
| 551 | NC_003098 | Streptococcus pneumonia R6 |
| 567 | NC_003485 | Streptococcus pyogenes MGAS8232 |
| 577 | NC_002695 | Escherichia coli O157 |
| 592 | NC_003028 | Streptococcus pneumonia TIGR4 |
| 702 | NC_003062 | Agrobacterium tumefaciens str. C58 (Cereon) circular chromosome |
| 729 | NC_001263 | Deinococcus radiodurans chromosome 1 |
| 918 | NC_003116 | Neisseria meningitidis Z2491 |
| 924 | NC_000908 | Mycoplasma genitalium |
| 960 | NC_002755 | Mycobacterium tuberculosis CDC1551 |
| 977 | NC_003112 | Neisseria meningitidis MC58 |
| 979 | NC_000921 | Helicobacter pylori J99 |
| 1015 | NC_000915 | Helicobacter pylori 26695 |
| 1189 | NC_000963 | Rickettsia prowazekii |
| 1284 | NC_001318 | Borrelia burgdorferi chromosome |
| 1331 | NC_002771 | Mycoplasma pulmonis |
| 1426 | NC_000912 | Mycoplasma pneumoniae |
| 1431 | NC_002528 | Buchnera sp. APS |
| 1463 | NC_000868 | Pyrococcus abyssi |
| 1468 | NC_000117 | Chlamydia trachomatis |
| 1468 | NC_002162 | Ureaplasma urealyticum |
| 1478 | NC_003212 | Listeria innocua |
| 1553 | NC_003210 | Listeria monocytogenes |
| 1577 | NC_000961 | Pyrococcus horikoshii |
| 1630 | NC_002620 | Chlamydia muridarum |
| 1636 | NC_003103 | Rickettsia conorii Malish 7 |
| 1769 | NC_003198 | Salmonella typhi |
| 1794 | NC_000913 | Escherichia coli K12 |
| 1894 | NC_002689 | Thermoplasma volcanium |
| 1996 | NC_003413 | Pyrococcus furiosis |
| 2081 | NC_002578 | Thermoplasma acidophilum |
| 2106 | NC_003197 | Salmonella typhimurium LT2 |
| 2137 | NC_003317 | Brucella melitensis chromosome I |
| 2402 | NC_002677 | Mycobacterium leprae |
| 2735 | NC_000918 | Aquifex aeolicus |
| 2803 | NC_002505 | Vibrio cholerae chromosome 1 |
| 2900 | NC_000907 | Haemophilus influenzae |
| 3000 | NC_003318 | Brucella melitensis chromosome II |
| 3120 | NC_000854 | Aeropyrum pernix |
| 3229 | NC_002662 | Lactococcus lactis |
| 3287 | NC_002607 | Halobacterium sp. NRC-1 |
| 3298 | NC_003454 | Fusobacterium nucleatum |
| 3497 | NC_001732 | Methanococcus jannaschii large extra-chromosomal element |
| 3548 | NC_002163 | Campylobacter jejuni |
| 3551 | NC_000853 | Thermotoga maritima |
| 3688 | NC_003106 | Sulfolobus tokodaii |
| 3775 | NC_002754 | Sulfolobus solfataricus |
| 3842 | NC_000919 | Treponema pallidum |
| 3921 | NC_003296 | Ralstonia solanacearum GMI1000 |
| 3940 | NC_000916 | Methanobacterium thermoautotrophicum |
| 4165 | NC_001264 | Deinococcus radiodurans chromosome 2 |
| 4271 | NC_003047 | Sinorhizobium meliloti 1021 chromosome |
| 4338 | NC_002663 | Pasteurella multocida |
| 4658 | NC_003364 | Pyrobaculum aerophilum |
| 5101 | NC_000917 | Archaeoglobus fulgidus |
| 5787 | NC_003366 | Clostridium perfringens |
| 5815 | NC_003450 | Corynebacterium glutamicum |
| 6520 | NC_002696 | Caulobacter crescentus |
| 6866 | NC_002506 | Vibrio cholerae chromosome 2 |
| 6891 | NC_003295 | Ralstonia solanacearum chromosome |
| 7078 | NC_002488 | Xylella fastidiosa chromosome |
| 8283 | NC_003143 | Yersinia pestis chromosome |
| 8320 | NC_000911 | Synechocystis PCC6803 |
| 8374 | NC_002570 | Bacillus halodurans |
| 8660 | NC_000964 | Bacillus subtilis |
| 8994 | NC_003030 | Clostridium acetobutylicum ATCC824 |
| 11725 | NC_003552 | Methanosarcina acetivorans |
| 12120 | NC_002516 | Pseudomonas aeruginosa |
| 12469 | NC_002678 | Mesorhizobium loti |
| 14022 | NC_003272 | Nostoc sp. PCC 7120 |

Example 3

Identification of Specific PETs

Figure 11:
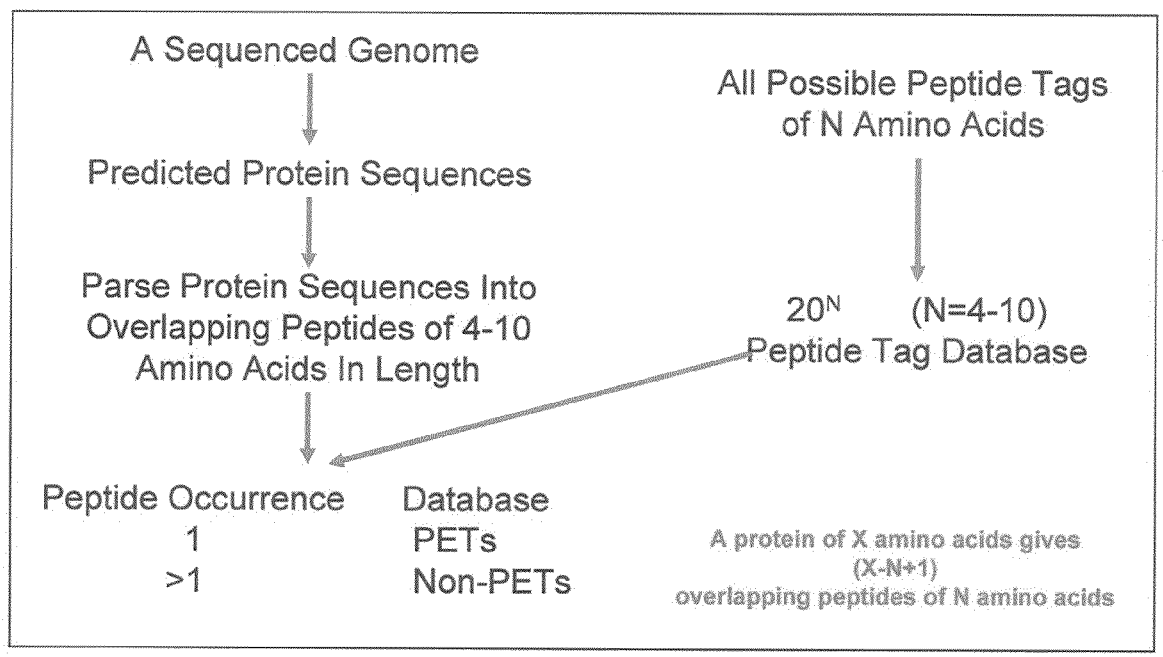
FIG. 11 illustrates a general approach to identify all PETs of a given length in an organism with sequenced genome or a sample with known proteome. Although in this illustrative figure, the protein sequences are parsed into overlapping peptides of 4-10 amino acids in length to identify PETs of 4-10 amino acids, the same scheme is to be used for PETs of any other lengths.

FIG. 11 outlines a general approach to identify all PETs of a given length in an organism with sequenced genome or a sample with known proteome. Briefly, all protein sequences within a sequenced genome can be readily identified using routine bioinformatic tools. These protein sequences are parsed into short overlapping peptides of 4-10 amino acids in length, depending on the desired length of PET. For example, a protein of X amino acids gives (X−N+1) overlapping peptides of N amino acids in length. Theoretically, all possible peptide tags for a given length of, for example, N amino acids, can be represented as $20^N$ (preferably, N=4-10). This is the so-called peptide tag database for this particular length (N) of peptide fragments. By comparing each and every sequence of the parsed short overlapping peptides with the peptide tag database, all PET (with one and only one occurrence in the peptide tag database) can be identified, while all non-PET (with more than one occurrence in the peptide tag database) can be eliminated.

As indicated above, each possible tetramer, pentamer or hexamer was searched against the human proteome (total number: 29,076; Source of human proteome: EBI Ensembl project release 4.28.1 on Mar. 12, 2002, http://www.ensembl.org/Homo_sapiens/) to identify unique recognition sequences (PETs).

Based on the foregoing searches, specific PETs were identified for the majority of the human proteome. FIG. 1 depicts the pentamer unique recognition sequences that were identified within the sequence of the Interleukin-8 receptor A. FIG. 2 depicts the pentamer unique recognition sequences that were identified within the Histamine H1 receptor that are not destroyed by trypsin digestion. Further Examples of pentamer unique recognition sequences that were identified within the human proteome are set forth below.

| Sequence ID* | Number of pentamer PETs | Pentamer PETs |
|---|---|---|
| ENSP00000000233 | 9 | AMPVS CATQG CFTVW ICFTV MPNAM PNAMP SRTWY TWYVQ WYVQA (SEQ ID NOs: 1-9) |
| ENSP00000000412 | 30 | CDFVC CGKEQ CWRTG DNFNP DNHCG FRVCR FYSCW GMEQF HLAFW IFNGS IMLIY IYIFR KGMEQ KTCDL MFPFY MISCN NETHI NWIML PFYSC QDCFY QFPHL RESWQ SNWIM VMISC YDNHC YIYIF YKGGD YLFEM YRGVG YSCWR (SEQ ID NOs: 10-39) |
| ENSP00000000442 | 2 | ASNEC PASNE (SEQ ID NOs: 40-41) |
| ENSP00000000449 | 9 | AQPWA ASTWR CLCLV FVICA LYCCP PRANR VNVLC YAQLW YCCPV (SEQ ID NOs: 42-50) |
| ENSP00000001008 | 20 | AIQRM AKPNE AMCHL AWDIA CQQRI ELKYE EMPMI FVHYT HSIVY HYTGW LYANM MIGDR QKSNT SWEMN SWLEY TEMPM WEMNS YAKPN YESSF YPNNK (SEQ ID NOs: 51-70) |
| ENSP00000001146 | 32 | ATRDK CPCEG DKSCK DTHDT EWPRS FEVYQ FQIPK FSGYR GCPCE GHLFE HDTAP IFSHE KEMTM KLQCT KSCKL KYGNV LKHPT MGEHH MTMQE MYSIR NVFDP QLWQL RGIQA RYLDC STEWP THDTA TRTFP VMYSI VRTCL VSTEW WQLRW WSVMY (SEQ ID NOs: 71-102) |
| ENSP00000001178 | 8 | ACKCF CKCFW FWLWY KCFWL LWYPH QKRRC WLWYP WYPHF (SEQ ID NOs: 103-110) |
| ENSP00000001380 | 26 | AMEQT APCTI AYMER CTIMK DGLCN EQTWR FRSYG GMAYM GYHMP HIPNY KGRIP KLDMG MAYME MEQTW MNKRE PGMNK QGYHM TMSPK TWRLD VEQGY VNDGL WDQTR WRLDP YEAME YHMPC YNPCQ (SEQ ID NOs: 111-136) |
| ENSP00000001567 | 137 | ATYYK CATYY CDNPY CEVVK CIKTD CINSR CKSPD CKSSN CNELP CQENY CSESF CYERE CYHFG CYMGK DFTWF DGWSA DIPIC DQTYP DREYH EEMHC EFDHN EFNCS EHGWA EINYR EKIPC EMHCS ESNTG ESTCG ESYAH EYHFG EYYCN FENAI FQYKC FTWFK GEWVA GNVFE GWTND HGRKF HGTIN HGWAQ HPGYA HPPSC HTVCI IHGVW IKHRT IMVCR INGRW IPCSQ IPVFM IVCGY IYKCR IYKEN KCNMG KGEWV KIPCS KPCDY KWSHP LPICY MENGW MGKWS MGYEY MIGHR NCSMA NDFTW NEGYQ NETTC NGWSD NMGYE NQNHG NSVQC NVFEY NYRDG NYREC PCDYP PEVNC PICYE PPQCE PPYYY PQCVA PYIPN QCYHF QIQLC QYKVG RDTSC REYHF RIKHR RKGEW RPCGH RVRYQ RWQSI SCDNP SDQTY SFTMI SITCG SRWTG STGWI SVEFN SWSDQ TAKCT TCIHG TCINS TCMEN TCYMG TMIGH TNDIP TSTGW TWFKL TYKCF VAIDK VCGYN VEFNC VFEYG VIMVC VNCSM VTYKC WDHIH WFKLN WIHTV WQSIP WSDQT WTNDI YCNPR YHENM YHFGQ YKCNM YKCRP YKIEG YMGKW YNGWS YNQNH YPDIK YQCRN YQYGE YSERG YWDHI YYKMD (SEQ ID NOs: 137-274) |
| ENSP00000001585 | 25 | CVSKG EIIII GINYE GMKHA GWDLK HGMKH HHPKF IEKCV IIMDA INYEI KGYVF MEMIV MIVRA NYTIG QMEMI SHHPK TGSFR TRYKG VYGWD YGESK YGWDL YIHGM YNERE YTIGE YVFQM (SEQ ID NOs: 275-299) |
| ENSP00000002125 | 7 | GRYQR KNMGI MGERF PIKQH QRNAR RYQRN YDMLM (SEQ ID NOs: 299-306) |

-continued

| Sequence ID* | Number of pentamer PETs | Pentamer PETs |
|---|---|---|
| ENSP00000002165 | 63 | AHSAT AKFFN CKWGW CMTID DKLSW DQAKF DVWYT EYSWN FDQAK FEWFH FNANQ FWWYW FYTCS HKWEN HPKAI HQMPC HTWRS IHQMP IPKYV IYETH KFFNA KWENC KWGWA KWPTS LMNIG LPHKW MPCKW MRPQE NANQW NCMTI NYPPS NYQPE PCKWG PDQYW PHKWE QMGSW QYWNS RNRTD SCGGN SKHHE TCSDR THTWR TIHQM TNDRW TPDVW TRFDP TVVTN VRGTV VVTND WENCM WFDQA WFWWY WGSEY WGWAL WNWNA WRSQN WWYWQ YEDFG YETHT YNPGH YSWNW YVEFM YYSLF (SEQ ID NOs: 307-369) |
| ENSP00000002494 | 74 | AMNDA ANHGE AQWRN CVKLP CVQYK DAHKR DCVQY DIEQR DMAER DPDKW DTANH EVSFM EYVID FEQYE FFEQY FGDCV FMNET HEIYR HERFL HFDQT HKQWK HKRAF HTAMN HWIQQ KHFDQ KMLNQ KQMTS KQYAQ KRAFH KWERF LNGRW LPHWI MFATM MKFMN MKMEF MLNQS MPQEG MYVKA NLPHW NTDAH NVLKH PHWIQ PVMDA QADEM QENCK QHTAM QNYVS QWKDL QYAQA RVPVM SFYDS SHERF TCDEM TDAHK TKLMP TVVRY TYQIL VMDAQ VMKFM VPVMD VRYLF VSFMN WDRYG WERFE WIIKY WIQQH WISTN WKDYT WKKHV YAQAD YEVTY YGRRE YTDCV YVKAD (SEQ ID NOs: 369-443) |
| ENSP00000002594 | 7 | CFKEN DGGFD FDLGD KLCFK KPMPN MPNPN PNPNH (SEQ ID NOs: 444-450) |
| ENSP00000002596 | 36 | DRCLH EEHYS EHYSH ENEVH EYFHE FFDWE FHEPN FSWPH FYNHM GRDRC GVAPN HEYFH HFFDW HIVDG HKPYP HMQKH HMQNW HPQVD HVHMQ KGRAH KHKPY KTPAY MQNWL NHMQK QKHKP QNWLR RVYSM SMNPS SWPHQ TFDWH TQVFY WEEHY YCLRD YHVHM YNHMQ YPSIE (SEQ ID NOs: 451-486) |
| ENSP00000002829 | 60 | ADIRM AWPSF CLVNK CQAYG CTYVN DHDRM DPSFI DRMYV GHCCL GIETH GYWRH HCCLV HDINR HDRMY HQYCQ HRCQA IETHF IFYLE IHQYC IIHWA INFMR IQPWN KMPYP KWLFQ LIIHW LIQPW MCTYV MPYPR MRSHP NNFKH NPIRQ NSRWL NTTDY NYQWM PIRQC PRNRR PVKTM PWNRT QDYIF QGYWR QTAMR RCQAY RMVFN SKDYV SNANK TGAWP VGVTH VINFM VKWLF WDGQA WPSFP WRHVP YAGVY YCQGY YNPMC YNSRW YPLQR YQAVY YQWMP YWRHV (SEQ ID NOs: 487- 546) |

*The Sequence IDs used are the ones provided in http://www.ensembl.org/Homo_sapiens/

Figure 12:
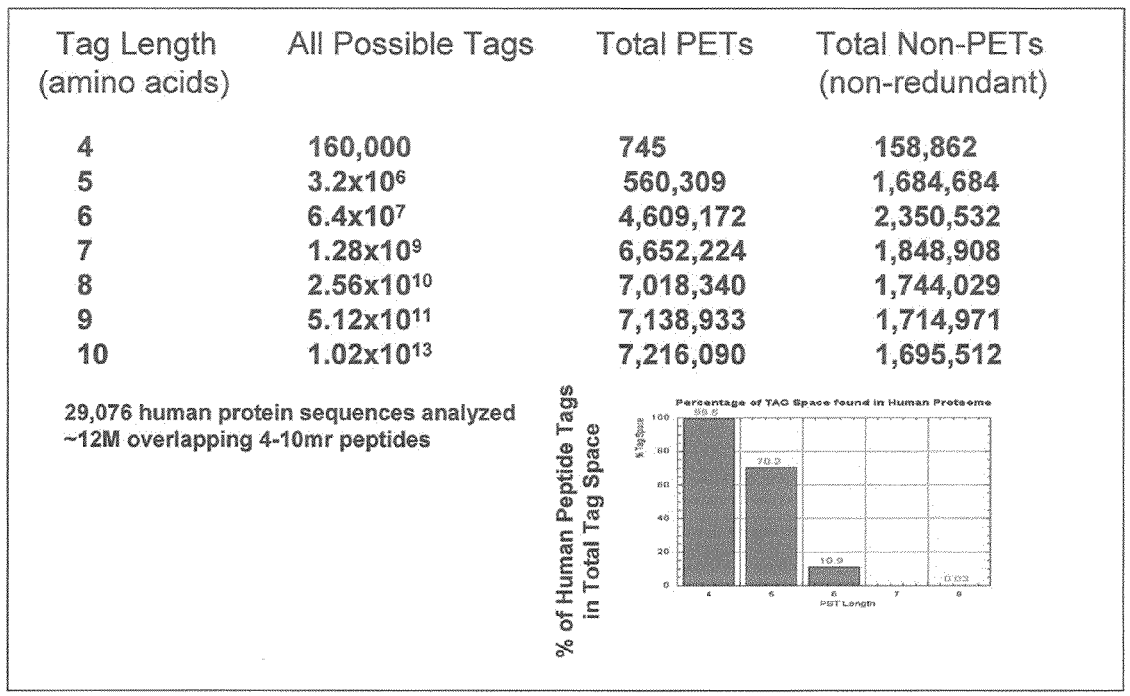
FIG. 12 lists the results of searching the whole human proteome (a total of 29,076 proteins, which correspond to about 12 million 4-10 overlapping peptides) for PETs, and the number of PETs identified for each N between 4-10.

FIG. 12 lists the results of searching the whole human proteome (a total of 29,076 proteins, which correspond to about 12 million 4-10 overlapping peptides) for PETs, and the number of PETs identified for each N between 4-10.

Figure 13:
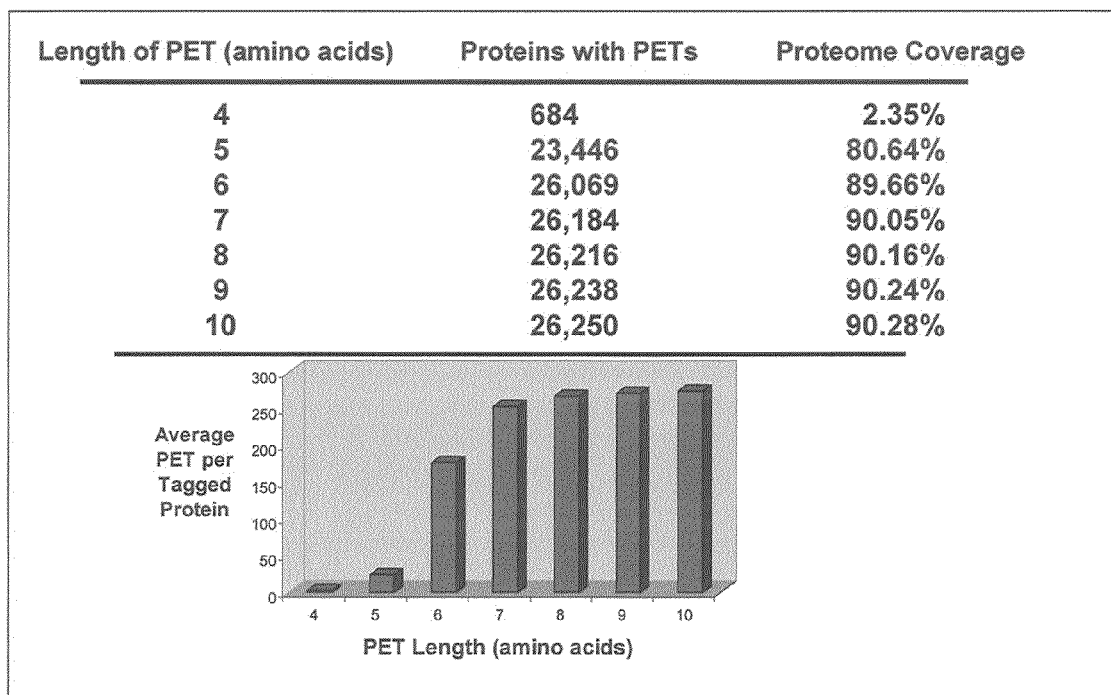
FIG. 13 shows the result of percentage of human proteins that have at least one PET(s).

FIG. 13 shows the result of percentage of human proteins that have at least one PET(s). It is shown that for a PET of 4 amino acids in length, only 684 (or about 2.35% of the total human proteins) proteins have at least one 4-mer PETs. However, if PETs of at least 6 amino acids are used, at least about 90% of all proteins have at least one PET. In addition, it is somewhat surprising that there is a significant increase in average number of PETs per protein from 5-mer PETs to 6-mer (or more) PETs (see lower panel of FIG. 13), and that average quickly reaches a plateau when 7- or 8-mer PETs are used. These data indicates that PETs of at least 6 amino acids, preferably 7-9 amino acids, most preferably 8 amino acids have the optimal length of PETs for most applications. It is easier to identify a useful PET of that length, partly because of the large average number of PETs per protein when a PET of that length is sought.

Figure 14:
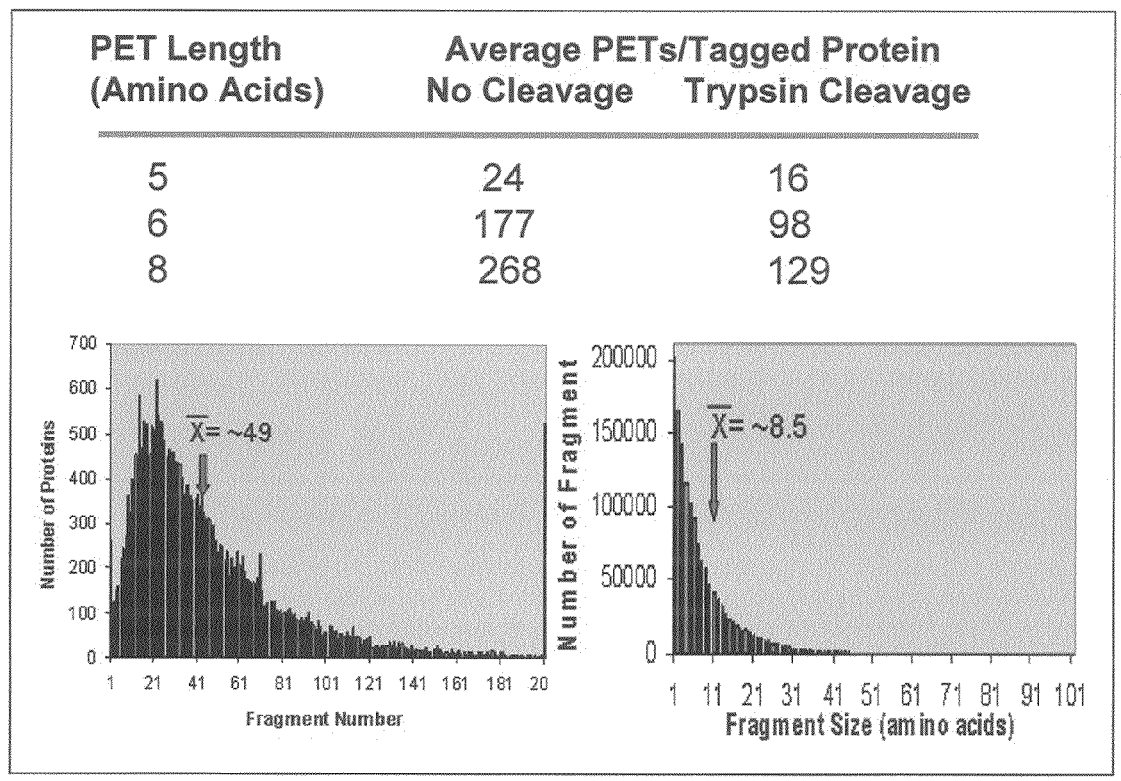
FIG. 14 provides further data resulting from tryptic digest of the human proteome.

FIG. 14 provides further data resulting from tryptic digest of the human proteome. Specifically, the top panel lists the average number of PETs per tagged protein (protein with at least one PETs), with or without trypsin digestion. Trypsin digestion reduces the average number of PETs per tagged protein by roughly ⅓ to ½. The bottom right panel shows the distribution of tryptic fragments in the human proteome, listed according to peptide length. On average, a typical tryptic fragment is about 8.5 amino acids in length. The bottom left panel shows the distribution of number of tryptic fragments generated from human proteins. On average, a human protein has about 49 tryptic fragments.

Example 6 below provides a detailed example of identifying SARS virus-specific 8-mer PETs. These PETs are potentially useful as SARS-specific antigens for immunization (vaccine production) in human or other mammals.

Example 4

Detection and Quantitation in a Complex Mixture of a Single Peptide Sequence with Two Non-Overlapping PET Sequences using Sandwich ELISA Assay A fluorescence sandwich immunoassay for specific capture and quantitation of a targeted peptide in a complex peptide mixture is illustrated herein.

Figure 15:
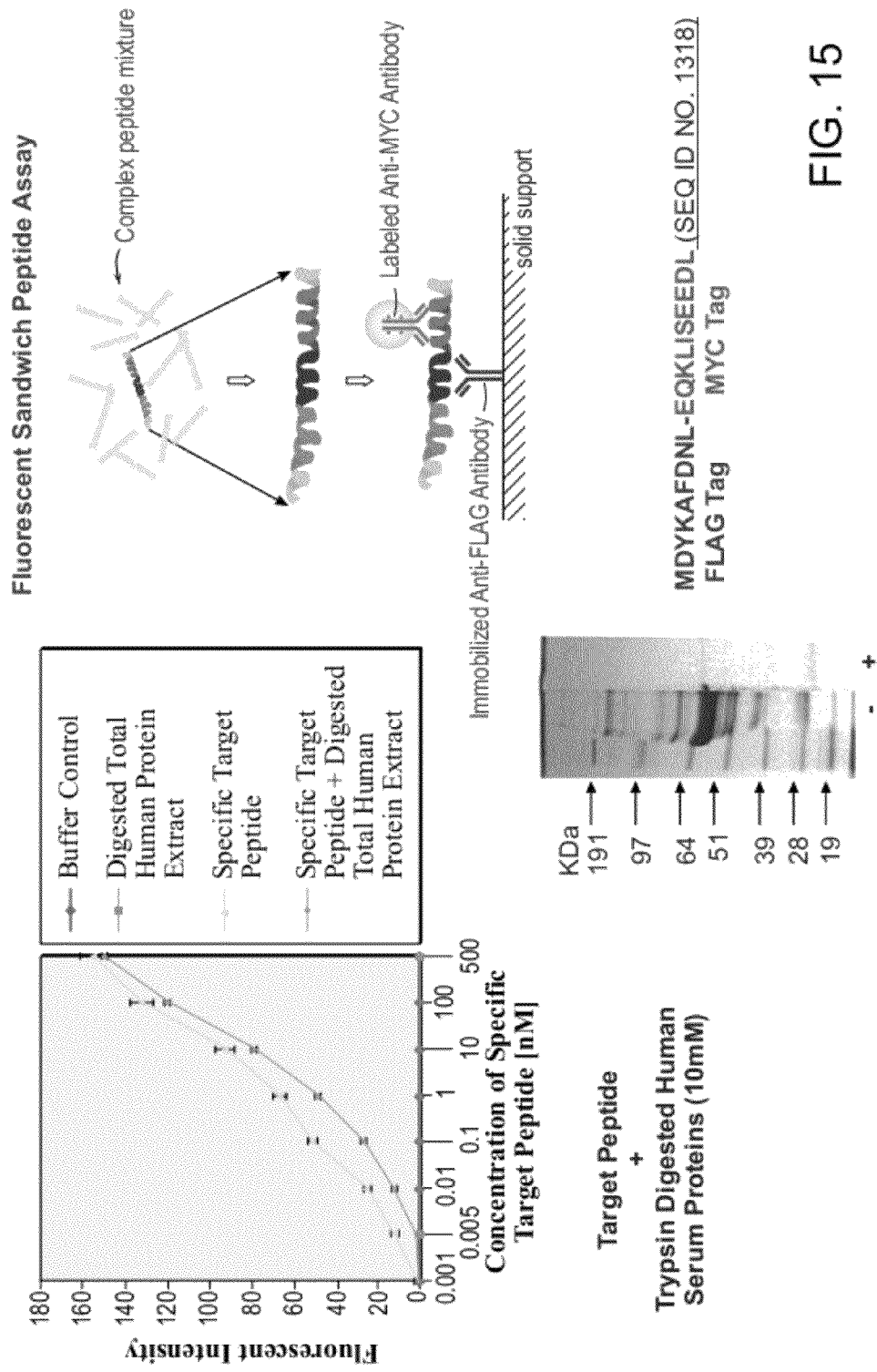
FIG. 15 illustrates a schematic drawing of fluorescence sandwich immunoassay for specific capture and quantitation of a targeted peptide in a complex peptide mixture, and results of readout fluorescent signal detected by the secondary antibody.

In the example shown here, a peptide consisting of three commonly used affinity epitope sequences (the HA tag, the FLAG tag and the MYC tag) is mixed with a large excess of unrelated peptides from digested human protein samples (FIG. 15). The FLAG epitope in the middle of the target peptide is first captured here by the FLAG antibody, then the labeled antibody (either HA mAb or MYC mAb) is used to detect the second epitope. The final signal is detected by fluorescence readout from the secondary antibody. FIG. 15 shows that picomolar concentrations of HA-FLAG-MYC peptide was detected in the presence of a billion molar excess of digested unrelated proteins. The detection limit of this method is typically about 10 pM or less.

Figure 16:
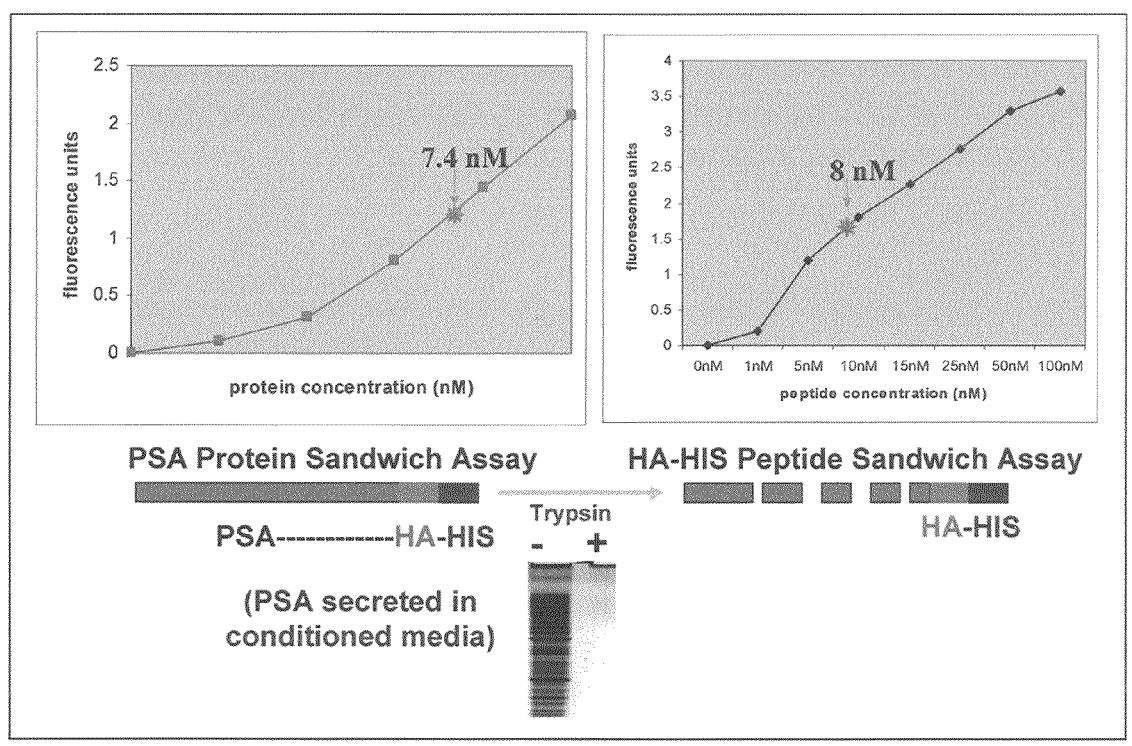
FIG. 16 illustrates the sandwich assay used to detect a tagged-human PSA protein.

The sandwich assay was used to detect a tagged-human PSA protein, both as full length protein secreted in conditioned media of cell cultures, and as tryptic peptides generated by digesting the same conditioned media. The result of this analysis is shown in FIG. 16. The PSA protein sandwich assay (left side of the figure) indicated that the PSA protein concentration is about 7.4 nM in conditioned media. SDS-PAGE analysis indicated that the tryptic digestion of all proteins in the sample was complete, manifested by the absence of any visible bands on the gel after digestion since most tryptic fragments are expected to be less than 1 kDa. The right side of the figure indicated that nearly the same concentration (8 nM) of the last fragment—the tag-containing portion of the recombinant PSA protein was present in the digested sample. The higher concentration could be attributed to the elimination of interfering substances in the sample, such as other proteins that bind the full-length PSA protein and mask its interaction with the antibody. Although this type of interference is not so severe in this example since the relatively simple conditioned media was used, it is expected to be much more prevalent in real biological samples, where large interference is expected from unknown proteins in a non-digested and complicated bodily fluid such as serum.

Figure 17:
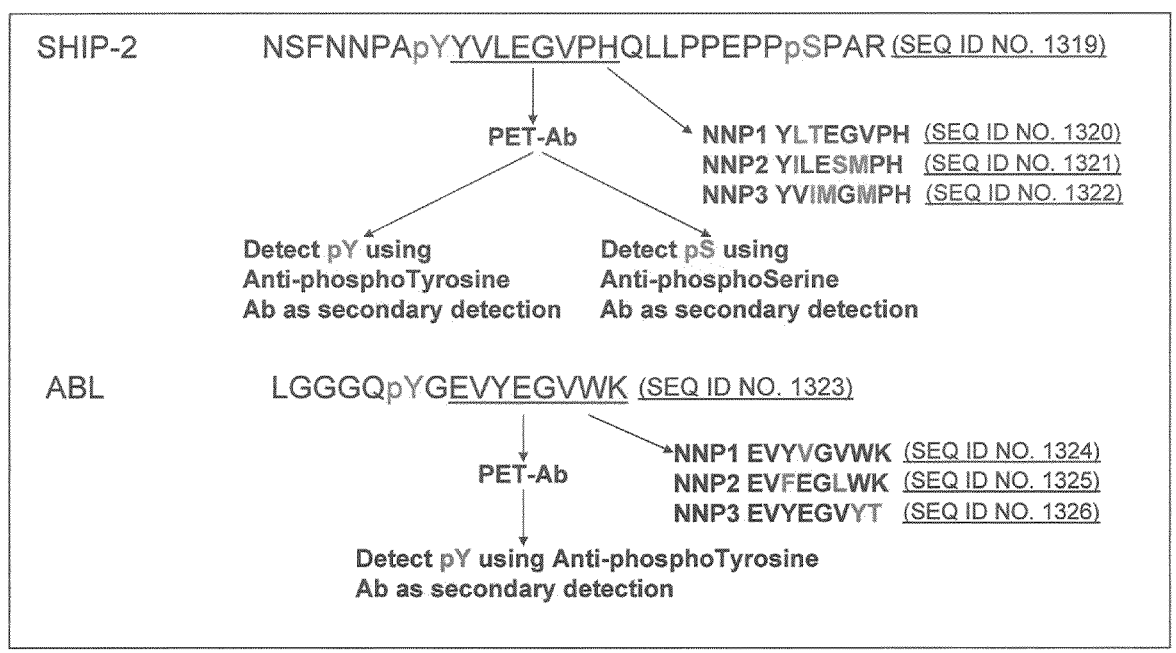
FIG. 17 illustrates the PETs and their nearest neighbors for the detection of phospho-peptides in SHIP-2 and ABL.

The same sandwich assay may be used for detecting modified amino acids, such as phosphorylated proteins using anti-tyrosine, anti-serine, or anti-threonine antibodies. For example, FIG. 17 shows that the phopshoprotein SHIP-2 contains a 28-amino acid tryptic fragment, which is phosphorylated on one tyrosine residue N-terminal to an 8-mer PET (YVLEGVPH) and on one serine residue C-terminal to the PET. Thus in the sandwich assay, the trypsin digested SHIP-2 protein can first be pulled-down using the PET-specific antibody, and the presence of phosphorylated tyrosine or serine may be detected/quantitated using the phospho-specific antibodies, such as those described elsewhere in the instant specification. Three of the nearest neighbors of the selected PET are also shown in the figure.

Similarly, the phosphoprotein ABL also contains an 8-mer PET on its tryptic fragment containing the phosphorylation site. The phosphorylated peptide is readily detectable by a phospho-tyrosine-specific antibody.

In fact, as a general approach, the sandwich assay may be used to detect N proteins with N+1 PET-specific antibodies: one PET is common to all N peptides to be detected, while each specific peptide also contains a unique PET. All N peptides can be pulled-down by a capture agent specific to the common PET, and the presence and quantity of each specific peptide can be individually assessed using antibodies specific to the unique PETs (see FIG. 18).

Figure 18:
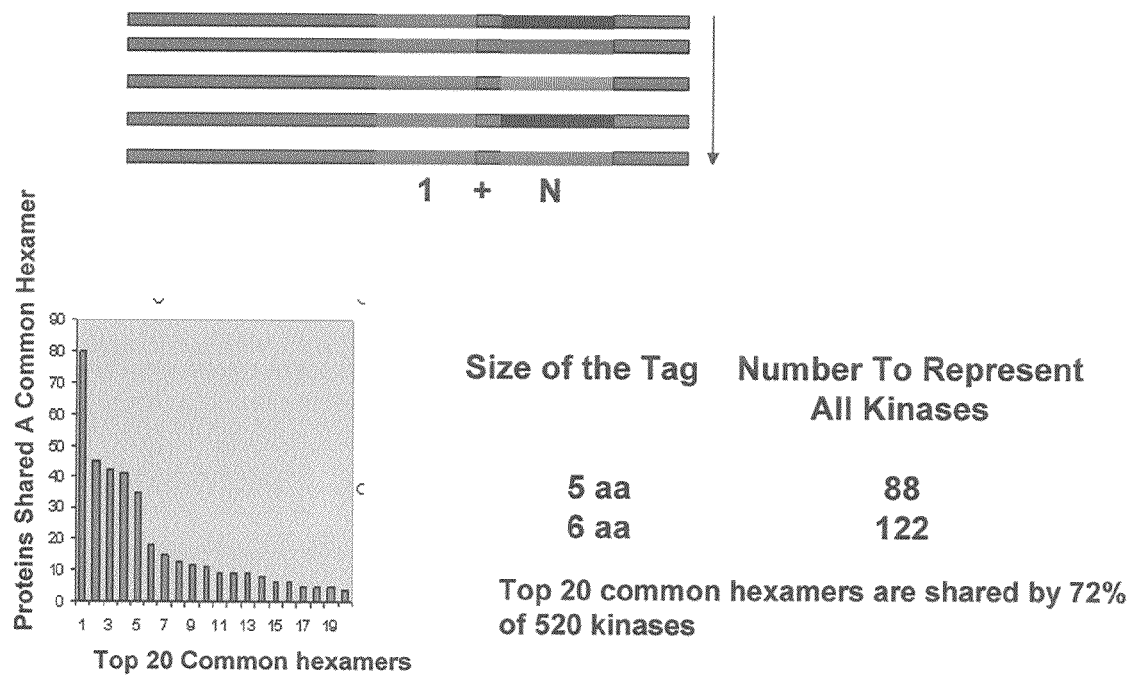
FIG. 18 illustrates a general approach to use the sandwich assay for detecting N proteins with N+1 PET-specific antibodies.

To illustrate, most kinases are somehow related by sharing similar catalytic structures and/or catalytic mechanisms. Thus, it is interesting that only 88 5-mer PETs are needed to represent all known 518 human kinases, and 122 6-mer PETs are needed for the same purpose. FIG. 18 also shows that the top 20 most common 6-mer PETs cover more than 70% of all known kinases. Since closely related kinases tend to share common features, the subject sandwich assay is suitable for simultaneous detection of family of kinases. FIG. 19 provides such an example, wherein one 5-mer PET is shared among tryptic fragments of 22 related kinases, each of which also has unique 7-mer or 8-mer PETs.

The same approach may be used for other protein families, including GPCRs, proteases, phosphotases, receptors, or specific enzymes. The Human Plasma Membrane Receptome is disclosed at http://receptome.stanford.edu/HPMR.

Example 5

Peptide Competition Assay

In certain embodiments of the invention, a peptide competition assay may be used to determine the binding specificity of a capture agent towards its target PET, as compared to several nearest neighbor sequences of the PET.

For a typical peptide competition assay, the following illustrative protocol may be used: 1 μg/100 μl/well of each target peptide is coated in Maxisorb Plates with coating buffer (carbonate buffer, pH 9.6) overnight at 4° C., or 1 hour at room temperature. The plates are washed with 300 μl of PBST (1× PBS/0.05% tween 20) for 4 times. Then 300 μl of blocking buffer (2% BSA/PBST) is added and the plates are incubated for 1 hour at room temperature. Following blocking, the plates are washed with 300 μl of PBST for 4 times.

Synthesized competition peptides are dissolved in water to a final concentration of 2 mM solution. Serial dilution of competition peptides (for example, from 100 pM to 100 μM) in digested human serum are prepared. These competition peptides at particular concentrations are then mixed with equal amounts of primary antibodies against the target peptide. These mixtures are then added to plate wells with immobilized target peptides respectively. Binding is allowed to proceed for 2 hours at room temperature. The plates are washed with 300 μl of PBST for 4 times. Then labeled secondary antibody against the primary antibody, such as 100 μl of 5,000× diluted anti-rabbit-IgG-HRP, is added and incubated for 1 more hour at room temperature. The plates are washed with 300 μl of PBST for 6 times. For detection of the HRP label activity, add 100 μl of TMB substrate (for HRP) and incubate for 15 minutes at room temperature. Add 100 μl of stop buffer (2N HCL) and read the plates at $OD_{450}$. A peptide competition curve is plotted using the ABS at $OD_{450}$ versus the competitor peptide concentrations.

Example 6

Identification of SARS-Specific PETs

Sequence Retrieval

A total of 2028 Coronavirus peptide sequences were obtained from the NCBI database (http://www.ncbi.nlm.nih.gov:80/genomes/SARS/SARS.html). These sequences represent at least 10 different species of Coronavirus. Among them, 1098 non-redundant peptide sequences were identified. Each sequence that appeared identically within (was subsumed in) a larger sequence was removed, leaving the larger sequence as the representative. The resulting sequences were then broken up into overlapping regions of eight amino acids (8-mers), with a sequence difference of 1 amino acid between successive 8-mers. These 8-mers were then queried against a database consisting of all 8-mers similarly generated and present in the proteome of the species in question (or any other set of protein sequences deemed necessary). 8-mers found to be present only once (the sequence identified only itself) were considered unique. The remainder of the sequences were initially classified as non-unique with the understanding that with more in-depth analysis, they might actually be as useful as those sequences initially determined to be unique. For example, an 8-mer may be present in another isoform of its parent sequence, so it would still be useful in uniquely detecting that parental sequence and that isoform from all other unrelated proteins.

A total of ~650,000 8-mer peptide sequences were generated, ~50,000 of which were determined to be PETs. Among these, 605 were SARS-specific and 602 were PETs relative to human.

PET Prioritization:

Once PETs have been identified, the best candidates for a particular application must be chosen from the pool of all PETs.

Generally, PETs are ranked based upon calculations used to predict their hydrophobicity, antigenicity, and solubility, with hydrophilic, antigenic, and soluble PETs given the highest priority. The PETs are then further ranked by determining each PET's closest nearest neighbors (similar looking 8-mers with at least one sequence difference(s)) in the proteome(s) in question. A matrix calculation is performed using a BLOSUM, PAM, or a similar proprietary matrix to determine sequence similarity and distance. PETs with the most distant nearest neighbors are given the priority.

The parental peptide sequence is then proteolytically cleaved in silico and the resulting fragments sorted by user-defined size/hydrophobicity/antigenicity/solubility criteria. The presence of PETs in each fragment is assessed, and fragments containing no PETs are discarded. The remaining fragments are analyzed in terms of PET placement within them depending upon the requirements of the type of assay to be performed. For example, a sandwich assay prefers two non-overlapping PETs in a single fragment. The ideal final choice would be the most antigenic PETs with only distantly-related nearest neighbors in an acceptable proteolytic fragment that fit the requirements of the assay to be performed.

Figure 20:
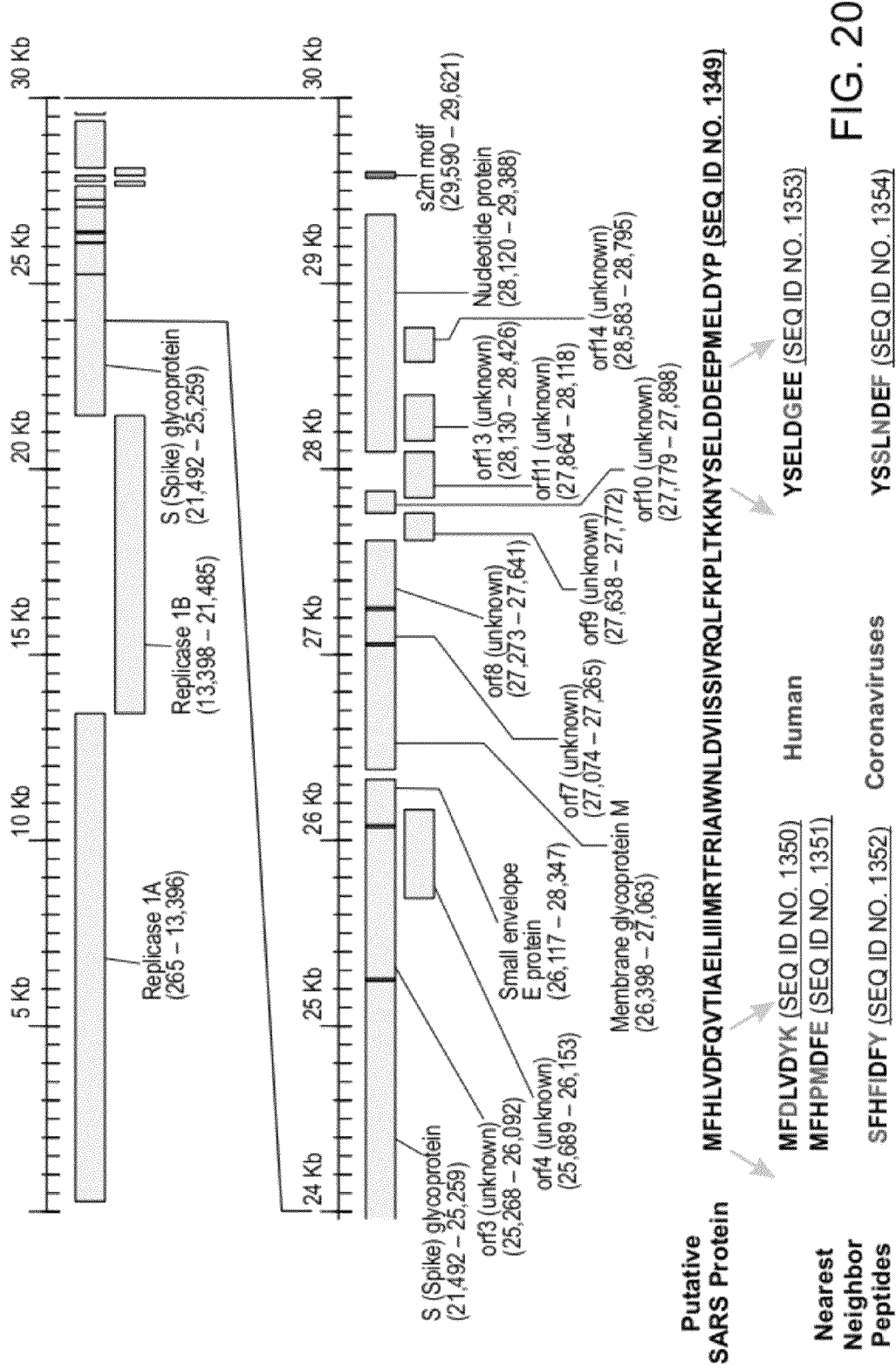
FIG. 20 shows two SARS-specific PETs and their nearest neighbors in both the human proteome and the related Coronaviruses.

FIG. 20 shows two SARS-specific PETs and their nearest neighbors in both the human proteome and the related Coronaviruses.

All SARS-specific PETs identified using this method is listed below in Table SARS.

TABLE SARS

List of SARS virus-specific PETs

>gi|30795153|gb|AAP41045.1| Orf10 [SARS coronavirus Tor2]     ISLCSCIC
(SEQ ID NO.663)

>gi|30795153|gb|AAP41045.1| Orf10 [SARS coronavirus Tor2]     SLCSCICT
(SEQ ID NO.664)

>gi|30795153|gb|AAP41045.1| Orf10 [SARS coronavirus Tor2]     LCSCICTV
(SEQ ID NO.665)

>gi|30795153|gb|AAP41045.1| Orf10 [SARS coronavirus Tor2]     CSCICTVV
(SEQ ID NO.666)

>gi|30795153|gb|AAP41045.1| Orf10 [SARS coronavirus Tor2]     SCICTVVQ
(SEQ ID NO.667)

>gi|30795153|gb|AAP41045.1| Orf10 [SARS coronavirus Tor2]     CICTVVQR
(SEQ ID NO.668)

>gi|30795153|gb|AAP41045.1| Orf10 [SARS coronavirus Tor2]     ICTVVQRC
(SEQ ID NO.669)

>gi|30795153|gb|AAP41045.1| Orf10 [SARS coronavirus Tor2]     CTVVQRCA
(SEQ ID NO.670)

>gi|30795153|gb|AAP41045.1| Orf10 [SARS coronavirus Tor2]     HVLEDPCK
(SEQ ID NO.671)

>gi|30795153|gb|AAP41045.1| Orf10 [SARS coronavirus Tor2]     VLEDPCKV
(SEQ ID NO.672)

>gi|30795153|gb|AAP41045.1| Orf10 [SARS coronavirus Tor2]     LEDPCKVQ
(SEQ ID NO.673)

>gi|30795153|gb|AAP41045.1| Orf10 [SARS coronavirus Tor2]     EDPCKVQH
(SEQ ID NO.674)

>gi|32187352|gb|AAP72981.1| Orf7b [SARS coronavirus HSR 1]     MNELTLID
(SEQ ID NO.675)

>gi|32187352|gb|AAP72981.1| Orf7b [SARS coronavirus HSR 1]     NELTLIDF
(SEQ ID NO.676)

TABLE SARS-continued

List of SARS virus-specific PETs

| | |
|---|---|
| >gi\|32187352\|gb\|AAP72981.1\| Orf7b [SARS coronavirus HSR 1] (SEQ ID NO.677) | ELTLIDFY |
| >gi\|32187352\|gb\|AAP72981.1\| Orf7b [SARS coronavirus HSR 1] (SEQ ID NO.678) | LTLIDFYL |
| >gi\|32187352\|gb\|AAP72981.1\| Orf7b [SARS coronavirus HSR 1] (SEQ ID NO.679) | TLIDFYLC |
| >gi\|32187352\|gb\|AAP72981.1\| Orf7b [SARS coronavirus HSR 1] (SEQ ID NO.680) | LIDFYLCF |
| >gi\|32187352\|gb\|AAP72981.1\| Orf7b [SARS coronavirus HSR 1] (SEQ ID NO.681) | IDFYLCFL |
| >gi\|32187352\|gb\|AAP72981.1\| Orf7b [SARS coronavirus HSR 1] (SEQ ID NO.682) | DFYLCFLA |
| >gi\|32187352\|gb\|AAP72981.1\| Orf7b [SARS coronavirus HSR 1] (SEQ ID NO.683) | FYLCFLAF |
| >gi\|32187352\|gb\|AAP72981.1\| Orf7b [SARS coronavirus HSR 1] (SEQ ID NO.684) | YLCFLAFL |
| >gi\|32187352\|gb\|AAP72981.1\| Orf7b [SARS coronavirus HSR 1] (SEQ ID NO.685) | LCFLAFLL |
| >gi\|32187352\|gb\|AAP72981.1\| Orf7b [SARS coronavirus HSR 1] (SEQ ID NO.686) | CFLAFLLF |
| >gi\|32187352\|gb\|AAP72981.1\| Orf7b [SARS coronavirus HSR 1] (SEQ ID NO.687) | FLAFLLFL |
| >gi\|32187352\|gb\|AAP72981.1\| Orf7b [SARS coronavirus HSR 1] (SEQ ID NO.688) | LAFLLFLV |
| >gi\|32187352\|gb\|AAP72981.1\| Orf7b [SARS coronavirus HSR 1] (SEQ ID NO.689) | AFLLFLVL |
| >gi\|32187352\|gb\|AAP72981.1\| Orf7b [SARS coronavirus HSR 1] (SEQ ID NO.690) | FLLFLVLI |
| >gi\|32187352\|gb\|AAP72981.1\| Orf7b [SARS coronavirus HSR 1] (SEQ ID NO.691) | LLFLVLIM |
| >gi\|32187352\|gb\|AAP72981.1\| Orf7b [SARS coronavirus HSR 1] (SEQ ID NO.692) | LFLVLIML |
| >gi\|32187352\|gb\|AAP72981.1\| Orf7b [SARS coronavirus HSR 1] (SEQ ID NO.693) | FLVLIMLI |
| >gi\|32187352\|gb\|AAP72981.1\| Orf7b [SARS coronavirus HSR 1] (SEQ ID NO.694) | LVLIMLII |
| >gi\|32187352\|gb\|AAP72981.1\| Orf7b [SARS coronavirus HSR 1] (SEQ ID NO.695) | VLIMLIIF |
| >gi\|32187352\|gb\|AAP72981.1\| Orf7b [SARS coronavirus HSR 1] (SEQ ID NO.696) | LIMLIIFW |
| >gi\|32187352\|gb\|AAP72981.1\| Orf7b [SARS coronavirus HSR 1] (SEQ ID NO.697) | IMLIIFWF |
| >gi\|32187352\|gb\|AAP72981.1\| Orf7b [SARS coronavirus HSR 1] (SEQ ID NO.698) | MLIIFWFS |
| >gi\|32187352\|gb\|AAP72981.1\| Orf7b [SARS coronavirus HSR 1] (SEQ ID NO.699) | LIIFWFSL |
| >gi\|32187352\|gb\|AAP72981.1\| Orf7b [SARS coronavirus HSR 1] (SEQ ID NO.700) | IIFWFSLE |
| >gi\|32187352\|gb\|AAP72981.1\| Orf7b [SARS coronavirus HSR 1] (SEQ ID NO.701) | IFWFSLEI |
| >gi\|32187352\|gb\|AAP72981.1\| Orf7b [SARS coronavirus HSR 1] (SEQ ID NO.702) | FWFSLEIQ |

TABLE SARS-continued

List of SARS virus-specific PETs

| | |
|---|---|
| >gi\|32187352\|gb\|AAP72981.1\| Orf7b [SARS coronavirus HSR 1] (SEQ ID NO.703) | WFSLEIQD |
| >gi\|32187352\|gb\|AAP72981.1\| Orf7b [SARS coronavirus HSR 1] (SEQ ID NO.704) | FSLEIQDL |
| >gi\|32187352\|gb\|AAP72981.1\| Orf7b [SARS coronavirus HSR 1] (SEQ ID NO.705) | SLEIQDLE |
| >gi\|32187352\|gb\|AAP72981.1\| Orf7b [SARS coronavirus HSR 1] (SEQ ID NO.706) | LEIQDLEE |
| >gi\|32187352\|gb\|AAP72981.1\| Orf7b [SARS coronavirus HSR 1] (SEQ ID NO.707) | EIQDLEEP |
| >gi\|32187352\|gb\|AAP72981.1\| Orf7b [SARS coronavirus HSR 1] (SEQ ID NO.708) | IQDLEEPC |
| >gi\|32187352\|gb\|AAP72981.1\| Orf7b [SARS coronavirus HSR 1] (SEQ ID NO.709) | QDLEEPCT |
| >gi\|32187352\|gb\|AAP72981.1\| Orf7b [SARS coronavirus HSR 1] (SEQ ID NO.710) | DLEEPCTK |
| >gi\|32187352\|gb\|AAP72981.1\| Orf7b [SARS coronavirus HSR 1] (SEQ ID NO.711) | LEEPCTKV |
| >gi\|32187350\|gb\|AAP72979.1\| Orf6 [SARS coronavirus HSR 1] (SEQ ID NO.712) | DEEPMELB |
| >gi\|32187350\|gb\|AAP72979.1\| Orf6 [SARS coronavirus HSR 1] (SEQ ID NO.713) | EEPMELBY |
| >gi\|32187350\|gb\|AAP72979.1\| Orf6 [SARS coronavirus HSR 1] (SEQ ID NO.714) | EPMELBYP |
| >gi\|30023959\|gb\|AAP13572.1\| unknown [SARS coronavirus CUHK-W1] (SEQ ID NO.715) | DEEPMELD |
| >gi\|300239S9\|gb\|AAP13572.1\| unknown [SARS coronavirus CUHK-W1] (SEQ ID NO.716) | EEPMELDY |
| >gi\|30023959\|gb\|AAP13572.1\| unknown [SARS coronavirus CUHK-W1] (SEQ ID NO.717) | EPMELDYP |
| >gi\|30275674\|gb\|AAP30035.1\| putative uncharacterized protein 3 [SARS coronavirus BJ01] (SEQ ID NO.718) | SELDDEEL |
| >gi\|30275674\|gb\|AAP30035.1\| putative uncharacterized protein 3 [SARS coronavirus BJ01] (SEQ ID NO.719) | ELDDEELM |
| >gi\|30275674\|gb\|AAP30035.1\| putative uncharacterized protein 3 [SARS coronavirus BJ01] (SEQ ID NO.720) | LDDEELME |
| >gi\|30275674\|gb\|AAP30035.1\| putative uncharacterized protein 3 [SARS coronavirus BJ01] (SEQ ID NO.721) | DDEELMEL |
| >gi\|30275674\|gb\|AAP30035.1\| putative uncharacterized protein 3 [SARS coronavirus BJ01] (SEQ ID NO.722) | DEELMELD |
| >gi\|30275674\|gb\|AAP30035.1\| putative uncharacterized protein 3 [SARS coronavirus BJ01] (SEQ ID NO.723) | EELMELDY |
| >gi\|30275674\|gb\|AAP30035.1\| putative uncharacterized protein 3 [SARS coronavirus BJ01] (SEQ ID NO.724) | ELMELDYP |
| >gi\|31747859\|gb\|AAP69660.1\| uncharacterized protein 9c [SARS coronavirus ZJ-HZ01] (SEQ ID NO.725) | MLPPCYNF |
| >gi\|31747859\|gb\|AAP69660.1\| uncharacterized protein 9c [SARS coronavirus ZJ-HZ01] (SEQ ID NO.726) | LPPCYNFL |
| >gi\|31747859\|gb\|AAP69660.1\| uncharacterized protein 9c [SARS coronavirus ZJ-HZ01] (SEQ ID NO.727) | PPCYNFLK |
| >gi\|31747859\|gb\|AAP69660.1\| uncharacterized protein 9c [SARS coronavirus ZJ-HZ01] (SEQ ID NO.728) | PCYNFLKE |

TABLE SARS-continued

| List of SARS virus-specific PETs | |
|---|---|
| >gi\|31747859\|gb\|AAP69660.1\| uncharacterized protein 9c [SARS coronavirus ZJ-HZ01] (SEQ ID NO.729) | CYNFLKEQ |
| >gi\|31747859\|gb\|AAP69660.1\| uncharacterized protein 9c [SARS coronavirus ZJ-HZ01] (SEQ ID NO.730) | YNFLKEQH |
| >gi\|31747859\|gb\|AAP69660.1\| uncharacterized protein 9c [SARS coronavirus ZJ-HZ01] (SEQ ID NO.731) | NFLKEQHC |
| >gi\|31747859\|gb\|AAP69660.1\| uncharacterized protein 9c [SARS coronavirus ZJ-HZ01] (SEQ ID NO.732) | FLKEQHCQ |
| >gi\|31747859\|gb\|AAP69660.1\| uncharacterized protein 9c [SARS coronavirus ZJ-HZ01] (SEQ ID NO.733) | LKEQHCQK |
| >gi\|31747859\|gb\|AAP69660.1\| uncharacterized protein 9c [SARS coronavirus ZJ-HZ01] (SEQ ID NO.734) | KEQHCQKA |
| >gi\|31747859\|gb\|AAP69660.1\| uncharacterized protein 9c [SARS coronavirus ZJ-HZ01] (SEQ ID NO.735) | EQHCQKAS |
| >gi\|31747859\|gb\|AAP69660.1\| uncharacterized protein 9c [SARS coronavirus ZJ-HZ01] (SEQ ID NO.736) | QHCQKAST |
| >gi\|31747859\|gb\|AAP69660.1\| uncharacterized protein 9c [SARS coronavirus ZJ-HZ01] (SEQ ID NO.737) | HCQKASTQ |
| >gi\|31747859\|gb\|AAP69660.1\| uncharacterized protein 9c [SARS coronavirus ZJ-HZ01] (SEQ ID NO.738) | CQKASTQR |
| >gi\|31747859\|gb\|AAP69660.1\| uncharacterized protein 9c [SARS coronavirus ZJ-HZ01] (SEQ ID NO.739) | QKASTQRE |
| >gi\|31747859\|gb\|AAP69660.1\| uncharacterized protein 9c [SARS coronavirus ZJ-HZ01] (SEQ ID NO.740) | KASTQREA |
| >gi\|31747859\|gb\|AAP69660.1\| uncharacterized protein 9c [SARS coronavirus ZJ-HZ01] (SEQ ID NO.741) | ASTQREAE |
| >gi\|31747859\|gb\|AAP69660.1\| uncharacterized protein 9c [SARS coronavirus ZJ-HZ01] (SEQ ID NO.742) | STQREAEA |
| >gi\|31747859\|gb\|AAP69660.1\| uncharacterized protein 9c [SARS coronavirus ZJ-HZ01] (SEQ ID NO.743) | TQREAEAA |
| >gi\|31747859\|gb\|AAP69660.1\| uncharacterized protein 9c [SARS coronavirus ZJ-HZ01] (SEQ ID NO.744) | QREAEAAV |
| >gi\|31747859\|gb\|AAP69660.1\| uncharacterized protein 9c [SARS coronavirus ZJ-HZ01] (SEQ ID NO.745) | REAEAAVK |
| >gi\|31747859\|gb\|AAP69660.1\| uncharacterized protein 9c [SARS coronavirus ZJ-HZ01] (SEQ ID NO.746) | EAEAAVKP |
| >gi\|31747859\|gb\|AAP69660.1\| uncharacterized protein 9c [SARS coronavirus ZJ-HZ01] (SEQ ID NO.747) | AEAAVKPL |
| >gi\|31747859\|gb\|AAP69660.1\| uncharacterized protein 9c [SARS coronavirus ZJ-HZ01] (SEQ ID NO.748) | EAAVKPLL |
| >gi\|31747859\|gb\|AAP69660.1\| uncharacterized protein 9c [SARS coronavirus ZJ-HZ01] (SEQ ID NO.749) | AAVKPLLA |
| >gi\|31747859\|gb\|AAP69660.1\| uncharacterized protein 9c [SARS coronavirus ZJ-HZ01] (SEQ ID NO.750) | AVKPLLAP |
| >gi\|31747859\|gb\|AAP69660.1\| uncharacterized protein 9c [SARS coronavirus ZJ-HZ01] (SEQ ID NO.751) | VKPLLAPH |
| >gi\|31747859\|gb\|AAP69660.1\| uncharacterized protein 9c [SARS coronavirus ZJ-HZ01] (SEQ ID NO.752) | KPLLAPHH |
| >gi\|31747859\|gb\|AAP69660.1\| uncharacterized protein 9c [SARS coronavirus ZJ-HZ01] (SEQ ID NO.753) | PLLAPHHV |
| >gi\|31747859\|gb\|AAP69660.1\| uncharacterized protein 9c [SARS coronavirus ZJ-HZ01] (SEQ ID NO.754) | LLAPHHVV |

TABLE SARS-continued

List of SARS virus-specific PETs

| | |
|---|---|
| >gi\|31747859\|gb\|AAP69660.1\| uncharacterized protein 9c [SARS coronavirus ZJ-HZ01] (SEQ ID NO.755) | LAPHHVVA |
| >gi\|31747859\|gb\|AAP69660.1\| uncharacterized protein 9c [SARS coronavirus ZJ-HZ01] (SEQ ID NO.756) | APHHVVAV |
| >gi\|31747859\|gb\|AAP69660.1\| uncharacterized protein 9c [SARS coronavirus ZJ-HZ01] (SEQ ID NO.757) | PHHVVAVI |
| >gi\|31747859\|gb\|AAP69660.1\| uncharacterized protein 9c [SARS coronavirus ZJ-HZ01] (SEQ ID NO.758) | HHVVAVIQ |
| >gi\|31747859\|gb\|AAP69660.1\| uncharacterized protein 9c [SARS coronavirus ZJ-HZ01] (SEQ ID NO.759) | HVVAVIQE |
| >gi\|31747859\|gb\|AAP69660.1\| uncharacterized protein 9c [SARS coronavirus ZJ-HZ01] (SEQ ID NO.760) | VVAVIQEI |
| >gi\|31747859\|gb\|AAP69660.1\| uncharacterized protein 9c [SARS coronavirus ZJ-HZ01] (SEQ ID NO.761) | VAVIQEIQ |
| >gi\|31747859\|gb\|AAP69660.1\| uncharacterized protein 9c [SARS coronavirus ZJ-HZ01] (SEQ ID NO.762) | AVIQEIQL |
| >gi\|31747859\|gb\|AAP69660.1\| uncharacterized protein 9c [SARS coronavirus ZJ-HZ01] (SEQ ID NO.763) | VIQEIQLL |
| >gi\|31747859\|gb\|AAP69660.1\| uncharacterized protein 9c [SARS coronavirus ZJ-HZ01] (SEQ ID NO.764) | IQEIQLLA |
| >gi\|31747859\|gb\|AAP69660.1\| uncharacterized protein 9c [SARS coronavirus ZJ-HZ01] (SEQ ID NO.765) | QEIQLLAA |
| >gi\|31747859\|gb\|AAP69660.1\| uncharacterized protein 9c [SARS coronavirus ZJ-HZ01] (SEQ ID NO.766) | EIQLLAAV |
| >gi\|31747859\|gb\|AAP69660.1\| uncharacterized protein 9c [SARS coronavirus ZJ-HZ01] (SEQ ID NO.767) | IQLLAAVG |
| >gi\|31747859\|gb\|AAP69660.1\| uncharacterized protein 9c [SARS coronavirus ZJ-HZ01] (SEQ ID NO.768) | QLLAAVGE |
| >gi\|31747859\|gb\|AAP69660.1\| uncharacterized protein 9c [SARS coronavirus ZJ-HZ01] (SEQ ID NO.769) | LLAAVGEI |
| >gi\|31747859\|gb\|AAP69660.1\| uncharacterized protein 9c [SARS coronavirus ZJ-HZ01] (SEQ ID NO.770) | LAAVGEIL |
| >gi\|31747859\|gb\|AAP69660.1\| uncharacterized protein 9c [SARS coronavirus ZJ-HZ01] (SEQ ID NO.771) | AAVGEILL |
| >gi\|31747859\|gb\|AAP69660.1\| uncharacterized protein 9c [SARS coronavirus ZJ-HZ01] (SEQ ID NO.772) | AVGEILLL |
| >gi\|31747859\|gb\|AAP69660.1\| uncharacterized protein 9c [SARS coronavirus ZJ-HZ01] (SEQ ID NO.773) | VGEILLLE |
| >gi\|31747859\|gb\|AAP69660.1\| uncharacterized protein 9c [SARS coronavirus ZJ-HZ01] (SEQ ID NO.774) | GEILLLEW |
| >gi\|31747859\|gb\|AAP69660.1\| uncharacterized protein 9c [SARS coronavirus ZJ-HZ01] (SEQ ID NO.775) | EILLLEWL |
| >gi\|31747859\|gb\|AAP69660.1\| uncharacterized protein 9c [SARS coronavirus ZJ-HZ01] (SEQ ID NO.776) | ILLLEWLA |
| >gi\|31747859\|gb\|AAP69660.1\| uncharacterized protein 9c [SARS coronavirus ZJ-HZ01] (SEQ ID NO.777) | LLLEWLAE |
| >gi\|31747859\|gb\|AAP69660.1\| uncharacterized protein 9c [SARS coronavirus ZJ-HZ01] (SEQ ID NO.778) | LLEWLAEV |
| >gi\|31747859\|gb\|AAP69660.1\| uncharacterized protein 9c [SARS coronavirus ZJ-HZ01] (SEQ ID NO.779) | LEWLAEVV |
| >gi\|31747859\|gb\|AAP69660.1\| uncharacterized protein 9c [SARS coronavirus ZJ-HZ01] (SEQ ID NO.780) | EWLAEVVK |

TABLE SARS-continued

| List of SARS virus-specific PETs | |
|---|---|
| >gi\|31747859\|gb\|AAP69660.1\| uncharacterized protein 9c [SARS coronavirus ZJ-HZ01] (SEQ ID NO.781) | WLAEVVKL |
| >gi\|31747859\|gb\|AAP69660.1\| uncharacterized protein 9c [SARS coronavirus ZJ-HZ01] (SEQ ID NO.782) | LAEVVKLP |
| >gi\|31747859\|gb\|AAP69660.1\| uncharacterized protein 9c [SARS coronavirus ZJ-HZ01] (SEQ ID NO.783) | AEVVKLPS |
| >gi\|31747859\|gb\|AAP69660.1\| uncharacterized protein 9c [SARS coronavirus ZJ-HZ01] (SEQ ID NO.784) | EVVKLPSR |
| >gi\|31747859\|gb\|AAP69660.1\| uncharacterized protein 9c [SARS coronavirus ZJ-HZ01] (SEQ ID NO.785) | VVKLPSRY |
| >gi\|31747859\|gb\|AAP69660.1\| uncharacterized protein 9c [SARS coronavirus ZJ-HZ01] (SEQ ID NO.786) | VKLPSRYC |
| >gi\|31747859\|gb\|AAP69660.1\| uncharacterized protein 9c [SARS coronavirus ZJ-HZ01] (SEQ ID NO.787) | KLPSRYCC |
| >gi\|31416298\|gb\|AAP51230.1\| envelope protein E [SARS coronavirus GZ01] (SEQ ID NO.788) | VLLFLAFM |
| >gi\|31416298\|gb\|AAP51230.1\| envelope protein E [SARS coronavirus GZ01] (SEQ ID NO.789) | LLFLAFMV |
| >gi\|31416298\|gb\|AAP51230.1\| envelope protein E [SARS coronavirus GZ01] (SEQ ID NO.790) | LFLAFMVF |
| >gi\|31416298\|gb\|AAP51230.1\| envelope protein E [SARS coronavirus GZ01] (SEQ ID NO.791) | FLAFMVFL |
| >gi\|31416298\|gb\|AAP51230.1\| envelope protein E [SARS coronavirus GZ01] (SEQ ID NO.792) | LAFMVFLL |
| >gi\|31416298\|gb\|AAP51230.1\| envelope protein E [SARS coronavirus GZ01] (SEQ ID NO.793) | AFMVFLLV |
| >gi\|31416298\|gb\|AAP51230.1\| envelope protein E [SARS coronavirus GZ01] (SEQ ID NO.794) | FMVFLLVT |
| >gi\|31416298\|gb\|AAP51230.1\| envelope protein E [SARS coronavirus GZ01] (SEQ ID NO.795) | MVFLLVTL |
| >gi\|29836499-ref-NP_828854.1\| small envelope protein; protein sM; protein E [SARS coronavirus] (SEQ ID NO.796) | VLLFLAFV |
| >gi\|29836499-ref-NP_828854.1\| small envelope protein; protein sM; protein E [SARS coronavirus] (SEQ ID NO.797) | LLFLAFVV |
| >gi\|29836499-ref-NP_828854.1\| small envelope protein; protein sM; protein E [SARS coronavirus] (SEQ ID NO.798) | LFLAFVVF |
| >gi\|29836499-ref-NP_828854.1\| small envelope protein; protein sM; protein E [SARS coronavirus] (SEQ ID NO.799) | FLAFVVFL |
| >gi\|29836499-ref-NP_828854.1\| small envelope protein; protein sM; protein E [SARS coronavirus] (SEQ ID NO.800) | LAFVVFLL |
| >gi\|29836499-ref-NP_828854.1\| small envelope protein; protein sM; protein E [SARS coronavirus] (SEQ ID NO.801) | AFVVFLLV |
| >gi\|29836499-ref-NP_828854.1\| small envelope protein; protein sM; protein E [SARS coronavirus] (SEQ ID NO.802) | FVVFLLVT |
| >gi\|29836499-ref-NP_828854.1\| small envelope protein; protein sM; protein E [SARS coronavirus] (SEQ ID NO.803) | VVFLLVTL |
| >gi\|32187354\|gb\|AAP72983.1\| Orf8b [SARS coronavirus HSR 1] (SEQ ID NO.804) | MCLKILVR |
| >gi\|32187354\|gb\|AAP72983.1\| Orf8b [SARS coronavirus HSR 1] (SEQ ID NO.805) | CLKILVRY |
| >gi\|32187354\|gb\|AAP72983.1\| Orf8b [SARS coronavirus HSR 1] (SEQ ID NO.806) | LKILVRYN |

TABLE SARS-continued

List of SARS virus-specific PETs

| | |
|---|---|
| >gi\|32187354\|gb\|AAP72983.1\| Orf8b [SARS coronavirus HSR 1] (SEQ ID NO.807) | KILVRYNT |
| >gi\|32187354\|gb\|AAP72983.1\| Orf8b [SARS coronavirus HSR 1] (SEQ ID NO.808) | ILVRYNTR |
| >gi\|32187354\|gb\|AAP72983.1\| Orf8b [SARS coronavirus HSR 1] (SEQ ID NO.809) | LVRYNTRG |
| >gi\|32187354\|gb\|AAP72983.1\| Orf8b [SARS coronavirus HSR 1] (SEQ ID NO.810) | VRYNTRGN |
| >gi\|32187354\|gb\|AAP72983.1\| Orf8b [SARS coronavirus HSR 1] (SEQ ID NO.811) | TAAFRDVL |
| >gi\|32187354\|gb\|AAP72983.1\| Orf8b [SARS coronavirus HSR 1] (SEQ ID NO.812) | AAFRDVLV |
| >gi\|32187354\|gb\|AAP72983.1\| Orf8b [SARS coronavirus HSR 1] (SEQ ID NO.813) | AFRDVLVV |
| >gi\|32187354\|gb\|AAP72983.1\| Orf8b [SARS coronavirus HSR 1] (SEQ ID NO.814) | FRDVLVVL |
| >gi\|32187354\|gb\|AAP72983.1\| Orf8b [SARS coronavirus HSR 1] (SEQ ID NO.815) | RDVLVVLN |
| >gi\|32187354\|gb\|AAP72983.1\| Orf8b [SARS coronavirus HSR 1] (SEQ ID NO.816) | DVLVVLNK |
| >gi\|32187354\|gb\|AAP72983.1\| Orf8b [SARS coronavirus HSR 1] (SEQ ID NO.817) | VLVVLNKR |
| >gi\|32187354\|gb\|AAP72983.1\| Orf8b [SARS coronavirus HSR 1] (SEQ ID NO.818) | LVVLNKRT |
| >gi\|31416303\|gb\|AAP51235.1\| BGI-PUP7 [SARS coronavirus GZ01] (SEQ ID NO.819) | MDPNQTNV |
| >gi\|31416303\|gb\|AAP51235.1\| BGI-PUP7 [SARS coronavirus GZ01] (SEQ ID NO.820) | DPNQTNVV |
| >gi\|31416303\|gb\|AAP51235.1\| BGI-PUP7 [SARS coronavirus GZ01] (SEQ ID NO.821) | PNQTNVVP |
| >gi\|31416303\|gb\|AAP51235.1\| BGI-PUP7 [SARS coronavirus GZ01] (SEQ ID NO.822) | NQTNVVPP |
| >gi\|31416303\|gb\|AAP51235.1\| BGI-PUP7 [SARS coronavirus GZ01] (SEQ ID NO.823) | QTNVVPPA |
| >gi\|31416303\|gb\|AAP51235.1\| BGI-PUP7 [SARS coronavirus GZ01] (SEQ ID NO.824) | TNVVPPAL |
| >gi\|31416303\|gb\|AAP51235.1\| BGI-PUP7 [SARS coronavirus GZ01] (SEQ ID NO.825) | NVVPPALH |
| >gi\|31416303\|gb\|AAP51235.1\| BGI-PUP7 [SARS coronavirus GZ01] (SEQ ID NO.826) | VVPPALHL |
| >gi\|31416303\|gb\|AAP51235.1\| BGI-PUP7 [SARS coronavirus GZ01] (SEQ ID NO.827) | VPPALHLV |
| >gi\|31416303\|gb\|AAP51235.1\| BGI-PUP7 [SARS coronavirus GZ01] (SEQ ID NO.828) | PPALHLVD |
| >gi\|31416303\|gb\|AAP51235.1\| BGI-PUP7 [SARS coronavirus GZ01] (SEQ ID NO.829) | PALHLVDP |
| >gi\|31416303\|gb\|AAP51235.1\| BGI-PUP7 [SARS coronavirus GZ01] (SEQ ID NO.830) | ALHLVDPQ |
| >gi\|31416303\|gb\|AAP51235.1\| BGI-PUP7 [SARS coronavirus GZ01] (SEQ ID NO.831) | LHLVDPQI |
| >gi\|31416303\|gb\|AAP51235.1\| BGI-PUP7 [SARS coronavirus GZ01] (SEQ ID NO.832) | HLVDPQIQ |

TABLE SARS-continued

List of SARS virus-specific PETs

| | |
|---|---|
| >gi\|31416303\|gb\|AAP51235.1\| BGI-PUP7 [SARS coronavirus GZ01] (SEQ ID NO.833) | LVDPQIQL |
| >gi\|31416303\|gb\|AAP51235.1\| BGI-PUP7 [SARS coronavirus GZ01] (SEQ ID NO.834) | VDPQIQLT |
| >gi\|31416303\|gb\|AAP51235.1\| BGI-PUP7 [SARS coronavirus GZ01] (SEQ ID NO.835) | DPQIQLTI |
| >gi\|31416303\|gb\|AAP51235.1\| BGI-PUP7 [SARS coronavirus GZ01] (SEQ ID NO.836) | PQIQLTIT |
| >gi\|31416303\|gb\|AAP51235.1\| BGI-PUP7 [SARS coronavirus GZ01] (SEQ ID NO.837) | QIQLTITR |
| >gi\|31416303\|gb\|AAP51235.1\| BGI-PUP7 [SARS coronavirus GZ01] (SEQ ID NO.838) | IQLTITRM |
| >gi\|31416303\|gb\|AAP51235.1\| BGI-PUP7 [SARS coronavirus GZ01] (SEQ ID NO.839) | QLTITRME |
| >gi\|31416303\|gb\|AAP51235.1\| BGI-PUP7 [SARS coronavirus GZ01] (SEQ ID NO.840) | LTITRMED |
| >gi\|31416303\|gb\|AAP51235.1\| BGI-PUP7 [SARS coronavirus GZ01] (SEQ ID NO.841) | TITRMEDA |
| >gi\|31416303\|gb\|AAP51235.1\| BGI-PUP7 [SARS coronavirus GZ01] (SEQ ID NO.842) | ITRMEDAM |
| >gi\|31416303\|gb\|AAP51235.1\| BGI-PUP7 [SARS coronavirus GZ01] (SEQ ID NO.843) | TRMEDAMG |
| >gi\|31416303\|gb\|AAP51235.1\| BGI-PUP7 [SARS coronavirus GZ01] (SEQ ID NO.844) | RMEDAMGQ |
| >gi\|31416303\|gb\|AAP51235.1\| BGI-PUP7 [SARS coronavirus GZ01] (SEQ ID NO.845) | MEDAMGQG |
| >gi\|31416303\|gb\|AAP51235.1\| BGI-PUP7 [SARS coronavirus GZ01] (SEQ ID NO.846) | EDAMGQGQ |
| >gi\|31416303\|gb\|AAP51235.1\| BGI-PUP7 [SARS coronavirus GZ01] (SEQ ID NO.847) | DAMGQGQN |
| >gi\|31416303\|gb\|AAP51235.1\| BGI-PUP7 [SARS coronavirus GZ01] (SEQ ID NO.848) | AMGQGQNS |
| >gi\|31416303\|gb\|AAP51235.1\| BGI-PUP7 [SARS coronavirus GZ01] (SEQ ID NO.849) | MGQGQNSA |
| >gi\|31416303\|gb\|AAP51235.1\| BGI-PUP7 [SARS coronavirus GZ01] (SEQ ID NO.850) | GQGQNSAD |
| >gi\|31416303\|gb\|AAP51235.1\| BGI-PUP7 [SARS coronavirus GZ01] (SEQ ID NO.851) | QGQNSADP |
| >gi\|31416303\|gb\|AAP51235.1\| BGI-PUP7 [SARS coronavirus GZ01] (SEQ ID NO.852) | GQNSADPK |
| >gi\|31416303\|gb\|AAP51235.1\| BGI-PUP7 [SARS coronavirus GZ01] (SEQ ID NO.853) | QNSADPKV |
| >gi\|31416303\|gb\|AAP51235.1\| BGI-PUP7 [SARS coronavirus GZ01] (SEQ ID NO.854) | NSADPKVY |
| >gi\|31416303\|gb\|AAP51235.1\| BGI-PUP7 [SARS coronavirus GZ01] (SEQ ID NO.855) | SADPKVYP |
| >gi\|31416303\|gb\|AAP51235.1\| BGI-PUP7 [SARS coronavirus GZ01] (SEQ ID NO.856) | ADPKVYPI |
| >gi\|31416303\|gb\|AAP51235.1\| BGI-PUP7 [SARS coronavirus GZ01] (SEQ ID NO.857) | DPKVYPII |
| >gi\|31416303\|gb\|AAP51235.1\| BGI-PUP7 [SARS coronavirus GZ01] (SEQ ID NO.858) | PKVYPIIL |

TABLE SARS-continued

List of SARS virus-specific PETs

| | |
|---|---|
| >gi\|31416303\|gb\|AAP51235.1\| BGI-PUP7 [SARS coronavirus GZ01] (SEQ ID NO.859) | KVYPIILR |
| >gi\|31416303\|gb\|AAP51235.1\| BGI-PUP7 [SARS coronavirus GZ01] (SEQ ID NO.860) | VYPIILRL |
| >gi\|31416303\|gb\|AAP51235.1\| BGI-PUP7 [SARS coronavirus GZ01] (SEQ ID NO.861) | YPIILRLG |
| >gi\|31416303\|gb\|AAP51235.1\| BGI-PUP7 [SARS coronavirus GZ01] (SEQ ID NO.862) | PIILRLGS |
| >gi\|31416303\|gb\|AAP51235.1\| BGI-PUP7 [SARS coronavirus GZ01] (SEQ ID NO.863) | IILRLGSQ |
| >gi\|31416303\|gb\|AAP51235.1\| BGI-PUP7 [SARS coronavirus GZ01] (SEQ ID NO.864) | ILRLGSQL |
| >gi\|31416303\|gb\|AAP51235.1\| BGI-PUP7 [SARS coronavirus GZ01] (SEQ ID NO.865) | LRLGSQLS |
| >gi\|31416303\|gb\|AAP51235.1\| BGI-PUP7 [SARS coronavirus GZ01] (SEQ ID NO.866) | RLGSQLSL |
| >gi\|31416303\|gb\|AAP51235.1\| BGI-PUP7 [SARS coronavirus GZ01] (SEQ ID NO.867) | LGSQLSLS |
| >gi\|31416303\|gb\|AAP51235.1\| BGI-PUP7 [SARS coronavirus GZ01] (SEQ ID NO.868) | GSQLSLSM |
| >gi\|31416303\|gb\|AAP51235.1\| BGI-PUP7 [SARS coronavirus GZ01] (SEQ ID NO.869) | SQLSLSMA |
| >gi\|31416303\|gb\|AAP51235.1\| BGI-PUP7 [SARS coronavirus GZ01] (SEQ ID NO.870) | QLSLSMAR |
| >gi\|31416303\|gb\|AAP51235.1\| BGI-PUP7 [SARS coronavirus GZ01] (SEQ ID NO.871) | LSLSMARR |
| >gi\|31416303\|gb\|AAP51235.1\| BGI-PUP7 [SARS coronavirus GZ01] (SEQ ID NO.872) | SLSMARRN |
| >gi\|31416303\|gb\|AAP51235.1\| BGI-PUP7 [SARS coronavirus GZ01] (SEQ ID NO.873) | LSMARRNL |
| >gi\|31416303\|gb\|AAP51235.1\| BGI-PUP7 [SARS coronavirus GZ01] (SEQ ID NO.874) | SMARRNLD |
| >gi\|31416303\|gb\|AAP51235.1\| BGI-PUP7 [SARS coronavirus GZ01] (SEQ ID NO.875) | MARRNLDS |
| >gi\|31416303\|gb\|AAP51235.1\| BGI-PUP7 [SARS coronavirus GZ01] (SEQ ID NO.876) | ARRNLDSL |
| >gi\|31416303\|gb\|AAP51235.1\| BGI-PUP7 [SARS coronavirus GZ01] (SEQ ID NO.877) | RRNLDSLE |
| >gi\|31416303\|gb\|AAP51235.1\| BGI-PUP7 [SARS coronavirus GZ01] (SEQ ID NO.878) | RNLDSLEA |
| >gi\|31416303\|gb\|AAP51235.1\| BGI-PUP7 [SARS coronavirus GZ01] (SEQ ID NO.879) | NLDSLEAR |
| >gi\|31416303\|gb\|AAP51235.1\| BGI-PUP7 [SARS coronavirus GZ01] (SEQ ID NO.880) | LDSLEARA |
| >gi\|31416303\|gb\|AAP51235.1\| BGI-PUP7 [SARS coronavirus GZ01] (SEQ ID NO.881) | DSLEARAF |
| >gi\|31416303\|gb\|AAP51235.1\| BGI-PUP7 [SARS coronavirus GZ01] (SEQ ID NO.882) | SLEARAFQ |
| >gi\|31416303\|gb\|AAP51235.1\| BGI-PUP7 [SARS coronavirus GZ01] (SEQ ID NO.883) | LEARAFQS |
| >gi\|31416303\|gb\|AAP51235.1\| BGI-PUP7 [SARS coronavirus GZ01] (SEQ ID NO.884) | EARAFQST |

TABLE SARS-continued

List of SARS virus-specific PETs

| | |
|---|---|
| >gi\|31416303\|gb\|AAP51235.1\| BGI-PUP7 [SARS coronavirus GZ01] (SEQ ID NO.885) | ARAFQSTP |
| >gi\|31416303\|gb\|AAP51235.1\| BGI-PUP7 [SARS coronavirus GZ01] (SEQ ID NO.886) | RAFQSTPI |
| >gi\|31416303\|gb\|AAP51235.1\| BGI-PUP7 [SARS coronavirus GZ01] (SEQ ID NO.887) | AFQSTPIV |
| >gi\|31416303\|gb\|AAP51235.1\| BGI-PUP7 [SARS coronavirus GZ01] (SEQ ID NO.888) | FQSTPIVV |
| >gi\|31416303\|gb\|AAP51235.1\| BGI-PUP7 [SARS coronavirus GZ01] (SEQ ID NO.889) | QSTPIVVQ |
| >gi\|31416303\|gb\|AAP51235.1\| BGI-PUP7 [SARS coronavirus GZ01] (SEQ ID NO.890) | STPIVVQM |
| >gi\|31416303\|gb\|AAP51235.1\| BGI-PUP7 [SARS coronavirus GZ01] (SEQ ID NO.891) | TPIVVQMT |
| >gi\|31416303\|gb\|AAP51235.1\| BGI-PUP7 [SARS coronavirus GZ01] (SEQ ID NO.892) | PIVVQMTK |
| >gi\|31416303\|gb\|AAP51235.1\| BGI-PUP7 [SARS coronavirus GZ01] (SEQ ID NO.893) | IVVQMTKL |
| >gi\|31416303\|gb\|AAP51235.1\| BGI-PUP7 [SARS coronavirus GZ01] (SEQ ID NO.894) | VVQMTKLA |
| >gi\|31416303\|gb\|AAP51235.1\| BGI-PUP7 [SARS coronavirus GZ01] (SEQ ID NO.895) | VQMTKLAT |
| >gi\|31416303\|gb\|AAP51235.1\| BGI-PUP7 [SARS coronavirus GZ01] (SEQ ID NO.896) | QMTKLATT |
| >gi\|31416303\|gb\|AAP51235.1\| BGI-PUP7 [SARS coronavirus GZ01] (SEQ ID NO.897) | MTKLATTE |
| >gi\|31416303\|gb\|AAP51235.1\| BGI-PUP7 [SARS coronavirus GZ01] (SEQ ID NO.898) | TKLATTEE |
| >gi\|31416303\|gb\|AAP51235.1\| BGI-PUP7 [SARS coronavirus GZ01] (SEQ ID NO.899) | KLATTEEL |
| >gi\|31416303\|gb\|AAP51235.1\| BGI-PUP7 [SARS coronavirus GZ01] (SEQ ID NO.900) | LATTEELP |
| >gi\|31416303\|gb\|AAP51235.1\| BGI-PUP7 [SARS coronavirus GZ01] (SEQ ID NO.901) | ATTEELPD |
| >gi\|31416303\|gb\|AAP51235.1\| BGI-PUP7 [SARS coronavirus GZ01] (SEQ ID NO.902) | TTEELPDE |
| >gi\|31416303\|gb\|AAP51235.1\| BGI-PUP7 [SARS coronavirus GZ01] (SEQ ID NO.903) | TEELPDEF |
| >gi\|31416303\|gb\|AAP51235.1\| BGI-PUP7 [SARS coronavirus GZ01] (SEQ ID NO.904) | EELPDEFV |
| >gi\|31416303\|gb\|AAP51235.1\| BGI-PUP7 [SARS coronavirus GZ01] (SEQ ID NO.905) | ELPDEFVV |
| >gi\|31416303\|gb\|AAP51235.1\| BGI-PUP7 [SARS coronavirus GZ01] (SEQ ID NO.906) | LPDEFVVV |
| >gi\|31416303\|gb\|AAP51235.1\| BGI-PUP7 [SARS coronavirus GZ01] (SEQ ID NO.907) | PDEFVVVT |
| >gi\|31416303\|gb\|AAP51235.1\| BGI-PUP7 [SARS coronavirus GZ01] (SEQ ID NO.908) | DEFVVVTA |
| >gi\|31416303\|gb\|AAP51235.1\| BGI-PUP7 [SARS coronavirus GZ01] (SEQ ID NO.909) | EFVVVTAK |
| >gi\|31416304\|gb\|AAP51236.1\| BGI-PUP(GZ29-nt-Ins) [SARS coronavirus GZ01] (SEQ ID NO.910) | ISLCSCIR |

TABLE SARS-continued

List of SARS virus-specific PETs

| | |
|---|---|
| >gi\|31416304\|gb\|AAP51236.1\| BGI-PUP(GZ29-nt-Ins) [SARS coronavirus GZ01] (SEQ ID NO.911) | SLCSCIRT |
| >gi\|31416304\|gb\|AAP51236.1\| BGI-PUP(GZ29-nt-Ins) [SARS coronavirus GZ01] (SEQ ID NO.912) | LCSCIRTV |
| >gi\|31416304\|gb\|AAP51236.1\| BGI-PUP(GZ29-nt-Ins) [SARS coronavirus GZ01] (SEQ ID NO.913) | CSCIRTVV |
| >gi\|31416304\|gb\|AAP51236.1\| BGI-PUP(GZ29-nt-Ins) [SARS coronavirus GZ01] (SEQ ID NO.914) | SGIRTVVQ |
| >gi\|31416304\|gb\|AAP51236.1\| BGI-PUP(GZ29-nt-Ins) [SARS coronavirus GZ01] (SEQ ID NO.915) | CIRTVVQR |
| >gi\|31416304\|gb\|AAP51236.1\| BGI-PUP(GZ29-nt-Ins) [SARS coronavirus GZ01] (SEQ ID NO.916) | IRTVVQRC |
| >gi\|31416304\|gb\|AAP51236.1\| BGI-PUP(GZ29-nt-Ins) [SARS coronavirus GZ01] (SEQ ID NO.917) | RTVVQRCA |
| >gi\|31416304\|gb\|AAP51236.1\| BGI-PUP(GZ29-nt-Ins) [SARS coronavirus GZ01] (SEQ ID NO.918) | HVLEDPCP |
| >gi\|31416304\|gb\|AAP51236.1\| BGI-PUP(GZ29-nt-Ins) [SARS coronavirus GZ01] (SEQ ID NO.919) | VLEDPCPT |
| >gi\|31416304\|gb\|AAP51236.1\| BGI-PUP(GZ29-nt-Ins) [SARS coronavirus GZ01] (SEQ ID NO.920) | LEDPCPTG |
| >gi\|31416304\|gb\|AAP51236.1\| BGI-PUP(GZ29-nt-Ins) [SARS coronavirus GZ01] (SEQ ID NO.921) | EDPCPTGY |
| >gi\|31416304\|gb\|AAP51236.1\| BGI-PUP(GZ29-nt-Ins) [SARS coronavirus GZ01] (SEQ ID NO.922) | DPCPTGYQ |
| >gi\|31416304\|gb\|AAP51236.1\| BGI-PUP(GZ29-nt-Ins) [SARS coronavirus GZ01] (SEQ ID NO.923) | PCPTGYQP |
| >gi\|31416304\|gb\|AAP51236.1\| BGI-PUP(GZ29-nt-Ins) [SARS coronavirus GZ01] (SEQ ID NO.924) | CPTGYQPE |
| >gi\|31416304\|gb\|AAP51236.1\| BGI-PUP(GZ29-nt-Ins) [SARS coronavirus GZ01] (SEQ ID NO.925) | PTGYQPEW |
| >gi\|31416304\|gb\|AAP51236.1\| BGI-PUP(GZ29-nt-Ins) [SARS coronavirus GZ01] (SEQ ID NO.926) | TGYQPEWN |
| >gi\|31416304\|gb\|AAP51236.1\| BGI-PUP(GZ29-nt-Ins) [SARS coronavirus GZ01] (SEQ ID NO.927) | GYQPEWNI |
| >gi\|31416304\|gb\|AAP51236.1\| BGI-PUP(GZ29-nt-Ins) [SARS coronavirus GZ01] (SEQ ID NO.928) | YQPEWNIR |
| >gi\|31416304\|gb\|AAP51236.1\| BGI-PUP(GZ29-nt-Ins) [SARS coronavirus GZ01] (SEQ ID NO.929) | QPEWNIRY |
| >gi\|31416304\|gb\|AAP51236.1\| BGI-PUP(GZ29-nt-Ins) [SARS coronavirus GZ01] (SEQ ID NO.930) | PEWNIRYN |
| >gi\|31416304\|gb\|AAP51236.1\| BGI-PUP(GZ29-nt-Ins) [SARS coronavirus GZ01] (SEQ ID NO.931) | EWNIRYNT |
| >gi\|31416304\|gb\|AAP51236.1\| BGI-PUP(GZ29-nt-Ins) [SARS coronavirus GZ01] (SEQ ID NO.932) | WNIRYNTR |
| >gi\|31416304\|gb\|AAP51236.1\| BGI-PUP(GZ29-nt-Ins) [SARS coronavirus GZ01] (SEQ ID NO.933) | NIRYNTRG |
| >gi\|31416304\|gb\|AAP51236.1\| BGI-PUP(GZ29-nt-Ins) [SARS coronavirus GZ01] (SEQ ID NO.934) | IRYNTRGN |
| >gi\|31416304\|gb\|AAP51236.1\| BGI-PUP(GZ29-nt-Ins) [SARS coronavirus GZ01] (SEQ ID NO.935) | TAAFRDVF |
| >gi\|31416304\|gb\|AAP51236.1\| BGI-PUP(GZ29-nt-Ins) [SARS coronavirus GZ01] (SEQ ID NO.936) | AAFRDVFV |

TABLE SARS-continued

List of SARS virus-specific PETs

| | |
|---|---|
| >gi\|31416

TABLE SARS-continued

List of SARS virus-specific PETs

| | |
|---|---|
| >gi\|31581511\|gb\|AAP33703.1\| Orf7a [SARS coronavirus Frankfurt 1] (SEQ ID NO.963) | QECVRGTT |
| >gi\|31581511\|gb\|AAP33703.1\| Orf7a [SARS coronavirus Frankfurt 1] (SEQ ID NO.964) | ECVRGTTV |
| >gi\|31581511\|gb\|AAP33703.1\| Orf7a [SARS coronavirus Frankfurt 1] (SEQ ID NO.965) | CVRGTTVL |
| >gi\|31581511\|gb\|AAP33703.1\| Orf7a [SARS coronavirus Frankfurt 1] (SEQ ID NO.966) | VRGTTVLL |
| >gi\|31581511\|gb\|AAP33703.1\| Orf7a [SARS coronavirus Frankfurt 1] (SEQ ID NO.967) | RGTTVLLK |
| >gi\|31581511\|gb\|AAP33703.1\| Orf7a [SARS coronavirus Frankfurt 1] (SEQ ID NO.968) | GTTVLLKE |
| >gi\|31581511\|gb\|AAP33703.1\| Orf7a [SARS coronavirus Frankfurt 1] (SEQ ID NO.969) | TTVLLKEP |
| >gi\|31581511\|gb\|AAP33703.1\| Orf7a [SARS coronavirus Frankfurt 1] (SEQ ID NO.970) | TVLLKEPC |
| >gi\|31581511\|gb\|AAP33703.1\| Orf7a [SARS coronavirus Frankfurt 1] (SEQ ID NO.971) | VLLKEPCP |
| >gi\|31581511\|gb\|AAP33703.1\| Orf7a [SARS coronavirus Frankfurt 1] (SEQ ID NO.972) | LLKEPCPS |
| >gi\|31581511\|gb\|AAP33703.1\| Orf7a [SARS coronavirus Frankfurt 1] (SEQ ID NO.973) | LKEPCPSG |
| >gi\|31581511\|gb\|AAP33703.1\| Orf7a [SARS coronavirus Frankfurt 1] (SEQ ID NO.974) | KEPCPSGT |
| >gi\|31581511\|gb\|AAP33703.1\| Orf7a [SARS coronavirus Frankfurt 1] (SEQ ID NO.975) | EPCPSGTY |
| >gi\|31581511\|gb\|AAP33703.1\| Orf7a [SARS coronavirus Frankfurt 1] (SEQ ID NO.976) | PCPSGTYE |
| >gi\|31581511\|gb\|AAP33703.1\| Orf7a [SARS coronavirus Frankfurt 1] (SEQ ID NO.977) | CPSGTYEG |
| >gi\|31581511\|gb\|AAP33703.1\| Orf7a [SARS coronavirus Frankfurt 1] (SEQ ID NO.978) | PSGTYEGN |
| >gi\|31581511\|gb\|AAP33703.1\| Orf7a [SARS coronavirus Frankfurt 1] (SEQ ID NO.979) | SGTYEGNS |
| >gi\|31581511\|gb\|AAP33703.1\| Orf7a [SARS coronavirus Frankfurt 1] (SEQ ID NO.980) | GTYEGNSP |
| >gi\|31581511\|gb\|AAP33703.1\| Orf7a [SARS coronavirus Frankfurt 1] (SEQ ID NO.981) | TYEGNSPF |
| >gi\|31581511\|gb\|AAP33703.1\| Orf7a [SARS coronavirus Frankfurt 1] (SEQ ID NO.982) | YEGNSPFH |
| >gi\|31581511\|gb\|AAP33703.1\| Orf7a [SARS coronavirus Frankfurt 1] (SEQ ID NO.983) | EGNSPFHP |
| >gi\|31581511\|gb\|AAP33703.1\| Orf7a [SARS coronavirus Frankfurt 1] (SEQ ID NO.984) | GNSPFHPL |
| >gi\|31581511\|gb\|AAP33703.1\| Orf7a [SARS coronavirus Frankfurt 1] (SEQ ID NO.985) | NSPFHPLA |
| >gi\|31581511\|gb\|AAP33703.1\| Orf7a [SARS coronavirus Frankfurt 1] (SEQ ID NO.986) | SPFHPLAD |
| >gi\|31581511\|gb\|AAP33703.1\| Orf7a [SARS coronavirus Frankfurt 1] (SEQ ID NO.987) | PFHPLADN |
| >gi\|31581511\|gb\|AAP33703.1\| Orf7a [SARS coronavirus Frankfurt 1] (SEQ ID NO.988) | FHPLADNK |

TABLE SARS-continued

List of SARS virus-specific PETs

| | |
|---|---|
| >gi\|31581511\|gb\|AAP33703.1\| Orf7a [SARS coronavirus Frankfurt 1] (SEQ ID NO.989) | HPLADNKF |
| >gi\|31581511\|gb\|AAP33703.1\| Orf7a [SARS coronavirus Frankfurt 1] (SEQ ID NO.990) | PLADNKFA |
| >gi\|31581511\|gb\|AAP33703.1\| Orf7a [SARS coronavirus Frankfurt 1] (SEQ ID NO.991) | LADNKFAL |
| >gi\|31581511\|gb\|AAP33703.1\| Orf7a [SARS coronavirus Frankfurt 1] (SEQ ID NO.992) | ADNKFALT |
| >gi\|31581511\|gb\|AAP33703.1\| Orf7a [SARS coronavirus Frankfurt 1] (SEQ ID NO.993) | DNKFALTC |
| >gi\|31581511\|gb\|AAP33703.1\| Orf7a [SARS coronavirus Frankfurt 1] (SEQ ID NO.994) | NKFALTCT |
| >gi\|31581511\|gb\|AAP33703.1\| Orf7a [SARS coronavirus Frankfurt 1] (SEQ ID NO.995) | KFALTCTS |
| >gi\|31581511\|gb\|AAP33703.1\| Orf7a [SARS coronavirus Frankfurt 1] (SEQ ID NO.996) | FALTCTST |
| >gi\|31581511\|gb\|AAP33703.1\| Orf7a [SARS coronavirus Frankfurt 1] (SEQ ID NO.997) | ALTCTSTH |
| >gi\|31581511\|gb\|AAP33703.1\| Orf7a [SARS coronavirus Frankfurt 1] (SEQ ID NO.998) | LTCTSTHF |
| >gi\|31581511\|gb\|AAP33703.1\| Orf7a [SARS coronavirus Frankfurt 1] (SEQ ID NO.999) | TCTSTHFA |
| >gi\|31581511\|gb\|AAP33703.1\| Orf7a [SARS coronavirus Frankfurt 1] (SEQ ID NO.1000) | CTSTHFAF |
| >gi\|31581511\|gb\|AAP33703.1\| Orf7a [SARS coronavirus Frankfurt 1] (SEQ ID NO.1001) | TSTHFAFA |
| >gi\|31581511\|gb\|AAP33703.1\| Orf7a [SARS coronavirus Frankfurt 1] (SEQ ID NO.1002) | STHFAFAC |
| >gi\|31581511\|gb\|AAP33703.1\| Orf7a [SARS coronavirus Frankfurt 1] (SEQ ID NO.1003) | THFAFACA |
| >gi\|31581511\|gb\|AAP33703.1\| Orf7a [SARS coronavirus Frankfurt 1] (SEQ ID NO.1004) | HFAFACAD |
| >gi\|31581511\|gb\|AAP33703.1\| Orf7a [SARS coronavirus Frankfurt 1] (SEQ ID NO.10005 | FAFACADG |
| >gi\|31581511\|gb\|AAP33703.1\| Orf7a [SARS coronavirus Frankfurt 1] (SEQ ID NO.1006) | AFACADGT |
| >gi\|31581511\|gb\|AAP33703.1\| Orf7a [SARS coronavirus Frankfurt 1] (SEQ ID NO.1007) | FACADGTR |
| >gi\|31581511\|gb\|AAP33703.1\| Orf7a [SARS coronavirus Frankfurt 1] (SEQ ID NO.1008) | ACADGTRH |
| >gi\|31581511\|gb\|AAP33703.1\| Orf7a [SARS coronavirus Frankfurt 1] (SEQ ID NO.1009) | CADGTRHT |
| >gi\|31581511\|gb\|AAP33703.1\| Orf7a [SARS coronavirus Frankfurt 1] (SEQ ID NO.1010) | ADGTRHTY |
| >gi\|31581511\|gb\|AAP33703.1\| Orf7a [SARS coronavirus Frankfurt 1] (SEQ ID NO.1011) | DGTRHTYQ |
| >gi\|31581511\|gb\|AAP33703.1\| Orf7a [SARS coronavirus Frankfurt 1] (SEQ ID NO.1012) | GTRHTYQL |
| >gi\|31581511\|gb\|AAP33703.1\| Orf7a [SARS coronavirus Frankfurt 1] (SEQ ID NO.1013) | TRHTYQLR |
| >gi\|31581511\|gb\|AAP33703.1\| Orf7a [SARS coronavirus Frankfurt 1] (SEQ ID NO.1014) | RHTYQLRA |

TABLE SARS-continued

List of SARS virus-specific PETs

| | |
|---|---|
| >gi\|31581511\|gb\|AAP33703.1\| Orf7a [SARS coronavirus Frankfurt 1] (SEQ ID NO.1015) | HTYQLRAR |
| >gi\|31581511\|gb\|AAP33703.1\| Orf7a [SARS coronavirus Frankfurt 1] (SEQ ID NO.1016) | TYQLRARS |
| >gi\|31581511\|gb\|AAP33703.1\| Orf7a [SARS coronavirus Frankfurt 1] (SEQ ID NO.1017) | YQLRARSV |
| >gi\|31581511\|gb\|AAP33703.1\| Orf7a [SARS coronavirus Frankfurt 1] (SEQ ID NO.1018) | QLRARSVS |
| >gi\|31581511\|gb\|AAP33703.1\| Orf7a [SARS coronavirus Frankfurt 1] (SEQ ID NO.1019) | LRARSVSP |
| >gi\|31581511\|gb\|AAP33703.1\| Orf7a [SARS coronavirus Frankfurt 1] (SEQ ID NO.1020) | RARSVSPK |
| >gi\|31581511\|gb\|AAP33703.1\| Orf7a [SARS coronavirus Frankfurt 1] (SEQ ID NO.1021) | ARSVSPKL |
| >gi\|31581511\|gb\|AAP33703.1\| Orf7a [SARS coronavirus Frankfurt 1] (SEQ ID NO.1022) | RSVSPKLF |
| >gi\|31581511\|gb\|AAP33703.1\| Orf7a [SARS coronavirus Frankfurt 1] (SEQ ID NO.1023) | SVSPKLFI |
| >gi\|31581511\|gb\|AAP33703.1\| Orf7a [SARS coronavirus Frankfurt 1] (SEQ ID NO.1024) | VSPKLFIR |
| >gi\|31581511\|gb\|AAP33703.1\| Orf7a [SARS coronavirus Frankfurt 1] (SEQ ID NO.1025) | SPKLFIRQ |
| >gi\|31581511\|gb\|AAP33703.1\| Orf7a [SARS coronavirus Frankfurt 1] (SEQ ID NO.1026) | PKLFIRQE |
| >gi\|31581511\|gb\|AAP33703.1\| Orf7a [SARS coronavirus Frankfurt 1] (SEQ ID NO.1027) | KLFIRQEE |
| >gi\|31581511\|gb\|AAP33703.1\| Orf7a [SARS coronavirus Frankfurt 1] (SEQ ID NO.1028) | LFIRQEEV |
| >gi\|31581511\|gb\|AAP33703.1\| Orf7a [SARS coronavirus Frankfurt 1] (SEQ ID NO.1029) | FIRQEEVQ |
| >gi\|31581511\|gb\|AAP33703.1\| Orf7a [SARS coronavirus Frankfurt 1] (SEQ ID NO.1030) | IRQEEVQQ |
| >gi\|31581511\|gb\|AAP33703.1\| Orf7a [SARS coronavirus Frankfurt 1] (SEQ ID NO.1031) | RQEEVQQE |
| >gi\|31581511\|gb\|AAP33703.1\| Orf7a [SARS coronavirus Frankfurt 1] (SEQ ID NO.1032) | QEEVQQEL |
| >gi\|31581511\|gb\|AAP33703.1\| Orf7a [SARS coronavirus Frankfurt 1] (SEQ ID NO.1033) | EEVQQELY |
| >gi\|31581511\|gb\|AAP33703.1\| Orf7a [SARS coronavirus Frankfurt 1] (SEQ ID NO.1034) | EVQQELYS |
| >gi\|31581511\|gb\|AAP33703.1\| Orf7a [SARS coronavirus Frankfurt 1] (SEQ ID NO.1035) | VQQELYSP |
| >gi\|31581511\|gb\|AAP33703.1\| Orf7a [SARS coronavirus Frankfurt 1] (SEQ ID NO.1036) | QQELYSPL |
| >gi\|31581511\|gb\|AAP33703.1\| Orf7a [SARS coronavirus Frankfurt 1] (SEQ ID NO.1037) | QELYSPLF |
| >gi\|31581511\|gb\|AAP33703.1\| Orf7a [SARS coronavirus Frankfurt 1] (SEQ ID NO.1038) | ELYSPLFL |
| >gi\|31581511\|gb\|AAP33703.1\| Orf7a [SARS coronavirus Frankfurt 1] (SEQ ID NO.1039) | LYSPLFLI |
| >gi\|31581511\|gb\|AAP33703.1\| Orf7a [SARS coronavirus Frankfurt 1] (SEQ ID NO.1040) | YSPLFLIV |

TABLE SARS-continued

| List of SARS virus-specific PETs | |
|---|---|
| >gi\|31581511\|gb\|AAP33703.1\| Orf7a [SARS coronavirus Frankfurt 1] (SEQ ID NO.1041) | SPLELIVA |
| >gi\|31581511\|gb\|AAP33703.1\| Orf7a [SARS coronavirus Frankfurt 1] (SEQ ID NO.1042) | PLFLIVAA |
| >gi\|31581511\|gb\|AAP33703.1\| Orf7a [SARS coronavirus Frankfurt 1] (SEQ ID NO.1043) | LFLIVAAL |
| >gi\|31581511\|gb\|AAP33703.1\| Orf7a [SARS coronavirus Frankfurt 1] (SEQ ID NO.1044) | FLIVAALV |
| >gi\|31581511\|gb\|AAP33703.1\| Orf7a [SARS coronavirus Frankfurt 1] (SEQ ID NO.1045) | LIVAALVF |
| >gi\|31581511\|gb\|AAP33703.1\| Orf7a [SARS coronavirus Frankfurt 1] (SEQ ID NO.1046) | IVAALVFL |
| >gi\|31581511\|gb\|AAP33703.1\| Orf7a [SARS coronavirus Frankfurt 1] (SEQ ID NO.1047) | VAALVFLI |
| >gi\|31581511\|gb\|AAP33703.1\| Orf7a [SARS coronavirus Frankfurt 1] (SEQ ID NO.1048) | AALVFLIL |
| >gi\|31581511\|gb\|AAP33703.1\| Orf7a [SARS coronavirus Frankfurt 1] (SEQ ID NO.1049) | ALVFLILC |
| >gi\|31581511\|gb\|AAP33703.1\| Orf7a [SARS coronavirus Frankfurt 1] (SEQ ID NO.1050) | LVFLILCF |
| >gi\|31581511\|gb\|AAP33703.1\| Orf7a [SARS coronavirus Frankfurt 1] (SEQ ID NO.1051) | VFLILCFT |
| >gi\|31581511\|gb\|AAP33703.1\| Orf7a [SARS coronavirus Frankfurt 1] (SEQ ID NO.1052) | FLILCFTI |
| >gi\|31581511\|gb\|AAP33703.1\| Orf7a [SARS coronavirus Frankfurt 1] (SEQ ID NO.1053) | LILCFTIK |
| >gi\|31581511\|gb\|AAP33703.1\| Orf7a [SARS coronavirus Frankfurt 1] (SEQ ID NO.1054) | ILCFTIKR |
| >gi\|31581511\|gb\|AAP33703.1\| Orf7a [SARS coronavirus Frankfurt 1] (SEQ ID NO.1055) | LCFTIKRK |
| >gi\|31581511\|gb\|AAP33703.1\| Orf7a [SARS coronavirus Frankfurt 1] (SEQ ID NO.1056) | CFTIKRKT |
| >gi\|31581511\|gb\|AAP33703.1\| Orf7a [SARS coronavirus Frankfurt 1] (SEQ ID NO.1057) | FTIKRKTE |
| >gi\|30026017\|gb\|AAP04587.1\| RNA-directed RNA polymerase [SARS coronavirus Taiwan] (SEQ ID NO.1058) | ILSDDGVX |
| >gi\|30026017\|gb\|AAP04587.1\| RNA-directed RNA polymerase [SARS coronavirus Taiwan] (SEQ ID NO.1059) | LSDDGVXV |
| >gi\|30026017\|gb\|AAP04587.1\| RNA-directed RNA polymerase [SARS coronavirus Taiwan] (SEQ ID NO.1060) | SDDGVXVL |
| >gi\|30026017\|gb\|AAP04587.1\| RNA-directed RNA polymerase [SARS coronavirus Taiwan] (SEQ ID NO.1061) | DDGVXVLN |
| >gi\|30275671\|gb\|AAP30032.1\| putative uncharacterized protein 2 [SARS coronavirus BJ01] (SEQ ID NO.1062) | LLIQQWIP |
| >gi\|30275671\|gb\|AAP30032.1\| putative uncharacterized protein 2 [SARS coronavirus BJ01] (SEQ ID NO.1063) | LIQQWIPF |
| >gi\|30275671\|gb\|AAP30032.1\| putative uncharacterized protein 2 [SARS coronavirus BJ01] (SEQ ID NO.1064) | IQQWIPFM |
| >gi\|30275671\|gb\|AAP30032.1\| putative uncharacterized protein 2 [SARS coronavirus BJ01] (SEQ ID NO.1065) | QQWIPFMM |
| >gi\|30275671\|gb\|AAP30032.1\| putative uncharacterized protein 2 [SARS coronavirus BJ01] (SEQ ID NO.1066) | QWIPFMMS |

TABLE SARS-continued

List of SARS virus-specific PETs

| | |
|---|---|
| >gi\|30275671\|gb\|AAP30032.1\| putative uncharacterized protein 2 [SARS coronavirus BJ01] (SEQ ID NO.1067) | WIPFMMSR |
| >gi\|30275671\|gb\|AAP30032.1\| putative uncharacterized protein 2 [SARS coronavirus BJ01] (SEQ ID NO.1068) | IPFMMSRR |
| >gi\|30275671\|gb\|AAP30032.1\| putative uncharacterized protein 2 [SARS coronavirus BJ01] (SEQ ID NO.1069) | PFMMSRRR |
| >gi\|31416297\|gb\|AAP51229.1\| BGI-PUP2 [SARS coronavirus GZ-1] (SEQ ID NO.1070) | QIQLSLLQ |
| >gi\|31416297\|gb\|AAP51229.1\| BGI-PUP2 [SARS coronavirus GZ-1] (SEQ ID NO.1071) | IQLSLLQV |
| >gi\|31416297\|gb\|AAP51229.1\| BGI-PUP2 [SARS coronavirus GZ-1] (SEQ ID NO.1072) | QLSLLQVT |
| >gi\|31416297\|gb\|AAP51229.1\| BGI-PUP2 [SARS coronavirus GZ-1] (SEQ ID NO.1073) | LSLLQVTA |
| >gi\|31416297\|gb\|AAP51229.1\| BGI-PUP2 [SARS coronavirus GZ-1] (SEQ ID NO.1074) | SLLQVTAF |
| >gi\|31416297\|gb\|AAP51229.1\| BGI-PUP2 [SARS coronavirus GZ-1] (SEQ ID NO.1075) | LLQVTAFQ |
| >gi\|31416297\|gb\|AAP51229.1\| BGI-PUP2 [SARS coronavirus GZ-1] (SEQ ID NO.1076) | LQVTAFQH |
| >gi\|31416297\|gb\|AAP51229.1\| BGI-PUP2 [SARS coronavirus GZ-1] (SEQ ID NO.1077) | QVTAFQHQ |
| >gi\|31416297\|gb\|AAP51229.1\| BGI-PUP2 [SARS coronavirus GZ-1] (SEQ ID NO.1078) | STALQELQ |
| >gi\|31416297\|gb\|AAP51229.1\| BGI-PUP2 [SARS coronavirus GZ-1] (SEQ ID NO.1079) | TALQELQI |
| >gi\|31416297\|gb\|AAP51229.1\| BGI-PUP2 [SARS coronavirus GZ-1] (SEQ ID NO.1080) | ALQELQIQ |
| >gi\|31416297\|gb\|AAP51229.1\| BGI-PUP2 [SARS coronavirus GZ-1] (SEQ ID NO.1081) | LQELQIQQ |
| >gi\|31416297\|gb\|AAP51229.1\| BGI-PUP2 [SARS coronavirus GZ-1] (SEQ ID NO.1082) | QELQIQQW |
| >gi\|31416297\|gb\|AAP51229.1\| BGI-PUP2 [SARS coronavirus GZ-1] (SEQ ID NO.1083) | ELQIQQWI |
| >gi\|31416297\|gb\|AAP51229.1\| BGI-PUP2 [SARS coronavirus GZ-1] (SEQ ID NO.1084) | LQIQQWIQ |
| >gi\|31416297\|gb\|AAP51229.1\| BGI-PUP2 [SARS coronavirus GZ-1] (SEQ ID NO.1085) | QIQQWIQF |
| >gi\|30795147\|gb\|AAP41039.1\| Orf4 [SARS coronavirus Tor2] (SEQ ID NO.1086) | LLIQQWIQ |
| >gi\|30795147\|gb\|AAP41039.1\| Orf4 [SARS coronavirus Tor2] (SEQ ID NO.1087) | LIQQWIQF |
| >gi\|30314342\|gb\|AAP06763.1\| RNA-directed RNA polymerase [SARS coronavirus Hong Kong/03/2003] (SEQ ID NO.1088) | QDAVASKI |
| >gi\|30314342\|gb\|AAP06763.1\| RNA-directed RNA polymerase [SARS coronavirus Hong Kong/03/2003] (SEQ ID NO.1089) | DAVASKIL |
| >gi\|30314342\|gb\|AAP06763.1\| RNA-directed RNA polymerase [SARS coronavirus Hong Kong/03/2003] (SEQ ID NO.1090) | YVDTENNL |
| >gi\|31581509\|gb\|AAP33701.1\| membrane protein M [SARS coronavirus Frankfurt 1] (SEQ ID NO.1091) | LACFVLAV |
| >gi\|31581509\|gb\|AAP33701.1\| membrane protein M [SARS coronavirus Frankfurt 1] (SEQ ID NO.1092) | ACFVLAVV |

TABLE SARS-continued

List of SARS virus-specific PETs

| | |
|---|---|
| >gi\|31581509\|gb\|AAP33701.1\| membrane protein M [SARS coronavirus Frankfurt 1] (SEQ ID NO.1093) | CFVLAVVY |
| >gi\|31581509\|gb\|AAP33701.1\| membrane protein M [SARS coronavirus Frankfurt 1] (SEQ ID NO.1094) | FVLAVVYR |
| >gi\|31581509\|gb\|AAP33701.1\| membrane protein M [SARS coronavirus Frankfurt 1] (SEQ ID NO.1095) | VLAVVYRI |
| >gi\|31581509\|gb\|AAP33701.1\| membrane protein M [SARS coronavirus Frankfurt 1] (SEQ ID NO.1096) | LAVVYRIN |
| >gi\|31581509\|gb\|AAP33701.1\| membrane protein M [SARS coronavirus Frankfurt 1] (SEQ ID NO.1097) | AVVYRINW |
| >gi\|31581509\|gb\|AAP33701.1\| membrane protein M [SARS coronavirus Frankfurt 1] (SEQ ID NO.1098) | VVYRINWV |
| >gi\|30027623\|gb\|AAP13444.1\| M protein [SARS coronavirus Urbani] (SEQ ID NO.1099) | HLRMAGHP |
| >gi\|30027623\|gb\|AAP13444.1\| M protein [SARS coronavirus Urbani] (SEQ ID NO.1100) | LRMAGHPL |
| >gi\|30027623\|gb\|AAP13444.1\| M protein [SARS coronavirus Urbani] (SEQ ID NO.1101) | RMAGHPLG |
| >gi\|30027623\|gb\|AAP13444.1\| M protein [SARS coronavirus Urbani] (SEQ ID NO.1102) | MAGHPLGR |
| >gi\|30027623\|gb\|AAP13444.1\| M protein [SARS coronavirus Urbani] (SEQ ID NO.1103) | AGHPLGRC |
| >gi\|30027623\|gb\|AAP13444.1\| M protein [SARS coronavirus Urbani] (SEQ ID NO.1104) | GHPLGRCD |
| >gi\|30027623\|gb\|AAP13444.1\| M protein [SARS coronavirus Urbani] (SEQ ID NO.1105) | HPLGRCDI |
| >gi\|30027623\|gb\|AAP13444.1\| M protein [SARS coronavirus Urbani] (SEQ ID NO.1106) | PLGRCDIK |
| >gi\|30275670\|gb\|AAP30031.1\| putative uncharacterized protein 1 [SARS coronavirus BJ01] (SEQ ID NO.1107) | LCWKCKSQ |
| >gi\|30275670\|gb\|AAP30031.1\| putative uncharacterized protein 1 [SARS coronavirus BJ01] (SEQ ID NO.1108) | CWKCKSQN |
| >gi\|30275670\|gb\|AAP30031.1\| putative uncharacterized protein 1 [SARS coronavirus BJ01] (SEQ ID NO.1109) | WKCKSQNP |
| >gi\|30275670\|gb\|AAP30031.1\| putative uncharacterized protein 1 [SARS coronavirus BJ01] (SEQ ID NO.1110) | KCKSQNPL |
| >gi\|30275670\|gb\|AAP30031.1\| putative uncharacterized protein 1 [SARS coronavirus BJ01] (SEQ ID NO.1111) | CKSQNPLL |
| >gi\|30275670\|gb\|AAP30031.1\| putative uncharacterized protein 1 [SARS coronavirus BJ01] (SEQ ID NO.1112) | KSQNPLLY |
| >gi\|30275670\|gb\|AAP30031.1\| putative uncharacterized protein 1 [SARS coronavirus BJ01] (SEQ ID NO.1113) | SQNPLLYD |
| >gi\|30275670\|gb\|AAP30031.1\| putative uncharacterized protein 1 [SARS coronavirus BJ01] (SEQ ID NO.1114) | QNPLLYDA |
| >gi\|31416296\|gb\|AAP51228.1\| BGI-PUP 1 [SARS coronavirus GZ-1] (SEQ ID NO.1115) | TDTIVVTA |
| >gi\|31416296\|gb\|AAP51228.1\| BGI-PUP 1 [SARS coronavirus GZ-1] (SEQ ID NO.1116) | DTIVVTAG |
| >gi\|31416296\|gb\|AAP51228.1\| BGI-PUP 1 [SARS coronavirus GZ-1] (SEQ ID NO.1117) | TIVVTAGD |
| >gi\|31416296\|gb\|AAP51228.1\| BGI-PUP 1 [SARS coronavirus GZ-1] (SEQ ID NO.1118) | IVVTAGDG |

TABLE SARS-continued

List of SARS virus-specific PETs

| | |
|---|---|
| >gi\|31416296\|gb\|AAP51228.1\| BGI-PUP 1 [SARS coronavirus GZ-1] (SEQ ID NO.1119) | VVTAGDGI |
| >gi\|31416296\|gb\|AAP51228.1\| BGI-PUP 1 [SARS coronavirus GZ-1] (SEQ ID NO.1120) | VTAGDGIS |
| >gi\|31416296\|gb\|AAP51228.1\| BGI-PUP 1 [SARS coronavirus GZ-1] (SEQ ID NO.1121) | TAGDGIST |
| >gi\|31416296\|gb\|AAP51228.1\| BGI-PUP 1 [SARS coronavirus GZ-1] (SEQ ID NO.1122) | AGDGISTP |
| >gi\|31416296\|gb\|AAP51228.1\| BGI-PUP 1 [SARS coronavirus GZ-1] (SEQ ID NO.1123) | IGGYSEDW |
| >gi\|31416296\|gb\|AAP51228.1\| BGI-PUP 1 [SARS coronavirus GZ-1] (SEQ ID NO.1124) | GGYSEDWH |
| >gi\|31416296\|gb\|AAP51228.1\| BGI-PUP 1 [SARS coronavirus GZ-1] (SEQ ID NO.1125) | GYSEDWHS |
| >gi\|31416296\|gb\|AAP51228.1\| BGI-PUP 1 [SARS coronavirus GZ-1] (SEQ ID NO.1126) | YSEDWHSG |
| >gi\|31416296\|gb\|AAP51228.1\| BGI-PUP 1 [SARS coronavirus GZ-1] (SEQ ID NO.1127) | SEDWHSGV |
| >gi\|31416296\|gb\|AAP51228.1\| BGI-PUP 1 [SARS coronavirus GZ-1] (SEQ ID NO.1128) | EDWHSGVK |
| >gi\|31416296\|gb\|AAP51228.1\| BGI-PUP 1 [SARS coronavirus GZ-1] (SEQ ID NO.1129) | DWHSGVKD |
| >gi\|31416296\|gb\|AAP51228.1\| BGI-PUP 1 [SARS coronavirus GZ-1] (SEQ ID NO.1130) | WHSGVKDY |
| >gi\|30795146\|gb\|AAP41038.1\| Orf3 [SARS coronavirus Tor2] (SEQ ID NO.1131) | FMRFFTLR |
| >gi\|30795146\|gb\|AAP41038.1\| Orf3 [SARS coronavirus Tor2] (SEQ ID NO.1132) | MRFFTLRS |
| >gi\|30795146\|gb\|AAP41038.1\| Orf3 [SARS coronavirus Tor2] (SEQ ID NO.1133) | RFFTLRSI |
| >gi\|30795146\|gb\|AAP41038.1\| Orf3 [SARS coronavirus Tor2] (SEQ ID NO.1134) | FFTLRSIT |
| >gi\|30795146\|gb\|AAP41038.1\| Orf3 [SARS coronavirus Tor2] (SEQ ID NO.1135) | FTLRSITA |
| >gi\|30795146\|gb\|AAP41038.1\| Orf3 [SARS coronavirus Tor2] (SEQ ID NO.1136) | TLRSITAQ |
| >gi\|30795146\|gb\|AAP41038.1\| Orf3 [SARS coronavirus Tor2] (SEQ ID NO.1137) | LRSITAQP |
| >gi\|30795146\|gb\|AAP41038.1\| Orf3 [SARS coronavirus Tor2] (SEQ ID NO.1138) | RSITAQPV |
| >gi\|30421455\|gb\|AAP30714.1\| putative nucleocapsid protein [SARS coronavirus CUHK-Su10] (SEQ ID NO.1139) | RSSSRSRC |
| >gi\|30421455\|gb\|AAP30714.1\| putative nucleocapsid protein [SARS coronavirus CUHK-Su10] (SEQ ID NO.1140) | SSSRSRCN |
| >gi\|30421455\|gb\|AAP30714.1\| putative nucleocapsid protein [SARS coronavirus CUHK-Su10] (SEQ ID NO.1141) | SSRSRCNS |
| >gi\|30421455\|gb\|AAP30714.1\| putative nucleocapsid protein [SARS coronavirus CUHK-Su10] (SEQ ID NO.1142) | SRSRCNSR |
| >gi\|30421455\|gb\|AAP30714.1\| putative nucleocapsid protein [SARS coronavirus CUHK-Su10] (SEQ ID NO.1143) | RSRCNSRN |
| >gi\|30421455\|gb\|AAP30714.1\| putative nucleocapsid protein [SARS coronavirus CUHK-Su10] (SEQ ID NO.1144) | SRCNSRNS |

TABLE SARS-continued

| List of SARS virus-specific PETs | |
|---|---|
| >gi\|30421455\|gb\|AAP30714.1\| putative nucleocapsid protein [SARS coronavirus CUHK-Su10] (SEQ ID NO.1145) | RCNSRNST |
| >gi\|30421455\|gb\|AAP30714.1\| putative nucleocapsid protein [SARS coronavirus CUHK-Su10] (SEQ ID NO.1146) | CNSRNSTP |
| >gi\|31540949\|gb\|AAP49024.1\| nucleocapsid protein [SARS coronavirus] (SEQ ID NO.1147) | PQGLPNNI |
| >gi\|31540949\|gb\|AAP49024.1\| nucleocapsid protein [SARS coronavirus] (SEQ ID NO.1148) | QGLPNNIA |
| >gi\|31540949\|gb\|AAP49024.1\| nucleocapsid protein [SARS coronavirus] (SEQ ID NO.1149) | GLPNNIAS |
| >gi\|31540949\|gb\|AAP49024.1\| nucleocapsid protein [SARS coronavirus] (SEQ ID NO.1150) | LPNNIASW |
| >gi\|31540949\|gb\|AAP49024.1\| nucleocapsid protein [SARS coronavirus] (SEQ ID NO.1151) | PNNIASWF |
| >gi\|31540949\|gb\|AAP49024.1\| nucleocapsid protein [SARS coronavirus] (SEQ ID NO.1152) | NNIASWFT |
| >gi\|31540949\|gb\|AAP49024.1\| nucleocapsid protein [SARS coronavirus] (SEQ ID NO.1153) | NIASWFTA |
| >gi\|31540949\|gb\|AAP49024.1\| nucleocapsid protein [SARS coronavirus] (SEQ ID NO.1154) | IASWFTAL |
| >gi\|31581505\|gb\|AAP33697.1\| spike protein S [SARS coronavirus Frankfurt 1] (SEQ ID NO.1155) | HTSPDVDF |
| >gi\|31581505\|gb\|AAP33697.1\| spike protein S [SARS coronavirus Frankfurt 1] (SEQ ID NO.1156) | TSPDVDFG |
| >gi\|31581505\|gb\|AAP33697.1\| spike protein S [SARS coronavirus Frankfurt 1] (SEQ ID NO.1157) | SPDVDFGD |
| >gi\|31581505\|gb\|AAP33697.1\| spike protein S [SARS coronavirus Frankfurt 1] (SEQ ID NO.1158) | PDVDFGDI |
| >gi\|31581505\|gb\|AAP33697.1\| spike protein S [SARS coronavirus Frankfurt 1] (SEQ ID NO.1159) | DVDFGDIS |
| >gi\|31581505\|gb\|AAP33697.1\| spike protein S [SARS coronavirus Frankfurt 1] (SEQ ID NO.1160) | VDFGDISG |
| >gi\|31581505\|gb\|AAP33697.1\| spike protein S [SARS coronavirus Frankfurt 1] (SEQ ID NO.1161) | DFGDISGI |
| >gi\|31581505\|gb\|AAP33697.1\| spike protein S [SARS coronavirus Frankfurt 1] (SEQ ID NO.1162) | FGDISGIN |
| >gi\|31416295\|gb\|AAP51227.1\| spike glycoprotein S [SARS coronavirus GZ01] (SEQ ID NO.1163) | RAILTAFL |
| >gi\|31416295\|gb\|AAP51227.1\| spike glycoprotein S [SARS coronavirus GZ01] (SEQ ID NO.1164) | AILTAFLP |
| >gi\|31416295\|gb\|AAP51227.1\| spike glycoprotein S [SARS coronavirus GZ01] (SEQ ID NO.1165) | ILTAFLPA |
| >gi\|31416295\|gb\|AAP51227.1\| spike glycoprotein S [SARS coronavirus GZ01] (SEQ ID NO.1166) | LTAFLPAQ |
| >gi\|31416295\|gb\|AAP51227.1\| spike glycoprotein S [SARS coronavirus GZ01] (SEQ ID NO.1167) | TAFLPAQD |
| >gi\|31416295\|gb\|AAP51227.1\| spike glycoprotein S [SARS coronavirus GZ01] (SEQ ID NO.1168) | AFLPAQDT |
| >gi\|31416295\|gb\|AAP51227.1\| spike glycoprotein S [SARS coronavirus GZ01] (SEQ ID NO.1169) | FLPAQDTW |
| >gi\|31416295\|gb\|AAP51227.1\| spike glycoprotein S [SARS coronavirus GZ01] (SEQ ID NO.1170) | LPAQDTWG |

TABLE SARS-continued

List of SARS virus-specific PETs

| | |
|---|---|
| >gi\|31416295\|gb\|AAP51227.1\| spike glycoprotein S [SARS coronavirus GZ01] (SEQ ID NO.1171) | NFRVVPSR |
| >gi\|31416295\|gb\|AAP51227.1\| spike glycoprotein S [SARS coronavirus GZ01] (SEQ ID NO.1172) | FRVVPSRD |
| >gi\|31416295\|gb\|AAP51227.1\| spike glycoprotein S [SARS coronavirus GZ01] (SEQ ID NO.1173) | RVVPSRDV |
| >gi\|31416295\|gb\|AAP51227.1\| spike glycoprotein S [SARS coronavirus GZ01] (SEQ ID NO.1174) | VVPSRDVV |
| >gi\|31416295\|gb\|AAP51227.1\| spike glycoprotein S [SARS coronavirus GZ01] (SEQ ID NO.1175) | VPSRDVVR |
| >gi\|31416295\|gb\|AAP51227.1\| spike glycoprotein S [SARS coronavirus GZ01] (SEQ ID NO.1176) | PSRDVVRF |
| >gi\|31416295\|gb\|AAP51227.1\| spike glycoprotein S [SARS coronavirus GZ01] (SEQ ID NO.1177) | SRDVVRFP |
| >gi\|31416295\|gb\|AAP51227.1\| spike glycoprotein S [SARS coronavirus GZ01] (SEQ ID NO.1178) | RDVVRFPN |
| >gi\|31416295\|gb\|AAP51227.1\| spike glycoprotein S [SARS coronavirus GZ01] (SEQ ID NO.1179) | VYAWERKR |
| >gi\|31416295\|gb\|AAP51227.1\| spike glycoprotein S [SARS coronavirus GZ01] (SEQ ID NO.1180) | YAWERKRI |
| >gi\|31416295\|gb\|AAP51227.1\| spike glycoprotein S [SARS coronavirus GZ01] (SEQ ID NO.1181) | AWERKRIS |
| >gi\|31416295\|gb\|AAP51227.1\| spike glycoprotein S [SARS coronavirus GZ01] (SEQ ID NO.1182) | WERKRISN |
| >gi\|31416295\|gb\|AAP51227.1\| spike glycoprotein S [SARS coronavirus GZ01] (SEQ ID NO.1183) | ERKRISNC |
| >gi\|31416295\|gb\|AAP51227.1\| spike glycoprotein S [SARS coronavirus GZ01] (SEQ ID NO.1184) | RKRISNCV |
| >gi\|31416295\|gb\|AAP51227.1\| spike glycoprotein S [SARS coronavirus GZ01] (SEQ ID NO.1185) | KRISNCVA |
| >gi\|31416295\|gb\|AAP51227.1\| spike glycoprotein S [SARS coronavirus GZ01] (SEQ ID NO.1186) | RISNCVAD |
| >gi\|31416295\|gb\|AAP51227.1\| spike glycoprotein S [SARS coronavirus GZ01] (SEQ ID NO.1187) | YRVVVLSY |
| >gi\|31416295\|gb\|AAP51227.1\| spike glycoprotein S [SARS coronavirus GZ01] (SEQ ID NO.1188) | RVVVLSYE |
| >gi\|31416295\|gb\|AAP51227.1\| spike glycoprotein S [SARS coronavirus GZ01] (SEQ ID NO.1189) | VVVLSYEL |
| >gi\|31416295\|gb\|AAP51227.1\| spike glycoprotein S [SARS coronavirus GZ01] (SEQ ID NO.1190) | VVLSYELL |
| >gi\|31416295\|gb\|AAP51227.1\| spike glycoprotein S [SARS coronavirus GZ01] (SEQ ID NO.1191) | VLSYELLN |
| >gi\|31416295\|gb\|AAP51227.1\| spike glycoprotein S [SARS coronavirus GZ01] (SEQ ID NO.1192) | LSYELLNA |
| >gi\|31416295\|gb\|AAP51227.1\| spike glycoprotein S [SARS coronavirus GZ01] (SEQ ID NO.1193) | SYELLNAP |
| >gi\|31416295\|gb\|AAP51227.1\| spike glycoprotein S [SARS coronavirus GZ01] (SEQ ID NO.1194) | YELLNAPA |
| >gi\|31416295\|gb\|AAP51227.1\| spike glycoprotein S [SARS coronavirus GZ01] (SEQ ID NO.1195) | YKTPTLKD |
| >gi\|31416295\|gb\|AAP51227.1\| spike glycoprotein S [SARS coronavirus GZ01] (SEQ ID NO.1196) | KTPTLKDF |

TABLE SARS-continued

List of SARS virus-specific PETs

| | |
|---|---|
| >gi\|31416295\|gb\|AAP51227.1\| spike glycoprotein S [SARS coronavirus GZ01] (SEQ ID NO.1197) | TPTLKDFG |
| >gi\|31416295\|gb\|AAP51227.1\| spike glycoprotein S [SARS coronavirus GZ01] (SEQ ID NO.1198) | PTLKDFGG |
| >gi\|31416295\|gb\|AAP51227.1\| spike glycoprotein S [SARS coronavirus GZ01] (SEQ ID NO.1199) | TLKDFGGF |
| >gi\|31416295\|gb\|AAP51227.1\| spike glycoprotein S [SARS coronavirus GZ01] (SEQ ID NO.1200) | LKDFGGFN |
| >gi\|31416295\|gb\|AAP51227.1\| spike glycoprotein S [SARS coronavirus GZ01] (SEQ ID NO.1201) | KDFGGFNF |
| >gi\|31416295\|gb\|AAP51227.1\| spike glycoprotein S [SARS coronavirus GZ01] (SEQ ID NO.1202) | DFGGFNFS |
| >gi\|31416295\|gb\|AAP51227.1\| spike glycoprotein S [SARS coronavirus GZ01] (SEQ ID NO.1203) | ILPDPLKS |
| >gi\|31416295\|gb\|AAP51227.1\| spike glycoprotein S [SARS coronavirus GZ01] (SEQ ID NO.1204) | LPDPLKST |
| >gi\|31416295\|gb\|AAP51227.1\| spike glycoprotein S [SARS coronavirus GZ01] (SEQ ID NO.1205) | PDPLKSTK |
| >gi\|31416295\|gb\|AAP51227.1\| spike glycoprotein S [SARS coronavirus GZ01] (SEQ ID NO.1206) | DPLKSTKR |
| >gi\|31416295\|gb\|AAP51227.1\| spike glycoprotein S [SARS coronavirus GZ01] (SEQ ID NO.1207) | PLKSTKRS |
| >gi\|31416295\|gb\|AAP51227.1\| spike glycoprotein S [SARS coronavirus GZ01] (SEQ ID NO.1208) | LKSTKRSF |
| >gi\|31416295\|gb\|AAP51227.1\| spike glycoprotein S [SARS coronavirus GZ01] (SEQ ID NO.1209) | KSTKRSFI |
| >gi\|31416295\|gb\|AAP51227.1\| spike glycoprotein S [SARS coronavirus GZ01] (SEQ ID NO.1210) | STKRSFIE |
| >gi\|30795145\|gb\|AAP41037.1\| spike glycoprotein [SARS coronavirus Tor2] (SEQ ID NO.1211) | ILDISPCA |
| >gi\|30795145\|gb\|AAP41037.1\| spike glycoprotein [SARS coronavirus Tor2] (SEQ ID NO.1212) | LDISPCAF |
| >gi\|30795145\|gb\|AAP41037.1\| spike glycoprotein [SARS coronavirus Tor2] (SEQ ID NO.1213) | DISPCAFG |
| >gi\|30795145\|gb\|AAP41037.1\| spike glycoprotein [SARS coronavirus Tor2] (SEQ ID NO.1214) | ISPCAFGG |
| >gi\|30795145\|gb\|AAP41037.1\| spike glycoprotein [SARS coronavirus Tor2] (SEQ ID NO.1215) | SPCAFGGV |
| >gi\|30795145\|gb\|AAP41037.1\| spike glycoprotein [SARS coronavirus Tor2] (SEQ ID NO.1216) | PCAFGGVS |
| >gi\|30795145\|gb\|AAP41037.1\| spike glycoprotein [SARS coronavirus Tor2] (SEQ ID NO.1217) | CAFGGVSV |
| >gi\|30795145\|gb\|AAP41037.1\| spike glycoprotein [SARS coronavirus Tor2] (SEQ ID NO.1218) | AFGGVSVI |
| >gi\|30023954\|gb\|AAP13567.1\| putative E2 glycoprotein precursor [SARS coronavirus CUHK-W1] (SEQ ID NO.1219) | AFSPAQDT |
| >gi\|30023954\|gb\|AAP13567.1\| putative E2 glycoprotein precursor [SARS coronavirus CUHK-W1] (SEQ ID NO.1220) | FSPAQDTW |
| >gi\|30023954\|gb\|AAP13567.1\| putative E2 glycoprotein precursor [SARS coronavirus CUHK-W1] (SEQ ID NO.1221) | SPAQDTWG |
| >gi\|31416293\|gb\|AAP51225.1\| orf1ab [SARS coronavirus GZ01] (SEQ ID NO.1222) | DALCEKAS |

TABLE SARS-continued

List of SARS virus-specific PETs

| | |
|---|---|
| >gi\|31416293\|gb\|AAP51225.1\| orf1ab [SARS coronavirus GZ01] (SEQ ID NO.1223) | ALCEKASK |
| >gi\|31416293\|gb\|AAP51225.1\| orf1ab [SARS coronavirus GZ01] (SEQ ID NO.1224) | LCEKASKY |
| >gi\|31416293\|gb\|AAP51225.1\| orf1ab [SARS coronavirus GZ01] (SEQ ID NO.1225) | CEKASKYL |
| >gi\|31416293\|gb\|AAP51225.1\| orf1ab [SARS coronavirus GZ01] (SEQ ID NO.1226) | EKASKYLP |
| >gi\|31416293\|gb\|AAP51225.1\| orf1ab [SARS coronavirus GZ01] (SEQ ID NO.1227) | KASKYLPI |
| >gi\|31416293\|gb\|AAP51225.1\| orf1ab [SARS coronavirus GZ01] (SEQ ID NO.1228) | ASKYLPID |
| >gi\|31416293\|gb\|AAP51225.1\| orf1ab [SARS coronavirus GZ01] (SEQ ID NO.1229) | SKYLPIDK |
| >gi\|31416293\|gb\|AAP51225.1\| orf1ab [SARS coronavirus GZ01] (SEQ ID NO.1230) | SVIDLLLN |
| >gi\|31416293\|gb\|AAP51225.1\| orf1ab [SARS coronavirus GZ01] (SEQ ID NO.1231) | LLLNDFVE |
| >gi\|31416293\|gb\|AAP51225.1\| orf1ab [SARS coronavirus GZ01] (SEQ ID NO.1232) | LLNDFVEI |
| >gi\|31416293\|gb\|AAP51225.1\| orf1ab [SARS coronavirus GZ01] (SEQ ID NO.1233) | LNDFVEII |
| >gi\|31416293\|gb\|AAP51225.1\| orf1ab [SARS coronavirus GZ01] (SEQ ID NO.1234) | NDFVEIIK |
| >gi\|31416293\|gb\|AAP51225.1\| orf1ab [SARS coronavirus GZ01] (SEQ ID NO.1235) | LVDSDLNE |
| >gi\|31416293\|gb\|AAP51225.1\| orf1ab [SARS coronavirus GZ01] (SEQ ID NO.1236) | VDSDLNEF |
| >gi\|31416293\|gb\|AAP51225.1\| orf1ab [SARS coronavirus GZ01] (SEQ ID NO.1237) | DSDLNEFV |
| >gi\|31416293\|gb\|AAP51225.1\| orf1ab [SARS coronavirus GZ01] (SEQ ID NO.1238) | SDLNEFVS |
| >gi\|31416293\|gb\|AAP51225.1\| orf1ab [SARS coronavirus GZ01] (SEQ ID NO.1239) | DLNEFVSD |
| >gi\|31416293\|gb\|AAP51225.1\| orf1ab [SARS coronavirus GZ01] (SEQ ID NO.1240) | LNEFVSDA |
| >gi\|31416293\|gb\|AAP51225.1\| orf1ab [SARS coronavirus GZ01] (SEQ ID NO.1241) | NEFVSDAD |
| >gi\|31416293\|gb\|AAP51225.1\| orf1ab [SARS coronavirus GZ01] (SEQ ID NO.1242) | EFVSDADS |
| >gi\|31416293\|gb\|AAP51225.1\| orf1ab [SARS coronavirus GZ01] (SEQ ID NO.1243) | ANYIFWRK |
| >gi\|31416293\|gb\|AAP51225.1\| orf1ab [SARS coronavirus GZ01] (SEQ ID NO.1244) | NYIFWRKT |
| >gi\|31416293\|gb\|AAP51225.1\| orf1ab [SARS coronavirus GZ01] (SEQ ID NO.1245) | YIFWRKTN |
| >gi\|31416293\|gb\|AAP51225.1\| orf1ab [SARS coronavirus GZ01] (SEQ ID NO.1246) | IFWRKTNP |

TABLE SARS-continued

| List of SARS virus-specific PETs | |
|---|---|
| >gi\|31416293\|gb\|AAP51225.1\| orf1ab [SARS coronavirus GZ01] (SEQ ID NO.1247) | FWRKTNPI |
| >gi\|31416293\|gb\|AAP51225.1\| orf1ab [SARS coronavirus GZ01] (SEQ ID NO.1248) | WRKTNPIQ |
| >gi\|31416293\|gb\|AAP51225.1\| orf1ab [SARS coronavirus GZ01] (SEQ ID NO.1249) | RKTNPIQL |
| >gi\|31416293\|gb\|AAP51225.1\| orf1ab [SARS coronavirus GZ01] (SEQ ID NO.1250) | KTNPIQLS |
| >gi\|30795144\|gb\|AAP41036.1\| replicase 1AB [SARS coronavirus Tor2] (SEQ ID NO.1251) | SADASTFF |
| >gi\|30795144\|gb\|AAP41036.1\| replicase 1AB [SARS coronavirus Tor2] (SEQ ID NO.1252) | ADASTFFK |
| >gi\|30795144\|gb\|AAP41036.1\| replicase 1AB [SARS coronavirus Tor2] (SEQ ID NO.1253) | DASTFFKR |
| >gi\|30795144\|gb\|AAP41036.1\| replicase 1AB [SARS coronavirus Tor2] (SEQ ID NO.1254) | ASTFFKRV |
| >gi\|30795144\|gb\|AAP41036.1\| replicase 1AB [SARS coronavirus Tor2] (SEQ ID NO.1255) | STFFKRVC |
| >gi\|30795144\|gb\|AAP41036.1\| replicase 1AB [SARS coronavirus Tor2] (SEQ ID NO.1256) | TFFKRVCG |
| >gi\|30795144\|gb\|AAP41036.1\| replicase 1AB [SARS coronavirus Tor2] (SEQ ID NO.1257) | FFKRVCGV |
| >gi\|30795144\|gb\|AAP41036.1\| replicase 1AB [SARS coronavirus Tor2] (SEQ ID NO.1258) | FKRVCGVS |
| >gi\|30795144\|gb\|AAP41036.1\| replicase 1AB [SARS coronavirus Tor2] (SEQ ID NO.1259) | KRVCGVSA |
| >gi\|31581504\|gb\|AAP33696.1\| polyprotein 1ab [SARS coronavirus Frankfurt 1] (SEQ ID NO.1260) | ELFYSYAI |
| >gi\|31581504\|gb\|AAP33696.1\| polyprotein 1ab [SARS coronavirus Frankfurt 1] (SEQ ID NO.1261) | LFYSYAIH |
| >gi\|31581504\|gb\|AAP33696.1\| polyprotein 1ab [SARS coronavirus Frankfurt 1] (SEQ ID NO.1262) | FYSYAIHH |
| >gi\|31581504\|gb\|AAP33696.1\| polyprotein 1ab [SARS coronavirus Frankfurt 1] (SEQ ID NO.1263) | YSYAIHHD |
| >gi\|31581504\|gb\|AAP33696.1\| polyprotein 1ab [SARS coronavirus Frankfurt 1] (SEQ ID NO.1264) | SYAIHHDK |
| >gi\|31581504\|gb\|AAP33696.1\| polyprotein 1ab [SARS coronavirus Frankfurt 1] (SEQ ID NO.1265) | YAIHHDKF |
| >gi\|31581504\|gb\|AAP33696.1\| polyprotein 1ab [SARS coronavirus Frankfurt 1] (SEQ ID NO.1266) | AIHHDKFT |
| >gi\|31581504\|gb\|AAP33696.1\| polyprotein 1ab [SARS coronavirus Frankfurt 1] (SEQ ID NO.1267) | IHHDKFTD |

Example 7

PET-Specific Antibodies are Highly Specific and have High Affinity for their PET Antigens There are numerous PET-specific antibodies that were shown to be highly specific and have high affinity for their respective antigens. The following table lists a few exemplary antibodies showing high affinity (low nanomolar to high picomolar range) for their respective antigens.

| Peptide Sequence | Length (aa) | Affinity ($K_D$ in nM) | Reference |
|---|---|---|---|
| GATPEDLNQKLAGN (SEQ ID NO.1268) | 14 | 1.4 | Cell 91: 799, 1997 |
| CRGTGSYNRSSFESSSG (SEQ ID NO.1269) | 17 | 2.8 | JIM 249: 253, 2001 |

| Peptide Sequence | Length (aa) | Affinity ($K_D$ in nM) | Reference |
|---|---|---|---|
| NYRAYATEPHAKKKS (SEQ ID NO.1270) | 15 | 0.5 | EJB 267: 1819, 2000 |
| RYDIEAKVTK (SEQ ID NO.1271) | 10 | 3.5 | JI 169: 6992, 2002 |
| DRVYIHPF (SEQ ID NO.1272) | 8 | 0.5 | JIM 254: 147, 2001 |
| PQSDPSVEPPLS (SEQ ID NO.1273) | 12 | 16 (a scFv) | NG 21: 163, 2003 |
| YDVPDYAS (HA tag) (SEQ ID NO.1274) | 8 | 2 | engeneOS |
| MDYKAFDN (FLAG tag) (SEQ ID NO.1275) | 8 | 2.3 | engeneOS |
| HHHHH (HIS tag) (SEQ ID NO.1276) | 5 | 25 | Novagen |

Further more, the table below shows three additional PET-specific antibodies with similar nanomolar-range affinity for the respective antigens:

| PET Sequence | Ab name | Affinity ($K_D$ in nM) | Parental Protein |
|---|---|---|---|
| EPAELTDA (SEQ ID NO.1277) | P1 | 5 | PSA |
| YEVQGEVF (SEQ ID NO.1278) | C1 | 31 | CRP |
| GYSIFSYA (SEQ ID NO.1279) | C2 | 200 | CRP |

These PETs are selected based on the criteria set forth in the instant specification, including nearest neighbor analysis. Listed below are several nearest neighbors of two of the PETs above.

| | PET | | AA Differences |
|---|---|---|---|
| | LSEPAELTDAVK | (SEQ ID NO. 1280) | |
| NNP1 | DEPVELTSAPTGHTFS | (SEQ ID NO. 1281) | 2 |
| NNP2 | AGEAAEL QDAEVESSAK | (SEQ ID NO. 1282) | 2 |
| NNP3 | LQEPAELVESDGVPK | (SEQ ID NO. 1283) | 3 |
| NNP4 | AQPAELVDSSGW | (SEQ ID NO. 1284) | 3 |
| NNP5 | GLDPTQLTDALTQR | (SEQ ID NO. 1285) | 3 |
| | YEVQGEVFTK | (SEQ ID NO. 1286) | |
| NNP1 | HVEVNGEVFQK | (SEQ ID NO. 1287) | 2 |
| NNP2 | SYEVLGEEFDR | (SEQ ID NO. 1288) | 2 |
| NNP3 | QYAVSGEIFVVDR | (SEQ ID NO. 1289) | 3 |
| NNP4 | VYEEQGEIILK | (SEQ ID NO. 1290) | 3 |
| NNP5 | LYEVRGETYLK | (SEQ ID NO. 1291) | 3 |

PET-specific antibodies are not only high affinity antibodies, but also highly specific antibodies showing little, if any cross-reactivity with other closely related peptide sequences.

For example, FIG. 24 shows peptide competition results using the peptide competition assay described in Example 5. The left panel shows that antibody P1, which is specific for the PSA-derived 8-mer PET sequence EPAELTDA, (SEQ ID NO: 1277) can be effectively competed away by the antigen PET (EPAELTDA) (SEQ ID NO: 1277), with a half-maximum effective peptide concentration of around 40 nM. However, two of its nearest-neighbor 8-mer PETs found in the human proteome with only two- or three-amino-acid differences, EPVELTSA (SEQ ID NO: 1292) and DPTQLTDA, (SEQ ID NO: 1293) are completely ineffective even at 1000 μM (25,000-fold higher concentration). Similarly, the right panel shows that antibody C1, which is specific for the CRP-derived 8-mer PET sequence YEVQGEVF (SEQ ID NO: 1277), can be effectively competed away by the antigen PET sequence YEVQGEVF (SEQ ID NO: 1278), with a half-maximum effective peptide concentration of around 1 μM. However, two of its nearest-neighbor 8-mer PETs found in the human proteome with only two-amino-acid differences, VEVNGEVF (SEQ ID NO: 1294) and YEVLGEEF (SEQ ID NO: 1295), are completely ineffective even at 1000 μM (at least 1,000-fold higher concentration).

Example 8

Antibody Cross-Reactivity: Kallikrein Ab's

The kallikreins are a subfamily of the serine protease enzyme family (Bhoola et al., *Pharmacol Rev* 44: 1-80, 1992; Clements J. *The molecular biology of the kallikreins and their roles in inflammation*. Farmer S. eds. *The kinin system* 1997: 71-97 Academic Press New York). The human kallikrein gene family was, until recently, thought to include only three members: KLK1, which encodes for pancreatic/renal kallikrein (hK1); KLK2, which encodes for human glandular kallikrein 2 (hK2); and KLK3, which encodes for prostate-specific antigen (PSA; hK3) (Riegman et al., *Genomics* 14: 6-11, 1992). The best known of the three classic human kallikreins is PSA, an important biomarker for prostate cancer diagnosis and monitoring. Recently, new serine proteases with high degrees of homology to the three classic kallikreins were cloned. These newly identified serine proteases have now been included in the expanded human kallikrein gene family. The entire human kallikrein gene locus on chromosome 19q13.4 now includes 15 genes, designated KLK1-KLK15; their respective proteins are known as hK1-hK15 (Diamandis et al., *Clin Chem* 46: 1855-1858, 2000).

KLK13, previously known as KLK-L4, is one of the newly identified kallikrein genes. The protein has 47% and 45% sequence identity with PSA and hK2, respectively (Yousef et al., *J Biol Chem* 275: 11891-11898, 2000). At the mRNA level, KLK13 expression is highest in the mammary gland, prostate, testis, and salivary glands (Yousef, supra). Although the function of KLK13 is still unknown, KLK13, like all other members of the human kallikrein family, is predicted to encode a secreted serine protease that is likely present in biological fluids. Given the prominent role of PSA as a cancer biomarker and the recent demonstration that other members of this gene family are also potential cancer biomarkers (Diamandis et al., *Clin Biochem* 33: 369-375, 2000; Luo et al., *Clin Chem* 47: 237-246, 2001; Diamandis et al., *Clin Biochem* 33: 579-583, 2000; Luo et al., *Clin Chim Acta* 7: 806-811, 2001; Diamandis et al., *Cancer Res* 62: 293-300, 2002), hK13 may also have utility as a disease biomarker. In order to develop a suitable method for measuring hK13 protein in biological fluids and tissues with high sensitivity and specificity, and to further investigate the diagnostic and other clinical applications of this protein, Kapadia et al. (*Clinical Chemistry* 49: 77-86, 2003) cloned and expressed the full-length recombinant human KLK13 in a yeast expression system, and raised KLK13-specific monoclonal and polyclonal antibodies. A sandwich-type assay revealed that the KLK13 antibody is quite specific—recombinant hK1, hK2, hK3, hK4, hK5, hK6, hK7, hK8, hK9, hK10, hK11, hK12, hK14, and hK15 proteins did not produce measurable readings, even at concentrations 1000-fold higher than that of hK13.

However, it should be noted that this type of antibody specificity defined by cross-reactivity to other related proteins, without any epitope information, can frequently be misleading, and thus the data presented in Kapadia et al. should be interpreted with caution. For one thing, unrelated proteins may have higher sequence homology or conformation similarity than family proteins. It may be pure luck that any hK13 antibody does not cross-react with other highly related family members. However, there is no guarantee that the specific epitope recognized by the hK13 antibody does not appear in other proteins, such as an un-identified kallikrein family member, or an alternative splicing form of hK13. Therefore, antibody specificity is better defined by reactivity to peptides most homologous to a selected PET (nearest neighbor peptides). Antibody cross-reactivity is now readily measurable using peptide competitive assays at a wide dynamic range.

On the other hand, in certain situations, detection for the whole protein family or a specific subset of the family are needed. For example, it has already been demonstrated that multiple kallikreins are overexpressed in ovarian carcinoma (reviewed in Yousef and Diamandis, *Minerva Endocrinol* 27: 157-166, 2002). There is experimental evidence that these kallikreins may form a cascade enzymatic pathway similar to the pathways of coagulation and fibrinolysis. Therefore, one single antibody specific for the subset of ovarian carcinoma-associated kallikreins is of particular interest in clinical setting. Lastly, the concentrations of competitors used is limited in Kapadia's assay.

These problems can be readily tackled with the approach of the instant invention. For example, the table below lists a common PET for hK1-hK11 (except hK6 and 7, which have their common PETs), as well as PETs specific for each hK proteins listed. In addition, both the family-specific PET and the protein-specific PET are within the same tryptic fragment.

| | | |
|---|---|---|
| hK1 | HSSQPWQVAVYSHGWAHCGGVLVHR | (SEQ ID NO. 1296) |
| hK2 | IVGGWECEQHSQPWQAALYHFSTFQCGGILVHK | (SEQ ID NO. 1297) |
| hK3 | GSQPWQVSLFNGLSFHCAGVLVDR | (SEQ ID NO. 1298) |
| hK4 | NSQPWQVGLFEGTSLR | (SEQ ID NO. 1299) |
| hK5 | HECQPHSQPWQAALFGQQLLCGGVLVGR | (SEQ ID NO. 1300) |
| hK8 | EDCSPHSQPWQAALVMENELFCSGVLVHR | (SEQ ID NO. 1301) |
| hK9 | VLNTNGTSGFLPGGYTCFPHSQPWQAALLVQGR | (SEQ ID NO. 1302) |
| hK10 | LLEGDECAPH SQPWQVALYER | (SEQ ID NO. 1303) |
| hK11 | PNSQPWQAGLFHLTR | (SEQ ID NO. 1304) |
| hK6 | CVTAGTSCLISGWGSTSSPQLR | (SEQ ID NO. 1305) |
| Hk7 | VMDLPTQEPALGTTCYASGWGSIEPEEFLTPK | (SEQ ID NO. 1306) |

By using these family- and individual-specific PET antibodies (or other suitable capture reagents), the same tryptic digestion can be used--for a sandwich-type assay that captures all interested tryptic peptides (using the family-specific PET antibodies), followed by selective detection/quantitation of specific family members (using for example, differentially labeled individual-specific antibodies, preferably in a single experiment.

In addition, the same approach may be used to detect the presence of alternative splicing isoforms of any protein. For example, there are three alternative splicing forms of hK15 (* represents trypsin digestion sites):

```
hK15-V1    R*LNPQVR*PAVLPTR*CPHPGEACVVSGWGLVSHEPGTAGSPR*SQG
           (SEQ ID NO. 1307)

hK15-V2    R*LNPQ----------------------------------
           (SEQ ID NO. 1308)

hK15-V3    R*LNPQGDSGGPLVCGGILQGIVSWGDVPCDNTTK*PGVYTK
           (SEQ ID NO. 1309)
```

Thus, SGWGLVSH (SEQ ID NO: 1310)is a PET for detecting V1, with the three nearest neighbor peptides being AGWGIVNH (SEQ ID NO: 1311), SGWGITNH (SEQ ID NO: 1312), and SGWGMVTE (SEQ ID NO: 1313). Similarly, WGDVPCDN (SEQ ID NO: 1314) is a PET for detecting V1, with the three nearest neighbor peptides being WKDVPCED (SEQ ID NO: 1315), WNDAPCDS (SEQ ID NO: 1316), and WNDAPCDK (SEQ ID NO: 1317).

Example 9

Detecting Serum Protein Levels

Due to the fundamental problems in measuring an antigen which exists in more than one form and/or present in different complexes, it may be difficult to reach a consensus on the level of total a serum protein (such as TGF-b1 protein) in normal human plasma. The instant invention provides a method that efficiently solves these problems.

Figure 21:
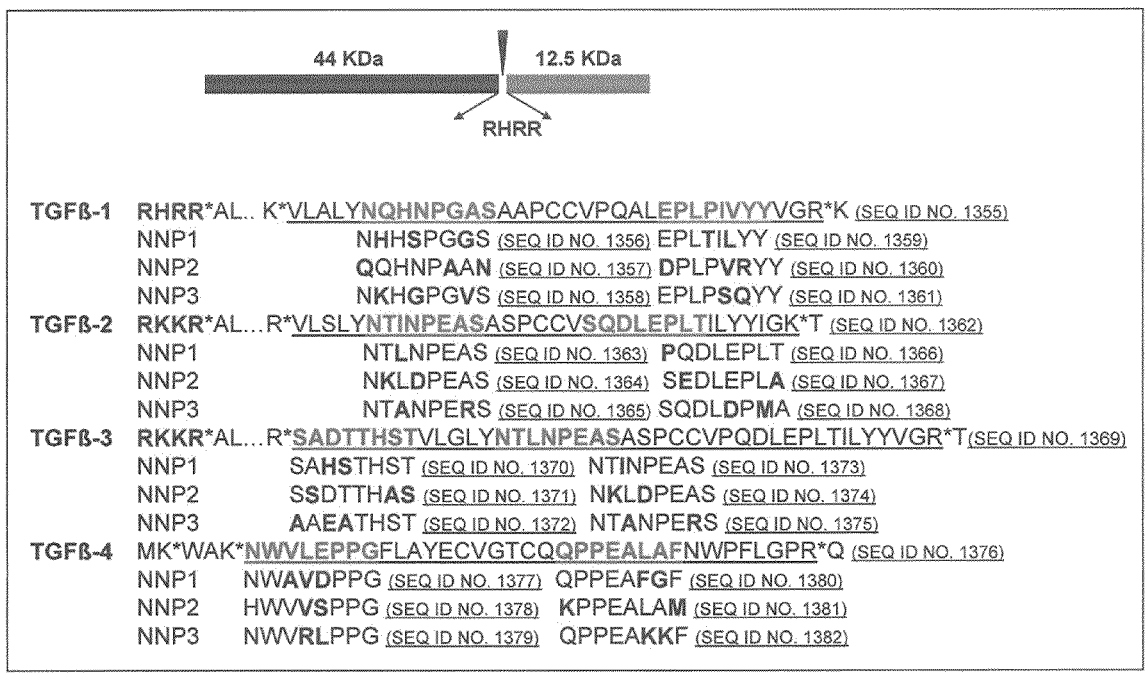
FIG. 21 shows a design for the PET-based assay for standardized serum TGF-beta measurement.

FIG. 21 shows a design for the PET-based assay for standardized serum TGF-beta measurement. The C-terminal monomer for the mature TGF-beta is represented in the top panel as a red bar. The sequences below indicates the PETs specific for each of the 4 TGF-beta isoforms and their respective nearest neighbors. The PET-based assay can be used to specifically detect one of the TGF-beta isoforms, as well as the total amount of all TGF-beta isoforms present in a serum sample.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for achieving high sensitivity detection and/or high accuracy quantitation of a target protein in a biological sample, the method comprising the steps of:
    (1) providing an addressable array of two or more different capture agents wherein each of which two or more capture agents is specific for binding naturally occurring peptide epitope tag (PET) within the target protein;
    (2) contacting the addressable array of two or more different capture agents with a solution of polypeptide analytes produced by denaturation and/or cleavage of the target protein in the test sample. such that the capture agents have access to the peptide epitope tags within the polypeptide analytes generated by the denaturation and/or cleavage of the target protein;
    (3) detecting a signal generated as a result of binding of a capture agent to a naturally occurring PET within a polypeptide analyte; and
    (4) averaging the signals generated in (3) from each of the capture agents specifically binding to a naturally occurring PET, if signals are present, thereby to quantitate the amount of the target protein in the sample.

2. The method of claim 1, wherein each of two or more different capture agent specifically binds a different PET within the target protein.

3. The method of claim 2, wherein each of the different capture agents belong to a same category.

4. The method of claim 3, wherein the category of capture agent is selected from the group consisting of an antibody, a non-antibody polypeptide, a PNA (peptide nucleic acids), a scaffolded peptide, a peptidomimetic compound, a polynucleotide, a carbohydrate, an artificial polymer, a plastibody, a chimeric binding agent derived from low-affinity ligand, and a small organic molecule.

5. The method of claim 2, wherein at least two of the different capture agents belong to different categories of capture agent selected from the group consisting of an antibody, a non-antibody polypeptide. a PNA (peptide nucleic acids), a scaffolded peptide, a peptidomimetic compound, a polynucleotide, a carbohydrate, an artificial polymers, a plastibody, a chimeric binding agent derived from low-affinity ligand. and a small organic molecule.

6. The method of claim 1, wherein a subset of the capture agents bind to the same PET, and wherein each of the capture agents of the subset belong. to a different category of capture agent selected from the group consisting of an antibody, a non-antibody polypeptide, a PNA (peptide nucleic acids), a scaffolded peptide, a peptidomimetic compound, a polynucleotide, a carbohydrate, an artificial polymer, a plastibody, a chimeric binding agent derived from low-affinity ligand. and a small organic molecule.

7. The method of claim 1, wherein the target protein has two or more different forms within the biological sample.

8. The method of claim 7, wherein the different forms include unprocessed/pro-form and processed/mature form.

9. The method of claim 7, wherein the different forms include different alternative splicing forms.

10. The method of claim 7, wherein the different forms include an unmodified and a posttranslationally modified form with respect to one or more post-translational modification(s).

11. The method of claim 10, wherein the one or more post-translational modification(s) is selected from the group consisting of acetylation, amidation, deamidation, prenylation, formylation, glycosylation, hydroxylation, methylation, myristoylation, phosphorylation. ubiquitination, ribosylation and sulphation.

12. The method of claim 7, wherein a subset of the capture agents are specific for PET(s) only found in certain forms but not in other forms.

13. The method of claim 12. further comprising determining the percentage of one form of the target protein as compared to the total target protein, or ratio of a first form of the target protein to a second form of the target protein.

14. The method of claim 1, further comprising detecting other target proteins within the biological sample with capture agents specific for PETs of the other target proteins.

15. The method of claim 14. wherein two or more different capture agents are used for detecting and/or quantitating at least one of the other target proteins.

16. The method of claim 1, wherein, for each capture agent, the method has a regression coefficient ($R^2$) of 0.95 or greater.

17. The method of claim 1, wherein the array has a recovery rate of at least 50 percent.

18. The method of claim 1. wherein the accuracy is 90%.

19. An array of capture agents for detecting and quantitating a target protein within a biological sample, the array comprising a plurality of capture agents, wherein each capture agent is immobilized on a distinct addressable location on a solid support, and wherein each of the capture agents. specifically binds a PET uniquely associated with a peptide fragment of the target protein that predictably results from a treatment of the biological sample.

20. A composition comprising a plurality of capture agents, wherein each of the capture agents recognizes and interacts with one PET within a target protein.

* * * * *